(12) United States Patent
Kaldor et al.

(10) Patent No.: US 12,312,336 B2
(45) Date of Patent: *May 27, 2025

(54) INHIBITORS OF RAF KINASES

(71) Applicant: PIERRE FABRE MEDICAMENT, Lavaur (FR)

(72) Inventors: Stephen W. Kaldor, San Diego, CA (US); Toufike Kanouni, Rancho Santa Fe, CA (US); John Tyhonas, San Diego, CA (US); Eric Murphy, San Marcos, CA (US)

(73) Assignee: PIERRE FABRE MÉDICAMENT, Lavaur (FR)

( * ) Notice: Subject to any disclaimer, the term of this patent is extended or adjusted under 35 U.S.C. 154(b) by 1088 days.

This patent is subject to a terminal disclaimer.

(21) Appl. No.: 17/213,036

(22) Filed: Mar. 25, 2021

(65) Prior Publication Data
US 2021/0300904 A1    Sep. 30, 2021

Related U.S. Application Data

(63) Continuation of application No. 17/079,152, filed on Oct. 23, 2020, now Pat. No. 11,098,031.

(60) Provisional application No. 63/044,898, filed on Jun. 26, 2020, provisional application No. 62/925,596, filed on Oct. 24, 2019.

(51) Int. Cl.
| | | |
|---|---|---|
| C07D 403/12 | (2006.01) | |
| C07D 401/12 | (2006.01) | |
| C07D 401/14 | (2006.01) | |
| C07D 403/14 | (2006.01) | |
| C07D 405/14 | (2006.01) | |
| C07D 413/14 | (2006.01) | |

(52) U.S. Cl.
CPC ......... *C07D 403/12* (2013.01); *C07D 401/12* (2013.01); *C07D 401/14* (2013.01); *C07D 403/14* (2013.01); *C07D 405/14* (2013.01); *C07D 413/14* (2013.01)

(58) Field of Classification Search
CPC .................................................. C07D 403/12
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 9,694,016 B2 | 7/2017 | Aversa et al. |
| 10,927,111 B2 | 2/2021 | Kaldaor et al. |
| 11,098,031 B1 * | 8/2021 | Kaldor .................... A61P 35/00 |
| 11,377,431 B2 | 7/2022 | Kaldor et al. |
| 11,407,737 B2 | 8/2022 | Kaldor et al. |
| 2004/0157827 A1 | 8/2004 | Pevarello et al. |
| 2005/0256174 A1 | 11/2005 | Wood et al. |
| 2007/0054916 A1 | 3/2007 | Patel et al. |
| 2007/0244120 A1 | 10/2007 | Dumas et al. |
| 2008/0114006 A1 | 5/2008 | Flynn et al. |
| 2009/0036419 A1 | 2/2009 | Chen et al. |
| 2009/0054436 A1 | 2/2009 | Borzilleri et al. |
| 2011/0183997 A1 | 7/2011 | Chianelli et al. |
| 2012/0040951 A1 | 2/2012 | Chuaqui et al. |
| 2014/0275003 A1 | 9/2014 | Barsanti et al. |
| 2015/0119392 A1 | 4/2015 | Flynn et al. |
| 2016/0075727 A1 | 3/2016 | Burger et al. |
| 2017/0260207 A1 | 9/2017 | Aversa et al. |
| 2019/0175606 A1 | 6/2019 | Aversa et al. |
| 2019/0175609 A1 | 6/2019 | Caponigro et al. |
| 2019/0358236 A1 | 11/2019 | Caponigro et al. |
| 2020/0347052 A1 | 11/2020 | Kaldor et al. |
| 2021/0246135 A1 | 8/2021 | Kaldor et al. |
| 2022/0340543 A1 | 10/2022 | Kaldor et al. |
| 2022/0356160 A1 | 11/2022 | Kaldor et al. |
| 2023/0081390 A1 | 3/2023 | Kaldaor et al. |
| 2023/0255977 A1 | 8/2023 | Franovic et al. |

FOREIGN PATENT DOCUMENTS

| | | |
|---|---|---|
| EP | 2112150 B1 | 10/2013 |
| JP | 2016-517417 A | 6/2016 |
| JP | 2017-526720 A | 9/2017 |
| JP | 2017-528475 A | 9/2017 |
| JP | 2022-525885 A | 5/2022 |
| WO | WO-03068229 A1 | 8/2003 |
| WO | WO-2006071940 A2 | 7/2006 |
| WO | WO-2008034008 A2 | 3/2008 |
| WO | WO-2013184119 A1 | 12/2013 |
| WO | WO-2014151616 A1 | 9/2014 |
| WO | WO 2016/038583 A1 | 3/2016 |
| WO | WO-2016038581 A1 | 3/2016 |
| WO | WO-2016038582 A1 | 3/2016 |
| WO | WO-2020168172 A1 | 8/2020 |
| WO | WO-2020198058 A1 | 10/2020 |
| WO | WO-2020227020 A1 | 11/2020 |
| WO | WO-2021081375 A1 | 4/2021 |

(Continued)

OTHER PUBLICATIONS

CAS Chemical Structure Search #3191415 Updated (Apr. 2020).
CAS Chemical Structure Search dated Apr. 24, 2019 .
Henry et al. Discovery of 1-(3,3-dimethylbutyl)-3-(2-fluoro-4-methyl-5-(7-methyl-2-(methylamino) pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
PCT/US2020/030786 International Search Report and Written Opinion dated Sep. 14, 2020.
PCT/US2020/030786 Invitation to Pay Additional Fees dated Jul. 14, 2020.
Lv et al. Design, synthesis and biological evaluation of novel 4-alkynylquinoline derivatives as PI3K/mTOR dual inhibitors. Eur J Med Chem 99:36-50 (2015).

(Continued)

*Primary Examiner* — Paul V Ward
(74) *Attorney, Agent, or Firm* — Birch, Stewart, Kolasch & Birch, LLP

(57) ABSTRACT

Provided herein are inhibitors of receptor tyrosine kinase effector, RAF, pharmaceutical compositions comprising said compounds, and methods for using said compounds for the treatment of diseases.

20 Claims, No Drawings

(56) References Cited

FOREIGN PATENT DOCUMENTS

| WO | WO-2022060996 A1 | 3/2022 |
| WO | WO-2022081469 A1 | 4/2022 |
| WO | WO-2022226221 A1 | 10/2022 |
| WO | WO-2022226261 A1 | 10/2022 |

OTHER PUBLICATIONS

Nishiguchi et al. Design and Discovery of N-(2-Methyl-5'-morpholino-6'-((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).
PCT/US2021/050690 International Search Report and Written Opinion dated Dec. 27, 2021.
PCT/US2021/054403 International Search Report and Written Opinion dated Dec. 28, 2021.
Ramurthy et al. Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).
Reg/Caplus and Marpat. Science IP Report dated Sep. 17, 2020.
Anastassiadis et al. Comprehensive assay of kinase catalytic activity reveals features of kinase inhibitor selectivity. Nat Biotechnol. 29(11):1039-45 (2011).
Berge et al. Pharmaceutical Salts. Journal of Pharmaceutical Sciences 66(1):1-19 (Jan. 1977).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
PCT/US2020/024009 International Search Report and Written Opinion dated Jul. 28, 2020.
PCT/US2020/024009 Invitation to Pay Additional Fees dated Jun. 2, 2020.
PCT/US2020/057132 International Search Report and Written Opinion dated Feb. 9, 2021.
PCT/US2020/057132 Invitation to Pay Additional Fees dated Dec. 8, 2020.
Rosse. Pyridyl Isonicotinamide Inhibitors of RAF Kinase. ACS Med. Chem. Lett. 7:1022-1023 (2016).
Science IP Report dated Jul. 13, 2020 (873 pgs).
CAS Search dated Apr. 26, 2023.
Chapman et al. Improved survival with vemurafenib in melanoma with BRAF V600E mutation. New England Journal of Medicine 364(26):2507-2516 (2011).
Chemical Structure Search report data Feb. 27, 2019.
Davies et al. Mutations of the BRAF Gene in Human Cancer. Nature 417:949-954 (2002).
Hauschild et al. Dabrafenib in BRAF-mutated Metastatic Melanoma: A Multicentre, Open-Label, Phase 3 Randomised Controlled Trial. Lancet 380(9839):358-65 (2012).
Kania et al. The Discovery of Exarafenib (KIN-2787), a Solution to the Challenges of Pan-RAF kinase Inhibition. PowerPoint presentation at Winter Conference on Medicinal & Bioorganic Chemistry (Jan. 2023).
Kinnate Biopharma. RAF Clinico-Genomic Landscape Study PowerPoint. (Nov. 2021).
Manabe. Antitumor activity of KIN-2787, a next-generation pan-RAF inhibitor, in preclinical models of human BRAF-alteration driven non-small cell lung cancer (NSCLC). Presentation from IASLC 2022 Targeted Therapies of Lung Cancer Meeting. Feb. 22-26, 2022.
McKean et al. Design and rationale of a first in human (FIH) phase 1/1b study evaluating KIN-2787, a potent and highly selective pan-RAF inhibitor, in adult patients with BRAF- and NRAS-mutation positive solid tumors. American Association for Cancer Research Annual Meeting. Poster #CT248 (2022).
Miller et al. Antitumor activity of KIN-2787, a next-generation pan-RAF inhibitor, in preclinical models of human RAF/RAS mutant melanoma. American Association for Cancer Research Poster #2674 (2022).
Owsley et al. Prevalence of class I-III BRAF mutations among 114,662 cancer patients in a large genomic database. Exp Biol Med (Maywood) 246(1):31-39 (2021).
PCT/US2022/025815 International Search Report and Written Opinion dated Jul. 28, 2022.
PCT/US2022/025875 International Search Report and Written Opinion dated Jul. 25, 2022.
Severson et al. Occurrence of BRAF class II and III alterations is common across solid tumors and is associated with inferior clinical outcomes in NSCLC and melanoma. American Association for Cancer Research Poster #4122 (2022).
Severson et al. Real-World Clinical Genomic Analysis of Patients with BRAF Mutated Cancers Identifies BRAF Class II and III as a Population of Unmet Medical Need. ESMO Targeted Anticancer Therapies Congress 2022. Poster 40P.
Spira et al. A Phase 1 Clinical Trial Evaluating Monotherapy With Exarafenib (KIN-2787), a Highly Selective Pan-RAF Inhibitor, in BRAF-Altered Solid Tumors and NRAS-Mutant Melanoma. PowerPoint Presentation American Association for Cancer Research Annual Meeting Apr. 14-19, 2023.
Subbiah et al. Pan-Cancer Efficacy of Vemurafenib in BRAF V600-Mutant Non-Melanoma Cancers. Cancer Discov 10(5):657-663 (2020).
U.S. Appl. No. 17/167,599 Office Action dated Oct. 31, 2022.
U.S. Appl. No. 17/738,327 Office Action dated Apr. 18, 2023.
U.S. Appl. No. 18/296,726 Office Action dated Jul. 18, 2023.
Wang et al. Exarafenib (KIN-2787) is a potent, selective pan-RAF inhibitor with activity in preclinical models of BRAF Class II/III mutant and NRAS mutant melanoma. American Association for Cancer Research Annual Meeting Poster #4927 (2023).
Yaeger et al. Targeting Alterations in the RAF-MEK Pathway. Cancer Discov 9(3):329-341 (2019).
Japanese Office Action for Japanese Application No. 2022-523904, dated Sep. 19, 2024, with English translation.

\* cited by examiner

INHIBITORS OF RAF KINASES

CROSS-REFERENCE TO RELATED APPLICATION

This application is a continuation of U.S. patent application Ser. No. 17/079,152, filed Oct. 23, 2020, and claims benefit of U.S. Patent Application No. 63/044,898, filed on Jun. 26, 2020, and U.S. Patent Application No. 62/925,596, filed on Oct. 24, 2019; all of which are hereby incorporated by reference in their entirety.

BACKGROUND

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY OF THE INVENTION

Provided herein are inhibitors of the receptor tyrosine kinase effector Raf (RAF), pharmaceutical compositions comprising said compounds, and methods for using said compounds for the treatment of diseases.

One embodiment provides a compound, or pharmaceutically acceptable salt or solvate thereof, having the structure of Formula (I):

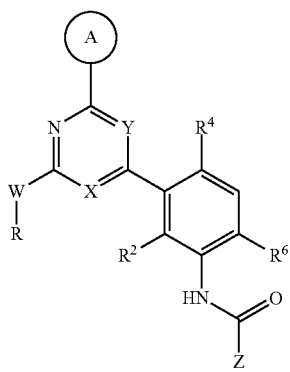

(I)

wherein,
ring A is a 5- or 6-membered optionally substituted heteroaryl, or 5- or 6-membered optionally substituted heterocyclyl;
W is NH, $NR^7$, or O;
X is N, C—H, C—F, or C—CN;
Y is N, C—F, or C—H;
R is H, C1-C8 optionally substituted alkyl, (C1-C8 optionally substituted alkylene)-$OPO(OH)_2$, C3-C6 optionally substituted cycloalkyl, (C3-C6 optionally substituted cycloalkylene)-$OPO(OH)_2$, C4-C8 optionally substituted cycloalkylalkyl, (C3-C6 optionally substituted cycloalkylalkylene)-$OPO(OH)_2$, C3-C6 optionally substituted heterocyclyl, (C3-C6 optionally substituted heterocyclyl)-$OPO(OH)_2$, C3-C6 optionally substituted heterocyclylalkyl, (C3-C6 optionally substituted heterocyclylalkyl)-$OPO(OH)_2$, or C1-C8 optionally substituted alkyl-CO—;
$R^2$ is H, D or F;
$R^4$ is halogen, optionally substituted C1-C3 alkyl, -$CD_3$, or optionally substituted C1-C3 alkoxy;
$R^6$ is H, D, Cl or F;
$R^7$ is C1-C8 optionally substituted alkyl; or R is not H, and R and $R^7$ optionally join to form an optionally substituted heterocyclyl ring;
Z is

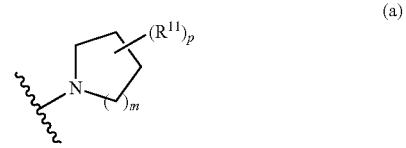

(a)

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo; or

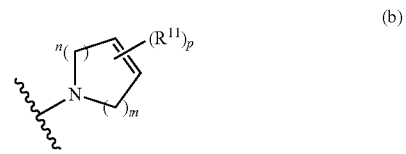

(b)

wherein m is 0, 1, 2, or 3; n is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$ C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

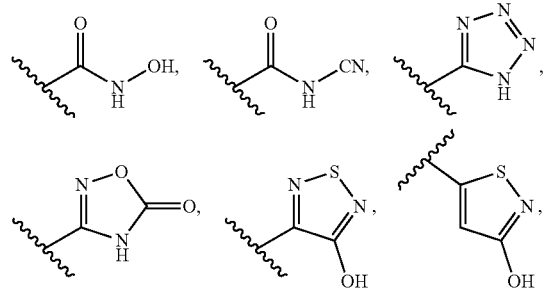

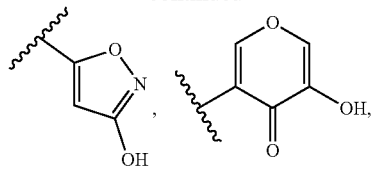

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—OR$^a$, —$R^b$—OC(O)—R$^a$, —$R^b$—OC(O)—OR$^a$, —$R^b$—OC(O)—N(R$^a$)$_2$, —$R^b$—N(R$^a$)$_2$, —$R^b$—C(O)R$^a$, —$R^b$—C(O)OR$^a$, —$R^b$—C(O)N(R$^a$)$_2$, —$R^b$—O—R$^c$—C(O)N(R$^a$)$_2$, —$R^b$—N(R$^a$)C(O)OR$^a$, —$R^b$—N(R$^a$)C(O)R$^a$, —$R^b$—N(R$^a$)S(O)$_t$R$^a$ (where t is 1 or 2), —$R^b$—S(O)$_t$R$^a$ (where t is 1 or 2), —$R^b$—S(O)$_t$OR$^a$ (where t is 1 or 2) and —$R^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above.

intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

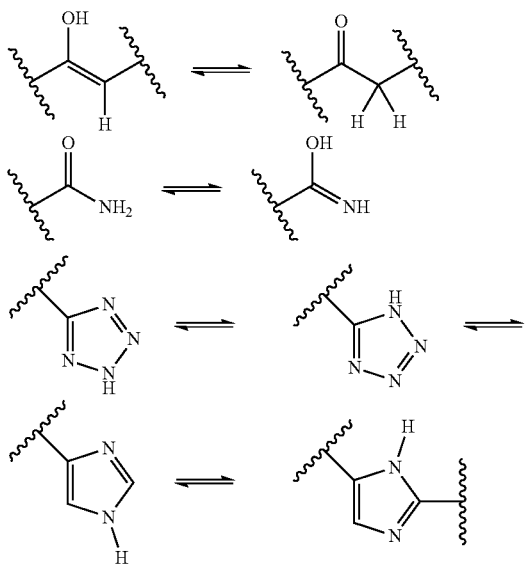
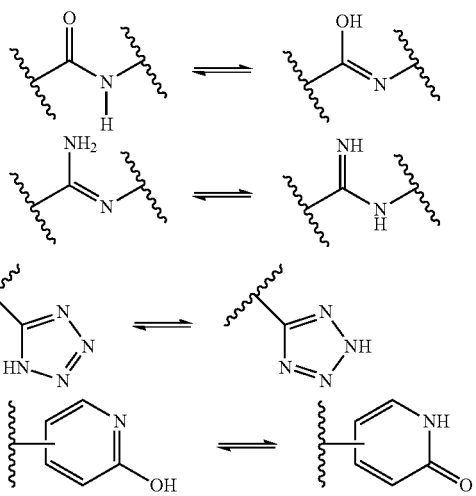

If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

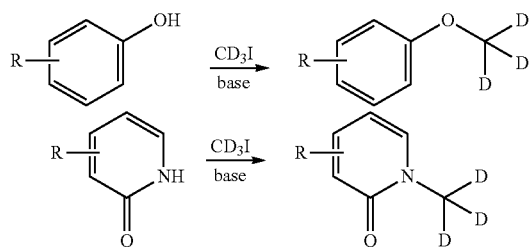

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

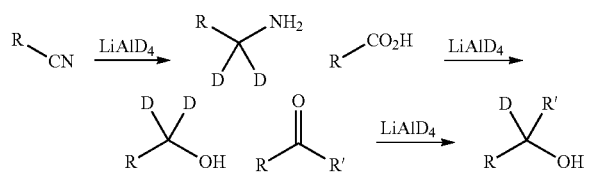

Deuterium gas and palladium catalyst are employed to reduce unsaturated carbon-carbon linkages and to perform a reductive substitution of aryl carbon-halogen bonds as illustrated, by way of example only, in the reaction schemes below.

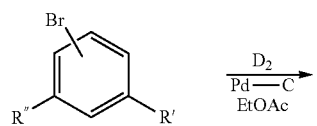

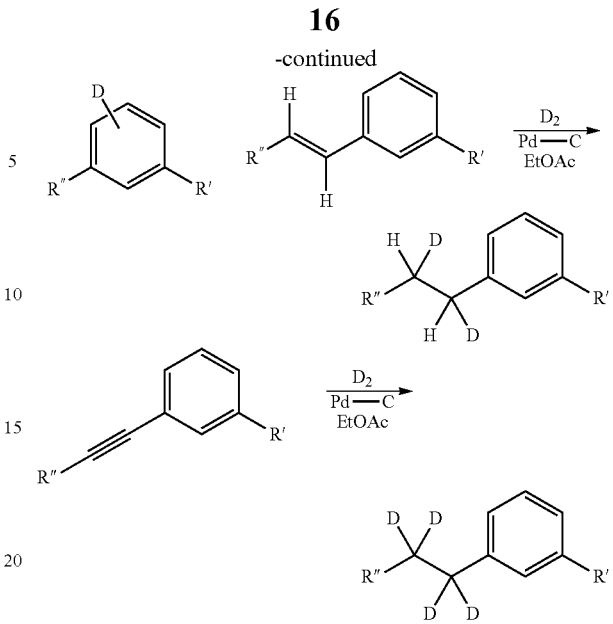

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heteroaromatic RAF inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms. The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The RAF Family of Kinases

The RAF kinases are a family of serine/threonine protein kinases constitute core components of the RAS-RAF-MEK-ERK mitogen activated protein kinase (MAPK) signalling cascade (also known as the MAPK/ERK pathway), a pathway that mediates signals from cell surface receptors to the nucleus to regulate cell growth, differentiation and survival. The RAF proteins are related to retroviral oncogenes and are structurally conserved from metazoans to mammals, as is the MAPK/ERK pathway. Their dysregulation leads to uncontrolled cellular proliferation, survival and dedifferentiation. Consequently, RAF kinases are altered or inappropriately activated in a majority of cancers.

The MAPK/ERK signalling pathway is a network of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, which communicate by adding phosphate groups to a neighboring protein, which acts as a molecular "on" or "off" switch, and overall the pathway can be divided into 3 steps: (i) Ras activation, (ii) a kinase signal transduction cascade, and (iii) regulation of translation and transcription. Briefly, an extracellular mitogen or a signaling molecule binds to the membrane receptor. This allows Ras (a small GTPase) to swap its GDP for a GTP and become active. Activated Ras activates the protein kinase activity of RAF kinase. RAF kinase phosphorylates and activates MEK (MEK1 and MEK2). MEK then phosphorylates and activates a MAPK (also known as ERK). MAPK activation regulates activities of several transcription factors and also alters the translation of mRNA to proteins. By altering the levels and activities of transcription factors, MAPK leads to altered transcription of genes that are important for the cell cycle.

There are three known mammalian RAF isoforms: C-RAF (also known as RAF-1, or c-RAF-1), B-RAF, and A-RAF. All RAF kinases share a common modular structure consisting of 3 conserved regions (CR1, CR2, and CR3) with distinct functions. CR1 contains (i) a Ras-binding domain (RBD), which is necessary for the interaction with Ras and with membrane phospholipids required for membrane recruitment, and (ii) a cysteine-rich domain (CRD), which is a secondary Ras-binding site and also necessary for the interaction of CR1 with the kinase domain for RAF autoinhibition. CR2 contains important inhibitory phosphorylation sites participating in the negative regulation of Ras binding and RAF activation. CR3 features the kinase domain, including the activation segment, whose phosphorylation is crucial for kinase activation.

Functionally, the RAF structure can be split into a regulatory N-terminal region, containing the RBD, which is critical for activation as well as inhibitory phosphorylation sites, and a catalytic C-terminal region, which includes phosphorylation sites necessary for the kinase activation.

The regulatory domain restrains the activity of the kinase domain, and its removal results in constitutive oncogenic activation. However, the activity of the isolated C-RAF kinase domain is subjected to further regulation and can be stimulated by phorbol esters, v-Src, and phosphorylation.

The common and key step in the activation of all 3 RAF kinase isoforms is membrane recruitment by a Ras family protein. The RAF kinases are located in the cytosol in their inactive state when bound to 14-3-3 proteins. In the presence of active Ras, they translocate to the plasma membrane. Membrane translocation triggers further activation events, such as the binding of PP2A to dephosphorylate the inhibitory pS259 site in RAF-1 (and presumably the corresponding sites in A-RAF and B-RAF) and the co-localization with the kinases responsible for the multiple activating phosphorylations. The sequences forming the binding interface are well conserved in the RAF as well as Ras family indicating that several members of the Ras family have the ability to bind RAF kinases. H-Ras, N-Ras, and K-Ras stimulate all 3 RAF isoforms and are the only Ras proteins that activate B-RAF. In contrast, A-RAF is also activated by R-Ras3, while C-RAF responds weakly to R-Ras3, Rit, and TC21 as well. But, all RAF kinases share MEK1/2 kinases as substrates. MEK1/2 in turn activate ERK1/2, and this pathway regulates many cellular functions such as cell proliferation, differentiation, migration, or apoptosis.

C-RAF

C-RAF was first to be identified and is a ubiquitously expressed isoform. In humans, C-RAF is encoded by the RAF1 gene. C-RAF also has a known splice variant preferentially expressed in the muscle and brain. C-RAF plays a critical role in mediating the cellular effects of growth factor signals. In the inactive state, C-RAF exists in a closed conformation in which the N-terminal regulatory region folds over and occludes the catalytic region. This conformation is stabilized by a 14-3-3 dimer binding to an N-terminal site, phospho-S259 (pS259), and a C-terminal site, pS621. Dephosphorylation of pS259 at the cell membrane by specific phosphatases (PP2A, PP1) releases 14-3-3 from its N-terminal binding site in C-RAF, thereby allowing conformational changes to occur that unmask the RBD and CRD domains in the CR1 region to enable Ras binding and membrane recruitment.

B-RAF

B-RAF is encoded in humans by the BRAF gene, also known as proto-oncogene B-RAF and v-RAF murine sarcoma viral oncogene homolog B. Alternative splicing gives rise to multiple B-RAF isoforms which are differentially expressed in various tissues. Whereas activation of A-RAF and C-RAF requires both phosphorylation and dephosphorylation of certain residues, as well as binding to other proteins, B-RAF becomes activated immediately upon translocation to the plasma membrane. B-RAF exhibits higher basal kinase activity than A-RAF and C-RAF. B-RAF requires Ras and 14-3-3 binding for its activation and is inhibited or activated by PKA depending on the levels of 14-3-3 expression, which need to be high for permitting activation. B-RAF activity is also regulated by splicing. B-RAF isoforms containing exon 8b are more phosphorylated on the inhibitory S365 site, leading to an increased interaction with 14-3-3 and strengthening the inhibitory interaction between N-terminal regulatory domain and kinase domain, altogether resulting in lower kinase activity.

A-RAF

Serine/threonine-protein kinase A-RAF or A-RAF is an enzyme encoded by the ARAF gene in humans. There are 2 known splice isoforms of A-RAF-DA-RAF1 and D-RAF2. They lack the kinase domain and act as dominant inhibitory mutants of Ras and ARF GTPases. DA-RAF1 is a positive regulator of myogenic differentiation by mediating the inhibition of the ERK pathway required for differentiation. There are several ways A-RAF is different from the other RAF kinases. A-RAF is the only steroid hormone-regulated Raf isoform. In addition, the A-RAFprotein has amino acid substitutions in a negatively charged region upstream of the kinase domain (N-region), which contributes to its low basal activity. A-RAF is also only weakly activated by oncogenic H-Ras and Src and also displays low kinase activity towards MEK (the lowest kinase activity towards MEK proteins in the Raf kinase family). In addition to phosphorylating MEK, A-RAF also inhibits MST2, a tumor suppressor and proapoptotic kinase not found in the MAPK pathway. By inhibiting MST2, A-RAF prevents apoptosis from occurring. However, this inhibition is only occurs when the splice factor heterogenous nuclear ribonucleoprotein H (hnRNP H) maintains the expression of a full-length A-RAF protein. Tumorous cells often overexpress hnRNP H which leads to full-length expression of A-Raf which then inhibits apoptosis, allowing cancerous cells that should be destroyed to stay alive. A-RAF also binds to pyruvate kinase M2 (PKM2), again outside the MAPK pathway. PKM2 is an isozyme of pyruvate kinase that is responsible for the Warburg effect in cancer cells. A-RAF upregulates the activity of PKM2 by promoting a conformational change in PKM2. This causes PKM2 to transition from its low-activity dimeric form to a highly active tetrameric form. This causes more glucose carbons to be converted to pyruvate and lactate, producing energy for the cell, linking A-Raf to energy metabolism regulation and cell transformation, both of which are very important in tumorigenesis.

RAF Kinase Inhibitors

Aberrant activation of the MAPK/ERK pathway is frequently found in various cancers and is a target for cancer therapeutics. In particular, B-RAF has emerged as one of the most attractive molecular targets for cancer therapeutics because somatic mutations of B-RAF have frequently been found in human tumors. Approximately 20% of all cancer samples tested to date harbor mutations in B-RAF. B-RAF-V600E, a missense mutation in the kinase domain generated by the substitution of glutamic acid with valine at position 600 is the most common B-RAF mutation. C-RAF is mutated in ~1% of the various tumor types tested and the rate of mutations in A-RAF is even lower. B-RAF and C-RAF form both homo- and heterodimers as part of their activation mechanism and A-RAF stabilizes the B-RAF:C-RAF complexes to sustain signaling efficiency. Also, it is C-RAF, not B-RAF, that transmits signals from oncogenic RAS to MEK. Therefore, in different contexts, each of the RAF isoforms act as a potential therapeutic target.

Sorafenib was the first RAF inhibitor to enter clinical trials. Sorafenib is a broad specificity drug that inhibits additional kinases, including vascular endothelial growth factor receptor family (VEGFR-2 and VEGFR-3), platelet-derived growth factor receptor family (PDGFR-b and KIT) and FLT3. Clinical trials showed no correlation between the clinical responses with B-RAF mutation status, indicating it is a poor inhibitor of B-RAF. This led to the development of a new generation of B-RAF inhibitors, including, but not limited to vemurafenib, SB-590885, and dabrafenib (GSK2118436). Although the initial results of the clinical studies in B-RAF-mutant melanoma were encouraging, as clinical testing began in other B-RAF-mutated cancers (such as thyroid and colorectal cancers) it became apparent that tumors of different cell types harboring B-RAF mutations responded differently to selective B-RAF inhibition. Moreover, the existence of both primary and secondary resistance to RAF inhibition poses as one of the greatest challenges to the progress of RAF kinase inhibitor therapy. The mechanisms of resistance fall into two broad categories. Intrinsic/primary resistance is displayed by approximately 50% of patients. The other 50% of the patients initially respond (>30% tumor shrinkage) to RAF inhibitor but subsequently develop progressive disease associated with acquired/secondary resistance to RAF inhibitor. These two categories are not mutually exclusive because nearly all responders have remaining disease and, thus, may display intrinsic resistance. The determinants of primary RAF inhibitor resistance seem to vary with tumor type, with alteration in RTK signaling also being involved. Potential mechanisms of secondary B-RAF inhibitor resistance include, but are not limited to, reactivation of ERK1/2 pathways, upregulation of RTK signaling, the upregulation of receptor tyrosine kinases, mutations in RAS, and upregulation of COT. B-Raf alternative splicing and amplification of B-RAF-V600E have also been implicated in ~30 and 20% of patients, respectively. Moreover, RAF kinase inhibitors cause paradoxical activation of the MAPK pathway, which, in some instances, leads to the development of secondary RAS mutation-driven malignancies. As such, there is a need in the field for new RAF kinase inhibitors that overcome the existing pitfalls and challenges posed by the current inhibitors.

Heteroaromatic RAF Inhibitory Compounds

In one aspect, provided herein is a heteroaromatic RAF inhibitory compound.

One embodiment provides a compound, or pharmaceutically acceptable salt or solvate thereof, having the structure of Formula (I):

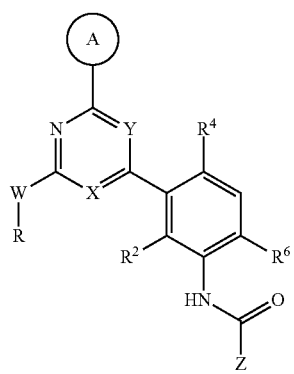

(I)

wherein,
ring A is a 5- or 6-membered optionally substituted heteroaryl, or 5- or 6-membered optionally substituted heterocyclyl;
W is NH, NR$^7$, or O;
X is N, C—H, C—F, or C—CN;
Y is N, C—F, or C—H;
R is H, C1-C8 optionally substituted alkyl, (C1-C8 optionally substituted alkylene)-OPO(OH)$_2$, C3-C6 optionally substituted cycloalkyl, (C3-C6 optionally substituted cycloalkylene)-OPO(OH)$_2$, C4-C8 optionally substituted cycloalkylalkyl, (C3-C6 optionally substituted cycloalkylalkylene)-OPO (OH)$_2$, C3-C6 optionally substituted heterocyclyl, (C3-C6 optionally substituted heterocyclyl)-OPO (OH)$_2$, C3-C6 optionally substituted heterocyclylalkyl, (C3-C6 optionally substituted heterocyclylalkyl)-OPO(OH)$_2$, or C1-C8 optionally substituted alkyl-CO—;
R$^2$ is H, D or F;
R$^4$ is halogen, optionally substituted C1-C3 alkyl, -CD$_3$, or optionally substituted C1-C3 alkoxy;
R$^6$ is H, D, Cl or F;
R$^7$ is C1-C8 optionally substituted alkyl; or R is not H, and R and R$^7$ optionally join to form an optionally substituted heterocyclyl ring;
Z is:

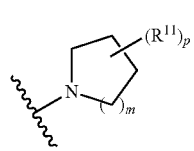

(a)

wherein m is 0, 1, 2, or 3; p is 0, 1, 2, 3, or 4; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two R$^{11}$ groups together form an oxo; or

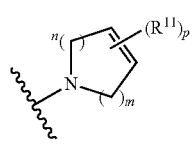

(b)

wherein m is 0, 1, 2, or 3; n is 0, 1, 2, or 3; p is 0, 1, 2, 3, or 4; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two R$^{11}$ groups together form an oxo.

Another embodiment provides the compound of Formula (I), or pharmaceutically acceptable salt or solvate thereof, wherein ring A is a 5- or 6-membered optionally substituted heteroaryl.

Another embodiment provides the compound of Formula (I), or pharmaceutically acceptable salt or solvate thereof, wherein ring A is an optionally substituted pyridine or optionally substituted pyrazole. Another embodiment provides the compound of Formula (I), or pharmaceutically acceptable salt or solvate thereof, wherein ring A is an optionally substituted 4-pyridinyl or optionally substituted 3-pyrrazole.

Another embodiment provides the compound of Formula (I), or pharmaceutically acceptable salt or solvate thereof, wherein ring A is a 5- or 6-membered optionally substituted heterocyclyl.

Another embodiment provides the compound of Formula (I), or pharmaceutically acceptable salt or solvate thereof, wherein ring A is an optionally substituted dihydropyran, optionally substituted tetrahydropyran, optionally substituted dihydrofuran, or optionally substituted tetrahydrofuran. Another embodiment provides the compound of Formula (I), or pharmaceutically acceptable salt or solvate thereof, wherein ring A is an optionally substituted dihydro-2H-pyran-4-yl, optionally substituted tetrahydropyran-4-yl, optionally substituted 2,5-dihydrofuran-3-yl, optionally substituted tetrahydrofuran-3-yl, 3-oxabicyclo[3.1.0]hexan-1-yl, or 3-oxabicyclo[4.1.0]heptan-6-yl.

Another embodiment provides the compound of Formula (I), or pharmaceutically acceptable salt or solvate thereof, wherein ring A is an optionally substituted morpholine.

Another embodiment provides the compound of Formula (I), or pharmaceutically acceptable salt or solvate thereof, having the structure of Formula (II):

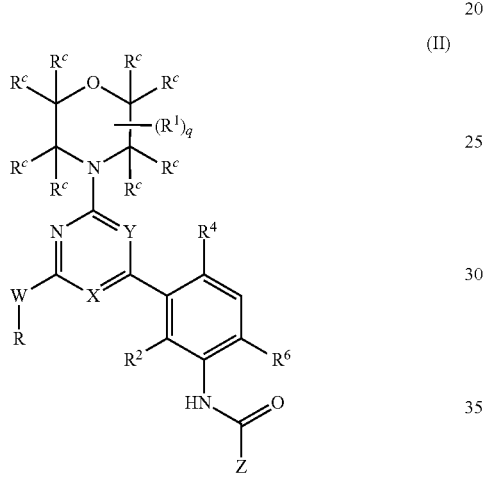

(II)

wherein,

W is NH, $NR^7$, or O;

X is N, C—H, C—F, or C—CN;

Y is N, C—F, or C—H;

R is H, C1-C8 optionally substituted alkyl, (C1-C8 optionally substituted alkylene)-OPO(OH)$_2$, C3-C6 optionally substituted cycloalkyl, (C3-C6 optionally substituted cycloalkylene)-OPO(OH)$_2$, C4-C8 optionally substituted cycloalkylalkyl, (C3-C6 optionally substituted cycloalkylalkylene)-OPO(OH)$_2$, C3-C6 optionally substituted heterocyclyl, (C3-C6 optionally substituted heterocyclyl)-OPO(OH)$_2$, C3-C6 optionally substituted heterocyclylalkyl, (C3-C6 optionally substituted heterocyclylalkyl)-OPO(OH)$_2$, or C1-C8 optionally substituted alkyl-CO—;

$R^1$ is C1-C3 optionally substituted alkyl, and q is 0, 1, or 2;

$R^2$ is H, D or F;

$R^4$ is halogen, optionally substituted C1-C3 alkyl, -CD$_3$, or optionally substituted C1-C3 alkoxy;

$R^6$ is H, D, Cl or F;

$R^7$ is C1-C8 optionally substituted alkyl; or R is not H, and R and $R^7$ optionally join to form an optionally substituted heterocyclyl ring;

$R^c$ is H or D;

Z is (a)

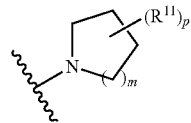

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo; or (b)

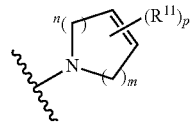

wherein n is 1, 2, or 3; m is 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo.

Another embodiment provides the compound of Formula (I), or pharmaceutically acceptable salt or solvate thereof, having the structure of Formula (III):

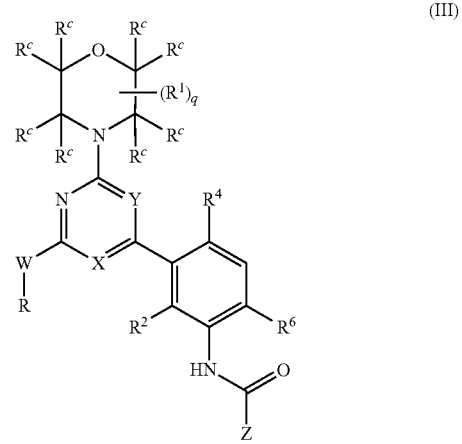

(III)

wherein,

W is NH or O;

X is N, C—H, or C—CN;

Y is N or C—H;

R is C1-C8 optionally substituted alkyl, —(C1-C8 optionally substituted alkylene)-OPO(OH)$_2$, C3-C6 optionally substituted cycloalkyl, —(C3-C6 optionally substituted cycloalkylene)-OPO(OH)$_2$, C4-C6 optionally substituted cycloalkylalkyl, —(C3-C6 optionally substituted cycloalkylalkylene)-OPO(OH)$_2$, C3-C6 optionally substituted heterocyclyl, —(C3-C6 optionally substituted heterocyclyl)-OPO(OH)$_2$, C3-C6 optionally substituted heterocyclylalkyl, —(C3-C6 optionally substituted heterocyclylalkyl)-OPO(OH)$_2$;

$R^1$ is C1-C3 optionally substituted alkyl, and q is 0, 1, or 2;

$R^2$ is H, D or F;

$R^4$ is halogen, optionally substituted C1-C3 alkyl, -CD$_3$, or optionally substituted C1-C3 alkoxy;

$R^6$ is H, D, Cl or F;

$R^c$ is H or D;

Z is

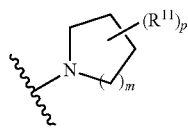

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo.

Another embodiment provides the compound of Formula (I)—(III), or pharmaceutically acceptable salt or solvate thereof, wherein W is NH.

Another embodiment provides the compound of Formula (I) or (II), or pharmaceutically acceptable salt or solvate thereof, wherein W is $NR^7$. Another embodiment provides the compound of Formula (I) or (II), or pharmaceutically acceptable salt or solvate thereof, wherein $R^7$ is optionally substituted C1 alkyl.

Another embodiment provides the compound of Formula (I) or (II), or pharmaceutically acceptable salt or solvate thereof, wherein W is $NR^7$, R is not H, and R and $R^7$ join to form an optionally substituted heterocyclyl ring. Another embodiment provides the compound of Formula (I) or (II), or pharmaceutically acceptable salt or solvate thereof, wherein the optionally substituted heterocyclyl ring is a 1-aztidinyl, 1-pyrrolidinyl, or 1-piperidinyl ring. Another embodiment provides the compound of Formula (I) or (II), or pharmaceutically acceptable salt or solvate thereof, wherein the optionally substituted heterocyclyl ring is substituted with at least one substituent selected from —OH, halogen, optionally substituted C1-C6 alkyl, or optionally substituted C1-C6 alkoxy.

Another embodiment provides the compound of Formula (I)—(III), or pharmaceutically acceptable salt or solvate thereof, wherein R is C1-C8 optionally substituted alkyl, C3-C6 optionally substituted cycloalkyl, C4-C8 optionally substituted cycloalkylalkyl, C3-C6 optionally substituted heterocyclyl, or C3-C6 optionally substituted heterocyclylalkyl.

Another embodiment provides the compound of Formula (I)—(III), or pharmaceutically acceptable salt or solvate thereof, wherein R is C1-C8 optionally substituted alkyl, C3-C6 optionally substituted cycloalkyl, C4-C6 optionally substituted cycloalkylalkyl, C3-C6 optionally substituted heterocyclyl, or C3-C6 optionally substituted heterocyclylalkyl. Another embodiment provides the compound of Formula (I)—(III), or pharmaceutically acceptable salt or solvate thereof, wherein R is C1-C8 optionally substituted alkyl. Another embodiment provides the compound of Formula (I)—(III), or pharmaceutically acceptable salt or solvate thereof, wherein R is C1-C6 optionally substituted alkyl. Another embodiment provides the compound of Formula (I)—(III), or pharmaceutically acceptable salt or solvate thereof, wherein R is C1-C4 optionally substituted alkyl. Another embodiment provides the compound of Formula (I)—(III), or pharmaceutically acceptable salt or solvate thereof, wherein R is C1-C3 optionally substituted alkyl. Another embodiment provides the compound of Formula (I)—(III), or pharmaceutically acceptable salt or solvate thereof, wherein R is C1-C2 optionally substituted alkyl. Another embodiment provides the compound of Formula (I)—(III), or pharmaceutically acceptable salt or solvate thereof, wherein R is C1-C6 optionally substituted alkyl and the alkyl is substituted with at least one hydroxyl.

Another embodiment provides the compound of Formula (I) or (II), or pharmaceutically acceptable salt or solvate thereof, wherein R is H.

Another embodiment provides the compound of Formula (I) or (II), or pharmaceutically acceptable salt or solvate thereof, wherein R is C1-C8 optionally substituted alkyl-CO—.

Another embodiment provides the compound of Formula (I)—(III), or pharmaceutically acceptable salt or solvate thereof, wherein R is C3-C6 optionally substituted cycloalkyl.

Another embodiment provides the compound of Formula (I)—(III), or pharmaceutically acceptable salt or solvate thereof, wherein R is C4-C6 optionally substituted cycloalkylalkyl.

Another embodiment provides the compound of Formula (I)—(III), or pharmaceutically acceptable salt or solvate thereof, wherein R is C3-C6 optionally substituted heterocyclyl.

Another embodiment provides the compound of Formula (I)—(III), or pharmaceutically acceptable salt or solvate thereof, wherein R is C3-C6 optionally substituted heterocyclylalkyl.

Another embodiment provides the compound of Formula (II)—(III), or pharmaceutically acceptable salt or solvate thereof, wherein $R^1$ is C1 optionally substituted alkyl. Another embodiment provides the compound of Formula (II)—(III), or pharmaceutically acceptable salt or solvate thereof, wherein q is 0. Another embodiment provides the compound of Formula (II)—(III), or pharmaceutically acceptable salt or solvate thereof, wherein q is 1.

Another embodiment provides the compound of Formula (I)—(III), or pharmaceutically acceptable salt or solvate thereof, wherein Z is Another embodiment provides the compound of Formula (I)—(III), or pharmaceutically acceptable salt or solvate thereof, wherein m is 0. Another embodiment provides the compound of Formula (I)—(III), or pharmaceutically acceptable salt or solvate thereof, wherein m is 1. Another embodiment provides the compound of Formula (I)—(III), or pharmaceutically acceptable salt or solvate thereof, wherein m is 2. Another embodiment provides the compound of Formula (I)—(III), or pharmaceutically acceptable salt or solvate thereof, wherein p is 1. Another embodiment provides the compound of Formula (I)—(III), or pharmaceutically acceptable salt or solvate thereof, wherein p is 2.

Another embodiment provides the compound of Formula (I)—(III), or pharmaceutically acceptable salt or solvate thereof, wherein $R^{11}$ is optionally substituted C1-C6 alkyl. Another embodiment provides the compound of Formula (I)—(III), or pharmaceutically acceptable salt or solvate thereof, wherein $R^{11}$ is optionally substituted C1-C4 alkyl. Another embodiment provides the compound of Formula (I)—(III), or pharmaceutically acceptable salt or solvate thereof, wherein $R^{11}$ is optionally substituted C1-C3 alkyl. Another embodiment provides the compound of Formula (I)—(III), or pharmaceutically acceptable salt or solvate thereof, wherein $R^{11}$ is optionally substituted C1-C2 alkyl. Another embodiment provides the compound of Formula (I)—(III), or pharmaceutically acceptable salt or solvate thereof, wherein $R^{11}$ is optionally substituted C1-C4 fluoroalkyl. Another embodiment provides the compound of Formula (I)—(III), or pharmaceutically acceptable salt or solvate thereof, wherein $R^{11}$ is —CH$_2$CF$_3$. Another embodiment provides the compound of Formula (I)—(III), or pharmaceutically acceptable salt or solvate thereof, wherein $R^{11}$ is optionally substituted C3-C6 cycloalkyl.

Another embodiment provides the compound of Formula (I)—(III), or pharmaceutically acceptable salt or solvate thereof, wherein Z is Another embodiment provides the compound of Formula (I)—(III), or pharmaceutically acceptable salt or solvate thereof, wherein m is 0. Another embodiment provides the compound of Formula (I)—(III), or pharmaceutically acceptable salt or solvate thereof, wherein m is 1. Another embodiment provides the compound of Formula (I)—(III), or pharmaceutically acceptable salt or solvate thereof, wherein m is 2. Another embodiment provides the compound of Formula (I)—(III), or pharmaceutically acceptable salt or solvate thereof, wherein n is 1. Another embodiment provides the compound of Formula (I)—(III), or pharmaceutically acceptable salt or solvate thereof, wherein n is 2. Another embodiment provides the compound of Formula (I)—(III), or pharmaceutically acceptable salt or solvate thereof, wherein p is 1. Another embodiment provides the compound of Formula (I)—(III), or pharmaceutically acceptable salt or solvate thereof, wherein p is 2.

Another embodiment provides the compound of Formula (I)—(III), or pharmaceutically acceptable salt or solvate thereof, wherein $R^{11}$ is optionally substituted C1-C6 alkyl. Another embodiment provides the compound of Formula (I)—(III), or pharmaceutically acceptable salt or solvate thereof, wherein $R^{11}$ is optionally substituted C1-C4 alkyl. Another embodiment provides the compound of Formula (I)—(III), or pharmaceutically acceptable salt or solvate thereof, wherein $R^{11}$ is optionally substituted C1-C3 alkyl. Another embodiment provides the compound of Formula (I)—(III), or pharmaceutically acceptable salt or solvate thereof, wherein $R^{11}$ is optionally substituted C1-C2 alkyl. Another embodiment provides the compound of Formula (I)—(III), or pharmaceutically acceptable salt or solvate thereof, wherein $R^{11}$ is optionally substituted C1-C4 fluoroalkyl. Another embodiment provides the compound of Formula (I)—(III), or pharmaceutically acceptable salt or solvate thereof, wherein $R^{11}$ is —CH$_2$CF$_3$. Another embodiment provides the compound of Formula (I)—(III), or pharmaceutically acceptable salt or solvate thereof, wherein $R^{11}$ is optionally substituted C3-C6 cycloalkyl.

Another embodiment provides the compound of Formula (I)—(III), or pharmaceutically acceptable salt or solvate thereof, wherein W is NH and ring A is an optionally substituted morpholine.

Another embodiment provides the compound of Formula (I)—(III), or pharmaceutically acceptable salt or solvate thereof, wherein W is NH and Z is 3-(2,2,2-trifluoroethyl)pyrrolidine.

Another embodiment provides the compound of Formula (I)—(III), or pharmaceutically acceptable salt or solvate thereof, wherein ring A is an optionally substituted morpholine and Z is 3-(2,2,2-trifluoroethyl)pyrrolidine.

Another embodiment provides the compound of Formula (I)—(III), or pharmaceutically acceptable salt or solvate thereof, wherein W is NH, ring A is an optionally substituted morpholine, and Z is 3-(2,2,2-trifluoroethyl)pyrrolidine.

Another embodiment provides the compound of Formula (I)—(III), or pharmaceutically acceptable salt or solvate thereof, wherein R is C1-C4 optionally substituted alkyl, W is NH and ring A is an optionally substituted morpholine.

Another embodiment provides the compound of Formula (I)—(III), or pharmaceutically acceptable salt or solvate thereof, wherein R is C1-C4 optionally substituted alkyl, W is NH and Z is 3-(2,2,2-trifluoroethyl)pyrrolidine.

Another embodiment provides the compound of Formula (I)—(III), or pharmaceutically acceptable salt or solvate thereof, wherein R is C1-C4 optionally substituted alkyl, ring A is an optionally substituted morpholine and Z is 3-(2,2,2-trifluoroethyl)pyrrolidine.

Another embodiment provides the compound of Formula (I)—(III), or pharmaceutically acceptable salt or solvate thereof, wherein R is C1-C4 optionally substituted alkyl, W is NH, ring A is an optionally substituted morpholine, and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, W is NH and ring A is an optionally substituted morpholine.

Another embodiment provides the compound of Formula (I)—(III), or pharmaceutically acceptable salt or solvate thereof, wherein X is C—H, Y is C—H, W is NH and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, ring A is an optionally substituted morpholine and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, W is NH, ring A is an optionally substituted morpholine, and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, R is C1-C4 optionally substituted alkyl, W is NH and ring A is an optionally substituted morpholine.

Another embodiment provides the compound of Formula (I)—(III), or pharmaceutically acceptable salt or solvate thereof, wherein X is C—H, Y is C—H, R is C1-C4 optionally substituted alkyl, W is NH and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, R is C1-C4 optionally substituted alkyl, ring A is an optionally substituted morpholine and Z is 3-(2,2,2-trifluoroethyl)pyrrolidine.

Another embodiment provides the compound of Formula (I)—(III), or pharmaceutically acceptable salt or solvate thereof, wherein X is C—H, Y is C—H, R is C1-C4 optionally substituted alkyl, W is NH, ring A is an optionally substituted morpholine, and Z is 3-(2,2,2-trifluoroethyl)pyrrolidine.

One embodiment provides a compound, or pharmaceutically acceptable salt or solvate thereof, having the structure of Formula (IV):

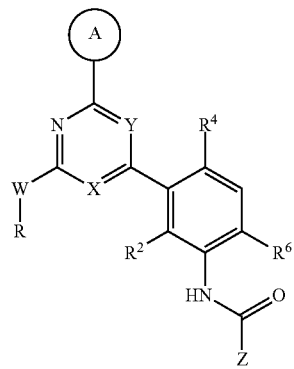

(IV)

wherein,
ring A is a 5- or 6-membered optionally substituted heteroaryl, or 5- or 6-membered optionally substituted heterocyclyl;
W is NH, or $NR^7$;
X is N, C—H, C—F, or C—CN;
Y is N, C—F, or C—H;
R is —$SO_2$—(C1-C8 optionally substituted alkyl), —$SO_2$—(C3-C6 optionally substituted cycloalkyl), —$SO_2$—(C4-C8 optionally substituted cycloalkylalkyl), —$SO_2$—(C3-C6 optionally substituted heterocyclyl), —$SO_2$—(C3-C6 optionally substituted heterocyclylalkyl), —$SO_2$—$N(R^8)R^9$—C1-C8 optionally substituted alkyl, —$CO_2$-C1-C8 optionally substituted alkyl, or —CO—$N(R^8)R^9$—C1-C8 optionally substituted alkyl;

$R^2$ is H, D or F;
$R^4$ is halogen, optionally substituted C1-C3 alkyl, -$CD_3$, or optionally substituted C1-C3 alkoxy;
$R^6$ is H, D, Cl or F;
$R^7$ is C1-C8 optionally substituted alkyl; or R and $R^7$ optionally join to form an optionally substituted heterocyclyl ring;
each $R^8$ and $R^9$ is independently selected from H or C1-C8 optionally substituted alkyl;
Z is (a)

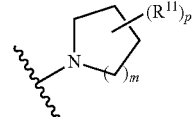

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo; or
(b)

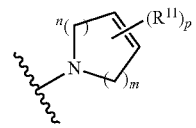

wherein m is 0, 1, 2, or 3; n is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo.

Another embodiment provides the compound of Formula (IV), or pharmaceutically acceptable salt or solvate thereof, wherein ring A is a 5- or 6-membered optionally substituted heteroaryl.

Another embodiment provides the compound of Formula (IV), or pharmaceutically acceptable salt or solvate thereof, wherein ring A is an optionally substituted pyridine or optionally substituted pyrazole. Another embodiment provides the compound of Formula (IV), or pharmaceutically acceptable salt or solvate thereof, wherein ring A is an optionally substituted 4-pyridinyl or optionally substituted 3-pyrrazole.

Another embodiment provides the compound of Formula (IV), or pharmaceutically acceptable salt or solvate thereof, wherein ring A is a 5- or 6-membered optionally substituted heterocyclyl.

Another embodiment provides the compound of Formula (IV), or pharmaceutically acceptable salt or solvate thereof, wherein ring A is an optionally substituted dihydropyran, optionally substituted tetrahydropyran, optionally substituted dihydrofuran, or optionally substituted tetrahydrofuran. Another embodiment provides the compound of Formula (IV), or pharmaceutically acceptable salt or solvate thereof, wherein ring A is an optionally substituted dihydro-2H-pyran-4-yl, optionally substituted tetrahydropyran-4-yl, optionally substituted 2,5-dihydrofuran-3-yl, optionally substituted tetrahydrofuran-3-yl, 3-oxabicyclo[3.1.0]hexan-1-yl, or 3-oxabicyclo[4.1.0]heptan-6-yl.

Another embodiment provides the compound of Formula (IV), or pharmaceutically acceptable salt or solvate thereof, wherein ring A is an optionally substituted morpholine.

Another embodiment provides the compound of Formula (IV), or pharmaceutically acceptable salt or solvate thereof, wherein W is NH.

Another embodiment provides the compound of Formula (IV), or pharmaceutically acceptable salt or solvate thereof, wherein $NR^7$. Another embodiment provides the compound of Formula (IV), or pharmaceutically acceptable salt or solvate thereof, wherein $R^7$ is C1-C8 optionally substituted alkyl. Another embodiment provides the compound of Formula (IV), or pharmaceutically acceptable salt or solvate thereof, wherein R and $R^7$ optionally join to form an optionally substituted heterocyclyl ring.

Another embodiment provides the compound of Formula (IV), or pharmaceutically acceptable salt or solvate thereof, wherein R is —SO$_2$—(C1-C8 optionally substituted alkyl).

Another embodiment provides the compound of Formula (IV), or pharmaceutically acceptable salt or solvate thereof, wherein R is —SO$_2$—(C3-C6 optionally substituted cycloalkyl).

Another embodiment provides the compound of Formula (IV), or pharmaceutically acceptable salt or solvate thereof, wherein R is —SO$_2$—(C4-C8 optionally substituted cycloalkylalkyl).

Another embodiment provides the compound of Formula (IV), or pharmaceutically acceptable salt or solvate thereof, wherein R is —SO$_2$—(C3-C6 optionally substituted heterocyclyl).

Another embodiment provides the compound of Formula (IV), or pharmaceutically acceptable salt or solvate thereof, wherein R is —SO$_2$—(C3-C6 optionally substituted heterocyclylalkyl).

Another embodiment provides the compound of Formula (IV), or pharmaceutically acceptable salt or solvate thereof, wherein R is —SO$_2$—N(R$^8$)R$^9$—C1-C8 optionally substituted alkyl. Another embodiment provides the compound of Formula (IV), or pharmaceutically acceptable salt or solvate thereof, wherein each R$^8$ and R$^9$ is independently selected from H or C1-C8 optionally substituted alkyl.

Another embodiment provides the compound of Formula (IV), or pharmaceutically acceptable salt or solvate thereof, wherein R is —CO$_2$-C1-C8 optionally substituted alkyl.

Another embodiment provides the compound of Formula (IV), or pharmaceutically acceptable salt or solvate thereof, wherein R is —CO—N(R$^8$)R$^9$—C1-C8 optionally substituted alkyl. Another embodiment provides the compound of Formula (IV), or pharmaceutically acceptable salt or solvate thereof, wherein each R$^8$ and R$^9$ is independently selected from H or C1-C8 optionally substituted alkyl.

Another embodiment provides the compound of Formula (IV), or pharmaceutically acceptable salt or solvate thereof, wherein Z is

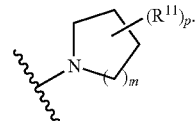

Another embodiment provides the compound of Formula (IV), or pharmaceutically acceptable salt or solvate thereof, wherein m is 0. Another embodiment provides the compound of Formula (IV), or pharmaceutically acceptable salt or solvate thereof, wherein m is 1. Another embodiment provides the compound of Formula (IV), or pharmaceutically acceptable salt or solvate thereof, wherein m is 2. Another embodiment provides the compound of Formula (IV), or pharmaceutically acceptable salt or solvate thereof, wherein p is 1. Another embodiment provides the compound of Formula (IV), or pharmaceutically acceptable salt or solvate thereof, wherein p is 2.

Another embodiment provides the compound of Formula (IV), or pharmaceutically acceptable salt or solvate thereof, wherein Z is

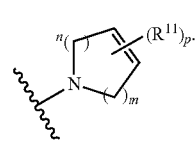

Another embodiment provides the compound of Formula (IV), or pharmaceutically acceptable salt or solvate thereof, wherein m is 0. Another embodiment provides the compound of Formula (IV), or pharmaceutically acceptable salt or solvate thereof, wherein m is 1. Another embodiment provides the compound of Formula (IV), or pharmaceutically acceptable salt or solvate thereof, wherein m is 2. Another embodiment provides the compound of Formula (IV), or pharmaceutically acceptable salt or solvate thereof, wherein n is 1. Another embodiment provides the compound of Formula (IV), or pharmaceutically acceptable salt or solvate thereof, wherein n is 2. Another embodiment provides the compound of Formula (IV), or pharmaceutically acceptable salt or solvate thereof, wherein p is 1. Another embodiment provides the compound of Formula (IV), or pharmaceutically acceptable salt or solvate thereof, wherein p is 2.

Another embodiment provides the compound of Formula (IV), or pharmaceutically acceptable salt or solvate thereof, wherein R$^{11}$ is optionally substituted C1-C6 alkyl. Another embodiment provides the compound of Formula (IV), or pharmaceutically acceptable salt or solvate thereof, wherein R$^{11}$ is optionally substituted C1-C4 alkyl. Another embodiment provides the compound of Formula (IV), or pharmaceutically acceptable salt or solvate thereof, wherein R$^{11}$ is optionally substituted C1-C3 alkyl. Another embodiment provides the compound of Formula (IV), or pharmaceutically acceptable salt or solvate thereof, wherein R$^{11}$ is optionally substituted C1-C2 alkyl. Another embodiment provides the compound of Formula (IV), or pharmaceutically acceptable salt or solvate thereof, wherein R$^{11}$ is optionally substituted C1-C4 fluoroalkyl. Another embodiment provides the compound of Formula (IV), or pharmaceutically acceptable salt or solvate thereof, wherein R$^{11}$ is —CH$_2$CF$_3$. Another embodiment provides the compound of Formula (IV), or pharmaceutically acceptable salt or solvate thereof, wherein $R^{11}$ is optionally substituted C3-C6 cycloalkyl.

Another embodiment provides the compound of Formula (IV), or pharmaceutically acceptable salt or solvate thereof, wherein W is NH and ring A is an optionally substituted morpholine.

Another embodiment provides the compound of Formula (IV), or pharmaceutically acceptable salt or solvate thereof, wherein W is NH and Z is 3-(2,2,2-trifluoroethyl)pyrrolidine.

Another embodiment provides the compound of Formula (IV), or pharmaceutically acceptable salt or solvate thereof, wherein ring A is an optionally substituted morpholine and Z is 3-(2,2,2-trifluoroethyl)pyrrolidine.

Another embodiment provides the compound of Formula (IV), or pharmaceutically acceptable salt or solvate thereof, wherein W is NH, ring A is an optionally substituted morpholine, and Z is 3-(2,2,2-trifluoroethyl)pyrrolidine.

Another embodiment provides the compound of Formula (IV), or pharmaceutically acceptable salt or solvate thereof, wherein X is C—H, Y is C—H, W is NH and ring A is an optionally substituted morpholine.

Another embodiment provides the compound of Formula (IV), or pharmaceutically acceptable salt or solvate thereof, wherein X is C—H, Y is C—H, W is NH and Z is 3-(2,2,2-trifluoroethyl)pyrrolidine.

Another embodiment provides the compound of Formula (IV), or pharmaceutically acceptable salt or solvate thereof, wherein X is C—H, Y is C—H, ring A is an optionally substituted morpholine and Z is 3-(2,2,2-trifluoroethyl)pyrrolidine.

Another embodiment provides the compound of Formula (IV), or pharmaceutically acceptable salt or solvate thereof, wherein X is C—H, Y is C—H, W is NH, ring A is an optionally substituted morpholine, and Z is 3-(2,2,2-trifluoroethyl)pyrrolidine.

Another embodiment provides the compound of Formula (I)—(IV), or pharmaceutically acceptable salt or solvate thereof, wherein X is N; and Y is C—H.

Another embodiment provides the compound of Formula (I)—(IV), or pharmaceutically acceptable salt or solvate thereof, wherein X is N; and Y is N.

Another embodiment provides the compound of Formula (I)—(IV), or pharmaceutically acceptable salt or solvate thereof, wherein X is C—H; and Y is C—H.

Another embodiment provides the compound of Formula (I)—(IV), or pharmaceutically acceptable salt or solvate thereof, wherein X is C—H; and Y is N.

Another embodiment provides the compound of Formula (I)—(IV), or pharmaceutically acceptable salt or solvate thereof, wherein X is C—F; and Y is C—H.

Another embodiment provides the compound of Formula (I)—(IV), or pharmaceutically acceptable salt or solvate thereof, wherein X is C—H; and Y is C—F.

Another embodiment provides the compound of Formula (I)—(IV), or pharmaceutically acceptable salt or solvate thereof, wherein $R^2$ is H.

Another embodiment provides the compound of Formula (I)—(IV), or pharmaceutically acceptable salt or solvate thereof, wherein $R^4$ is optionally substituted C1-C3 alkyl.

Another embodiment provides the compound of Formula (I)—(IV), or pharmaceutically acceptable salt or solvate thereof, wherein $R^4$ is optionally substituted C1 alkyl.

Another embodiment provides the compound of Formula (I)—(IV), or pharmaceutically acceptable salt or solvate thereof, wherein $R^4$ is $CH_3$.

Another embodiment provides the compound of Formula (I)—(IV), or pharmaceutically acceptable salt or solvate thereof, wherein $R^6$ is H.

In some embodiments, the heteroaromatic RAF kinase inhibitory compound as described herein has a structure provided in Table 1.

TABLE 1

| Synthetic Chemistry Example | Compound Structure | Compound Name |
|---|---|---|
| 1 | 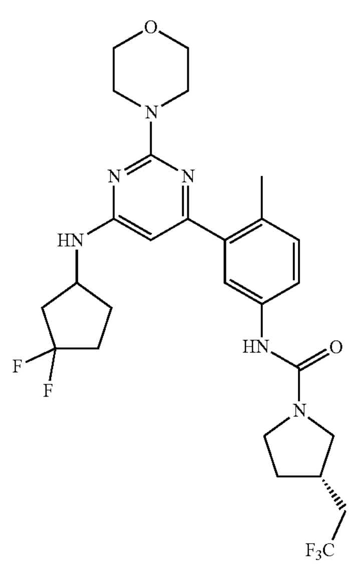 [SMILES: Cc1ccc(NC(=O)N2CC[C@@H](CC(F)(F)F)C2)cc1-c1cc(NC2CCC(F)(F)C2)nc(N2CCOCC2)n1] | (3S)-N-(3-(6-((3,3-difluorocyclopentyl)amino)-2-morpholinopyrimidin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 2 | 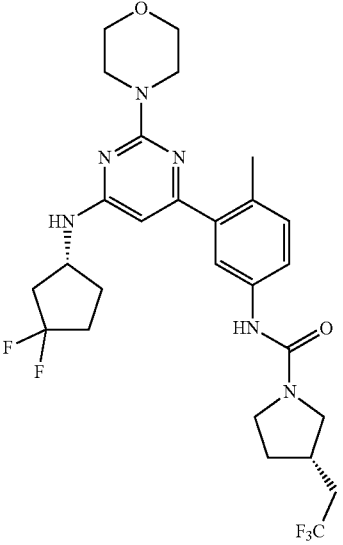 [SMILES: Cc1ccc(NC(=O)N2CC[C@@H](CC(F)(F)F)C2)cc1-c1cc(N[C@@H]2CCC(F)(F)C2)nc(N2CCOCC2)n1] | (S)-N-(3-(6-(((R)-3,3-difluorocyclopentyl)amino)-2-morpholinopyrimidin-4-yl)-4-methylphenyl)-3-(2,2,2-trifluoroethyl)pyrrolidine-1-carboxamide |
| 3 | 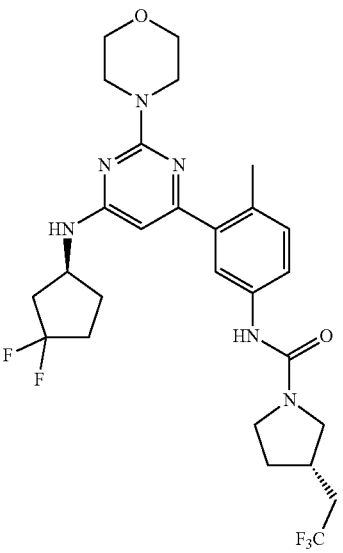 [SMILES: Cc1ccc(NC(=O)N2CC[C@@H](CC(F)(F)F)C2)cc1-c1cc(N[C@H]2CCC(F)(F)C2)nc(N2CCOCC2)n1] | (S)-N-(3-(6-(((S)-3,3-difluorocyclopentyl)amino)-2-morpholinopyrimidin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 4 and 5 | 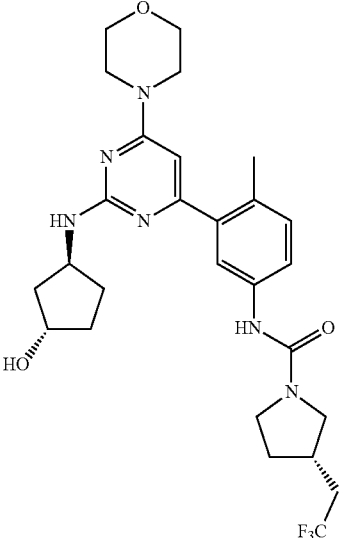 [SMILES: Cc1ccc(NC(=O)N2CC[C@@H](CC(F)(F)F)C2)cc1-c1cc(N2CCOCC2)nc(N[C@H]2CC[C@H](O)C2)n1]<br>+<br>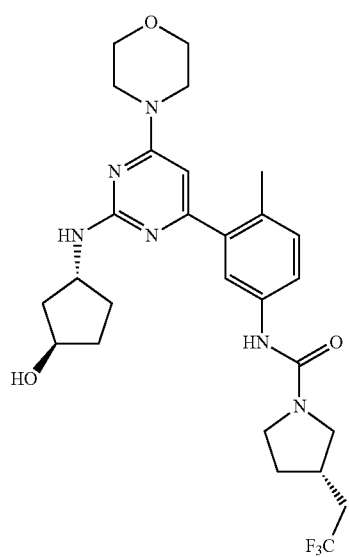 [SMILES: Cc1ccc(NC(=O)N2CC[C@@H](CC(F)(F)F)C2)cc1-c1cc(N2CCOCC2)nc(N[C@@H]2CC[C@@H](O)C2)n1] | (S)-N-(3-(2-(((1S,3S)-3-hydroxycyclopentyl)amino)-6-morpholinopyrimidin-4-yl)-4-methylphenyl)-3-(2,2,2-trifluoroethyl)pyrrolidine-1-carboxamide and (S)-N-(3-(2-(((1R,3R)-3-hydroxycyclopentyl)amino)-6-morpholinopyrimidin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 6 | 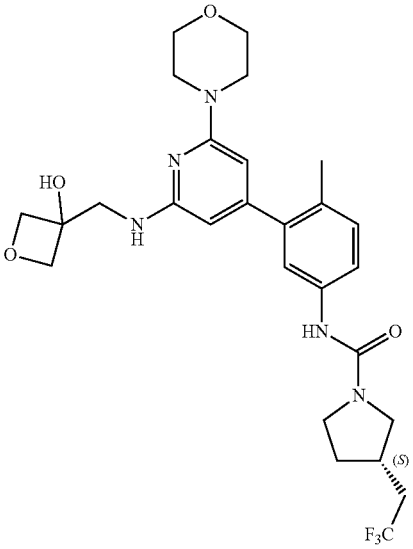 | (S)-N-(3-(2-(((3-hydroxyoxetan-3-yl)methyl)amino)-6-morpholinopyridin-4-yl)-4-methylphenyl)-3-(2,2,2-trifluoroethyl)pyrrolidine-1-carboxamide |
| 7 | 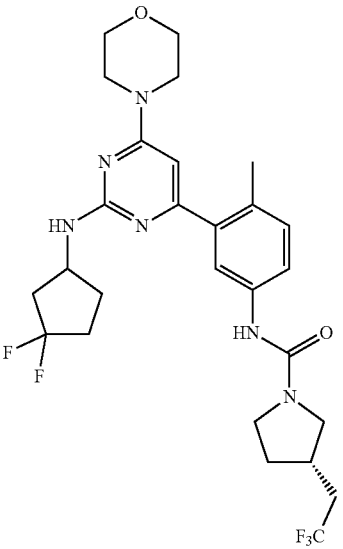 [SMILES: Cc1ccc(NC(=O)N2CC[C@@H](CC(F)(F)F)C2)cc1-c1cc(N2CCOCC2)nc(NC2CCC(F)(F)C2)n1] | (3S)-N-(3-(2-((3,3-difluorocyclopentyl)amino)-6-morpholinopyrimidin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 8 and 9 | 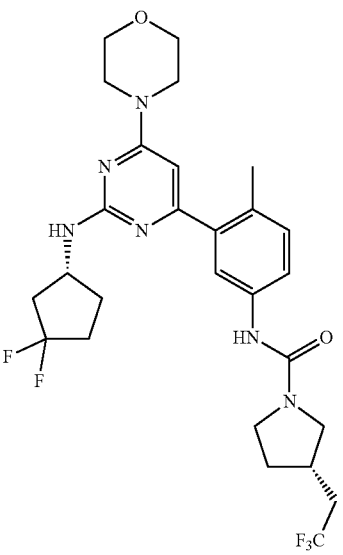 [SMILES: Cc1ccc(NC(=O)N2CC[C@@H](CC(F)(F)F)C2)cc1-c1cc(N2CCOCC2)nc(N[C@@H]2CCC(F)(F)C2)n1] <br> + <br> 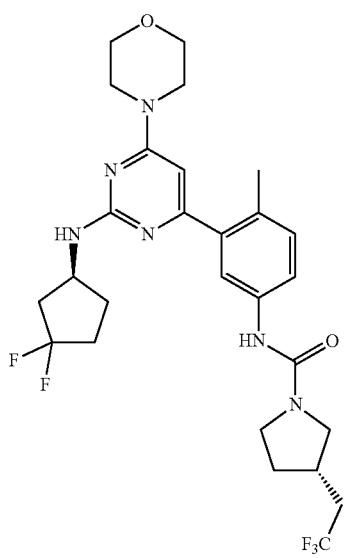 [SMILES: Cc1ccc(NC(=O)N2CC[C@@H](CC(F)(F)F)C2)cc1-c1cc(N2CCOCC2)nc(N[C@H]2CCC(F)(F)C2)n1] | (S)-N-(3-(2-(((R)-3,3-difluorocyclopentyl)amino)-6-morpholinopyrimidin-4-yl)-4-methylphenyl)-3-(2,2,2-trifluoroethyl)pyrrolidine-1-carboxamide and (S)-N-(3-(2-(((S)-3,3-difluorocyclopentyl)amino)-6-morpholinopyrimidin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 10 | 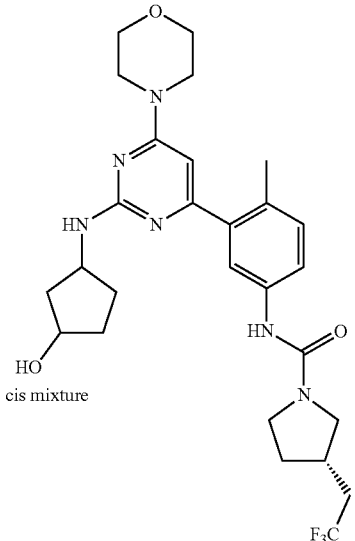 [SMILES: Cc1ccc(NC(=O)N2CC[C@@H](CC(F)(F)F)C2)cc1-c1cc(N2CCOCC2)nc(NC2CCC(O)C2)n1] cis mixture | (3S)-N-[3-(2-[(cis-3-hydroxycyclopentyl]amino]-6-(morpholin-4-yl)pyrimidin-4-yl)-4-methylphenyl]-3-(2,2,2-trifluoroethyl)pyrrolidine-1-carboxamide |
| 11 and 12 | 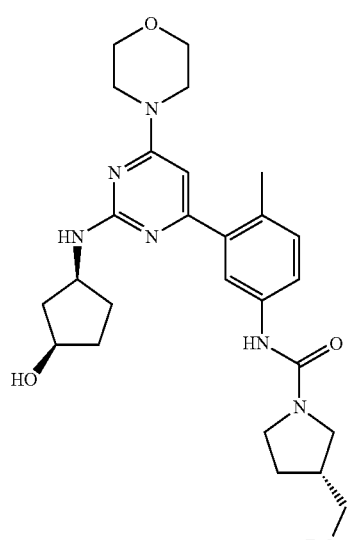 | (S)-N-(3-(2-(((1S,3R)-3-hydroxycyclopentyl)amino)-6-morpholinopyrimidin-4-yl)-4-methylphenyl)-3-(2,2,2-trifluoroethyl)pyrrolidine-1-carboxamide and (S)-N-(3-(2-(((1R,3S)-3-hydroxycyclopentyl)amino)-6-morpholinopyrimidin-4-yl)-4-methylphenyl)-3-(2,2,2-trifluoroethyl)pyrrolidine-1-carboxamide |

+

TABLE 1-continued
| Synthetic Chemistry Example | Compound Structure | Compound Name |
|---|---|---|
| | 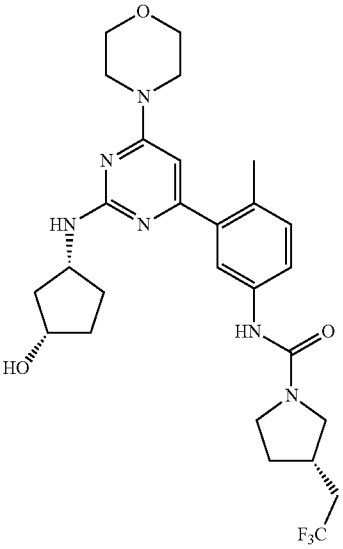 [SMILES: Cc1ccc(NC(=O)N2CC[C@@H](CC(F)(F)F)C2)cc1-c1cc(N2CCOCC2)nc(N[C@@H]2CC[C@H](O)C2)n1] | |
| 13 | 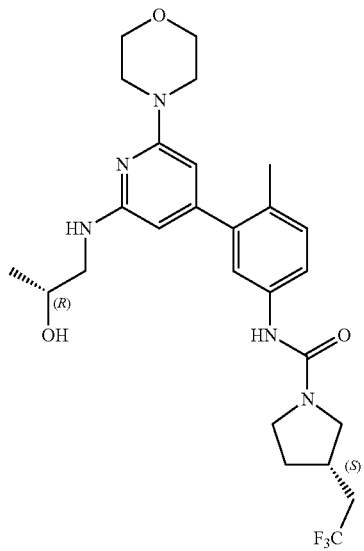 | (S)-N-(3-(2-(((R)-2-hydroxypropyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 14 | 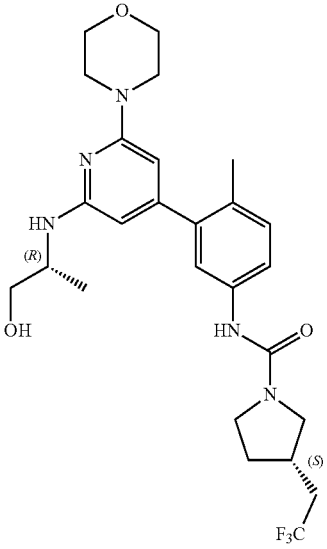 | (S)-N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide |
| 15 | 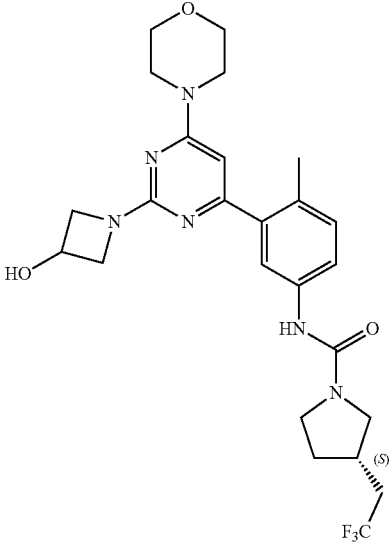 | (S)-N-(3-(2-(3-hydroxyazetidin-1-yl)-6-morpholinopyrimidin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 16 | 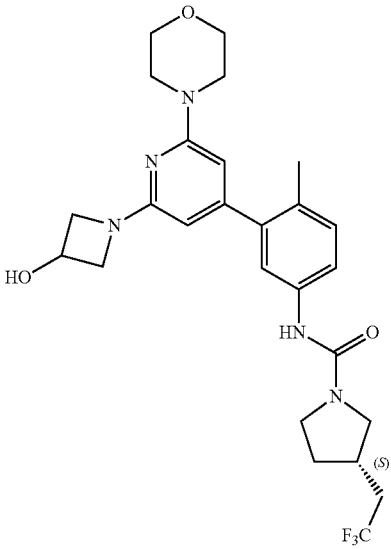 | (S)-N-(3-(2-(3-hydroxyazetidin-1-yl)-6-morpholinopyridin-4-yl)-4-methylphenyl)-3-(2,2,2-trifluoroethyl)pyrrolidine-1-carboxamide |
| 17 | 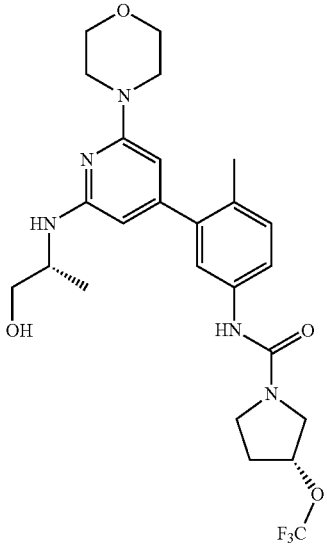 [SMILES: Cc1ccc(NC(=O)N2CC[C@@H](OC(F)(F)F)C2)cc1-c1cc(N[C@H](C)CO)nc(N2CCOCC2)c1] | (R)-N-(3-(2-(((R)-1-hydroxypropan-2-yl)amino)-6-morpholinopyridin-4-yl)-4-methylphenyl)-3-(trifluoromethoxy)pyrrolidine-1-carboxamide |

TABLE 1-continued
| Synthetic Chemistry Example | Compound Structure | Compound Name |
|---|---|---|
| 18 | 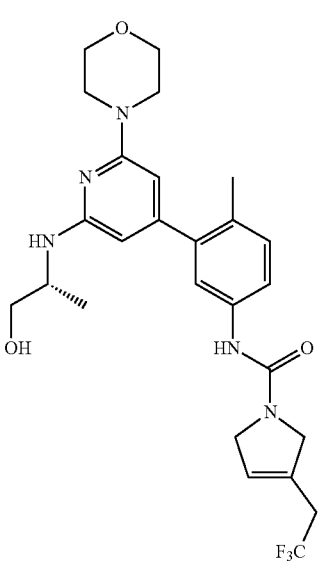 [SMILES: Cc1ccc(NC(=O)N2CC=C(CC(F)(F)F)C2)cc1-c1cc(N[C@H](C)CO)nc(N2CCOCC2)c1] | (R)-N-(3-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide |
| 19 | 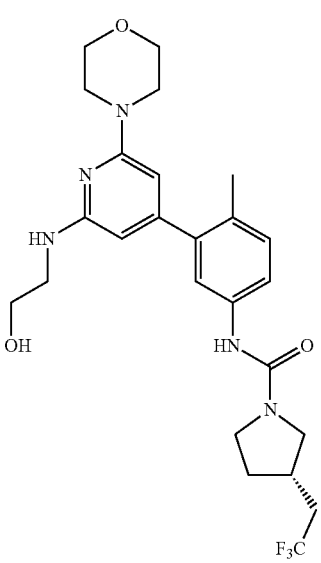 [SMILES: Cc1ccc(NC(=O)N2CC=C(CC(F)(F)F)C2)cc1-c1cc(NCCO)nc(N2CCOCC2)c1] | (S)-N-(3-(2-((2-hydroxyethyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 20 | 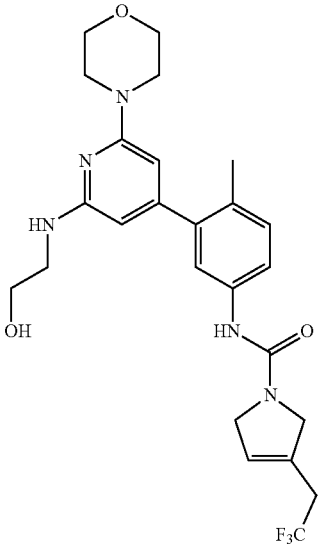 | N-(3-(2-((2-hydroxyethyl)amino)-6-morpholinopyridin-4-yl)-4-methylphenyl)-3-(2,2,2-trifluoroethyl)-2,5-dihydro-1H-pyrrole-1-carboxamide |
| 21 | 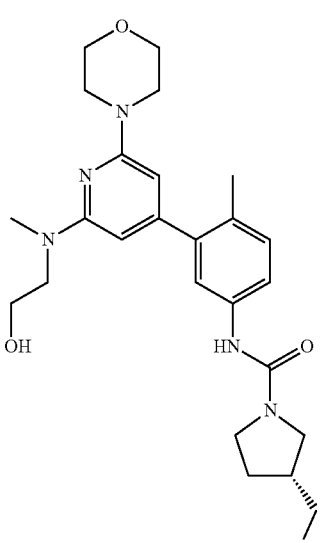 | (S)-N-(3-(2-((2-hydroxyethyl)(methyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 22 | 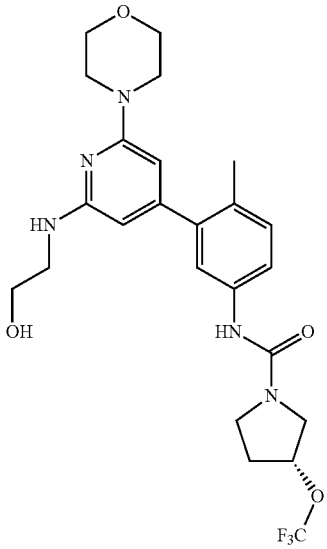 [SMILES: Cc1ccc(NC(=O)N2CC[C@@H](OC(F)(F)F)C2)cc1-c1cc(NCCO)nc(N2CCOCC2)c1] | (R)-N-(3-(2-((2-hydroxyethyl)amino)-6-morpholinopyridin-4-yl)-4-methylphenyl)-3-(trifluoromethoxy)pyrrolidine-1-carboxamide |
| 23 | 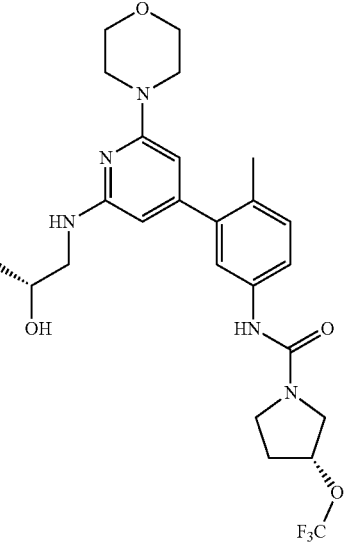 | (R)-N-(3-(2-(((R)-2-hydroxypropyl)amino)-6-morpholinopyridin-4-yl)-4-methylphenyl)-3-(trifluoromethoxy)pyrrolidine-1-carboxamide |

TABLE 1-continued
| Synthetic Chemistry Example | Compound Structure | Compound Name |
|---|---|---|
| 24 | 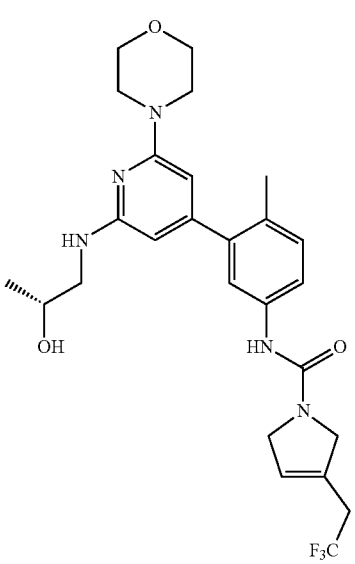 [SMILES: Cc1ccc(NC(=O)N2CC=C(CC(F)(F)F)C2)cc1-c1cc(NC[C@@H](C)O)nc(N2CCOCC2)c1] | (R)-N-(3-(2-((2-hydroxypropyl)amino)-6-morpholinopyridin-4-yl)-4-methylphenyl)-3-(2,2,2-trifluoroethyl)-2,5-dihydro-1H-pyrrole-1-carboxamide |
| 25 | 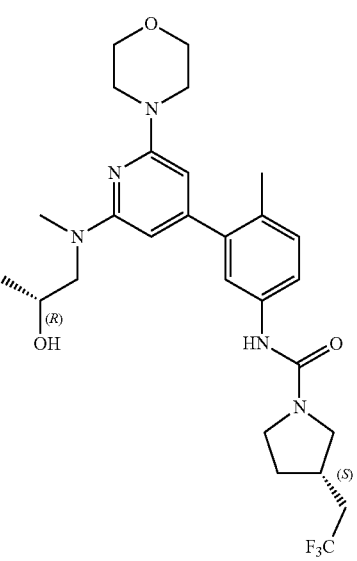 | (S)-N-(3-(2-(((R)-2-hydroxypropyl)(methyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 26 | 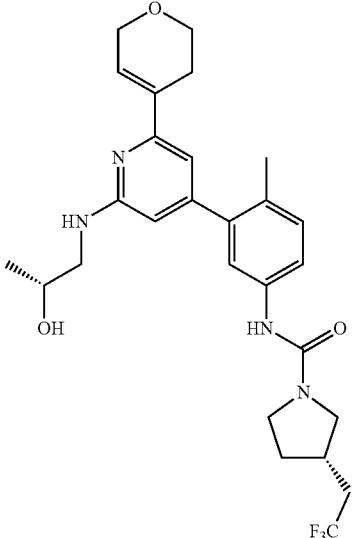 [SMILES: Cc1ccc(NC(=O)N2CC[C@@H](CC(F)(F)F)C2)cc1-c1cc(NC[C@@H](C)O)nc(C2=CCOCC2)c1] | (S)-N-(3-(2-(3,6-dihydro-2H-pyran-4-yl)-6-(((R)-2-hydroxypropyl)amino)pyridin-4-yl)-4-methylphenyl)-3-(2,2,2-trifluoroethyl)pyrrolidine-1-carboxamide |
| 27 | 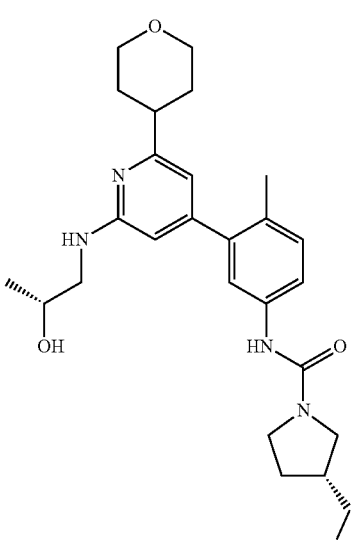 | (S)-N-(3-(2-(((R)-2-hydroxypropyl)amino)-6-(tetrahydro-2H-pyran-4-yl)pyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 28 | 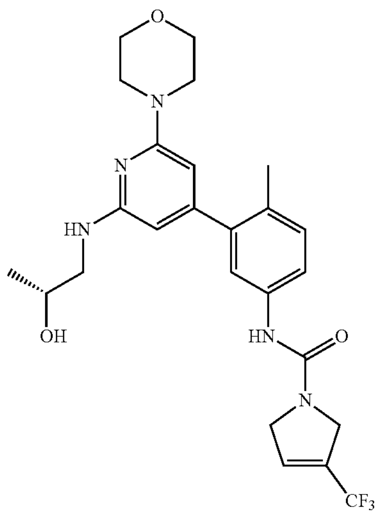 [SMILES: Cc1ccc(NC(=O)N2CC=C(C(F)(F)F)C2)cc1-c1cc(NC[C@@H](C)O)nc(N2CCOCC2)c1] | (R)-N-(3-(2-((2-hydroxypropyl)amino)-6-morpholinopyridin-4-yl)-4-methylphenyl)-3-(trifluoromethyl)-2,5-dihydro-1H-pyrrole-1-carboxamide |
| 29 | 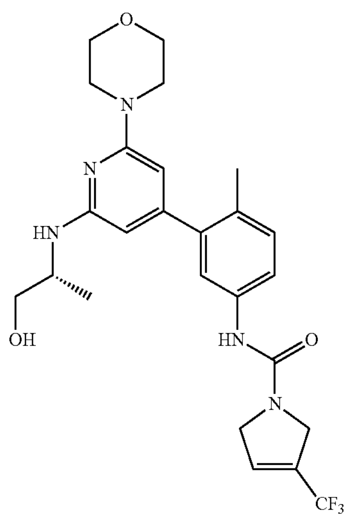 [SMILES: Cc1ccc(NC(=O)N2CC=C(C(F)(F)F)C2)cc1-c1cc(N[C@H](C)CO)nc(N2CCOCC2)c1] | (R)-N-(3-(2-((1-hydroxypropan-2-yl)amino)-6-morpholinopyridin-4-yl)-4-methylphenyl)-3-(trifluoromethyl)-2,5-dihydro-1H-pyrrole-1-carboxamide |
| 30 | 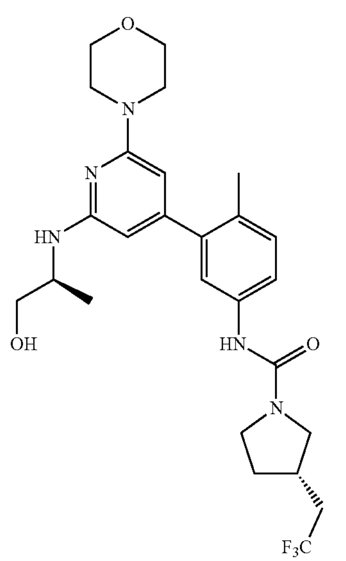 [SMILES: Cc1ccc(NC(=O)N2CC[C@@H](CC(F)(F)F)C2)cc1-c1cc(N[C@@H](C)CO)nc(N2CCOCC2)c1] | (S)-N-(3-(2-(((S)-1-hydroxypropan-2-yl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 31 | 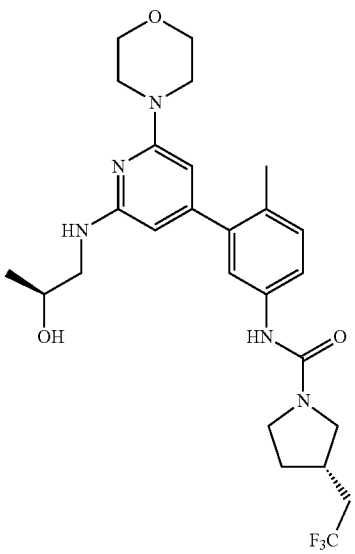 [SMILES: Cc1ccc(NC(=O)N2CC[C@@H](CC(F)(F)F)C2)cc1-c1cc(NC[C@H](C)O)nc(N2CCOCC2)c1] | (S)-N-(3-(2-(((S)-2-hydroxypropyl)amino)-6-morpholinopyridin-4-yl)-4-methylphenyl)-3-(2,2,2-trifluoroethyl)pyrrolidine-1-carboxamide |
| 32 | 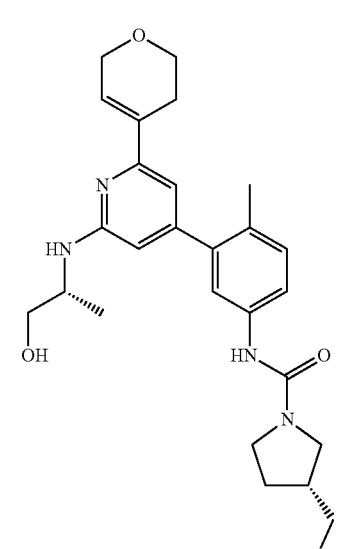 | (S)-N-(3-(2-(3,6-dihydro-2H-pyran-4-yl)-6-(((R)-1-hydroxypropan-2-yl)amino)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 33 | 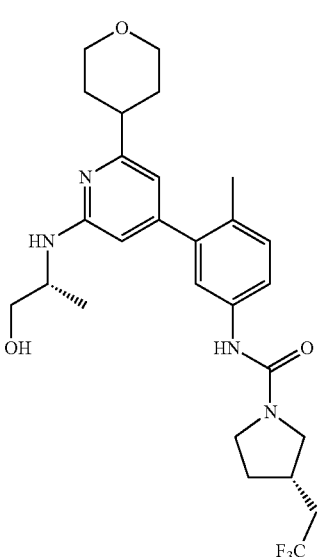 | (S)-N-(3-(2-(((R)-1-hydroxypropan-2-yl)amino)-6-(tetrahydro-2H-pyran-4-yl)pyridin-4-yl)-4-methylphenyl)-3-(2,2,2-trifluoroethyl)pyrrolidine-1-carboxamide |
| 34 | 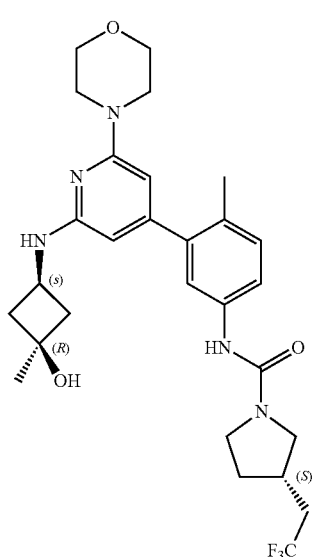 | (S)-N-(3-(2-(((1S,3R)-3-hydroxy-3-methylcyclobutyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 35 | 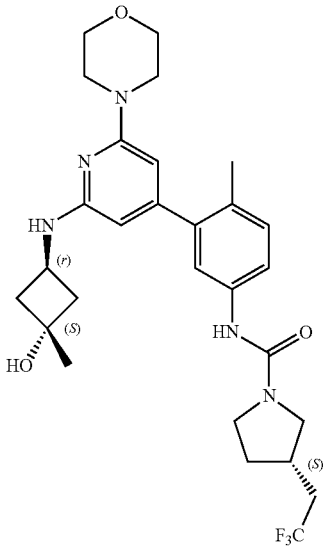 | (S)-N-(3-(2-(((1R,3S)-3-hydroxy-3-methylcyclobutyl)amino)-6-morpholinopyridin-4-yl)-4-methylphenyl)-3-(2,2,2-trifluoroethyl)pyrrolidine-1-carboxamide |
| 36 | 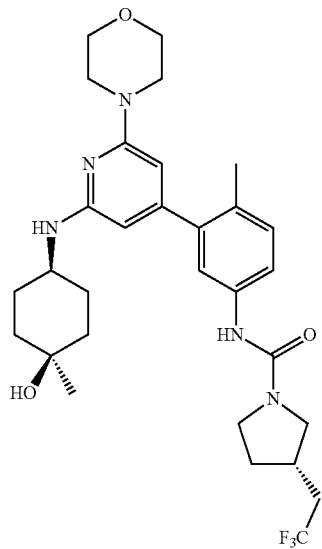 [SMILES: Cc1ccc(NC(=O)N2CC[C@@H](CC(F)(F)F)C2)cc1-c1cc(N[C@H]2CC[C@@](C)(O)CC2)nc(N2CCOCC2)c1] | (S)-N-(3-(2-(((1S,4R)-4-hydroxy-4-methylcyclohexyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 37 | 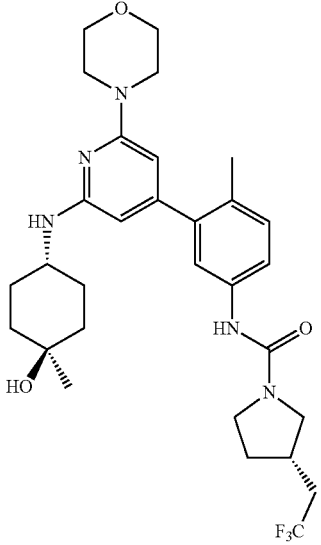 [SMILES: Cc1ccc(NC(=O)N2CC[C@@H](CC(F)(F)F)C2)cc1-c1cc(N[C@H]2CC[C@](C)(O)CC2)nc(N2CCOCC2)c1] | (S)-N-(3-(2-(((1R,4S)-4-hydroxy-4-methylcyclohexyl)amino)-6-morpholinopyridin-4-yl)-4-methylphenyl)-3-(2,2,2-trifluoroethyl)pyrrolidine-1-carboxamide |
| 38 | 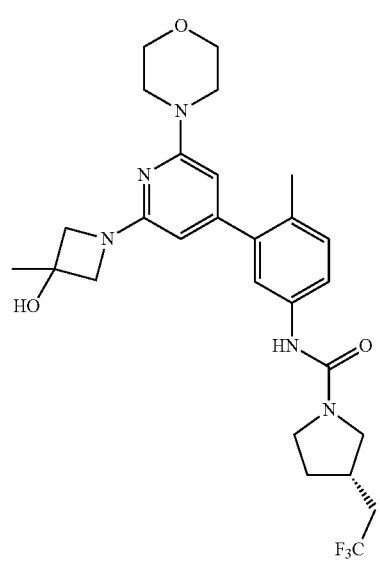 [SMILES: Cc1ccc(NC(=O)N2CC[C@@H](CC(F)(F)F)C2)cc1-c1cc(N2CCOCC2)nc(N2CC(C)(O)C2)c1] | (S)-N-(3-(2-(3-hydroxy-3-methylazetidin-1-yl)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 39 | 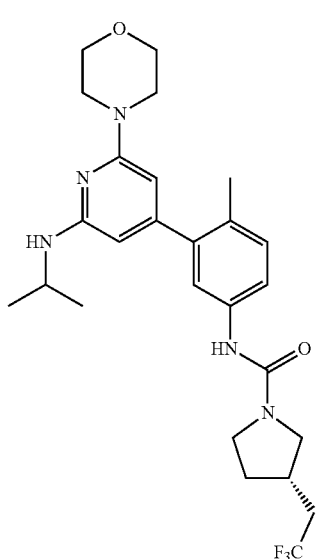 | (S)-N-(3-(2-(isopropylamino)-6-morpholinopyridin-4-yl)-4-methylphenyl)-3-(2,2,2-trifluoroethyl)pyrrolidine-1-carboxamide |
| 40 | 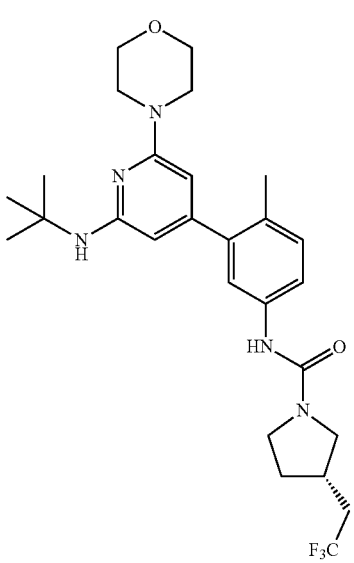 [SMILES: Cc1ccc(NC(=O)N2CC[C@@H](CC(F)(F)F)C2)cc1-c1cc(NC(C)(C)C)nc(N2CCOCC2)c1] | (S)-N-(3-(2-(tert-butylamino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 41 | 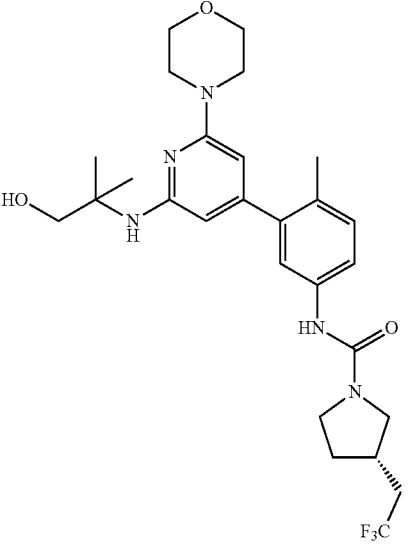 [SMILES: Cc1ccc(NC(=O)N2CC[C@@H](CC(F)(F)F)C2)cc1-c1cc(NC(C)(C)CO)nc(N2CCOCC2)c1] | (S)-N-(3-(2-((1-hydroxy-2-methylpropan-2-yl)amino)-6-morpholinopyridin-4-yl)-4-methylphenyl)-3-(2,2,2-trifluoroethyl)pyrrolidine-1-carboxamide |
| 42 | 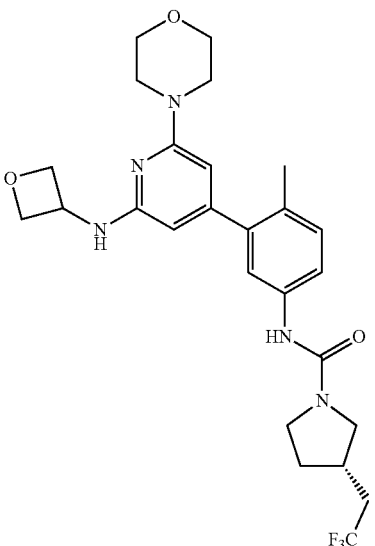 [SMILES: Cc1ccc(NC(=O)N2CC[C@@H](CC(F)(F)F)C2)cc1-c1cc(NC2COC2)nc(N2CCOCC2)c1] | (S)-N-(4-methyl-3-(2-morpholino-6-(oxetan-3-ylamino)pyridin-4-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 43 | 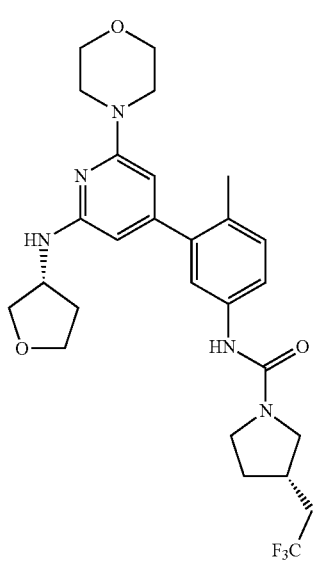 [SMILES: Cc1ccc(NC(=O)N2CC[C@@H](CC(F)(F)F)C2)cc1-c1cc(N[C@@H]2CCOC2)nc(N2CCOCC2)c1] | (S)-N-(4-methyl-3-(2-morpholino-6-(((R)-tetrahydrofuran-3-yl)amino)pyridin-4-yl)phenyl)-3-(2,2,2-trifluoroethyl)pyrrolidine-1-carboxamide |
| 44 | 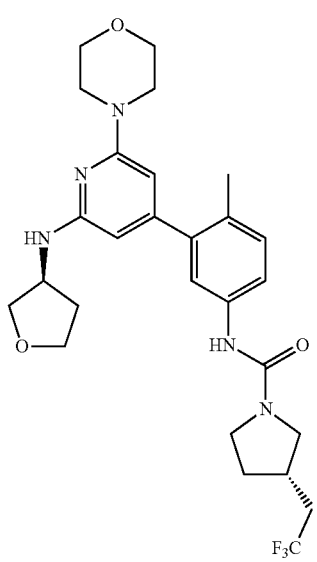 [SMILES: Cc1ccc(NC(=O)N2CC[C@@H](CC(F)(F)F)C2)cc1-c1cc(N[C@H]2CCOC2)nc(N2CCOCC2)c1] | (S)-N-(4-methyl-3-(2-morpholino-6-(((S)-tetrahydrofuran-3-yl)amino)pyridin-4-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 45 | 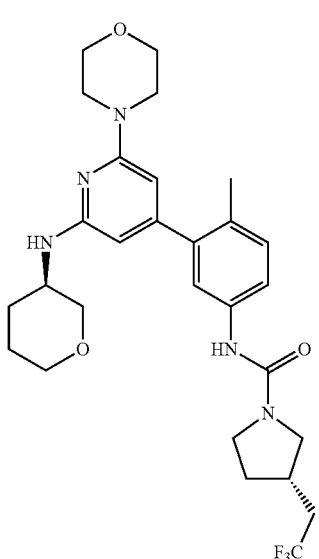 [SMILES: Cc1ccc(NC(=O)N2CC[C@@H](CC(F)(F)F)C2)cc1-c1cc(N[C@@H]2CCCOC2)nc(N2CCOCC2)c1] | (S)-N-(4-methyl-3-(2-morpholino-6-(((R)-tetrahydro-2H-pyran-3-yl)amino)pyridin-4-yl)phenyl)-3-(2,2,2-trifluoroethyl)pyrrolidine-1-carboxamide |
| 46 | 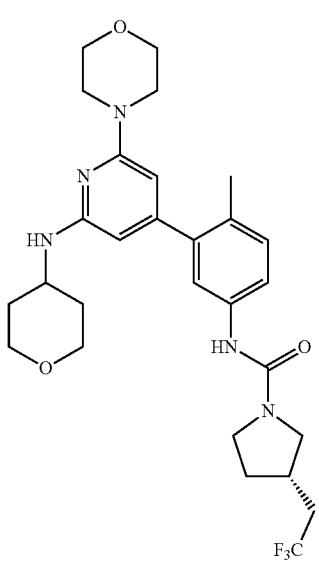 [SMILES: Cc1ccc(NC(=O)N2CC[C@@H](CC(F)(F)F)C2)cc1-c1cc(NC2CCOCC2)nc(N2CCOCC2)c1] | (S)-N-(4-methyl-3-(2-morpholino-6-((tetrahydro-2H-pyran-4-yl)amino)pyridin-4-yl)phenyl)-3-(2,2,2-trifluoroethyl)pyrrolidine-1-carboxamide |

| Synthetic Chemistry Example | Compound Structure | Compound Name |
|---|---|---|
| 47 | 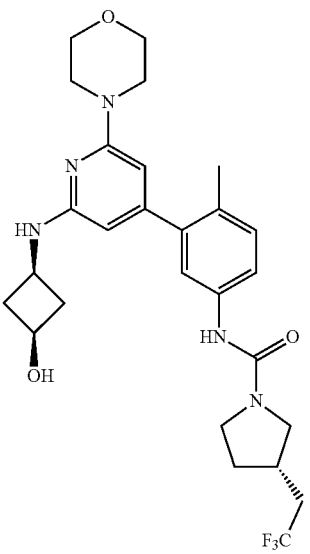 [SMILES: Cc1ccc(NC(=O)N2CC[C@@H](CC(F)(F)F)C2)cc1-c1cc(N[C@H]2C[C@@H](O)C2)nc(N2CCOCC2)c1] | (S)-N-(3-(2-(((1S,3R)-3-hydroxycyclobutyl)amino)-6-morpholinopyridin-4-yl)-4-methylphenyl)-3-(2,2,2-trifluoroethyl)pyrrolidine-1-carboxamide |
| 48 | 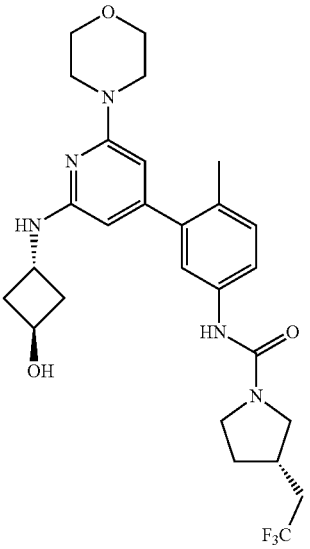 [SMILES: Cc1ccc(NC(=O)N2CC[C@@H](CC(F)(F)F)C2)cc1-c1cc(N[C@H]2C[C@H](O)C2)nc(N2CCOCC2)c1] | (S)-N-(3-(2-(((1R,3S)-3-hydroxycyclobutyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 49 | 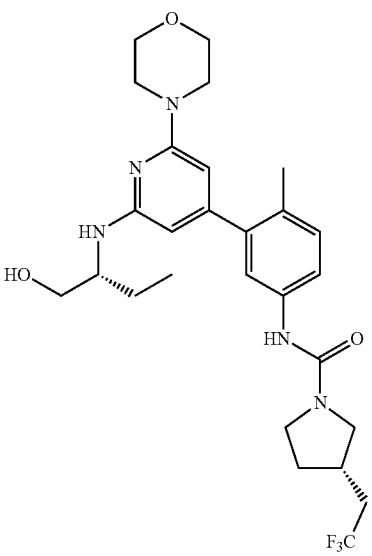 [SMILES: CC[C@H](CO)Nc1cc(-c2cc(NC(=O)N3CC[C@@H](CC(F)(F)F)C3)ccc2C)cc(N2CCOCC2)n1] | (S)-N-(3-(2-(((R)-1-hydroxybutan-2-yl)amino)-6-morpholinopyridin-4-yl)-4-methylphenyl)-3-(2,2,2-trifluoroethyl)pyrrolidine-1-carboxamide |
| 50 | 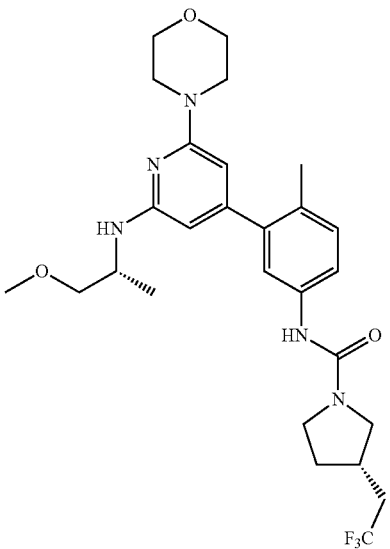 [SMILES: COC[C@@H](C)Nc1cc(-c2cc(NC(=O)N3CC[C@@H](CC(F)(F)F)C3)ccc2C)cc(N2CCOCC2)n1] | (S)-N-(3-(2-(((R)-1-methoxypropan-2-yl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 51 | 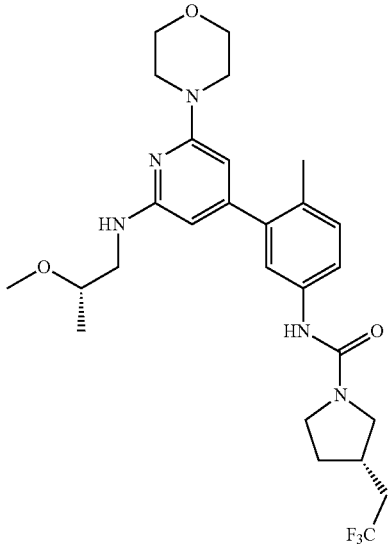 [SMILES: CO[C@@H](C)CNc1cc(-c2cc(NC(=O)N3CC[C@@H](CC(F)(F)F)C3)ccc2C)cc(N2CCOCC2)n1] | (S)-N-(3-(2-(((S)-2-methoxypropyl)amino)-6-morpholinopyridin-4-yl)-4-methylphenyl)-3-(2,2,2-trifluoroethyl)pyrrolidine-1-carboxamide |
| 52 | 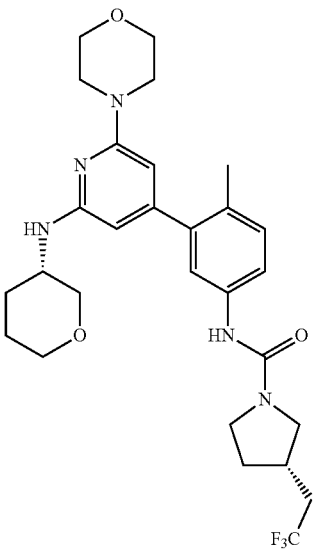 [SMILES: Cc1ccc(NC(=O)N2CC[C@@H](CC(F)(F)F)C2)cc1-c1cc(N[C@H]2CCCOC2)nc(N2CCOCC2)c1] | (S)-N-(4-methyl-3-(2-morpholino-6-(((S)-tetrahydro-2H-pyran-3-yl)amino)pyridin-4-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 53 | 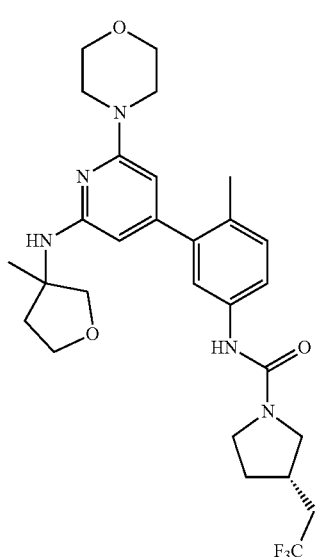 [SMILES: Cc1ccc(NC(=O)N2CC[C@@H](CC(F)(F)F)C2)cc1-c1cc(NC2(C)CCOC2)nc(N2CCOCC2)c1] | (3S)-N-(4-methyl-3-(2-((3-methyltetrahydrofuran-3-yl)amino)-6-morpholinopyridin-4-yl)phenyl)-3-(2,2,2-trifluoroethyl)pyrrolidine-1-carboxamide |
| 54 | 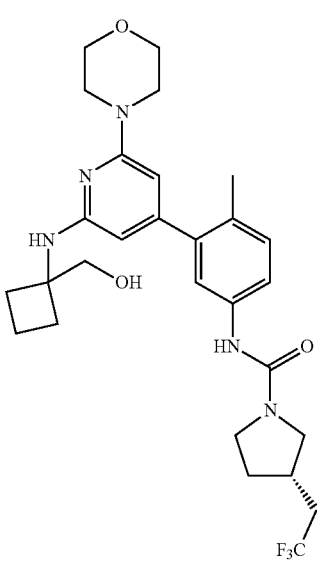 [SMILES: Cc1ccc(NC(=O)N2CC[C@@H](CC(F)(F)F)C2)cc1-c1cc(NC2(CO)CCC2)nc(N2CCOCC2)c1] | (S)-N-(3-(2-((1-(hydroxymethyl)cyclobutyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 55 | 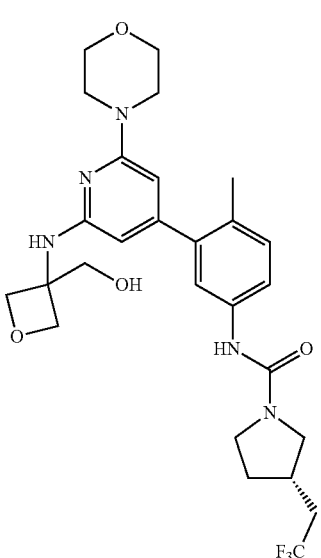 | (S)-N-(3-(2-((3-(hydroxymethyl)oxetan-3-yl)amino)-6-morpholinopyridin-4-yl)-4-methylphenyl)-3-(2,2,2-trifluoroethyl)pyrrolidine-1-carboxamide |
| 56 | 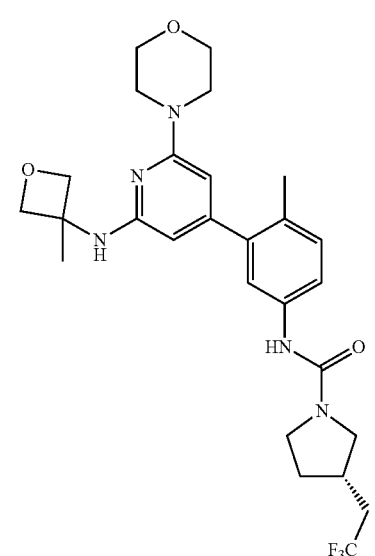 [SMILES: Cc1ccc(NC(=O)N2CC[C@@H](CC(F)(F)F)C2)cc1-c1cc(NC2(C)COC2)nc(N2CCOCC2)c1] | (S)-N-(4-methyl-3-(2-((3-methyloxetan-3-yl)amino)-6-morpholinopyridin-4-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 57 | 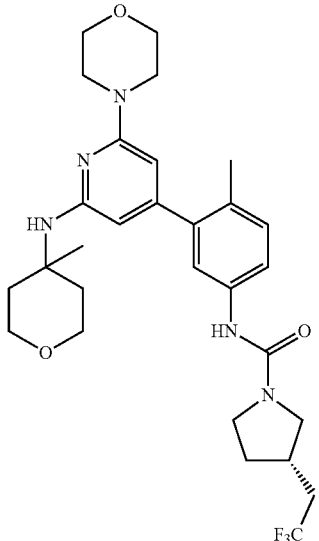 | (S)-N-(4-methyl-3-(2-((4-methyltetrahydro-2H-pyran-4-yl)amino)-6-morpholinopyridin-4-yl)phenyl)-3-(2,2,2-trifluoroethyl)pyrrolidine-1-carboxamide |
| 58 | 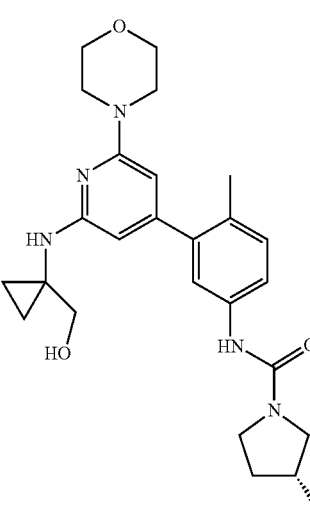 | (S)-N-(3-(2-((1-(hydroxymethyl)cyclopropyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 59 and 60 | 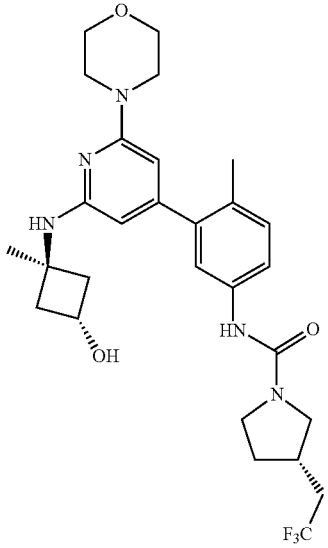 [SMILES: Cc1ccc(NC(=O)N2CC[C@@H](CC(F)(F)F)C2)cc1-c1cc(N[C@]2(C)C[C@@H](O)C2)nc(N2CCOCC2)c1]<br>+<br>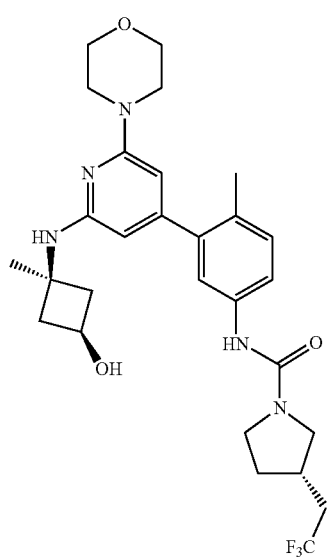 [SMILES: Cc1ccc(NC(=O)N2CC[C@@H](CC(F)(F)F)C2)cc1-c1cc(N[C@]2(C)C[C@H](O)C2)nc(N2CCOCC2)c1] | (S)-N-(3-(2-(((1R,3S)-3-hydroxy-1-methylcyclobutyl)amino)-6-morpholinopyridin-4-yl)-4-methylphenyl)-3-(2,2,2-trifluoroethyl)pyrrolidine-1-carboxamide and (S)-N-(3-(2-(((1S,3R)-3-hydroxy-1-methylcyclobutyl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 61 | 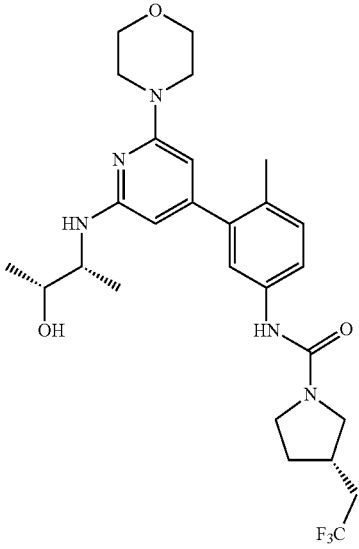 [SMILES: Cc1ccc(NC(=O)N2CC[C@@H](CC(F)(F)F)C2)cc1-c1cc(N[C@H](C)[C@@H](C)O)nc(N2CCOCC2)c1] | (S)-N-(3-(2-(((2R,3R)-3-hydroxybutan-2-yl)amino)-6-morpholinopyridin-4-yl)-4-methylphenyl)-3-(2,2,2-trifluoroethyl)pyrrolidine-1-carboxamide |
| 62 | 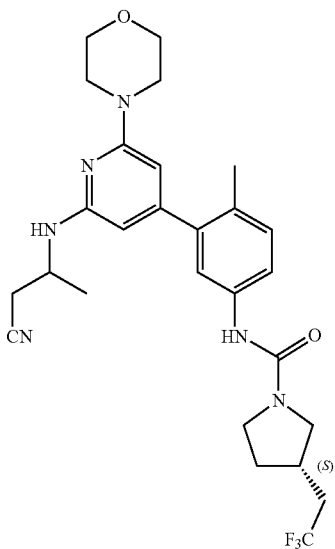 | (3S)-N-(3-(2-((1-cyanopropan-2-yl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 63 and 64 | 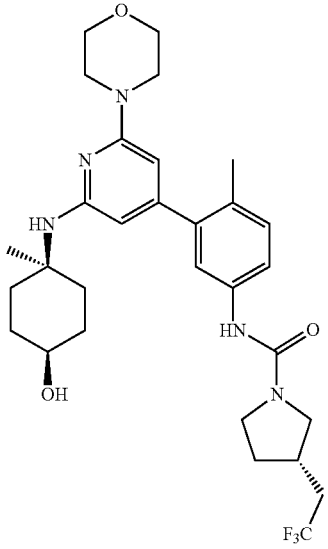 [SMILES: Cc1ccc(NC(=O)N2CC[C@@H](CC(F)(F)F)C2)cc1-c1cc(N[C@]2(C)CC[C@H](O)CC2)nc(N2CCOCC2)c1] | (S)-N-(3-(2-(((1S,4R)-4-hydroxy-1-methylcyclohexyl)amino)-6-morpholinopyridin-4-yl)-4-methylphenyl)-3-(2,2,2-trifluoroethyl)pyrrolidine-1-carboxamide And (S)-N-(3-(2-(((1R,4S)-4-hydroxy-1-methylcyclohexyl)amino)-6-morpholinopyridin-4-yl)-4-methylphenyl)-3-(2,2,2-trifluoroethyl)pyrrolidine-1-carboxamide |
+
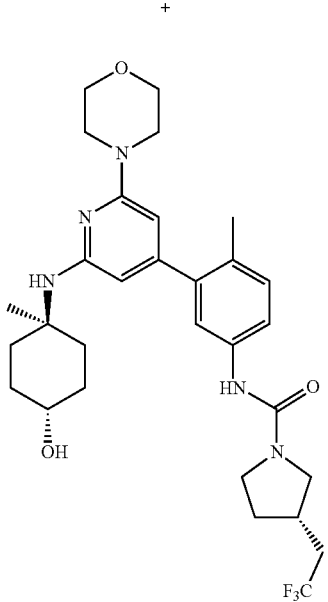

TABLE 1-continued
| Synthetic Chemistry Example | Compound Structure | Compound Name |
|---|---|---|
| 65 | 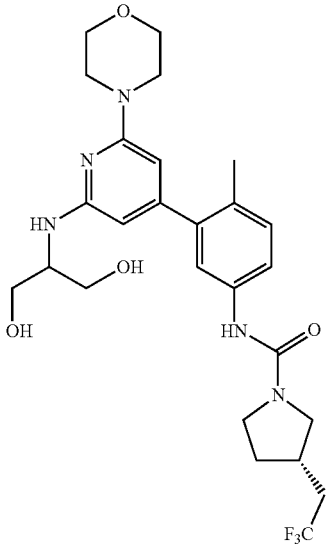 [SMILES: Cc1ccc(NC(=O)N2CC[C@@H](CC(F)(F)F)C2)cc1-c1cc(NC(CO)CO)nc(N2CCOCC2)c1] | (S)-N-(3-(2-((1,3-dihydroxypropan-2-yl)amino)-6-morpholinopyridin-4-yl)-4-methylphenyl)-3-(2,2,2-trifluoroethyl)pyrrolidine-1-carboxamide |
| 66 | 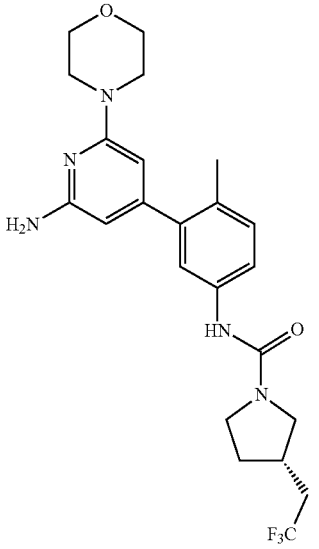 [SMILES: Cc1ccc(NC(=O)N2CC[C@@H](CC(F)(F)F)C2)cc1-c1cc(N)nc(N2CCOCC2)c1] | (S)-N-(3-(2-amino-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 67 | 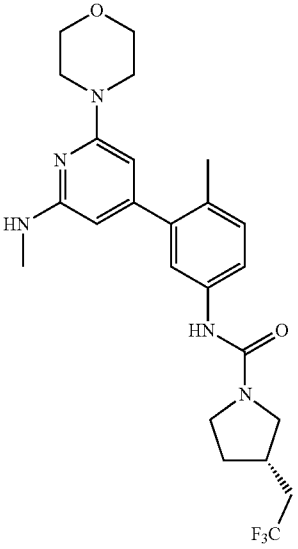 [SMILES: CNc1cc(-c2cc(NC(=O)N3CC[C@@H](CC(F)(F)F)C3)ccc2C)cc(N2CCOCC2)n1] | (S)-N-(4-methyl-3-(2-(methylamino)-6-morpholinopyridin-4-yl)phenyl)-3-(2,2,2-trifluoroethyl)pyrrolidine-1-carboxamide |
| 68 | 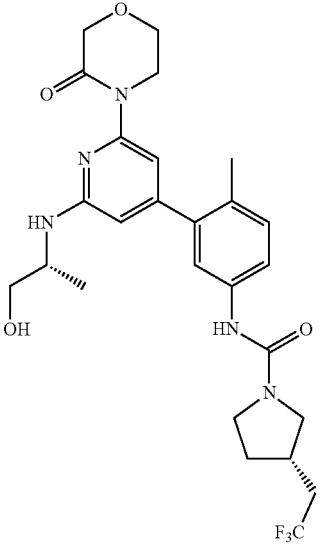 [SMILES: Cc1ccc(NC(=O)N2CC[C@@H](CC(F)(F)F)C2)cc1-c1cc(N[C@H](C)CO)nc(N2CCOCC2=O)c1] | (S)-N-(3-(2-(((R)-1-hydroxypropan-2-yl)amino)-6-(3-oxomorpholino)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 69 | 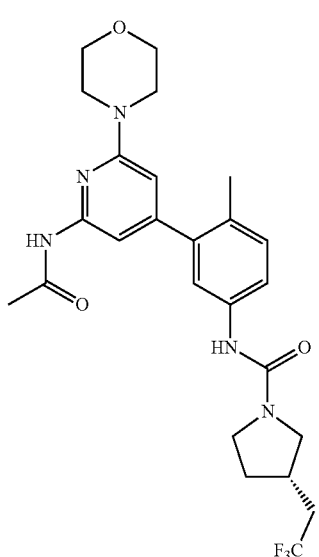 [SMILES: CC(=O)Nc1cc(-c2cc(NC(=O)N3CC[C@@H](CC(F)(F)F)C3)ccc2C)cc(N2CCOCC2)n1] | (S)-N-(3-(2-acetamido-6-morpholinopyridin-4-yl)-4-methylphenyl)-3-(2,2,2-trifluoroethyl)pyrrolidine-1-carboxamide |
| 70 | 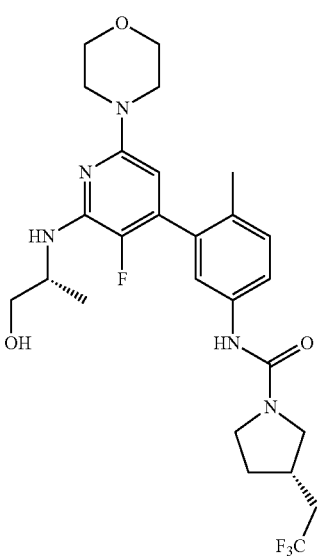 [SMILES: Cc1ccc(NC(=O)N2CC[C@@H](CC(F)(F)F)C2)cc1-c1cc(N2CCOCC2)nc(N[C@H](C)CO)c1F] | (S)-N-(3-(3-fluoro-2-(((R)-1-hydroxypropan-2-yl)amino)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 71 | 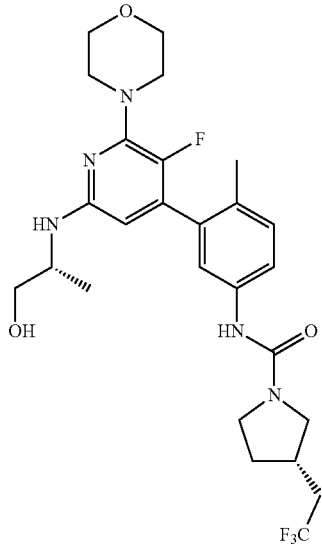 [SMILES: Cc1ccc(NC(=O)N2CC[C@@H](CC(F)(F)F)C2)cc1-c1cc(N[C@H](C)CO)nc(N2CCOCC2)c1F] | (S)-N-(3-(3-fluoro-6-(((R)-1-hydroxypropan-2-yl)amino)-2-morpholinopyridin-4-yl)-4-methylphenyl)-3-(2,2,2-trifluoroethyl)pyrrolidine-1-carboxamide |
| 72 and 73 | 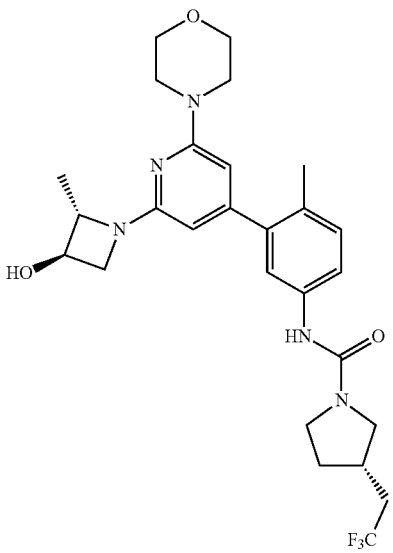 [SMILES: Cc1ccc(NC(=O)N2CC[C@@H](CC(F)(F)F)C2)cc1-c1cc(N2CCOCC2)nc(N2C[C@@H](O)[C@@H]2C)c1] | (S)-N-(3-(2-((2S,3R)-3-hydroxy-2-methylazetidin-1-yl)-6-morpholinopyridin-4-yl)-4-methylphenyl)-3-(2,2,2-trifluoroethyl)pyrrolidine-1-carboxamide and (S)-N-(3-(2-((2S,3S)-3-hydroxy-2-methylazetidin-1-yl)-6-morpholinopyridin-4-yl)-4-methylphenyl)-3-(2,2,2-trifluoroethyl)pyrrolidine-1-carboxamide |

| Synthetic Chemistry Example | Compound Structure | Compound Name |
|---|---|---|
| | 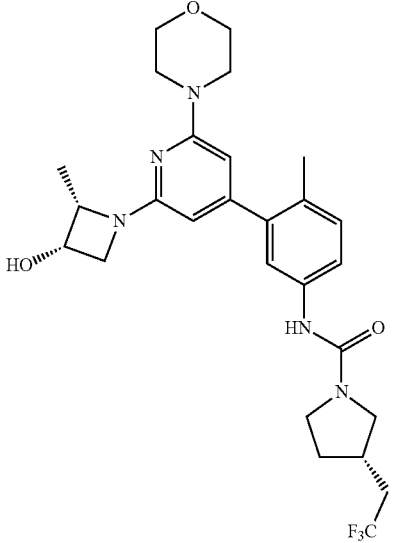 [SMILES: Cc1ccc(NC(=O)N2CC[C@@H](CC(F)(F)F)C2)cc1-c1cc(N2CCOCC2)nc(N2C[C@H](O)[C@@H]2C)c1] | |
| 74 | 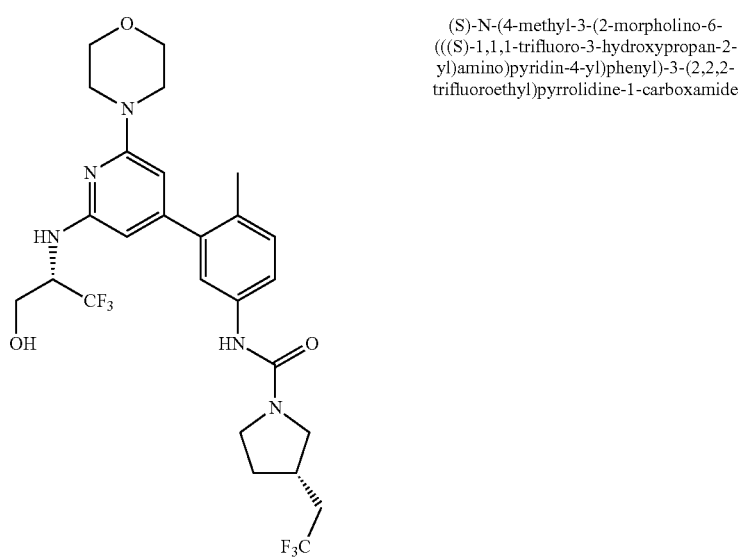 | (S)-N-(4-methyl-3-(2-morpholino-6-(((S)-1,1,1-trifluoro-3-hydroxypropan-2-yl)amino)pyridin-4-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 75 | 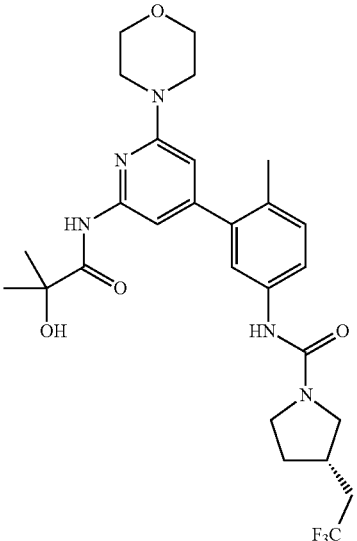 [SMILES: Cc1ccc(NC(=O)N2CC[C@@H](CC(F)(F)F)C2)cc1-c1cc(NC(=O)C(C)(C)O)nc(N2CCOCC2)c1] | (S)-N-(3-(2-(2-hydroxy-2-methylpropanamido)-6-morpholinopyridin-4-yl)-4-methylphenyl)-3-(2,2,2-trifluoroethyl)pyrrolidine-1-carboxamide |
| 76 | 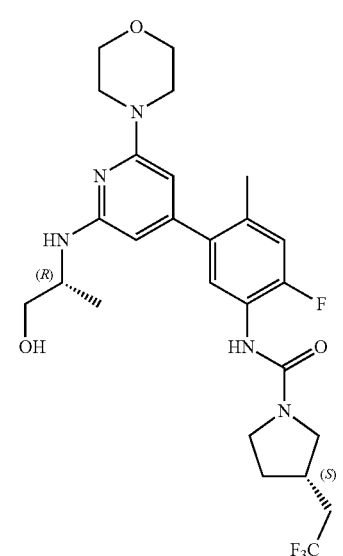 | (S)-N-(2-fluoro-5-(2-(((R)-1-hydroxypropan-2-yl)amino)-6-morpholinopyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 77 | 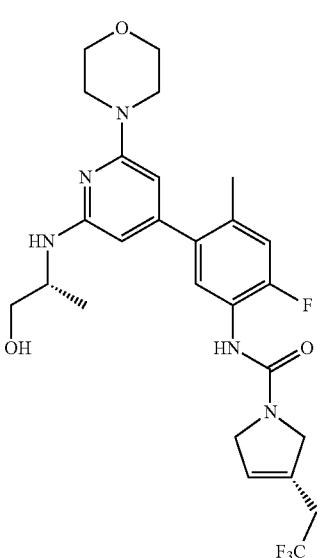 | (R)-N-(2-fluoro-5-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide |
| 78 | 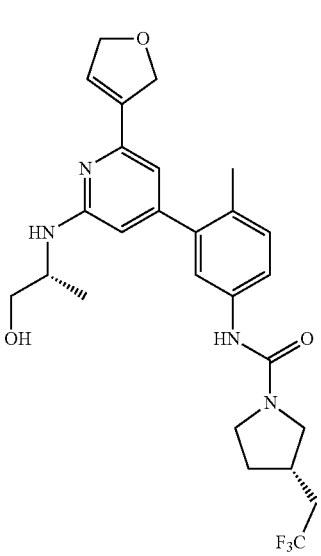 [SMILES: Cc1ccc(NC(=O)N2CC[C@@H](CC(F)(F)F)C2)cc1-c1cc(N[C@H](C)CO)nc(C2=CCOC2)c1] | (S)-N-(3-(2-(2,5-dihydrofuran-3-yl)-6-(((R)-1-hydroxypropan-2-yl)amino)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 79 | 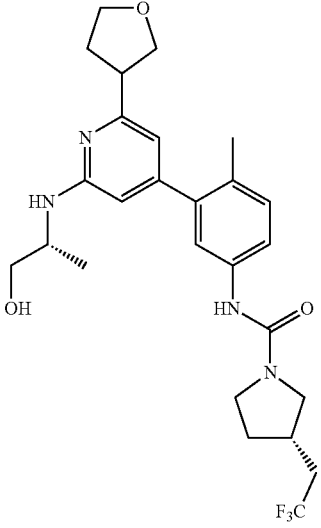 [SMILES: Cc1ccc(NC(=O)N2CC[C@@H](CC(F)(F)F)C2)cc1-c1cc(N[C@H](C)CO)nc(C2CCOC2)c1] | (3S)-N-(3-(2-(((R)-1-hydroxypropan-2-yl)amino)-6-(tetrahydrofuran-3-yl)pyridin-4-yl)-4-methylphenyl)-3-(2,2,2-trifluoroethyl)pyrrolidine-1-carboxamide |
| 80 | 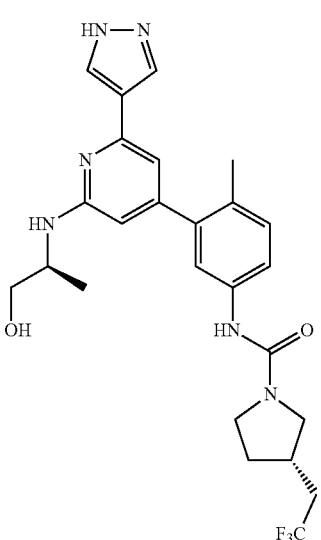 [SMILES: Cc1ccc(NC(=O)N2CC[C@@H](CC(F)(F)F)C2)cc1-c1cc(N[C@@H](C)CO)nc(-c2cn[nH]c2)c1] | (S)-N-(3-(2-(((S)-1-hydroxypropan-2-yl)amino)-6-(1H-pyrazol-4-yl)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 81 | 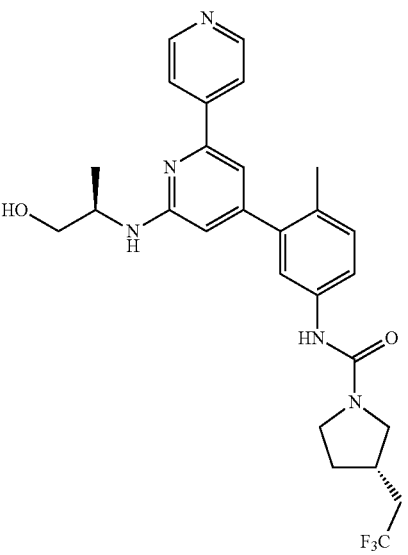 [SMILES: Cc1ccc(NC(=O)N2CC[C@@H](CC(F)(F)F)C2)cc1-c1cc(N[C@H](C)CO)nc(-c2ccncc2)c1] | (S)-N-(3-(6-(((R)-1-hydroxypropan-2-yl)amino)-[2,4'-bipyridin]-4-yl)-4-methylphenyl)-3-(2,2,2-trifluoroethyl)pyrrolidine-1-carboxamide |
| 82 | 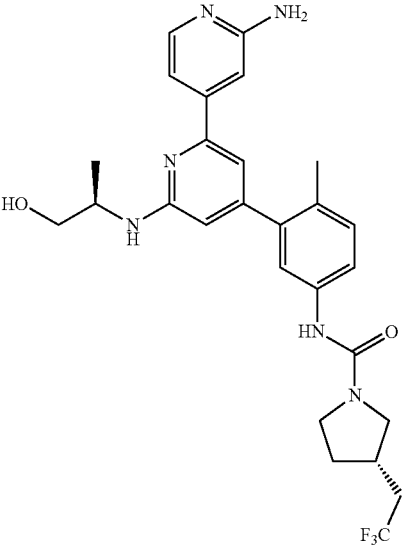 [SMILES: Cc1ccc(NC(=O)N2CC[C@@H](CC(F)(F)F)C2)cc1-c1cc(N[C@H](C)CO)nc(-c2ccnc(N)c2)c1] | (S)-N-(3-(2'-amino-6-(((R)-1-hydroxypropan-2-yl)amino)-[2,4'-bipyridin]-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 83 | 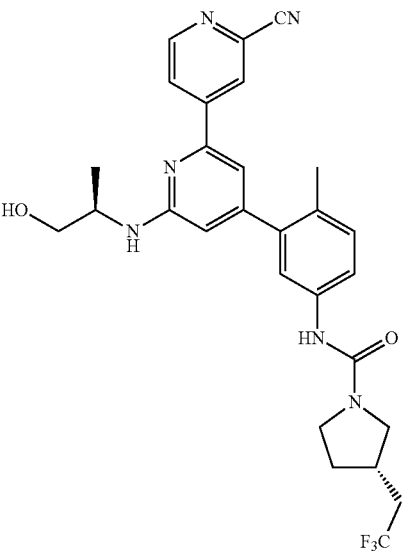 [SMILES: Cc1ccc(NC(=O)N2CC[C@@H](CC(F)(F)F)C2)cc1-c1cc(N[C@H](C)CO)nc(-c2ccnc(C#N)c2)c1] | (S)-N-(3-(2'-cyano-6-(((R)-1-hydroxypropan-2-yl)amino)-[2,4'-bipyridin]-4-yl)-4-methylphenyl)-3-(2,2,2-trifluoroethyl)pyrrolidine-1-carboxamide |
| 84 and 85 | 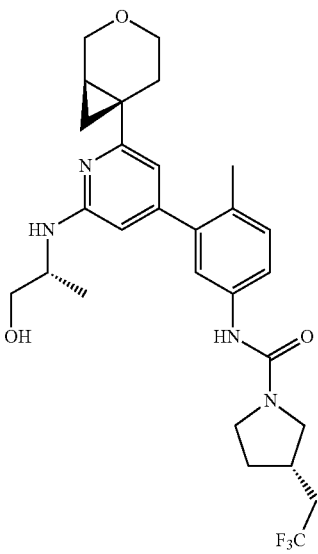 [SMILES: Cc1ccc(NC(=O)N2CC[C@@H](CC(F)(F)F)C2)cc1-c1cc(N[C@H](C)CO)nc([C@@]23CCOC[C@@H]2C3)c1] | (S)-N-(3-(2-((1R,6S)-3-oxabicyclo[4.1.0]heptan-6-yl)-6-(((R)-1-hydroxypropan-2-yl)amino)pyridin-4-yl)-4-methylphenyl)-3-(2,2,2-trifluoroethyl)pyrrolidine-1-carboxamide and (S)-N-(3-(2-((1S,6R)-3-oxabicyclo[4.1.0]heptan-6-yl)-6-(((R)-1-hydroxypropan-2-yl)amino)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| | 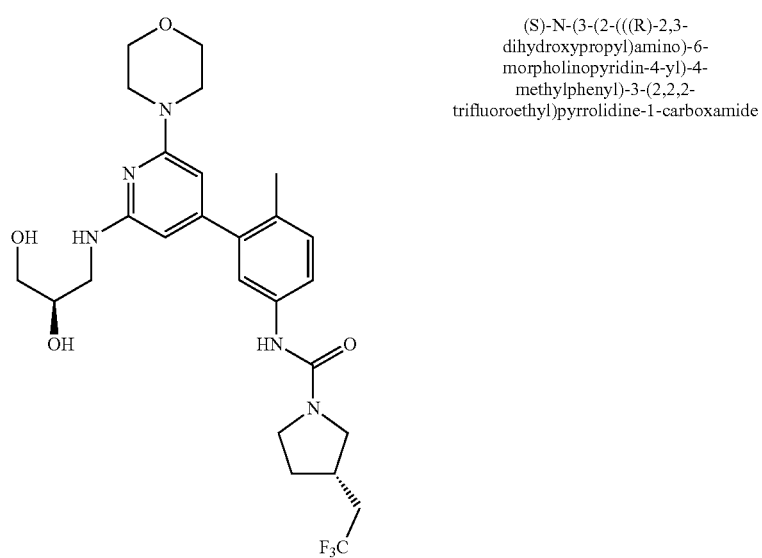 | |
| 86 | 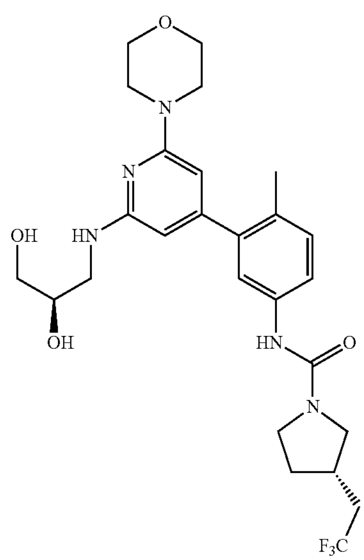 [SMILES: Cc1ccc(NC(=O)N2CC[C@@H](CC(F)(F)F)C2)cc1-c1cc(NC[C@@H](O)CO)nc(N2CCOCC2)c1] | (S)-N-(3-(2-(((R)-2,3-dihydroxypropyl)amino)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 87 | 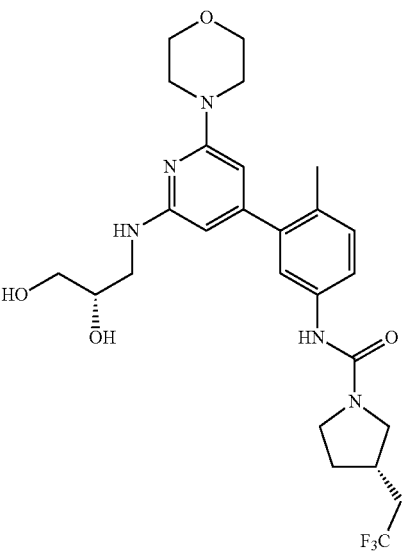 [SMILES: Cc1ccc(NC(=O)N2CC[C@@H](CC(F)(F)F)C2)cc1-c1cc(NC[C@H](O)CO)nc(N2CCOCC2)c1] | (S)-N-(3-(2-(((S)-2,3-dihydroxypropyl)amino)-6-morpholinopyridin-4-yl)-4-methylphenyl)-3-(2,2,2-trifluoroethyl)pyrrolidine-1-carboxamide |
| 88 and 89 | 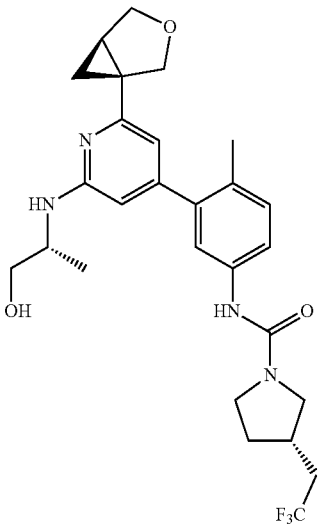 [SMILES: Cc1ccc(NC(=O)N2CC[C@@H](CC(F)(F)F)C2)cc1-c1cc(N[C@H](C)CO)nc([C@@]23COC[C@@H]2C3)c1] | (S)-N-(3-(2-((1S,5R)-3-oxabicyclo[3.1.0]hexan-1-yl)-6-(((R)-1-hydroxypropan-2-yl)amino)pyridin-4-yl)-4-methylphenyl)-3-(2,2,2-trifluoroethyl)pyrrolidine-1-carboxamide and (S)-N-(3-(2-((1R,5S)-3-oxabicyclo[3.1.0]hexan-1-yl)-6-(((R)-1-hydroxypropan-2-yl)amino)pyridin-4-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| | 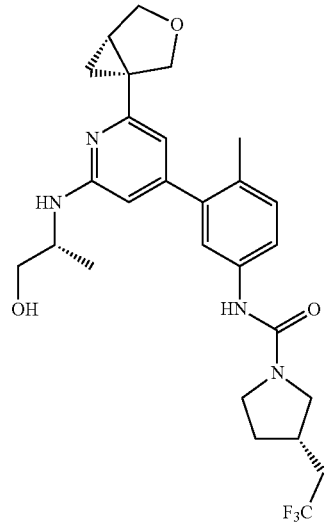 [SMILES: Cc1ccc(NC(=O)N2CC[C@@H](CC(F)(F)F)C2)cc1-c1cc(N[C@H](C)CO)nc([C@]23COC[C@H]2C3)c1] | |
| 90 and 91 | 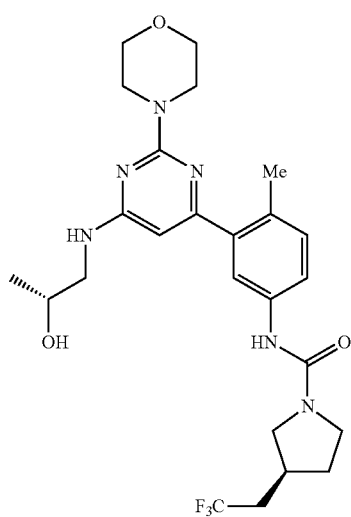 [SMILES: Cc1ccc(NC(=O)N2CC[C@@H](CC(F)(F)F)C2)cc1-c1cc(NC[C@@H](C)O)nc(N2CCOCC2)n1] | (S)-N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide and (R)-N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide |
+

TABLE 1-continued

| Synthetic Chemistry Example | Compound Structure | Compound Name |
|---|---|---|
| 92 | 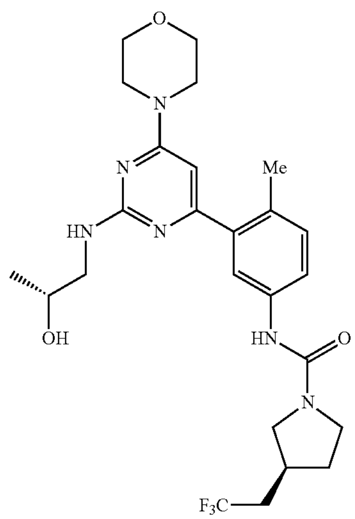 [SMILES: Cc1ccc(NC(=O)N2CC[C@@H](CC(F)(F)F)C2)cc1-c1cc(N2CCOCC2)nc(NC[C@@H](C)O)n1] | (S)-N-(3-(2-(((R)-2-hydroxypropyl)amino)-6-morpholinopyrimidin-4-yl)-4-methylphenyl)-3-(2,2,2-trifluoroethyl)pyrrolidine-1-carboxamide |
| 93 | 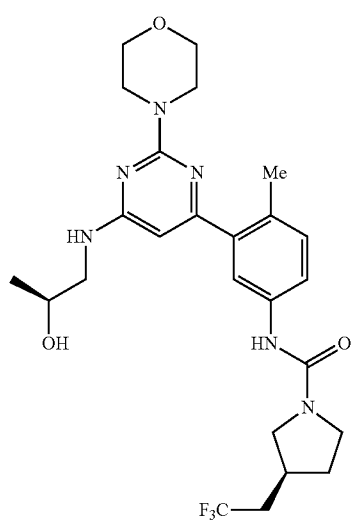 [SMILES: Cc1ccc(NC(=O)N2CC[C@@H](CC(F)(F)F)C2)cc1-c1cc(NC[C@H](C)O)nc(N2CCOCC2)n1] | (S)-N-(3-(6-(((S)-2-hydroxypropyl)amino)-2-morpholinopyrimidin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 94 | 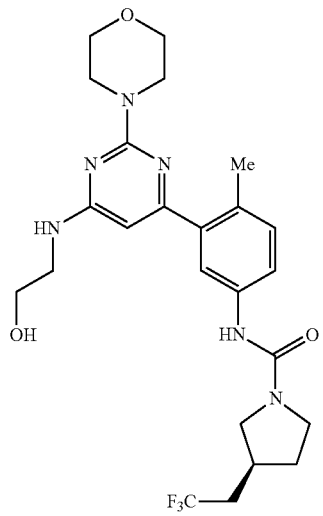 [SMILES: Cc1ccc(NC(=O)N2CC[C@@H](CC(F)(F)F)C2)cc1-c1cc(NCCO)nc(N2CCOCC2)n1] | (S)-N-(3-(6-((2-hydroxyethyl)amino)-2-morpholinopyrimidin-4-yl)-4-methylphenyl)-3-(2,2,2-trifluoroethyl)pyrrolidine-1-carboxamide |
| 95 | 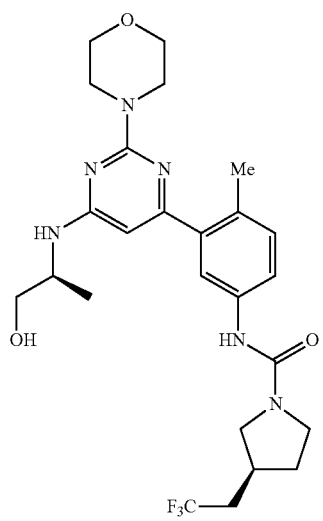 | (S)-N-(3-(6-(((S)-1-hydroxypropan-2-yl)amino)-2-morpholinopyrimidin-4-yl)-4-methylphenyl)-3-(2,2,2-trifluoroethyl)pyrrolidine-1-carboxamide |
| 96 | 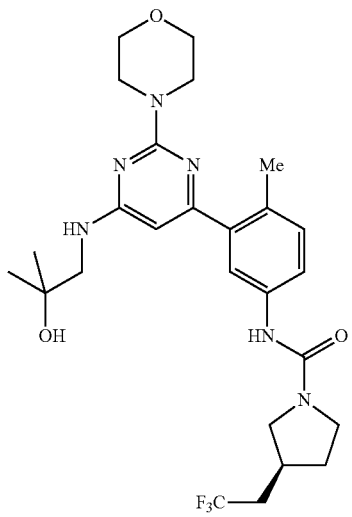 [SMILES: Cc1ccc(NC(=O)N2CC[C@@H](CC(F)(F)F)C2)cc1-c1cc(NCC(C)(C)O)nc(N2CCOCC2)n1] | (S)-N-(3-(6-((2-hydroxy-2-methylpropyl)amino)-2-morpholinopyrimidin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 97 | 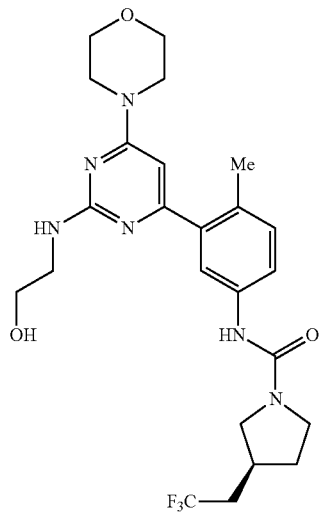 [SMILES: Cc1ccc(NC(=O)N2CC[C@@H](CC(F)(F)F)C2)cc1-c1cc(N2CCOCC2)nc(NCCO)n1] | (S)-N-(3-(2-((2-hydroxyethyl)amino)-6-morpholinopyrimidin-4-yl)-4-methylphenyl)-3-(2,2,2-trifluoroethyl)pyrrolidine-1-carboxamide |
| 98 | 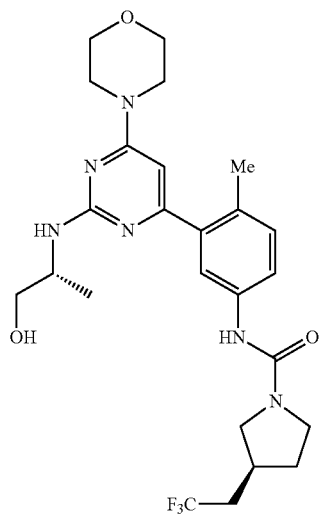 | (S)-N-(3-(2-(((R)-1-hydroxypropan-2-yl)amino)-6-morpholinopyrimidin-4-yl)-4-methylphenyl)-3-(2,2,2-trifluoroethyl)pyrrolidine-1-carboxamide |
| 99 | 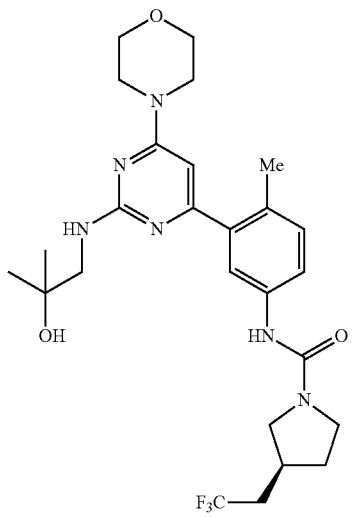 [SMILES: Cc1ccc(NC(=O)N2CC[C@@H](CC(F)(F)F)C2)cc1-c1cc(N2CCOCC2)nc(NCC(C)(C)O)n1] | (S)-N-(3-(2-((2-hydroxy-2-methylpropyl)amino)-6-morpholinopyrimidin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 100 | 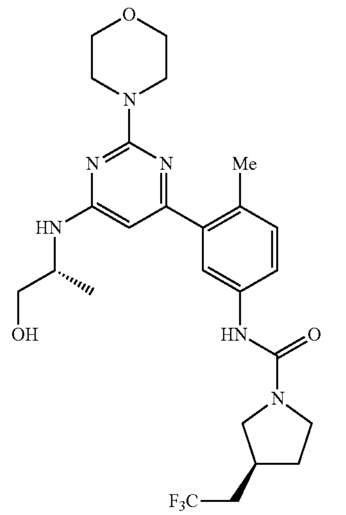 [SMILES: Cc1ccc(NC(=O)N2CC[C@@H](CC(F)(F)F)C2)cc1-c1cc(N[C@H](C)CO)nc(N2CCOCC2)n1] | (S)-N-(3-(6-(((R)-1-hydroxypropan-2-yl)amino)-2-morpholinopyrimidin-4-yl)-4-methylphenyl)-3-(2,2,2-trifluoroethyl)pyrrolidine-1-carboxamide |
| 101 | 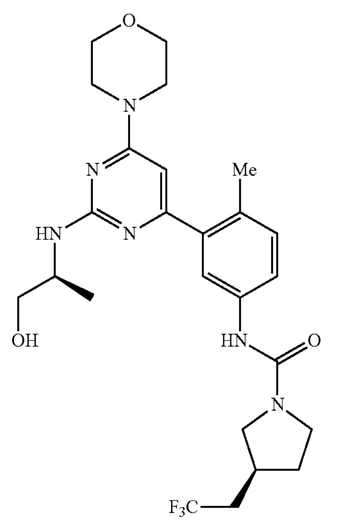 [SMILES: Cc1ccc(NC(=O)N2CC[C@@H](CC(F)(F)F)C2)cc1-c1cc(N2CCOCC2)nc(N[C@@H](C)CO)n1] | (S)-N-(3-(2-(((S)-1-hydroxypropan-2-yl)amino)-6-morpholinopyrimidin-4-yl)-4-methylphenyl)-3-(2,2,2-trifluoroethyl)pyrrolidine-1-carboxamide |
| 102 and 103 | 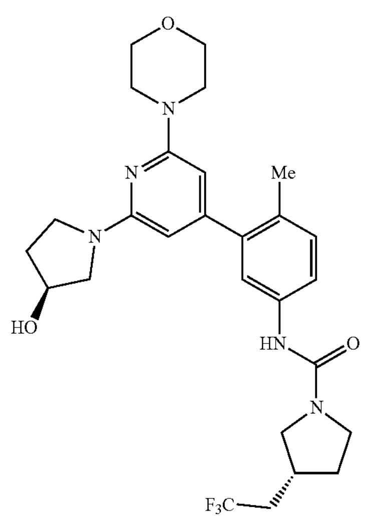 [SMILES: Cc1ccc(NC(=O)N2CC[C@H](CC(F)(F)F)C2)cc1-c1cc(N2CCOCC2)nc(N2CC[C@H](O)C2)c1] | (R)-N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide and (S)-N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide |

+

TABLE 1-continued
| Synthetic Chemistry Example | Compound Structure | Compound Name |
|---|---|---|
| | 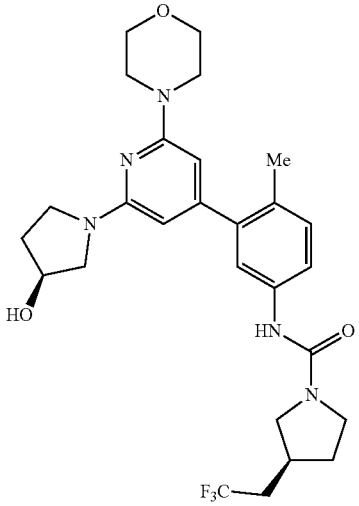 [SMILES: Cc1ccc(NC(=O)N2CC[C@@H](CC(F)(F)F)C2)cc1-c1cc(N2CCOCC2)nc(N2CC[C@H](O)C2)c1] | |
| 104 | 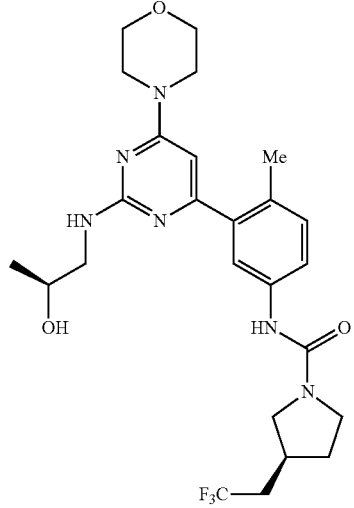 [SMILES: Cc1ccc(NC(=O)N2CC[C@@H](CC(F)(F)F)C2)cc1-c1cc(N2CCOCC2)nc(NC[C@H](C)O)n1] | (S)-N-(3-(2-(((S)-2-hydroxypropyl)amino)-6-morpholinopyrimidin-4-yl)-4-methylphenyl)-3-(2,2,2-trifluoroethyl)pyrrolidine-1-carboxamide |
| 105 | 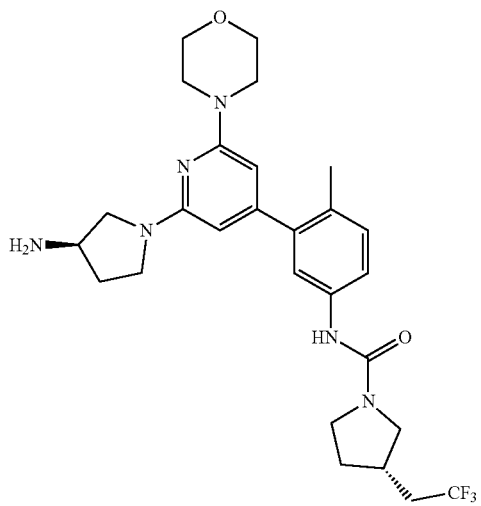 [SMILES: Cc1ccc(NC(=O)N2CC[C@@H](CC(F)(F)F)C2)cc1-c1cc(N2CCOCC2)nc(N2CC[C@@H](N)C2)c1] | (3S)-N-(3-[2-[(3R)-3-aminopyrrolidin-1-yl]-6-(morpholin-4-yl)pyridin-4-yl]-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 106 | 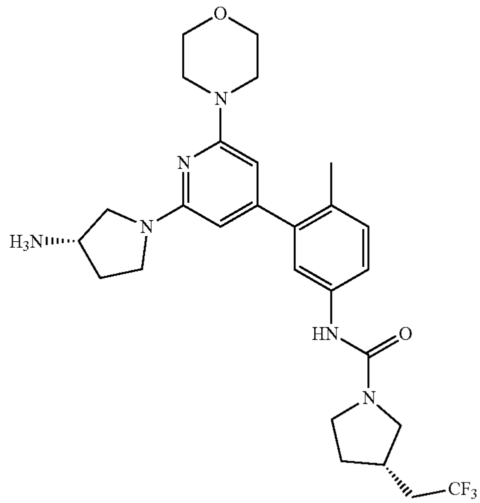 [SMILES: Cc1ccc(NC(=O)N2CC[C@@H](CC(F)(F)F)C2)cc1-c1cc(N2CCOCC2)nc(N2CC[C@H](N)C2)c1] | (3S)-N-(3-[2-[(3S)-3-aminopyrrolidin-1-yl]-6-(morpholin-4-yl)pyridin-4-yl]-4-methylphenyl)-3-(2,2,2-trifluoroethyl)pyrrolidine-1-carboxamide |
| 107 | 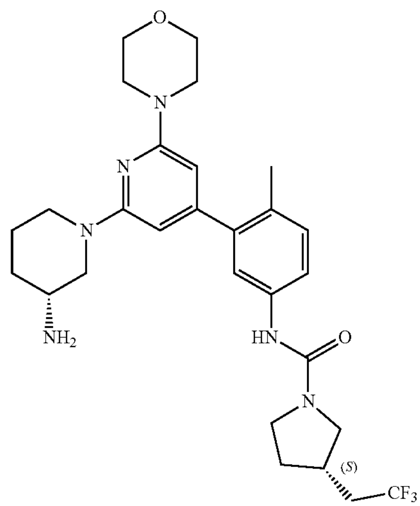 | (3S)-N-(3-[2-[(3R)-3-aminopiperidin-1-yl]-6-(morpholin-4-yl)pyridin-4-yl]-4-methylphenyl)-3-(2,2,2-trifluoroethyl)pyrrolidine-1-carboxamide |
| 108 | 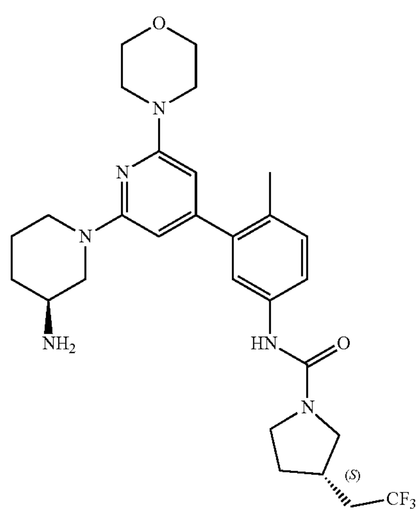 | (3S)-N-(3-[2-[(3S)-3-aminopiperidin-1-yl]-6-(morpholin-4-yl)pyridin-4-yl]-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 109 | 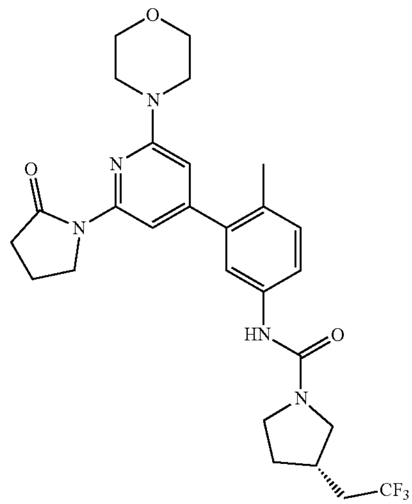 [SMILES: Cc1ccc(NC(=O)N2CC[C@@H](CC(F)(F)F)C2)cc1-c1cc(N2CCOCC2)nc(N2CCCC2=O)c1] | (3S)-N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide |
| 110 | 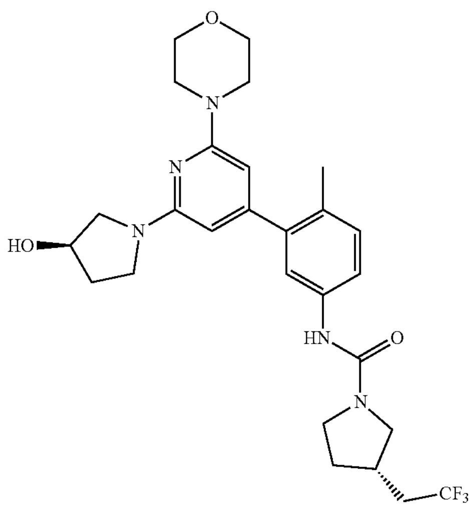 [SMILES: Cc1ccc(NC(=O)N2CC[C@@H](CC(F)(F)F)C2)cc1-c1cc(N2CCOCC2)nc(N2CC[C@@H](O)C2)c1] | (3S)-N-(3-[2-[(3R)-3-hydroxypyrrolidin-1-yl]-6-(morpholin-4-yl)pyridin-4-yl]-4-methylphenyl)-3-(2,2,2-trifluoroethyl)pyrrolidine-1-carboxamide |
| 111 | 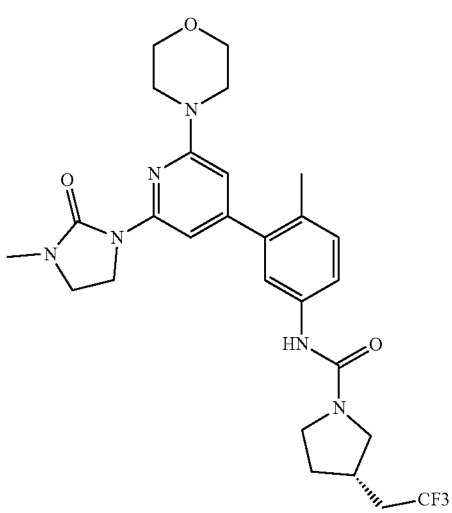 [SMILES: Cc1ccc(NC(=O)N2CC[C@@H](CC(F)(F)F)C2)cc1-c1cc(N2CCOCC2)nc(N2CCN(C)C2=O)c1] | (3S)-N-[4-methyl-3-[2-(3-methyl-2-oxoimidazolidin-1-yl)-6-(morpholin-4-yl)pyridin-4-yl]phenyl]-3-(2,2,2-trifluoroethyl)pyrrolidine-1-carboxamide |

TABLE 1-continued
| Synthetic Chemistry Example | Compound Structure | Compound Name |
|---|---|---|
| 112 | 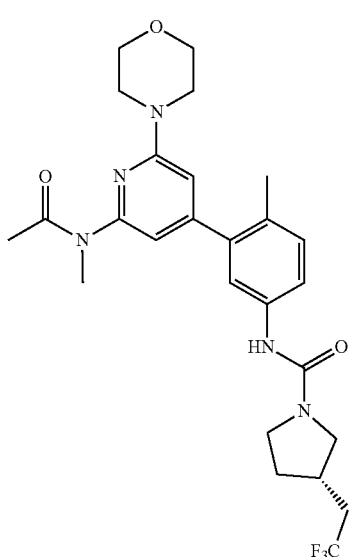 [SMILES: CC(=O)N(C)c1cc(-c2cc(NC(=O)N3CC[C@@H](CC(F)(F)F)C3)ccc2C)cc(N2CCOCC2)n1] | (3S)-N-[4-methyl-3-[2-(N-methylacetamido)-6-(morpholin-4-yl)pyridin-4-yl]phenyl]-3-(2,2,2-trifluoroethyl)pyrrolidine-1-carboxamide |
| 113 | 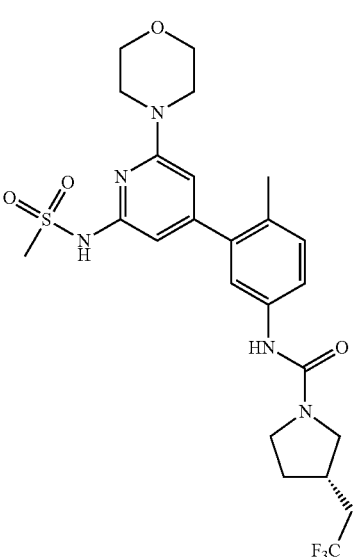 [SMILES: Cc1ccc(NC(=O)N2CC[C@@H](CC(F)(F)F)C2)cc1-c1cc(NS(C)(=O)=O)nc(N2CCOCC2)c1] | (3S)-N-[3-[2-methanesulfonamido-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 114 | 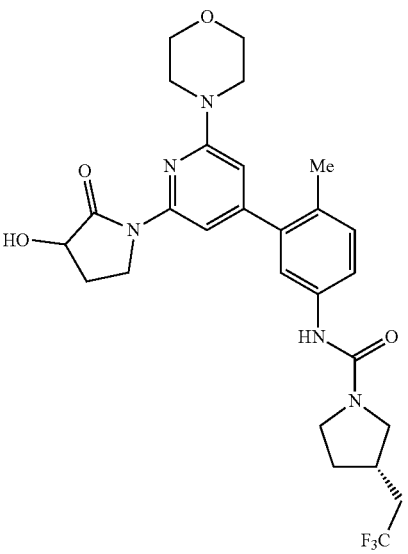 [SMILES: Cc1ccc(NC(=O)N2CC[C@@H](CC(F)(F)F)C2)cc1-c1cc(N2CCOCC2)nc(N2CCC(O)C2=O)c1] | (3S)-N-[3-[2-(3-hydroxy-2-oxopyrrolidin-1-yl)-6-(morpholin-4-yl)pyridin-4-yl]-4-methylphenyl]-3-(2,2,2-trifluoroethyl)pyrrolidine-1-carboxamide |
| 115 | 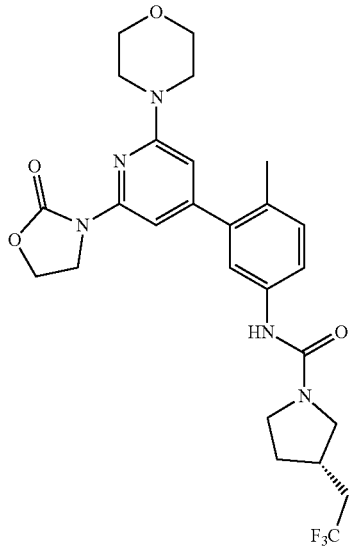 [SMILES: Cc1ccc(NC(=O)N2CC[C@@H](CC(F)(F)F)C2)cc1-c1cc(N2CCOCC2)nc(N2CCOC2=O)c1] | (3S)-N-[4-methyl-3-[2-(morpholin-4-yl)-6-(2-oxo-1,3-oxazolidin-3-yl)pyridin-4-yl]phenyl]-3-(2,2,2-trifluoroethyl)pyrrolidine-1-carboxamide |

TABLE 1-continued
| Synthetic Chemistry Example | Compound Structure | Compound Name |
|---|---|---|
| 116 | 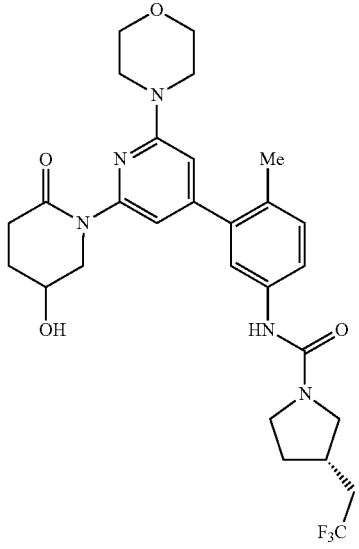 [SMILES: Cc1ccc(NC(=O)N2CC[C@@H](CC(F)(F)F)C2)cc1-c1cc(N2CCOCC2)nc(N2CC(O)CCC2=O)c1] | (3S)-N-(3-[2-[(5R)-5-hydroxy-2-oxopiperidin-1-yl]-6-(morpholin-4-yl)pyridin-4-yl]-4-methylphenyl)-3-(2,2,2-trifluoroethyl)pyrrolidine-1-carboxamide |
| 117 | 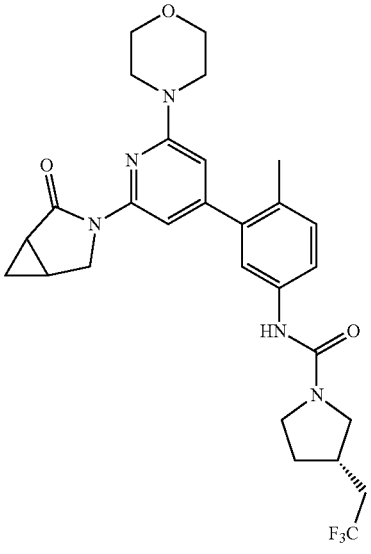 [SMILES: Cc1ccc(NC(=O)N2CC[C@@H](CC(F)(F)F)C2)cc1-c1cc(N2CCOCC2)nc(N2CC3CC3C2=O)c1] | (3S)-N-(4-methyl-3-(2-morpholino-6-(2-oxo-3-azabicyclo[3.1.0]hexan-3-yl)pyridin-4-yl)phenyl)-3-(2,2,2-trifluoroethyl)pyrrolidine-1-carboxamide |

TABLE 1-continued

| Synthetic Chemistry Example | Compound Structure | Compound Name |
|---|---|---|
| 118 | 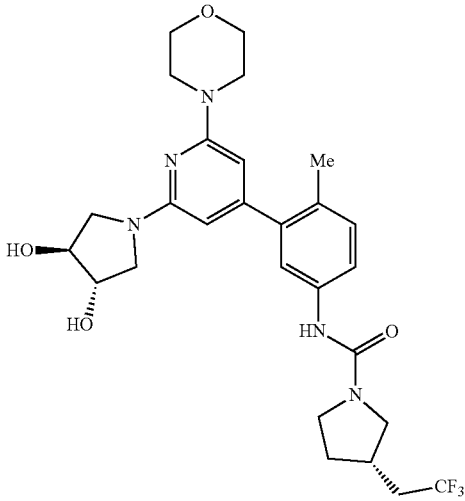 [SMILES: Cc1ccc(NC(=O)N2CC[C@@H](CC(F)(F)F)C2)cc1-c1cc(N2CCOCC2)nc(N2C[C@H](O)[C@@H](O)C2)c1] | (S)-N-(3-(2-((3S,4S)-3,4-dihydroxypyrrolidin-1-yl)-6-morpholinopyridin-4-yl)-4-methylphenyl)-3-(2,2,2-trifluoroethyl)pyrrolidine-1-carboxamide |
| 119 | 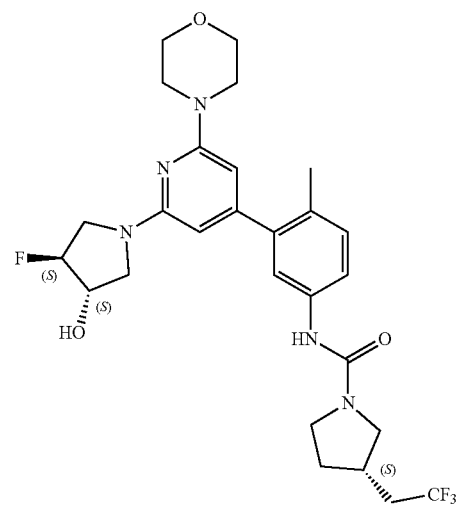 | (S)-N-(3-(2-((3S,4S)-3-fluoro-4-hydroxypyrrolidin-1-yl)-6-morpholinopyridin-4-yl)-4-methylphenyl)-3-(2,2,2-trifluoroethyl)pyrrolidine-1-carboxamide |
| 120 | 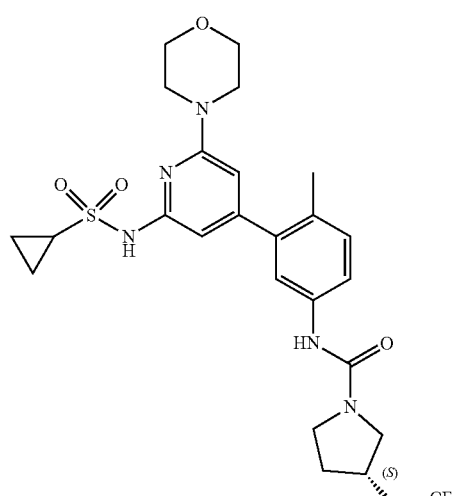 | (3S)-N-[3-[2-cyclopropanesulfonamido-6-(morpholin-4-yl)pyridin-4-yl]-4-methylphenyl]-3-(2,2,2 trifluoroethyl)pyrrolidine-1-carboxamide |

TABLE 1-continued

| Synthetic Chemistry Example | Compound Structure | Compound Name |
|---|---|---|
| 121 | 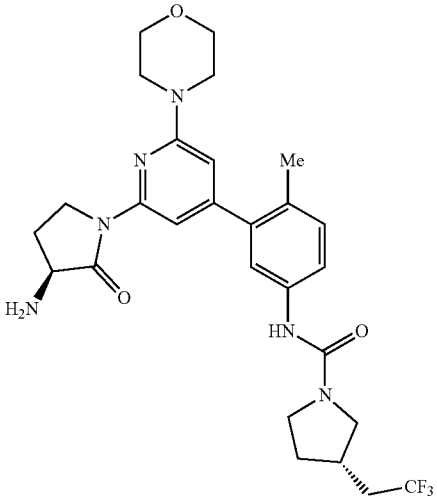 [SMILES: Cc1ccc(NC(=O)N2CC[C@@H](CC(F)(F)F)C2)cc1-c1cc(N2CCOCC2)nc(N2CC[C@H](N)C2=O)c1] | (S)-N-(3-(2-((S)-3-amino-2-oxopyrrolidin-1-yl)-6-morpholinopyridin-4-yl)-4-methylphenyl)-3-(2,2,2-trifluoroethyl)pyrrolidine-1-carboxamide |
| 122 | 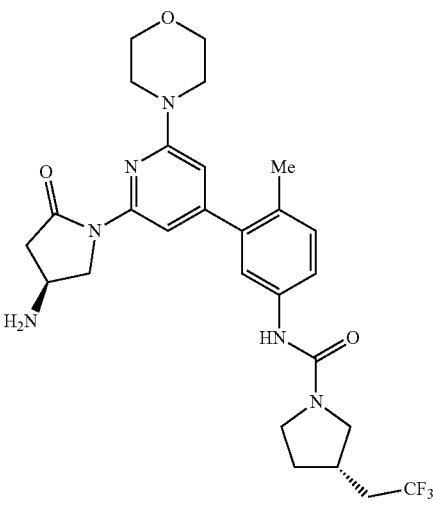 [SMILES: Cc1ccc(NC(=O)N2CC[C@@H](CC(F)(F)F)C2)cc1-c1cc(N2CCOCC2)nc(N2C[C@@H](N)CC2=O)c1] | (S)-N-(3-(2-((S)-4-amino-2-oxopyrrolidin-1-yl)-6-morpholinopyridin-4-yl)-4-methylphenyl)-3-(2,2,2-trifluoroethyl)pyrrolidine-1-carboxamide |
| 123 | 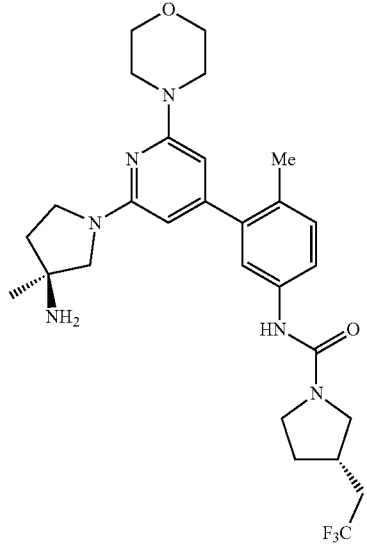 [SMILES: Cc1ccc(NC(=O)N2CC[C@@H](CC(F)(F)F)C2)cc1-c1cc(N2CCOCC2)nc(N2CC[C@](C)(N)C2)c1] | (S)-N-(3-(2-((S)-3-amino-3-methylpyrrolidin-1-yl)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 124 | 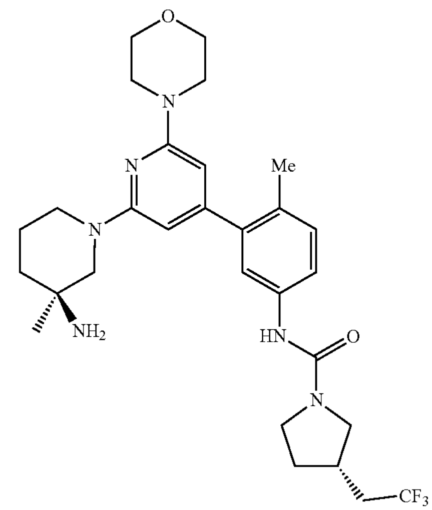 [SMILES: Cc1ccc(NC(=O)N2CC[C@@H](CC(F)(F)F)C2)cc1-c1cc(N2CCOCC2)nc(N2CCC[C@](C)(N)C2)c1] | (S)-N-(3-(2-((S)-3-amino-3-methylpiperidin-1-yl)-6-morpholinopyridin-4-yl)-4-methylphenyl)-3-(2,2,2-trifluoroethyl)pyrrolidine-1-carboxamide |
| 125 | 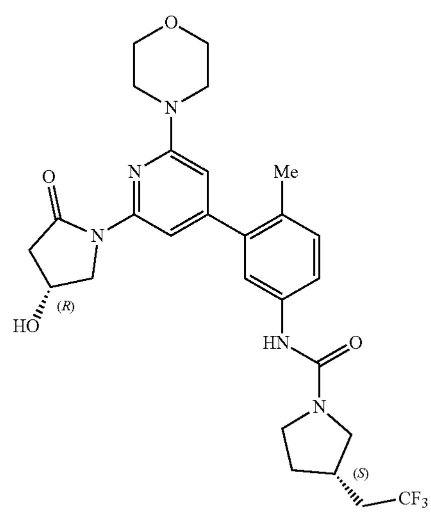 | (3S)-N-(3-[2-[(4R)-4-hydroxy-2-oxopyrrolidin-1-yl]-6-(morpholin-4-yl)pyridin-4-yl]-4-methylphenyl)-3-(2,2,2-trifluoroethyl)pyrrolidine-1-carboxamide |
| 126 | 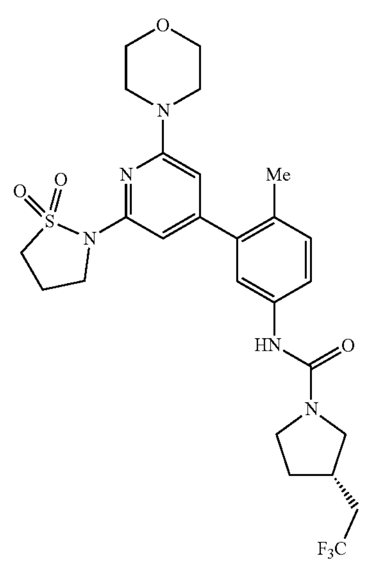 [SMILES: Cc1ccc(NC(=O)N2CC[C@@H](CC(F)(F)F)C2)cc1-c1cc(N2CCOCC2)nc(N2CCCS2(=O)=O)c1] | (3S)-N-[3-[2-(1,1-dioxo-1lambda6,2-thiazolidin-2-yl)-6-(morpholin-4-yl)pyridin-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 127 | 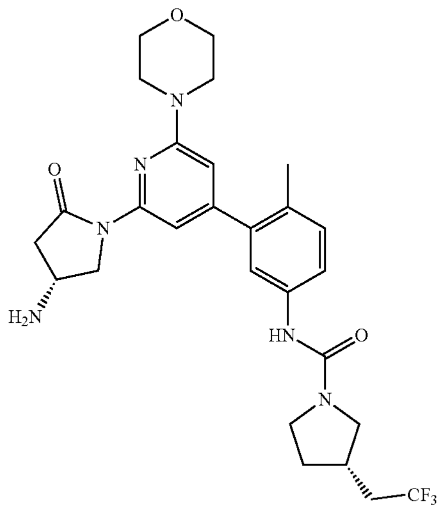 [SMILES: Cc1ccc(NC(=O)N2CC[C@@H](CC(F)(F)F)C2)cc1-c1cc(N2CCOCC2)nc(N2C[C@H](N)CC2=O)c1] | (S)-N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide |
| 128 and 129 | | (S)-N-(3-(2-((R)-3,3-difluoro-4-hydroxypyrrolidin-1-yl)-6-morpholinopyridin-4-yl)-4-methylphenyl)-3-(2,2,2-trifluoroethyl)pyrrolidine-1-carboxamide and (S)-N-(3-(2-((S)-3,3-difluoro-4-hydroxypyrrolidin-1-yl)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 130 and 131 | 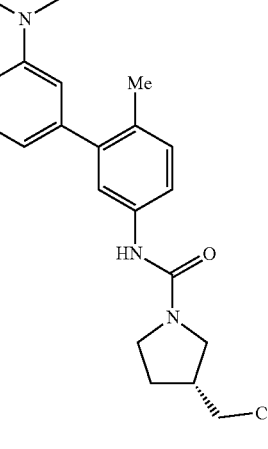 | (3S)-N-(3-(2-((1R)-1-amino-3-azabicyclo[3.1.0]hexan-3-yl)-6-morpholinopyridin-4-yl)-4-methylphenyl)-3-(2,2,2-trifluoroethyl)pyrrolidine-1-carboxamide and (3S)-N-(3-(2-((1S)-1-amino-3-azabicyclo[3.1.0]hexan-3-yl)-6-morpholinopyridin-4-yl)-4-methylphenyl)-3-(2,2,2-trifluoroethyl)pyrrolidine-1-carboxamide |
| 132 | 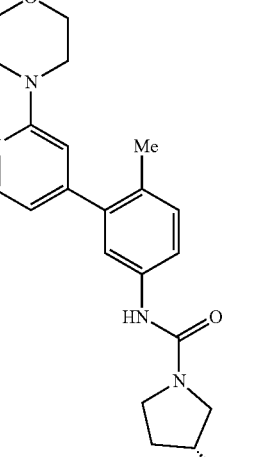 | (S)-N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide |
| 133 and 134 | 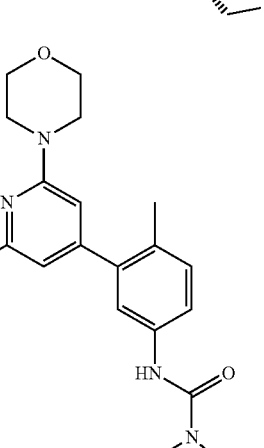 | (S)-N-(3-(2-((R)-4-amino-3,3-difluoropyrrolidin-1-yl)-6-morpholinopyridin-4-yl)-4-methylphenyl)-3-(2,2,2-trifluoroethyl)pyrrolidine-1-carboxamide and (S)-N-(3-(2-((S)-4-amino-3,3-difluoropyrrolidin-1-yl)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 135 and 136 | | (3S)-N-(3-{2-[(3R,4R)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide and (3S)-N-(3-{2-[(3S,4S)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 137 | 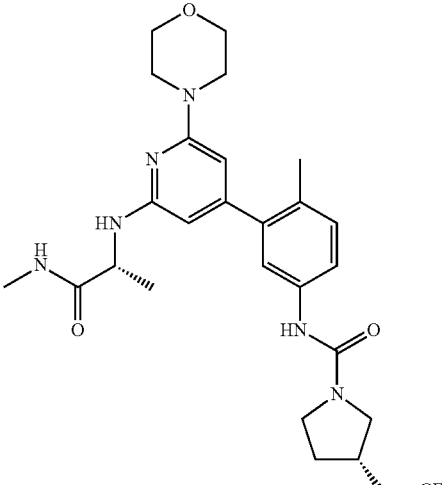 | (S)-N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide |
| 138 | 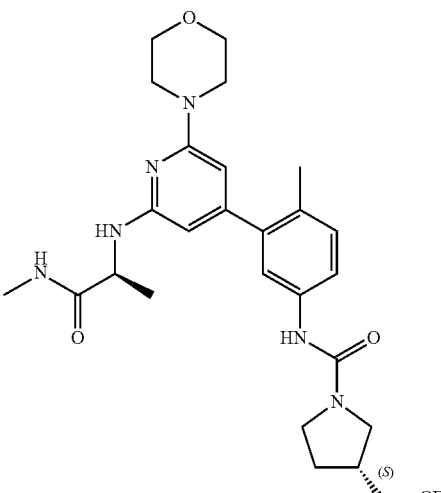 | (S)-N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide |
| 139 | 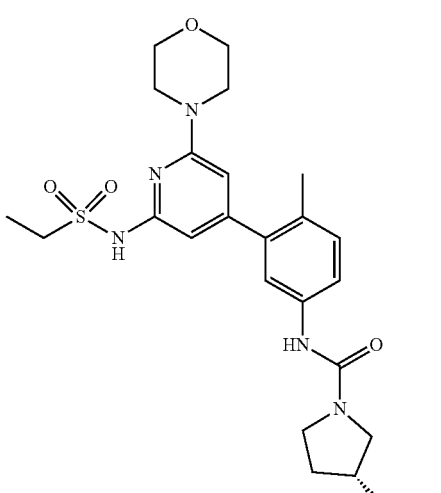 | (3S)-N-{3-[2-ethanesulfonamido-6-(morpholin-4-yl)pyridin-4-yl]-4-methylphenyl}-3-(2,2,2-trifluoroethyl)pyrrolidine-1-carboxamide |

TABLE 1-continued

| Synthetic Chemistry Example | Compound Structure | Compound Name |
|---|---|---|
| 140 | 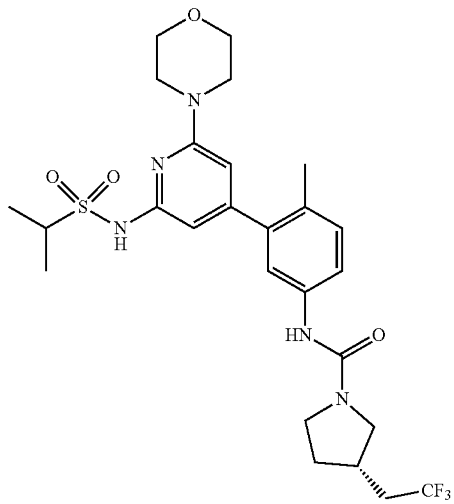 [SMILES: Cc1ccc(NC(=O)N2CC[C@@H](CC(F)(F)F)C2)cc1-c1cc(NS(=O)(=O)C(C)C)nc(N2CCOCC2)c1] | (3S)-N-{4-methyl-3-[2-(morpholin-4-yl)-6-(propane-2-sulfonamido)pyridin-4-yl]phenyl}-3-(2,2,2-trifluoroethyl)pyrrolidine-1-carboxamide |
| 141 | 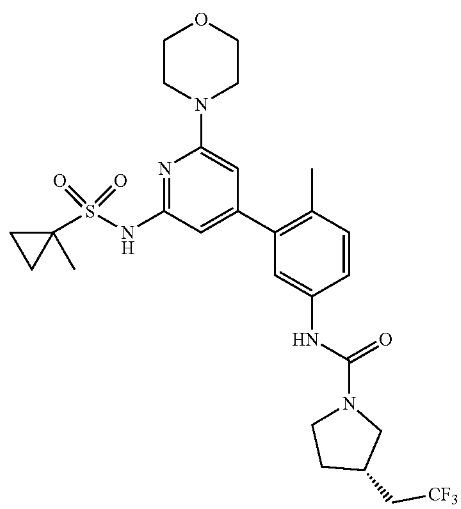 [SMILES: Cc1ccc(NC(=O)N2CC[C@@H](CC(F)(F)F)C2)cc1-c1cc(NS(=O)(=O)C2(C)CC2)nc(N2CCOCC2)c1] | (3S)-N-{4-methyl-3-[2-(1-methylcyclopropanesulfonamido)-6-(morpholin-4-yl)pyridin-4-yl]phenyl}-3-(2,2,2-trifluoroethyl)pyrrolidine-1-carboxamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis:

Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heteroaromatic RAF kinase inhibitory compound described herein is administered as a pure chemical. In other embodiments, the heteroaromatic RAF kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one heteroaromatic RAF kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I)—(IV), or a pharmaceutically acceptable salt or solvate thereof.

One embodiment provides a method of preparing a pharmaceutical composition comprising mixing a compound of Formula (I)—(IV), or a pharmaceutically acceptable salt or solvate thereof, and a pharmaceutically acceptable carrier.

In certain embodiments, the heteroaromatic RAF kinase inhibitory compound as described by Formula (I)—(IV), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the heteroaromatic RAF kinase inhibitory compound as described by Formula (I)—(IV), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic RAF kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I)—(IV), or a pharmaceutically acceptable salt or solvate thereof, for use in a method of treatment of the human or animal body.

One embodiment provides a compound of Formula (I)—(IV), or a pharmaceutically acceptable salt or solvate thereof, for use in a method of treatment of cancer or neoplastic disease.

One embodiment provides a use of a compound of Formula (I)—(IV), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I)—(IV), or a pharmaceutically acceptable salt or solvate thereof. In some embodiments, described herein is a method of treating cancer in a patient in need thereof comprising administering to the patient a pharmaceutical composition comprising a compound of Formula (I)—(IV), or a pharmaceutically acceptable salt or solvate thereof, and a pharmaceutically acceptable excipient.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic RAF kinase inhibitory compounds disclosed herein are synthesized according to the following examples. As used below, and throughout the description of the invention, the following abbreviations, unless otherwise indicated, shall be understood to have the following meanings:

° C. degrees Celsius
δH chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
S singlet (spectral)
t triplet (spectral)
T temperature
TFA trifluoroacetic acid
THF tetrahydrofuran Example 1: (3S)—N-(3-[6-[(3,3-difluorocyclopentyl)amino]-2-(morpholin-4-yl)pyrimidin-4-yl]-4-methylphenyl)-3-(2,2,2-trifluoroethyl)pyrrolidine-1-carboxamide

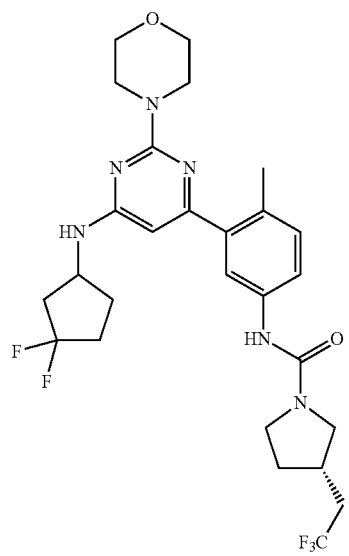 [SMILES: Cc1ccc(NC(=O)N2CC[C@@H](CC(F)(F)F)C2)cc1-c1cc(NC2CCC(F)(F)C2)nc(N2CCOCC2)n1]

Synthetic Scheme

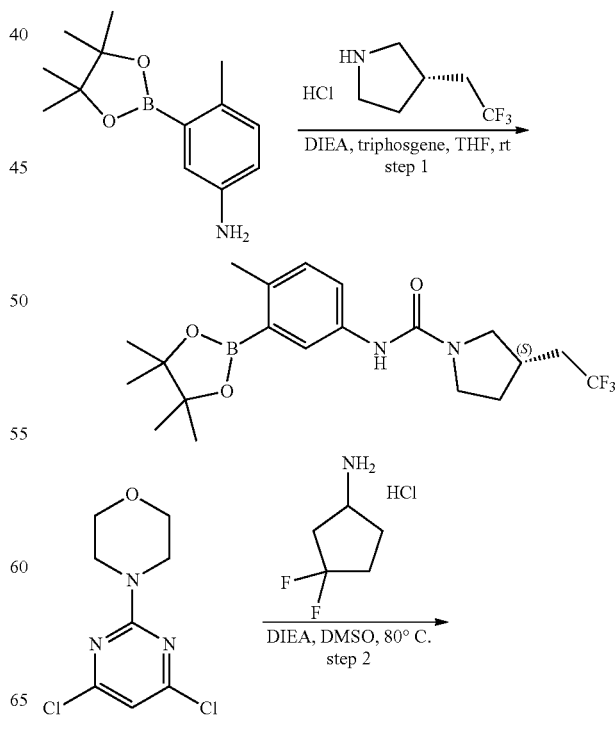

-continued

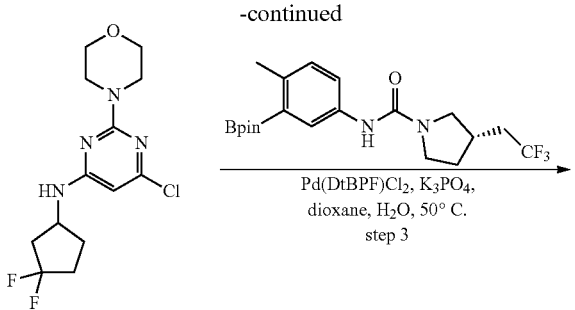

Pd(DtBPF)Cl₂, K₃PO₄,
dioxane, H₂O, 50° C.
step 3

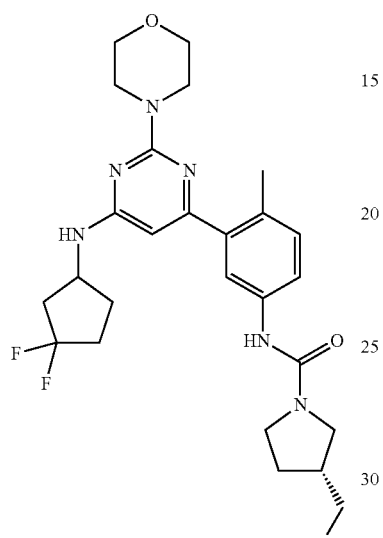

Preparation 1A: (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide

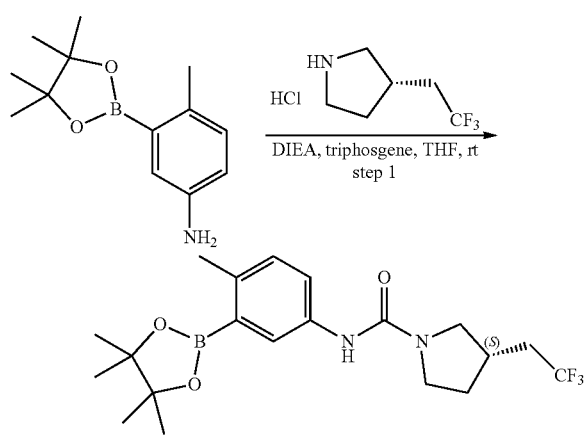

To a stirred solution of 4-methyl-3-(4,4,5,5-tetramethyl-1,3,2-dioxaborolan-2-yl)aniline (11.0 g, 47.186 mmol, 1.00 equiv) in THF (1000 mL) were added DIEA (30.5 g, 235.930 mmol, 5.00 equiv) and triphosgene (5.6 g, 18.874 mmol, 0.40 equiv) at ambient temperature under nitrogen atmosphere. The resulting mixture was stirred at ambient temperature for 30 min. To this was added a solution of (3S)-3-(2,2,2-trifluoroethyl)pyrrolidine hydrochloride (8.95 g, 47.186 mmol, 1.00 equiv) in THF (100 mL). The resulting mixture was stirred at ambient temperature for 3 h. The reaction mixture was concentrated under reduced pressure. The residue was purified by silica gel column chromatography, eluted with EtOAc in PE (5%-45%) to afford (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (16.3 g, 84%) as a white solid. MS ESI calculated for C₂₀H₂₈BF₃N₂O₃ [M+H]⁺, 413.21, found 413.25. ¹H NMR (300 MHz, chloroform-d) δ 7.75 (dd, J=8.4, 2.7 Hz, 1H), 7.44 (d, J=2.7 Hz, 1H), 7.14 (d, J=8.4 Hz, 1H), 6.14 (s, 1H), 3.86-3.74 (m, 1H), 3.69-3.56 (m, 1H), 3.43 (td, J=9.6, 6.6 Hz, 1H), 3.11 (t, J=9.6 Hz, 1H), 2.58 (dd, J=16.5, 8.4 Hz, 1H), 2.50 (s, 3H), 2.37-2.18 (m, 3H), 1.82-1.75 (m, 1H), 1.36 (s, 12H). ¹⁹F NMR (282 MHz, chloroform-d) δ-64.95.

Preparation 1B: N-(3,3-dimethylcyclopentyl)-6-methyl-2-(morpholin-4-yl)pyrimidin-4-amine

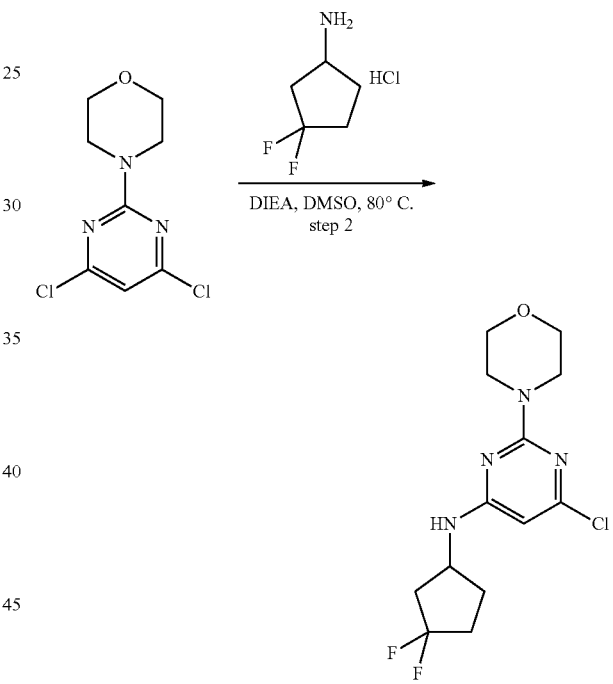

To a stirred solution of 4-(4,6-dichloropyrimidin-2-yl)morpholine (140 mg, 0.598 mmol) and 3,3-difluorocyclopentan-1-amine hydrochloride (104 mg, 0.658 mmol) in DMSO (1 mL) was added DIEA (386 mg, 2.990 mmol) dropwise at 0° C. under nitrogen atmosphere. The resulting mixture was stirred for 16 at room temperature under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na₂SO₄. After filtration, the filtrate was concentrated under reduced pressure. The residue was purified by silica gel column chromatography, eluted with PE/(EA/EtOH=3:1)(3:1) to afford N-(3,3-dimethylcyclopentyl)-6-methyl-2-(morpholin-4-yl)pyrimidin-4-amine (160 mg, 92%) as an off-white solid. MS ESI calculated for C₁₃H₁₇ClF₂N₄O [M+H]⁺, 319.11, found 319.15. ¹H NMR (400 MHz, DMSO-d₆) δ 7.55 (s, 1H), 5.81 (s, 1H), 4.36 (s, 1H), 3.61 (s, 8H), 3.42 (s, 2H), 2.62-2.55 (m, 1H), 2.28-1.92 (m, 2H), 1.73-1.63 (m, 1H). $^{19}$F NMR (376 MHz, DMSO-d$_6$) δ −87.90 (2F).

Example 1: (3S)—N-(3-[6-[(3,3-difluorocyclopentyl)amino]-2-(morpholin-4-yl)pyrimidin-4-yl]-4-methylphenyl)-3-(2,2,2-trifluoroethyl)pyrrolidine-1-carboxamide

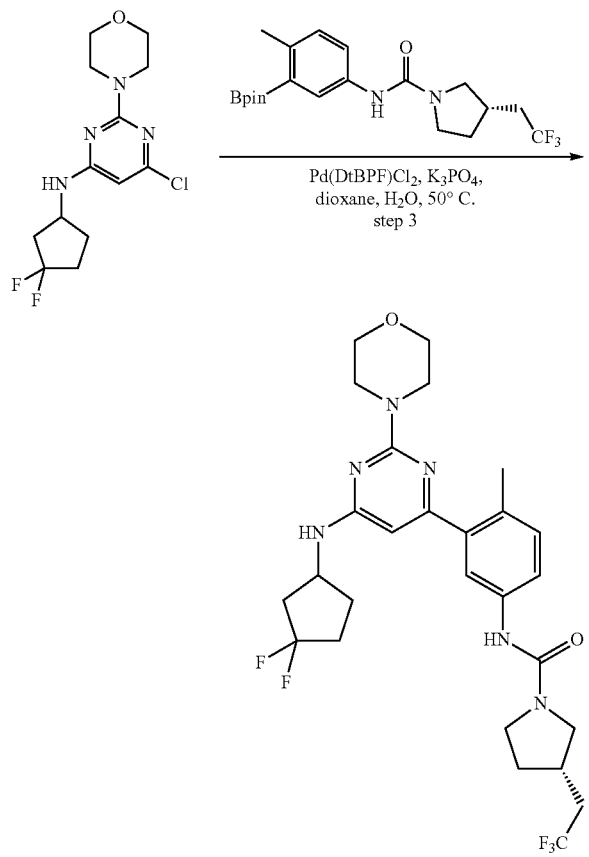

To a stirred solution of 6-chloro-N-(3,3-difluorocyclopentyl)-2-(morpholin-4-yl)pyrimidin-4-amine (140 mg, 0.439 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (181 mg, 0.439 mmol) and K$_3$PO$_4$ (186 mg, 0.878 mmol,) in dioxane:H$_2$O=2:1 (2 mL) was added Pd(DtBPF)Cl$_2$ (29 mg, 0.044 mmol) at room temperature under nitrogen atmosphere. The resulting mixture was stirred for 16 h at 60° C. under nitrogen atmosphere. The reaction was monitored by LCMS. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/(EA/EtOH=3:1) (2:1) to afford 150 mg crude product. The residue was purified by reverse flash chromatography with the following conditions: Column: XBridge C18 OBD Prep Column, 100 Å, 10 μm, 19 mm×250 mm; Mobile Phase A: Water (10 MMOL/L NH$_4$HCO$_3$), Mobile Phase B: CH$_3$CN; Flow rate: 20 mL/min; Gradient:40% B to 80% B in 5.8 min; 210/254 nm to afford (3S)—N-(3-[6-[(3,3-difluorocyclopentyl)amino]-2-(morpholin-4-yl)pyrimidin-4-yl]-4-methylphenyl)-3-(2,2,2-trifluoroethyl)pyrrolidine-1-carboxamide (130 mg, 52%) as an off-white solid. MS ESI calculated for C$_{27}$H$_{33}$F$_5$N$_6$O$_2$ [M+H]$^+$, 569.26, found 569.25. $^1$H NMR (400 MHz, DMSO-d$_6$) δ 8.13 (s, 1H), 7.52 (m, 1H), 7.42-7.41 (m, 1H), 7.30-7.28 (m, 1H), 7.09-7.06 (m, 1H), 5.86 (s, 1H), 4.40 (s, 1H), 3.69-3.64 (m, 9H), 3.55-3.50 (m, 1H), 3.31-3.28 (m, 1H), 3.05-3.00 (m, 1H), 2.59-2.51 (m, 1H), 2.49-2.40 (m, 3H), 2.26-2.13 (m, 5H), 2.13-2.03 (m, 3H), 1.75-1.66 (m, 2H). $^{19}$F NMR (376 MHz, DMSO-d$_6$) δ −63.36 (3F), −87.70-87.80 (2F).

Examples 2 and 3: (3S)—N-[3-(6-[[(1R)-3,3-difluorocyclopentyl]amino]-2-(morpholin-4-yl)pyrimidin-4-yl)-4-methylphenyl]-3-(2,2,2-trifluoroethyl)pyrrolidine-1-carboxamide, (3S)—N-[3-(6-[[(1S)-3,3-difluorocyclopentyl]amino]-2-(morpholin-4-yl)pyrimidin-4-yl)-4-methylphenyl]-3-(2,2,2-trifluoroethyl)pyrrolidine-1-carboxamide

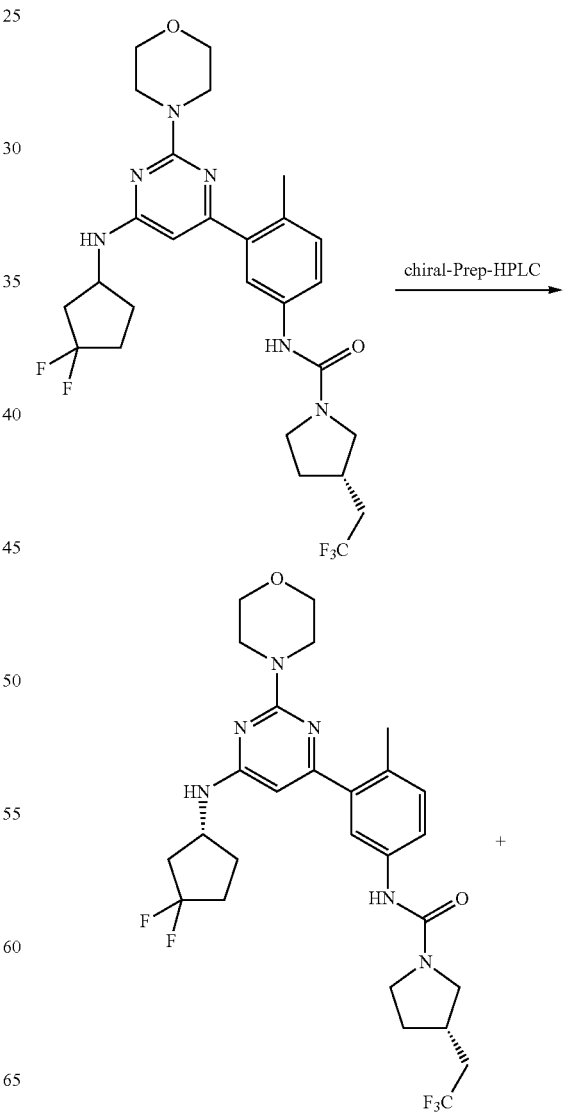

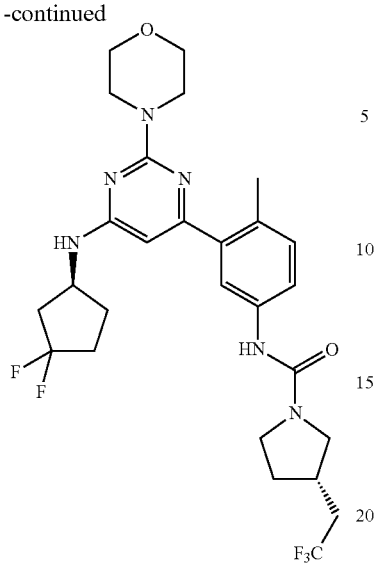

(3S)—N-(3-[6-[(3,3-difluorocyclopentyl)amino]-2-(morpholin-4-yl)pyrimidin-4-yl]-4-methylphenyl)-3-(2,2,2-trifluoroethyl)pyrrolidine-1-carboxamide (130 mg) was purified by Chiral-Prep-HPLC with the following conditions (Column: CHIRALPAK AD-H, 2.0 cm*25 cm; Mobile Phase A: Hex (8 mmol/L NH$_3$·MeOH), Mobile Phase B: EtOH; Flow rate: 20 mL/min; Gradient:20 B to 20 B in 18 min; 220/254 nm) to afford (3S)—N-[3-(6-[[(1R)-3,3-difluorocyclopentyl]amino]-2-(morpholin-4-yl)pyrimidin-4-yl]-4-methylphenyl]-3-(2,2,2-trifluoroethyl)pyrrolidine-1-carboxamide (41 mg, 32%) as an off-white solid, MS ESI calculated for C$_{27}$H$_{33}$F$_5$N$_6$O$_2$ [M+H]$^+$, 569.26, found 569.25. $^1$H NMR (400 MHz, DMSO-d$_6$) δ 8.14 (s, 1H), 7.52 (m, 1H), 7.43-7.41 (m, 1H), 7.30 (s, 1H), 7.09-7.07 (m, 1H), 5.86 (s, 1H), 4.40 (s, 1H), 3.69-3.64 (m, 9H), 3.55-3.50 (m, 1H), 3.31-3.28 (m, 1H), 3.05-3.00 (m, 1H), 2.61-2.55 (m, 1H), 2.46-2.38 (m, 3H), 2.26-2.13 (m, 5H), 2.13-1.91 (m, 3H), 1.78-1.61 (m, 2H). $^{19}$F NMR (376 MHz, DMSO-d$_6$) δ −63.33 (3F), −87.67 (2F).

Also afforded (3S)—N-[3-(6-[[(1S)-3,3-difluorocyclopentyl]amino]-2-(morpholin-4-yl)pyrimidin-4-yl]-4-methylphenyl]-3-(2,2,2-trifluoroethyl)pyrrolidine-1-carboxamide (44 mg, 34%) as an off-white solid. MS ESI calculated for C$_{27}$H$_{33}$F$_5$N$_6$O$_2$ [M+H]$^+$, 569.26, found 569.25. $^1$H NMR (400 MHz, DMSO-d$_6$) δ 8.14 (s, 1H), 7.52 (m, 1H), 7.43-7.40 (m, 1H), 7.30 (s, 1H), 7.09-7.06 (m, 1H), 5.86 (s, 1H), 4.40 (s, 1H), 3.69-3.64 (m, 9H), 3.55-3.50 (m, 1H), 3.31-3.28 (m, 1H), 3.05-3.00 (m, 1H), 2.61-2.55 (m, 1H), 2.46-2.38 (m, 3H), 2.26-2.13 (m, 5H), 2.13-1.91 (m, 3H), 1.78-1.61 (m, 2H). $^{19}$F NMR (376 MHz, DMSO-d$_6$) δ −63.36 (3F), −87.68 (2F).

Examples 4 and 5: (3S)—N-[3-(2-[[(1S,3S)-3-hydroxycyclopentyl]amino]-6-(morpholin-4-yl)pyrimidin-4-yl)-4-methylphenyl]-3-(2,2,2-trifluoroethyl)pyrrolidine-1-carboxamide, (3S)—N-[3-(2-[[(1R,3R)-3-hydroxycyclopentyl]amino]-6-(morpholin-4-yl)pyrimidin-4-yl]-4-methylphenyl]-3-(2,2,2-trifluoroethyl)pyrrolidine-1-carboxamide

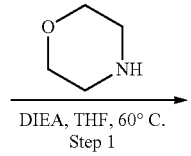
DIEA, THF, 60° C.
Step 1

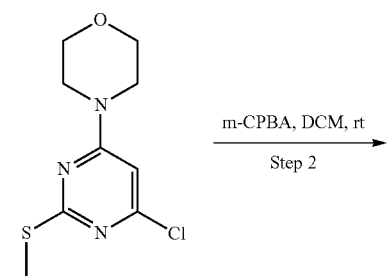
m-CPBA, DCM, rt
Step 2

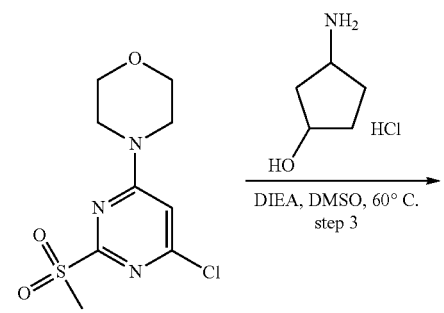
DIEA, DMSO, 60° C.
step 3

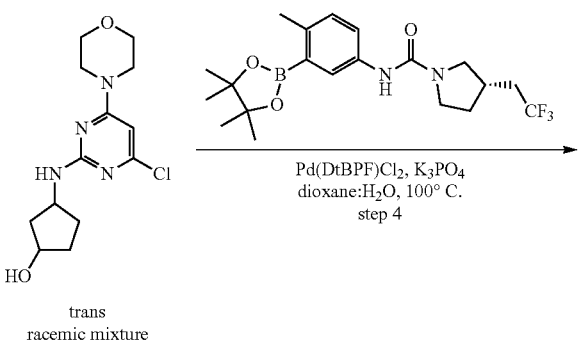
trans racemic mixture
Pd(DtBPF)Cl$_2$, K$_3$PO$_4$
dioxane:H$_2$O, 100° C.
step 4

-continued

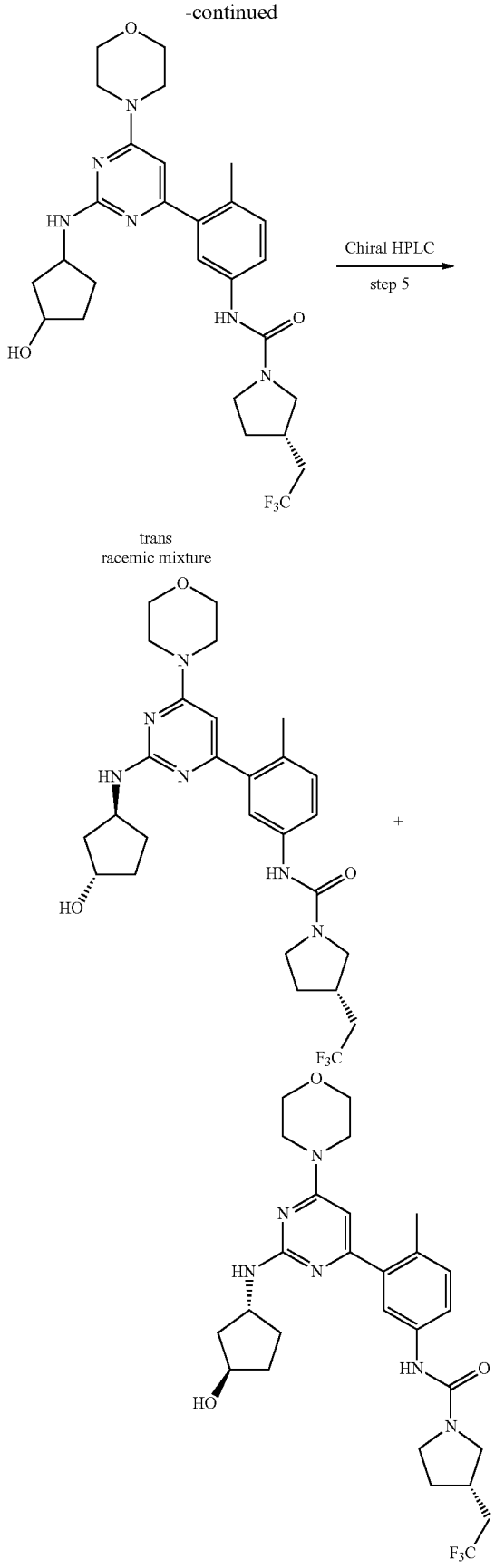

trans
racemic mixture

→ Chiral HPLC
step 5

Preparation 4A: 4-[6-chloro-2-(methylsulfanyl)pyrimidin-4-yl]morpholine

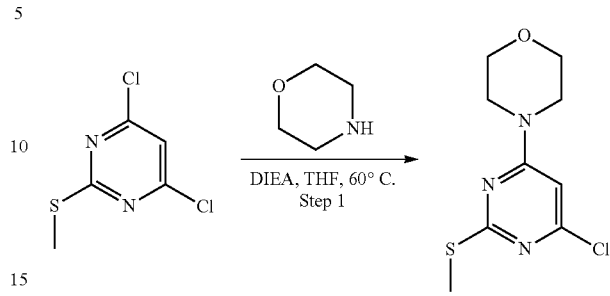

DIEA, THF, 60° C.
Step 1

To a stirred solution of 4,6-dichloro-2-(methylsulfanyl) pyrimidine (2.20 g, 11.28 mmol) in THF (29 mL) was added DIPEA (1.60 g, 12.41 mmol), morpholine (1.08 g, 12.40 mmol) dropwise at room temperature under nitrogen atmosphere. The resulting mixture was stirred for overnight at 60° C. under nitrogen atmosphere. The mixture was allowed to cool down to room temperature. The resulting mixture was diluted with water (50 mL). The precipitated solids were collected by filtration to afford 4-[6-chloro-2-(methylsulfanyl)pyrimidin-4-yl]morpholine (2.7 g, 97%) as a light yellow solid. MS ESI calculated for $C_9H_{12}ClN_3OS$ $[M+H]^+$, 246.04; found 245.95. $^1H$ NMR (400 MHz, DMSO-$d_6$) δ 6.68 (s, 1H), 3.68-3.64 (m, 8H), 2.45 (s, 3H).

Preparation 4B: 4-(6-chloro-2-methanesulfonylpyrimidin-4-yl)morpholine

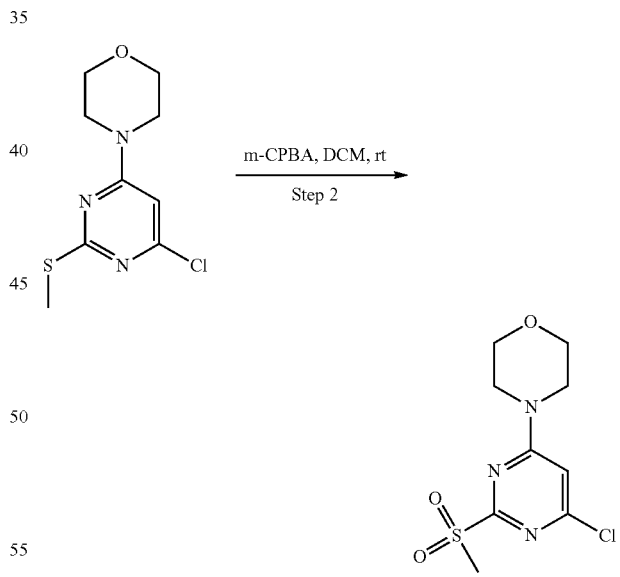

m-CPBA, DCM, rt
Step 2

To a stirred solution of 4-[6-chloro-2-(methylsulfanyl) pyrimidin-4-yl]morpholine (12.33 g, 50.18 mmol) and m-CPBA (23.43 g, 115.41 mmol, 85%) in DCM (172.6 mL) at room temperature under nitrogen atmosphere. The resulting mixture was stirred for 2 h at room temperature under nitrogen atmosphere. The resulting mixture was concentrated under reduced pressure. The reaction was quenched by the addition of $NaHCO_3$ aq. (200 mL) at 0° C. The resulting mixture was extracted with EtOAc (3×150 mL). The combined organic layers were washed with $NaHCO_3$ aq.

(200 mL), dried over anhydrous Na$_2$SO$_4$. After filtration, the filtrate was concentrated under reduced pressure. The residue was purified by silica gel column chromatography, eluted with hexane/EtOAc (1:1) to afford 4-(6-chloro-2-methanesulfonylpyrimidin-4-yl)morpholine (13.3 g, 95%) as a white solid. MS ESI calculated for C$_9$H$_{12}$ClN$_3$O$_3$S [M+H]$^+$, 278.03; found 277.95. $^1$H NMR (300 MHz, chloroform-d) δ 6.62 (s, 1H), 3.82-3.75 (m, 8H), 3.36-3.31 (m, 3H).

Preparation 4C: trans-3-[[4-chloro-6-(morpholin-4-yl)pyrimidin-2-yl]amino]cyclopentan-1-ol

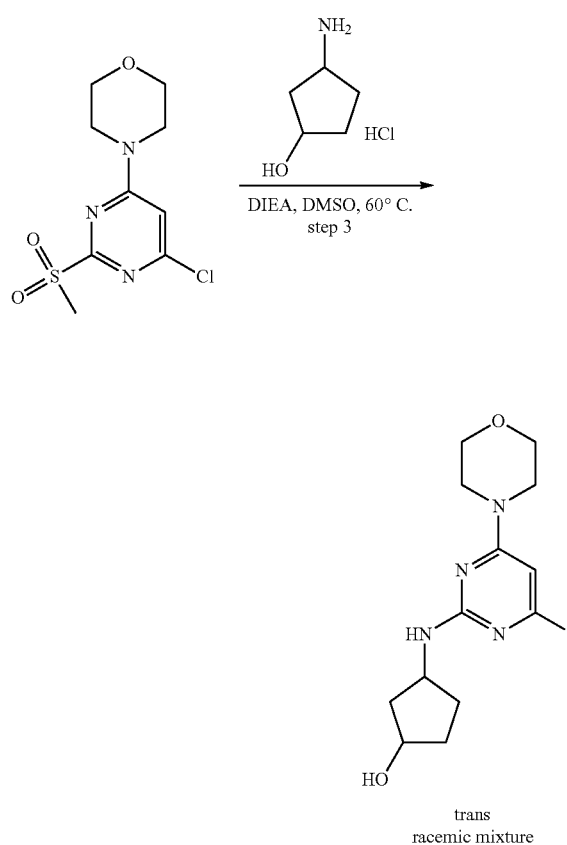

A mixture of 4-(6-chloro-2-methanesulfonylpyrimidin-4-yl)morpholine (1.00 g, 3.60 mmol), (trans)-3-aminocyclopentan-1-ol hydrochloride (0.55 g, 4.00 mmol) and DIEA (1.40 g, 10.80 mmol) in DMSO (10 mL) was stirred for overnight at 60° C. under nitrogen atmosphere. The resulting mixture was diluted with water (10 mL). The resulting mixture was extracted with EtOAc (3×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/(EtOAc:EtOH=3:1) (1:1) to afford trans-3-[[4-chloro-6-(morpholin-4-yl)pyrimidin-2-yl]amino]cyclopentan-1-ol (0.38 g, 33%) as an off-white solid. MS ESI calculated for C$_{13}$H$_{19}$ClN$_4$O$_2$ [M+H]$^+$, 299.77, found 299.10. $^1$H NMR (300 MHz, DMSO-d$_6$) δ 6.07 (s, 1H), 4.29 (m, 1H), 4.18 (m, 1H), 3.64 (m, 4H), 3.54 (m, 4H), 3.40 (m, 2H), 2.05 (m, 1H), 1.86 (m, 2H), 1.64-1.58 (m, 1H), 1.41 (m, 2H).

Preparation 4D: (3S)—N-[3-(2-[[trans-3-hydroxycyclopentyl]amino]-6-(morpholin-4-yl)pyrimidin-4-yl]-4-methylphenyl]-3-(2,2,2-trifluoroethyl)pyrrolidine-1-carboxamide

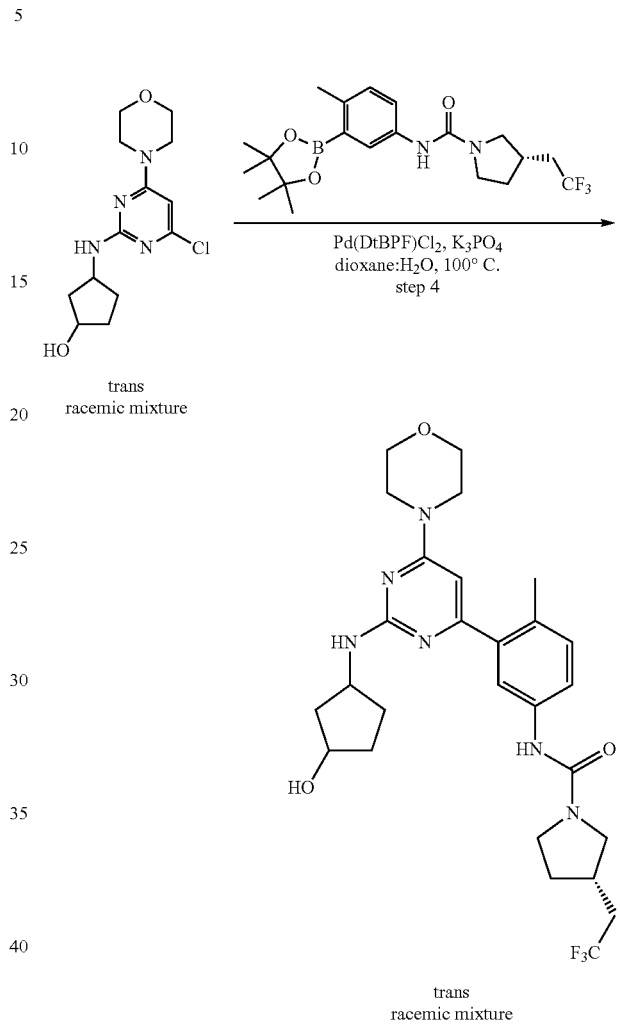

A mixture of trans-3-[[4-chloro-6-(morpholin-4-yl)pyrimidin-2-yl]amino]cyclopentan-1-ol (200 mg, 0.669 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (276 mg, 0.669 mmol), Pd(DtBPF)Cl$_2$ (44 mg, 0.067 mmol) and K$_3$PO$_4$ (284 mg, 1.339 mmol) in 1,4-dioxane (3.6 mL) and H$_2$O (0.9 mL) was stirred for overnight at 80° C. under nitrogen atmosphere. The resulting mixture was concentrated under vacuum. The residue was purified by silica gel column chromatography, eluted with PE/((EtOAc:EtOH=3:1):NH$_4$OH=20:1)(1:1). The crude product was purified by reverse flash chromatography with the following conditions: Column: XBridge C$^{18}$ OBD Prep Column, 100 Å, 10 μm, 19 mm×250 mm; Mobile Phase A: water (10 mmol/L NH$_4$HCO$_3$), Mobile Phase B: CH$_3$CN; Flow rate:20 mL/min; Gradient:35 B to 70 B in 5.8 min; 210/254 nm to afford (3S)—N-[3-(2-[[(trans)-3-hydroxycyclopentyl]amino]-6-(morpholin-4-yl)pyrimidin-4-yl)-4-methylphenyl]-3-(2,2,2-trifluoroethyl)pyrrolidine-1-carboxamide (180 mg, 29%) as an off-white solid. MS ESI calculated for C$_{27}$H$_{35}$F$_3$N$_6$O$_3$ [M+H]$^+$, 549.27; found 549.30.

Example 4: (3S)—N-[3-(2-[[(1S,3S)-3-hydroxycyclopentyl]amino]-6-(morpholin-4-yl)pyrimidin-4-yl)-4-methylphenyl]-3-(2,2,2-trifluoroethyl)pyrrolidine-1-carboxamide Examples 4 and 5: (3S)—N-[3-(2-[[(1R,3R)-3-hydroxycyclopentyl]amino]-6-(morpholin-4-yl)pyrimidin-4-yl)-4-methylphenyl]-3-(2,2,2-trifluoroethyl)pyrrolidine-1-carboxamide

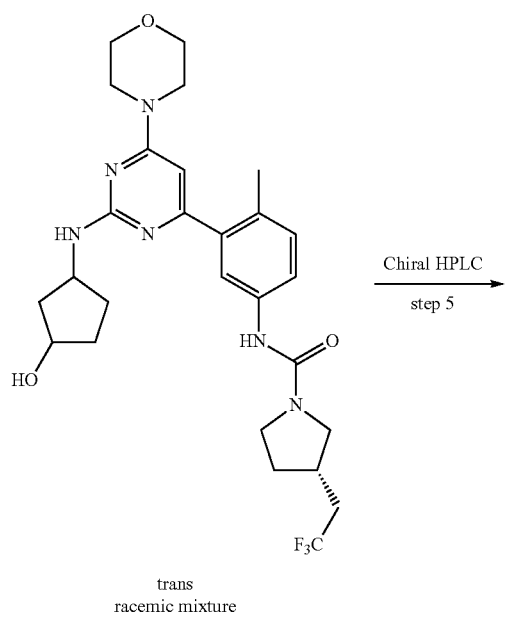

trans
racemic mixture

Chiral HPLC
step 5

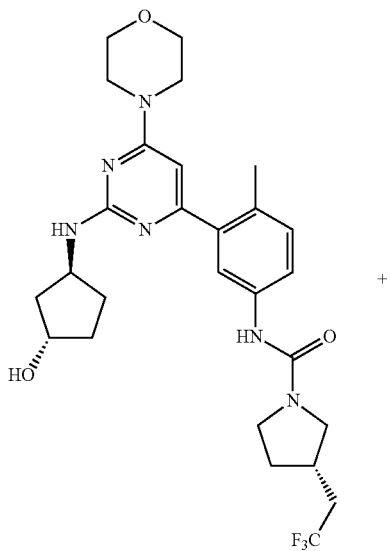

+

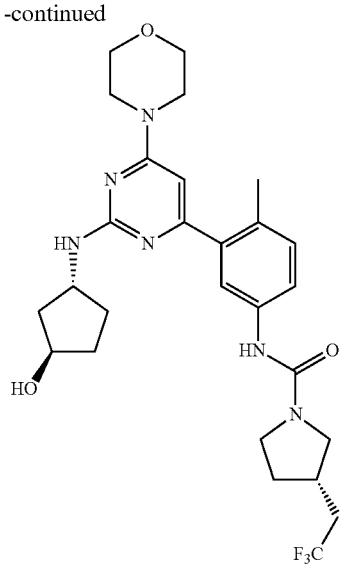

(3S)—N-[3-(2-[[(trans)-3-hydroxycyclopentyl]amino]-6-(morpholin-4-yl)pyrimidin-4-yl)-4-methylphenyl]-3-(2,2,2-trifluoroethyl)pyrrolidine-1-carboxamide (180 mg) was resolved by Chiral-HPLC with the following conditions (Column: Reg-AD, 30×250 mm, 5 um; Mobile Phase A: Hex (8 mmol/L NH$_3$·MeOH), Mobile Phase B: IPA; Flow rate: 45 mL/min; Gradient: 20 B to 20 B in 25 min; 220/254 nm) to afford 75 mg (44%) as an off-white solid. MS ESI calculated for $C_{27}H_{35}F_3N_6O_3$ [M+H]$^+$, 549.61; found 549.30. $^1$H NMR (300 MHz, DMSO-d$_6$) δ 8.11 (s, 1H), 7.46-7.43 (m, 2H), 7.09-7.06 (m, 1H), 6.52-6.50 (m, 1H), 5.99 (s, 1H), 4.41-4.36 (m, 2H), 4.18-4.17 (m, 1H), 3.70-3.43 (m, 10H), 3.35-3.28 (m, 1H), 3.05-2.99 (m, 1H), 2.50-2.32 (m, 3H), 2.25-2.16 (m, 3H), 2.08-1.91 (m, 2H), 1.90-1.75 (m, 2H), 1.74-1.65 (m, 2H), 1.64-1.30 (m, 2H). $^{19}$F NMR (282 MHz, DMSO-d$_6$) δ −63.39-63.45 (3F), and (3S)—N-[3-(2-[[(1R,3R)-3-hydroxycyclopentyl]amino]-6-(morpholin-4-yl)pyrimidin-4-yl)-4-methylphenyl]-3-(2,2,2-trifluoroethyl)pyrrolidine-1-carboxamide (77 mg, 45%) as an off-white solid. MS ESI calculated for $C_{27}H_{35}F_3N_6O_3$ [M+H]$^+$, 549.61; found 549.30. $^1$H NMR (300 MHz, DMSO-d$_6$) δ 8.11 (s, 1H), 7.46-7.43 (m, 2H), 7.09-7.06 (m, 1H), 6.52 (m, 1H), 5.99 (s, 1H), 4.41-4.32 (m, 2H), 4.17 (m, 1H), 3.69-3.64 (m, 5H), 3.55-3.50 (m, 5H), 3.35-3.26 (m, 1H), 3.05-2.99 (m, 1H), 2.51-2.40 (m, 3H), 2.25 (s, 3H), 2.07-1.99 (m, 2H), 1.93-1.85 (m, 2H), 1.70-1.55 (m, 2H), 1.54-1.25 (m, 2H). $^{19}$F NMR (376 MHz, DMSO-d$_6$) δ −63.35 (3F).

Example 6: (3S)—N-[3-(2-[[(3-hydroxyoxetan-3-yl)methyl]amino]-6-(morpholin-4-yl)pyridin-4-yl)-4-methylphenyl]-3-(2,2,2-trifluoroethyl)pyrrolidine-1-carboxamide
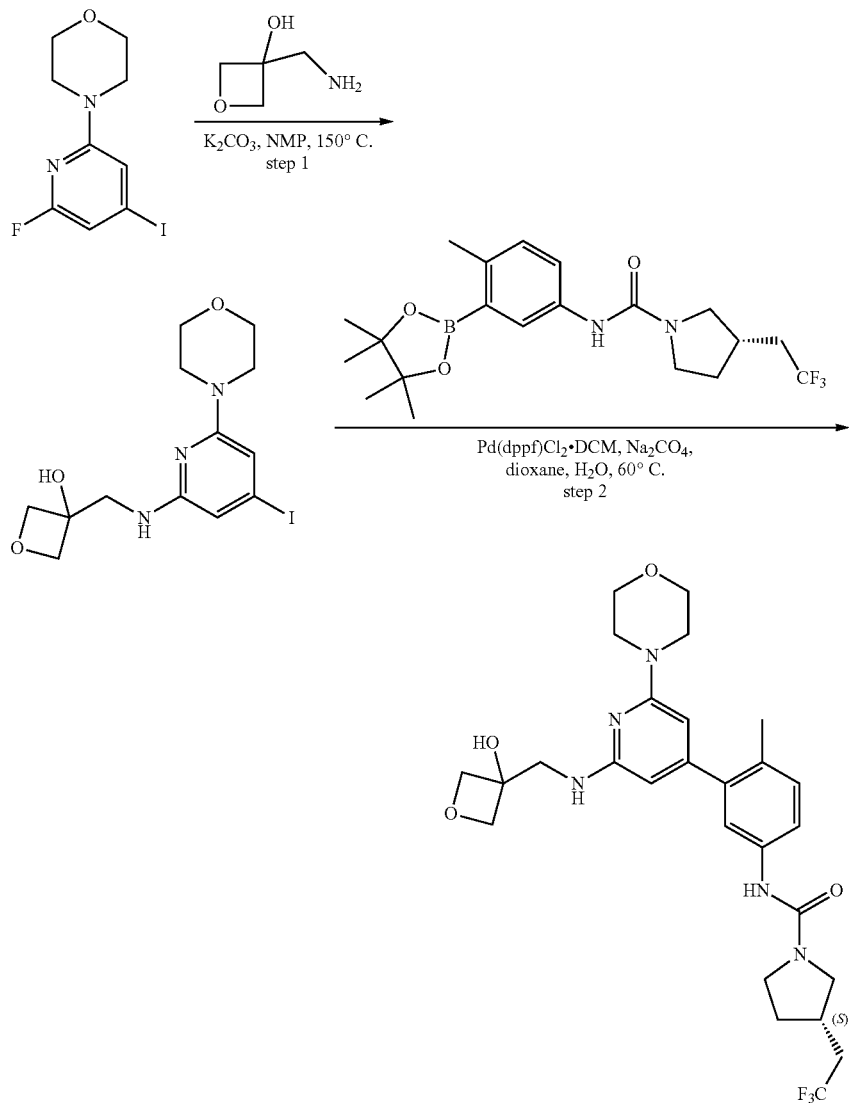
Preparation 6A: 3-([[4-iodo-6-(morpholin-4-yl)pyridin-2-yl]amino]methyl)oxetan-3-ol
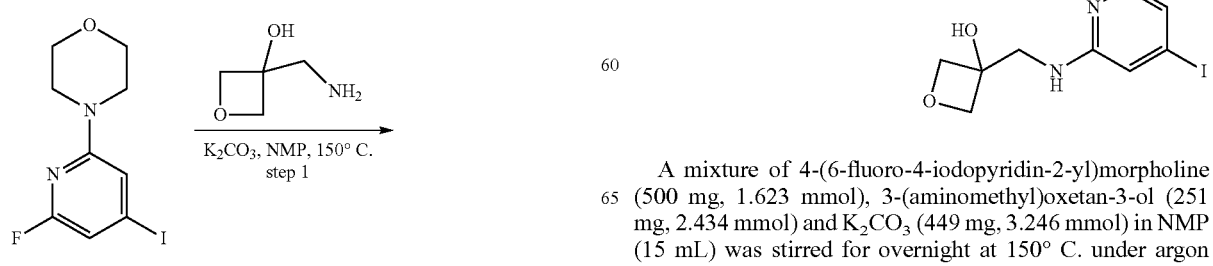
A mixture of 4-(6-fluoro-4-iodopyridin-2-yl)morpholine (500 mg, 1.623 mmol), 3-(aminomethyl)oxetan-3-ol (251 mg, 2.434 mmol) and K$_2$CO$_3$ (449 mg, 3.246 mmol) in NMP (15 mL) was stirred for overnight at 150° C. under argon atmosphere. The resulting mixture was concentrated under reduced pressure. The residue was purified by silica gel column chromatography, eluted with DCM/MeOH (20/1) to afford crude product. The residue was purified by reverse flash chromatography with the following conditions: column, C18 silica gel; mobile phase, MeCN in water, 20% to 50% gradient in 30 min; detector, UV 254 nm. to afford 3-([[4-iodo-6-(morpholin-4-yl)pyridin-2-yl]amino]methyl) oxetan-3-ol (148 mg, 23%) as a light brown solid. MS ESI calculated for $C_{13}H_{18}IN_3O_3$ [M+H]$^+$, 392.04, found 392.00. $^1$H NMR (400 MHz, DMSO-d$_6$) δ 6.56-6.53 (m, 1H), 6.33 (m, 1H), 6.23 (m, 1H), 5.90 (s, 1H), 4.41-4.36 (m, 4H), 3.66-3.63 (m, 4H), 3.54-3.53 (m, 2H), 3.36-3.34 (m, 4H).

Example 6: (3S)—N-[3-(2-[[(3-hydroxyoxetan-3-yl) methyl]amino]-6-(morpholin-4-yl)pyridin-4-yl)-4-methylphenyl]-3-(2,2,2-trifluoroethyl)pyrrolidine-1-carboxamide

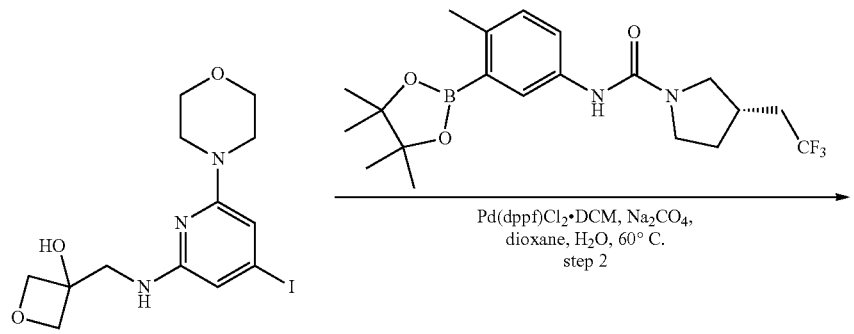

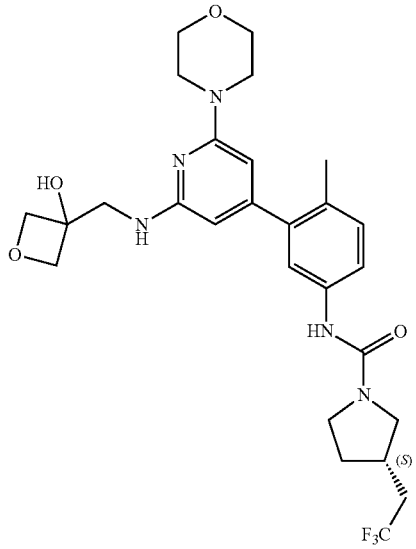

To a stirred solution of 3-([[4-iodo-6-(morpholin-4-yl) pyridin-2-yl]amino]methyl)oxetan-3-ol (140 mg, 0.358 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (162 mg, 0.394 mmol) and Na$_2$CO$_3$ (114 mg, 1.074 mmol) in dioxane:H$_2$O=4:1 (2.00 mL) was added Pd(dppf)Cl$_2$·CH$_2$Cl$_2$ (29 mg, 0.036 mmol) at 25° C. under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/(EA/EtOH=3:1)(2:1) to afford 150 mg crude product. The residue was purified by reverse flash chromatography with the following conditions: Column: XBridge Shield RP18 OBD Column, 5 um, 19*150 mm; Mobile Phase A: Water (10 MMOL/L NH$_4$HCO$_3$), Mobile Phase B: CH$_3$CN; Flow rate: 20 mL/min; Gradient: 45 B to 60 B in 4.5 min; 254/210 nm to afford (3S)—N-[3-(2-[[(3-hydroxyoxetan-3-yl)methyl]amino]-6-(morpholin-4-yl)pyridin-4-yl)-4-methylphenyl]-3-(2,2,2-trifluoroethyl)pyrrolidine-1-carboxamide (100 mg, 51%) as an off-white solid. MS ESI calculated for $C_{27}H_{34}F_3N_5O_4$ [M+H]$^+$, 550.26, found 550.25. $^1$H NMR (300 MHz, DMSO-d$_6$) δ 8.11 (s, 1H), 7.44-7.35 (m, 2H), 7.11-7.09 (m, 1H), 6.45-6.42 (m, 1H), 6.05 (s, 1H), 5.86-5.81 (m, 2H), 4.46-4.39 (m, 4H), 3.69-3.64 (m, 5H), 3.61-3.59 (m, 2H), 3.55-3.50 (m, 1H), 3.39-3.34 (m, 4H), 3.30-3.27 (m, 1H), 3.05-3.00 (m, 1H), 2.48-2.36 (m, 3H), 2.16 (s, 3H), 2.10-2.07 (m, 1H), 1.71-1.61 (m, 1H). $^{19}$F NMR (376 MHz, DMSO-d$_6$) δ −63.38 (3F).

Example 7: (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide

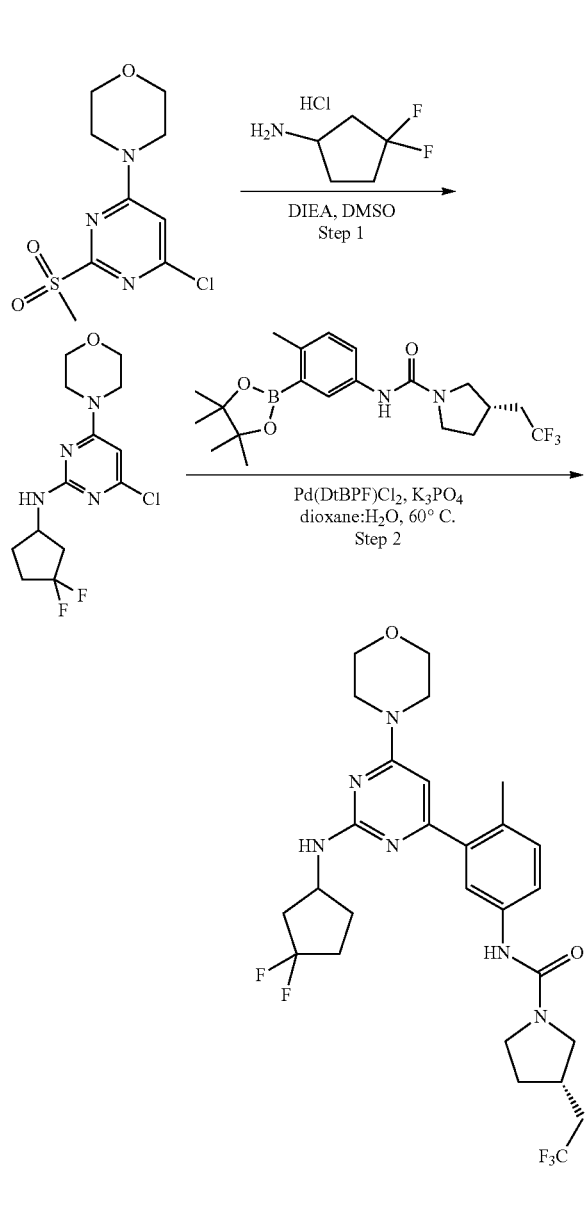

Preparation 7A: 4-chloro-N-(3,3-difluorocyclopentyl)-6-(morpholin-4-yl)pyrimidin-2-amine

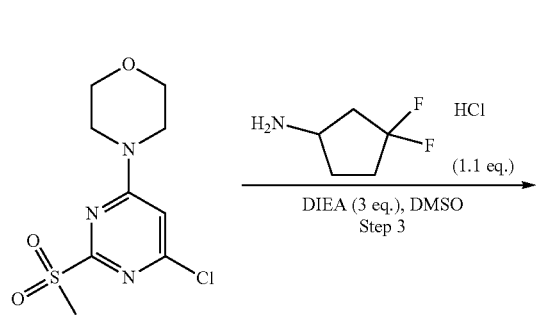

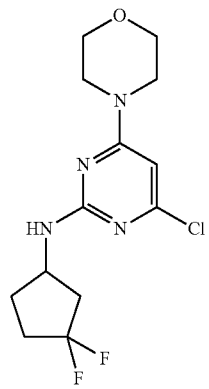

To a stirred solution of 4-(6-chloro-2-methanesulfonylpyrimidin-4-yl)morpholine (200 mg, 0.720 mmol) and 3,3-difluorocyclopentan-1-amine hydrochloride (125 mg, 0.79 mmol) in DMSO (4 mL) was added DIEA (279 mg, 2.16 mmol) dropwise at room temperature under nitrogen atmosphere. The resulting mixture was stirred for overnight at 60° C. under nitrogen atmosphere. The resulting mixture was diluted with water (15 mL). The resulting mixture was extracted with EtOAc (3×20 mL). The combined organic layers were washed with brine (15 mL), dried over anhydrous $Na_2SO_4$. After filtration, the filtrate was concentrated under reduced pressure. The residue was purified by silica gel column chromatography, eluted with hexane/EtOAc (1:1) to afford 4-chloro-N-(3,3-difluorocyclopentyl)-6-(morpholin-4-yl)pyrimidin-2-amine (84 mg, 37%) as a white solid. MS ESI calculated for $C_{13}H_{17}ClF_2N_4O$ [M+H]$^+$, 319.11; found 319.15. $^1$H NMR (300 MHz, DMSO-d$_6$) δ 5.93 (s, 1H), 5.16 (s, 1H), 4.47-4.42 (m, 1H), 3.79-3.76 (m, 4H), 3.60-3.57 (m, 4H), 2.70-2.53 (m, 1H), 2.32-1.82 (m, 4H), 1.79-1.73 (m, 1H).

Example 7: (3S)—N-(3-[2-[(3,3-difluorocyclopentyl)amino]-6-(morpholin-4-yl)pyrimidin-4-yl]-4-methylphenyl)-3-(2,2,2-trifluoroethyl)pyrrolidine-1-carboxamide

-continued

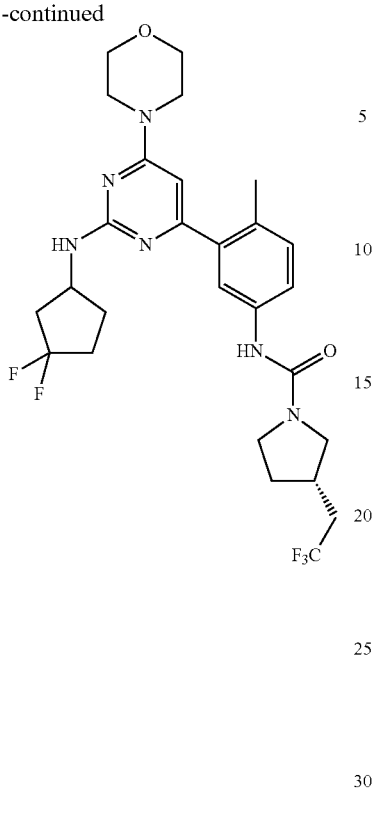

Examples 8 and 9: (3S)—N-[3-(2-[[(1R)-3,3-difluorocyclopentyl]amino]-6-(morpholin-4-yl)pyrimidin-4-yl)-4-methylphenyl]-3-(2,2,2-trifluoroethyl)pyrrolidine-1-carboxamide, (3S)—N-[3-(2-[[(1S)-3,3-difluorocyclopentyl]amino]-6-(morpholin-4-yl)pyrimidin-4-yl)-4-methylphenyl]-3-(2,2,2-trifluoroethyl)pyrrolidine-1-carboxamide Chiral Prep-HPLC →

To a stirred solution of 4-chloro-N-(3,3-difluorocyclopentyl)-6-(morpholin-4-yl)pyrimidin-2-amine (160 mg, 0.502 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (248 mg, 0.602 mmol), K₃PO₄ (213 mg, 1.004 mmol) in dioxane (3.2 mL), H₂O (0.8 mL) was added Pd(DtBPF)Cl₂ (33 mg, 0.050 mmol) at room temperature under nitrogen atmosphere. The resulting mixture was stirred for 2 h at 80° C. under nitrogen atmosphere. The resulting mixture was concentrated under vacuum. The residue was purified by silica gel column chromatography, eluted with hexane/(EtOAc:EtOH=3:1)(1:1) to afford crude. The crude product (150 mg) was purified by Prep-HPLC with the following conditions (Column: XSelect CSH Prep C18 OBD Column, 19×250 mm, 5 um; Mobile Phase A: Water (0.1% FA), Mobile Phase B: CH₃CN; Flow rate: 20 mL/min; Gradient: 30 B to 40 B in 6.5 min; 254/210 nm to afford (3S)—N-(3-[2-[(3,3-difluorocyclopentyl)amino]-6-(morpholin-4-yl)pyrimidin-4-yl]-4-methylphenyl)-3-(2,2,2-trifluoroethyl)pyrrolidine-1-carboxamide (85 mg, 30%) as a white solid. MS ESI calculated for $C_{27}H_{33}F_5N_6O_2$ [M+H]⁺, 569.26, found 569.20. ¹H NMR (400 MHz, DMSO-d₆) δ 8.14 (s, 1H), 7.47-7.45 (m, 2H), 7.11-7.09 (m, 2H), 6.07 (s, 1H), 4.37-4.35 (m, 1H), 3.67-3.51 (m, 10H), 3.05-3.00 (m, 1H), 2.44-2.42 (m, 6H), 2.34-2.21 (m, 3H), 2.09-2.08 (m, 4H), 1.79-1.63 (m, 2H). ¹⁹F NMR (376 MHz, DMSO-d₆) δ −63.37 (3F), −87.50 (2F).

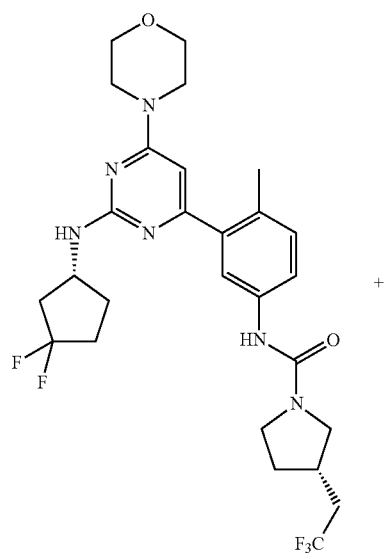

+

183

-continued

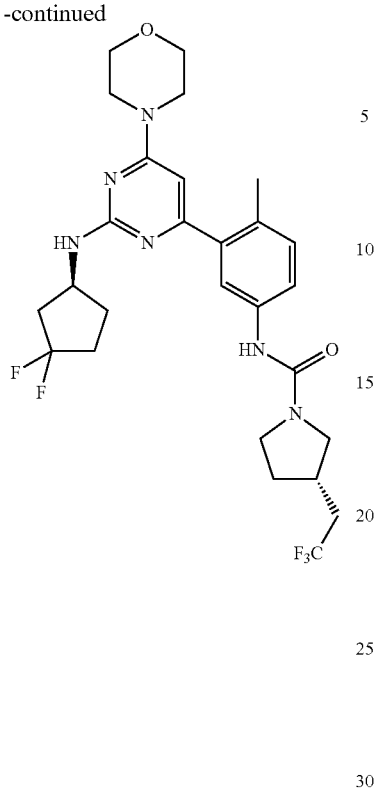

(3S)—N-(3-[2-[(3,3-difluorocyclopentyl)amino]-6-(morpholin-4-yl)pyrimidin-4-yl]-4-methylphenyl)-3-(2,2,2-trifluoroethyl)pyrrolidine-1-carboxamide (80 mg) was resolved by Prep-CHIRAL-HPLC with the following conditions (Column: CHIRALPAK ADH, 2×25 cm, 5 um; Mobile Phase A: Hex (8 mmol/L NH$_3$·MeOH)-HPLC, Mobile Phase B: IPA-HPLC; Flow rate: 20 mL/min; Gradient:20 B to 20 B in 35 min; 220/254 nm) to afford 33 mg (41%) as a white solid. MS ESI calculated for $C_{27}H_{33}F_5N_6O_2$ [M+H]$^+$, 569.26, found 569.25. $^1$H NMR (400 MHz, DMSO-d$_6$) δ 8.13 (s, 1H), 7.47-7.44 (m, 2H), 7.10-7.08 (m, 2H), 6.06 (s, 1H), 4.36-4.34 (m, 1H), 3.69-3.51 (m, 11H), 3.05-3.00 (m, 1H), 2.47-2.27 (m, 7H), 2.11-2.08 (m, 5H), 1.75-1.66 (m, 2H). $^{19}$F NMR (376 MHz, DMSO-d$_6$) δ −63.37 (3F), −87.50 (2F), and 33 mg (41%) as a white solid. MS ESI calculated for $C_{27}H_{33}F_5N_6O_2$ [M+H]$^+$, 569.26, found 569.25. $^1$H NMR (400 MHz, DMSO-d$_6$) δ 8.13 (s, 1H), 7.47-7.44 (m, 2H), 7.10-7.08 (m, 1H), 6.93-6.82 (m, 1H), 6.06 (s, 1H), 4.39-4.27 (m, 1H), 3.66-3.55 (m, 11H), 3.05-3.00 (m, 1H), 2.47-2.27 (m, 7H), 2.19-2.03 (m, 5H), 1.79-1.66 (m, 2H). $^{19}$F NMR (376 MHz, DMSO-d$_6$) δ −63.37 (3F), −87.51 (2F).

184

Example 10: (3S)—N-[3-(2-[[(cis-3-hydroxycyclopentyl]amino]-6-(morpholin-4-yl)pyrimidin-4-yl)-4-methylphenyl]-3-(2,2,2-trifluoroethyl)pyrrolidine-1-carboxamide

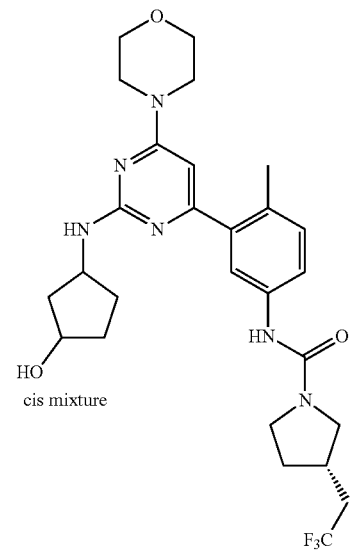 [SMILES: Cc1ccc(NC(=O)N2CC[C@@H](CC(F)(F)F)C2)cc1-c1cc(N2CCOCC2)nc(NC2CCC(O)C2)n1]
cis mixture

Synthetic Scheme

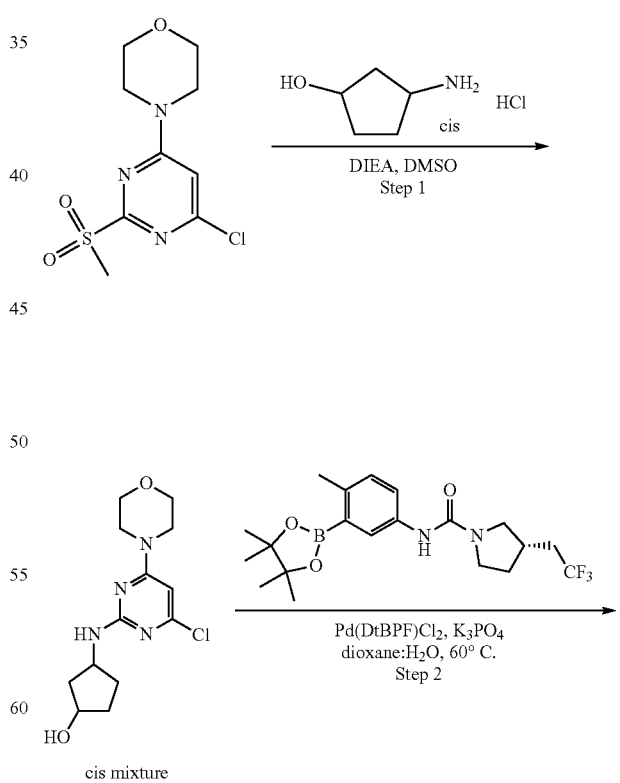

-continued

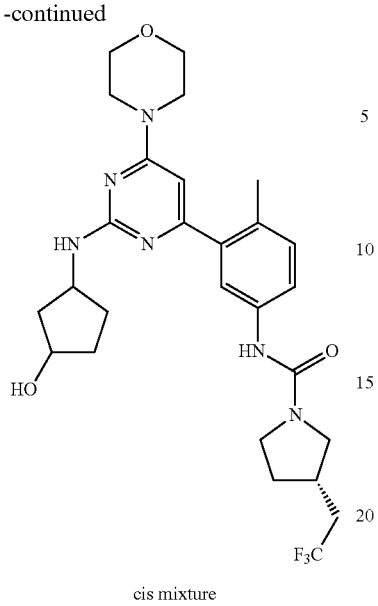

cis mixture

Preparation 10A: cis-3-[[4-chloro-6-(morpholin-4-yl)pyrimidin-2-yl]amino]cyclopentan-1-ol

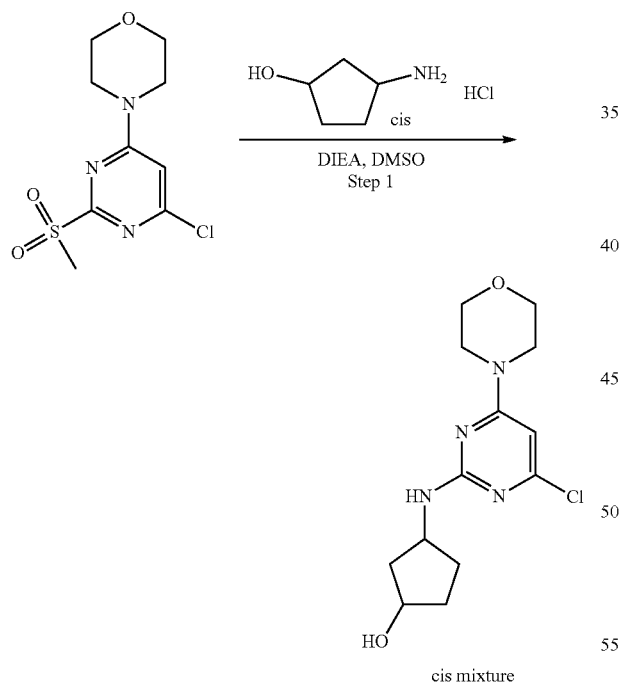

cis mixture

To a stirred solution of 4-(6-chloro-2-methanesulfonylpyrimidin-4-yl)morpholine (500 mg, 1.800 mmol) and cis-3-aminocyclopentan-1-ol hydrochloride (273 mg, 1.980 mmol) in DMSO (9 mL) were added DIEA (698 mg, 5.401 mmol) dropwise at room temperature under nitrogen atmosphere. The resulting mixture was stirred for overnight at 60° C. under nitrogen atmosphere. The resulting mixture was diluted with water (30 mL). The resulting mixture was extracted with EtOEt (4×30 mL). The combined organic layers were washed with brine (30 mL), dried over anhydrous Na₂SO₄. After filtration, the filtrate was concentrated under reduced pressure. The residue was purified by silica gel column chromatography, eluted with hexane/(EtOAc: EtOH=3:1) (1:1) to afford (cis)-3-[[4-chloro-6-(morpholin-4-yl)pyrimidin-2-yl]amino]cyclopentan-1-ol (221 mg, 42%) as a white solid. MS ESI calculated for $C_{13}H_{19}ClN_4O_2$ [M+H]⁺, 299.12; found 299.15 ¹H NMR (300 MHz, chloroform-d) δ 5.88-5.87 (m, 1H), 5.57 (m, 1H), 5.34-5.32 (m, 1H). 4.43-4.35 (m, 2H), 3.78-3.75 (m, 4H), 3.60-3.56 (m, 4H), 2.23-2.07 (m, 2H), 1.94-1.80 (m, 4H).

Example 10: (3S)—N-[3-(2-[[(cis-3-hydroxycyclopentyl]amino]-6-(morpholin-4-yl)pyrimidin-4-yl)-4-methylphenyl]-3-(2,2,2-trifluoroethyl)pyrrolidine-1-carboxamide

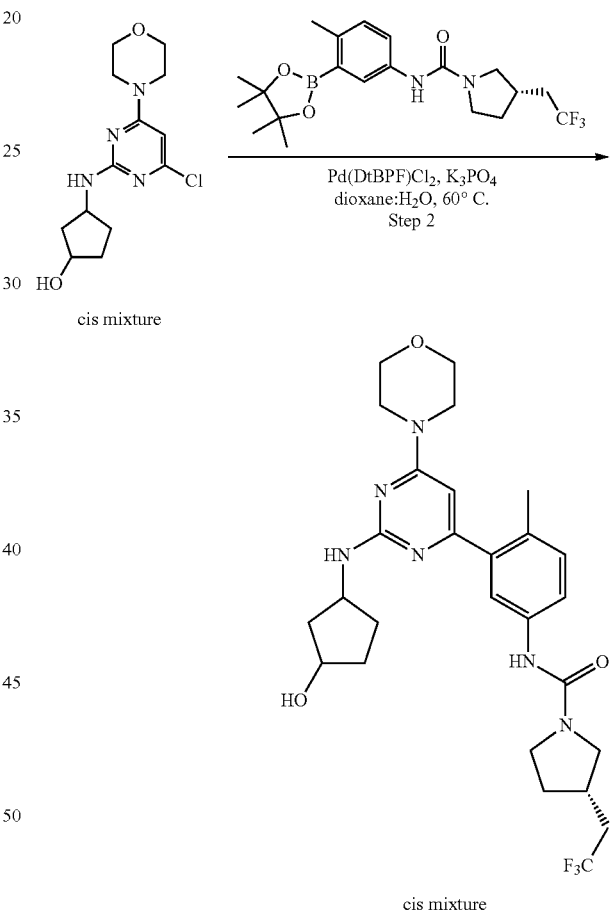

cis mixture

To a stirred mixture of (cis)-3-[[4-chloro-6-(morpholin-4-yl)pyrimidin-2-yl]amino]cyclopentan-1-ol (270 mg, 0.904 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (447 mg, 1.084 mmol), K₃PO₄ (384 mg, 1.807 mmol) in dioxane (5.4 mL), H₂O (1.35 mL) were added Pd(DtBPF)Cl₂ (59 mg, 0.090 mmol) at room temperature under nitrogen atmosphere. The resulting mixture was stirred for 2 h at 80° C. under nitrogen atmosphere. The resulting mixture was concentrated under vacuum. The residue was purified by silica gel column chromatography, eluted with hexane/(EtOAc:EtOH=3:1)(1:1) to afford crude.

The crude product (277 mg) was purified by Prep-HPLC with the following conditions (Column: XBridge Shield RP18 OBD Column, 5 um, 19×150 mm; Mobile Phase A: Water (10 MMOL/L NH$_4$HCO$_3$), Mobile Phase B: CH$_3$CN; Flow rate: 20 mL/min; Gradient: 28 B to 40 B in 4.3 min; 254/210 nm to afford (3S)—N-[3-(2-[[(cis)-3-hydroxycyclopentyl]amino]-6-(morpholin-4-yl)pyrimidin-4-yl)-4-methylphenyl]-3-(2,2,2-trifluoroethyl)pyrrolidine-1-carboxamide (165 mg, 33%) as a white solid. MS ESI calculated for C$_{27}$H$_{35}$F$_3$N$_6$O$_3$ [M+H]$^+$, 549.27; found 549.30. $^1$H NMR (300 MHz, DMSO-d$_6$) δ 8.12 (s, 1H), 7.44-7.42 (m, 2H), 7.08-7.06 (m, 1H), 6.41-6.39 (m, 1H), 6.00 (s, 1H), 4.60-5.59 (m, 1H), 4.17-4.08 (m, 2H), 3.69-3.42 (m, 10H), 3.05-2.99 (m, 1H), 2.46-2.39 (m, 3H), 2.24-2.15 (m, 3H), 2.10-2.07 (m, 3H), 1.88-1.85 (m, 1H), 1.82-1.77 (m, 5H). $^{19}$F NMR (282 MHz, DMSO-d$_6$) δ −63.35 (3F).

Examples 11 and 12: (3S)—N-[3-(2-[[(1S,3R)-3-hydroxycyclopentyl]amino]-6-(morpholin-4-yl)pyrimidin-4-yl)-4-methylphenyl]-3-(2,2,2-trifluoroethyl)pyrrolidine-1-carboxamide, (3S)—N-[3-(2-[[(1R,3S)-3-hydroxycyclopentyl]amino]-6-(morpholin-4-yl)pyrimidin-4-yl)-4-methylphenyl]-3-(2,2,2-trifluoroethyl)pyrrolidine-1-carboxamide

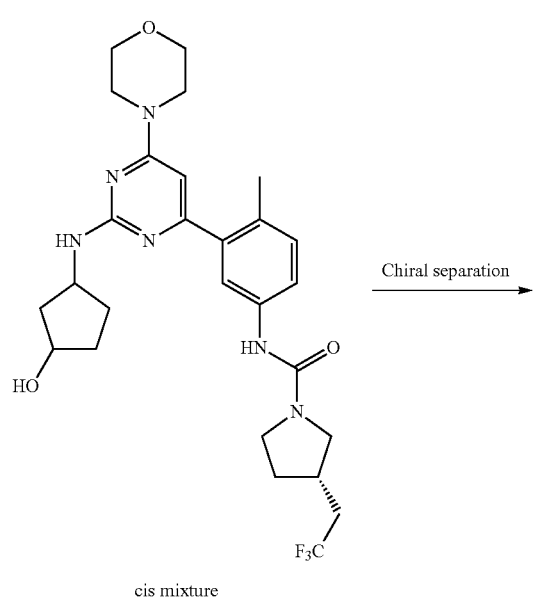

cis mixture

Chiral separation →

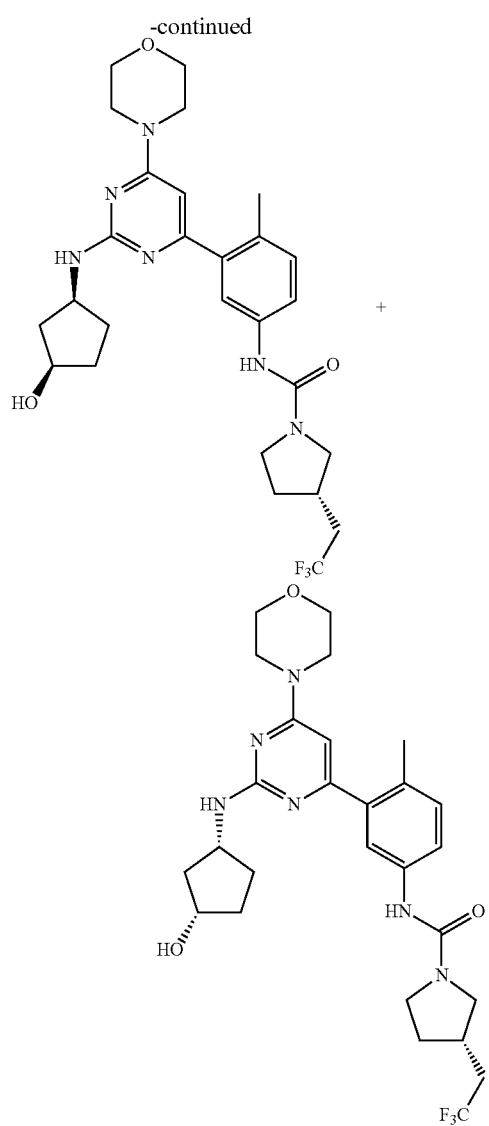

(3S)—N-[3-(2-[[(cis)-3-hydroxycyclopentyl]amino]-6-(morpholin-4-yl)pyrimidin-4-yl)-4-methylphenyl]-3-(2,2,2-trifluoroethyl)pyrrolidine-1-carboxamide (160 mg) was resolved by Prep-CHIRAL-HPLC with the following conditions (Column: CHIRALPAK ADH, 2×25 cm, 5 um; Mobile Phase A: Hex (8 mmol/L NH$_3$·MeOH)-HPLC, Mobile Phase B: IPA-HPLC; Flow rate: 20 mL/min; Gradient:30 B to 30 B in 15 min; 220/254 nm) to afford 66 mg (41%) as a white solid. MS ESI calculated for C$_{27}$H$_{35}$F$_3$N$_6$O$_3$ [M+H]$^+$, 549.27; found 549.30. $^1$H NMR (400 MHz, DMSO-d$_6$) δ 8.15-8.13 (m, 1H), 7.49-7.46 (m, 2H), 7.11-7.08 (m, 1H), 6.52-6.33 (m, 1H), 6.01 (s, 1H), 4.63-4.61 (m, 1H), 4.23-4.02 (m, 2H), 3.79-3.52 (m, 11H), 3.13-3.02 (m, 1H), 2.46-2.44 (m, 3H), 2.39-2.12 (m, 3H), 2.17-2.05 (m, 2H), 1.93-1.86 (m, 1H), 1.73-1.46 (m, 5H). $^{19}$F NMR (376 MHz, DMSO-d$_6$) δ −63.37 (3F), and 67 mg (42%) as a white solid. MS ESI calculated for C$_{27}$H$_{35}$F$_3$N$_6$O$_3$ [M+H]$^+$, 549.27; found 549.30. $^1$H NMR (400 MHz, DMSO-d$_6$) δ8.15-8.13 (m, 1H), 7.57-7.40 (m, 2H), 7.11-7.08 (m, 1H), 6.52-6.43 (m, 1H), 6.10-5.96 (m, 1H), 4.63-5.61 (m, 1H), 4.17-4.10 (m, 2H), 3.82-3.41 (m, 11H), 3.10-3.02 (m, 1H), 2.46-2.39 (m, 3H), 2.24-2.19 (m, 3H), 2.17-2.07 (m, 2H), 1.88-1.68 (m, 1H), 1.65-1.46 (m, 5H). $^{19}$F NMR (376 MHz, DMSO-d$_6$) δ −63.34-63.37 (3F).

Example 13: (3S)—N-[3-(2-[[(2R)-2-hydroxypropyl]amino]-6-(morpholin-4-yl)pyridin-4-yl)-4-methylphenyl]-3-(2,2,2-trifluoroethyl)pyrrolidine-1-carboxamide

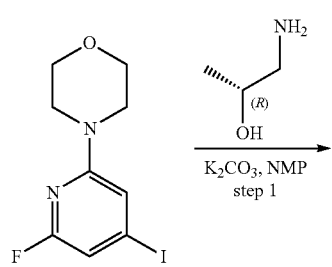

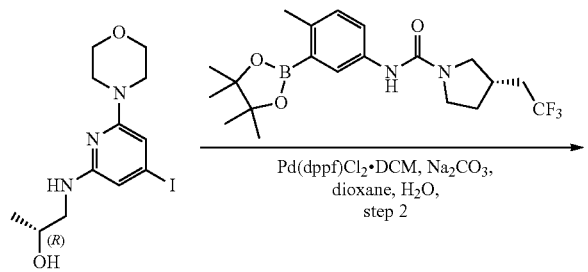

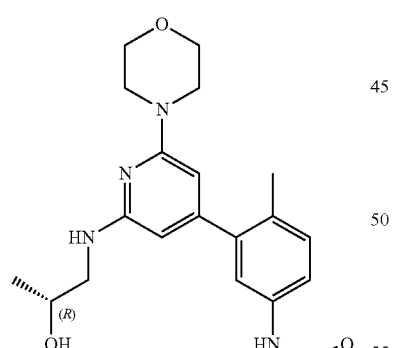

Preparation 13A: (2R)-1-[[4-iodo-6-(morpholin-4-yl)pyridin-2-yl]amino]propan-2-ol

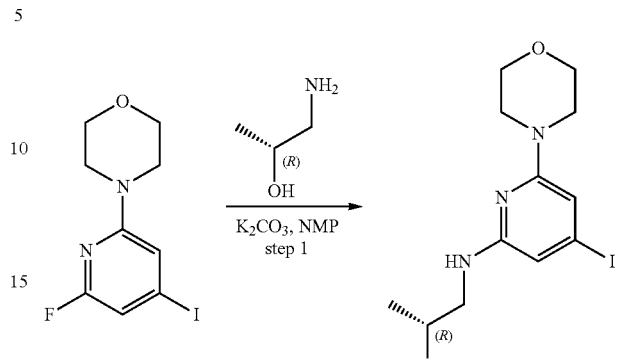

To a stirred solution of 4-(6-fluoro-4-iodopyridin-2-yl)morpholine (400 mg, 1.298 mmol) and K$_2$CO$_3$ (359 mg, 2.597 mmol) in NMP (4 mL) was added (R)-1-amino-2-propanol (146 mg, 1.947 mmol) at room temperature under nitrogen atmosphere. The resulting mixture was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2:1) to afford (2R)-1-[[4-iodo-6-(morpholin-4-yl)pyridin-2-yl]amino]propan-2-ol (200 mg, 42%) as an off-white solid. MS ESI calculated for C$_{12}$H$_{18}$IN$_3$O$_2$ [M+H]$^+$, 364.04, found 363.90. $^1$H NMR (400 MHz, DMSO-d$_6$) δ 6.37 (m, 1H), 6.25 (m, 1H), 6.19 (m, 1H), 4.64-4.63 (m, 1H), 3.77-3.71 (m, 1H), 3.66-3.63 (m, 4H), 3.34-3.33 (m, 4H), 3.17-3.06 (m, 2H), 1.06-1.04 (m, 3H).

Example 13: (3S)—N-[3-(2-[[(2R)-2-hydroxypropyl]amino]-6-(morpholin-4-yl)pyridin-4-yl)-4-methylphenyl]-3-(2,2,2-trifluoroethyl)pyrrolidine-1-carboxamide

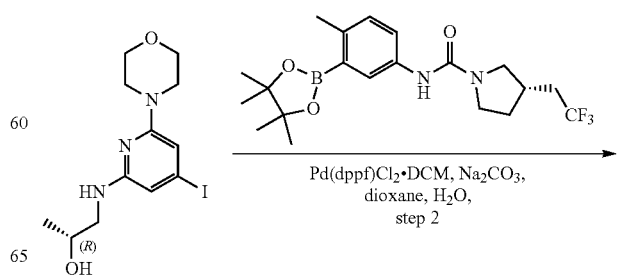

-continued

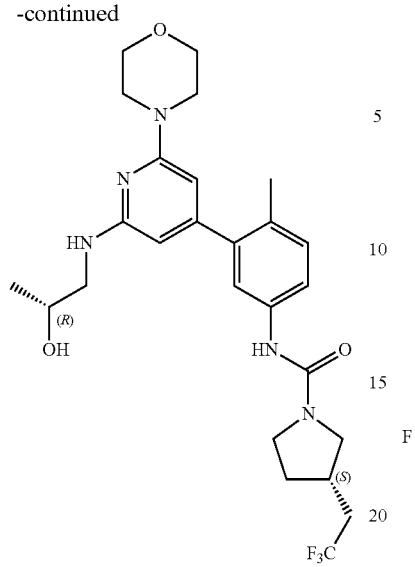

To a stirred solution of (2R)-1-[[4-iodo-6-(morpholin-4-yl)pyridin-2-yl]amino]propan-2-ol (50 mg, 0.138 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (60 mg, 0.145 mmol) and Na$_2$CO$_3$ (44 mg, 0.413 mmol) in dioxane (0.8 mL) and H$_2$O (0.2 mL) was added Pd(dppf)Cl$_2$·CH$_2$Cl$_2$ (11 mg, 0.014 mmol) at room temperature under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EA/EtOH (8/3/1) to afford 50 mg crude product. The residue was purified by reverse flash chromatography with the following conditions: Column: XBridge Prep Amide OBD Column, 19×150 mm 5 um 13 nm; Mobile Phase A: Water (10 mmol/L NH$_4$HCO$_3$), Mobile Phase B: CH$_3$CN; Flow rate: 20 mL/min; Gradient:40 B to 70 B in 4.3 min; 210/254 nm. This resulted in (3S)—N-[3-(2-[[(2R)-2-hydroxypropyl]amino]-6-(morpholin-4-yl)pyridin-4-yl)-4-methylphenyl]-3-(2,2,2-trifluoroethyl)pyrrolidine-1-carboxamide (38 mg, 53%) as an off-white solid. MS ESI calculated for C$_{26}$H$_{34}$F$_3$N$_5$O$_3$ [M+H]$^+$. 522.26, found 522.15. $^1$H NMR (400 MHz, DMSO-d$_6$) δ 8.11 (s, 1H), 7.43-7.40 (m, 1H), 7.34-7.33 (m, 1H), 7.10-7.08 (m, 1H), 6.22-6.19 (m, 1H), 5.78-5.76 (m, 2H), 4.70-4.69 (m, 1H), 3.83-3.77 (m, 1H), 3.69-3.55 (m, 5H), 3.53-3.50 (m, 1H), 3.38-3.36 (m, 4H), 3.31-3.27 (m, 1H), 3.22-3.13 (m, 2H), 3.04-3.00 (m, 1H), 2.48-2.38 (m, 3H), 2.16 (s, 3H), 2.11-2.07 (m, 1H), 1.68-1.63 (m, 1H), 1.09-1.07 (m, 3H). $^{19}$F NMR (376 MHz, DMSO-d$_6$) δ −63.36 (3F).

Example 14: (3S)—N-[3-(2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide

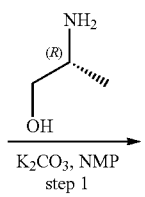

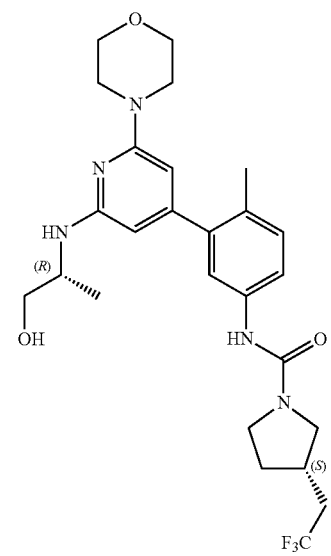

Preparation 14A: (2R)-2-[[4-iodo-6-(morpholin-4-yl)pyridin-2-yl]amino]propan-1-ol

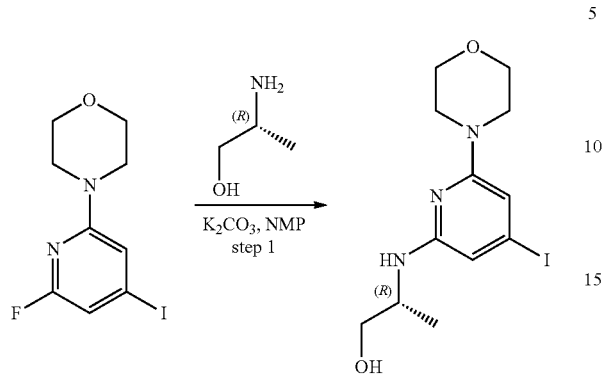

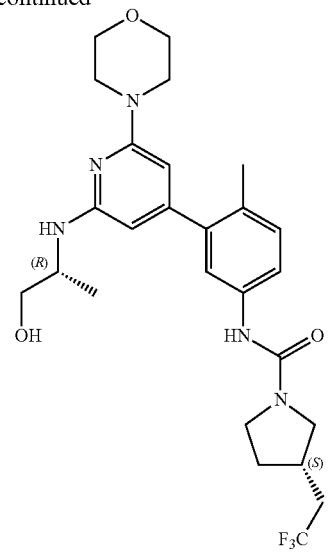

To a stirred solution of 4-(6-fluoro-4-iodopyridin-2-yl)morpholine (300 mg, 0.974 mmol) and K₂CO₃ (269 mg, 1.947 mmol) in NMP (3 mL) was added (R)-(−)-2-amino-1-propanol (110 mg, 1.461 mmol) at room temperature under nitrogen atmosphere. The resulting mixture was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na₂SO₄. After filtration, the filtrate was concentrated under reduced pressure. The residue was purified by silica gel column chromatography, eluted with PE/EtOAc (2:1) to afford (2R)-2-[[4-iodo-6-(morpholin-4-yl)pyridin-2-yl]amino]propan-1-ol (85 mg, 24%) as an off-white solid. MS ESI calculated for $C_{12}H_{18}IN_3O_2$ [M+H]⁺, 364.04, found 364.10. ¹H NMR (400 MHz, DMSO-d₆) δ 6.23 (s, 1H), 6.18-6.13 (m, 2H), 4.63-4.60 (m, 1H), 3.86-3.80 (m, 1H), 3.66-3.63 (m, 4H), 3.45-3.41 (m, 1H), 3.38-3.34 (m, 4H), 3.28-3.22 (m, 1H), 1.09-1.07 (m, 3H).

Example 14: (3S)—N-[3-(2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide

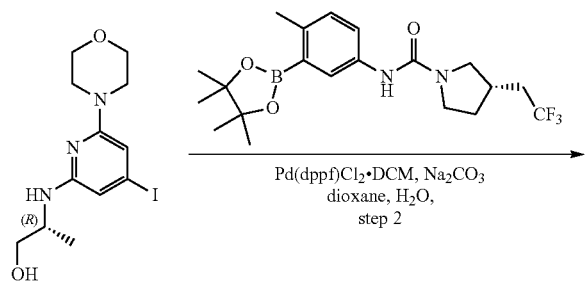

To a stirred solution of (2R)-2-[[4-iodo-6-(morpholin-4-yl)pyridin-2-yl]amino]propan-1-ol (50 mg, 0.138 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (57 mg, 0.138 mmol) and Na₂CO₃ (44 mg, 0.413 mmol) in dioxane (0.8 mL) and H₂O (0.2 mL) was added Pd(dppf)Cl₂·CH₂Cl₂ (11 mg, 0.014 mmol) at room temperature under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na₂SO₄. After filtration, the filtrate was concentrated under reduced pressure. The residue was purified by silica gel column chromatography, eluted with PE/EA/EtOH (8/3/1) to afford 50 mg crude product. The residue was purified by reverse flash chromatography with the following conditions: Column: XBridge Shield RP18 OBD Column, 30*150 mm, 5 um; Mobile Phase A: Water (10 mmol/l NH₄HCO₃), Mobile Phase B: CH₃CN; Flow rate: 20 mL/min; Gradient:35 B to 65 B in 8 min; 210/254 nm. This resulted in (3S)—N-[3-(2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide (31 mg, 43%) as an off-white solid. MS ESI calculated for $C_{26}H_{34}F_3N_5O_3$ [M+H]⁺. 522.26, found 522.10. ¹H NMR (400 MHz, DMSO-d₆) δ 8.11 (s, 1H), 7.42-7.40 (m, 1H), 7.34 (m, 1H), 7.10-7.08 (m, 1H), 5.98-5.96 (m, 1H), 5.75 (m, 2H), 4.66-4.64 (m, 1H), 3.91-3.87 (m, 1H), 3.69-3.65 (m, 5H), 3.52-3.47 (m, 2H), 3.38-3.36 (m, 4H), 3.32-3.26 (m, 2H), 3.04-3.00 (m, 1H), 2.48-2.38 (m, 3H), 2.16 (s, 3H), 2.10-2.07 (m, 1H), 1.71-1.61 (m, 1H), 1.13-1.12 (m, 3H). ¹⁹F NMR (376 MHz, DMSO-d₆) δ −63.36 (3F).

Example 15: (3S)—N-[3-[2-(3-hydroxyazetidin-1-yl)-6-(morpholin-4-yl)pyrimidin-4-yl]-4-methylphenyl]-3-(2,2,2-trifluoroethyl)pyrrolidine-1-carboxamide
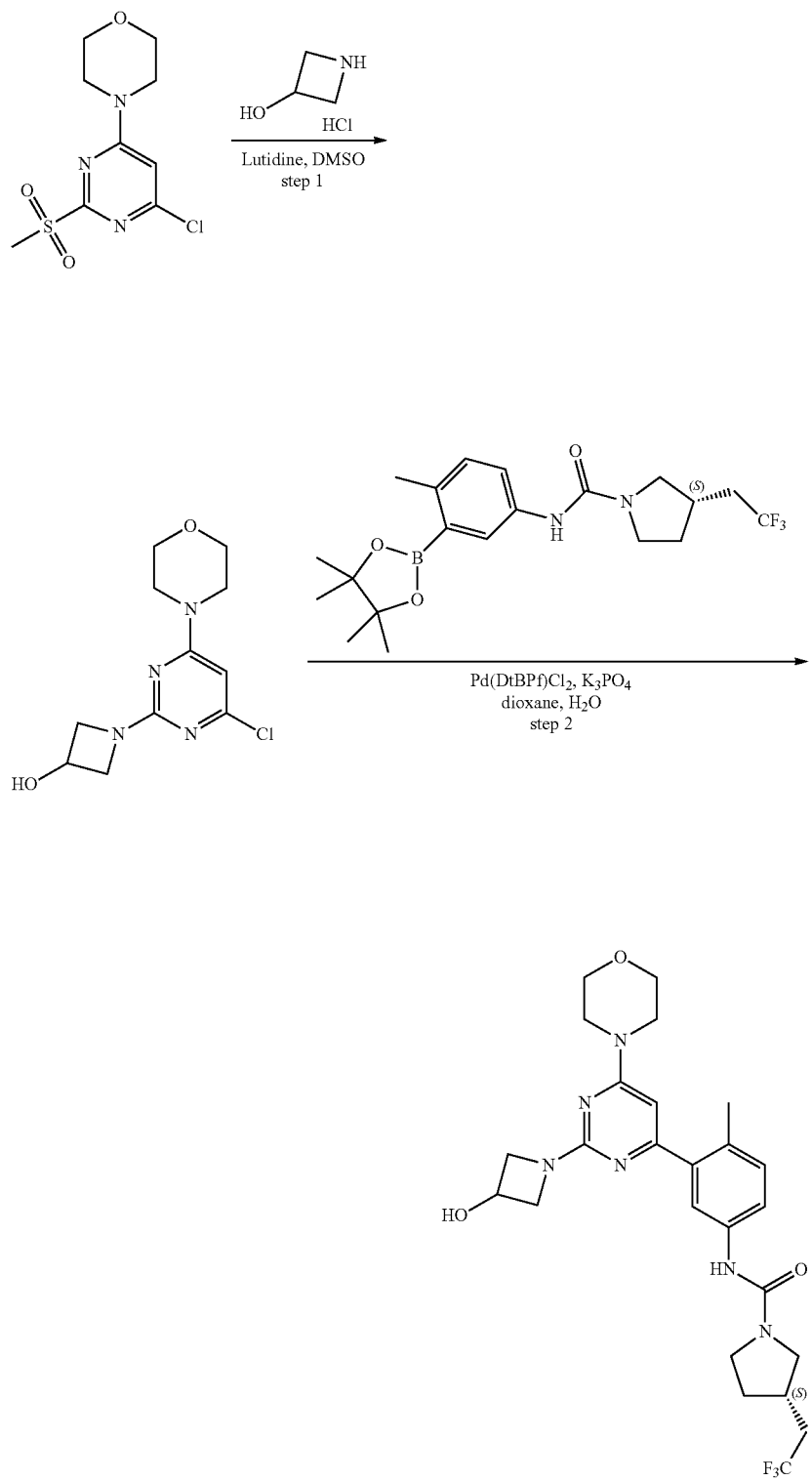

Preparation 15A: 1-[4-chloro-6-(morpholin-4-yl)pyrimidin-2-yl]azetidin-3-ol

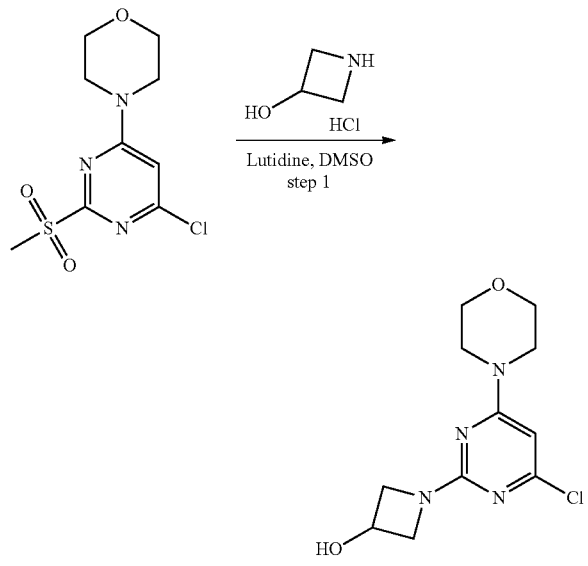

A mixture of 4-(6-chloro-2-methanesulfonylpyrimidin-4-yl)morpholine (200 mg, 0.720 mmol), azetidin-3-ol hydrochloride (87 mg, 0.792 mmol) and 2,6-Dimethylpyridine (232 mg, 2.160 mmol) in DMSO (2 mL) was stirred for 16 h at 60° C. under nitrogen atmosphere. The reaction was quenched by the addition of Water (20 mL) at room temperature. The resulting mixture was extracted with EtOAc (5×20 mL). The combined organic layers were dried over anhydrous $Na_2SO_4$. After filtration, the filtrate was concentrated under reduced pressure. The residue was purified by silica gel column chromatography, eluted with PE/EtOAc/EtOH (4/3/1) to afford 1-[4-chloro-6-(morpholin-4-yl)pyrimidin-2-yl]azetidin-3-ol (110 mg, 48%) as an off-white solid. MS ESI calculated for $C_{11}H_{15}ClN_4O_2$ [M+H]$^+$, 271.09, found 271.05. $^1$H NMR (400 MHz, DMSO-d$_6$) δ6.15 (s, 1H), 5.64 (d, J=6.4 Hz, 1H), 4.51-4.44 (m, 1H), 4.15-4.11 (m, 2H), 3.70-3.66 (m, 2H), 3.61-3.59 (m, 4H), 3.52-3.50 (m, 4H).

Example 15: (3S)—N-[3-[2-(3-hydroxyazetidin-1-yl)-6-(morpholin-4-yl)pyrimidin-4-yl]-4-methylphenyl]-3-(2,2,2-trifluoroethyl)pyrrolidine-1-carboxamide

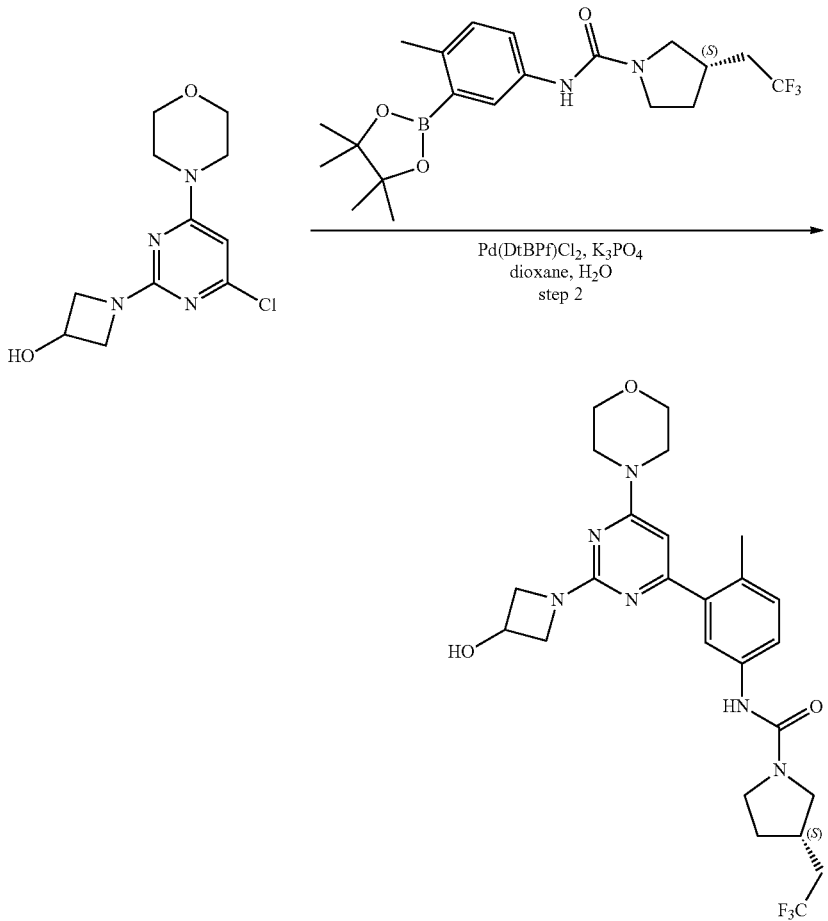

A mixture of 1-[4-chloro-6-(morpholin-4-yl)pyrimidin-2-yl]azetidin-3-ol (50 mg, 0.185 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (76 mg, 0.185 mmol), Pd(DtBPF)Cl$_2$ (12 mg, 0.018 mmol) and K$_3$PO$_4$ (78 mg, 0.369 mmol) in dioxane (0.9 mL) and H$_2$O (0.2 mL) was stirred for 16 h at 80° C. under nitrogen atmosphere. The resulting mixture was concentrated under vacuum. The residue was purified by silica gel column chromatography, eluted with PE/EtOAc/EtOH (4/3/1), the crude product (50 mg) was purified by Prep-HPLC with the following conditions: (Column: XBridge Prep C18 OBD Column, 19×150 mm 5 um; Mobile Phase A: Water (10 mmol/L NH$_4$HCO$_3$), Mobile Phase B: CH$_3$CN; Flow rate: 20 mL/min; Gradient:40 B to 75 B in 4.3 min; 210/254 nm) to afford (3S)—N-[3-[2-(3-hydroxyazetidin-1-yl)-6-(morpholin-4-yl)pyrimidin-4-yl]-4-methylphenyl]-3-(2,2,2-trifluoroethyl)pyrrolidine-1-carboxamide (38 mg, 39%) as an off-white solid. MS ESI calculated for C$_{25}$H$_{31}$F$_3$N$_6$O$_3$ [M+H]$^+$, 521.24, found 521.25. $^1$H NMR (400 MHz, DMSO-d$_6$) δ 8.15 (s, 1H), 7.48-7.45 (m, 2H), 7.10-7.08 (m, 1H), 6.10 (s, 1H), 5.60-5.58 (m, 1H), 4.52-4.50 (m, 1H), 4.18-4.14 (m, 2H), 3.83 (m, 2H), 3.74-3.64 (m, 5H), 3.56-3.51 (m, 5H), 3.31-3.30 (m, 1H), 3.05-3.00 (m, 1H), 2.51-2.41 (m, 3H), 2.24 (s, 3H), 2.08 (m, 1H), 1.75-1.55 (m, 1H). $^{19}$F NMR (376 MHz, DMSO-d$_6$) δ −63.36 (3F).

Example 16: (3S)—N-[3-[2-(3-hydroxyazetidin-1-yl)-6-(morpholin-4-yl)pyridin-4-yl]-4-methylphenyl]-3-(2,2,2-trifluoroethyl)pyrrolidine-1-carboxamide Preparation 16A: 1-[4-iodo-6-(morpholin-4-yl)pyridin-2-yl]azetidin-3-ol

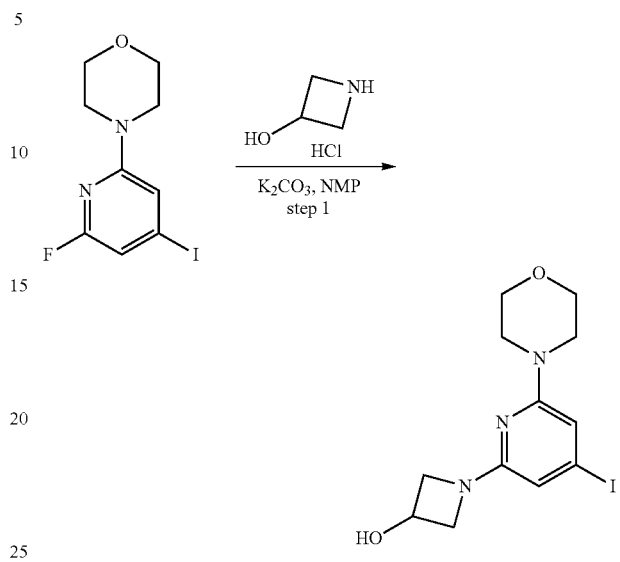

To a stirred solution of 4-(6-fluoro-4-iodopyridin-2-yl)morpholine (300 mg, 0.974 mmol) and K$_2$CO$_3$ (269 mg, 1.947 mmol) in NMP (3 mL) was added azetidin-3-ol hydrochloride (160 mg, 1.461 mmol) at room temperature

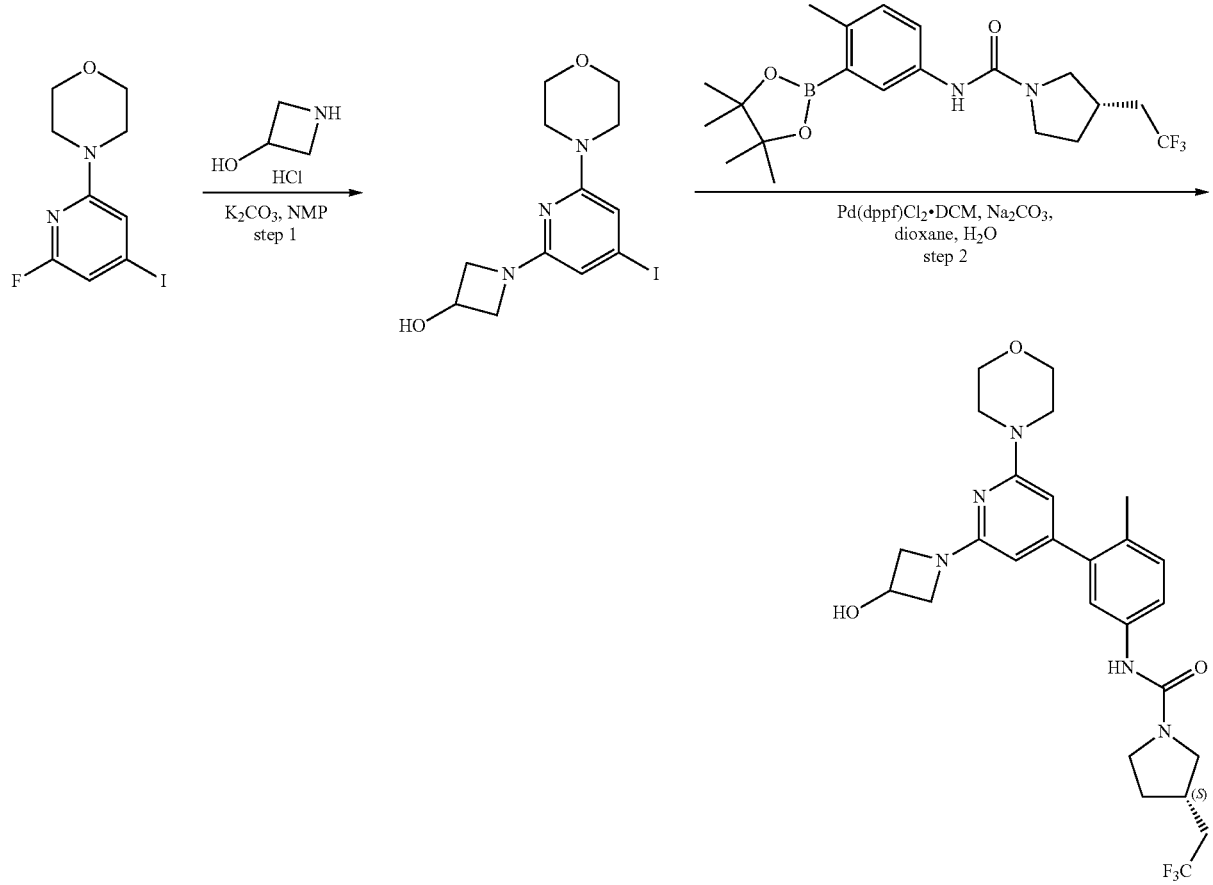

under nitrogen atmosphere. The resulting mixture was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EtOAc (2:1) to afford 1-[4-iodo-6-(morpholin-4-yl)pyridin-2-yl]azetidin-3-ol (90 mg, 26%) as an off-white solid. MS ESI calculated for $C_{12}H_{16}IN_3O_2$ [M+H]$^+$, 361.03, found 361.90. $^1$H NMR (400 MHz, DMSO-$d_6$) δ 6.37 (m, 1H), 6.06-6.05 (m, 1H), 5.61-5.59 (m, 1H), 4.53-4.43 (m, 1H), 4.09-4.03 (m, 2H), 3.65-3.58 (m, 6H), 3.37-3.35 (m, 4H].

Example 16: (3S)—N-[3-[2-(3-hydroxyazetidin-1-yl)-6-(morpholin-4-yl)pyridin-4-yl]-4-methylphenyl]-3-(2,2,2-trifluoroethyl)pyrrolidine-1-carboxamide

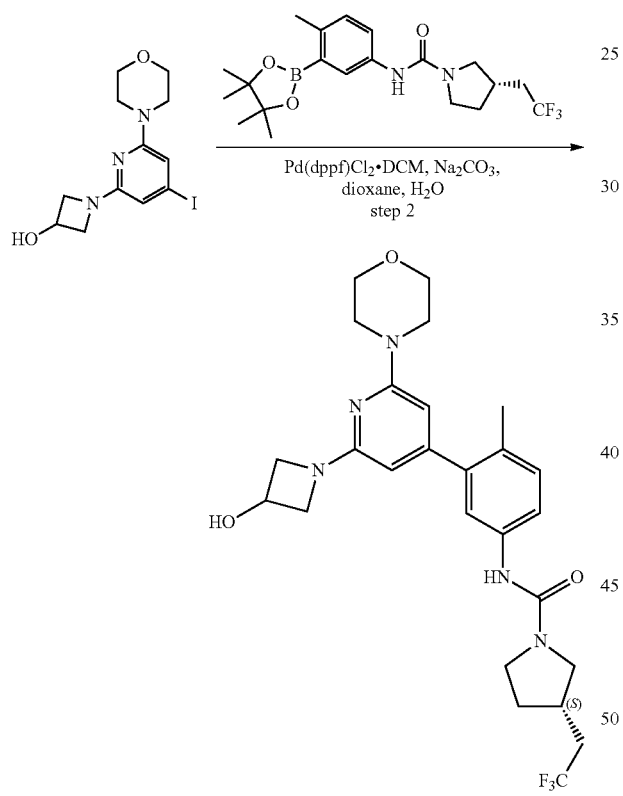

To a stirred solution of 1-[4-iodo-6-(morpholin-4-yl)pyridin-2-yl]azetidin-3-ol (50 mg, 0.138 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (60 mg, 0.145 mmol) and $Na_2CO_3$ (44 mg, 0.415 mmol) in dioxane (0.8 mL) and $H_2O$ (0.2 mL) was added Pd(dppf)$Cl_2$·$CH_2Cl_2$ (11 mg, 0.014 mmol) at room temperature under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EA/EtOH (8/3/1) to afford 50 mg crude product. The residue was purified by reverse flash chromatography with the following conditions: Column: XBridge Prep C18 OBD Column, 30*100 mm, 5 um; Mobile Phase A: Water (10 mmol/l $NH_4HCO_3$), Mobile Phase B: $CH_3CN$; Flow rate: 20 mL/min; Gradient:35 B to 65 B in 8 min; 210/254 nm. This resulted in (3S)—N-[3-[2-(3-hydroxyazetidin-1-yl)-6-(morpholin-4-yl)pyridin-4-yl]-4-methylphenyl]-3-(2,2,2-trifluoroethyl)pyrrolidine-1-carboxamide (33 mg, 46%) as an off-white solid. MS ESI calculated for $C_{26}H_{32}F_3N_5O_3$ [M+H]$^+$. 519.25, found 520.15. $^1$H NMR (400 MHz, DMSO-$d_6$) δ 8.12 (s, 1H), 7.45-7.42 (m, 1H), 7.34-7.33 (m, 1H), 7.12-7.10 (m, 1H), 5.93 (s, 1H), 5.61-5.57 (m, 2H), 4.56-4.52 (m, 1H), 4.12-4.08 (m, 2H), 3.69-3.61 (m, 7H), 3.59-3.50 (m, 1H), 3.41-3.39 (m, 4H), 3.31-3.27 (m, 1H), 3.04-3.00 (m, 1H), 2.47-2.38 (m, 2H), 2.16 (s, 3H), 2.10-2.08 (m, 1H), 1.71-1.63 (m, 1H), 1.24 (m, 1H). $^{19}$F NMR (376 MHz, DMSO-$d_6$) δ −63.36 (3F).

Example 17: (3R)—N-[3-(2-[[(2R)-1-hydroxypropan-2-yl]amino]-6-(morpholin-4-yl)pyridin-4-yl)-4-methylphenyl]-3-(trifluoromethoxy)pyrrolidine-1-carboxamide

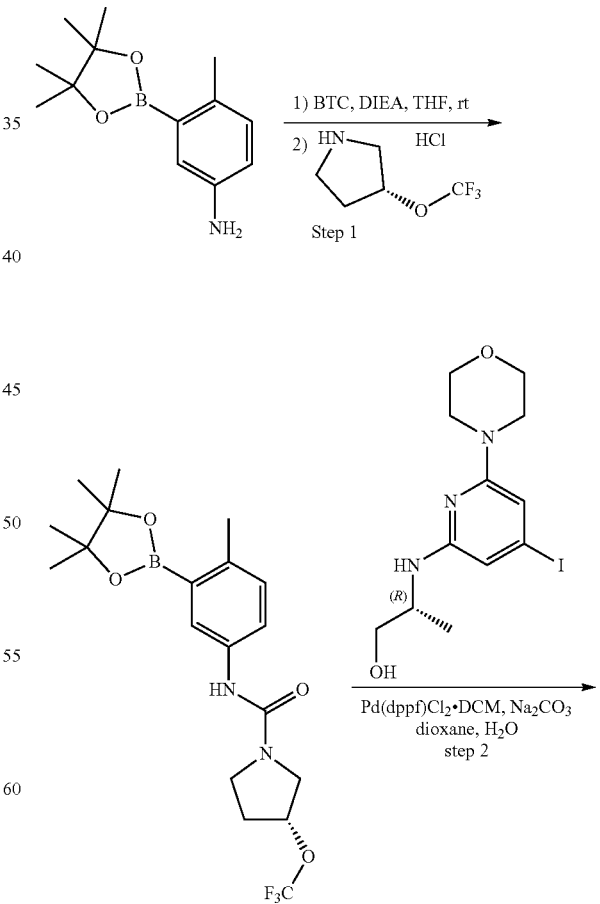

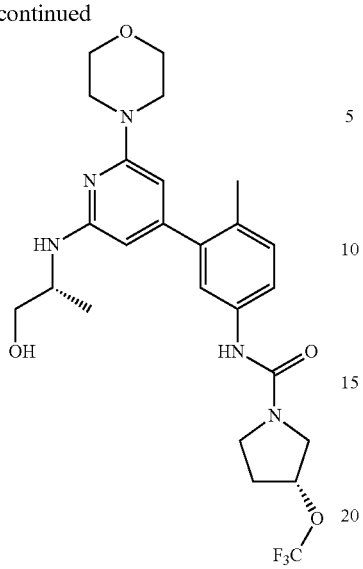

Preparation 17A: (3R)—N-[4-methyl-3-(4,4,5,5-tetramethyl-1,3,2-dioxaborolan-2-yl)phenyl]-3-(trifluoromethoxy)pyrrolidine-1-carboxamide

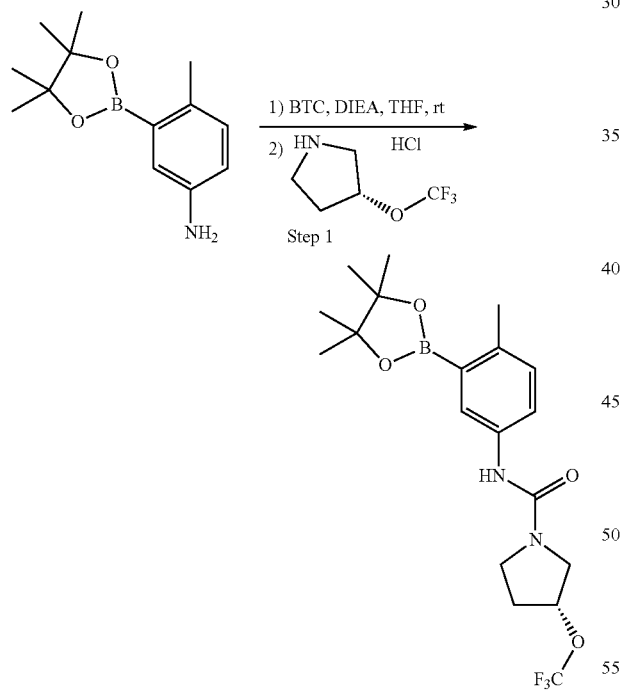

To a stirred solution of (3R)-3-(trifluoromethoxy)pyrrolidine hydrochloride (150 mg, 0.64 mmol) and DIEA (415.80 mg, 3.22 mmol) in THF (5 mL) was added triphosgene (76 mg, 0.26 mmol,) at room temperature. The resulting mixture was stirred for 30 min at room temperature. To this was added (3R)-3-(trifluoromethoxy)pyrrolidine hydrochloride (136 mg, 0.708 mmol). The solution was stirred for 1 h at room temperature. The resulting mixture was concentrated under vacuum. The residue was purified by silica gel column chromatography, eluted with EA/PE (0~60%) to afford (3R)—N-[4-methyl-3-(4,4,5,5-tetramethyl-1,3,2-dioxaborolan-2-yl)phenyl]-3-(trifluoromethoxy)pyrrolidine-1-carboxamide (250 mg, 94%) as an off-white solid. MS ESI calculated for $C_{19}H_{26}BF_3N_2O_4$ [M+H]$^+$, 415.19, found 415.25. $^1$H NMR (400 MHz, Chloroform-d) δ 7.73-7.71 (m, 1H), 7.46-7.45 (m, 1H), 7.16-7.14 (m, 1H), 6.14 (s, 1H), 4.95-4.92 (m, 1H), 3.80-3.71 (m, 2H), 3.64-3.61 (m, 2H), 2.51 (s, 3H), 2.37-2.20 (m, 2H), 1.37 (s, 12H). $^{19}$F NMR (376 MHz, Chloroform-d) δ −58.70 (3F).

Example 17: (3R)—N-[3-(2-[[(2R)-1-hydroxypropan-2-yl]amino]-6-(morpholin-4-yl)pyridin-4-yl)-4-methylphenyl]-3-(trifluoromethoxy)pyrrolidine-1-carboxamide

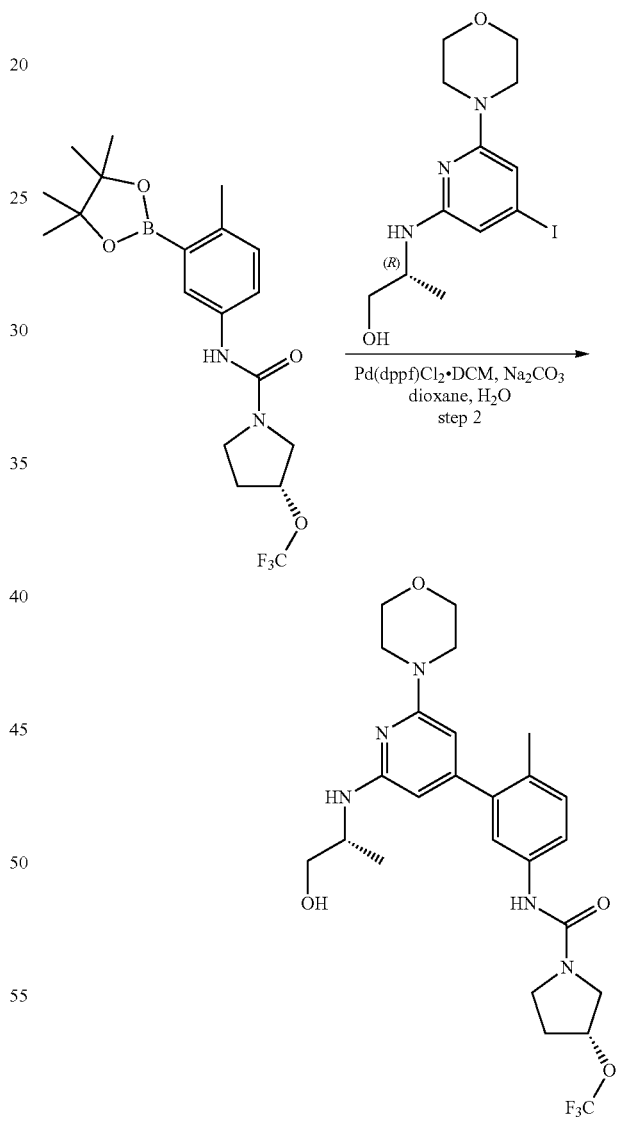

To a stirred solution of (2R)-2-[[4-iodo-6-(morpholin-4-yl)pyridin-2-yl]amino]propan-1-ol (109 mg, 0.300 mmol) in dioxane (2 mL) and H$_2$O (0.2 mL) were added (3R)—N-[4-methyl-3-(4,4,5,5-tetramethyl-1,3,2-dioxaborolan-2-yl)phenyl]-3-(trifluoromethoxy)pyrrolidine-1-carboxamide (149 mg, 0.360 mmol), Na$_2$CO$_3$ (191 mg, 0.900 mmol) and Pd(dppf)Cl₂CH₂Cl₂ (25 mg, 0.030 mmol) at room temperature under nitrogen atmosphere. The resulting mixture was stirred for 1 h at 80° C. under nitrogen atmosphere. The resulting mixture was filtered, the filter cake was washed with EtOAc (3×10 mL). The filtrate was concentrated under reduced pressure. The residue was purified by silica gel column chromatography, eluted with EtOAc in PE (0-82%) to afford crude product as a brown solid. The crude product (201 mg) was purified by Prep-HPLC with the following conditions: Column: Atlantis Prep T3 OBD Column, 19*250 mm 10 u; Mobile Phase A: Water (0.1% FA), Mobile Phase B: CH₃CN; Flow rate: 20 mL/min; Gradient:25 B to 50 B in 6 min; 210/254 nm to afford (3R)—N-[3-(2-[[(2R)-1-hydroxypropan-2-yl]amino]-6-(morpholin-4-yl)pyridin-4-yl)-4-methylphenyl]-3-(trifluoromethoxy)pyrrolidine-1-carboxamide (83 mg, 53%) as an off-white solid. MS ESI calculated for $C_{25}H_{33}F_3N_5O_4$ [M+H]⁺, 524.25, 526.25, found 524.10, 526.10. ¹H NMR (300 MHz, DMSO-d₆) δ 8.24 (s, 1H), 7.47-7.34 (m, 2H), 7.12 (d, J=8.4 Hz, 1H), 5.98 (d, J=7.7 Hz, 1H), 5.77 (s, 2H), 5.16 (s, 1H), 4.65 (s, 1H), 3.90 (t, J=6.5 Hz, 1H), 3.82-3.59 (m, 7H), 3.55-3.37 (m, 6H), 2.18 (s, 6H), 1.14 (d, J=6.6 Hz, 3H).

Example 18: N-[3-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide

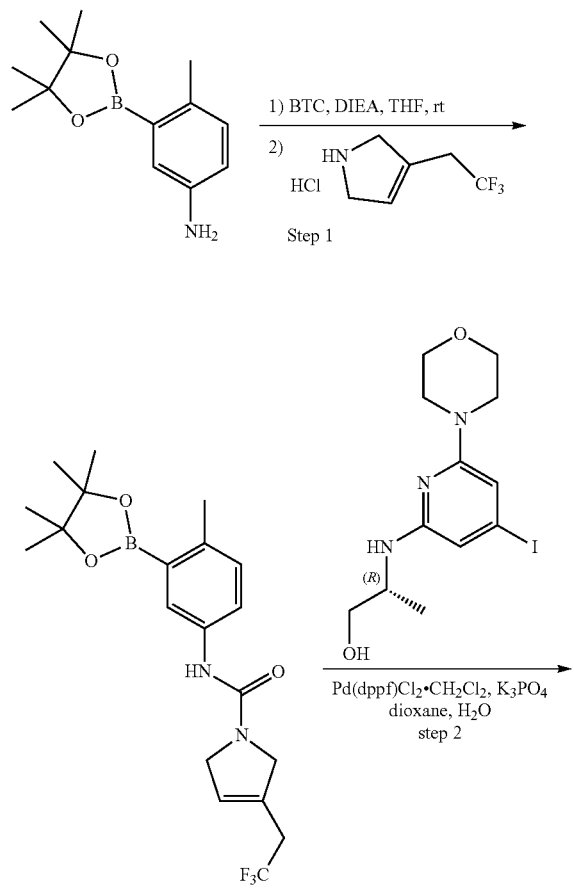

Preparation 18A: N-[4-methyl-3-(4,4,5,5-tetramethyl-1,3,2-dioxaborolan-2-yl)phenyl]-3-(2,2,2-trifluoroethyl)-2,5-dihydropyrrole-1-carboxamide

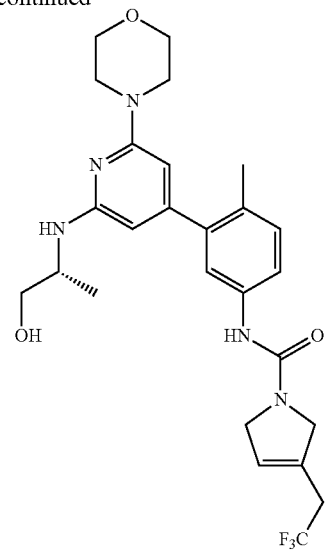

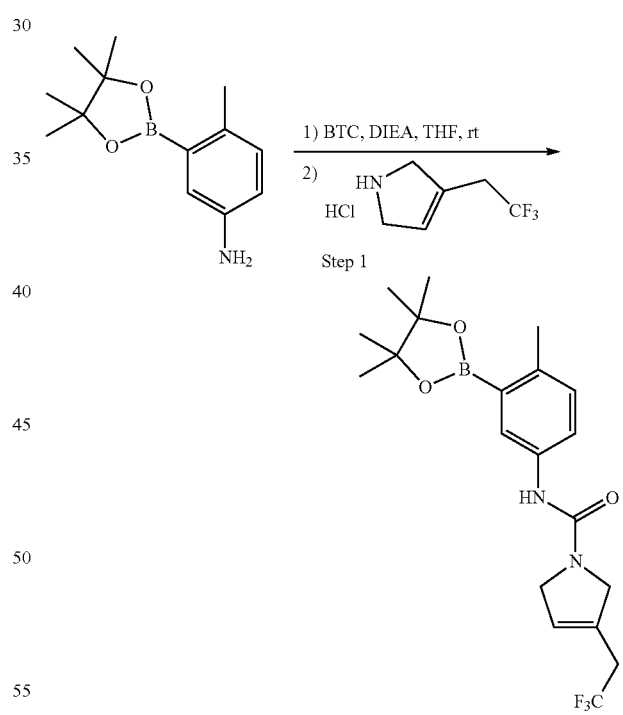

To a stirred mixture of 4-methyl-3-(4,4,5,5-tetramethyl-1,3,2-dioxaborolan-2-yl)aniline (68 mg, 0.292 mmol, 1.00 equiv) in THF (4 mL) were added DIEA (188 mg, 1.458 mmol), Triphosgene (35 mg, 0.117 mmol) at room temperature. The resulting mixture was stirred for 0.5 h at room temperature. To this was added 3-(2,2,2-trifluoroethyl)-2,5-dihydro-1H-pyrrole hydrochloride (60 mg, 0.321 mmol) in THF (3 mL) was dropwised at room temperature. The resulting mixture was stirred for 2 h at room temperature. The resulting mixture was diluted with MeOH (10 mL) and concentrated under vacuum. The residue was purified by silica gel column chromatography, eluted with hexane/(EtOAc:EtOH=3:1)(1:1) to afford N-[4-methyl-3-(4,4,5,5-tetramethyl-1,3,2-dioxaborolan-2-yl)phenyl]-3-(2,2,2-trifluoroethyl)-2,5-dihydropyrrole-1-carboxamide (100 mg, 84%) as a light brown oil. MS ESI calculated for $C_{20}H_{26}BF_3N_2O_3$ [M+H]$^+$, 411.20, found 411.20. $^1$H NMR (300 MHz, DMSO-d$_6$) δ 8.22 (s, 1H), 7.69 (d, J=2.4 Hz, 1H), 7.64 (d, J=8.4 Hz, 1H), 7.06 (d, J=8.4 Hz, 1H), 5.95 (s, 1H), 4.21 (s, 4H), 3.32 (q, J=11.7 Hz, 2H), 2.40 (s, 3H), 1.31 (s, 12H).

Example 18: N-[3-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide

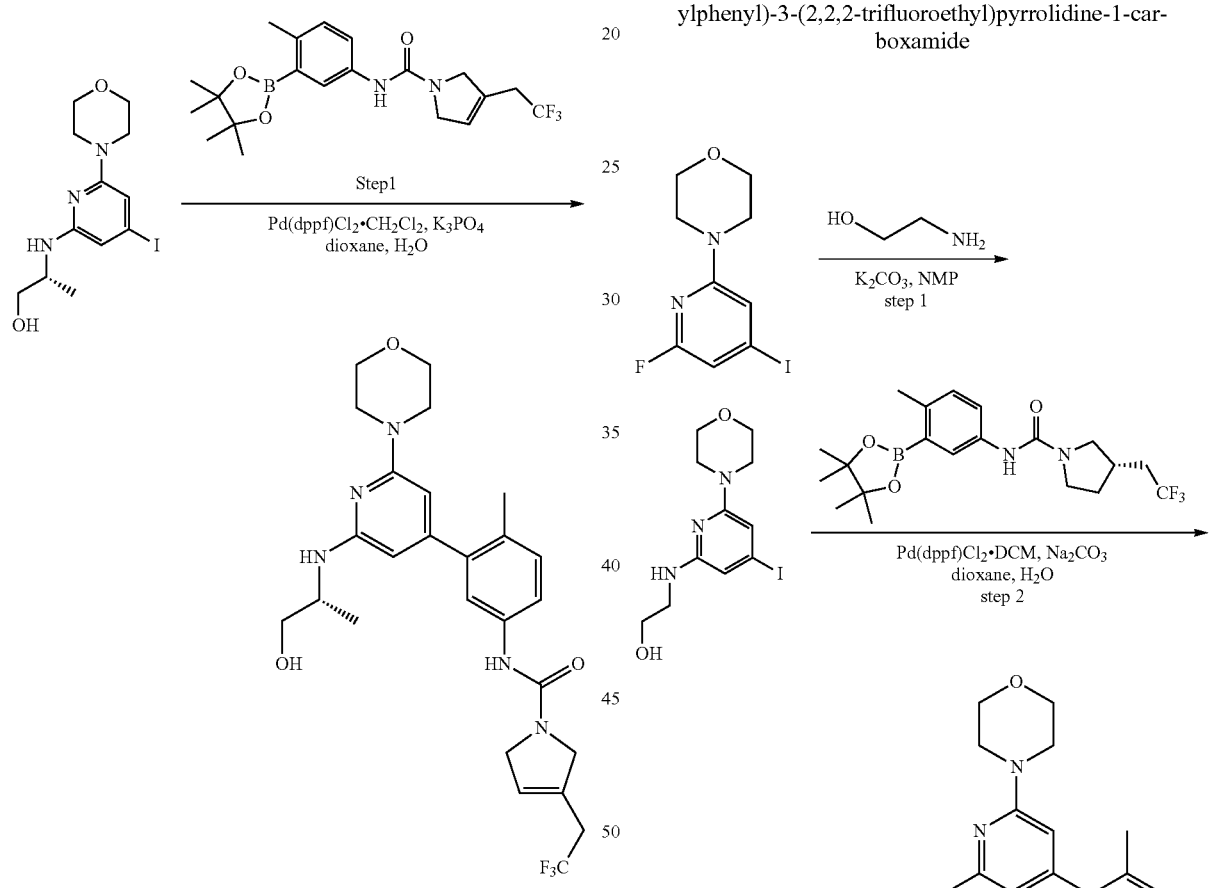

To a solution of (2R)-2-[[4-iodo-6-(morpholin-4-yl)pyridin-2-yl]amino]propan-1-ol (132 mg, 0.36 mmol) and N-[4-methyl-3-(4,4,5,5-tetramethyl-1,3,2-dioxaborolan-2-yl)phenyl]-3-(2,2,2-trifluoroethyl)-2,5-dihydropyrrole-1-carboxamide (149 mg, 0.363 mmol) in 1,4-dioxane (2 mL) and H$_2$O (0.2 mL) were added Pd(dppf)Cl$_2$·CH$_2$Cl$_2$ (30 mg, 0.030 mmol) and K$_3$PO$_4$ (231 mg, 1.090 mmol). After stirring for 1 h at 80° C. under a nitrogen atmosphere, the resulting mixture was concentrated under reduced pressure. The residue was purified by silica gel column chromatography, eluted with EtOAc in PE (0-50%) to afford the crude product. The crude product was purified by Prep-HPLC with the following conditions: Column: Spherical C18, 19×150 mm 5 um; Mobile Phase A: Water (0.1% FA), Mobile Phase B: CH$_3$CN: Flow rate: 20 mL/min; Gradient:30% B to 60% B in 4.3 min; Detector: UV 210 & 254 nm to afford N-[3-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide (82 mg, 44%) as a light pink solid. MS ESI calculated for $C_{26}H_{34}F_3N_5O_3$ [M+H]$^+$, 520.25, found 520.10. $^1$H NMR (400 MHz, DMSO-d$_6$) δ 8.19 (s, 1H), 7.43 (dd, J=8.2, 2.3 Hz, 1H), 7.35 (d, J=2.3 Hz, 1H), 7.11 (d, J=8.3 Hz, 1H), 6.00-5.91 (m, 2H), 5.76 (d, J=1.6 Hz, 2H), 4.64 (t, J=5.5 Hz, 1H), 4.18 (S, 4H) 3.89 (p, J=6.5 Hz, 1H), 3.72-3.64 (m, 4H), 3.50 (dt, J=10.0, 5.0 Hz, 1H), 3.37 (t, J=4.9 Hz, 4H), 3.32-3.25 (m, 2H), 2.17 (s, 3H), 1.13 (d, J=6.5 Hz, 3H). $^{19}$F NMR (376 MHz, DMSO-d$_6$) δ −63.28 (3F)

Example 19: (3S)—N-(3-[2-[(2-hydroxyethyl)amino]-6-(morpholin-4-yl)pyridin-4-yl]-4-methylphenyl)-3-(2,2,2-trifluoroethyl)pyrrolidine-1-carboxamide

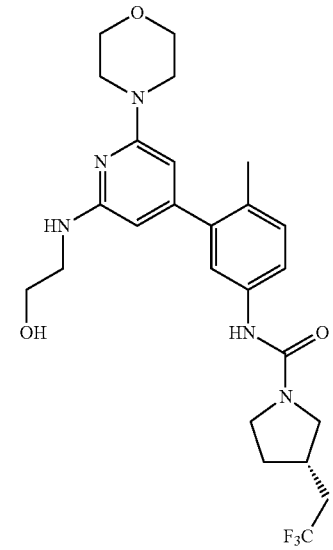

Preparation 19A: 2-[[4-iodo-6-(morpholin-4-yl)pyridin-2-yl]amino]ethanol

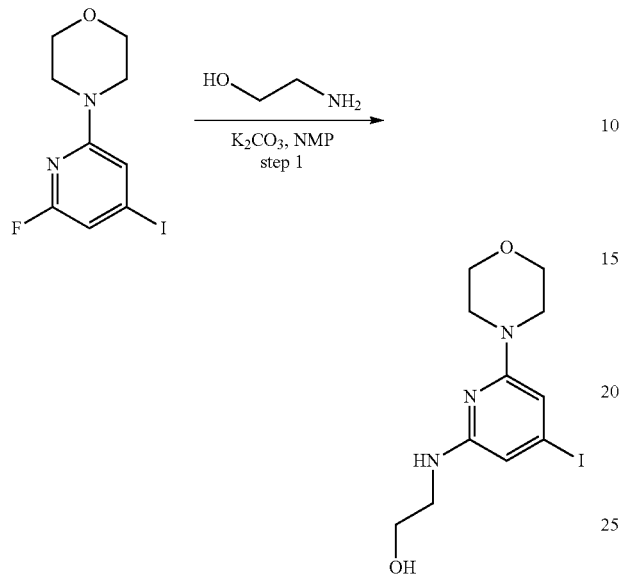

To a stirred mixture of 4-(6-fluoro-4-iodopyridin-2-yl)morpholine (2.00 g, 6.492 mmol) and K$_2$CO$_3$ (1.79 g, 12.983 mmol) in NMP (20 mL) was added ethanolamine (595 mg, 9.737 mmol) at room temperature. The resulting mixture was stirred for 16 h at 150° C. The mixture was allowed to cool down to room temperature. The reaction was quenched with Water (20 mL) at room temperature. The resulting mixture was extracted with EtOAc (3×20 mL). The combined organic layers were washed with brine (1×20 mL), dried over anhydrous Na$_2$SO$_4$. After filtration, the filtrate was concentrated under reduced pressure. The residue was purified by silica gel column chromatography, eluted with PE/EtOAc (1:1) to afford 2-[[4-iodo-6-(morpholin-4-yl)pyridin-2-yl]amino]ethanol (2 g, 88%) as a yellow oil. MS ESI calculated for C$_{15}$H$_{20}$BrN$_3$O$_2$ [M+H]$^+$350.03 found 350.00. $^1$H NMR (300 MHz, DMSO-d$_6$) δ 6.23 (m, 2H), 4.64 (m, 1H), 3.66 (t, J=4.6 Hz, 4H), 2.72 (d, J=1.2 Hz, 8H).

Example 19: (3S)—N-(3-[2-[(2-hydroxyethyl)amino]-6-(morpholin-4-yl)pyridin-4-yl]-4-methylphenyl)-3-(2,2,2-trifluoroethyl)pyrrolidine-1-carboxamide

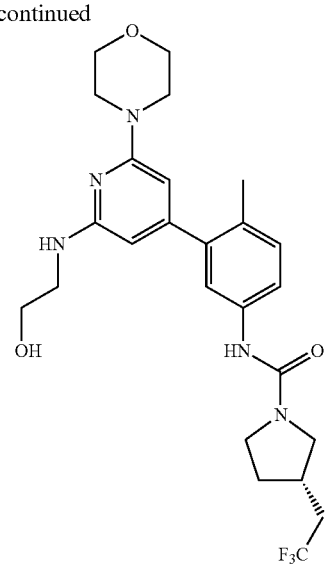

To a stirred mixture of 2-[[4-iodo-6-(morpholin-4-yl)pyridin-2-yl]amino]ethanol (150 mg, 0.430 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (142 mg, 0.344 mmol) in dioxane (4 mL) and H$_2$O (1 mL) were added Na$_2$CO$_3$ (137 mg, 1.289 mmol) and Pd(dppf)Cl$_2$CH$_2$Cl$_2$ (35 mg, 0.043 mmol) in portions at 60° C. under nitrogen atmosphere. The reaction was quenched with (20 mL) Water at room temperature. The resulting mixture was extracted with EtOAc (3×60 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EtOAc (1:1) to afford (3S)—N-(3-[2-[(2-hydroxyethyl)amino]-6-(morpholin-4-yl)pyridin-4-yl]-4-methylphenyl)-3-(2,2,2-trifluoroethyl)pyrrolidine-1-carboxamide (95 mg, 43%) as a light green solid. MS ESI calculated for C$_{15}$H$_{20}$BrN$_3$O$_2$ [M+H]$^+$508.25 found 508.00. $^1$H NMR (400 MHz, DMSO-d$_6$) δ 8.11 (s, 1H), 7.49-7.27 (m, 2H), 7.09 (d, J=8.4 Hz, 1H), 6.21 (s, 1H), 5.76 (s, 2H), 4.66 (t, J=5.5 Hz, 1H), 3.68 (s, 3H), 3.53 (d, J=7.4 Hz, 3H), 3.38 (s, 9H), 3.02 (t, J=9.4 Hz, 1H), 2.44 (s, 3H), 2.12 (d, J=29.5 Hz, 4H), 1.66 (t, J=10.6 Hz, 1H).

Example 20: N-(3-[2-[(2-hydroxyethyl)amino]-6-(morpholin-4-yl)pyridin-4-yl]-4-methylphenyl)-3-(2,2,2-trifluoroethyl)-2,5-dihydropyrrole-1-carboxamide

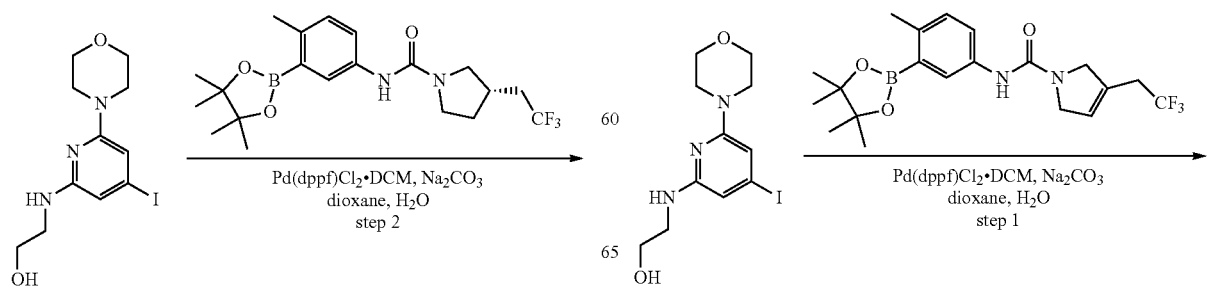

211
-continued

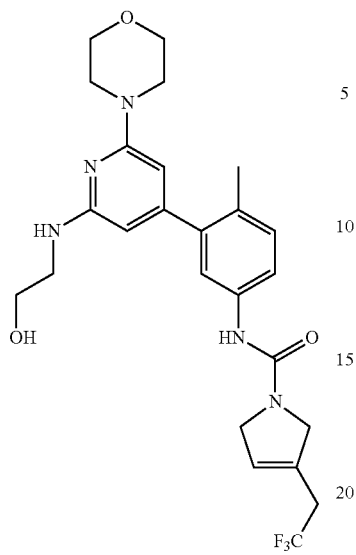

To a stirred mixture of 2-[[4-iodo-6-(morpholin-4-yl)pyridin-2-yl]amino]ethanol (150 mg, 0.430 mmol) and N-[4-methyl-3-(4,4,5,5-tetramethyl-1,3,2-dioxaborolan-2-yl)phenyl]-3-(2,2,2-trifluoroethyl)-2,5-dihydropyrrole-1-carboxamide (141 mg, 0.344 mmol) in dioxane (4 mL) and H₂O (1 mL) were added Na₂CO₃ (137 mg, 1.289 mmol) and Pd(dppf)Cl₂CH₂Cl₂ (35 mg, 0.043 mmol) in portions at 60° C. under nitrogen atmosphere. The reaction was quenched by the addition of Water (20 mL) at room temperature. The resulting mixture was extracted with EtOAc (3×60 mL). The combined organic layers were washed with brine (3×10 mL), dried over anhydrous Na₂SO₄. After filtration, the filtrate was concentrated under reduced pressure. The residue was purified by silica gel column chromatography, eluted with PE/EtOAc (1:1) to afford N-(3-[2-[(2-hydroxyethyl)amino]-6-(morpholin-4-yl)pyridin-4-yl]-4-methylphenyl)-3-(2,2,2-trifluoroethyl)-2,5-dihydropyrrole-1-carboxamide (97 mg, 44%) as a light green solid. MS ESI calculated for $C_{25}H_{30}F_3N_5O_3$ [M+H]⁺506.23 found 506.00. ¹H NMR (400 MHz, DMSO-d₆) δ 8.20 (s, 1H), 7.49-7.30 (m, 2H), 7.11 (d, J=8.4 Hz, 1H), 6.23 (s, 1H), 5.94 (s, 1H), 5.77 (s, 2H), 4.66 (s, 1H), 4.20 (s, 4H), 3.68 (s, 4H), 3.54 (s, 2H), 3.36 (d, J=18.2 Hz, 8H), 2.17 (s, 3H).

Example 21: (3S)—N-[3-[2-(3-hydroxyazetidin-1-yl)-6-(morpholin-4-yl)pyrimidin-4-yl]-4-methylphenyl]-3-(2,2,2-trifluoroethyl)pyrrolidine-1-carboxamide

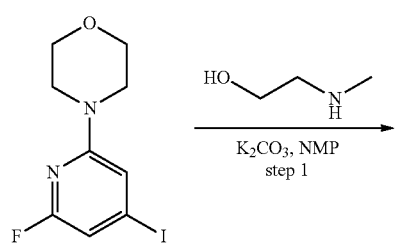

212
-continued

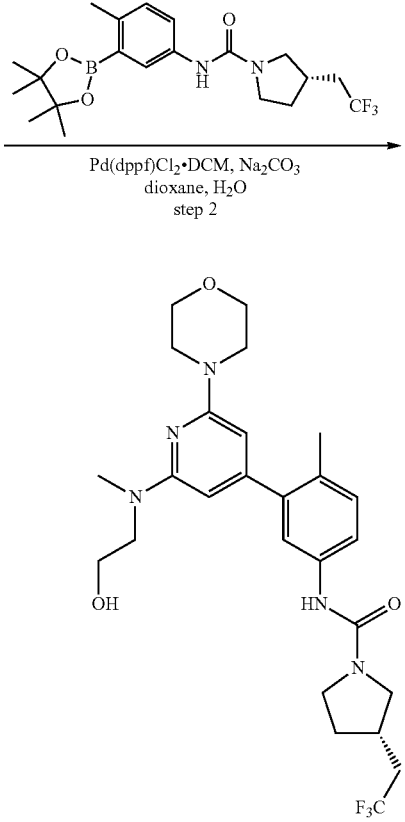

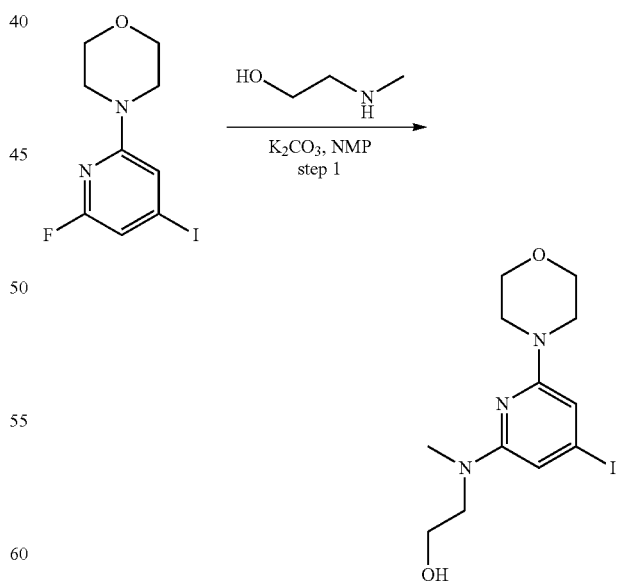

Preparation 21A: 2-[[4-iodo-6-(morpholin-4-yl)pyridin-2-yl](methyl)amino]ethanol To a stirred mixture of 4-(6-fluoro-4-iodopyridin-2-yl)morpholine (500 mg, 1.623 mmol) and K₂CO₃ (449 mg, 3.246 mmol) in NMP (5 mL) was added methylethanolamine (183 mg, 2.434 mmol) at room temperature. The resulting mixture was stirred for 16 h at 150° C. The mixture was allowed to cool down to room temperature. The reaction was quenched with water (20 mL) at room temperature. The resulting mixture was extracted with EtOAc (3×20 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EtOAc (1/1) to afford 2-[[4-iodo-6-(morpholin-4-yl)pyridin-2-yl](methyl)amino]ethanol (480 mg, 81%) as a yellow oil. MS ESI calculated for $C_{12}H_{18}IN_3O_2$ $[M+H]^+$, 363.95, found 363.95. $^1H$ NMR (300 MHz, chloroform-d) δ 6.34-6.26 (m, 2H), 3.80 (m, 6H), 3.70 (dd, J=5.5, 4.4 Hz, 2H), 3.47-3.36 (m, 4H), 3.02 (s, 3H).

Example 21: (3S)—N-[3-[2-(3-hydroxyazetidin-1-yl)-6-(morpholin-4-yl)pyrimidin-4-yl]-4-methylphenyl]-3-(2,2,2-trifluoroethyl)pyrrolidine-1-carboxamide

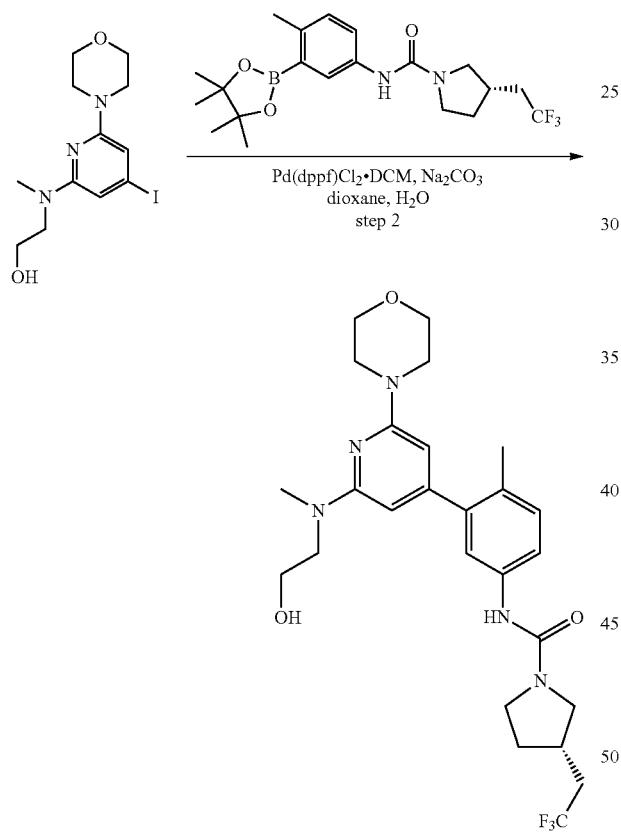

To a stirred solution of 2-[[4-iodo-6-(morpholin-4-yl)pyridin-2-yl](methyl)amino]ethanol (200 mg, 0.551 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (227 mg, 0.551 mmol) in 1,4-dioxane (2 mL) and $H_2O$ (0.5 mL) were added $Na_2CO_3$ (175 mg, 1.652 mmol) and Pd(dppf)Cl$_2$CH$_2$Cl$_2$ (40 mg, 0.055 mmol) at room temperature under nitrogen atmosphere. The resulting mixture was stirred for 16 h at 70° C. under nitrogen atmosphere. The mixture was allowed to cool down to room temperature. The reaction was quenched by the addition of Water (10 mL) at room temperature. The resulting mixture was extracted with EtOAc (3×10 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EtOAc/EtOH (4/3/1) to afford (3S)—N-(3-[2-[(2-hydroxyethyl)(methyl)amino]-6-(morpholin-4-yl)pyridin-4-yl]-4-methylphenyl)-3-(2,2,2-trifluoroethyl)pyrrolidine-1-carboxamide (172 mg, 60%) as a light brown solid. MS ESI calculated for $C_{26}H_{34}F_3N_5O_3$ $[M+H]^+$, 522.15, found 522.15. $^1H$ NMR (400 MHz, DMSO-d$_6$) δ 8.12 (s, 1H), 7.44 (dd, J=8.3, 2.3 Hz, 1H), 7.34 (d, J=2.3 Hz, 1H), 7.11 (d, J=8.4 Hz, 1H), 5.84 (d, J=13.6 Hz, 2H), 4.68-4.59 (m, 1H), 3.69 (d, J=5.2 Hz, 5H), 3.61-3.48 (m, 5H), 3.40 (t, J=4.7 Hz, 4H), 3.03 (s, 4H), 2.44 (t, J=10.4 Hz, 3H), 2.17 (s, 3H), 2.09 (s, 1H), 2.01 (s, 1H), 1.73-1.60 (m, 1H). $^{19}F$ NMR (376 MHz, DMSO-d$_6$) δ -63.36 (3F).

Example 22: (3R)—N-(3-[2-[(2-hydroxyethyl)amino]-6-(morpholin-4-yl)pyridin-4-yl]-4-methylphenyl)-3-(trifluoromethoxy)pyrrolidine-1-carboxamide

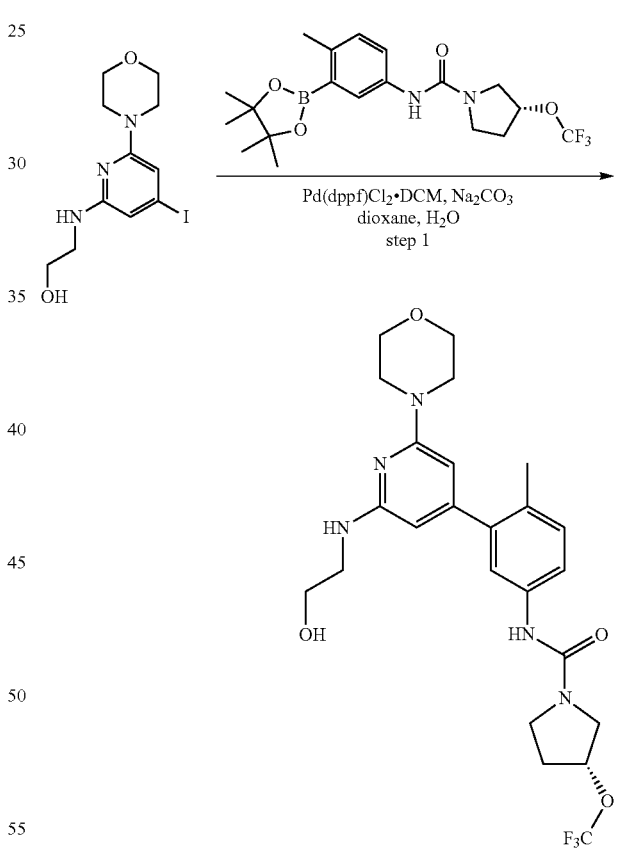

To a stirred mixture of 2-[[4-iodo-6-(morpholin-4-yl)pyridin-2-yl]amino]ethanol (150 mg, 0.430 mmol) and (3R)—N-[4-methyl-3-(4,4,5,5-tetramethyl-1,3,2-dioxaborolan-2-yl)phenyl]-3-(trifluoromethoxy)pyrrolidine-1-carboxamide (142 mg, 0.344 mmol) in dioxane (4 ml) and $H_2O$ (1 mL) were added $Na_2CO_3$ (137 mg, 1.289 mmol) and Pd(dppf)Cl$_2$CH$_2$Cl$_2$ (35 mg, 0.043 mmol) in portions at 60° C. under nitrogen atmosphere. The reaction was quenched by the addition of Water (20 mL) at room temperature. The resulting mixture was extracted with EtOAc (3×60 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EtOAc (1/1) to afford (3R)—N-(3-[2-[(2-hydroxyethyl)amino]-6-(morpholin-4-yl)pyridin-4-yl]-4-methylphenyl)-3-(trifluoromethoxy)pyrrolidine-1-carboxamide (74.3 mg, 34%) as a light green solid. MS ESI calculated for C$_{24}$H$_{30}$F$_3$N$_5$O$_4$ [M+H]$^+$, 510.22 found 510.00. $^1$H NMR (400 MHz, DMSO-d$_6$) δ 8.24 (s, 1H), 7.53-7.24 (m, 2H), 7.11 (d, J=8.3 Hz, 1H), 6.22 (t, J=5.9 Hz, 1H), 5.77 (s, 2H), 5.15 (s, 1H), 4.66 (t, J=5.5 Hz, 1H), 3.78-3.62 (m, 5H), 3.56 (dd, J=14.2, 8.1 Hz, 3H), 3.46 (d, J=8.9 Hz, 1H), 3.38 (s, 3H), 3.34 (s, 3H), 3.31 (d, J=5.9 Hz, 1H), 2.20-2.00 (m, 5H).

Example 23: (3R)—N-[3-(2-[[(2R)-2-hydroxypropyl]amino]-6-(morpholin-4-yl)pyridin-4-yl)-4-methylphenyl]-3-(trifluoromethoxy)pyrrolidine-1-carboxamide saturated brine (3×50 mL), dried over anhydrous Na$_2$SO$_4$. After filtration, the filtrate was concentrated under reduced pressure. The residue was purified by silica gel column chromatography, eluted with PE/EA/EtOH (8/3/1) to afford 125 mg crude product. The residue was purified by reverse flash chromatography with the following conditions: Column: XBridge Prep C18 OBD Column, 19×150 mm 5 um; Mobile Phase A: water (10 mmol/l NH$_4$HCO$_3$), Mobile Phase B: CH$_3$CN; Flow rate: 20 mL/min; Gradient:40 B to 75 B in 4.3 min; 210/254 nm. This resulted in (3R)—N-[3-(2-[[(2R)-2-hydroxypropyl]amino]-6-(morpholin-4-yl)pyridin-4-yl)-4-methylphenyl]-3-(trifluoromethoxy)pyrrolidine-1-carboxamide (102 mg, 54%) as a light green solid. MS ESI calculated for C$_{25}$H$_{32}$F$_3$N$_5$O$_4$ [M+H]$^+$, 524.24, found 524.15. $^1$H NMR (400 MHz, DMSO-d$_6$) δ 8.22 (s, 1H), 7.42-7.33 (m, 2H), 7.12-7.09 (m, 1H), 6.20-6.15 (m, 1H), 5.83-5.76 (m, 2H), 5.14 (s, 1H), 4.69-4.67 (m, 1H), 3.83-3.76 (m, 1H), 3.67-3.55 (m, 7H), 3.48-3.37 (m, 5H), 3.20-3.14 (m, 2H), 2.24-2.16 (m, 5H), 1.09-1.07 (m, 3H). $^{19}$F NMR (376 MHz, DMSO-d$_6$) δ −56.69 (3F).

Example 24: N-[3-(2-[[(2R)-2-hydroxypropyl]amino]-6-(morpholin-4-yl)pyridin-4-yl)-4-methylphenyl]-3-(2,2,2-trifluoroethyl)-2,5-dihydropyrrole-1-carboxamide

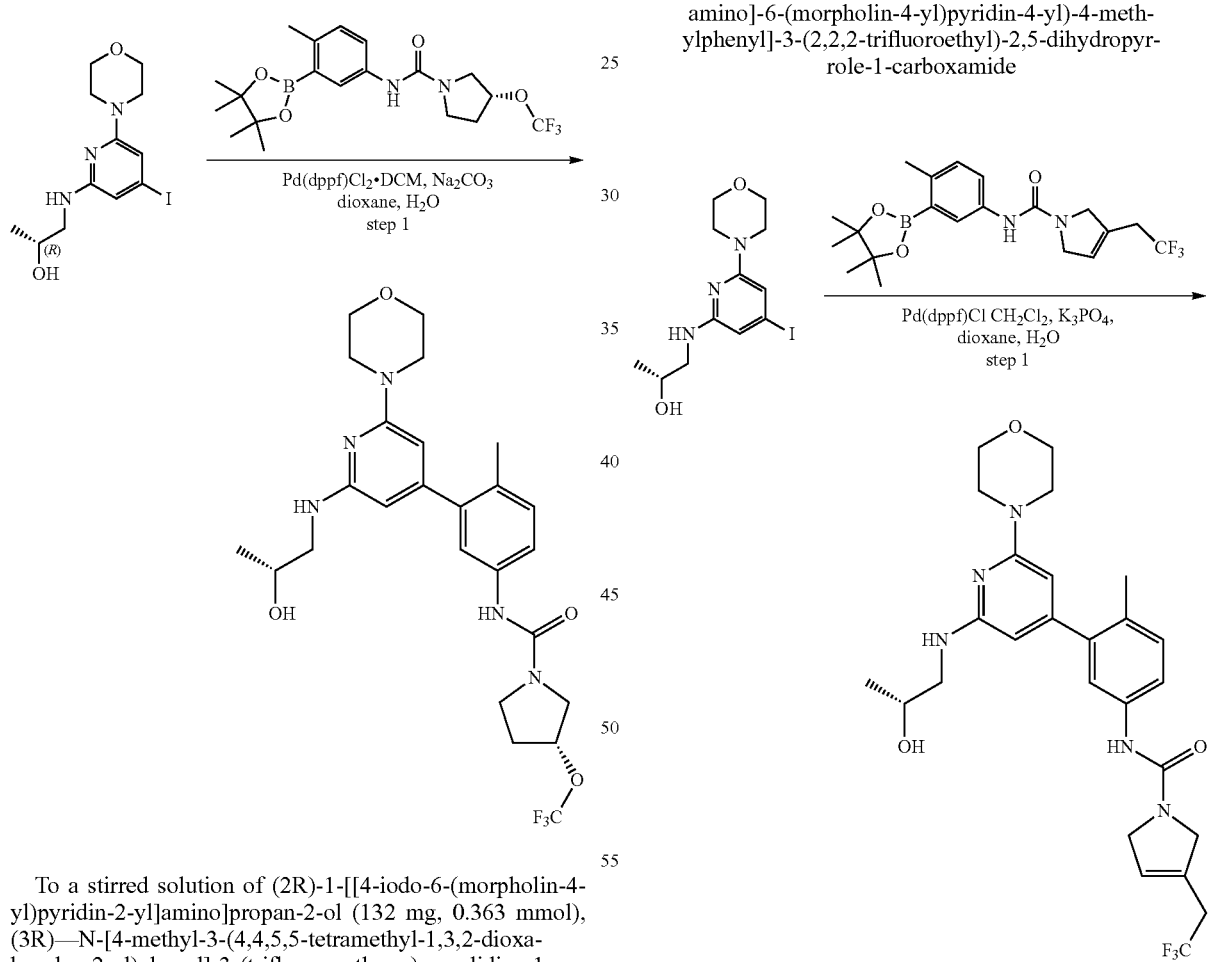

To a stirred solution of (2R)-1-[[4-iodo-6-(morpholin-4-yl)pyridin-2-yl]amino]propan-2-ol (132 mg, 0.363 mmol), (3R)—N-[4-methyl-3-(4,4,5,5-tetramethyl-1,3,2-dioxaborolan-2-yl)phenyl]-3-(trifluoromethoxy)pyrrolidine-1-carboxamide (151 mg, 0.363 mmol) and Na$_2$CO$_3$ (116 mg, 1.090 mmol) in dioxane (0.8 mL) and water (0.2 mL) was added Pd(dppf)Cl$_2$·CH$_2$Cl$_2$ (30 mg, 0.036 mmol) at room temperature under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with A mixture of (2R)-1-[[4-iodo-6-(morpholin-4-yl)pyridin-2-yl]amino]propan-2-ol (133 mg, 0.366 mmol), N-[4-methyl-3-(4,4,5,5-tetramethyl-1,3,2-dioxaborolan-2-yl)phenyl]-3-(2,2,2-trifluoroethyl)-2,5-dihydropyrrole-1-carboxamid (150 mg, 0.370 mmol), Pd(dppf)Cl$_2$·CH$_2$Cl$_2$ (30 mg, 0.040 mmol) and K$_3$PO$_4$ (233 mg, 1.100 mmol) in dioxane (3 mL) and H$_2$O (0.3 mL) was stirred for 2 hour at 80° C. under N₂ atmosphere. The mixture was cooled. The resulting mixture was added water (5 mL) and extracted with EtOAc (3×10 mL). The combined organic layers were washed with water (2×10 mL), dried over anhydrous Na₂SO₄. After filtration, the filtrate was concentrated under reduced pressure. The residue was purified by silica gel column chromatography, eluted with PE/EtOAc (50-100%) to afford the crude product. The residue was purified by Prep-HPLC with the following conditions: Column: X-Bridge Prep C18 OBD Column, 19×150 mm 5 um; mobile phase A: water (10 mmol/L NH₄HCO₃), mobile phase B: ACN; Flow rate: 20 mL/min; Gradient:20 B to 55 B in 4.3 min; 210/254 nm to afford N-[3-(2-[[(2R)-2-hydroxypropyl]amino]-6-(morpholin-4-yl)pyridin-4-yl)-4-methylphenyl]-3-(2,2,2-trifluoroethyl)-2,5-dihydropyrrole-1-carboxamide (97 mg, 51%) as a white solid. MS ESI calculated for C₁₉H₂₅BrN₄O₃ [M+H]⁺, 437.11, found 437.00. ¹H NMR (400 MHz, CDCL3) δ 7.37 (dd, J=8.2, 2.4 Hz, 1H), 7.24 (d, J=2.4 Hz, 1H), 7.18 (d, J=8.2 Hz, 1H), 6.13 (s, 1H), 5.88-5.82 (m, 3H), 4.70 (brs, 1H), 4.32-4.30 (m, 4H), 4.06-3.98 (m, 1H), 3.84-3.81 (m, 4H), 3.54-3.43 (m, 5H), 3.31-3.28 (m, 1H), 3.05-2.98 (m, 2H), 2.24 (s, 3H), 1.25 (d, J=6.3 Hz, 3H).

Example 25: (3S)—N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide

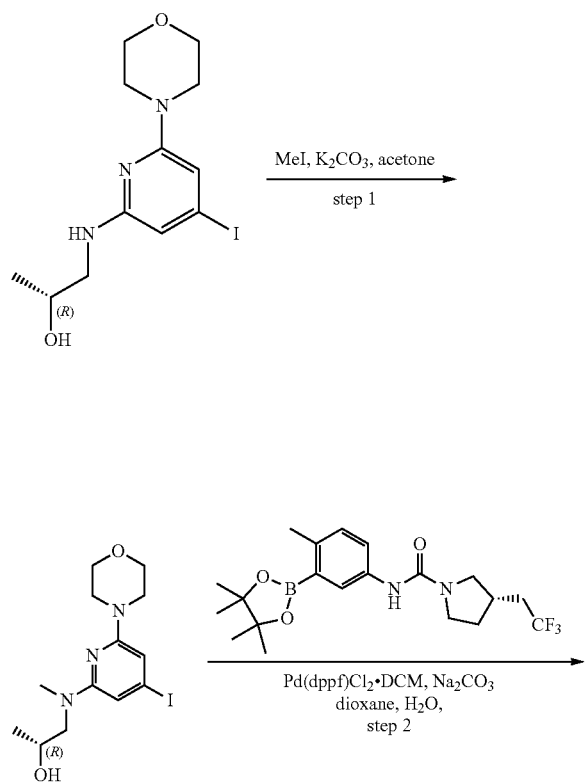

Preparation 25A: (2R)-1-[[4-iodo-6-(morpholin-4-yl)pyridin-2-yl](methyl)amino]propan-2-ol

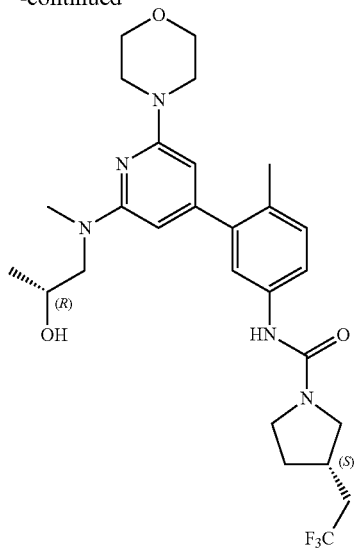

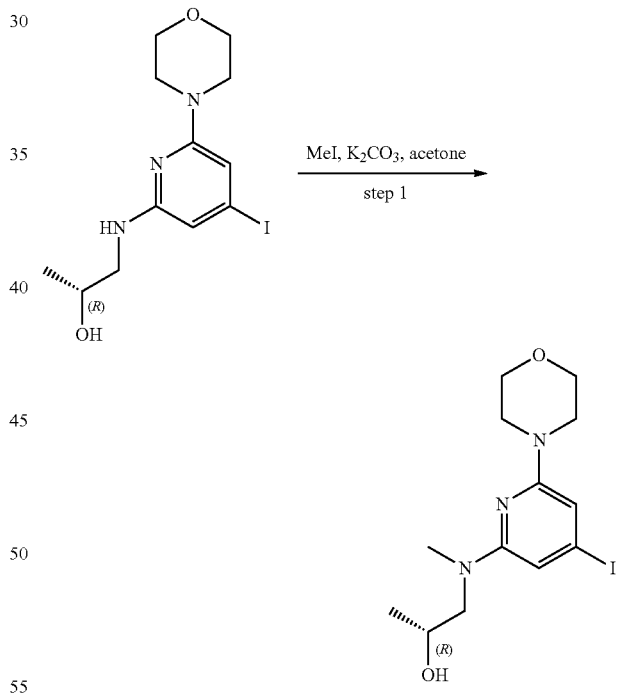

To a stirred solution of (2R)-1-[[4-iodo-6-(morpholin-4-yl)pyridin-2-yl]amino]propan-2-ol (500 mg, 1.377 mmol) and K₂CO₃ (571 mg, 4.130 mmol) in acetone (10 mL) was added methyl iodide (234 mg, 1.652 mmol) at 0° C. under nitrogen atmosphere. The resulting mixture was stirred for 48 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na₂SO₄. After filtration, the filtrate was concentrated under reduced pressure. The residue was purified by silica gel column chromatography, eluted with PE/EtOAc (2/1) to afford (2R)-1-[[4-iodo-6-(morpholin-4-yl)pyridin-2-yl](methyl)amino]propan-2-ol (150 mg, 29%) as an off-white solid. MS ESI calculated for C₁₃H₂₀IN₃O₂ [M+H]⁺, 378.06, found 378.10. ¹H NMR (400 MHz, CDCL₃) δ 6.33-6.30 (m, 2H), 4.16-4.09 (m, 1H), 3.81-3.79 (m, 4H), 1.66-1.61 (m, 1H), 3.48-3.42 (m, 5H), 3.04 (s, 3H), 1.23-1.22 (m, 3H).

Example 25: (3S)—N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide

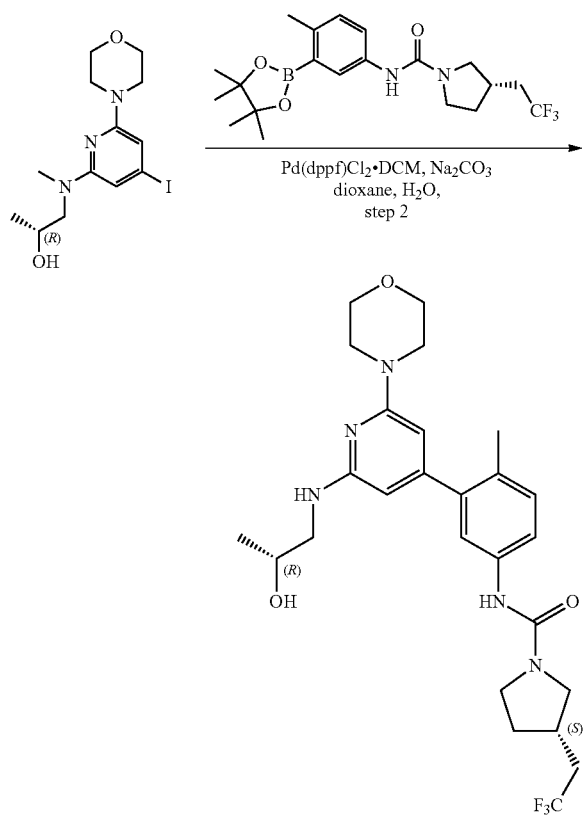

To a stirred solution of (2R)-1-[[4-iodo-6-(morpholin-4-yl)pyridin-2-yl](methyl)amino]propan-2-ol (200 mg, 0.530 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (219 mg, 0.530 mmol) and Na₂CO₃ (169 mg, 1.591 mmol) in dioxane (1.6 mL) and H₂O (0.4 mL) was added Pd(dppf)Cl₂·CH₂Cl₂ (43 mg, 0.053 mmol) at room temperature under nitrogen atmosphere. The resulting mixture was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na₂SO₄. After filtration, the filtrate was concentrated under reduced pressure. The residue was purified by silica gel column chromatography, eluted with PE/EA/EtOH (8/3/1) to afford 70 mg crude product. The residue was purified by reverse flash chromatography with the following conditions: Column: XBridge Prep C18 OBD Column, 19×150 mm 5 um; Mobile Phase A: Water (10 mmol/l NH₄HCO₃), Mobile Phase B: CH₃CN; Flow rate: 20 mL/min; Gradient: 40 B to 70 B in 4.3 min; 210/254 nm. This resulted in (3S)—N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide (144 mg, 51%) as a light green solid. MS ESI calculated for C₂₇H₃₆F₃N₅O₃ [M+H]⁺, 536.28, found 536.20. ¹H NMR (400 MHz, DMSO-d₆) δ 8.11 (s, 1H), 7.44-7.40 (m, 1H), 7.33-7.32 (m, 1H), 7.11-7.08 (m, 1H), 5.84-5.79 (m, 2H), 4.66-4.65 (m, 1H), 3.92-3.86 (m, 1H), 3.69-3.63 (m, 5H), 3.55-3.44 (m, 2H), 3.40-3.37 (m, 4H), 3.29-3.26 (m, 2H), 3.02-2.98 (m, 4H), 2.46-2.39 (m, 3H), 2.15-2.06 (m, 4H), 1.71-1.61 (m, 1H), 1.06-1.04 (m, 3H). ¹⁹F NMR (376 MHz, DMSO-d₆) δ −63.35 (3F).

Example 26: (3S)—N-[3-[2-(3,6-dihydro-2H-pyran-4-yl)-6-[[(2R)-2-hydroxypropyl]amino]pyridin-4-yl]-4-methylphenyl]-3-(2,2,2-trifluoroethyl)pyrrolidine-1-carboxamide

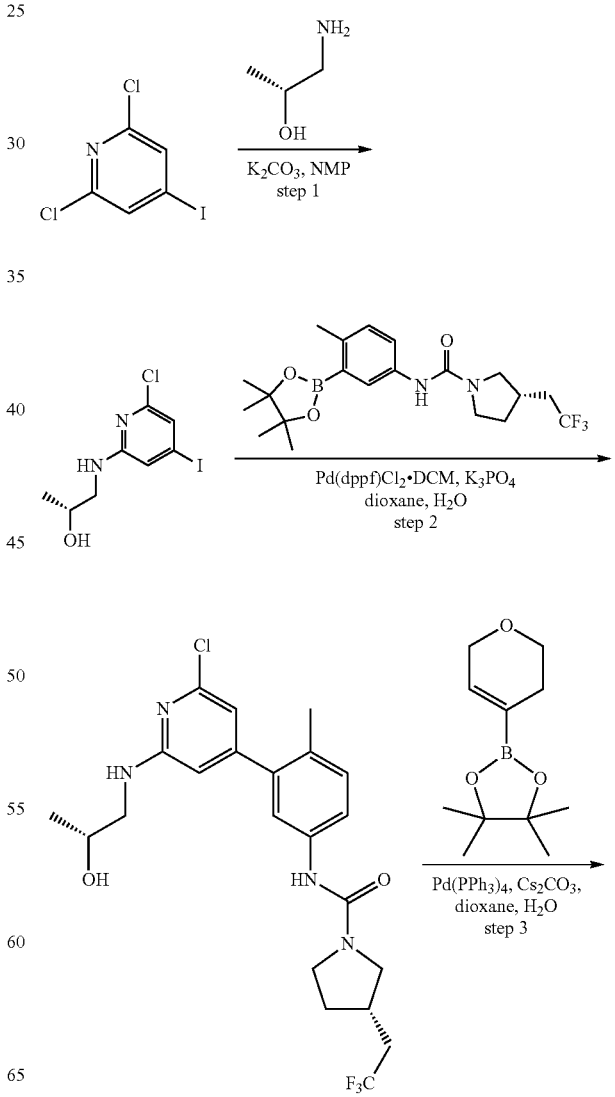

-continued

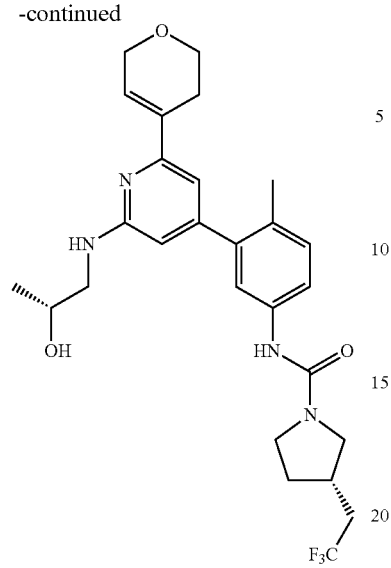

Preparation 26A: (2R)-1-[(6-chloro-4-iodopyridin-2-yl)amino]propan-2-ol

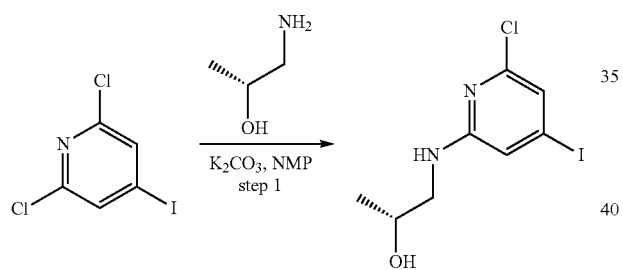

To a stirred solution of 2,6-dichloro-4-iodopyridine (1 g, 3.651 mmol) and $K_2CO_3$ (1 g, 7.302 mmol) in NMP (20 mL) was added (R)-1-amino-2-propanol (274 mg, 3.651 mmol) at room temperature. The part of resulting mixture was stirred for 16 h at 100° C. The reaction was quenched by the addition of water (70 mL). The resulting mixture was extracted with EtOAc (3×150 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EtOAc (2/1) to afford (2R)-1-[(6-chloro-4-iodopyridin-2-yl)amino]propan-2-ol (410 mg, 36%) as a yellow oil. MS ESI calculated for $C_8H_{10}ClIN_2O$ [M+H]$^+$, 312.54, found 312.95. $^1$H NMR (300 MHz, chloroform-d) δ 6.96 (d, J=1.0 Hz, 1H), 6.74 (d, J=1.1 Hz, 1H), 5.31 (s, 1H), 3.46 (dd, J=13.7, 3.1 Hz, 2H), 3.19 (dd, J=13.7, 7.7 Hz, 1H), 1.26 (d, J=6.2 Hz, 3H).

Preparation 26B: (3S)—N-[3-(2-chloro-6-[[(2R)-2-hydroxypropyl]amino]pyridin-4-yl)-4-methylphenyl]-3-(2,2,2-trifluoroethyl)pyrrolidine-1-carboxamide

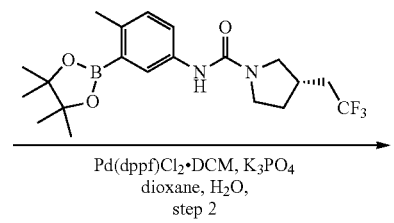

To a stirred mixture of (2R)-1-[(6-chloro-4-iodopyridin-2-yl)amino]propan-2-ol (380 mg, 1.216 mmol) and (3S)—N-[4-methyl-3-(4,4,5,5-tetramethyl-1,3,2-dioxaborolan-2-yl)phenyl]-3-(2,2,2-trifluoroethyl) pyrrod-ine-1-carboxamide (501 mg, 1.216 mmol), $K_3PO_4$ (774 mg, 3.648 mmol) in dioxane (4 mL), $H_2O$ (0.4 mL) was added Pd(dppf)Cl$_2$CH$_2$Cl$_2$ (99 mg, 0.122 mmol) in portions at room temperature under nitrogen atmosphere. The resulting mixture was stirred for 1 h at 50° C. under nitrogen atmosphere. The resulting mixture was quenched with water (100 mL), and extracted with EtOAc (3×300 mL). The combined organic layers were washed with brine (2×70 mL), dried over anhydrous $Na_2SO_4$ and concentrated under reduced pressure. The residue was purified by silica gel column chromatography, eluted with 0% to 50% EtOAc in PE to afford (3S)—N-[3-(2-chloro-6-[[(2R)-2-hydroxypropyl]amino]pyridin-4-yl)-4-methylphenyl]-3-(2,2,2-trifluoroethyl)pyrrolidine-1-carboxamide (510 mg, 89%) as a yellow solid. MS ESI calculated for $C_{22}H_{26}ClF_3N_4O_2$ [M+H]$^+$, 471.17, found 471.20. $^1$H NMR (300 MHz, DMSO-d$_6$) δ 8.19 (s, 1H), 7.49 (s, 1H), 7.41 (s, 1H), 7.15 (s, 1H), 7.00 (s, 1H), 6.44 (d, J=1.1 Hz, 2H), 4.75 (s, 1H), 4.05-3.98 (m, 1H), 3.69-3.60 (m, 1H), 3.55-3.51 (m, 1H), 3.33-3.29 (m, 2H), 3.21-3.18 (m, 1H), 2.19 (s, 1H), 2.16-2.05 (m, 2H), 2.01 (d, J=1.1 Hz, 1H), 1.67-1.61 (m, 2H), 1.07 (s, 3H).

Example 26: (3S)—N-[3-[2-(3,6-dihydro-2H-pyran-4-yl)-6-[[(2R)-2-hydroxypropyl]amino]pyridin-4-yl]-4-methylphenyl]-3-(2,2,2-trifluoroethyl)pyrrolidine-1-carboxamide

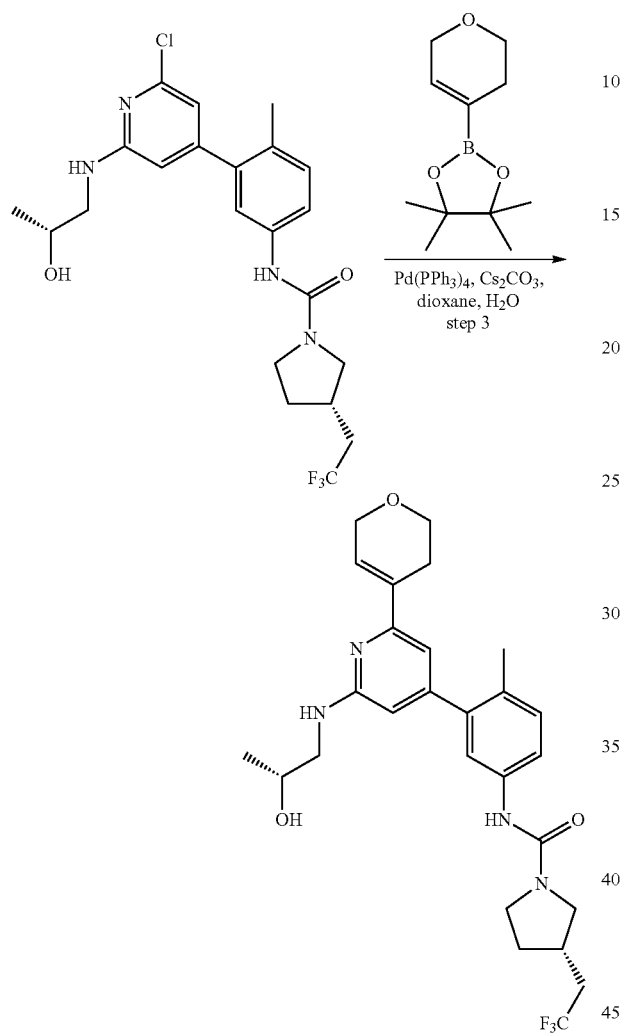

To a stirred mixture of (3S)—N-[3-(2-chloro-6-[[(2R)-2-hydroxypropyl]amino]pyridin-4-yl)-4-methylphenyl]-3-(2,2,2-trifluoroethyl)pyrrolidine-1-carboxamide (430 mg, 0.913 mmol) and 2-(3,6-dihydro-2H-pyran-4-yl)-4,4,5,5-tetramethyl-1,3,2-dioxaborolane (384 mg, 1.826 mmol), $Cs_2CO_3$ (893 mg, 2.739 mmol) in dioxane (5 mL), $H_2O$ (0.5 mL) was added $Pd(dppf)Cl_2CH_2Cl_2$ (75 mg, 0.091 mmol) in portions at room temperature under nitrogen atmosphere. The resulting mixture was stirred for 1 h at 100° C. under nitrogen atmosphere. The resulting mixture was quenched with water (50 mL), and extracted with EtOAc (3×100 mL). The combined organic layers were washed with brine (2×30 mL), dried over anhydrous $Na_2SO_4$ and concentrated under reduced pressure. The residue was purified by silica gel column chromatography, eluted with 0% to 90% EtOAc in PE to afford (3S)—N-[3-[2-(3,6-dihydro-2H-pyran-4-yl)-6-[[(2R)-2-hydroxypropyl]amino]pyridin-4-yl]-4-methylphenyl]-3-(2,2,2-trifluoroethyl)pyrrolidine-1-carboxamide (310 mg, 65%) as a yellow solid. MS ESI calculated for $C_{27}H_{33}F_3N_4O_3$ $[M+H]^+$, 519.25, found 519.15. $^1H$ NMR (300 MHz, DMSO-$d_6$) δ 8.17 (s, 1H), 7.47-7.45 (m, 2H), 7.40 (s, 1H), 7.16-7.13 (m, 1H), 6.73 (s, 1H), 6.53 (s, 1H), 6.36 (s, 1H), 4.84-4.83 (m, 1H), 4.27 (s, 2H), 3.81 (s, 3H), 3.71-3.69 (m, 2H), 3.57-3.31 (m, 4H), 3.07-3.01 (m, 1H), 2.52-2.42 (m, 4H), 2.18-2.10 (m, 4H), 1.70-1.64 (m, 1H), 1.12-1.10 (m, 3H).

Example 27: (3S)—N-[3-(2-[[(2R)-2-hydroxypropyl]amino]-6-(oxan-4-yl)pyridin-4-yl)-4-methylphenyl]-3-(2,2,2-trifluoroethyl)pyrrolidine-1-carboxamide

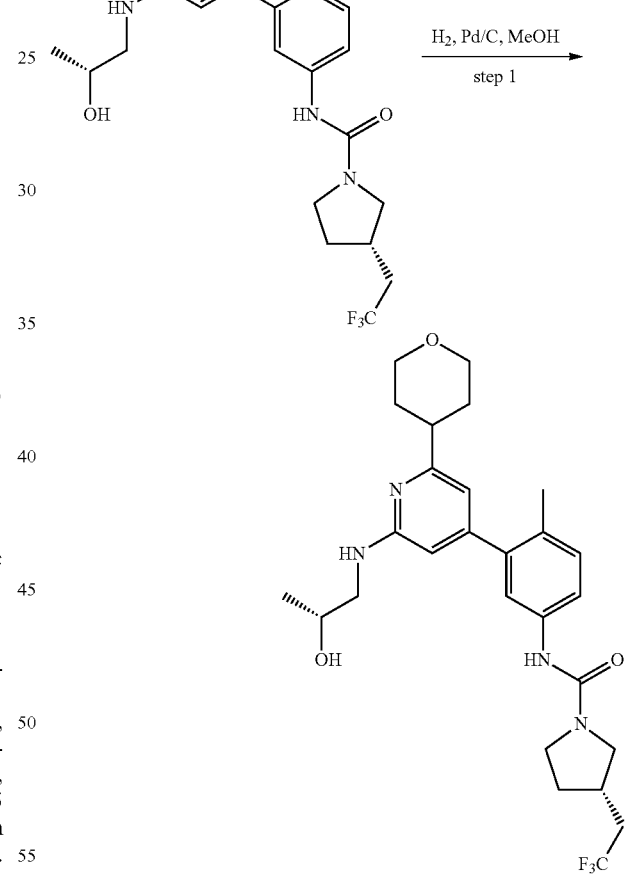

To a solution of (3S)—N-[3-[2-(3,6-dihydro-2H-pyran-4-yl)-6-[[(2R)-2-hydroxypropyl]amino]pyridin-4-yl]-4-methylphenyl]-3-(2,2,2-trifluoroethyl)pyrrolidine-1-carboxamide (150 mg, 0.289 mmol) in MeOH (2 mL), $CH_3COOH$ (0.1 mL) was added Pd/C (92 mg, 0.868 mmol) under nitrogen atmosphere. The mixture was hydrogenated at room temperature for 2 h under hydrogen atmosphere using a hydrogen balloon, filtered through a Celite pad and concentrated under reduced pressure. The crude product (200 mg) was purified by Prep-HPLC with the following conditions (Column: XBridge Prep C18 OBD Column, 150 mm 5 um; Mobile Phase A: Water (10 mmol/L $NH_4HCO_3$), Mobile Phase B: $CH_3CN$; Flow rate: 20 mL/min; Gradient: 20 B to 50 B in 4.3 min; 210/254 nm) to afford (3S)—N-[3-(2-[[(2R)-2-hydroxypropyl]amino]-6-(oxan-4-yl)pyridin-4-yl)-4-methylphenyl]-3-(2,2,2-trifluoroethyl)pyrrolidine-1-carboxamide (115 mg, 76%) as a white solid. MS ESI calculated for $C_{27}H_{35}F_3N_4O_3$ $[M+H]^+$, 521.27, found 521.15. $^1H$ NMR (300 MHz, DMSO-$d_6$) δ 8.14 (s, 1H), 7.41 (s, 2H), 7.36-7.35 (m, 1H), 7.13-7.10 (m, 1H), 6.29-6.27 (m, 2H), 4.84 (s, 1H), 3.95 (s, 2H), 3.91 (s, 1H), 3.41 (s, 1H), 3.37-3.33 (m, 3H), 3.27-3.25 (m, 2H), 3.10-2.98 (m, 1H), 2.78 (s, 1H), 2.50-2.42 (m, 4H), 2.15-2.10 (m, 4H), 1.75-1.71 (m, 5H), 1.09-1.07 (m, 3H).

Example 28: N-[3-(2-[[(2R)-2-hydroxypropyl]amino]-6-(morpholin-4-yl)pyridin-4-yl)-4-methylphenyl]-3-(trifluoromethyl)-2,5-dihydropyrrole-1-carboxamide

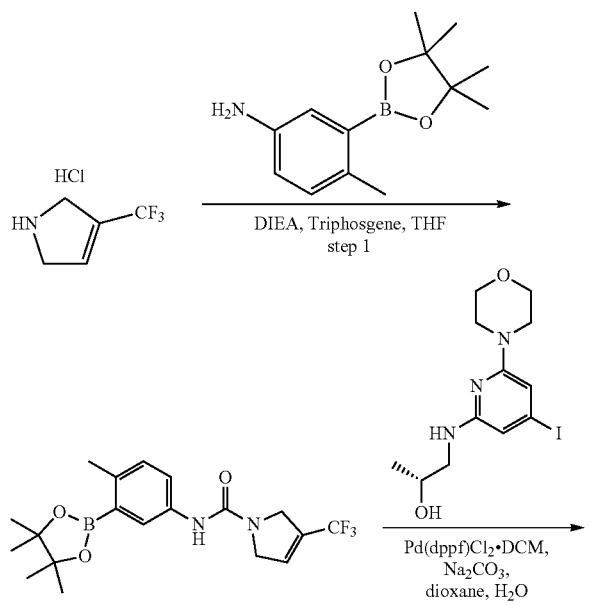

Preparation 28A: N-[4-methyl-3-(4,4,5,5-tetramethyl-1,3,2-dioxaborolan-2-yl)phenyl]-3-(trifluoromethyl)-2,5-dihydropyrrole-1-carboxamide

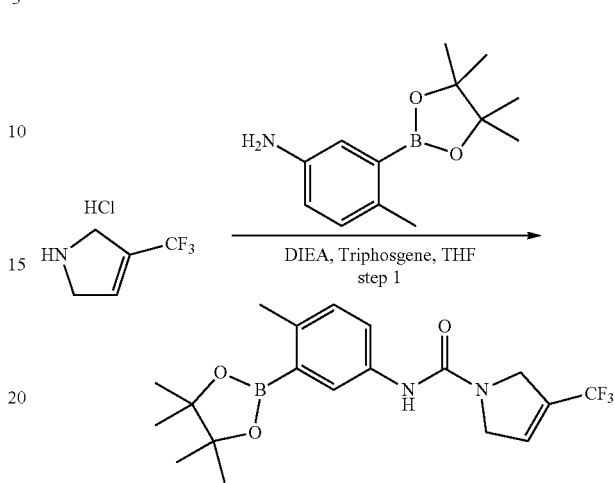

To a solution of 4-methyl-3-(4,4,5,5-tetramethyl-1,3,2-dioxaborolan-2-yl)aniline (435 mg, 1.867 mmol) and triphosgene (246 mg, 0.830 mmol) in THF (40 mL) was added DIEA (1.81 mL, 13.977 mmol) at room temperature under nitrogen atmosphere. The mixture was stirred for 30 min at room temperature. To this was added 3-(trifluoromethyl)-2,5-dihydro-1H-pyrrole hydrochloride (180 mg, 1.037 mmol) and the mixture was stirred for 3 h at room temperature. The resulting mixture was concentrated under reduced pressure. The residue was purified by silica gel column chromatography, eluted with PE/EtOAc (2/1) to afford N-[4-methyl-3-(4,4,5,5-tetramethyl-1,3,2-dioxaborolan-2-yl)phenyl]-3-(trifluoromethyl)-2,5-dihydropyrrole-1-carboxamide (500 mg, 61%) as a yellow oil. MS ESI calculated for $C_{19}H_{24}F_3N_2O_3$ $[M+H]^+$, 397.25, found 397.25. $^1H$ NMR (400 MHz, $CDCl_3$-d) δ 7.71 (dd, J=8.3, 2.5 Hz, 1H), 7.48 (d, J=2.6 Hz, 1H), 7.15 (d, J=8.3 Hz, 1H), 6.45-6.40 (m, 1H), 6.16 (s, 1H), 4.44 (s, 4H), 2.50 (s, 3H), 1.36 (s, 12H). $^{19}F$ NMR (376 MHz, $CDCl_3$-d) δ −65.69 (3F).

Example 28: N-[3-(2-[[(2R)-2-hydroxypropyl]amino]-6-(morpholin-4-yl)pyridin-4-yl)-4-methylphenyl]-3-(trifluoromethyl)-2,5-dihydropyrrole-1-carboxamide

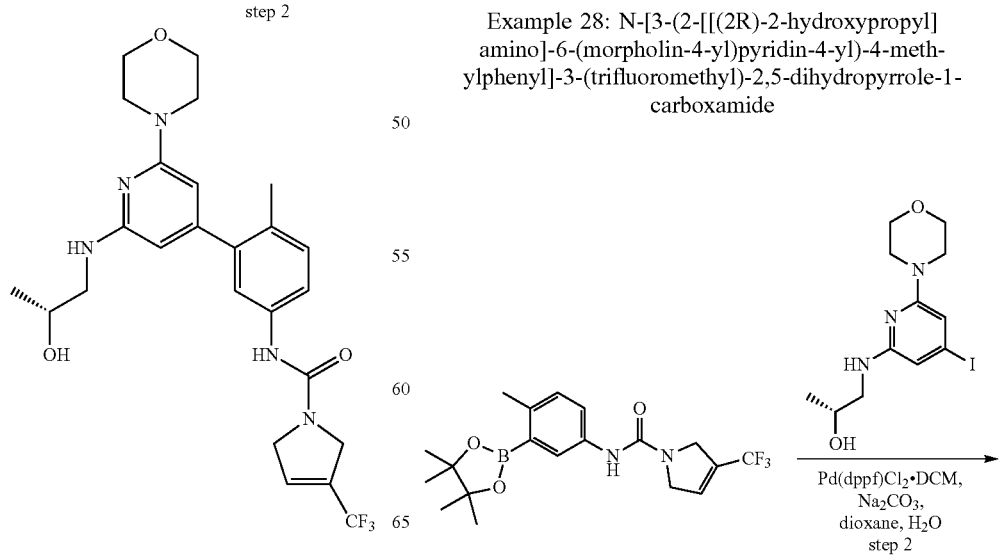

227

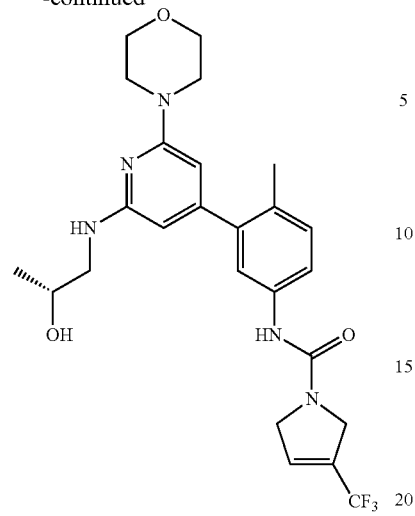

To a stirred solution of (2R)-1-[[4-iodo-6-(morpholin-4-yl)pyridin-2-yl]amino]propan-2-ol (160 mg, 0.441 mmol) and N-[4-methyl-3-(4,4,5,5-tetramethyl-1,3,2-dioxaborolan-2-yl)phenyl]-3-(trifluoromethyl)-2,5-dihydropyrrole-1-carboxamide (174 mg, 0.441 mmol) in 1,4-dioxane (2 mL) and H₂O (0.5 mL) were added Pd(dppf)Cl₂·CH₂Cl₂ (36 mg, 0.044 mmol) and Na₂CO₃ (140 mg, 1.322 mmol). The resulting mixture was stirred for 16 h at 60° C. under nitrogen atmosphere. The mixture was allowed to cool down to room temperature. The reaction was quenched by the addition of water (10 mL) at room temperature. The resulting mixture was extracted with EtOAc (3×10 mL). The combined organic layers were washed with brine (10 mL), dried over anhydrous Na₂SO₄. After filtration, the filtrate was concentrated under reduced pressure. The residue was purified by silica gel column chromatography, eluted with PE/EtOAc (1/2) to afford N-[3-(2-[[(2R)-2-hydroxypropyl]amino]-6-(morpholin-4-yl)pyridin-4-yl)-4-methylphenyl]-3-(trifluoromethyl)-2,5-dihydropyrrole-1-carboxamide (116 mg, 44%) as a light green solid. MS ESI calculated for C₂₅H₃₀F₃N₅O₃ [M+H]⁺, 506.05, found 506.05. ¹H NMR (300 MHz, DMSO-d6) δ8.31 (s, 1H), 7.45 (dd, J=8.2, 2.3 Hz, 1H), 7.37 (d, J=2.3 Hz, 1H), 7.14 (d, J=8.3 Hz, 1H), 6.75 (d, J=2.6 Hz, 1H), 6.23 (s, 1H), 5.79 (d, J=6.5 Hz, 2H), 4.70 (s, 1H), 4.41 (s, 4H), 3.81 (s, 1H), 3.70 (t, J=4.8 Hz, 4H), 3.39 (t, J=4.8 Hz, 4H), 3.23-3.09 (m, 2H), 2.19 (s, 3H), 1.10 (d, J=6.2 Hz, 3H). ¹⁹F NMR (282 MHz, DMSO-d6) δ −63.98 (3F).

Example 29: N-[3-(2-[[(2R)-1-hydroxypropan-2-yl]amino]-6-(morpholin-4-yl)pyridin-4-yl)-4-methylphenyl]-3-(trifluoromethyl)-2,5-dihydropyrrole-1-carboxamide

228

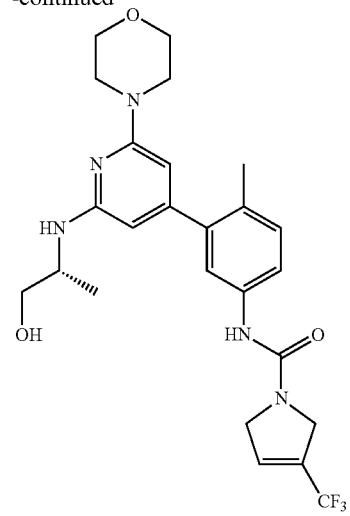

To a stirred solution of (2R)-2-[[4-iodo-6-(morpholin-4-yl)pyridin-2-yl]amino]propan-1-ol (150 mg, 0.413 mmol) and N-[4-methyl-3-(4,4,5,5-tetramethyl-1,3,2-dioxaborolan-2-yl)phenyl]-3-(trifluoromethyl)-2,5-dihydropyrrole-1-carboxamide (164 mg, 0.413 mmol) in 1,4-dioxane (2 mL) and H₂O (0.4 mL) were added Na₂CO₃ (131 mg, 1.239 mmol) and Pd(dppf)Cl₂·CH₂Cl₂ (34 mg, 0.041 mmol). The resulting mixture was stirred for 16 h at 60° C. under nitrogen atmosphere. The mixture was allowed to cool down to room temperature. The reaction was quenched by the addition of water (10 mL) at room temperature. The resulting mixture was extracted with EtOAc (3×10 mL). The combined organic layers were washed with brine (10 mL), dried over anhydrous Na₂SO₄. After filtration, the filtrate was concentrated under reduced pressure. The residue was purified by silica gel column chromatography, eluted with PE/EtOAc (1/2) to afford N-[3-(2-[[(2R)-1-hydroxypropan-2-yl]amino]-6-(morpholin-4-yl)pyridin-4-yl)-4-methylphenyl]-3-(trifluoromethyl)-2,5-dihydropyrrole-1-carboxamide (116 mg, 56%) as a light yellow solid. MS ESI calculated for C₂₅H₃₀F₃N₅O₃ [M+H]⁺, 506.10, found 506.10. ¹H NMR (400 MHz, DMSO-d₆) δ8.29 (s, 1H), 7.45-7.40 (m, 1H), 7.36 (d, J=2.3 Hz, 1H), 7.13 (d, J=8.4 Hz, 1H), 6.76-672 (m, 1H), 5.99 (s, 1H), 5.76 (s, 2H), 4.65 (s, 1H), 4.39 (s, 4H), 3.93-3.85 (m, 1H), 3.71-3.64 (m, 4H), 3.49 (dd, J=10.3, 4.9 Hz, 1H), 3.37 (t, J=4.8 Hz, 4H), 3.34-3.33 (m, 1H), 2.17 (s, 3H), 1.13 (d, J=6.5 Hz, 3H). ¹⁹F NMR (376 MHz, DMSO-d₆) δ −63.99 (3F).

Example 30: (3S)—N-[3-(2-[[(2S)-1-hydroxypropan-2-yl]amino]-6-(morpholin-4-yl)pyridin-4-yl)-4-methylphenyl]-3-(2,2,2-trifluoroethyl)pyrrolidine-1-carboxamide

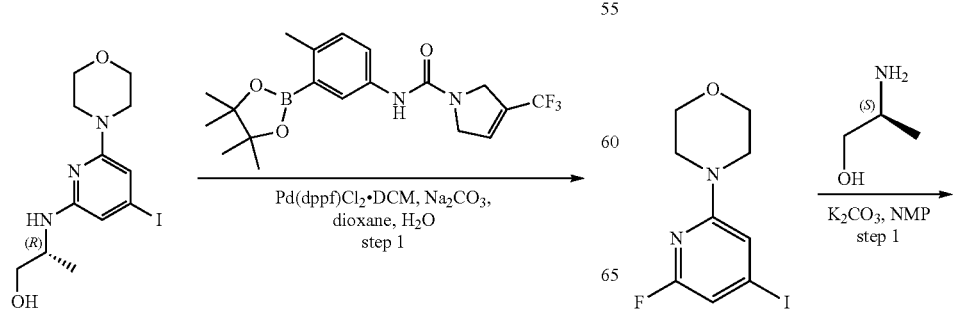

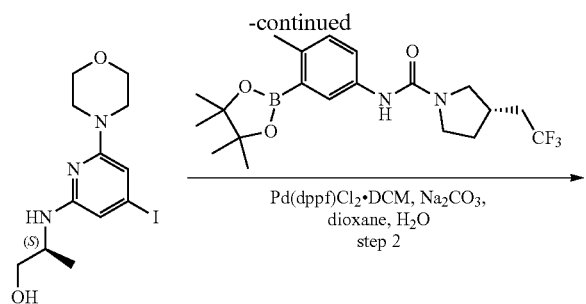

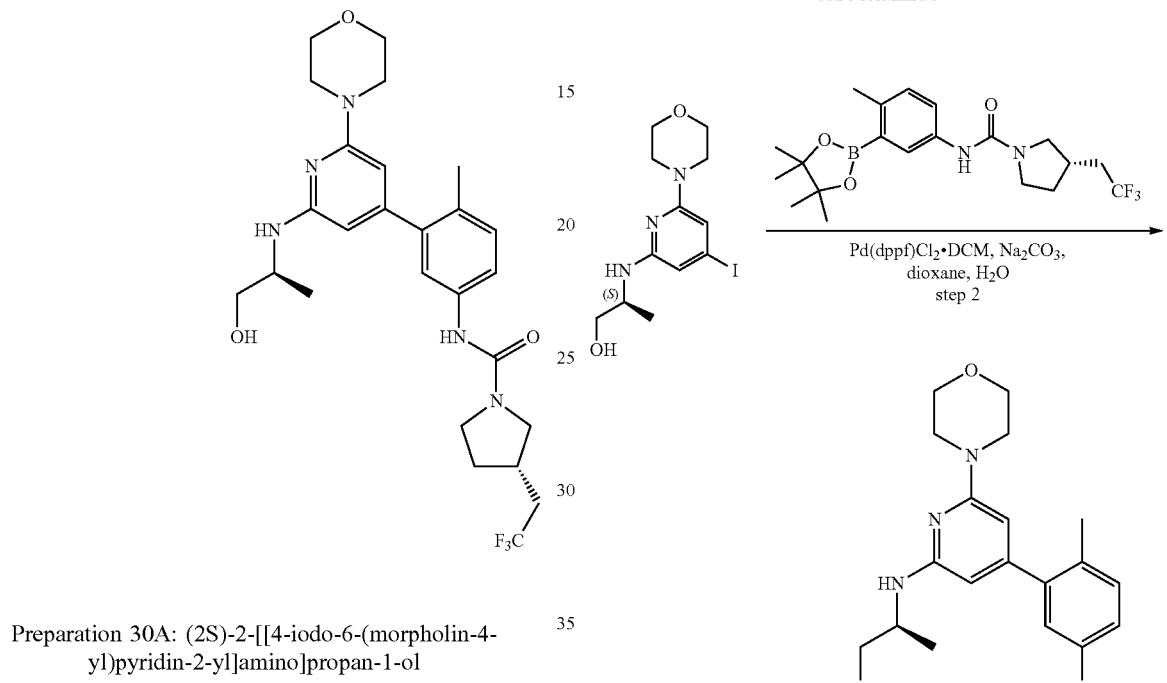

Preparation 30A: (2S)-2-[[4-iodo-6-(morpholin-4-yl)pyridin-2-yl]amino]propan-1-ol

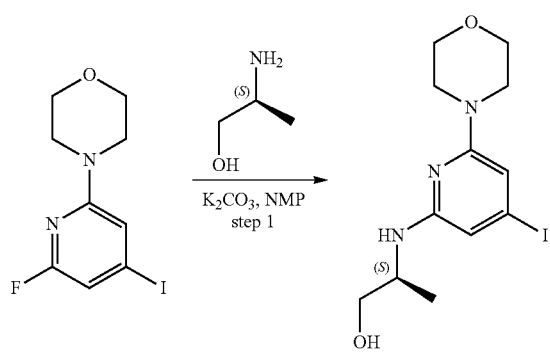

To a stirred solution of 4-(6-fluoro-4-iodopyridin-2-yl)morpholine (300 mg, 0.974 mmol) and K$_2$CO$_3$ (269 mg, 1.947 mmol) in NMP (3 mL) was added (2S)-2-aminopropan-1-ol (110 mg, 1.461 mmol) at room temperature under nitrogen atmosphere. The resulting mixture was stirred for 16 h at 150° C. under nitrogen atmosphere. The reaction was quenched by the addition of water (100 mL). The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with PE/EtOAc (1/1) to afford (2S)-2-[[4-iodo-6-(morpholin-4-yl)pyridin-2-yl]amino]propan-1-ol (198 mg, 55%) as an off-white solid. MS ESI calculated for C$_{12}$H$_{18}$IN$_3$O$_2$ [M+H]$^+$, 364.04, found 364.10. $^1$H NMR (400 MHz, CDCL$_3$) δ 6.29-6.25 (m, 2H), 4.32-4.28 (m, 1H), 4.02 (s, 1H), 3.81-3.72 (m, 5H), 3.58-3.54 (m, 1H), 3.45-3.43 (m, 4H), 1.23-1.22 (m, 3H).

Example 30: (3S)—N-[3-(2-[[(2S)-1-hydroxypropan-2-yl]amino]-6-(morpholin-4-yl)pyridin-4-yl)-4-methylphenyl]-3-(2,2,2-trifluoroethyl)pyrrolidine-1-carboxamide A mixture of (2S)-2-[[4-iodo-6-(morpholin-4-yl)pyridin-2-yl]amino]propan-1-ol (200 mg, 0.551 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (227 mg, 0.551 mmol), Na$_2$CO$_3$ (175 mg, 1.652 mmol), 1,4-dioxane (1.6 mL), H$_2$O (0.4 mL) and Pd(dppf)Cl$_2$·CH$_2$Cl$_2$ (45 mg, 0.055 mmol) was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc/EtOH=(8/3/1) followed by reverse flash chromatography with the following conditions: Column: SunFire Prep C18 OBD Column, 19×150 mm 5 um 10 nm; Mobile Phase A: water (0.05% TFA), Mobile Phase B: CH$_3$CN; Flow rate:20 mL/min; Gradient:25 B to 65 B in 5.3 min; 254/210 nm. This resulted in (3S)—N-[3-(2-[[(2S)-1-hydroxypropan-2-yl]amino]-6-(morpholin-4-yl)pyridin-4-yl)-4-methylphenyl]-3-(2,2,2-trifluoroethyl)pyrrolidine-1-carboxamide (111 mg, 37%) as an off-white solid. MS ESI calculated for $C_{26}H_{34}F_3N_5O_3$ [M+H]$^+$, 522.26, found 522.30. $^1$H NMR (400 MHz, DMSO-d$_6$) δ 8.11 (s, 1H), 7.42-7.40 (m, 1H), 7.34-7.33 (m, 1H), 7.10-7.08 (m, 1H), 5.98-5.96 (m, 1H), 5.75 (m, 2H), 4.65 (s, 1H), 3.90-3.87 (m, 1H), 3.69-3.65 (m, 5H), 3.55-3.48 (m, 2H), 3.38-3.34 (m, 5H), 3.04-2.99 (m, 1H), 2.48-2.41 (m, 3H), 2.16 (s, 3H), 2.10-2.07 (m, 1H), 1.70-1.60 (m, 1H), 1.13-1.12 (m, 3H). $^{19}$F NMR (376 MHz, DMSO-d$_6$) δ −63.37 (3F).

Example 31: (3S)—N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide

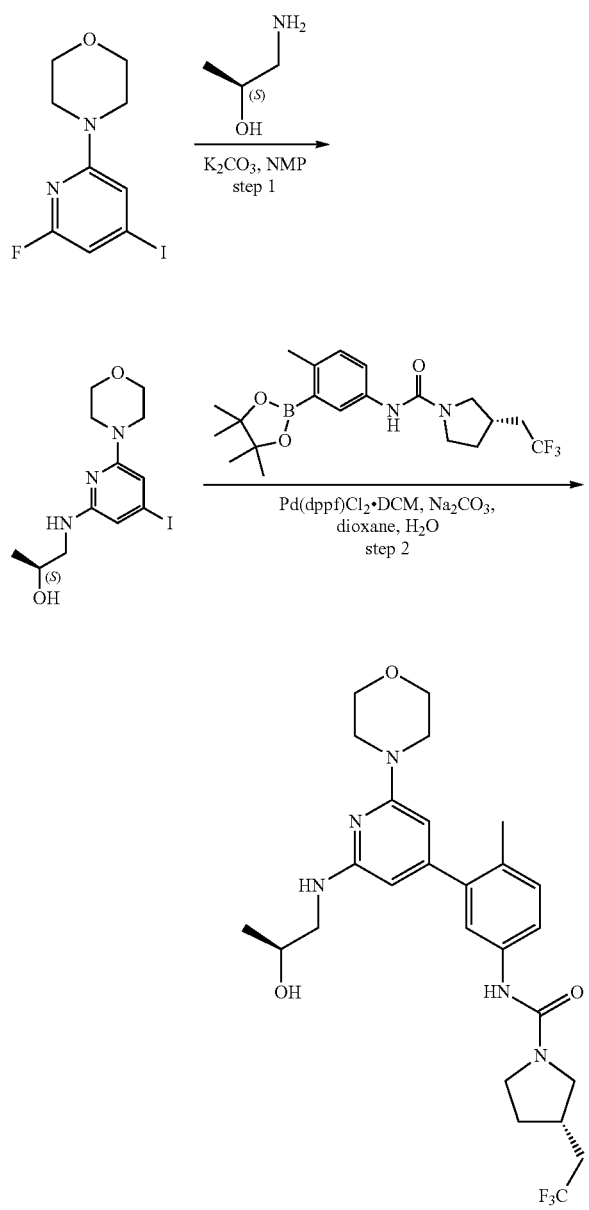

Preparation 31A: (2R)-1-[[4-iodo-6-(morpholin-4-yl)pyridin-2-yl](methyl)amino]propan-2-ol

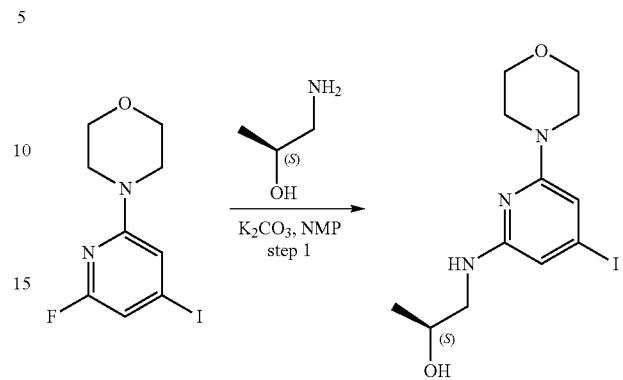

A mixture of 4-(6-fluoro-4-iodopyridin-2-yl)morpholine (300 mg, 0.974 mmol), K$_2$CO$_3$ (269 mg, 1.947 mmol), NMP (3 mL) and (2S)-1-aminopropan-2-ol (110 mg, 1.461 mmol) was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (1/1) to afford (2S)-1-[[4-iodo-6-(morpholin-4-yl)pyridin-2-yl]amino]propan-2-ol (222 mg, 63%) as an off-white solid. MS ESI calculated for $C_{12}H_{18}IN_3O_2$ [M+H]$^+$, 364.04, found 364.10. $^1$H NMR (400 MHz, chloroform-d) δ 6.29-6.25 (m, 2H), 4.65 (s, 1H), 4.05-3.97 (m, 1H), 3.81-3.78 (m, 4H), 3.47-3.41 (m, 5H), 3.25-3.18 (m, 1H), 1.25-1.23 (m, 3H).

Example 31: (3S)—N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide

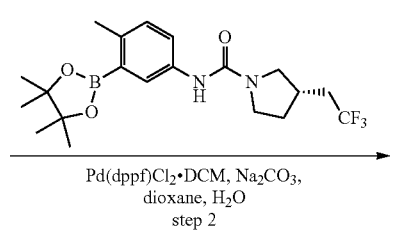

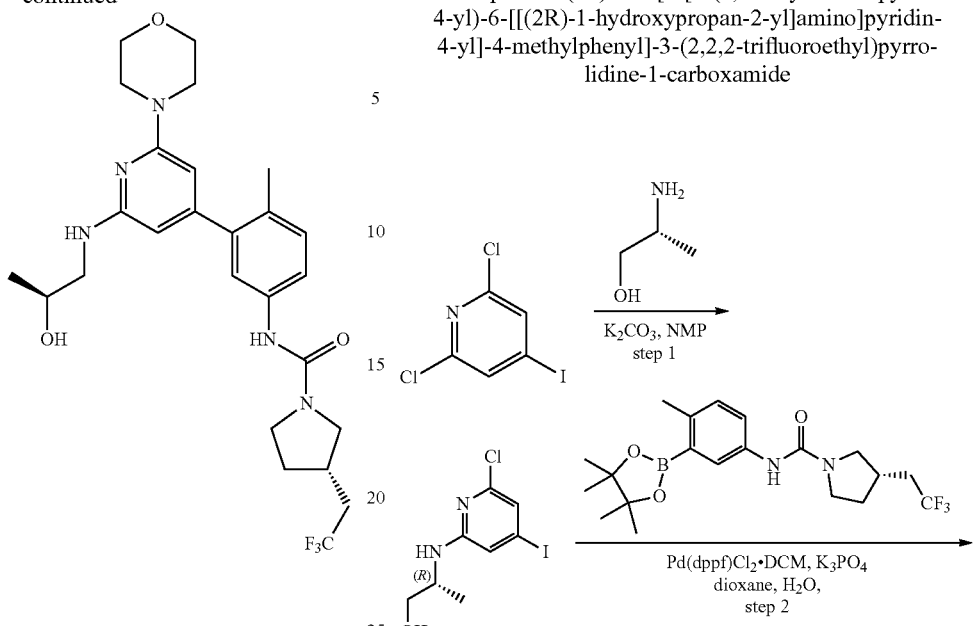

Example 32: (3S)—N-[3-[2-(3,6-dihydro-2H-pyran-4-yl)-6-[[(2R)-1-hydroxypropan-2-yl]amino]pyridin-4-yl]-4-methylphenyl]-3-(2,2,2-trifluoroethyl)pyrrolidine-1-carboxamide

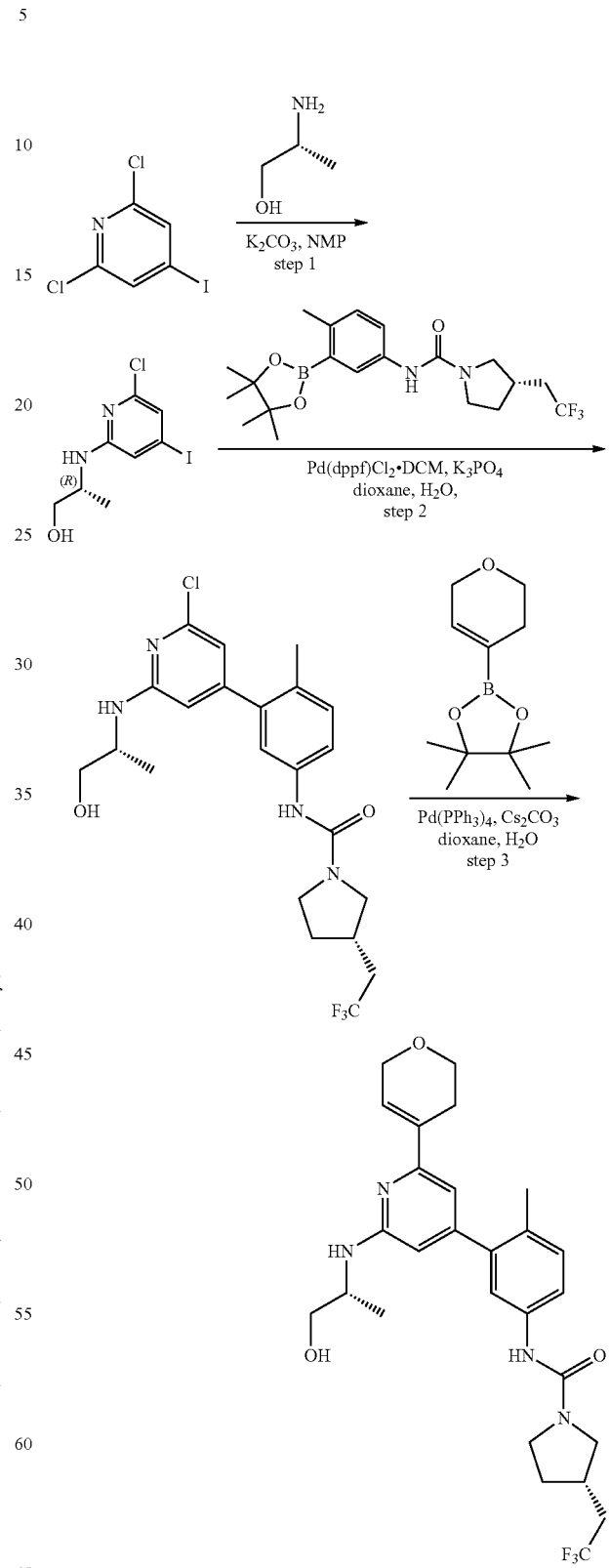

A mixture of (2S)-1-[[4-iodo-6-(morpholin-4-yl)pyridin-2-yl]amino]propan-2-ol (200 mg, 0.551 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (227 mg, 0.551 mmol), Na$_2$CO$_3$ (175 mg, 1.652 mmol), dioxane:H$_2$O=4:1 (2 mL) and Pd(dppf)Cl$_2$·CH$_2$Cl$_2$ (45 mg, 0.055 mmol) was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EA/EtOH=(8/3/1) followed by reverse flash chromatography with the following conditions: Column: SunFire Prep C18 OBD Column, 19×150 mm 5 um 10 nm; Mobile Phase A: water (0.1% FA), Mobile Phase B: CH$_3$CN; Flow rate: 20 mL/min; Gradient:25 B to 65 B in 5.3 min; 254/210 nm. This resulted in (3S)—N-[3-(2-[[(2S)-2-hydroxypropyl]amino]-6-(morpholin-4-yl)pyridin-4-yl)-4-methylphenyl]-3-(2,2,2-trifluoroethyl)pyrrolidine-1-carboxamide (145 mg, 49%) as an off-white solid. MS ESI calculated for C$_{26}$H$_{34}$F$_3$N$_5$O$_3$ [M+H]$^+$, 522.26, found 522.25. $^1$H NMR (400 MHz, DMSO-d$_6$) δ 8.11 (s, 1H), 7.43-7.40 (m, 1H), 7.34-7.33 (m, 1H), 7.10-7.08 (m, 1H), 6.22-6.19 (m, 1H), 5.78-5.76 (m, 2H), 4.70 (s, 1H), 3.82-3.77 (m, 1H), 3.69-3.65 (m, 5H), 3.55-3.50 (m, 1H), 3.38-3.36 (m, 4H), 3.23-3.11 (m, 2H), 3.04-2.99 (m, 1H), 2.48-2.36 (m, 3H), 2.16 (s, 3H), 2.11-2.07 (m, 1H), 1.70-1.60 (m, 1H), 1.09-1.07 (m, 3H). $^{19}$F NMR (376 MHz, DMSO-d$_6$) δ −63.37 (3F).

Preparation 32A: (2R)-2-[(6-chloro-4-iodopyridin-2-yl)amino]propan-1-ol

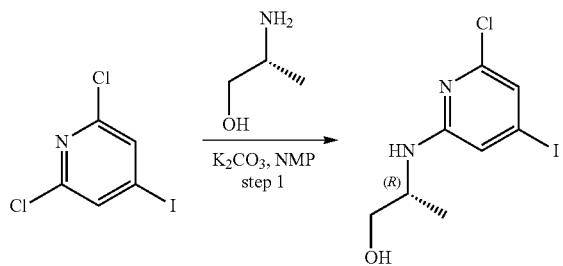

To a stirred solution of 2,6-dichloro-4-iodopyridine (1 g, 3.651 mmol) and $K_2CO_3$ (1 g, 7.302 mmol) in NMP (20 mL) was added (R)-(−)-2-amino-1-propanol (274 mg, 3.651 mmol) at room temperature. The part of resulting mixture was stirred for 16 h at 100° C. The reaction was quenched by the addition of water (70 mL). The resulting mixture was extracted with EtOAc (3×150 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EtOAc (2/1) to afford (2R)-2-[(6-chloro-4-iodopyridin-2-yl)amino]propan-1-ol (240 mg, 21%) as a yellow oil. MS ESI calculated for $C_8H_{10}ClIN_2O$ [M+H]$^+$, 312.95, found 312.95. $^1$H NMR (300 MHz, chloroform-d) δ 6.97 (d, J=1.0 Hz, 1H), 6.77 (d, J=1.1 Hz, 1H), 4.90 (s, 1H), 3.76 (dd, J=13.7, 3.1 Hz, 2H), 3.61 (dd, J=13.7, 7.7 Hz, 1H), 1.28 (d, J=6.2 Hz, 3H).

Preparation 32B: (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide To a stirred mixture of (2R)-2-[(6-chloro-4-iodopyridin-2-yl)amino]propan-1-ol (230 mg, 0.736 mmol) and (3S)—N-[4-methyl-3-(4,4,5,5-tetramethyl-1,3,2-dioxaborolan-2-yl)phenyl]-3-(2,2,2-trifluoroethyl) pyrrolidine-1-carboxamide (303 mg, 0.736 mmol), $K_3PO_4$ (469 mg, 2.208 mmol) in dioxane (3 mL), $H_2O$ (0.3 mL) was added Pd(dppf)$Cl_2$$CH_2Cl_2$ (60 mg, 0.074 mmol) in portions at room temperature under nitrogen atmosphere. The resulting mixture was stirred for 1 h at 50° C. under nitrogen atmosphere. The resulting mixture was quenched with water (50 mL), and extracted with EtOAc (3×100 mL). The combined organic layers were washed with brine (2×30 mL), dried over anhydrous $Na_2SO_4$ and concentrated under reduced pressure. The residue was purified by silica gel column chromatography, eluted with 0% to 90% EtOAc in PE to afford (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (310 mg, 89%) as a yellow solid. MS ESI calculated for $C_{22}H_{26}ClF_3N_4O_2$ [M+H]$^+$, 471.17, found 471.05. $^1$H NMR (300 MHz, DMSO-$d_6$) δ 8.17 (s, 1H), 7.48-7.45 (m, 1H), 7.40-7.34 (m, 1H), 7.15-7.12 (m, 1H), 6.87-6.81 (m, 1H), 6.41 (s, 1H), 7.41 (s, 1H), 6.36 (s, 1H), 4.04-4.02 (m, 1H), 3.90 (s, 1H), 3.67 (s, 1H), 3.52 (s, 2H), 3.36-3.25 (m, 2H), 3.03 (s, 1H), 2.51-2.34 (m, 3H), 2.17 (s, 3H), 2.13-2.05 (m, 1H), 1.73-1.59 (m, 1H), 1.26-1.10 (m, 4H).

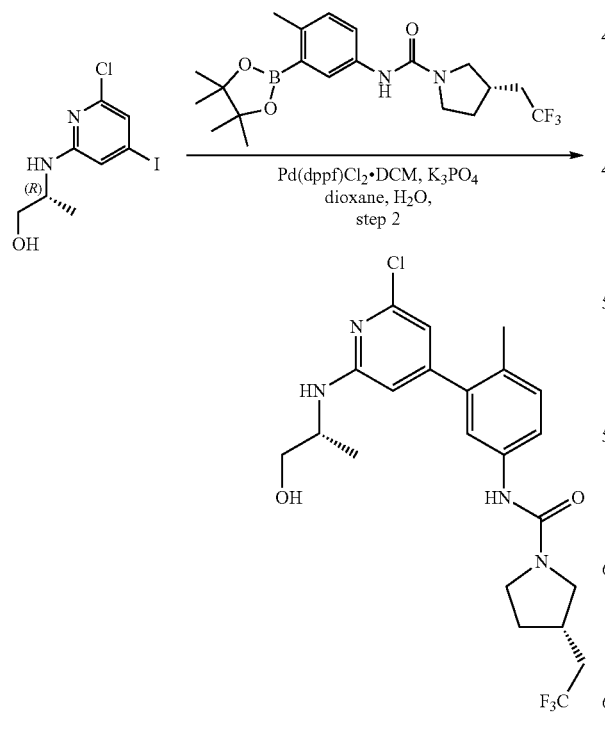

Example 32: (3S)—N-[3-[2-(3,6-dihydro-2H-pyran-4-yl)-6-[[(2R)-1-hydroxypropan-2-yl]amino]pyridin-4-yl]-4-methylphenyl]-3-(2,2,2-trifluoroethyl)pyrrolidine-1-carboxamide

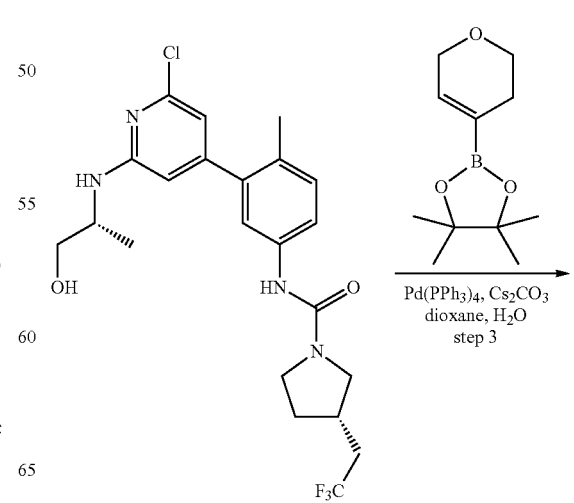

-continued

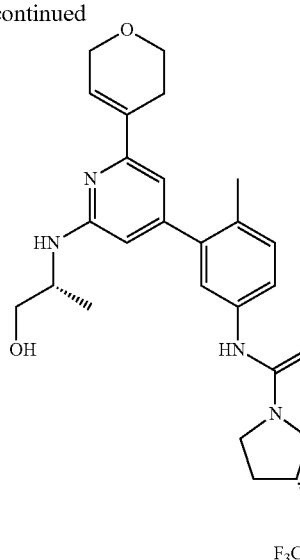

To a stirred mixture of (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (310 mg, 0.658 mmol) and 2-(3,6-dihydro-2H-pyran-4-yl)-4,4,5,5-tetramethyl-1,3,2-dioxaborolane (277 mg, 1.317 mmol), $Cs_2CO_3$ (643 mg, 1.975 mmol) in dioxane (4 mL), $H_2O$ (0.4 mL) was added Pd(dppf)$Cl_2CH_2Cl_2$ (54 mg, 0.066 mmol) in portions at room temperature under nitrogen atmosphere. The resulting mixture was stirred for 12 h at 100° C. under nitrogen atmosphere. The resulting mixture was quenched with water (50 mL), and extracted with EtOAc (3×100 mL). The combined organic layers were washed with brine (2×30 mL), dried over anhydrous $Na_2SO_4$ and concentrated under reduced pressure. The residue was purified by silica gel column chromatography, eluted with 0% to 90% EtOAc in PE to afford (3S)—N-[3-[2-(3,6-dihydro-2H-pyran-4-yl)-6-[[(2R)-1-hydroxypropan-2-yl]amino]pyridin-4-yl]-4-methylphenyl]-3-(2,2,2-trifluoroethyl)pyrrolidine-1-carboxamide (130 mg, 38%) as a yellow solid. MS ESI calculated for $C_{27}H_{33}F_3N_4O_3$ [M+H]$^+$, 519.25, found 519.15. $^1$H NMR (300 MHz, DMSO-d$_6$) δ 8.15 (s, 1H), 7.45-7.39 (m, 2H), 7.14-7.12 (m, 1H), 6.71 (s, 1H), 6.50 (s, 1H), 6.31 (s, 2H), 4.85-4.83 (m, 1H), 4.25-4.24 (m, 2H), 4.07 (s, 1H), 3.81 (s, 2H), 3.67-3.66 (m, 1H), 3.52-3.50 (m, 2H), 3.33-3.29 (m, 2H), 3.02 (s, 1H), 2.51-2.43 (m, 5H), 2.41-2.17 (m, 4H), 1.75-1.70 (m, 1H), 1.16-1.14 (m, 3H).

Example 33: (3S)—N-[3-(2-[[(2R)-1-hydroxypropan-2-yl]amino]-6-(oxan-4-yl)pyridin-4-yl)-4-methylphenyl]-3-(2,2,2-trifluoroethyl)pyrrolidine-1-carboxamide

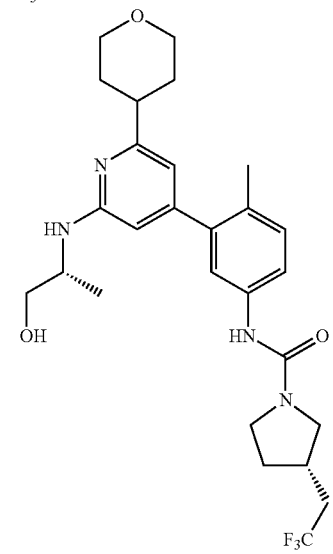

To a solution of (3S)—N-[3-[2-(3,6-dihydro-2H-pyran-4-yl)-6-[[(2R)-1-hydroxypropan-2-yl]amino]pyridin-4-yl]-4-methylphenyl]-3-(2,2,2-trifluoroethyl)pyrrolidine-1-carboxamide (130 mg, 0.251 mmol) in MeOH (2 mL), CH$_3$COOH (0.1 mL) was added Pd/C (80 mg, 0.752 mmol) under nitrogen atmosphere. The mixture was hydrogenated at room temperature for 2 h under hydrogen atmosphere using a hydrogen balloon. The reaction mixture was filtered through a celite pad and concentrated under reduced pressure. The crude product (200 mg) was purified by Prep-HPLC with the following conditions (Column: XBridge Prep C18 OBD Column, 150 mm 5 um; Mobile Phase A: water (10 mmol/L NH$_4$HCO$_3$), Mobile Phase B: CH$_3$CN; Flow rate: 20 mL/min; Gradient:20 B to 50 B in 4.3 min; 210/254 nm) to afford (3S)—N-[3-(2-[[(2R)-1-hydroxypropan-2-yl]amino]-6-(oxan-4-yl)pyridin-4-yl)-4-methylphenyl]-3-(2,2,2-trifluoroethyl)pyrrolidine-1-carboxamide (63 mg, 48%) as a white solid. MS ESI calculated for C$_{27}$H$_{35}$F$_3$N$_4$O$_3$ [M+H]$^+$, 521.27, found 521.15. $^1$H NMR (300 MHz, DMSO-d$_6$) δ 8.13 (s, 1H), 7.43-7.41 (m, 2H), 7.36 (s, 1H), 6.26-6.19 (m, 3H), 4.77 (s, 1H), 3.95-3.91 (m, 3H), 3.63 (s, 1H), 3.55-3.25 (m, 5H), 3.04-2.98 (m, 1H), 2.76 (s, 1H), 2.50-2.39 (m, 4H), 2.27-2.06 (m, 4H), 1.78-1.61 (m, 5H), 1.23-1.13 (m, 3H).

Example 34: (S)—N-(3-(2-(((1S,3R)-3-hydroxy-3-methylcyclobutyl)amino)-6-morpholinopyridin-4-yl)-4-methylphenyl)-3-(2,2,2-trifluoroethyl)pyrrolidine-1-carboxamide

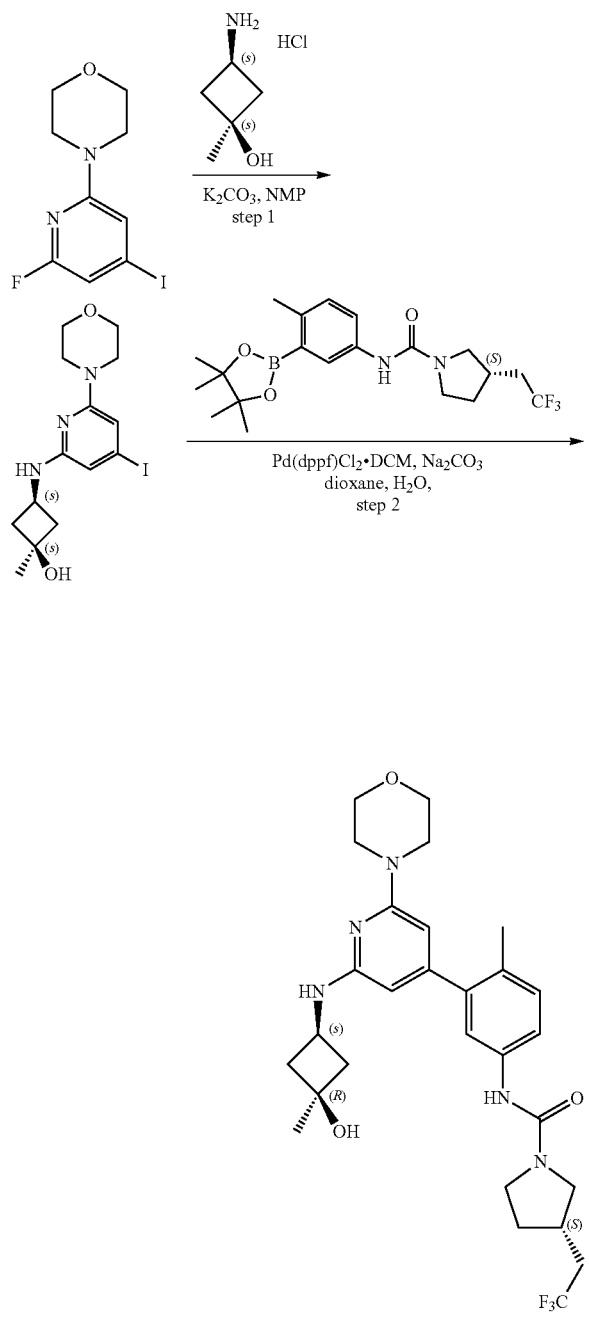

Preparation 34A: (1S,3S)-3-((4-iodo-6-morpholinopyridin-2-yl)amino)-1-methylcyclobutan-1-ol

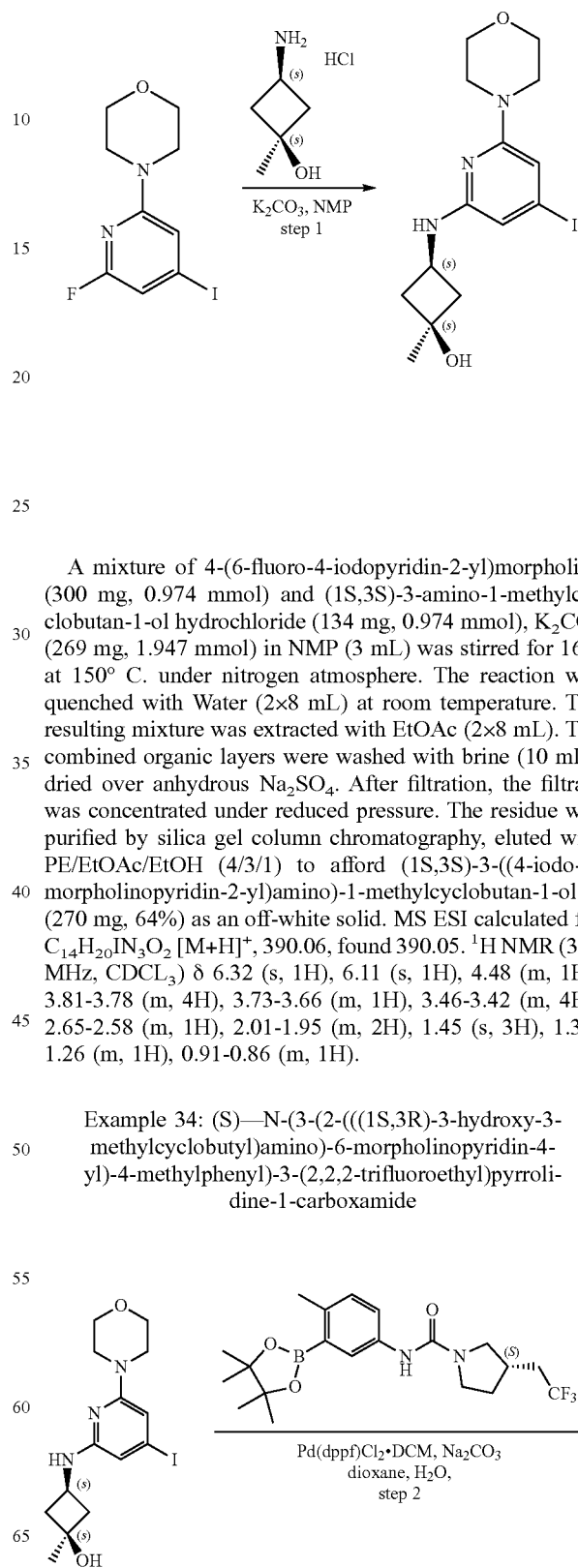

A mixture of 4-(6-fluoro-4-iodopyridin-2-yl)morpholine (300 mg, 0.974 mmol) and (1S,3S)-3-amino-1-methylcyclobutan-1-ol hydrochloride (134 mg, 0.974 mmol), K$_2$CO$_3$ (269 mg, 1.947 mmol) in NMP (3 mL) was stirred for 16 h at 150° C. under nitrogen atmosphere. The reaction was quenched with Water (2×8 mL) at room temperature. The resulting mixture was extracted with EtOAc (2×8 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc/EtOH (4/3/1) to afford (1S,3S)-3-((4-iodo-6-morpholinopyridin-2-yl)amino)-1-methylcyclobutan-1-ol (270 mg, 64%) as an off-white solid. MS ESI calculated for C$_{14}$H$_{20}$IN$_3$O$_2$ [M+H]$^+$, 390.06, found 390.05. $^1$H NMR (300 MHz, CDCL$_3$) δ 6.32 (s, 1H), 6.11 (s, 1H), 4.48 (m, 1H), 3.81-3.78 (m, 4H), 3.73-3.66 (m, 1H), 3.46-3.42 (m, 4H), 2.65-2.58 (m, 1H), 2.01-1.95 (m, 2H), 1.45 (s, 3H), 1.31-1.26 (m, 1H), 0.91-0.86 (m, 1H).

Example 34: (S)—N-(3-(2-(((1S,3R)-3-hydroxy-3-methylcyclobutyl)amino)-6-morpholinopyridin-4-yl)-4-methylphenyl)-3-(2,2,2-trifluoroethyl)pyrrolidine-1-carboxamide -continued

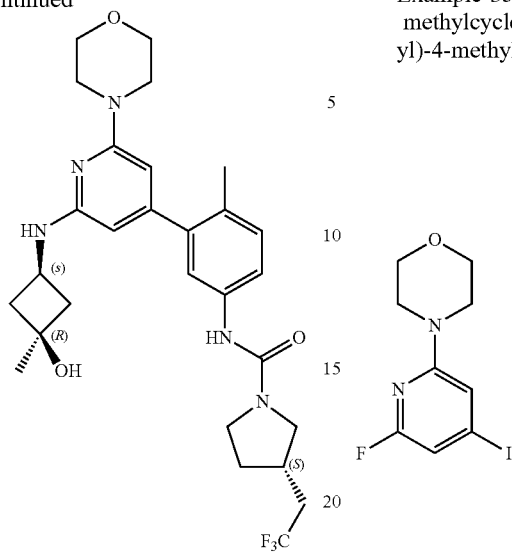

Example 35: (S)—N-(3-(2-(((1R,3S)-3-hydroxy-3-methylcyclobutyl)amino)-6-morpholinopyridin-4-yl)-4-methylphenyl)-3-(2,2,2-trifluoroethyl)pyrrolidine-1-carboxamide

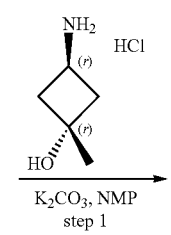

A mixture of (1S,3S)-3-((4-iodo-6-morpholinopyridin-2-yl)amino)-1-methylcyclobutan-1-ol (142 mg, 0.364 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (150 mg, 0.364 mmol), Pd(dppf)Cl$_2$·CH$_2$Cl$_2$ (30 mg, 0.036 mmol) and Na$_2$CO$_3$ (116 mg, 1.092 mmol) in dioxane (1.2 mL) and H$_2$O (0.3 mL) was stirred for 16 h at 60° C. under nitrogen atmosphere. The reaction was quenched by the addition of water (3 mL) at room temperature. The resulting mixture was extracted with EtOAc (2×10 mL). The combined organic layers were washed with brine (5 mL), dried over anhydrous Na$_2$SO$_4$. After filtration, the filtrate was concentrated under reduced pressure. The residue was purified by silica gel column chromatography, eluted with PE/EtOAc/EtOH (4/3/1), the crude product was purified by reverse flash chromatography with the following conditions: Column: SunFire Prep C18 OBD Column, 19×150 mm 5 um 10 nm; Mobile Phase A: water (0.1% FA), Mobile Phase B: CH$_3$CN; Flow rate: 20 mL/min; Gradient: 35 B to 70 B in 4.3 min; 210/254 nm. This resulted in (S)—N-(3-(2-(((1S,3R)-3-hydroxy-3-methylcyclobutyl)amino)-6-morpholinopyridin-4-yl)-4-methylphenyl)-3-(2,2,2-trifluoroethyl)pyrrolidine-1-carboxamide (117 mg, 58%) as an off-white solid. MS ESI calculated for C$_{28}$H$_{36}$F$_3$N$_5$O$_3$ [M+H]$^+$, 548.28, found 548.20. $^1$H NMR (300 MHz, DMSO-d$_6$) δ 8.13-8.11 (m, 1H), 7.42-7.40 (m, 1H), 7.33 (s, 1H), 7.10-7.07 (m, 1H), 6.44-6.32 (m, 1H), 5.77-5.69 (m, 2H), 4.90-4.87 (m, 1H), 3.89-3.60 (m, 6H), 3.55-3.49 (m, 1H), 3.37-3.29 (m, 5H), 3.07-2.99 (m, 1H), 2.51-2.34 (m, 5H), 2.20-1.94 (m, 4H), 1.90-1.81 (m, 2H), 1.80-1.50 (m, 1H), 1.45-1.05 (m, 3H). $^{19}$F NMR (282 MHz, DMSO-d$_6$) δ −63.35 (3F).

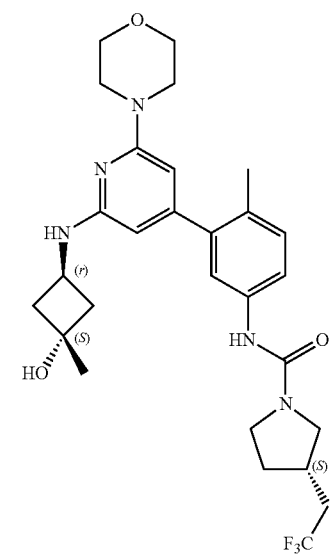

243

Preparation 35A: (1R,3R)-3-((4-iodo-6-morpholino-pyridin-2-yl)amino)-1-methylcyclobutan-1-ol

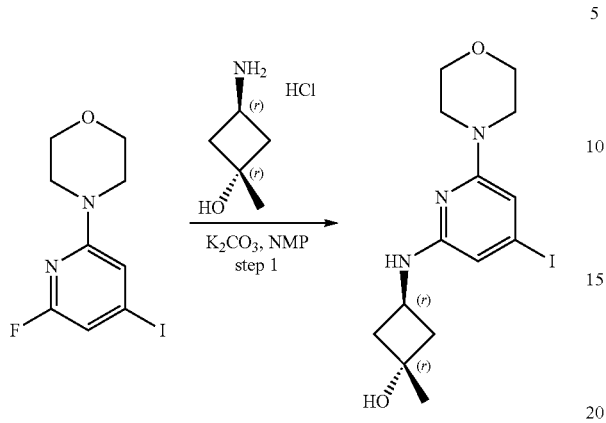

A mixture of 4-(6-fluoro-4-iodopyridin-2-yl)morpholine (300 mg, 0.974 mmol) and (trans)-3-amino-1-methylcyclobutan-1-ol hydrochloride (201 mg, 1.461 mmol), $K_2CO_3$ (269 mg, 1.947 mmol) in NMP (3 mL) was stirred for 16 h at 150° C. under nitrogen atmosphere. The reaction was quenched by the addition of Water (30 mL) at room temperature. The resulting mixture was extracted with EtOAc (2×20 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EtOAc/EtOH=(4/3/1) to afford (1R,3R)-3-((4-iodo-6-morpholinopyridin-2-yl)amino)-1-methylcyclobutan-1-ol (370 mg, 88%) as an off-white solid. MS ESI calculated for $C_{14}H_{20}IN_3O_2$ [M+H]$^+$, 390.06, found 390.05. $^1$H NMR (300 MHz, chloroform-d) δ 6.33-6.32 (m, 1H), 6.11-6.10 (s, 1H), 4.47-4.45 (m, 1H), 4.23-4.11 (m, 1H), 3.80-3.77 (m, 4H), 3.45-3.42 (m, 4H), 2.60-2.53 (m, 1H), 2.00-1.93 (m, 2H), 1.46 (s, 3H), 1.31-1.26 (m, 1H), 0.91-0.88 (m, 1H).

Example 35: (S)—N-(3-(2-(((1R,3S)-3-hydroxy-3-methylcyclobutyl)amino)-6-morpholinopyridin-4-yl)-4-methylphenyl)-3-(2,2,2-trifluoroethyl)pyrrolidine-1-carboxamide

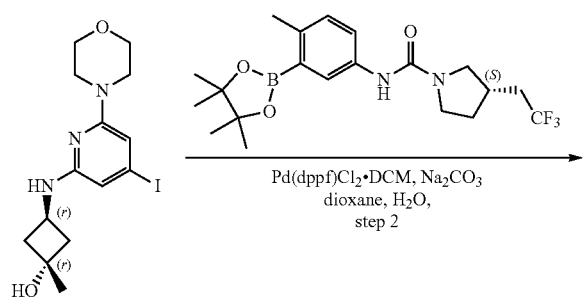

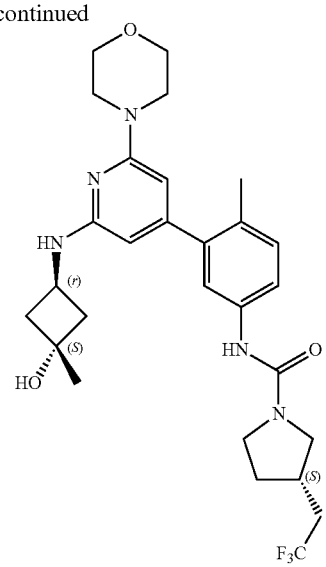

A mixture of (1R,3R)-3-((4-iodo-6-morpholinopyridin-2-yl)amino)-1-methylcyclobutan-1-ol (142 mg, 0.364 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (150 mg, 0.364 mmol), Pd(dppf)Cl$_2$·CH$_2$Cl$_2$ (30 mg, 0.036 mmol) and Na$_2$CO$_3$ (116 mg, 1.092 mmol) in dioxane (1.2 mL) and H$_2$O (0.3 mL) was stirred for 16 h at 60° C. under hydrogen atmosphere. The reaction was quenched by the addition of water (5 mL) at room temperature. The resulting mixture was extracted with EtOAc (2×10 mL). The combined organic layers were washed with brine (5 mL), dried over anhydrous Na$_2$SO$_4$. After filtration, the filtrate was concentrated under reduced pressure. The residue was purified by silica gel column chromatography, eluted with PE/EtOAc/EtOH=(4/3/1), the crude product was purified by reverse flash chromatography with the following conditions: Column: SunFire Prep C$^{18}$ OBD Column, 19×150 mm 5 um 10 nm; Mobile Phase A: water (0.1% FA), Mobile Phase B: CH$_3$CN; Flow rate: 20 mL/min; Gradient: 35 B to 70 B in 4.3 min; 210/254 nm. This resulted in (S)—N-(3-(2-(((1R,3S)-3-hydroxy-3-methylcyclobutyl)amino)-6-morpholinopyridin-4-yl)-4-methylphenyl)-3-(2,2,2-trifluoroethyl)pyrrolidine-1-carboxamide (114 mg, 56%) as an off-white solid. MS ESI calculated for $C_{28}H_{36}F_3N_5O_3$ [M+H]$^+$, 548.28, found 548.15. $^1$H NMR (300 MHz, DMSO-d$_6$) δ 8.13-8.11 (m, 1H), 7.43-7.40 (m, 1H), 7.33 (s, 1H), 7.10-7.08 (m, 1H), 6.42 (m, 1H), 5.77 (s, 1H), 5.64 (s, 1H), 4.83-4.23 (m, 1H), 4.45-4.05 (m, 1H), 3.80-3.67 (m, 5H), 3.57-3.55 (m, 1H), 3.52-3.38 (m, 5H), 3.10-2.99 (m, 1H), 2.46-2.32 (m, 5H), 2.29-2.08 (m, 4H), 1.94-1.84 (m, 2H), 1.72-1.62 (m, 1H), 1.27-1.06 (m, 3H). $^{19}$F NMR (282 MHz, DMSO-d$_6$) δ −63.35-63.42 (3F).

Example 36: (S)—N-(3-(2-(((1S,4R)-4-hydroxy-4-methylcyclohexyl)amino)-6-morpholinopyridin-4-yl)-4-methylphenyl)-3-(2,2,2-trifluoroethyl)pyrrolidine-1-carboxamide Preparation 36A: (1S,4S)-4-((4-iodo-6-morpholinopyridin-2-yl)amino)-1-methylcyclohexan-1-ol

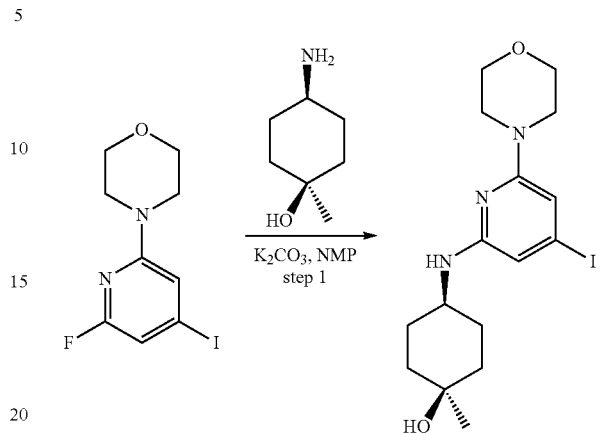

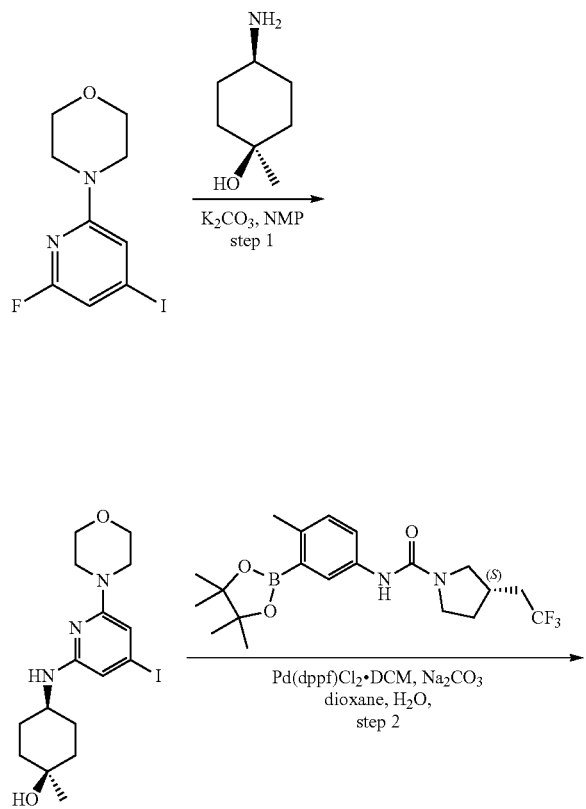

To a stirred mixture of 4-(6-fluoro-4-iodopyridin-2-yl)morpholine (300 mg, 0.974 mmol) and K$_2$CO$_3$ (407 mg, 2.921 mmol) in NMP (3 mL) was added (cis)-4-amino-1-methylcyclohexan-1-ol (189 mg, 1.461 mmol) at room temperature. The resulting mixture was stirred for 16 h at 150° C. The mixture was allowed to cool down to room temperature. The residue was purified by reverse flash chromatography with the following conditions: column, C18 silica gel; mobile phase, CH$_3$CN in water, 30% to 70% gradient in 20 min; detector, UV 254 nm to afford (1S,4S)-4-((4-iodo-6-morpholinopyridin-2-yl)amino)-1-methylcyclohexan-1-ol (290 mg, 71%) as a light brown solid. MS ESI calculated for C$_{16}$H$_{24}$IN$_3$O$_2$ 418.09, found 417.95. $^1$H NMR (300 MHz, chloroform-d) δ 6.26 (s, 1H), 6.16 (s, 1H), 4.24 (d, J=8.0 Hz, 1H), 3.84-3.75 (m, 4H), 3.45-3.42 (m, 5H), 2.00-1.40 (m, 8H), 1.29 (s, 3H), 1.13 (s, 1H).

Example 36: (S)—N-(3-(2-(((1S,4R)-4-hydroxy-4-methylcyclohexyl)amino)-6-morpholinopyridin-4-yl)-4-methylphenyl)-3-(2,2,2-trifluoroethyl)pyrrolidine-1-carboxamide

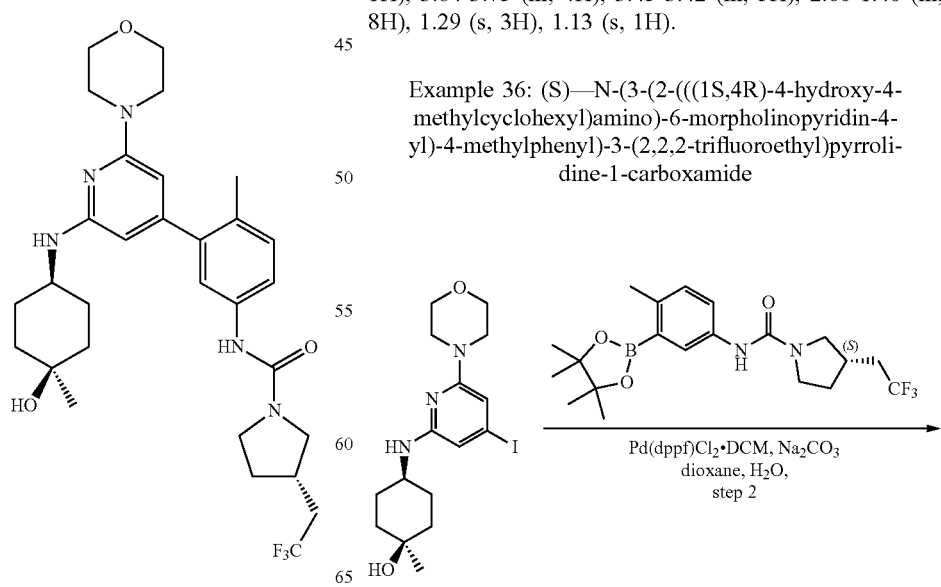

-continued

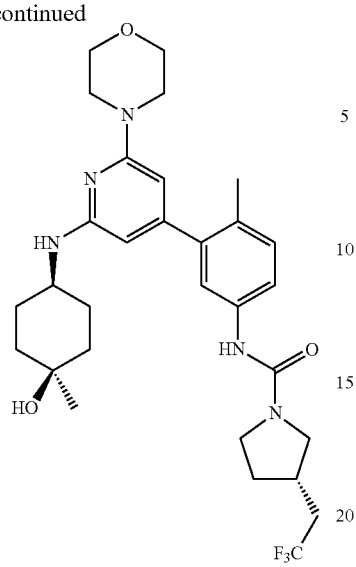

To a stirred mixture of (1S,4S)-4-((4-iodo-6-morpholinopyridin-2-yl)amino)-1-methylcyclohexan-1-ol (150 mg, 0.359 mmol) and (3S)—N-[4-methyl-3-(4,4,5-trimethyl-1,3,2-dioxaborolan-2-yl)phenyl]-3-(2,2,2-trifluoroethyl)pyrrolidine-1-carboxamide (143 mg, 0.359 mmol) in 1,4-dioxane (4 mL) and H$_2$O (1 mL) were added Na$_2$CO$_3$ (114 mg, 1.078 mmol) and Pd(dppf)Cl$_2$·DCM (29 mg, 0.036 mmol) at 70° C. under nitrogen atmosphere. The reaction was quenched by the addition of water (20 mL) at room temperature. The resulting mixture was extracted with EtOAc (3×50 mL). The combined organic layers were washed with brine (2×5 mL), dried over anhydrous Na$_2$SO$_4$. After filtration, the filtrate was concentrated under reduced pressure. The residue was purified by silica gel column chromatography, eluted with PE/EtOAc (1:1) to afford (S)—N-(3-(2-(((1S,4R)-4-hydroxy-4-methylcyclohexyl)amino)-6-morpholinopyridin-4-yl)-4-methylphenyl)-3-(2,2,2-trifluoroethyl)pyrrolidine-1-carboxamide (98 mg, 47%) as a light green solid. MS ESI calculated for C$_{30}$H$_{40}$F$_3$N$_5$O$_3$, 576.31 found 576.20. $^1$H NMR (300 MHz, DMSO-d$_6$) δ 8.12 (s, 1H), 7.41 (dd, J=8.2, 2.3 Hz, 1H), 7.33 (d, J=2.3 Hz, 1H), 7.09 (d, J=8.4 Hz, 1H), 6.07 (d, J=7.4 Hz, 1H), 5.73 (s, 2H), 4.02 (s, 1H), 3.68 (dd, J=5.9, 3.7 Hz, 5H), 3.52 (td, J=9.4, 8.3, 5.3 Hz, 2H), 3.37 (s, 3H), 3.02 (t, J=9.4 Hz, 1H), 2.44 (dd, J=12.6, 8.1 Hz, 3H), 2.16 (s, 3H), 2.09 (d, J=11.9 Hz, 1H), 1.69 (t, J=7.9 Hz, 3H), 1.56 (p, J=9.9, 8.8 Hz, 5H), 1.43-1.28 (m, 3H), 1.24 (s, 1H), 1.12 (s, 3H).

Example 37: (S)—N-(3-(2-(((1R,4S)-4-hydroxy-4-methylcyclohexyl)amino)-6-morpholinopyridin-4-yl)-4-methylphenyl)-3-(2,2,2-trifluoroethyl)pyrrolidine-1-carboxamide

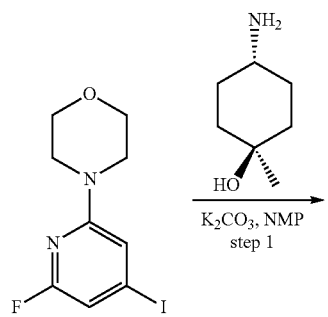

-continued

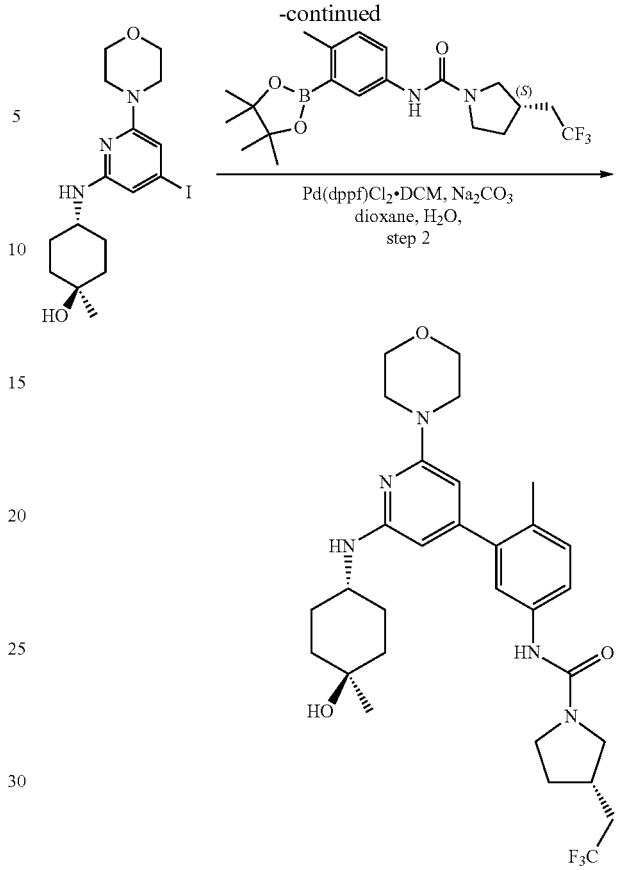

Preparation 37A: (1R,4R)-4-((4-iodo-6-morpholinopyridin-2-yl)amino)-1-methylcyclohexan-1-ol

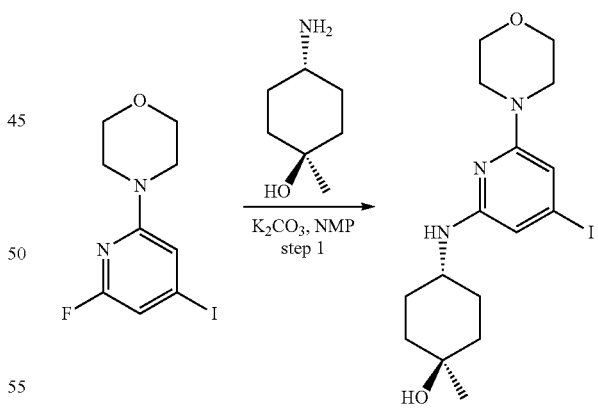

To a stirred mixture of 4-(6-fluoro-4-iodopyridin-2-yl)morpholine (300 mg, 0.974 mmol) and K$_2$CO$_3$ (404 mg, 2.921 mmol) in NMP (3 mL) was added (1R,4R)-4-amino-1-methylcyclohexan-1-ol (189 mg, 1.461 mmol) at room temperature. The resulting mixture was stirred for 16 h at 150° C. The mixture was allowed to cool down to room temperature. The residue was purified by reverse flash chromatography with the following conditions: column, C18 silica gel; mobile phase, CH$_3$CN in water, 30% to 70% gradient in 20 min; detector, UV 254 nm to afford (1R,4R)-

4-((4-iodo-6-morpholinopyridin-2-yl)amino)-1-methylcyclohexan-1-ol (320 mg, 79%) as a light brown solid. MS ESI calculated for $C_{16}H_{24}IN_3O_2$ [M+H]$^+$418.09 found 418.00. $^1$H NMR (300 MHz, chloroform-d) δ 6.28 (s, 1H), 6.18 (s, 1H), 4.27 (s, 1H), 3.84-3.75 (m, 4H), 3.63-3.39 (m, 5H), 2.02-1.36 (m, 8H), 1.31 (s, 3H), 1.27 (s, 1H).

Example 37: (S)—N-(3-(2-(((1R,4S)-4-hydroxy-4-methylcyclohexyl)amino)-6-morpholinopyridin-4-yl)-4-methylphenyl)-3-(2,2,2-trifluoroethyl)pyrrolidine-1-carboxamide

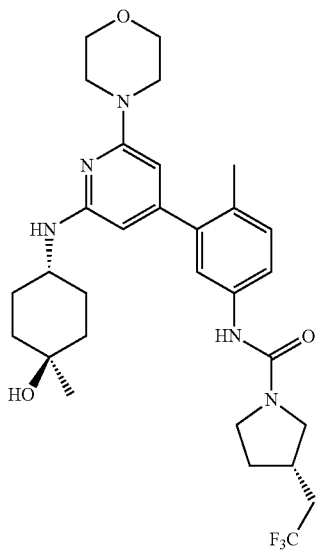 [SMILES: Cc1ccc(NC(=O)N2CC[C@@H](CC(F)(F)F)C2)cc1-c1cc(N[C@H]2CC[C@](C)(O)CC2)nc(N2CCOCC2)c1]

A mixture of (1R,4R)-4-((4-iodo-6-morpholinopyridin-2-yl)amino)-1-methylcyclohexan-1-ol (220 mg, 0.527 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (217 mg, 0.527 mmol), 1,4-dioxane (5.3 mL), H$_2$O (1.3 mL), Na$_2$CO$_3$ (168 mg, 1.582 mmol) and Pd(dppf)Cl$_2$·DCM (43 mg, 0.053 mmol) was stirred for 2 h at 70° C. under nitrogen atmosphere. The reaction was quenched by the addition of water (20 mL) at room temperature. The resulting mixture was extracted with EtOAc (3×50 mL). The combined organic layers were washed with brine (2×5 mL), dried over anhydrous Na$_2$SO$_4$. After filtration, the filtrate was concentrated under reduced pressure. The residue was purified by silica gel column chromatography, eluted with PE/EtOAc (1/1) to afford (S)—N-(3-(2-(((1R,4S)-4-hydroxy-4-methylcyclohexyl)amino)-6-morpholinopyridin-4-yl)-4-methylphenyl)-3-(2,2,2-trifluoroethyl)pyrrolidine-1-carboxamide (153 mg, 50%) as a light green solid. MS ESI calculated for $C_{30}H_{40}F_3N_5O_3$ [M+H]$^+$576.31, found 576.15. $^1$H NMR (300 MHz, DMSO-d$_6$) δ 8.12 (s, 1H), 7.41 (dd, J=8.3, 2.3 Hz, 1H), 7.34 (d, J=2.3 Hz, 1H), 7.09 (d, J=8.4 Hz, 1H), 6.08 (d, J=7.3 Hz, 1H), 5.74 (d, J=4.4 Hz, 2H), 4.20 (s, 1H), 3.67 (q, J=8.3, 6.4 Hz, 6H), 3.57-3.50 (m, 1H), 3.44-3.27 (m, 5H), 3.02 (t, J=9.4 Hz, 1H), 2.47 (d, J=19.5 Hz, 3H), 2.18-2.16 (m, 4H), 1.93-1.81 (m, 2H), 1.75-1.53 (m, 3H), 1.41 (h, J=10.4 Hz, 4H), 1.14 (s, 3H).

Example 38: (3S)—N-[3-[2-(3-hydroxy-3-methylazetidin-1-yl)-6-(morpholin-4-yl)pyridin-4-yl]-4-methylphenyl]-3-(2,2,2-trifluoroethyl)pyrrolidine-1-carboxamide

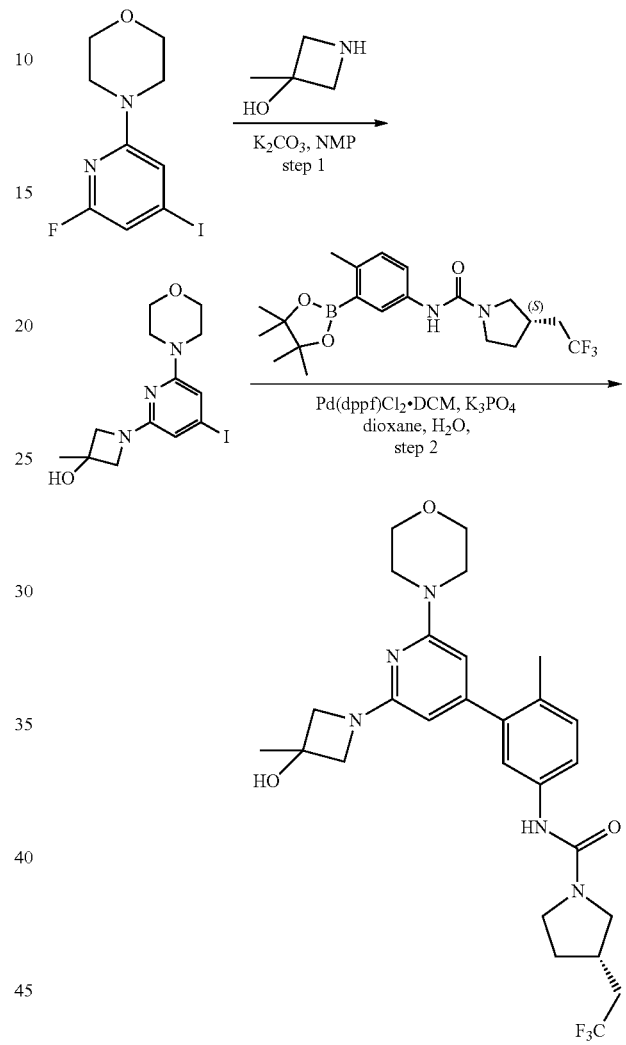

Preparation 38A: 1-[4-iodo-6-(morpholin-4-yl)pyridin-2-yl]-3-methylazetidin-3-ol

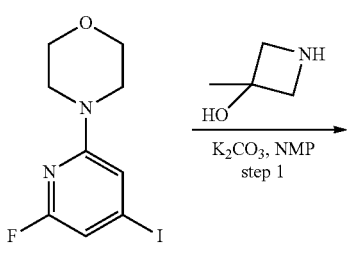

251

-continued

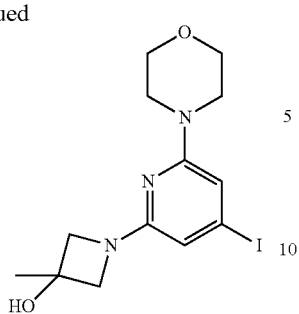

To a stirred solution/mixture of 4-(6-fluoro-4-iodopyridin-2-yl)morpholine (300 mg, 0.974 mmol) and 3-methylazetidin-3-ol (127 mg, 1.461 mmol) in NMP (3 mL) was added $K_2CO_3$ (404 mg, 3.00 equiv) at room temperature. The resulting mixture was stirred for 16 h at 150° C. The residue was purified by reverse flash chromatography with the following conditions: column, C18 silica gel; mobile phase, MeOH in water, 10% to 50% gradient in 30 min; detector, UV 254 nm. to afford 1-[4-iodo-6-(morpholin-4-yl)pyridin-2-yl]-3-methylazetidin-3-ol (270 mg, 74%) as an off-white solid. MS ESI calculated for $C_{13}H_{18}IN_3O_2$, $[M+H]^+$, 376.21, found 376.00. $^1H$ NMR (300 MHz, chloroform-d) δ 6.32 (s, 1H), 6.10 (s, 1H), 3.89 (q, J=8.6 Hz, 4H), 3.83-3.75 (m, 4H), 3.50-3.41 (m, 4H), 1.60 (s, 3H)

Example 38: (3S)—N-[3-[2-(3-hydroxy-3-methylazetidin-1-yl)-6-(morpholin-4-yl)pyridin-4-yl]-4-methylphenyl]-3-(2,2,2-trifluoroethyl)pyrrolidine-1-carboxamide

252

A mixture of 1-[4-iodo-6-(morpholin-4-yl)pyridin-2-yl]-3-methylazetidin-3-ol (150 mg, 0.400 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (181 mg, 0.440 mmol), 1,4-dioxane (1.6 mL), $H_2O$ (0.4 mL), $K_3PO_4$ (255 mg, 1.199 mmol) and Pd(dppf)$Cl_2$·DCM (43 mg, 0.053 mmol) at room temperature under $N_2$ atmosphere. The resulting mixture was stirred for 1 h at 80° C. under $N_2$ atmosphere. The resulting mixture was concentrated under reduced pressure. The residue was purified by silica gel column chromatography, eluted with PE/EtOAc (1/1) to afford (3S)—N-[3-[2-(3-hydroxy-3-methylazetidin-1-yl)-6-(morpholin-4-yl)pyridin-4-yl]-4-methylphenyl]-3-(2,2,2-trifluoroethyl)pyrrolidine-1-carboxamide (79 mg, 37%) as an off-white solid. MS ESI calculated for $C_{27}H_{34}F_3N_5O_3$ $[M+H]^+$, 534.26, found 534.15. $^1H$ NMR (400 MHz, DMSO-$d_6$) δ 8.12 (s, 1H), 7.43 (dd, J=8.3, 2.3 Hz, 1H), 7.33 (d, J=2.4 Hz, 1H), 7.10 (d, J=8.4 Hz, 1H), 5.93 (d, J=1.0 Hz, 1H), 5.61 (d, J=0.9 Hz, 1H), 5.49 (s, 1H), 3.80-3.62 (m, 9H), 3.52 (ddd, J=10.4, 8.3, 2.3 Hz, 1H), 3.40 (t, J=4.9 Hz, 4H), 3.32 (d, J=2.5 Hz, 1H), 3.02 (t, J=9.5 Hz, 1H), 2.45 (d, J=11.3 Hz, 1H), 2.41 (s, 2H), 2.15 (s, 3H), 2.12-2.00 (m, 1H), 1.65 (p, J=9.9 Hz, 1H), 1.43 (s, 3H). $^{19}F$ NMR (376 MHz, DMSO-$d_6$) δ −63.12.

Example 39: (3S)—N-[3-[2-(isopropylamino)-6-(morpholin-4-yl)pyridin-4-yl]-4-methylphenyl]-3-(2,2,2-trifluoroethyl)pyrrolidine-1-carboxamide

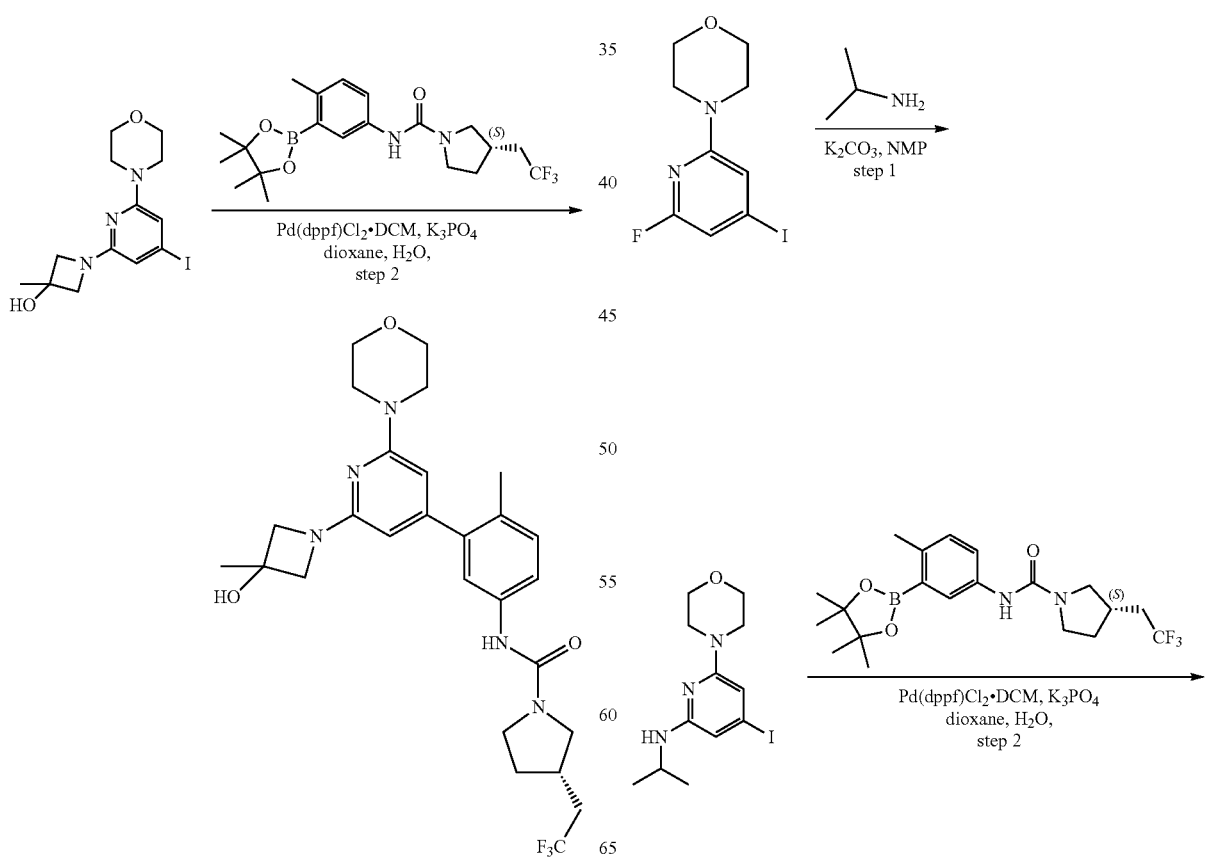

-continued

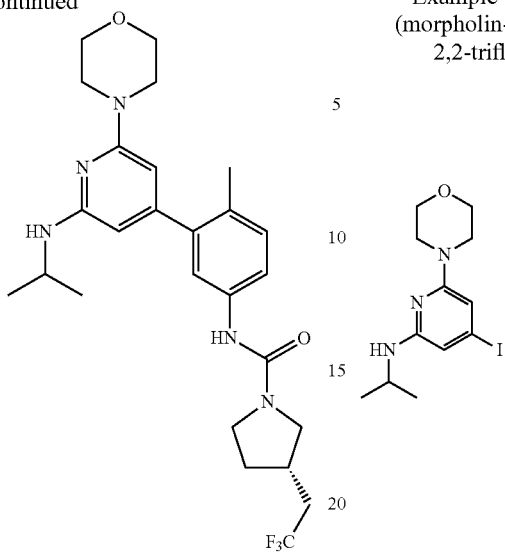

Preparation 39A: 4-iodo-N-isopropyl-6-(morpholin-4-yl)pyridin-2-amine

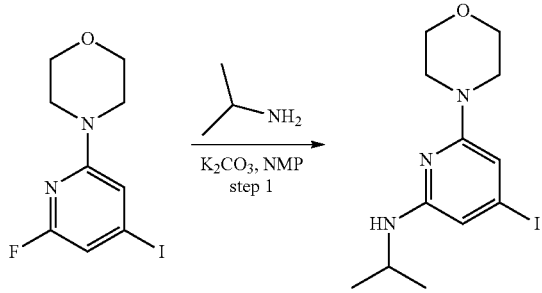

A mixture of 4-(6-fluoro-4-iodopyridin-2-yl)morpholine (300 mg, 0.974 mmol), isopropylamine (86 mg, 1.461 mmol), NMP (3 mL) and K$_2$CO$_3$ (404 mg, 2.921 mmol) was stirred for 16 h at 150° C. The resulting mixture was concentrated under reduced pressure. The residue was purified by silica gel column chromatography, eluted with PE/EtOAc (0-50%) to afford 4-iodo-N-isopropyl-6-(morpholin-4-yl)pyridin-2-amine (210 mg, 62%) as a white solid. MS ESI calculated for C$_{12}$H$_{18}$IN$_3$O [M+H]$^+$, 348.05, found 348.10. $^1$H NMR (300 MHz, chloroform-d) δ 6.27 (s, 1H), 6.16 (s, 1H), 4.17 (d, J=7.7 Hz, 1H), 3.92-3.74 (m, 5H), 3.48-3.39 (m, 4H), 1.22 (d, J=6.4 Hz, 6H).

Example 39: (3S)—N-[3-[2-(isopropylamino)-6-(morpholin-4-yl)pyridin-4-yl]-4-methylphenyl]-3-(2,2,2-trifluoroethyl)pyrrolidine-1-carboxamide

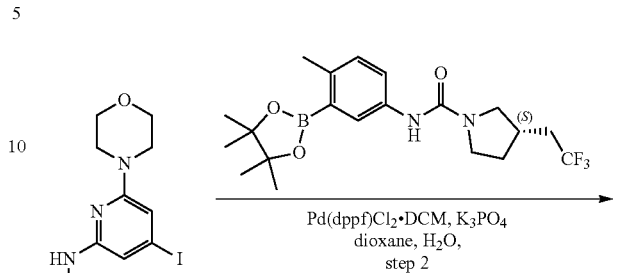

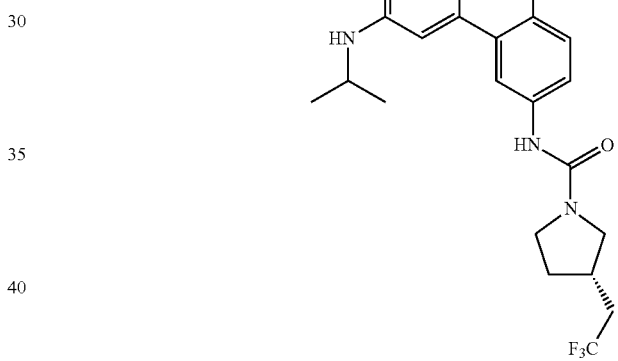

A mixture of 4-iodo-N-isopropyl-6-(morpholin-4-yl)pyridin-2-amine (150 mg, 0.432 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (196 mg, 0.475 mmol), 1,4-dioxane (2 mL), H$_2$O (0.5 mL), K$_3$PO$_4$ (275 mg, 1.296 mmol) and Pd (dppf)Cl$_2$·DCM (43 mg, 0.053 mmol) was stirred for 1 h at 80° C. under N$_2$ atmosphere. The resulting mixture was concentrated under reduced pressure. The residue was purified by silica gel column chromatography, eluted with PE/EtOAc (1/1) to afford (3S)—N-[3-[2-(isopropylamino)-6-(morpholin-4-yl)pyridin-4-yl]-4-methylphenyl]-3-(2,2,2-trifluoroethyl)pyrrolidine-1-carboxamide (86 mg, 40%) as an off-white solid. MS ESI calculated for C$_{26}$H$_{34}$F$_3$N$_5$O$_2$ [M+H]$^+$, 506.27, found 506.15. $^1$H NMR (400 MHz, DMSO-d$_6$) δ 8.13 (d, J=17.1 Hz, 1H), 7.41 (dd, J=8.3, 2.3 Hz, 1H), 7.33 (d, J=2.4 Hz, 1H), 7.09 (d, J=8.4 Hz, 1H), 6.05 (d, J=7.5 Hz, 1H), 5.72 (dd, J=8.5, 1.0 Hz, 2H), 3.96 (h, J=6.6 Hz, 1H), 3.71-3.62 (m, 5H), 3.57-3.47 (m, 1H), 3.36-3.30 (m, 5H), 3.02 (t, J=9.4 Hz, 1H), 2.50-2.42 (m, 1H), 2.41-2.39 (m, 2H), 2.16 (s, 3H), 2.08 (s, 1H), 1.67 (q, J=10.5, 10.1 Hz, 1H), 1.15 (d, J=6.5 Hz, 6H).

Example 40: (3S)—N-[3-[2-(tert-butylamino)-6-(morpholin-4-yl)pyridin-4-yl]-4-methylphenyl]-3-(2,2,2-trifluoroethyl)pyrrolidine-1-carboxamide

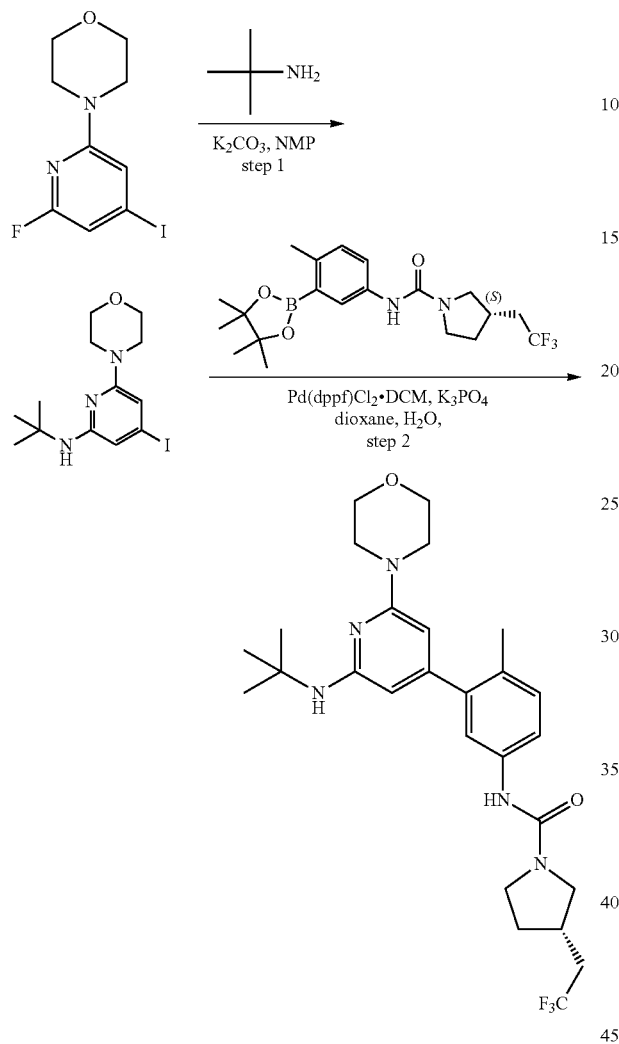

Preparation 40A: N-tert-butyl-4-iodo-6-(morpholin-4-yl)pyridin-2-amine

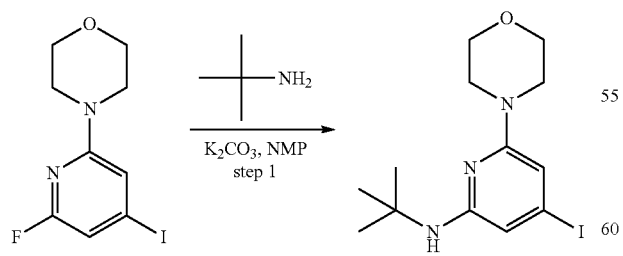

A mixture of 4-(6-fluoro-4-iodopyridin-2-yl)morpholine (300 mg, 0.974 mmol), 3-methylazetidin-3-ol (127 mg, 1.461 mmol), NMP (3 mL) and $K_2CO_3$ (404 mg, 2.921 mmol) was stirred for 16 h at 150° C. The reaction was monitored by LCMS. The residue was purified by silica gel column chromatography, eluted with PE/EtOAc (1/1) to afford N-tert-butyl-4-iodo-6-(morpholin-4-yl)pyridin-2-amine (120 mg, 34%) as a white solid. MS ESI calculated for $C_{13}H_{20}IN_3O$ [M+H]$^+$, 362.07, found 362.05. $^1$H NMR (400 MHz, DMSO-d$_6$) δ 6.28 (d, J=1.0 Hz, 1H), 6.19-6.11 (m, 2H), 3.66 (t, J=4.9 Hz, 4H), 3.44-3.29 (m, 4H), 1.34 (s, 9H).

Example 40: (3S)—N-[3-[2-(tert-butylamino)-6-(morpholin-4-yl)pyridin-4-yl]-4-methylphenyl]-3-(2,2,2-trifluoroethyl)pyrrolidine-1-carboxamide

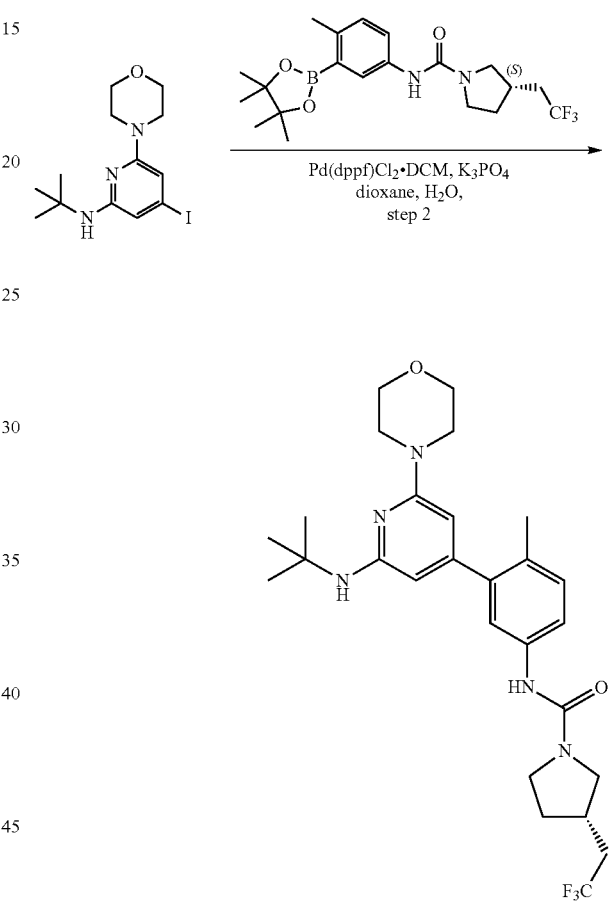

To a stirred mixture of N-tert-butyl-4-iodo-6-(morpholin-4-yl)pyridin-2-amine (100 mg, 0.277 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (126 mg, 0.305 mmol) in dioxane (1 mL) H$_2$O (0.2 mL), were added K$_3$PO$_4$ (176 mg, 0.831 mmol) and Pd(dppf)Cl$_2$·CH$_2$Cl$_2$ (23 mg, 0.028 mmol) in portions at room temperature under N$_2$ atmosphere. The resulting mixture was stirred for 1 h at 80° C. under N$_2$ atmosphere. The resulting mixture was concentrated under reduced pressure. The residue was purified by silica gel column chromatography, eluted with PE/EtOAc (1:1). The residue was purified by reverse flash chromatography with the following conditions: Column: XBridge Prep Phenyl OBD Column, 19×150 mm 5 um 13 nm; Mobile Phase A: Water (10 mmol/l NH$_4$HCO$_3$), Mobile Phase B: CH$_3$CN; Flow rate: 20 mL/min; Gradient:30 B to 70 B in 4.2 min; 254/210 nm. The fractions contained desired product were combined and concentrated to afford (3S)—N-[3-[2-(tert-butylamino)-6-(morpholin-4-yl)pyridin-4-yl]-4-methylphenyl]-3-(2,2,2-trifluoroethyl)pyrrolidine-1-carboxamide (86 mg, 60%) as a white solid. MS ESI calculated for $C_{27}H_{36}F_3N_5O_2$ [M+H]$^+$, 520.28, found 520.15. $^1$H NMR (400 MHz, DMSO-d$_6$) δ 8.10 (s, 1H), 7.40 (dd, J=8.2, 2.3 Hz, 1H), 7.34 (d, J=2.3 Hz, 1H), 7.09 (d, J=8.3 Hz, 1H), 5.98 (s, 1H), 5.81 (s, 1H), 5.73 (s, 1H), 3.69 (q, J=8.0, 6.3 Hz, 5H), 3.57-3.48 (m, 1H), 3.37 (s, 1H), 3.32 (s, 1H), 3.02 (t, J=9.4 Hz, 1H), 2.45 (d, J=11.3 Hz, 1H), 2.41 (s, 2H), 2.16 (s, 3H), 2.12-2.05 (m, 1H), 1.70-1.61 (m, 1H), 1.40 (s, 9H). $^{19}$F NMR (376 MHz, DMSO-d$_6$) δ −63.37 (3F).

Example 41: (3S)—N-(3-[2-[(1-hydroxy-2-methylpropan-2-yl)amino]-6-(morpholin-4-yl)pyridin-4-yl]-4-methylphenyl)-3-(2,2,2-trifluoroethyl)pyrrolidine-1-carboxamide Preparation 41A: 2-[[4-iodo-6-(morpholin-4-yl)pyridin-2-yl]amino]-2-methylpropan-1-ol

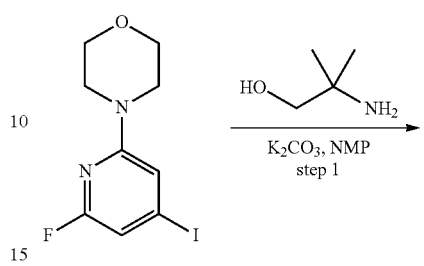

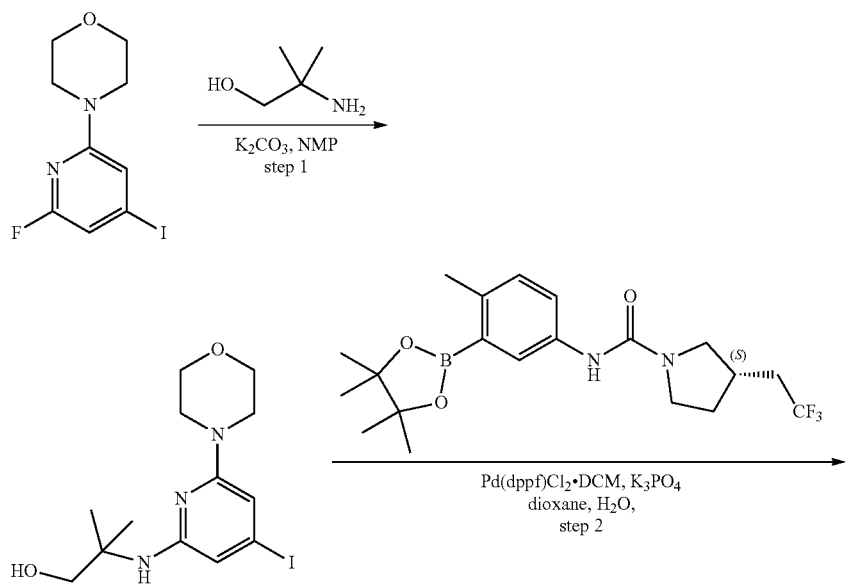

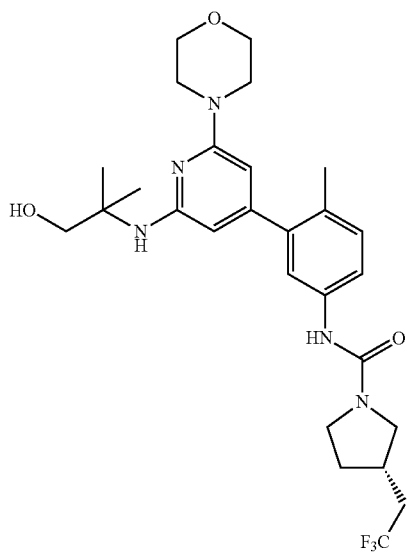

-continued

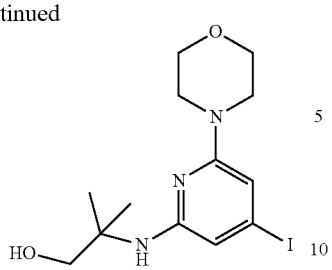

To a stirred solution of 4-(6-fluoro-4-iodopyridin-2-yl)morpholine (300 mg, 0.974 mmol) and 2-amino-2-methyl-1-propanol (130 mg, 1.461 mmol) in NMP (3 mL) was added $K_2CO_3$ (404 mg, 2.922 mmol) in portions at room temperature. The resulting mixture was stirred for 16 h at 150° C. The residue was purified by silica gel column chromatography, eluted with PE/EtOAc (0-50%) to afford 2-[[4-iodo-6-(morpholin-4-yl)pyridin-2-yl]amino]-2-methylpropan-1-ol (160 mg, 44%) as a light blue solid. MS ESI calculated for $C_{13}H_{20}IN_3O_2$ [M+H]$^+$, 378.06, found 378.10. $^1$H NMR (400 MHz, DMSO-d$_6$) δ 6.67 (s, 1H), 6.49 (s, 1H), 3.87 (s, 2H), 3.67 (t, J=4.7 Hz, 4H), 3.42 (t, J=4.8 Hz, 4H), 1.57 (s, 2H), 1.05 (s, 6H).

Example 41: (3S)—N-(3-[2-[(1-hydroxy-2-methylpropan-2-yl)amino]-6-(morpholin-4-yl)pyridin-4-yl]-4-methylphenyl)-3-(2,2,2-trifluoroethyl)pyrrolidine-1-carboxamide To a stirred mixture of 2-[[4-iodo-6-(morpholin-4-yl)pyridin-2-yl]amino]-2-methylpropan-1-ol (100 mg, 0.265 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (120 mg, 0.292 mmol) in dioxane (2 mL), $H_2O$ (0.5 mL), were added $K_3PO_4$ (169 mg, 0.795 mmol) and Pd(dppf)Cl$_2$·CH$_2$Cl$_2$ (22 mg, 0.027 mmol) in portions at room temperature under $N_2$ atmosphere. The resulting mixture was stirred for 1 h at 80° C. under $N_2$ atmosphere. The resulting mixture was concentrated under reduced pressure. The residue was purified by silica gel column chromatography, eluted with EA. The residue was purified by reverse flash chromatography with the following conditions: Column: XBridge Prep Phenyl OBD Column, 19×150 mm 5 um 13 nm; Mobile Phase A: Water (10 mmol/l $NH_4HCO_3$), Mobile Phase B: $CH_3CN$; Flow rate: 20 mL/min; Gradient:40 B to 75 B in 4.3 min; 254/210 nm. The fractions contained desired product were combined and concentrated to afford (3S)—N-(3-[2-[(1-hydroxy-2-methylpropan-2-yl)amino]-6-(morpholin-4-yl)pyridin-4-yl]-4-methylphenyl)-3-(2,2,2-trifluoroethyl)pyrrolidine-1-carboxamide (31 mg, 22%) as a light blue solid. MS ESI calculated for $C_{27}H_{36}F_3N_5O_2$ [M+H]$^+$, 536.28, found 536.15. $^1$H NMR (400 MHz, DMSO-d$_6$) δ 8.11 (s, 1H), 7.40 (dd, J=8.2, 2.4 Hz, 1H), 7.35 (d, J=2.3 Hz, 1H), 7.09 (d, J=8.3 Hz, 1H), 5.82 (d, J=14.0 Hz, 2H), 5.75 (s, 1H), 4.90 (t, J=5.7 Hz, 1H), 3.73-3.62 (m, 5H), 3.58-3.48 (m, 3H), 3.32 (dd, J=16.9, 10.3 Hz, 3H), 3.02 (t, J=9.4 Hz, 1H), 2.51-2.34 (m, 2H), 2.17 (s, 3H), 2.08 (t, J=5.8 Hz, 1H), 1.67 (q, J=10.0 Hz, 1H), 1.32 (s, 6H). $^{19}$F-NMR (376 MHz, DMSO-d$_6$) δ −63.37 (3F).

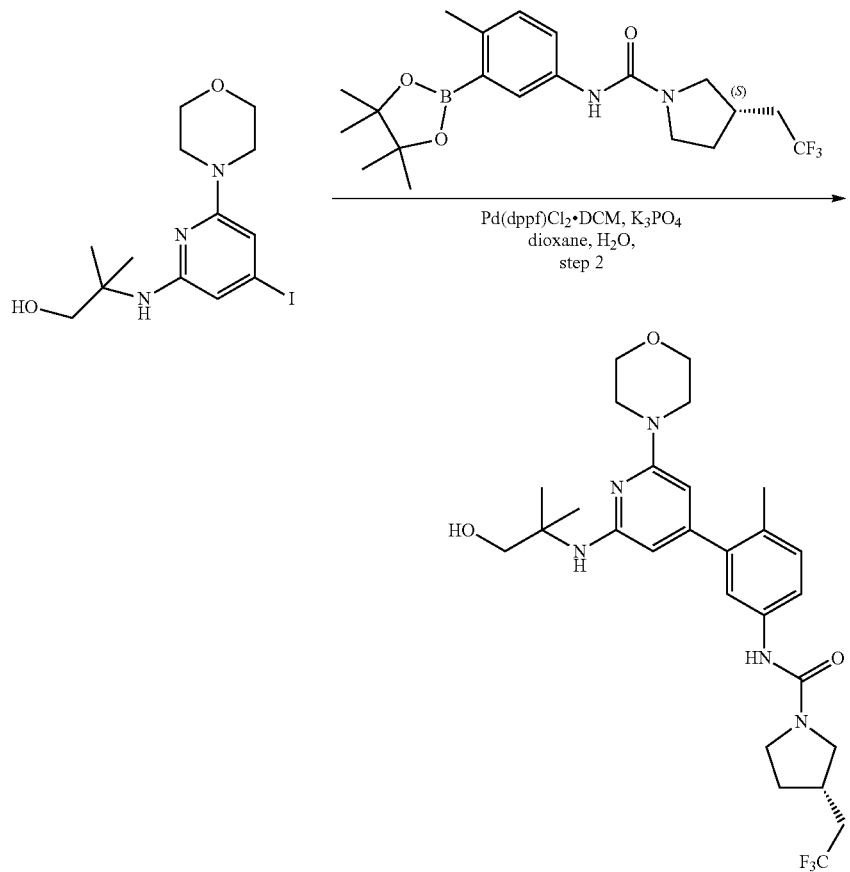

Example 42: (3S)—N-[4-methyl-3-[2-(morpholin-4-yl)-6-(oxetan-3-ylamino)pyridin-4-yl]phenyl]-3-(2,2,2-trifluoroethyl)pyrrolidine-1-carboxamide

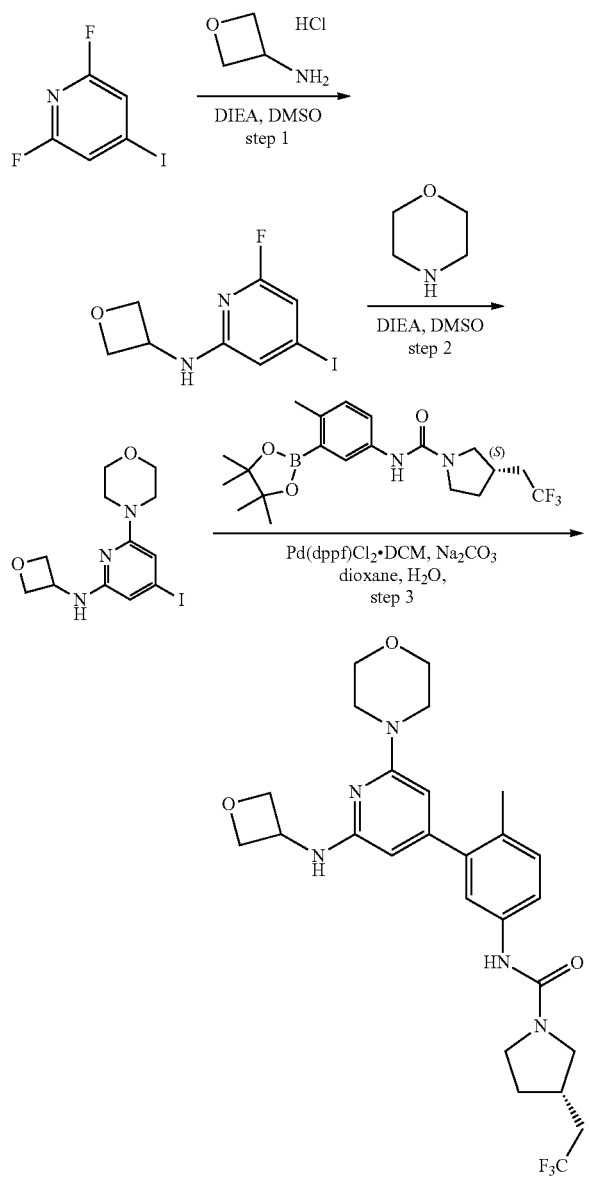

Preparation 42A: 6-fluoro-4-iodo-N-(oxetan-3-yl)pyridin-2-amine

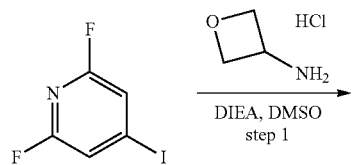

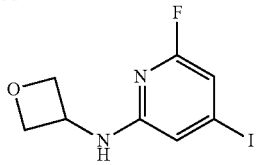

To a stirred mixture of 2,6-difluoro-4-iodopyridine (300 mg, 1.245 mmol) and oxetan-3-amine hydrochloride (150 mg, 1.369 mmol), DIEA (354 mg, 2.739 mmol) in DMSO (4 mL) at room temperature under nitrogen atmosphere. The resulting mixture was stirred for 3 h at 70° C. under nitrogen atmosphere. No further workup and used in next step directly. MS ESI calculated for $C_8H_8FIN_2O[M+H]^+$, 294.97, found 295.05.

Preparation 42B: 4-iodo-6-(morpholin-4-yl)-N-(oxetan-3-yl)pyridin-2-amine

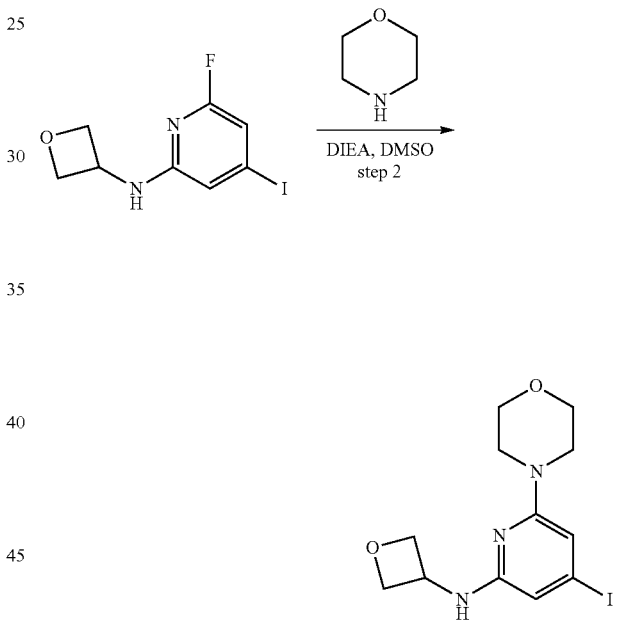

To a stirred mixture of 6-fluoro-4-iodo-N-(oxetan-3-yl)pyridin-2-amine (300 mg, 1.020 mmol) and morpholine (444 mg, 5.101 mmol), DIEA (145 mg, 1.122 mmol) in DMSO (4.5 mL) at room temperature under nitrogen atmosphere. The resulting mixture was stirred for 16 h at 70° C. under nitrogen atmosphere. The resulting mixture was diluted with water (50 mL). The resulting mixture was extracted with EtOAc (3×60 mL). The combined organic layers were washed with brine (2×50 mL), dried over anhydrous $Na_2SO_4$ After filtration, the filtrate was concentrated under reduced pressure. The residue was purified by silica gel column chromatography, eluted with PE/EtOAc/EtOH=(4/3/1) to afford 4-iodo-6-(morpholin-4-yl)-N-(oxetan-3-yl)pyridin-2-amine (395 mg, 90%) as an off-white solid. MS ESI calculated for $C_{12}H_{16}IN_3O_2$ $[M+H]^+$, 362.03, found 362.00. $^1H$ NMR (400 MHz, chloroform-d) δ 6.35-6.34 (m, 1H), 6.15 (s, 1H), 4.99-4.95 (m, 2H), 4.57-4.55 (m, 2H), 3.81-3.87 (m, 4H), 3.86-3.43 (m, 5H).

Example 42: (3S)—N-[4-methyl-3-[2-(morpholin-4-yl)-6-(oxetan-3-ylamino)pyridin-4-yl]phenyl]-3-(2,2,2-trifluoroethyl)pyrrolidine-1-carboxamide Example 43: (3S)—N-[4-methyl-3-[2-(morpholin-4-yl)-6-[(3R)-oxolan-3-ylamino]pyridin-4-yl]phenyl]-3-(2,2,2-trifluoroethyl)pyrrolidine-1-carboxamide

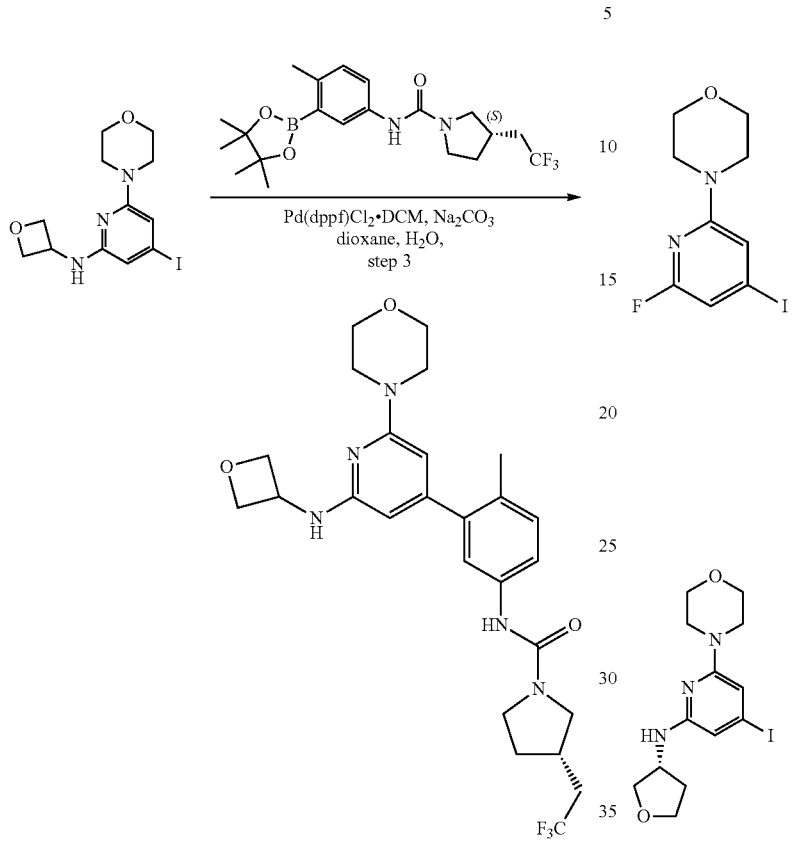

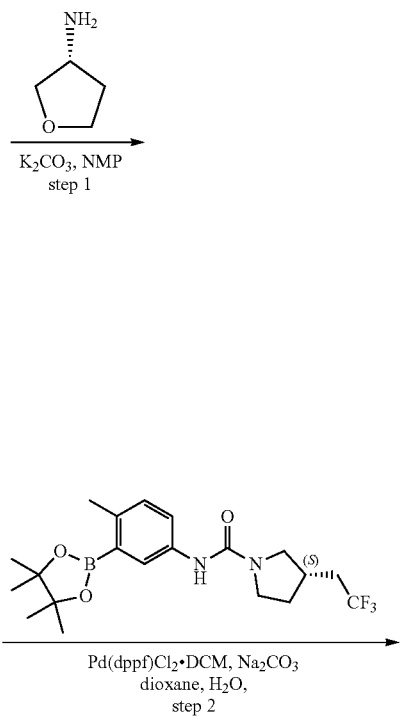

A mixture of 4-iodo-6-(morpholin-4-yl)-N-(oxetan-3-yl)pyridin-2-amine (200 mg, 0.554 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (228 mg, 0.554 mmol), $Na_2CO_3$ (176 mg, 1.661 mmol), dioxane (1.6 mL), $H_2O$ (0.4 mL) and $Pd(dppf)Cl_2 \cdot CH_2Cl_2$ (45 mg, 0.055 mmol) was stirred for 16 h at 60° C. The resulting mixture was diluted with $H_2O$ (20 mL). The resulting mixture was extracted with EtOAc (3×20 mL). The combined organic layers were washed with brine (2×15 mL), dried over anhydrous $Na_2SO_4$. After filtration, the filtrate was concentrated under reduced pressure. The residue was purified by silica gel column chromatography, eluted with PE/EtOAc/EtOH=(4/3/1) followed by Prep-HPLC with the following conditions (Column: SunFire Prep C18 OBD Column, 19×150 mm 5 um 10 nm; Mobile Phase A: water (0.1% FA), Mobile Phase B: $CH_3CN$; Flow rate: 20 mL/min; Gradient:20 B to 50 B in 4.3 min; 210/254 nm to afford (3S)—N-[4-methyl-3-[2-(morpholin-4-yl)-6-(oxetan-3-ylamino)pyridin-4-yl]phenyl]-3-(2,2,2-trifluoroethyl)pyrrolidine-1-carboxamide (160 mg, 55%) as a white solid. MS ESI calculated for $C_{26}H_{32}F_3N_5O_3$ $[M+H]^+$, 520.25, found 520.15. $^1H$ NMR (400 MHz, DMSO-$d_6$) δ 8.13 (s, 1H), 7.54-7.34 (m, 2H), 7.11-7.01 (m, 2H), 5.83-5.74 (m, 2H), 4.87-4.77 (m, 3H), 4.48-4.32 (m, 2H), 3.76-3.60 (m, 6H), 3.54-3.21 (m, 5H), 3.04-2.99 (m, 1H), 2.45-2.41 (m, 3H), 2.34-2.07 (m, 4H), 1.68-1.63 (m, 1H). $^{19}F$ NMR (376 MHz, DMSO-$d_6$) δ −63.36 (3F).

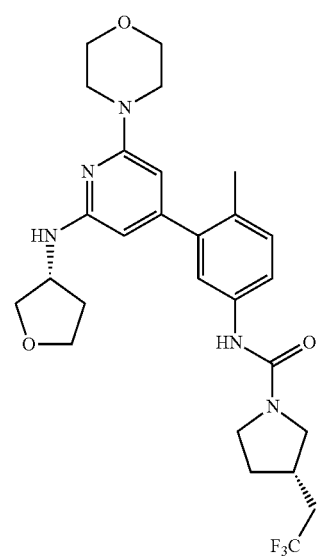

Preparation 43A: 4-iodo-6-(morpholin-4-yl)-N-[(3R)-oxolan-3-yl]pyridin-2-amine

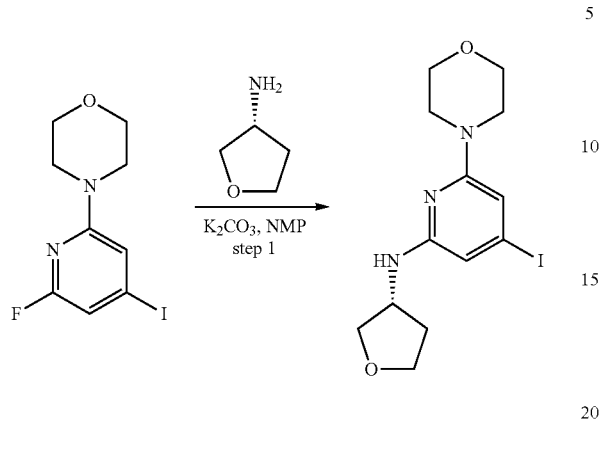

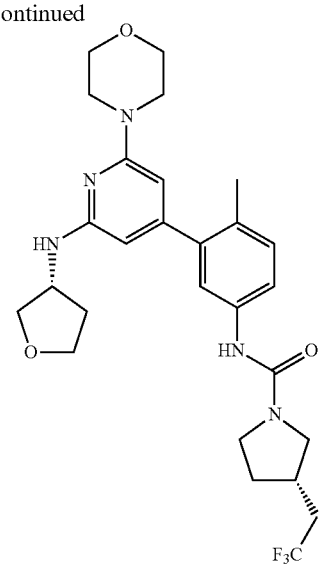

To a stirred mixture of 4-(6-fluoro-4-iodopyridin-2-yl)morpholine (300 mg, 0.974 mmol) and K$_2$CO$_3$ (404 mg, 2.921 mmol) in NMP (3 mL) was added (3R)-oxolan-3-amine (127 mg, 1.461 mmol) at room temperature. The resulting mixture was stirred for 16 h at 150° C. The mixture was allowed to cool down to room temperature. The residue was purified by reverse flash chromatography with the following conditions: column, C18 silica gel; mobile phase, CH$_3$CN in water, 30% to 70% gradient in 20 min; detector, UV 254 nm to afford 4-iodo-6-(morpholin-4-yl)-N-[(3R)-oxolan-3-yl]pyridin-2-amine (230 mg, 63%) as a brown solid. MS ESI calculated for C$_{13}$H$_{18}$IN$_3$O$_2$ [M+H]$^+$376.04 found 375.90. $^1$H NMR (300 MHz, chloroform-d) δ 6.32 (d, J=1.0 Hz, 1H), 6.20 (d, J=1.0 Hz, 1H), 4.47-4.28 (m, 2H), 4.04-3.91 (m, 2H), 3.91-3.81 (m, 1H), 3.85-3.75 (m, 4H), 3.68 (dd, J=9.2, 3.3 Hz, 1H), 3.56-3.40 (m, 4H), 2.38-2.20 (m, 1H), 1.92-1.79 (m, 1H).

Example 43: (3S)—N-[4-methyl-3-[2-(morpholin-4-yl)-6-[(3R)-oxolan-3-ylamino]pyridin-4-yl]phenyl]-3-(2,2,2-trifluoroethyl)pyrrolidine-1-carboxamide

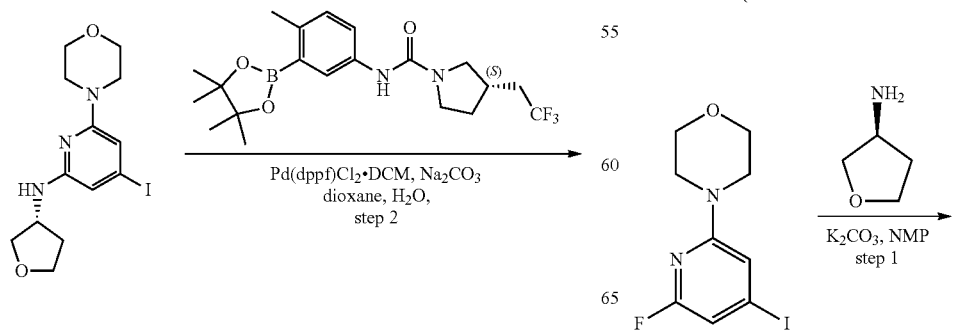

To a stirred mixture of 4-iodo-6-(morpholin-4-yl)-N-[(3R)-oxolan-3-yl]pyridin-2-amine (130 mg, 0.346 mmol,) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (142.84 mg, 0.346 mmol,) in 1,4-dioxane (4 mL) and H$_2$O (1 mL) were added Na$_2$CO$_3$ (110 mg, 1.039 mmol) and Pd(dppf)Cl$_2$·CH$_2$Cl$_2$ (29 mg, 0.035 mmol) at 70° C. under nitrogen atmosphere. The reaction was quenched by the addition of water (10 mL) at room temperature. The resulting mixture was extracted with EtOAc (3×40 mL). The combined organic layers were washed with brine (2×4 mL), dried over anhydrous Na$_2$SO$_4$. After filtration, the filtrate was concentrated under reduced pressure. The residue was purified by silica gel column chromatography, eluted with PE/EtOAc (1:1) to afford (3S)—N-[4-methyl-3-[2-(morpholin-4-yl)-6-[(3R)-oxolan-3-ylamino]pyridin-4-yl]phenyl]-3-(2,2,2-trifluoroethyl)pyrrolidine-1-carboxamide (55 mg, 30%) as a light green solid. MS ESI calculated for C$_{27}$H$_{34}$F$_3$N$_5$O$_4$ [M+H]$^+$534.26 found 534.10. $^1$H NMR (300 MHz, DMSO-d$_6$) δ 8.12 (s, 1H), 7.49-7.30 (m, 2H), 7.10 (d, J=8.3 Hz, 1H), 6.53 (s, 1H), 5.79 (d, J=6.6 Hz, 2H), 4.33 (s, 1H), 3.92 (dd, J=8.7, 6.0 Hz, 1H), 3.84 (dd, J=8.3, 7.0 Hz, 1H), 3.77-3.64 (m, 6H), 3.59-3.46 (m, 2H), 3.39 (d, J=4.8 Hz, 4H), 3.29 (dd, J=10.1, 6.7 Hz, 1H), 3.02 (t, J=9.3 Hz, 1H), 2.44 (dd, J=12.8, 7.7 Hz, 3H), 2.36-1.94 (m, 5H), 1.89-1.74 (m, 1H), 1.67 (q, J=9.8 Hz, 1H).

Example 44: (3S)—N-[4-methyl-3-[2-(morpholin-4-yl)-6-[(3S)-oxolan-3-ylamino]pyridin-4-yl]phenyl]-3-(2,2,2-trifluoroethyl)pyrrolidine-1-carboxamide (FT002912 PH-FNT-KIN-04-1601-0)

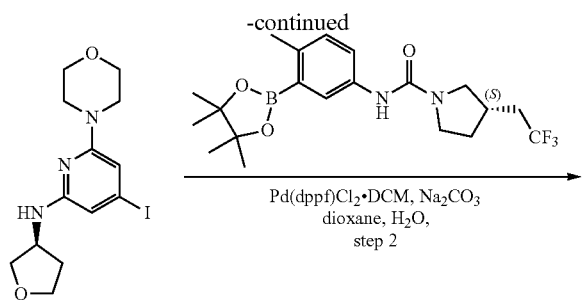

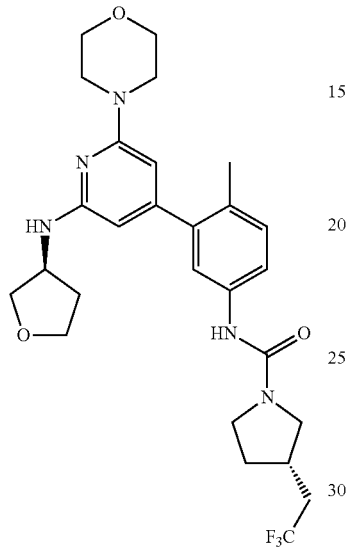

Preparation 44A: 4-iodo-6-(morpholin-4-yl)-N-[(3S)-oxolan-3-yl]pyridin-2-amine

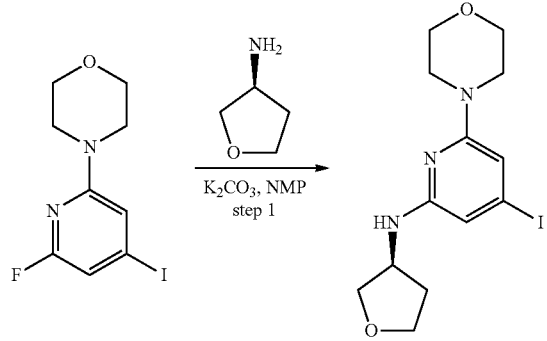 [SMILES: Fc1cc(I)cc(N2CCOCC2)n1 ; N[C@H]1CCOC1 ; Ic1cc(N[C@H]2CCOC2)nc(N2CCOCC2)c1]

To a stirred mixture of 4-(6-fluoro-4-iodopyridin-2-yl)morpholine (300 mg, 0.974 mmol) and K₂CO₃ (404 mg, 2.921 mmol) in NMP (3 mL) was added (3S)-oxolan-3-amine (127 mg, 1.461 mmol) at room temperature. The resulting mixture was stirred for 16 h at 150° C. The reaction was quenched by the addition of water (20 mL) at room temperature. The resulting mixture was extracted with EtOAc (3×50 mL). The combined organic layers were washed with brine (2×5 mL), dried over anhydrous Na₂SO₄. After filtration, the filtrate was concentrated under reduced pressure. The residue was purified by silica gel column chromatography eluted with PE/EtOAc (1/1) to afford 4-iodo-6-(morpholin-4-yl)-N-[(3S)-oxolan-3-yl]pyridin-2-amine (304 mg, 83%) as a light green solid. MS ESI calculated for C₁₃H₁₈IN₃O₂ 376.04, found 375.95. ¹H NMR (400 MHz, chloroform-d) δ 6.32 (d, J=1.1 Hz, 1H), 6.20 (d, J=1.0 Hz, 1H), 4.42 (s, 1H), 3.98 (dd, J=9.0, 5.7 Hz, 2H), 3.86 (td, J=8.4, 5.6 Hz, 1H), 3.80 (t, J=4.9 Hz, 4H), 3.69 (dd, J=9.1, 3.2 Hz, 1H), 3.45 (s, 4H), 2.36-2.22 (m, 1H), 1.60 (s, 1H), 1.28 (s, 1H).

Example 44: (3S)—N-[4-methyl-3-[2-(morpholin-4-yl)-6-[(3S)-oxolan-3-ylamino]pyridin-4-yl]phenyl]-3-(2,2,2-trifluoroethyl)pyrrolidine-1-carboxamide

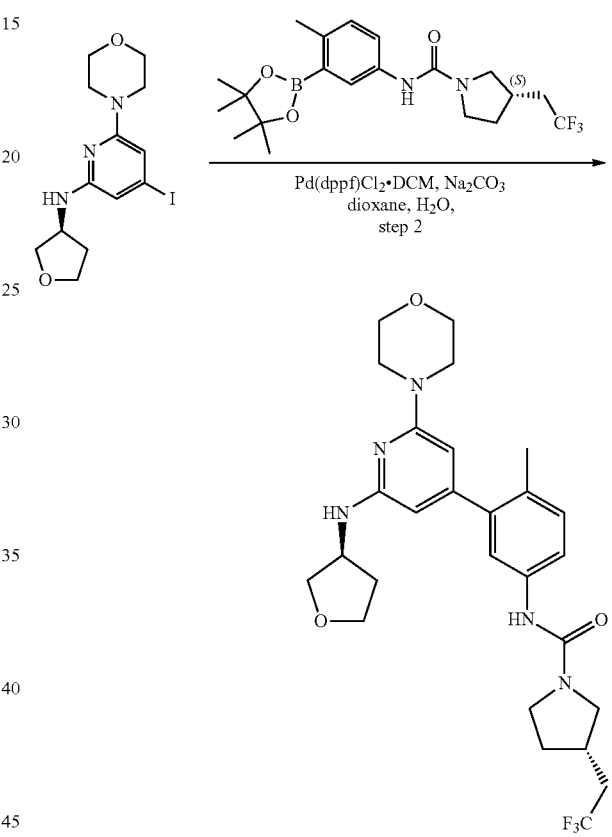

To a stirred mixture of 4-iodo-6-(morpholin-4-yl)-N-[(3S)-oxolan-3-yl]pyridin-2-amine (150 mg, 0.400 mmol) and (3R)—N-[4-methyl-3-(4,4,5,5-tetramethyl-1,3,2-dioxaborolan-2-yl)phenyl]-3-(2,2,2-trifluoroethyl)cyclopentane-1-carboxamide (132 mg, 0.321 mmol) in 1,4-dioxane (4 mL) and H₂O (1 mL) were added Na₂CO₃ (127 mg, 1.199 mmol) and Pd(dppf)Cl₂·CH₂Cl₂ (33 mg, 0.040 mmol) at 150° C. under nitrogen atmosphere. The reaction was quenched by the addition of water (20 mL) at room temperature. The resulting mixture was extracted with EtOAc (3×60 mL). The combined organic layers were washed with brine (2×20 mL), dried over anhydrous Na₂SO₄. After filtration, the filtrate was concentrated under reduced pressure. The residue was purified by Prep-HPLC with the following conditions: Column: SunFire Prep C18 OBD Column, 19×150 mm 5 um 10 nm; Mobile Phase A: Water (0.1% FA), Mobile Phase B: CH₃CN; Flow rate: 20 mL/min; Gradient:35 B to 70 B in 5.3 min; 254/210 nm to afford (3S)—N-[4-methyl-3-[2-(morpholin-4-yl)-6-[(3S)-oxolan-3-ylamino]pyridin-4-yl]phenyl]-3-(2,2,2-trifluoroethyl)pyrrolidine-1-carboxamide (61 mg, 29%) as a light green solid. MS ESI calculated for 534.26, found 534.15. $^1$H NMR (400 MHz, DMSO-$d_6$) δ 8.11 (s, 1H), 7.51-7.25 (m, 2H), 7.10 (d, J=8.3 Hz, 1H), 6.51 (d, J=5.8 Hz, 1H), 5.88-5.64 (m, 2H), 4.33 (s, 1H), 3.92 (dd, J=8.7, 6.0 Hz, 1H), 3.82 (q, J=7.5 Hz, 1H), 3.68 (t, J=4.9 Hz, 6H), 3.51 (dd, J=8.7, 3.9 Hz, 3H), 3.39 (d, J=5.4 Hz, 5H), 3.02 (t, J=9.4 Hz, 1H), 2.44 (t, J=10.9 Hz, 2H), 2.16 (s, 4H), 2.12-2.04 (m, 1H), 1.80 (dq, J=12.3, 6.0 Hz, 1H), 1.67 (q, J=10.0 Hz, 1H).

Example 45: (3S)—N-[4-methyl-3-[2-(morpholin-4-yl)-6-[(3R)-oxan-3-ylamino]pyridin-4-yl]phenyl]-3-(2,2,2-trifluoroethyl)pyrrolidine-1-carboxamide

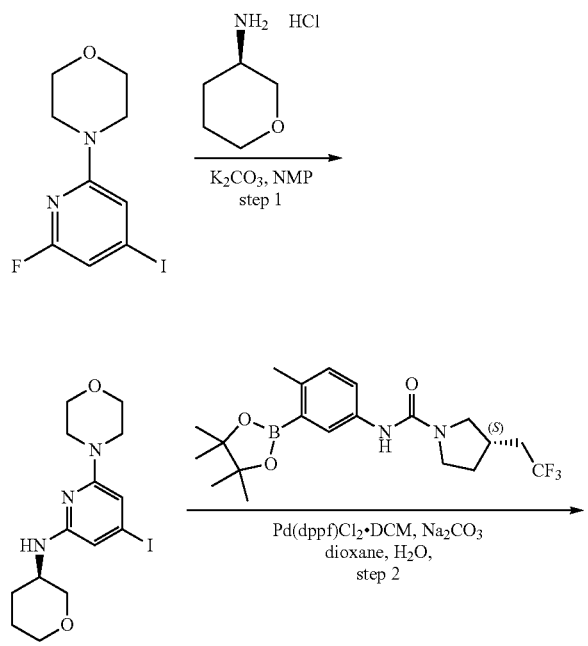

Preparation 45A: 4-iodo-6-(morpholin-4-yl)-N-[(3R)-oxan-3-yl]pyridin-2-amine

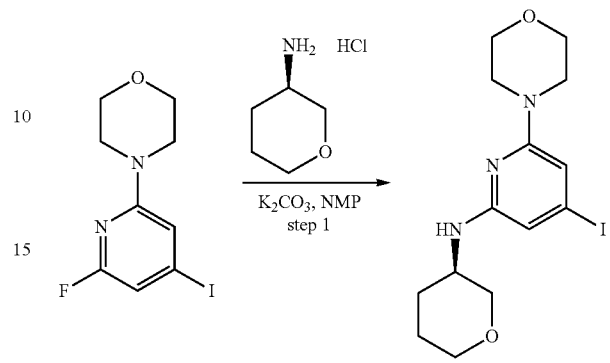

To a stirred mixture of 4-(6-fluoro-4-iodopyridin-2-yl)morpholine (300 mg, 0.974 mmol) and K$_2$CO$_3$ (673 mg, 4.869 mmol), (3R)-oxan-3-amine hydrochloride (670 mg, 4.869 mmol) in NMP (3 mL) at room temperature under nitrogen atmosphere. The resulting mixture was stirred for 16 h at 150° C. under nitrogen atmosphere. The resulting mixture was diluted with water (50 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with hexane/EtOAc/EtOH (4/3/1) to afford 4-iodo-6-(morpholin-4-yl)-N-[(3R)-oxan-3-yl]pyridin-2-amine (322 mg, 85%) as a white solid. MS ESI calculated for C$_{14}$H$_{20}$IN$_3$O$_2$ [M+H]$^+$, 390.06, found 389.95.

Example 45: (3S)—N-[4-methyl-3-[2-(morpholin-4-yl)-6-[(3R)-oxan-3-ylamino]pyridin-4-yl]phenyl]-3-(2,2,2-trifluoroethyl)pyrrolidine-1-carboxamide

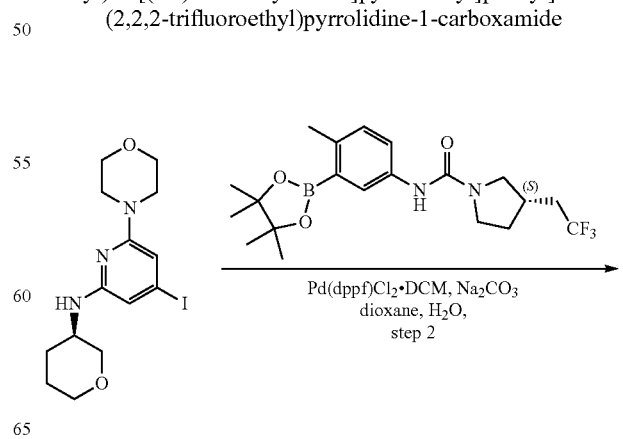

271

-continued

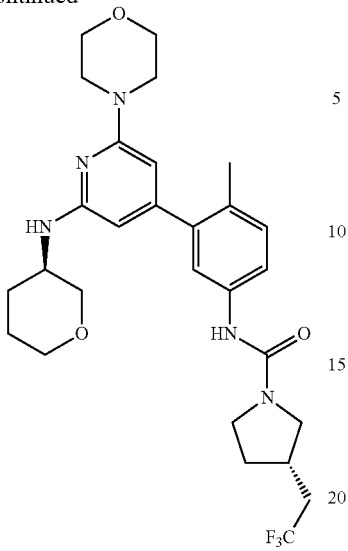

To a stirred mixture of 4-iodo-6-(morpholin-4-yl)-N-[(3R)-oxan-3-yl]pyridin-2-amine (150 mg, 0.385 mmol) and (3R)—N-[4-methyl-3-(4,4,5,5-tetramethyl-1,3,2-dioxaborolan-2-yl)phenyl]-3-(2,2,2-trifluoroethyl)cyclopentane-1-carboxamide (127 mg, 0.308 mmol) in 1,4-dioxane (4 mL) and H₂O (1 mL) were added Na₂CO₃ (122 mg, 1.156 mmol) and Pd(dppf)Cl₂·CH₂Cl₂ (31 mg, 0.039 mmol) was stirred for 2 h at 150° C. under nitrogen atmosphere. The reaction was quenched by the addition of water (20 mL) at room temperature. The resulting mixture was extracted with EtOAc (3×60 mL). The combined organic layers were washed with brine (2×10 mL), dried over anhydrous Na₂SO₄. After filtration, the filtrate was concentrated under reduced pressure. The residue was purified by silica gel column chromatography, eluted with PE/EtOAc (1:1) to afford (3S)—N-[4-methyl-3-[2-(morpholin-4-yl)-6-[(3R)-oxan-3-ylamino]pyridin-4-yl]phenyl]-3-(2,2,2-trifluoroethyl)pyrrolidine-1-carboxamide (25 mg, 12%) as a light green solid. MS ESI calculated for $C_{28}H_{36}F_3N_5O_3$ [M+H]⁺, 547.28 found 548.15. ¹H NMR (400 MHz, DMSO-d₆) δ 8.13 (s, 1H), 7.49-7.29 (m, 2H), 7.10 (d, J=8.3 Hz, 1H), 6.20 (brs, 1H), 5.81 (s, 2H), 3.92 (s, 1H), 3.81 (s, 1H), 3.73-3.62 (m, 6H), 3.52 (ddd, J=10.3, 8.3, 2.3 Hz, 1H), 3.36-3.30 (m, 8H), 2.48-2.32 (m, 3H), 2.16 (s, 3H), 2.11-2.06 (m, 1H), 1.92-1.90 (m, 1H), 1.76-1.59 (m, 4H).

Example 46: (3S)—N-[4-methyl-3-[2-(morpholin-4-yl)-6-(oxan-4-ylamino)pyridin-4-yl]phenyl]-3-(2,2,2-trifluoroethyl)pyrrolidine-1-carboxamide

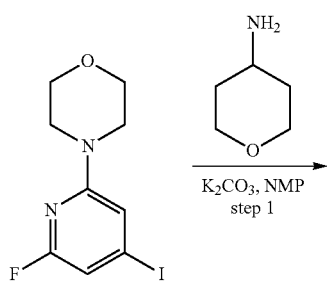

272

-continued

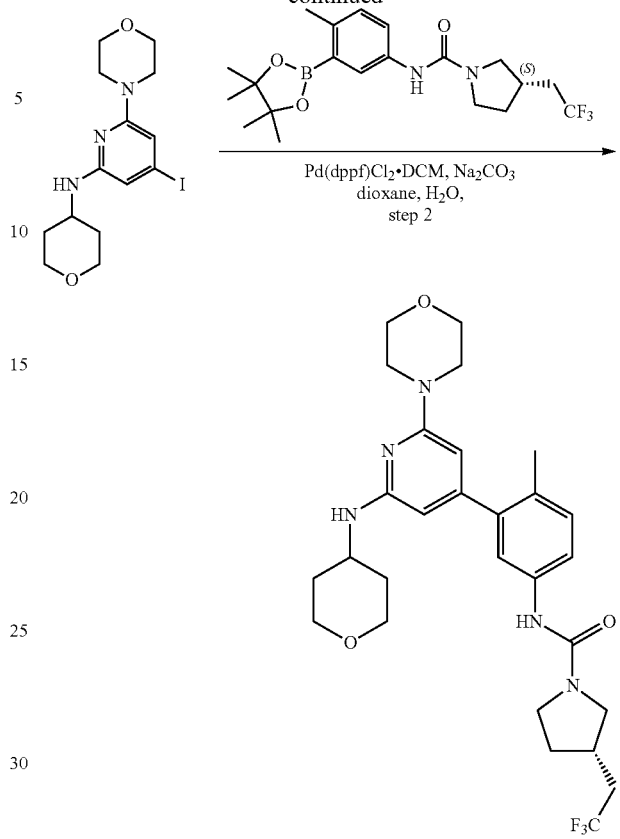

Preparation 46A: 4-iodo-6-(morpholin-4-yl)-N-(oxan-4-yl)pyridin-2-amine

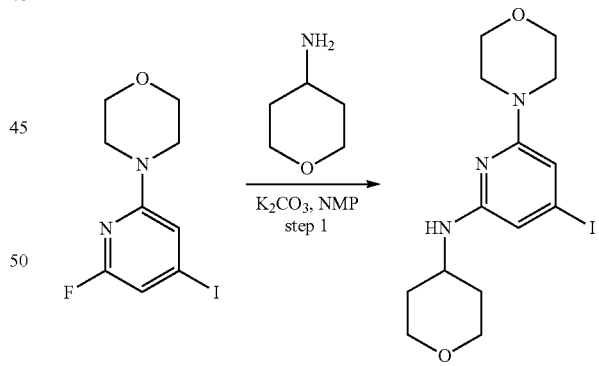

To a stirred mixture of 4-(6-fluoro-4-iodopyridin-2-yl)morpholine (300 mg, 0.974 mmol) and oxan-4-amine (541.70 mg, 5.355 mmol) in NMP (3 mL) was added K₂CO₃ (269.15 mg, 1.947 mmol) at 60° C. under nitrogen atmosphere. The reaction was quenched by the addition of water (10 mL) at room temperature. The resulting mixture was extracted with EtOAc (3×50 mL). The combined organic layers were washed with brine (2×5 mL), dried over anhydrous Na₂SO₄. After filtration, the filtrate was concentrated under reduced pressure. The residue was purified by silica gel column chromatography, eluted with PE/EtOAc (1:1) to afford 4-iodo-6-(morpholin-4-yl)-N-(oxan-4-yl)pyridin-2- amine (150 mg, 40%) as a light green solid. MS ESI calculated for $C_{14}H_{20}IN_3O_2$ [M+H]$^+$, 390.06, found 389.95 $^1$H NMR (400 MHz, DMSO-d$_6$) δ 6.38 (d, J=7.3 Hz, 1H), 6.23 (d, J=1.0 Hz, 1H), 6.20 (d, J=1.0 Hz, 1H), 3.84 (dt, J=11.7, 3.7 Hz, 2H), 3.68-3.61 (m, 4H), 3.44-3.30 (m, 4H), 1.84 (d, J=12.2 Hz, 2H), 1.49-1.30 (m, 2H), 1.24 (s, 1H), 0.89 (dd, J=29.8, 6.5 Hz, 2H).

Example 46: (3S)—N-[4-methyl-3-[2-(morpholin-4-yl)-6-(oxan-4-ylamino)pyridin-4-yl]phenyl]-3-(2,2,2-trifluoroethyl)pyrrolidine-1-carboxamide

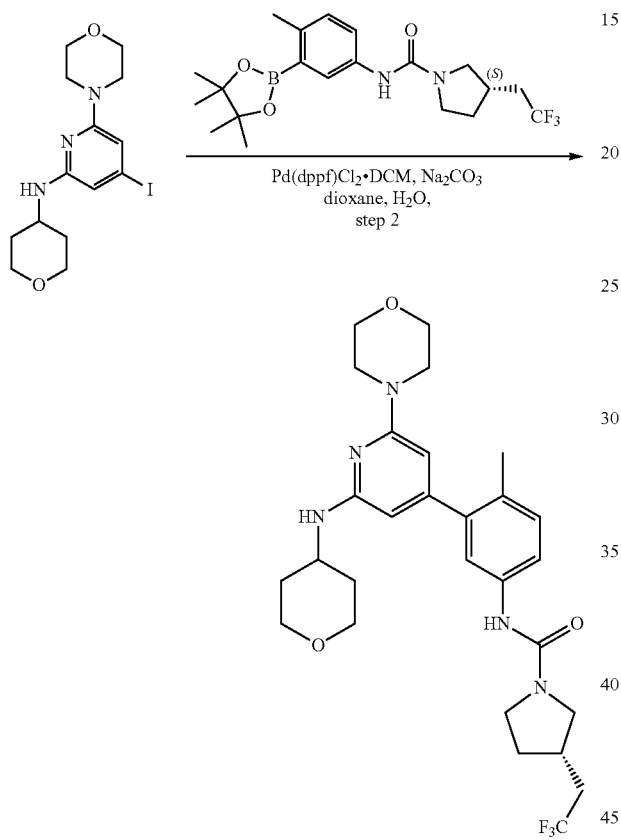

To a stirred mixture of 4-iodo-6-(morpholin-4-yl)-N-(oxan-4-yl)pyridin-2-amine (150 mg, 0.385 mmol) and (3R)—N-[4-methyl-3-(4,4,5,5-tetramethyl-1,3,2-dioxaborolan-2-yl)phenyl]-3-(2,2,2-trifluoroethyl)cyclopentane-1-carboxamide (127 mg, 0.308 mmol) in 1,4-dioxane (4 mL) and H$_2$O (1 mL) were added Na$_2$CO$_3$ (122 mg, 1.156 mmol) and Pd(dppf)Cl$_2$·CH$_2$Cl$_2$ (31 mg, 0.039 mmol) at 150° C. under nitrogen atmosphere. The reaction was quenched by the addition of water (20 mL) at room temperature. The resulting mixture was extracted with EtOAc (3×60 mL). The combined organic layers were washed with brine (2×20 mL), dried over anhydrous Na$_2$SO$_4$. After filtration, the filtrate was concentrated under reduced pressure. The residue was purified by Prep-HPLC with the following conditions: Column: SunFire Prep C18 OBD Column, 19×150 mm 5 um 10 nm; Mobile Phase A: Water (0.1% FA), Mobile Phase B: CH$_3$CN; Flow rate: 20 mL/min; Gradient:30 B to 75 B in 5.5 min; 254/210 nm to afford (3S)—N-[4-methyl-3-[2-(morpholin-4-yl)-6-(oxan-4-ylamino)pyridin-4-yl]phenyl]-3-(2,2,2-trifluoroethyl)pyrrolidine-1-carboxamide (89 mg, 42%) as a light green solid. MS ESI calculated for $C_{28}H_{36}F_3N_5O_3$ [M+H]$^+$, 548.28, found 548.15. $^1$H NMR (400 MHz, DMSO-d$_6$) δ 8.13 (d, J=14.5 Hz, 1H), 7.41 (dd, J=8.3, 2.4 Hz, 1H), 7.34 (d, J=2.3 Hz, 1H), 7.09 (d, J=8.4 Hz, 1H), 6.21 (d, J=7.4 Hz, 1H), 5.76 (s, 2H), 3.95-3.76 (m, 4H), 3.76-3.59 (m, 6H), 3.52 (t, J=8.8 Hz, 1H), 3.45-3.39 (m, 5H), 3.02 (t, J=9.5 Hz, 1H), 2.44 (t, J=11.0 Hz, 3H), 2.16 (s, 3H), 2.08 (s, 1H), 1.90 (d, J=13.2 Hz, 2H), 1.66 (p, J=10.1 Hz, 1H), 1.52-1.32 (m, 2H).

Example 47: (S)—N-(3-(2-(((1S,3R)-3-hydroxycyclobutyl)amino)-6-morpholinopyridin-4-yl)-4-methylphenyl)-3-(2,2,2-trifluoroethyl)pyrrolidine-1-carboxamide

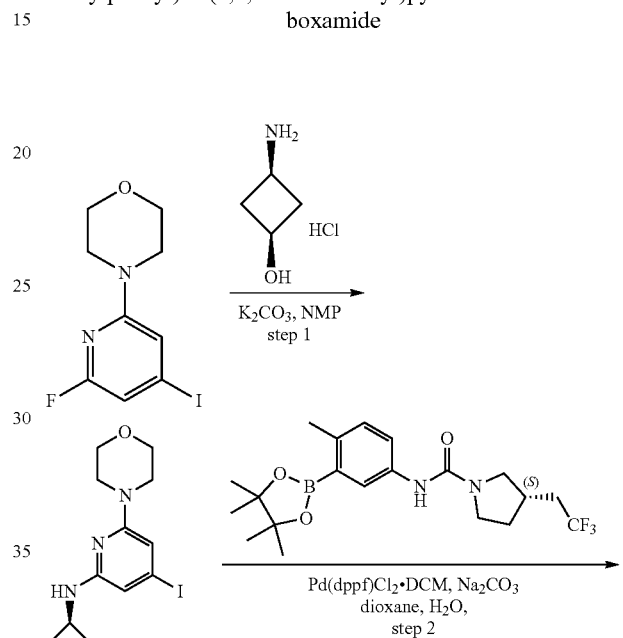

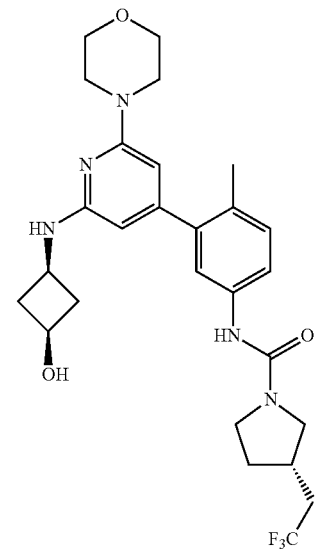

Preparation 47A: (1S,3S)-3-((4-iodo-6-morpholino-pyridin-2-yl)amino)cyclobutan-1-ol

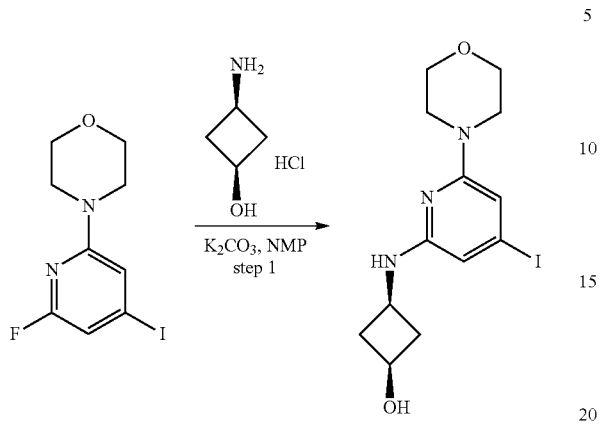

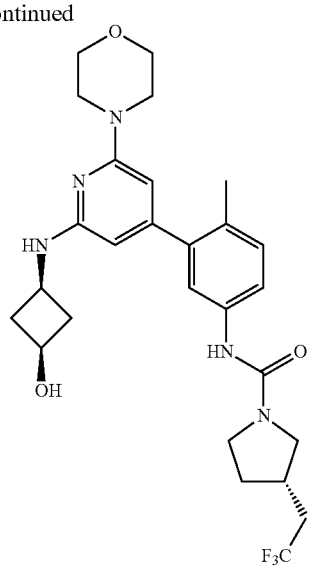

A mixture of 4-(6-fluoro-4-iodopyridin-2-yl)morpholine (300 mg, 0.974 mmol), (cis)-3-aminocyclobutan-1-ol hydrochloride (181 mg, 1.461 mmol) and K$_2$CO$_3$ (404 mg, 2.921 mmol) in NMP (5 mL) was stirred for 16 h at 150° C. under nitrogen atmosphere. The mixture was allowed to cool down to room temperature. The reaction was quenched by the addition of water (50 mL) at room temperature. The resulting mixture was extracted with EtOAc (3×30 mL). The combined organic layers were washed with brine (50 mL), dried over anhydrous Na$_2$SO$_4$. After filtration, the filtrate was concentrated under reduced pressure The residue was purified by silica gel column chromatography, eluted with EtOAc in PE (80%) to afford (1S,3S)-3-((4-iodo-6-morpholinopyridin-2-yl)amino)cyclobutan-1-ol (300 mg, 80%) as an off-white solid. MS ESI calculated for C$_{13}$H$_{18}$IN$_3$O$_2$ [M+H]$^+$, 376.04, found 375.95. $^1$H NMR (400 MHz, chloroform-d) δ 6.31 (s, 1H), 6.12 (s, 1H), 4.45-4.44 (m, 1H), 4.17-4.10 (m, 1H), 3.80-3.78 (m, 4H), 3.68-3.62 (m, 1H), 3.46-3.43 (m, 4H), 2.92-2.85 (m, 1H), 1.83-1.81 (m, 4H).

Example 47: (S)—N-(3-(2-(((1S,3R)-3-hydroxycyclobutyl)amino)-6-morpholinopyridin-4-yl)-4-methylphenyl)-3-(2,2,2-trifluoroethyl)pyrrolidine-1-carboxamide A mixture of (1S,3S)-3-((4-iodo-6-morpholinopyridin-2-yl)amino)cyclobutan-1-ol (200 mg, 0.533 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (242 mg, 0.586 mmol), Pd(dppf)Cl$_2$·CH$_2$Cl$_2$ (43 mg, 0.053 mmol), Na$_2$CO$_3$ (169 mg, 1.599 mmol), 1,4-dioxane (6 mL) and water (1.5 mL) was stirred for 16 h at 60° C. under nitrogen atmosphere. The reaction mixture was cooled to room temperature and concentrated under reduced pressure. The residue was purified by silica gel column chromatography, eluted with EA/EtOH (3/1) in PE (65%) followed by trituration with DCM/Hexane (1/5) to afford (S)—N-(3-(2-(((1S,3R)-3-hydroxycyclobutyl)amino)-6-morpholinopyridin-4-yl)-4-methylphenyl)-3-(2,2,2-trifluoroethyl)pyrrolidine-1-carboxamide (214 mg, 74%) as a light yellow solid. MS ESI calculated for C$_{27}$H$_{34}$F$_3$N$_5$O$_3$ [M+H]$^+$, 534.26, found 534.20. $^1$H NMR (400 MHz, DMSO-d$_6$) δ 8.12 (s, 1H), 7.42-7.40 (m, 1H), 7.40 (s, 1H), 7.33-7.32 (m, 1H), 7.10-7.08 (m, 1H), 5.76 (s, 1H), 5.68 (s, 1H), 5.00 (s, 1H), 3.86-3.84 (m, 1H), 3.69-3.65 (m, 6H), 3.52-3.50 (m, 1H), 3.38-3.29 (m, 5H), 3.04-2.99 (m, 1H), 2.63-2.41 (m, 5H), 2.15-2.07 (m, 4H), 1.74-1.66 (m, 3H). $^{19}$F NMR (376 MHz, DMSO-d$_6$) δ −63.37 (3F).

Example 48: (S)—N-(3-(2-(((1R,3S)-3-hydroxycyclobutyl)amino)-6-morpholinopyridin-4-yl)-4-methylphenyl)-3-(2,2,2-trifluoroethyl)pyrrolidine-1-carboxamide

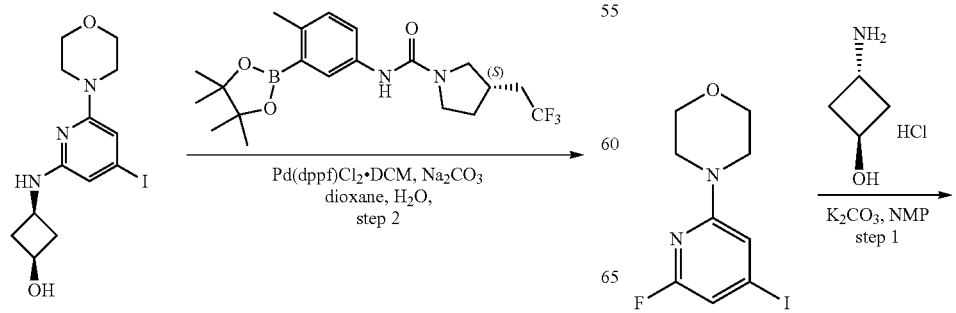

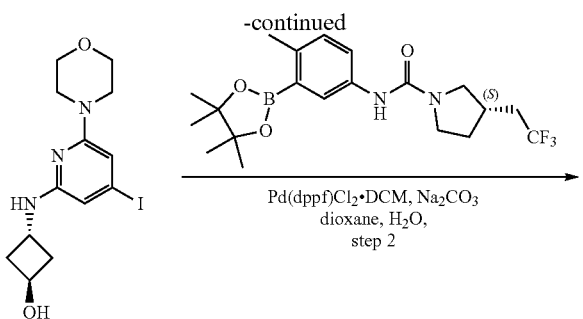

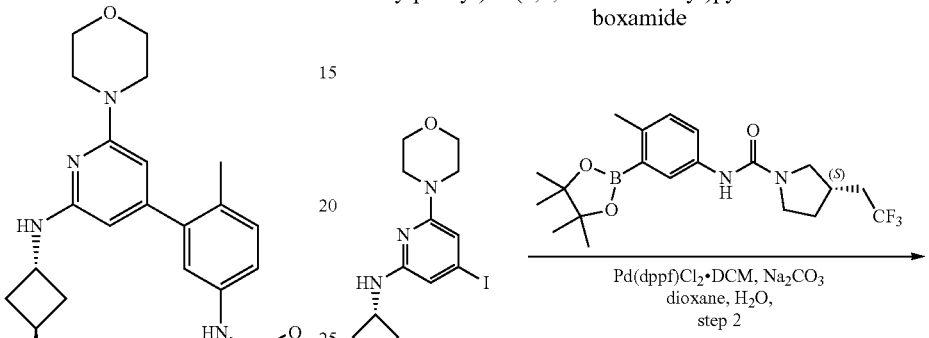

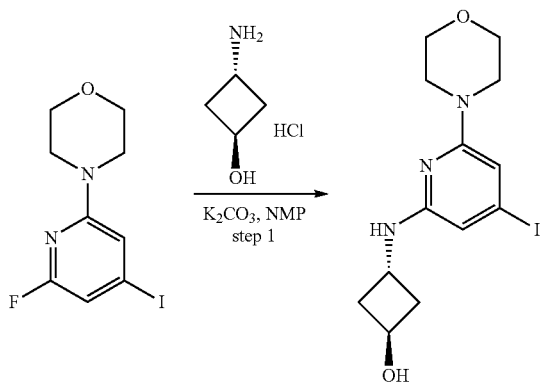 [SMILES: Fc1cc(I)cc(N2CCOCC2)n1 ; N[C@H]1C[C@H](O)C1 ; Cl ; O[C@H]1C[C@H](Nc2cc(I)cc(N3CCOCC3)n2)C1]

Preparation 48A: (1R,3R)-3-((4-iodo-6-morpholino-pyridin-2-yl)amino)cyclobutan-1-ol A mixture of 4-(6-fluoro-4-iodopyridin-2-yl)morpholine (300 mg, 0.974 mmol), (1R,3R)-3-aminocyclobutan-1-ol hydrochloride (181 mg, 1.461 mmol) and K$_2$CO$_3$ (404 mg, 2.921 mmol) in NMP (5 mL) was stirred for 16 h at 150° C. under nitrogen atmosphere. The mixture was allowed to cool down to room temperature. The reaction was quenched by the addition of water (50 mL) at room temperature. The resulting mixture was extracted with EtOAc (3×30 mL). The combined organic layers were washed with brine (50 mL), dried over anhydrous Na$_2$SO$_4$. After filtration, the filtrate was concentrated under reduced pressure The residue was purified by silica gel column chromatography, eluted with EtOAc in PE (80%) to afford (1R,3R)-3-((4-iodo-6-morpholinopyridin-2-yl)amino)cyclobutan-1-ol (270 mg, 74%) as a light yellow solid. MS ESI calculated for C$_{13}$H$_{18}$IN$_3$O$_2$ [M+H]$^+$, 376.04, found 375.90. $^1$H NMR (400 MHz, DMSO-d$_6$) δ 6.63-6.60 (m, 1H), 6.22 (s, 1H), 6.11 (s, 1H), 4.96 (s, 1H), 4.29-4.13 (m, 2H), 3.65-3.63 (m, 4H), 3.41-3.33 (m, 4H), 2.16-2.06 (m, 4H).

Example 48: (S)—N-(3-(2-(((1R,3S)-3-hydroxycyclobutyl)amino)-6-morpholinopyridin-4-yl)-4-methylphenyl)-3-(2,2,2-trifluoroethyl)pyrrolidine-1-carboxamide

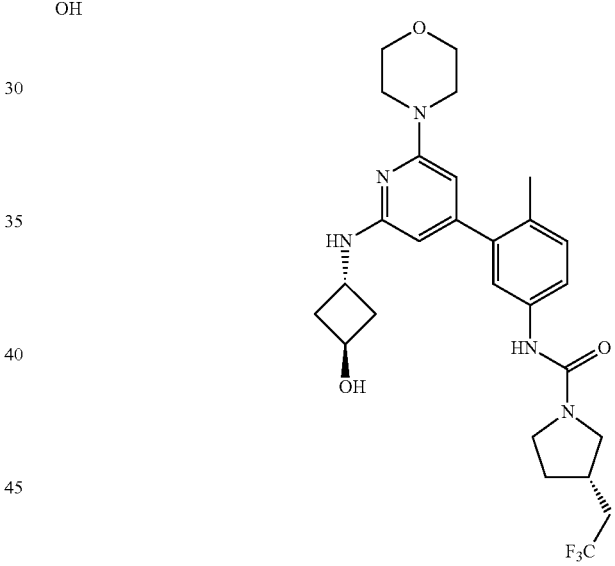

A mixture of (1R,3R)-3-((4-iodo-6-morpholinopyridin-2-yl)amino)cyclobutan-1-ol (200 mg, 0.533 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (242 mg, 0.586 mmol), Pd(dppf)Cl$_2$·CH$_2$Cl$_2$ (43 mg, 0.053 mmol), Na$_2$CO$_3$ (169 mg, 1.599 mmol), 1,4-dioxane (6 mL) and water (1.5 mL). The resulting mixture was stirred for 16 h at 60° C. under nitrogen atmosphere. The reaction mixture was cooled to room temperature and concentrated under reduced pressure. The residue was purified by silica gel column chromatography, eluted with EA/EtOH (3/1) in PE (65%) followed by trituration with DCM/Hexane (1/5) to afford (S)—N-(3-(2-(((1R,3S)-3-hydroxycyclobutyl)amino)-6-morpholinopyridin-4-yl)-4-methylphenyl)-3-(2,2,2-trifluoroethyl)pyrrolidine-1-carboxamide (190 mg, 65%) as a brown yellow solid. MS ESI calculated for C$_{27}$H$_{34}$F$_3$N$_5$O$_3$ [M+H]$^+$, 534.26, found 534.30. $^1$H NMR (400 MHz, DMSO-d$_6$) δ 8.12 (s, 1H), 7.42-7.41 (m, 1H), 7.40 (s, 1H), 7.33-7.32 (m, 1H), 7.10-7.08 (m, 1H), 5.78 (s, 1H), 5.63 (s, 1H), 4.97-4.95 (m, 1H), 4.31-4.18 (m, 2H), 3.69-3.50 (m, 6H), 3.39-3.29 (m, 5H), 3.04-2.99 (m, 1H), 2.50-2.41 (m, 3H), 2.16-2.08 (m, 8H), 1.68-1.66 (m, 1H). $^{19}$F NMR (376 MHz, DMSO-$d_6$) δ −63.37 (3F).

Example 49: (3S)—N-[3-(2-[[(2R)-1-hydroxybutan-2-yl]amino]-6-(morpholin-4-yl)pyridin-4-yl)-4-methylphenyl]-3-(2,2,2-trifluoroethyl)pyrrolidine-1-carboxamide

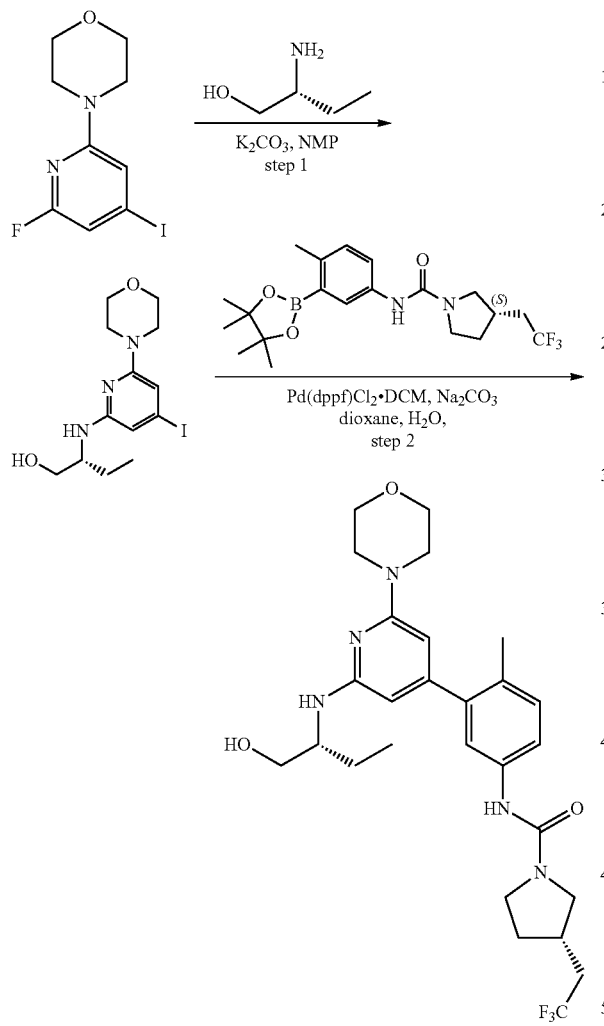

Preparation 49A: (2R)-2-[[4-iodo-6-(morpholin-4-yl)pyridin-2-yl]amino]butan-1-ol

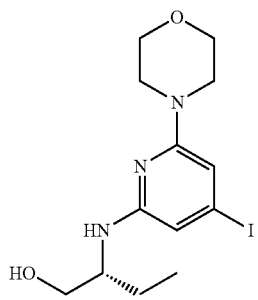

A mixture of 4-(6-fluoro-4-iodopyridin-2-yl)morpholine (300 mg, 0.974 mmol) and K$_2$CO$_3$ (269 mg, 1.947 mmol), NMP (3 mL) and (2R)-2-aminobutan-1-ol (130 mg, 1.461 mmol) was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2/1) to afford (2R)-2-[[4-iodo-6-(morpholin-4-yl)pyridin-2-yl]amino]butan-1-ol (90 mg, 24%) as an off-white solid. MS ESI calculated for C$_{13}$H$_{20}$IN$_3$O$_2$ [M+H]$^+$, 378.06, found 377.90. $^1$H NMR (300 MHz, CDCL$_3$) δ 6.29-6.26 (m, 2H), 4.23 (s, 1H), 3.81-3.76 (m, 6H), 3.62-3.55 (m, 1H), 3.45-3.42 (m, 4H), 3.14 (s, 1H), 1.77-1.63 (m, 1H), 1.57-1.43 (m, 1H), 1.03-0.96 (m, 3H).

Example 49: (3S)—N-[3-(2-[[(2R)-1-hydroxybutan-2-yl]amino]-6-(morpholin-4-yl)pyridin-4-yl)-4-methylphenyl]-3-(2,2,2-trifluoroethyl)pyrrolidine-1-carboxamide

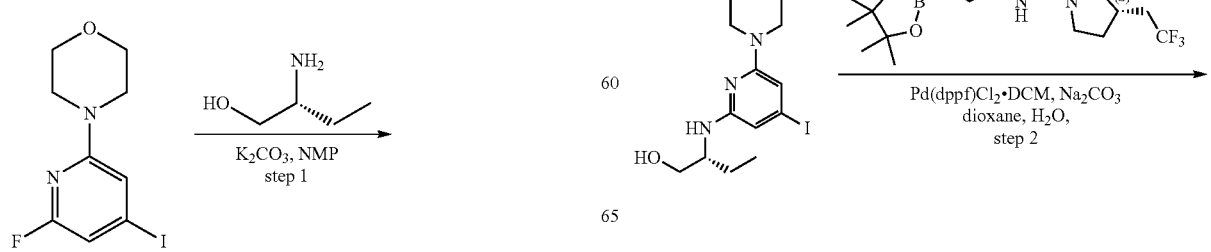

281

-continued

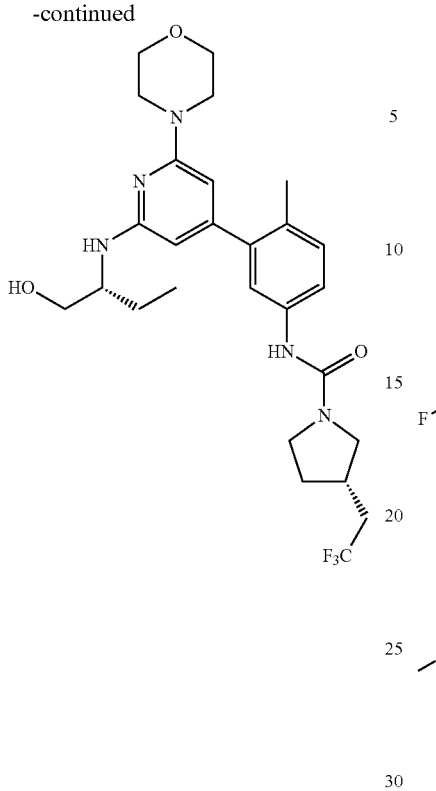

A mixture of (2R)-2-[[4-iodo-6-(morpholin-4-yl)pyridin-2-yl]amino]butan-1-ol (90 mg, 0.239 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (98 mg, 0.239 mmol), Na$_2$CO$_3$ (76 mg, 0.716 mmol), dioxane:H$_2$O=4:1 (1 mL) and Pd(dppf)Cl$_2$·CH$_2$Cl$_2$ (19 mg, 0.024 mmol) was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EA/EtOH (8/3/1) to afford 70 mg crude product. The residue was purified by reverse flash chromatography with the following conditions: Column: SunFire Prep C18 OBD Column, 19×150 mm 5 um 10 nm; Mobile Phase A: water (0.1% FA), Mobile Phase B: CH$_3$CN; Flow rate: 20 mL/min; Gradient:25 B to 65 B in 5.1 min; 254/210 nm. This resulted in (3S)—N-[3-(2-[[(2R)-1-hydroxybutan-2-yl]amino]-6-(morpholin-4-yl)pyridin-4-yl)-4-methylphenyl]-3-(2,2,2-trifluoroethyl)pyrrolidine-1-carboxamide (59 mg, 46%) as an off-white solid. MS ESI calculated for C$_{27}$H$_{36}$F$_3$N$_5$O$_3$ [M+H]$^+$. 536.28, found 536.15. $^1$H NMR (400 MHz, DMSO-d$_6$) δ 8.11 (s, 1H), 7.42-7.40 (m, 1H), 7.34-7.33 (m, 1H), 7.10-7.08 (m, 1H), 5.95-5.93 (m, 1H), 5.78-5.73 (m, 2H), 4.59 (s, 1H), 3.75-3.64 (m, 6H), 3.55-3.48 (m, 2H), 3.38-3.36 (m, 4H), 3.31-3.27 (m, 2H), 3.04-2.99 (m, 1H), 2.48-2.38 (m, 3H), 2.16 (s, 3H), 2.12-2.07 (m, 1H), 1.70-1.60 (m, 2H), 1.48-1.37 (m, 1H), 0.91-0.88 (m, 3H). $^{19}$F NMR (376 MHz, DMSO-d$_6$) δ −63.37 (3F).

282

Example 50: (3S)—N-[3-(2-[[(2R)-1-methoxypropan-2-yl]amino]-6-(morpholin-4-yl)pyridin-4-yl)-4-methylphenyl]-3-(2,2,2-trifluoroethyl)pyrrolidine-1-carboxamide

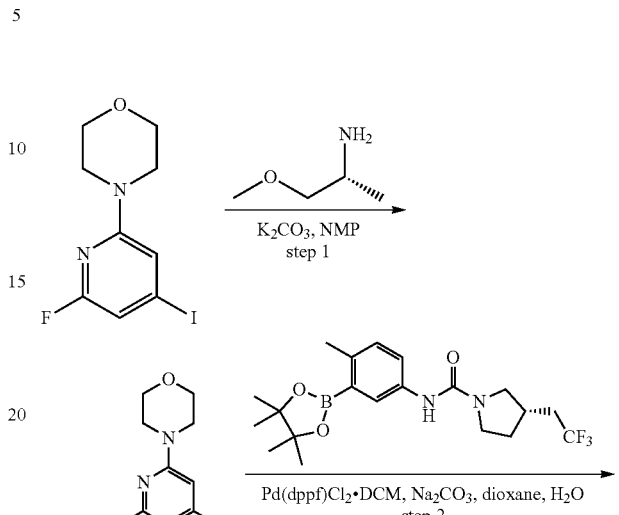

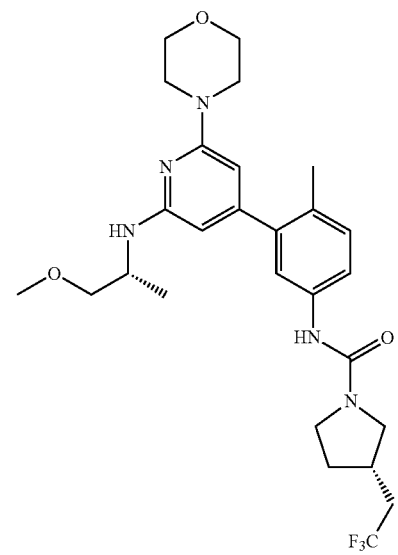

Preparation 50A: 4-iodo-N-[(2R)-1-methoxypropan-2-yl]-6-(morpholin-4-yl)pyridin-2-amine

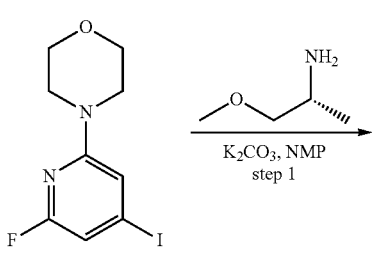

283
-continued

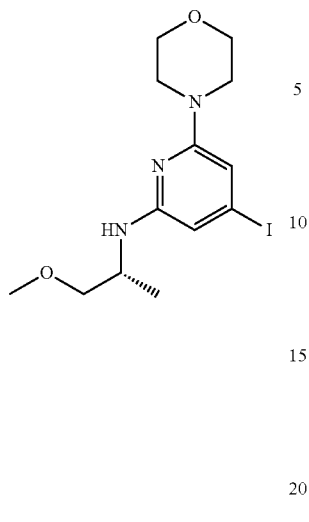

A mixture of 4-(6-fluoro-4-iodopyridin-2-yl)morpholine (300 mg, 0.974 mmol) and K$_2$CO$_3$ (269 mg, 1.947 mmol), NMP (3 mL) and (2R)-1-methoxypropan-2-amine (434 mg, 4.869 mmol) was stirred for 16 h at 150° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2:1) to afford 4-iodo-N-[(2R)-1-methoxypropan-2-yl]-6-(morpholin-4-yl)pyridin-2-amine (150 mg, 41%) as an off-white solid. MS ESI calculated for C$_{13}$H$_{20}$IN$_3$O$_2$ [M+H]$^+$, 378.06, found 377.95. $^1$H NMR (400 MHz, CDCL$_3$) δ 6.27 (m, 1H), 6.20 (s, 1H), 4.45-4.43 (m, 1H), 4.00-3.97 (m, 1H), 3.84-3.78 (m, 4H), 3.53-3.27 (m, 8H), 1.28-1.23 (m, 3H).

Example 50: (3S)—N-[3-(2-[[(2R)-1-methoxypropan-2-yl]amino]-6-(morpholin-4-yl)pyridin-4-yl)-4-methylphenyl]-3-(2,2,2-trifluoroethyl)pyrrolidine-1-carboxamide

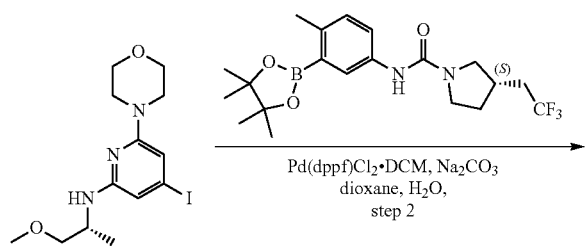

284
-continued

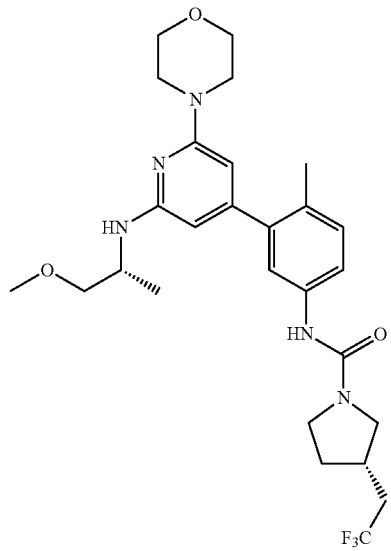

A mixture of 4-iodo-N-[(2R)-1-methoxypropan-2-yl]-6-(morpholin-4-yl)pyridin-2-amine (150 mg, 0.398 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (172 mg, 0.418 mmol), Na$_2$CO$_3$ (126 mg, 1.193 mmol), dioxane:H$_2$O=4:1 (2 mL) was added Pd(dppf)Cl$_2$·CH$_2$Cl$_2$ (32 mg, 0.040 mmol) was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EA/EtOH (8/3/1) to afford 70 mg crude product. The residue was purified by reverse flash chromatography with the following conditions: Column: Welch Xtimate C18, 21.2*250 mm, 5 um; Mobile Phase A: water (0.1% FA), Mobile Phase B: CH$_3$CN; Flow rate: 20 mL/min; Gradient: 20 B to 60 B in 5.5 min; 254/210 nm; This resulted in (3S)—N-[3-(2-[[(2R)-1-methoxypropan-2-yl]amino]-6-(morpholin-4-yl)pyridin-4-yl)-4-methylphenyl]-3-(2,2,2-trifluoroethyl)pyrrolidine-1-carboxamide (41 mg, 19%) as an off-white solid. MS ESI calculated for C$_{27}$H$_{36}$F$_3$N$_5$O$_3$ [M+H]$^+$. 536.28, found 536.20. $^1$H NMR (400 MHz, DMSO-d$_6$) δ 8.13 (s, 1H), 7.44-7.36 (m, 2H), 7.12-7.09 (m, 1H), 6.12-6.09 (m, 1H), 5.77 (s, 2H), 4.14-4.10 (m, 1H), 3.77-3.69 (m, 6H), 3.57-3.36 (m, 5H), 3.29 (s, 4H), 3.27-3.22 (m, 1H), 3.07-3.00 (m, 1H), 32.48-2.41 (m, 3H), 2.17 (s, 3H), 2.08-2.03 (m, 1H), 1.71-1.64 (m, 1H), 1.16-1.14 (m, 3H). $^{19}$F NMR (376 MHz, DMSO-d$_6$) δ −63.36 (3F).

Example 51: (3S)—N-[3-(2-[[(2S)-2-methoxypropyl]amino]-6-(morpholin-4-yl)pyridin-4-yl)-4-methylphenyl]-3-(2,2,2-trifluoroethyl)pyrrolidine-1-carboxamide

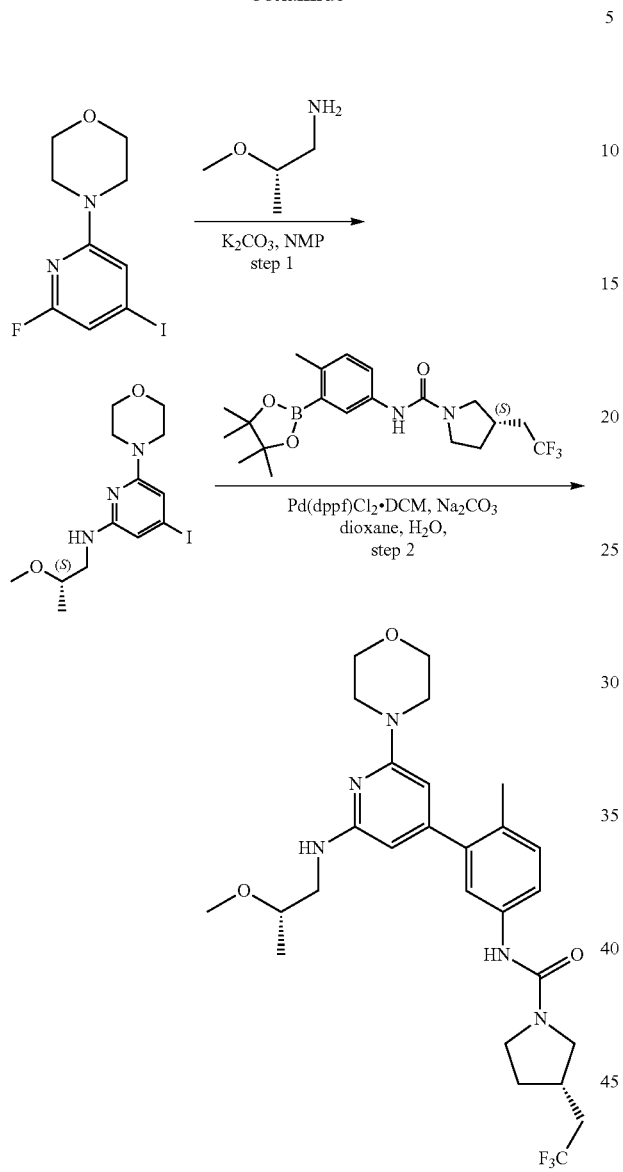

Preparation 51A: 4-iodo-N-[(2S)-2-methoxypropyl]-6-(morpholin-4-yl)pyridin-2-amine

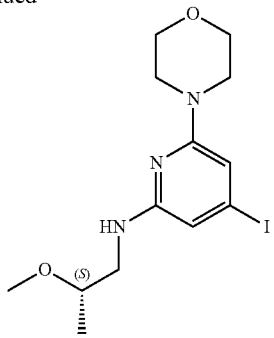

A mixture of 4-(6-fluoro-4-iodopyridin-2-yl)morpholine (300 mg, 0.974 mmol) and (2S)-2-methoxypropan-1-amine (87 mg, 0.974 mmol), NMP (3 mL) and K$_2$CO$_3$ (269 mg, 1.947 mmol) was stirred for 16 h at 60° C. under nitrogen atmosphere. The reaction was quenched by the addition of water (15 mL) at room temperature. The resulting mixture was extracted with EtOAc (3×30 mL). The combined organic layers were washed with brine (2×8 mL), dried over anhydrous Na$_2$SO$_4$. After filtration, the filtrate was concentrated under reduced pressure. The residue was purified by silica gel column chromatography, eluted with PE/EtOAc (1/1) to afford 4-iodo-N-[(2S)-2-methoxypropyl]-6-(morpholin-4-yl)pyridin-2-amine (120 mg, crude) as a light green solid, which was used for next step without further purification. MS ESI calculated for C$_{13}$H$_{20}$IN$_3$O$_2$ 378.06, found 378.00.

Example 51: (3S)—N-[3-(2-[[(2S)-2-methoxypropyl]amino]-6-(morpholin-4-yl)pyridin-4-yl)-4-methylphenyl]-3-(2,2,2-trifluoroethyl)pyrrolidine-1-carboxamide

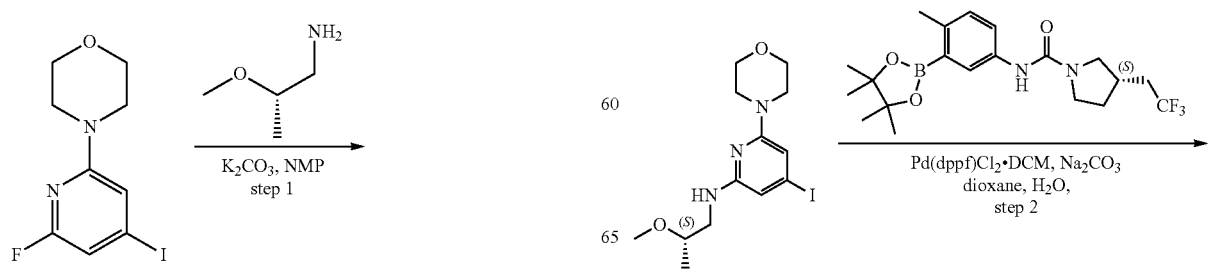

-continued

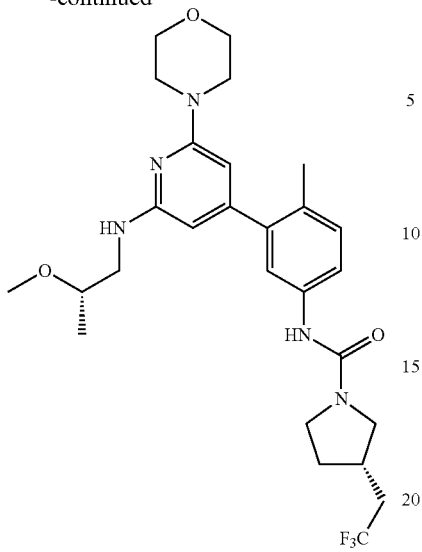

A mixture of 4-iodo-N-[(2S)-2-methoxypropyl]-6-(morpholin-4-yl)pyridin-2-amine (112 mg, 0.297 mmol), (3R)—N-[4-methyl-3-(4,4,5,5-tetramethyl-1,3,2-dioxaborolan-2-yl)phenyl]-3-(2,2,2-trifluoroethyl)cyclopentane-1-carboxamide (98 mg, 0.238 mmol), 1,4-dioxane (4 mL), H$_2$O (1 mL), Na$_2$CO$_3$ (94 mg, 0.891 mmol) and Pd(dppf)Cl$_2$·CH$_2$Cl$_2$ (24 mg, 0.030 mmol) was stirred at 70° C. under nitrogen atmosphere. The reaction was quenched by the addition of water (10 mL) at room temperature. The resulting mixture was extracted with EtOAc (3×30 mL). The combined organic layers were washed with brine (2×8 mL), dried over anhydrous Na$_2$SO$_4$. After filtration, the filtrate was concentrated under reduced pressure. The residue was purified by silica gel column chromatography, eluted with PE/EtOAc (1/1) to afford (3S)—N-[3-(2-[[(2S)-2-methoxypropyl]amino]-6-(morpholin-4-yl)pyridin-4-yl)-4-methylphenyl]-3-(2,2,2-trifluoroethyl)pyrrolidine-1-carboxamide (22 mg, %) as a light green solid. MS ESI calculated for C$_{27}$H$_{36}$F$_3$N$_5$O$_3$ 536.28, found 536.00. $^1$H NMR (400 MHz, DMSO-d$_6$) δ 8.12 (s, 1H), 7.42 (dd, J=8.3, 2.3 Hz, 1H), 7.33 (d, J=2.4 Hz, 1H), 7.09 (d, J=8.4 Hz, 1H), 6.29 (t, J=5.9 Hz, 1H), 5.78 (d, J=15.3 Hz, 2H), 3.71-3.62 (m, 5H), 3.57-3.45 (m, 2H), 3.38 (t, J=4.9 Hz, 4H), 3.32 (s, 6H), 3.02 (t, J=9.4 Hz, 1H), 2.50 (s, 3H), 2.16 (s, 3H), 2.12-2.05 (m, 1H), 1.64 (q, J=10.2 Hz, 1H), 1.10 (d, J=6.2 Hz, 3H).

Example 52: (3S)—N-[4-methyl-3-[2-(morpholin-4-yl)-6-[(3S)-oxan-3-ylamino]pyridin-4-yl]phenyl]-3-(2,2,2-trifluoroethyl)pyrrolidine-1-carboxamide

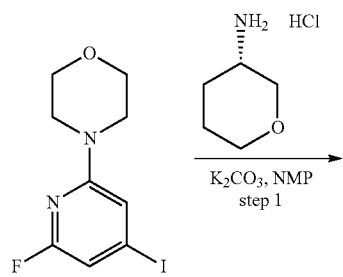

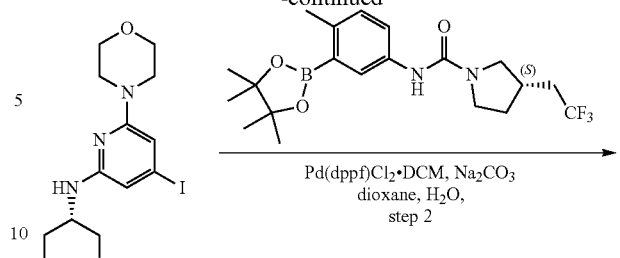

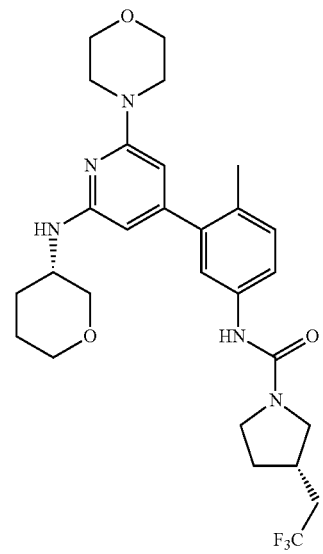

Preparation 52A: 4-iodo-6-(morpholin-4-yl)-N-[(3S)-oxan-3-yl]pyridin-2-amine

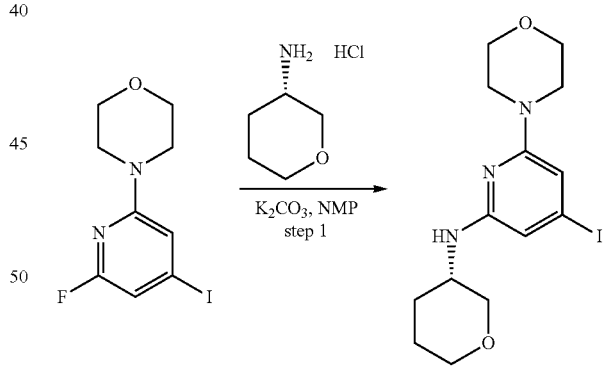

To a stirred mixture of 4-(6-fluoro-4-iodopyridin-2-yl)morpholine (300 mg, 0.974 mmol) and K$_2$CO$_3$ (673 mg, 4.869 mmol), (3S)-oxan-3-amine hydrochloride (670 mg, 4.869 mmol) in NMP (3 mL) at room temperature under nitrogen atmosphere. The resulting mixture was stirred for 16 h at 150° C. under nitrogen atmosphere. The resulting mixture was diluted with water (50 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with hexane/EtOAc/EtOH (4/3/1) to afford 4-iodo-6-(morpholin-4-yl)-N-[(3S)-oxan-3-yl]pyridin-2-amine (260 mg, 69%) as a white solid. MS ESI calculated for $C_{14}H_{20}IN_3O_2$ [M+H]$^+$, 390.06, found 389.95. $^1$H NMR (300 MHz, chloroform-d) δ 6.33-6.32 (m, 1H), 6.11-6.10 (s, 1H), 4.47-4.45 (m, 1H), 4.23-4.11 (m, 1H), 3.80-3.77 (m, 4H), 3.45-3.42 (m, 4H), 2.60-2.53 (m, 1H), 2.00-1.93 (m, 2H), 1.46 (s, 3H), 1.31-1.26 (m, 1H), 0.91-0.88 (m, 1H).

Example 52: (3S)—N-[4-methyl-3-[2-(morpholin-4-yl)-6-[(3S)-oxan-3-ylamino]pyridin-4-yl]phenyl]-3-(2,2,2-trifluoroethyl)pyrrolidine-1-carboxamide

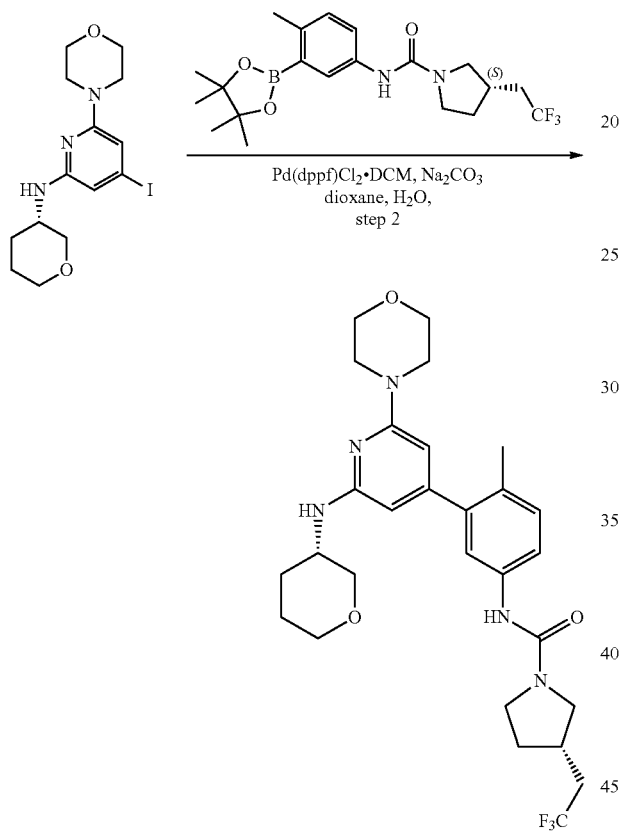

A mixture of 4-iodo-6-(morpholin-4-yl)-N-[(3S)-oxan-3-yl]pyridin-2-amine (200 mg, 0.514 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (212 mg, 0.514 mmol), dioxane (2 mL), H$_2$O (0.5 mL), Pd(dppf)Cl$_2$·CH$_2$Cl$_2$ (42 mg, 0.051 mmol) and Na$_2$CO$_3$ (163 mg, 1.541 mmol) was stirred for 3 h at 80° C. under nitrogen atmosphere. The mixture was allowed to cool down to rt. The resulting mixture was concentrated under vacuum. The residue was purified by silica gel column chromatography, eluted with PE/EtOAc (0% to 80%) followed by Prep-HPLC with the following conditions Column: SunFire Prep C18 OBD Column, 19?150 mm 5 um 10 nm; Mobile Phase A: water (0.1% FA), Mobile Phase B: CH$_3$CN; Flow rate: 20 mL/min; Gradient:25 B to 65 B in 5.3 min; 254/210 nm to afford (3S)—N-[4-methyl-3-[2-(morpholin-4-yl)-6-[(3S)-oxan-3-ylamino]pyridin-4-yl]phenyl]-3-(2,2,2-trifluoroethyl)pyrrolidine-1-carboxamide (120 mg, 43%) as a off-white solid. MS ESI calculated for $C_{28}H_{36}F_3N_5O_3$ [M+H]$^+$, 548.28, found 548.10. $^1$H NMR (400 MHz, DMSO-d$_6$) δ 8.11 (s, 1H), 7.41 (dd, J=8.3, 2.3 Hz, 1H), 7.34 (d, J=2.4 Hz, 1H), 7.09 (d, J=8.3 Hz, 1H), 6.19 (s, 1H), 5.78 (d, J=4.9 Hz, 2H), 3.94 (dd, J=10.8, 4.0 Hz, 1H), 3.82 (dt, J=13.4, 6.3 Hz, 1H), 3.77-3.62 (m, 6H), 3.52 (ddd, J=10.5, 8.3, 2.3 Hz, 1H), 3.41-3.25 (m, 6H), 3.05 (dt, J=24.7, 9.5 Hz, 2H), 2.51-2.34 (m, 3H), 2.16 (s, 3H), 2.08 (dd, J=9.6, 3.5 Hz, 1H), 1.99-1.90 (m, 1H), 1.75-1.50 (m, 4H).

Example 53: (3S)—N-(4-methyl-3-[2-[(3-methyloxolan-3-yl)amino]-6-(morpholin-4-yl)pyridin-4-yl]phenyl)-3-(2,2,2-trifluoroethyl)pyrrolidine-1-carboxamide

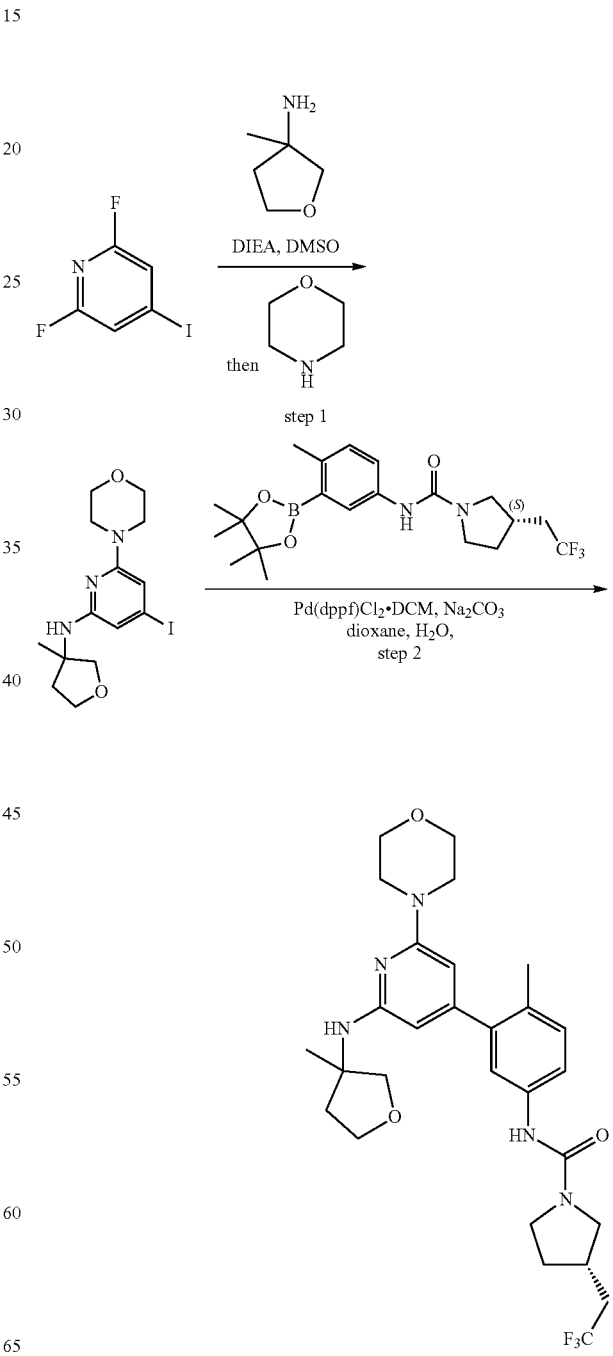

Preparation 53A: 4-iodo-N-(3-methyloxolan-3-yl)-6-(morpholin-4-yl)pyridin-2-amine

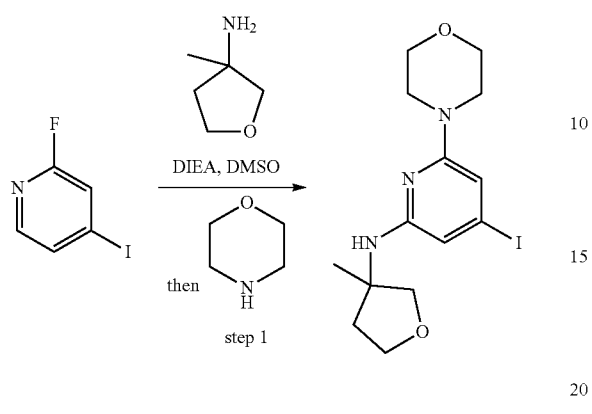

A mixture of 2,6-difluoro-4-iodopyridine (300 mg, 1.245 mmol), 3-methyloxolan-3-amine (138 mg, 1.369 mmol), DMSO (3 mL) and DIEA (0.48 mL, 3.691 mmol) was stirred for 4 h at 110° C. To the above mixture was added morpholine (361 mg, 4.150 mmol) at room temperature. The resulting mixture was stirred for 16 h at 110° C. The mixture was allowed to cool down to room temperature and quenched with water (50 mL). The resulting mixture was extracted with EtOAc (3×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (4:1) to afford 4-iodo-N-(3-methyloxolan-3-yl)-6-(morpholin-4-yl)pyridin-2-amine (230 mg, 47%) as a yellow solid. MS ESI calculated for C$_{14}$H$_{20}$IN$_3$O$_2$ [M+H]$^+$, 390.05, found 390.05. $^1$H NMR (300 MHz, chloroform-d) δ 6.28 (d, J=1.0 Hz, 1H), 6.20 (d, J=1.0 Hz, 1H), 4.39 (s, 1H), 4.00-3.91 (m, 3H), 3.82-3.76 (m, 5H), 3.51-3.37 (m, 4H), 2.41-2.31 (m, 1H), 2.03-1.93 (m, 1H), 1.57 (s, 3H).

Example 53: (3S)—N-(4-methyl-3-[2-[(3-methyloxolan-3-yl)amino]-6-(morpholin-4-yl)pyridin-4-yl]phenyl)-3-(2,2,2-trifluoroethyl)pyrrolidine-1-carboxamide

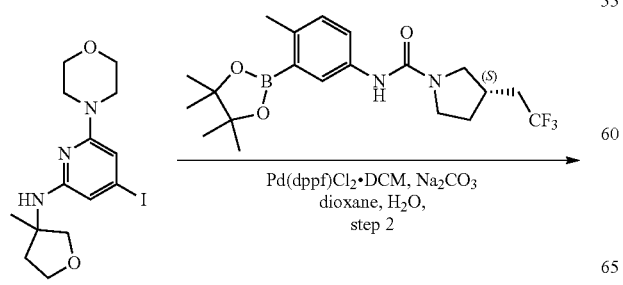

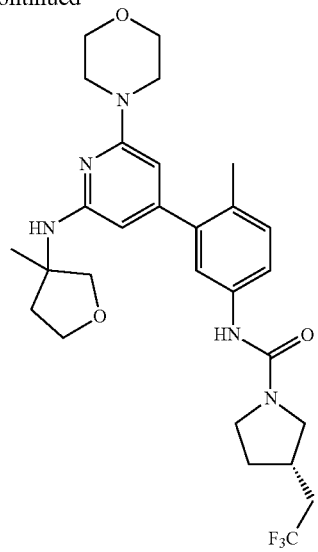

A mixture of 4-iodo-N-(3-methyloxolan-3-yl)-6-(morpholin-4-yl)pyridin-2-amine (230 mg, 0.591 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (244 mg, 0.591 mmol), 1,4-dioxane (3 mL), H$_2$O (0.6 mL), Na$_2$CO$_3$ (188 mg, 1.773 mmol) and Pd(dppf)Cl$_2$·CH$_2$Cl$_2$ (48 mg, 0.059 mmol) was stirred for 16 h at 60° C. under nitrogen atmosphere. The mixture was allowed to cool down to room temperature. The reaction was quenched by the addition of water (10 mL) at room temperature. The resulting mixture was extracted with EtOAc (3×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (1:2) to afford (3S)—N-(4-methyl-3-[2-[(3-methyloxolan-3-yl)amino]-6-(morpholin-4-yl)pyridin-4-yl]phenyl)-3-(2,2,2-trifluoroethyl)pyrrolidine-1-carboxamide (200 mg, 62%) as a light pink solid. MS ESI calculated for C$_{28}$H$_{36}$F$_3$N$_5$O$_3$ [M+H]$^+$, 548.15, found 548.15. $^1$H NMR (400 MHz, DMSO-d$_6$) δ 8.11 (s, 1H), 7.40 (dd, J=8.3, 2.3 Hz, 1H), 7.35 (d, J=2.3 Hz, 1H), 7.09 (d, J=8.4 Hz, 1H), 6.45 (s, 1H), 5.80 (dd, J=10.3, 1.0 Hz, 2H), 3.95 (d, J=8.5 Hz, 1H), 3.86-3.74 (m, 2H), 3.73-3.67 (m, 6H), 3.57-3.44 (m, 1H), 3.39-3.22 (m, 5H), 3.02 (t, J=9.4 Hz, 1H), 2.49-2.36 (m, 3H), 2.33-2.22 (m, 1H), 2.16 (s, 3H), 2.08 (d, J=11.2 Hz, 1H), 1.95-1.86 (m, 1H), 1.70-1.61 (m, 1H), 1.50 (s, 3H). $^{19}$F NMR (376 MHz, DMSO-d$_6$) δ −63.61 (3F).

Example 54: (3S)—N-[3-(2-[[1-(hydroxymethyl)cyclobutyl]amino]-6-(morpholin-4-yl)pyridin-4-yl)-4-methylphenyl]-3-(2,2,2-trifluoroethyl)pyrrolidine-1-carboxamide

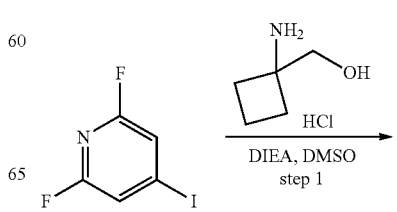

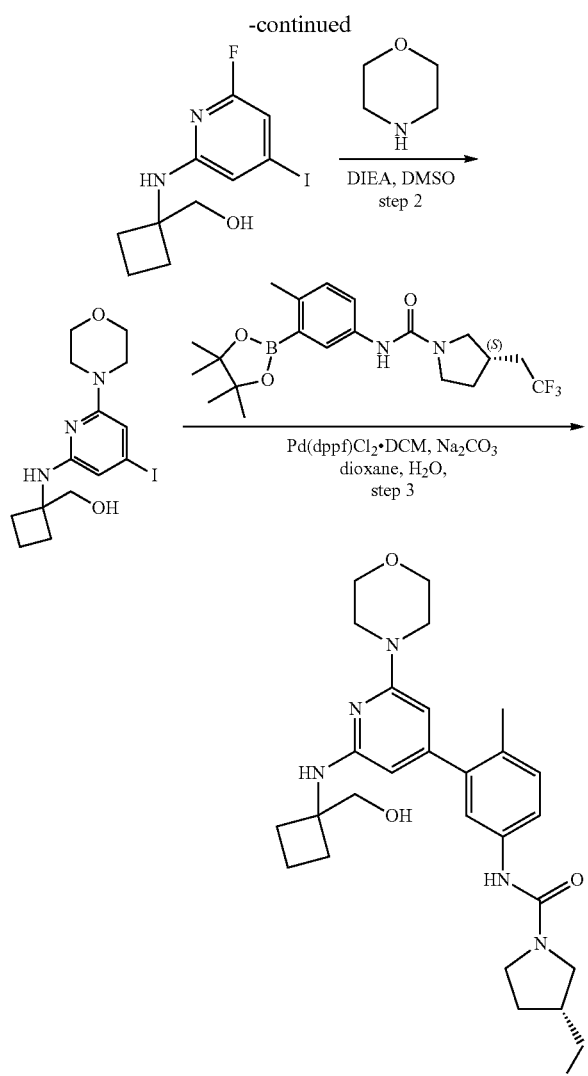

Preparation 54A: [1-[(6-fluoro-4-iodopyridin-2-yl)amino]cyclobutyl]methanol

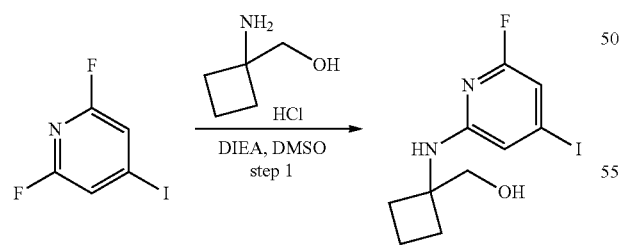

To a mixture of 2,6-difluoro-4-iodopyridine (550 mg, 2.282 mmol), (1-aminocyclobutyl)methanol hydrochloride (345 mg, 2.511 mmol) and DMSO (6 mL) was added DIEA (944 mg, 7.304 mmol) at 0° C. under nitrogen atmosphere. The resulting mixture was stirred for 3 h at 70° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2/1) to afford [1-[(6-fluoro-4-iodopyridin-2-yl)amino]cyclobutyl]methanol (320 mg, 43%) as an off-white solid. MS ESI calculated for C$_{10}$H$_{12}$FIN$_2$O [M+H]$^+$, 323.00, found 322.85. $^1$H NMR (300 MHz, chloroform-d) δ 6.60-6.55 (m, 2H), 3.86 (s, 2H), 2.35-2.25 (m, 2H), 2.17-2.07 (m, 2H), 2.06-1.83 (m, 2H).

Preparation 54B: (1-[[4-iodo-6-(morpholin-4-yl)pyridin-2-yl]amino]cyclobutyl)methanol

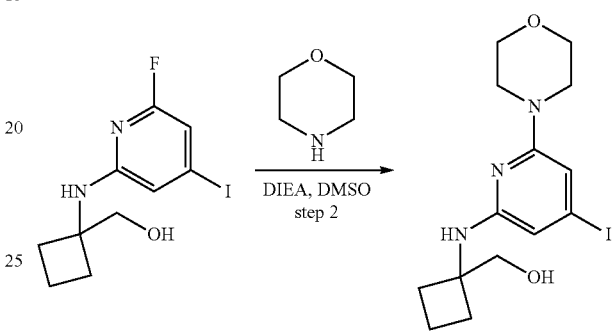

To a stirred solution of [1-[(6-fluoro-4-iodopyridin-2-yl)amino]cyclobutyl]methanol (210 mg, 0.652 mmol) and morpholine (125 mg, 1.434 mmol) in DMSO (2.1 mL) was added DIEA (185 mg, 1.434 mmol) at 0° C. under nitrogen atmosphere. The resulting mixture was stirred for 16 h at 110° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2/1) to afford (1-[[4-iodo-6-(morpholin-4-yl)pyridin-2-yl]amino]cyclobutyl)methanol (195 mg, 77%) as a light yellow oil. MS ESI calculated for C$_{14}$H$_{20}$IN$_3$O$_2$ [M+H]$^+$, 390.06, found 389.95. $^1$H NMR (300 MHz, DMSO-d$_6$) δ 6.45 (s, 1H), 6.24-6.18 (m, 2H), 4.71 (s, 1H), 3.66-3.63 (m, 6H), 3.32-3.29 (m, 4H), 2.13-2.08 (m, 4H), 1.84-1.66 (m, 2H).

Example 54: (3S)—N-[3-(2-[[1-(hydroxymethyl)cyclobutyl]amino]-6-(morpholin-4-yl)pyridin-4-yl)-4-methylphenyl]-3-(2,2,2-trifluoroethyl)pyrrolidine-1-carboxamide

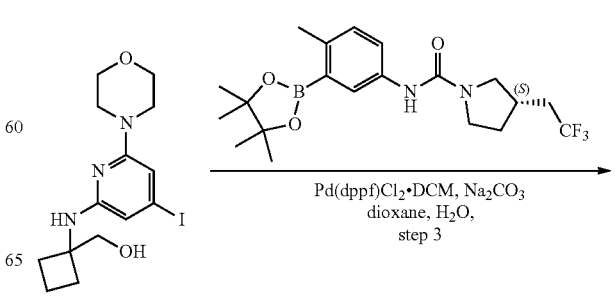

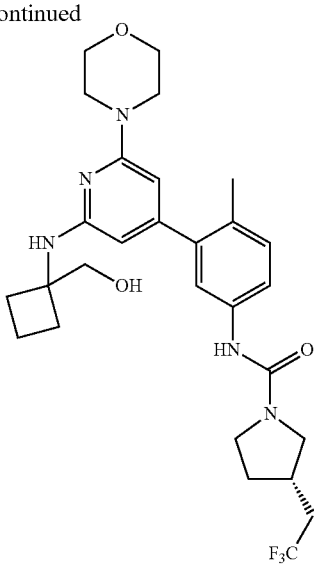

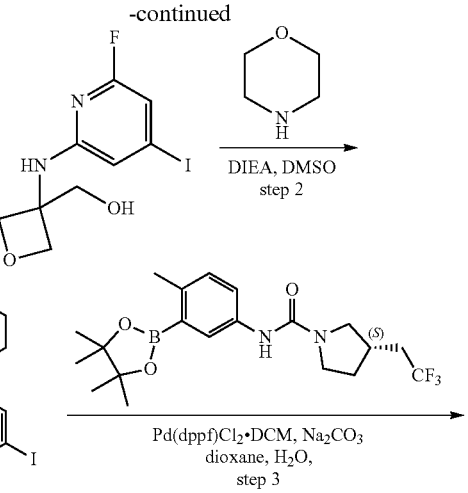

A mixture of (1-[[4-iodo-6-(morpholin-4-yl)pyridin-2-yl]amino]cyclobutyl)methanol (190 mg, 0.488 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (201 mg, 0.488 mmol), Na$_2$CO$_3$ (155.21 mg, 1.464 mmol), dioxane:H$_2$O=4:1 (2 mL) and Pd(dppf)Cl$_2$·CH$_2$Cl$_2$ (40 mg, 0.049 mmol) was stirred for 16 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EA/EtOH (8/3/1) to afford 200 mg crude product followed by reverse flash chromatography with the following conditions: column, C18 silica gel; mobile phase, CH$_3$CN in water (10 mmol/l NH$_4$HCO$_3$), 10% to 80% gradient in 30 min; detector, UV 254 nm. This resulted in (3S)—N-[3-(2-[[1-(hydroxymethyl)cyclobutyl]amino]-6-(morpholin-4-yl)pyridin-4-yl)-4-methylphenyl]-3-(2,2,2-trifluoroethyl)pyrrolidine-1-carboxamide (160 mg, 60%) as an off-white solid. MS ESI calculated for C$_{28}$H$_{36}$F$_3$N$_5$O$_3$ [M+H]$^+$: 548.28, found 548.15. $^1$H NMR (400 MHz, DMSO-d$_6$) δ 8.11 (s, 1H), 7.41-7.35 (m, 2H), 7.11-7.08 (m, 1H), 6.29 (s, 1H), 5.75 (s, 2H), 4.86-4.82 (m, 1H), 3.69-3.67 (m, 8H), 3.56-3.50 (m, 1H), 3.32 (s, 3H), 3.05-2.99 (m, 1H), 2.47-2.40 (m, 3H), 2.16-2.13 (m, 9H), 1.83-1.59 (m, 3H). $^{19}$F NMR (376 MHz, DMSO-d$_6$) δ −63.36 (3F).

Example 55: (3S)—N-[3-(2-[[3-(hydroxymethyl)oxetan-3-yl]amino]-6-(morpholin-4-yl)pyridin-4-yl)-4-methylphenyl]-3-(2,2,2-trifluoroethyl)pyrrolidine-1-carboxamide

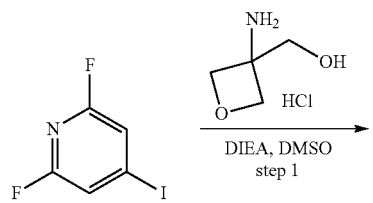

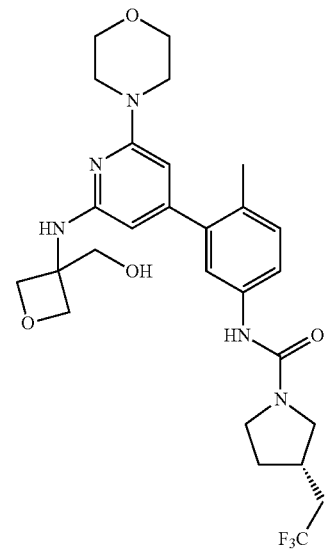

Preparation 55A: [3-[(6-fluoro-4-iodopyridin-2-yl)amino]oxetan-3-yl]methanol

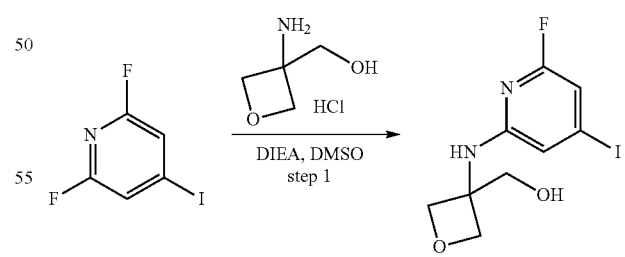

To a stirred mixture of 2,6-difluoro-4-iodopyridine (1.00 g, 4.150 mmol) and (3-aminooxetan-3-yl)methanol (0.51 g, 4.980 mmol) in DMSO (8 mL) was added DIEA (1.34 g, 10.374 mmol) in portions at room temperature under nitrogen atmosphere. The resulting mixture was stirred for 16 h at 100° C. under nitrogen atmosphere. The resulting mixture was diluted with EtOAc (100 mL). The combined organic layers were washed with brine (2×50 mL), dried over anhydrous Na$_2$SO$_4$. After filtration, the filtrate was concentrated under reduced pressure to afford (3-((6-fluoro-4-iodopyridin-2-yl)amino)oxetan-3-yl)methanol (1 g, crude) as light yellow oil. The crude product was used for next step without further purification. MS ESI calculated for C$_9$H$_{10}$FIN$_2$O$_2$ [M+H]$^+$, 324.98, found 324.95.

Preparation 55B: (3-[[4-iodo-6-(morpholin-4-yl)pyridin-2-yl]amino]oxetan-3-yl)methanol

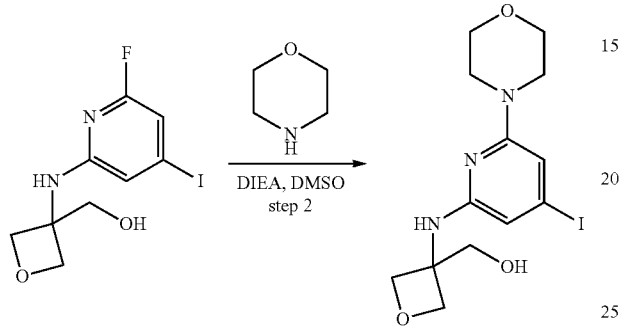

To a stirred mixture of [3-[(6-fluoro-4-iodopyridin-2-yl)amino]oxetan-3-yl]methanol (600 mg, 1.851 mmol, 1.00 equiv) and morpholine (177 mg, 2.036 mmol) in DMSO (4 mL) was added DIEA (526 mg, 4.073 mmol) in portions at room temperature under nitrogen atmosphere. The resulting mixture was stirred for 16 h at 100° C. under nitrogen atmosphere. The resulting mixture was extracted with EtOAc (3×300 mL). The combined organic layers were washed with brine (2×500 mL), dried over anhydrous Na$_2$SO$_4$. After filtration, the filtrate was concentrated under reduced pressure. The residue was purified by silica gel column chromatography, eluted with PE/EtOAc (2:1) to afford (3-[[4-iodo-6-(morpholin-4-yl)pyridin-2-yl]amino]oxetan-3-yl)methanol (300 mg, 41.42%) as a white solid. MS ESI calculated for C$_{13}$H$_{18}$IN$_3$O$_3$ [M+H]$^+$, 392.04, found 392.04. $^1$H NMR (400 MHz, Chloroform-d) δ 7.28 (s, 1H), 6.34 (d, J=1.0 Hz, 1H), 6.28 (s, 1H), 4.73 (d, J=6.4 Hz, 1H), 4.63 (d, J=6.5 Hz, 2H), 4.14 (s, 1H), 3.81-3.77 (m, 2H), 3.37 (s, 2H), 3.13 (s, 1H), 1.59 (s, 2H), 1.34-1.23 (m, 2H), 0.93-0.81 (m, 2H).

Example 55: (3S)—N-[3-(2-[[3-(hydroxymethyl)oxetan-3-yl]amino]-6-(morpholin-4-yl)pyridin-4-yl)-4-methylphenyl]-3-(2,2,2-trifluoroethyl)pyrrolidine-1-carboxamide

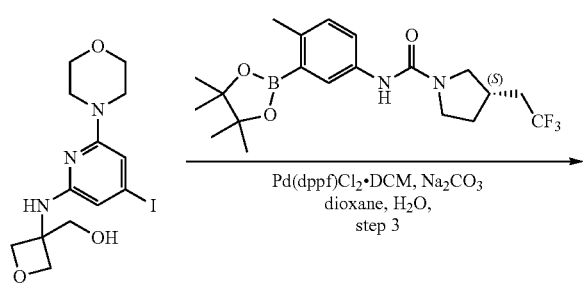

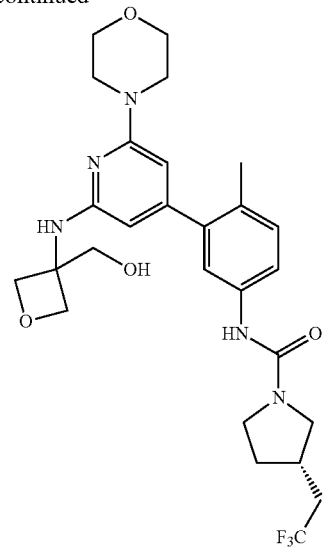

A mixture of (3-[[4-iodo-6-(morpholin-4-yl)pyridin-2-yl]amino]oxetan-3-yl)methanol (250 mg, 0.639 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (263 mg, 0.639 mmol), H$_2$O (0.75 mL) and 1,4-dioxane (3 mL), Pd(dppf)Cl$_2$·CH$_2$Cl$_2$ (52 mg, 0.064 mmol) and Na$_2$CO$_3$ (203 mg, 1.917 mmol) was stirred for 2 h at 60° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with EtOAc followed by reverse phase flash chromatography with the following conditions: Column: Spherical C18, 20-40 um, 40 g; Mobile Phase A: water (5 mM NH$_4$HCO$_3$); Mobile Phase B: CH$_3$CN; Flow rate: 60 mL/min; Gradient:5%-5% B, 10 min, 5%-40% B, 35 min, 40% B-98% B gradient in 10 min; Detector: 220 nm to afford (3S)—N-[3-(2-[[3-(hydroxymethyl)oxetan-3-yl]amino]-6-(morpholin-4-yl)pyridin-4-yl)-4-methylphenyl]-3-(2,2,2-trifluoroethyl)pyrrolidine-1-carboxamide (186 mg, 53%) as a light blue solid. MS ESI calculated for C$_{27}$H$_{34}$F$_3$N$_5$O$_4$ [M+H]$^+$, 550.26, found 550.3. $^1$H NMR (400 MHz, DMSO-d$_6$) δ 8.12 (s, 1H), 7.43-7.33 (m, 2H), 7.10 (d, J=8.3 Hz, 1H), 6.81 (s, 1H), 5.87-5.73 (m, 2H), 5.03 (t, J=5.7 Hz, 1H), 4.56 (q, J=6.1 Hz, 4H), 3.81 (d, J=5.8 Hz, 2H), 3.66 (dd, J=5.9, 3.9 Hz, 5H), 3.52 (ddd, J=10.4, 8.4, 2.3 Hz, 1H), 3.32 (s, 5H), 3.02 (t, J=9.4 Hz, 1H), 2.44 (t, J=10.8 Hz, 3H), 2.16 (s, 3H), 2.09 (q, J=5.3, 4.7 Hz, 1H), 1.65 (p, J=10.0 Hz, 1H).

Example 56: (3S)—N-(4-methyl-3-[2-[(3-methyl-oxetan-3-yl)amino]-6-(morpholin-4-yl)pyridin-4-yl]phenyl)-3-(2,2,2-trifluoroethyl)pyrrolidine-1-carboxamide

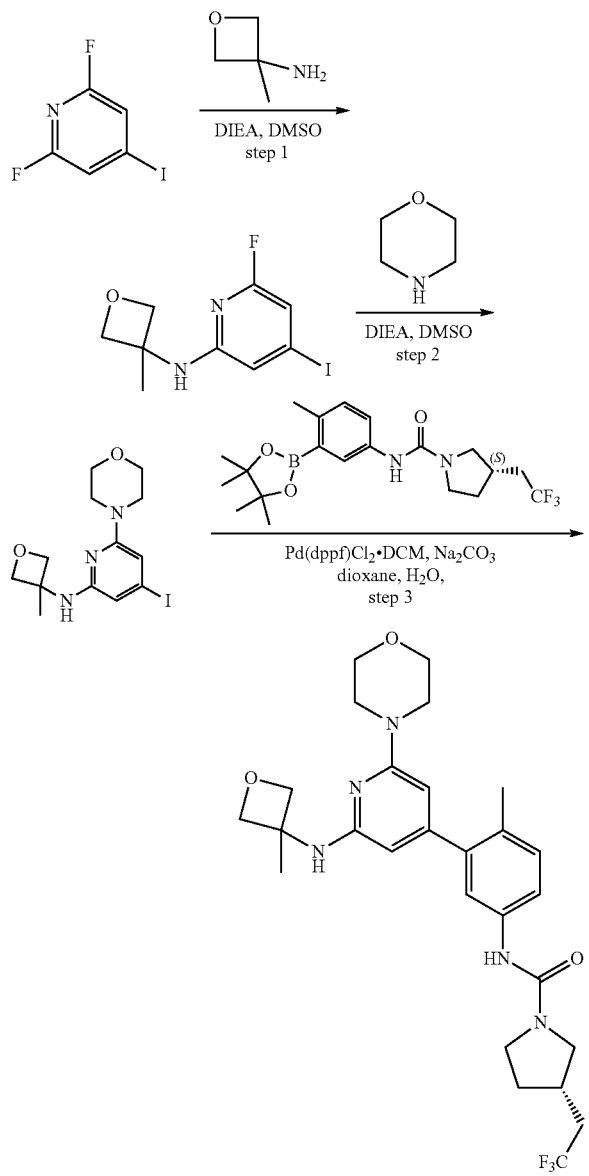

Preparation 56A: 6-fluoro-4-iodo-N-(3-methyl-oxetan-3-yl)pyridin-2-amine

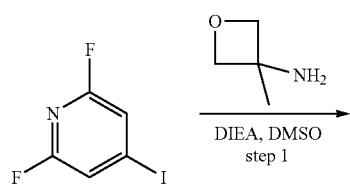

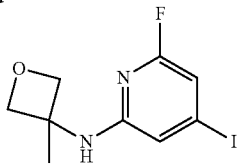

A solution of 2,6-difluoro-4-iodopyridine (500 mg, 2.075 mmol), 3-methyloxetan-3-amine (181 mg, 2.075 mmol) and DIEA (295 mg, 2.282 mmol) in DMSO (5 mL) was stirred for 16 h at 70° C. under nitrogen atmosphere. The resulting mixture was cooled down to room temperature and diluted with water (50 mL) and extracted with EtOAc (3×30 mL). The combined organic layers was washed with brine (100 mL), dried over anhydrous $Na_2SO_4$. After filtration, the filtrate was concentrated under reduced pressure. The residue was purified by silica gel column chromatography, eluted with EtOAc in PE (50%) to afford 6-fluoro-4-iodo-N-(3-methyloxetan-3-yl)pyridin-2-amine (450 mg, 70%) as an off-white solid. MS ESI calculated for $C_9H_{10}FIN_2O$ [M+H]$^+$, 309.09, found 308.85. $^1$H NMR (400 MHz, DMSO-$d_6$) δ 7.62 (s, 1H), 6.74-6.73 (m, 1H), 6.59-6.58 (m, 1H), 4.59-4.58 (m, 2H), 4.39-4.38 (m, 2H), 1.58 (s, 3H). $^{19}$F NMR (376 MHz, DMSO-$d_6$) δ −69.76 (1F).

Preparation 56B: 4-iodo-N-(3-methyloxetan-3-yl)-6-(morpholin-4-yl)pyridin-2-amine

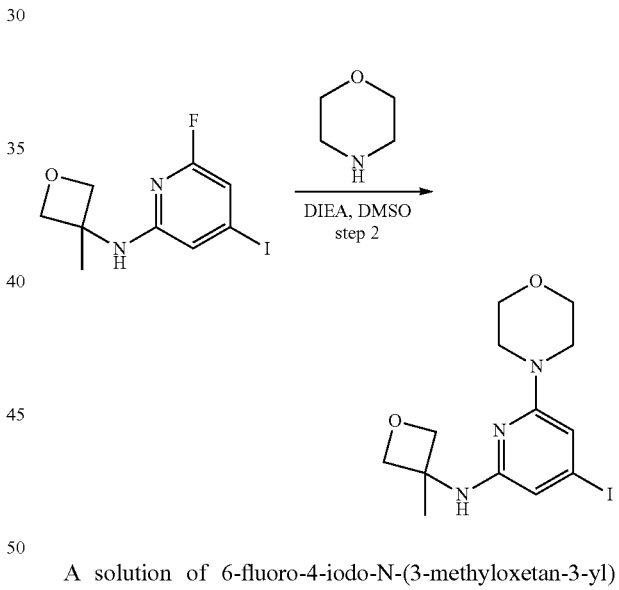

A solution of 6-fluoro-4-iodo-N-(3-methyloxetan-3-yl)pyridin-2-amine (400 mg, 1.298 mmol), morpholine (124 mg, 1.428 mmol) and DIEA (335 mg, 2.597 mmol) in DMSO (4 mL) was stirred for 16 h at 100° C. under nitrogen atmosphere. The resulting mixture was cooled down to room temperature and diluted with water (50 mL) and extracted with EtOAc (3×30 mL). The combined organic layers was washed with brine (100 mL), dried over anhydrous $Na_2SO_4$. After filtration, the filtrate was concentrated under reduced pressure. The residue was purified by silica gel column chromatography, eluted with EtOAc in PE (50%) to afford 4-iodo-N-(3-methyloxetan-3-yl)-6-(morpholin-4-yl)pyridin-2-amine (270 mg, 55%) as a light yellow solid. MS ESI calculated for $C_{13}H_{18}IN_3O_2$ [M+H]$^+$, 376.21, found 375.90. $^1$H NMR (400 MHz, DMSO-$d_6$) δ 6.90 (s, 1H), 6.25 (s, 1H), 6.20 (s, 1H), 4.63-4.60 (m, 2H), 4.36-4.34 (m, 2H), 3.65-3.62 (m, 4H), 3.31-3.28 (m, 4H), 1.59 (s, 3H).

Example 56: (3S)—N-(4-methyl-3-[2-[(3-methyl-oxetan-3-yl)amino]-6-(morpholin-4-yl)pyridin-4-yl]phenyl)-3-(2,2,2-trifluoroethyl)pyrrolidine-1-carboxamide

Example 57: (3S)—N-(4-methyl-3-[2-[(4-methyl-oxan-4-yl)amino]-6-(morpholin-4-yl)pyridin-4-yl]phenyl)-3-(2,2,2-trifluoroethyl)pyrrolidine-1-carboxamide

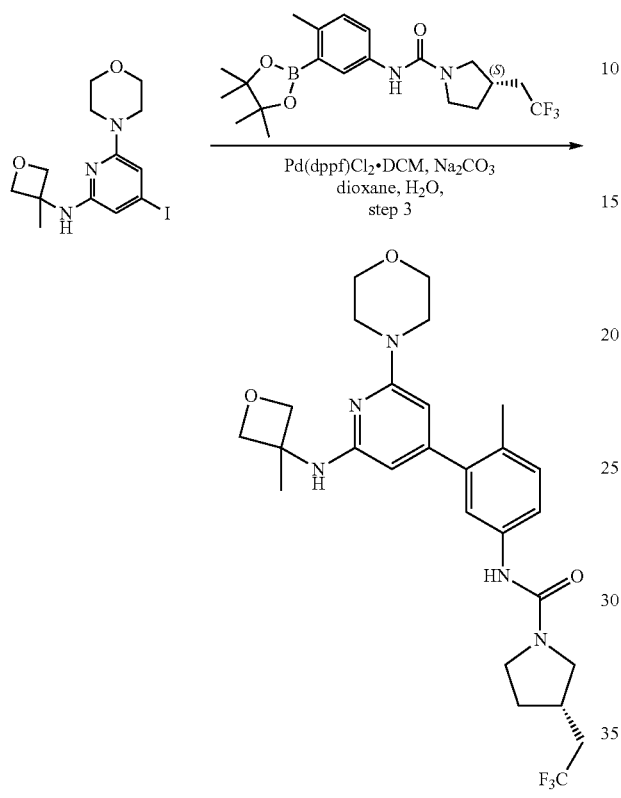

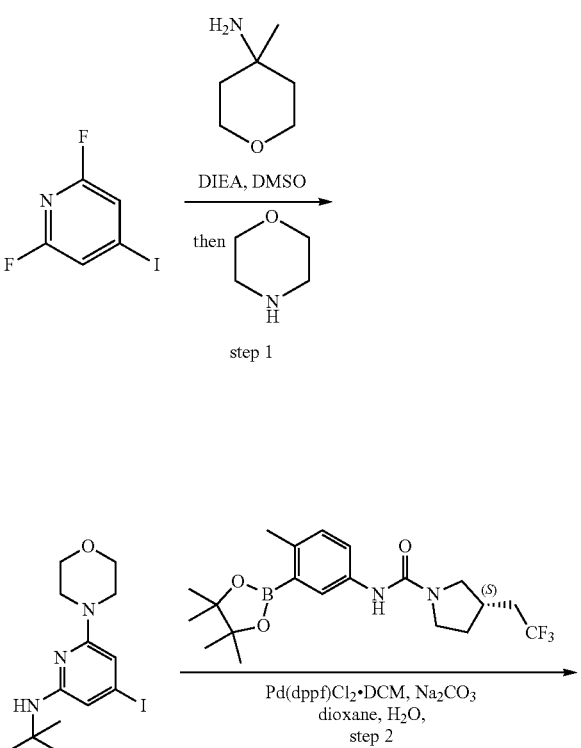

A mixture of 4-iodo-N-(3-methyloxetan-3-yl)-6-(morpholin-4-yl)pyridin-2-amine (200 mg, 0.533 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (242 mg, 0.586 mmol), Pd(dppf)Cl$_2$·CH$_2$Cl$_2$ (43 mg, 0.053 mmol), Na$_2$CO$_3$ (169 mg, 1.599 mmol), 1,4-dioxane (6 mL) and H$_2$O (1.5 mL) was stirred for 16 h at 60° C. under nitrogen atmosphere. The reaction mixture was cooled to room temperature and concentrated under reduced pressure. The residue was purified by silica gel column chromatography, eluted with EA/EtOH (3/1) in PE (58%) followed by prep-HPLC with the following conditions: Column: XBridge Prep Phenyl OBD Column, 19×150 mm 5 um 13 nm; Mobile Phase A: water (10 mmol/L NH$_4$HCO$_3$), Mobile Phase B: acetonitrile; Flow rate: 20 mL/min; Gradient:40 B to 65 B in 5.5 min; 254/210 nm to afford (3S)—N-(4-methyl-3-[2-[(3-methyloxetan-3-yl)amino]-6-(morpholin-4-yl)pyridin-4-yl]phenyl)-3-(2,2,2-trifluoroethyl)pyrrolidine-1-carboxamide (97 mg, 33%) as an off-white solid. MS ESI calculated for C$_{27}$H$_{34}$F$_3$N$_5$O$_3$ [M+H]$^+$, 534.26, found 534.25. $^1$H NMR (400 MHz, DMSO-d$_6$) δ8.12 (s, 1H), 7.42-7.35 (m, 2H), 7.11-7.09 (m, 1H), 6.77 (s, 1H), 5.81 (s, 1H), 5.73 (s, 1H), 4.70-4.69 (m, 2H), 4.40-4.38 (m, 2H), 3.68-3.64 (m, 5H), 3.52-3.50 (m, 1H), 3.35-3.29 (m, 5H), 3.04-2.99 (m, 1H), 2.52-2.41 (m, 3H), 2.16 (s, 3H), 2.06-2.04 (m, 1H), 1.75-1.60 (m, 4H). $^{19}$F NMR (376 MHz, DMSO-d$_6$) δ −63.37 (3F).

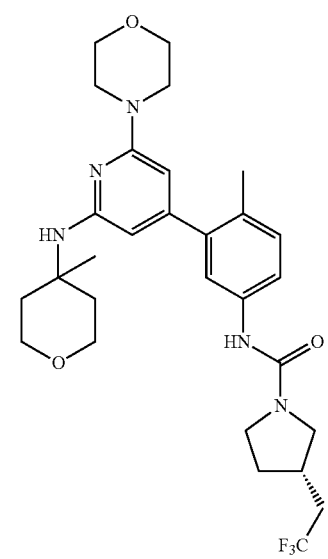

Preparation 57A: 4-iodo-N-(4-methyloxan-4-yl)-6-(morpholin-4-yl)pyridin-2-amine

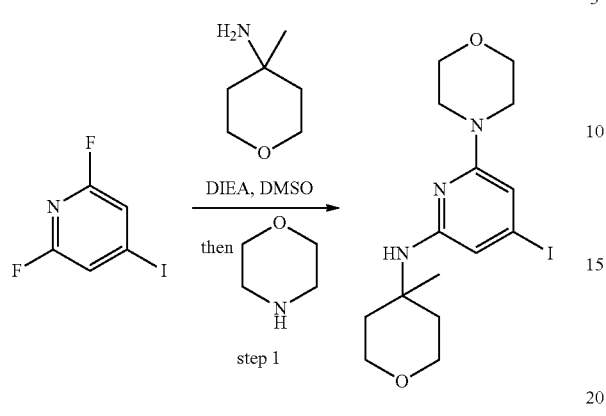

A solution of 2,6-difluoro-4-iodopyridine (200 mg, 0.830 mmol), 4-methyloxan-4-amine (105 mg, 0.913 mmol), DMSO (2 mL) and DIEA (0.32 mL, 2.461 mmol) was stirred for 4 h at 110° C. To this was added morpholine (361 mg, 4.150 mmol). The resulting mixture was stirred for 16 h at 110° C. The mixture was allowed to cool down to room temperature and quenched with water (10 mL). The resulting mixture was extracted with EtOAc (3×10 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EtOAc (4:1) to afford 4-iodo-N-(4-methyloxan-4-yl)-6-(morpholin-4-yl)pyridin-2-amine (220 mg, 66%) as a yellow solid. MS ESI calculated for $C_{15}H_{22}IN_3O_2$ [M+H]$^+$, 404.10, found 404.10. $^1$H NMR (300 MHz, CDCl$_3$-d) δ 6.23 (dd, J=10.0, 1.0 Hz, 2H), 4.05 (s, 1H), 3.86-3.67 (m, 11H), 3.43-3.35 (m, 5H), 2.10 (t, J=12.3 Hz, 3H).

Example 57: (3S)—N-(4-methyl-3-[2-[(4-methyloxan-4-yl)amino]-6-(morpholin-4-yl)pyridin-4-yl]phenyl)-3-(2,2,2-trifluoroethyl)pyrrolidine-1-carboxamide

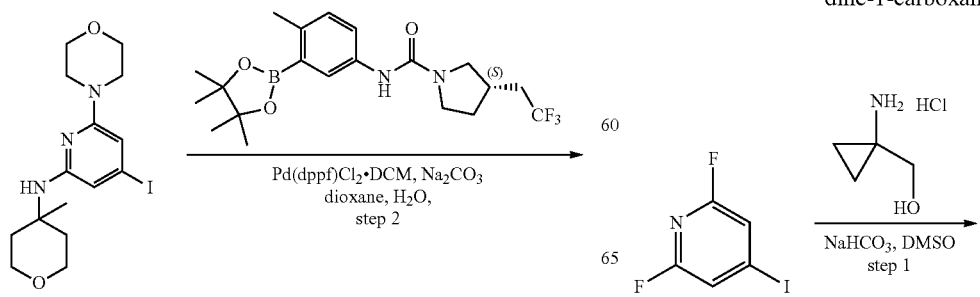

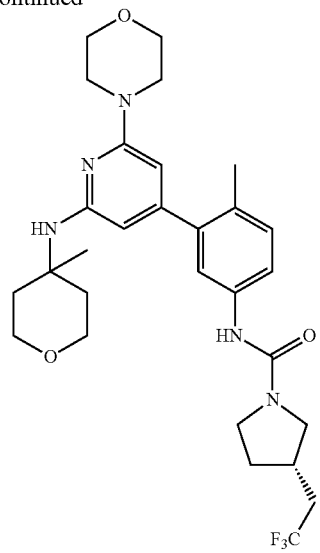

A mixture of 4-iodo-N-(4-methyloxan-4-yl)-6-(morpholin-4-yl)pyridin-2-amine (220 mg, 0.546 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (225 mg, 0.546 mmol), 1,4-dioxane (2 mL), H$_2$O (0.4 mL), Na$_2$CO$_3$ (173 mg, 1.637 mmol) and Pd(dppf)Cl$_2$·CH$_2$Cl$_2$ (44 mg, 0.055 mmol) was stirred for 16 h at 60° C. under nitrogen atmosphere. The mixture was allowed to cool down to room temperature. The reaction was quenched by the addition of water (10 mL) at room temperature. The resulting mixture was extracted with EtOAc (3×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (1/2) to afford (3S)—N-(4-methyl-3-[2-[(4-methyloxan-4-yl)amino]-6-(morpholin-4-yl)pyridin-4-yl]phenyl)-3-(2,2,2-trifluoroethyl)pyrrolidine-1-carboxamide (158 mg, 52%) as a light yellow solid. MS ESI calculated for C$_{29}$H$_{38}$F$_3$N$_5$O$_3$ [M+H]$^+$, 562.15, found 562.15. $^1$H NMR (400 MHz, DMSO-d$_6$) δ 8.11 (s, 1H), 7.42 (dd, J=8.3, 2.4 Hz, 1H), 7.35 (d, J=2.3 Hz, 1H), 7.09 (d, J=8.4 Hz, 1H), 5.97 (s, 1H), 5.91 (d, J=0.9 Hz, 1H), 5.75 (d, J=1.0 Hz, 1H), 3.72-3.54 (m, 9H), 3.52-3.49 (m, 1H), 3.36-3.32 (m, 5H), 3.02 (t, J=9.5 Hz, 1H), 2.47-2.35 (m, 3H), 2.21 (s, 1H), 2.17 (s, 4H), 2.09 (dd, J=12.4, 6.2 Hz, 1H), 1.73-1.53 (m, 3H), 1.46 (s, 3H). $^{19}$F NMR (376 MHz, DMSO-d$_6$) δ −63.36 (3F).

Example 58: (3S)—N-[3-(2-[[1-(hydroxymethyl)cyclopropyl]amino]-6-(morpholin-4-yl)pyridin-4-yl)-4-methylphenyl]-3-(2,2,2-trifluoroethyl)pyrrolidine-1-carboxamide

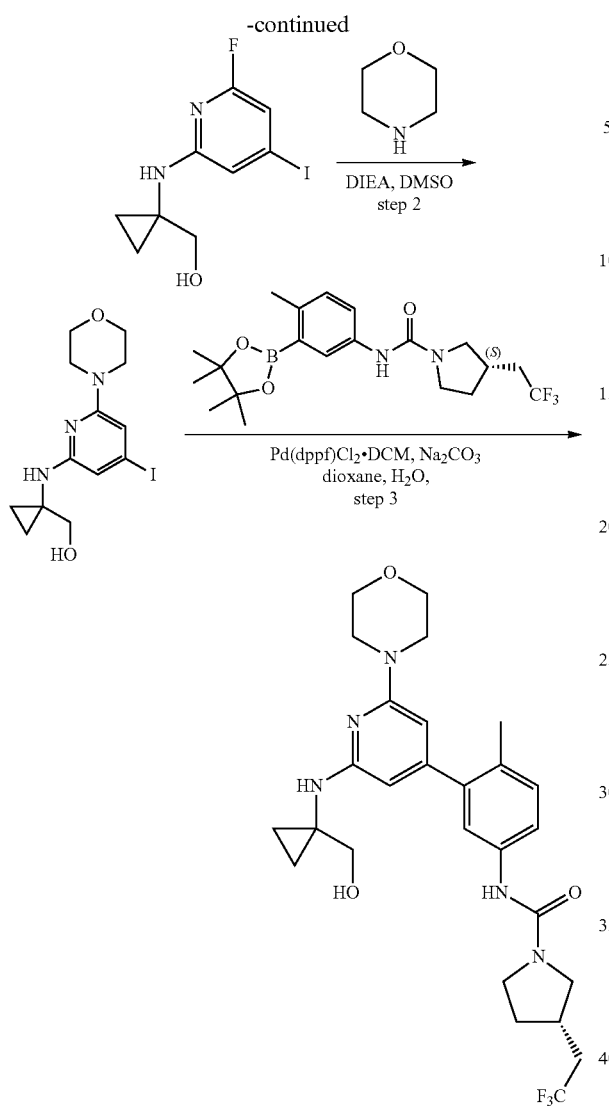

Preparation 58A: [1-[(6-fluoro-4-iodopyridin-2-yl)amino]cyclopropyl]methanol

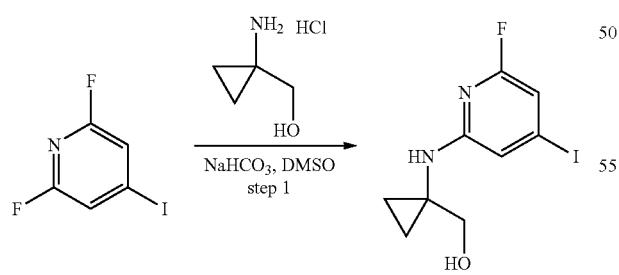

A mixture of 2,6-difluoro-4-iodopyridine (500 mg, 2.075 mmol), (1-aminocyclopropyl)methanol hydrochloride (282 mg, 2.282 mmol) and NaHCO₃ (523 mg, 6.225 mmol) in DMSO (5 mL) was stirred for 3 h at 100° C. under nitrogen atmosphere. The resulting mixture was cooled down to room temperature and diluted with water (50 mL) and extracted with EtOAc (3×30 mL). The combined organic layers was washed with brine (100 mL), dried over anhydrous Na₂SO₄. After filtration, the filtrate was concentrated under reduced pressure. The residue was purified by silica gel column chromatography, eluted with EtOAc in PE (58%) to afford [1-[(6-fluoro-4-iodopyridin-2-yl)amino]cyclopropyl]methanol (575 mg, 90%) as light yellow oil. MS ESI calculated for C₉H₁₀FIN₂O [M+H]⁺, 309.09, found 308.90. ¹H NMR (400 MHz, DMSO-d₆) δ 7.42 (s, 1H), 6.84 (s, 1H), 6.59 (s, 1H), 4.77 (brs, 1H), 3.48-3.42 (m, 2H), 0.80-0.74 (m, 2H), 0.61-0.55 (m, 2H). ¹⁹F NMR (376 MHz, DMSO-d₆) δ −70.00 (1F).

Preparation 58B: (1-[[4-iodo-6-(morpholin-4-yl)pyridin-2-yl]amino]cyclopropyl)methanol

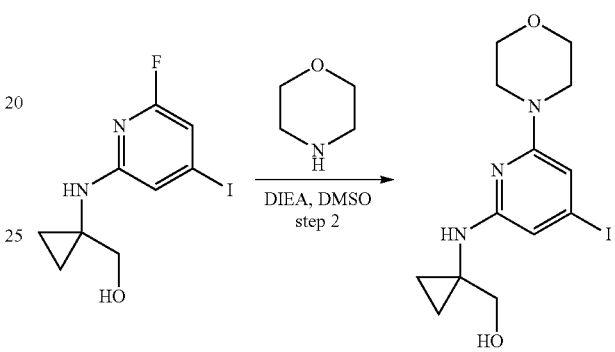

A solution of [1-[(6-fluoro-4-iodopyridin-2-yl)amino]cyclopropyl]methanol (575 mg, 1.866 mmol), morpholine (179 mg, 2.053 mmol) and DIEA (482 mg, 3.733 mmol) in DMSO (6 mL) was stirred for 16 h at 100° C. under nitrogen atmosphere. The resulting mixture was cooled down to room temperature and quenched with water (60 mL) and extracted with EtOAc (3×30 mL). The combined organic layers was washed with brine (100 mL), dried over anhydrous Na₂SO₄. After filtration, the filtrate was concentrated under reduced pressure. The residue was purified by silica gel column chromatography, eluted with EtOAc in PE (76%) to afford (1-[[4-iodo-6-(morpholin-4-yl)pyridin-2-yl]amino]cyclopropyl)methanol (315 mg, 45%) as a light yellow solid. MS ESI calculated for C₁₃H₁₈IN₃O₂ [M+H]⁺, 376.21, found 375.90. ¹H NMR (400 MHz, DMSO-d₆) δ 6.60 (s, 1H), 6.29-6.27 (m, 2H), 4.68 (brs, 1H), 3.64-3.62 (m, 4H), 3.50-3.41 (m, 2H), 3.33-3.30 (m, 4H), 0.75-0.72 (m, 2H), 0.57-0.55 (m, 2H).

Example 58: (3S)—N-[3-(2-[[1-(hydroxymethyl)cyclopropyl]amino]-6-(morpholin-4-yl)pyridin-4-yl)-4-methylphenyl]-3-(2,2,2-trifluoroethyl)pyrrolidine-1-carboxamide

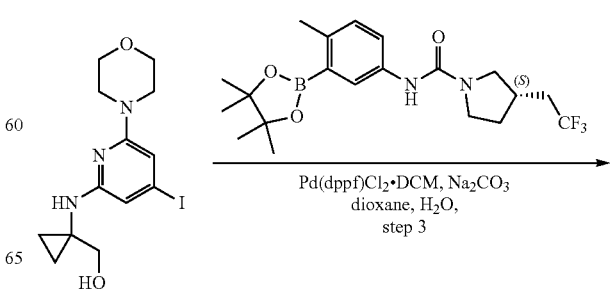

307

-continued

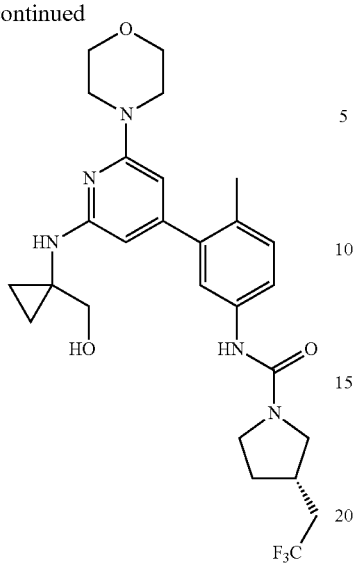

A mixture of (1-[[4-iodo-6-(morpholin-4-yl)pyridin-2-yl]amino]cyclopropyl)methanol (200 mg, 0.533 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (242 mg, 0.586 mmol), Pd(dppf)Cl$_2$·CH$_2$Cl$_2$ (43 mg, 0.053 mmol), Na$_2$CO$_3$ (169 mg, 1.599 mmol), 1,4-dioxane (6 mL) and water (1.5 mL) was stirred for 16 h at 60° C. under nitrogen atmosphere. The reaction mixture was cooled to room temperature and concentrated under reduced pressure. The residue was purified by silica gel column chromatography, eluted with EA/EtOH (3/1) in PE (60%) followed by prep-HPLC with the following conditions: Column: XBridge Prep Phenyl OBD Column, 19×150 mm 5 um 13 nm; Mobile Phase A: water (10 mmol/L NH$_4$HCO$_3$), Mobile Phase B: acetonitrile; Flow rate: 20 mL/min; Gradient:45 B to 65 B in 5.5 min; 254/210 nm to afford (3S)—N-[3-(2-[[1-(hydroxymethyl)cyclopropyl]amino]-6-(morpholin-4-yl)pyridin-4-yl)-4-methylphenyl]-3-(2,2,2-trifluoroethyl)pyrrolidine-1-carboxamide (151 mg, 51%) as an off-white solid. MS ESI calculated for C$_{27}$H$_{34}$F$_3$N$_5$O$_3$ [M+H]$^+$, 534.59, found 534.25. $^1$H NMR (400 MHz, DMSO-d$_6$) δ 8.12 (s, 1H), 7.43-7.33 (m, 2H), 7.11-7.09 (m, 1H), 6.43 (s, 1H), 5.85-5.83 (m, 2H), 4.75-4.74 (m, 1H), 3.68-3.66 (m, 5H), 3.52-3.49 (m, 3H), 3.38-3.30 (m, 5H), 3.03-3.02 (m, 1H), 2.52-2.44 (m, 3H), 2.16 (s, 3H), 2.08-2.06 (m, 1H), 1.78-1.65 (m, 1H), 0.76-0.75 (m, 2H), 0.63-0.62 (m, 2H). $^{19}$F NMR (376 MHz, DMSO-d$_6$) δ −63.36 (3F).

Examples 59 and 60: (S)—N-(3-(2-(((1R,3S)-3-hydroxy-1-methylcyclobutyl)amino)-6-morpholinopyridin-4-yl)-4-methylphenyl)-3-(2,2,2-trifluoroethyl)pyrrolidine-1-carboxamide, (S)—N-(3-(2-(((1S,3R)-3-hydroxy-1-methylcyclobutyl)amino)-6-morpholinopyridin-4-yl)-4-methylphenyl)-3-(2,2,2-trifluoroethyl)pyrrolidine-1-carboxamide

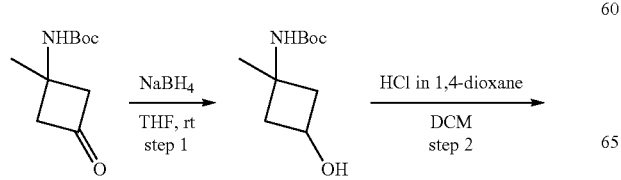

308

-continued

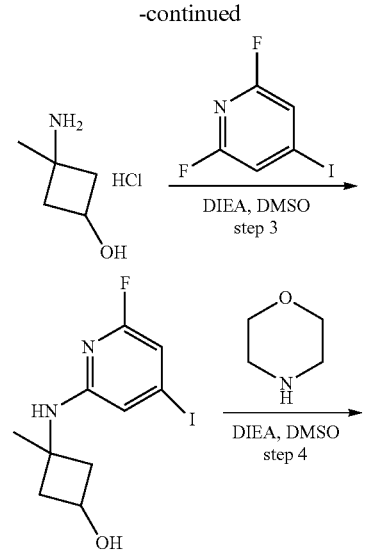

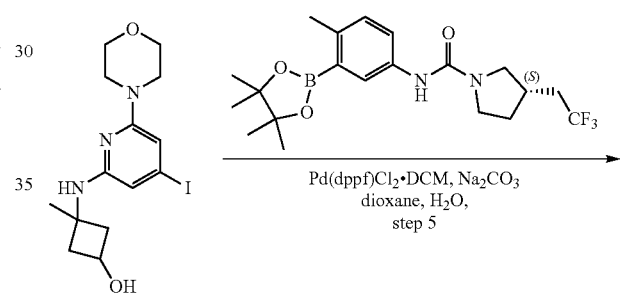

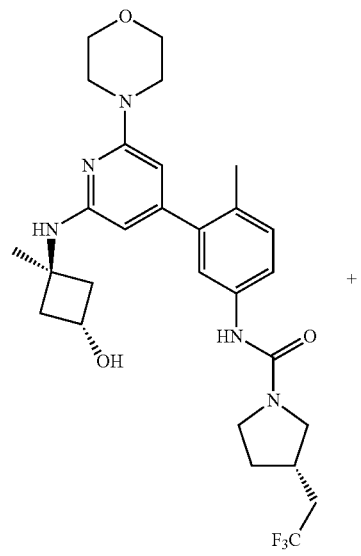

+

-continued

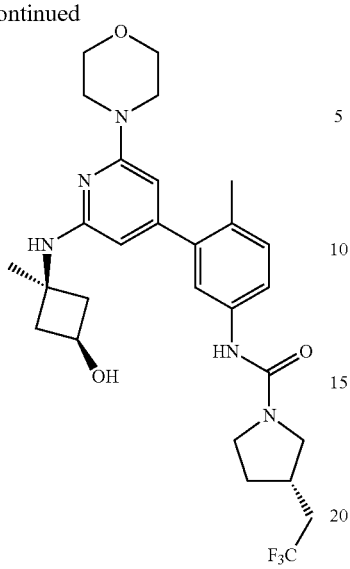

Preparation 59A: tert-butyl (3-hydroxy-1-methylcyclobutyl)carbamate

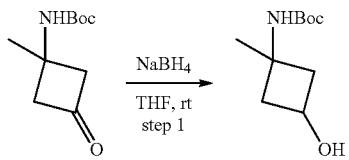

To a solution of tert-butyl N-(1-methyl-3-oxocyclobutyl) carbamate (2.00 g, 10.04 mmol) in THF (20 mL) was added NaBH$_4$ (0.76 g, 20.07 mmol) dropwise at 0° C. under nitrogen atmosphere. The resulting mixture was stirred for 16 h at room temperature. The reaction was quenched with sat. NH$_4$Cl (100 mL) at 0° C. The resulting mixture was extracted with EtOAc (3×100 mL). The combined organic layers were washed with brine (50 mL), dried over anhydrous Na$_2$SO$_4$. After filtration, the filtrate was concentrated under reduced pressure. The resulting mixture was used in the next step directly without further purification. $^1$H NMR (400 MHz, chloroform-d) δ 4.72 (s, 1H), 4.17-4.10 (m, 2H), 1.99-1.86 (m, 2H), 1.30 (d, J=20.8 Hz, 9H).

Preparation 59B: 3-amino-3-methylcyclobutan-1-ol hydrochloride

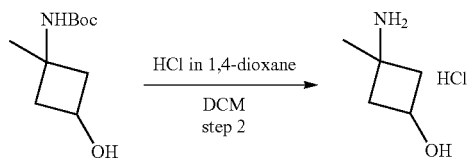

To a solution tert-butyl (3-hydroxy-1-methylcyclobutyl) carbamate (1.50 g, 7.46 mmol) in DCM (4 mL) was added HCl (gas) in 1,4-dioxane (2 mL, 65.82 mmol, 4 M) at 0° C. The resulting mixture was stirred for 1 h at room temperature. The resulting mixture was concentrated under reduced pressure. The resulting mixture was used in the next step directly without further purification. $^1$H NMR (400 MHz, DMSO-d$_6$) δ 8.37 (s, 2H), 4.43-4.35 (m, 1H), 4.04 (p, J=7.1 Hz, 1H), 2.26 (ddt, J=9.3, 7.1, 2.3 Hz, 2H), 2.17-2.08 (m, 2H), 1.33 (s, 3H).

Preparation 59C: 3-((6-fluoropyridin-2-yl)amino)-3-methylcyclobutan-1-ol

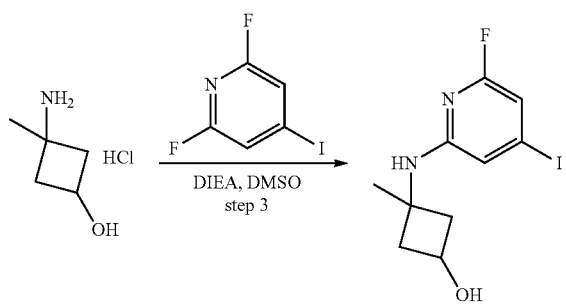

To a solution of 3-amino-3-methylcyclobutan-1-ol hydrochloride (1.3 g, 9.489 mmol) in DMSO (13 mL) were added 2,6-difluoro-4-iodopyridine (1.37 g, 5.67 mmol) and DIEA (6.10 g, 47.23 mmol) at room temperature under. The resulting mixture was stirred for 16 h at 110° C. The reaction was quenched by the addition of water (130 mL) at room temperature. The resulting mixture was extracted with EtOAc (3×100 mL). The combined organic layers were washed with brine (200 mL), dried over anhydrous Na$_2$SO$_4$. After filtration, the filtrate was concentrated under reduced pressure. The residue was purified by silica gel column chromatography, eluted with PE/EtOAc (3:1) to afford 3-((6-fluoropyridin-2-yl)amino)-3-methylcyclobutan-1-ol (800 mg, 26%) as a light yellow oil. MS ESI calculated for C$_{10}$H$_{13}$FN$_2$O [M+H]$^+$, 323.00, found 323.05. $^1$H NMR (400 MHz, chloroform-d) δ 6.55-6.45 (m, 2H), 4.63 (d, J=53.3 Hz, 1H), 4.23 (p, J=6.9 Hz, 1H), 4.13-4.03 (m, 1H), 2.51-2.43 (m, 2H), 2.37-2.25 (m, 2H), 1.34-1.22 (m, 3H).

Preparation 59D: 3-((4-iodo-6-morpholinopyridin-2-yl)amino)-3-methylcyclobutan-1-ol

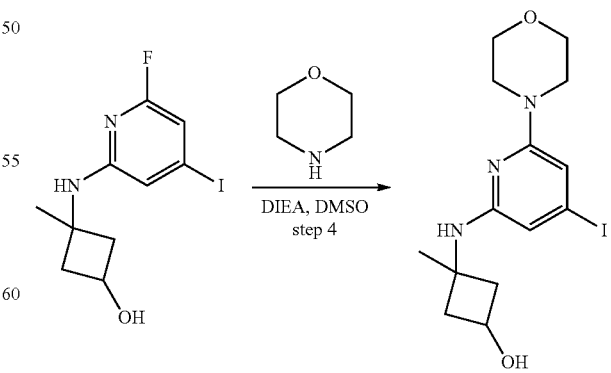

To a solution of 3-((6-fluoro-4-iodopyridin-2-yl)amino)-3-methylcyclobutan-1-ol (980 mg, 3.043 mmol) in DMSO (10 mL) was added DIEA (786 mg, 6.085 mmol) at room temperature. The resulting mixture was stirred for 16 h at 110° C. The reaction was quenched with water (100 mL). The resulting mixture was extracted with EtOAc (3×50 mL). The combined organic layers were washed with brine (100 mL), dried over anhydrous Na$_2$SO$_4$. After filtration, the filtrate was concentrated under reduced pressure. The residue was purified by silica gel column chromatography, eluted with PE/EtOAc (1:1) to afford 3-((4-iodo-6-morpholinopyridin-2-yl)amino)-3-methylcyclobutan-1-ol (200 mg, 17%) as a light yellow oil. MS ESI calculated for C$_{14}$H$_{20}$IN$_3$O$_2$ [M+H]$^+$, 390.06, found 389.95. $^1$H NMR (400 MHz, DMSO-d$_6$) δ 6.17 (d, J=1.1 Hz, 1H), 6.14 (d, J=1.0 Hz, 1H), 4.03 (q, J=7.1 Hz, 3H), 3.90 (t, J=7.3 Hz, 1H), 3.64 (dd, J=5.8, 3.9 Hz, 4H), 2.39 (ddd, J=12.0, 6.0, 2.6 Hz, 2H), 2.23-2.20 (m, 2H), 1.21 (s, 3H).

Examples 59 and 60: (S)—N-(3-(2-(((1R,3S)-3-hydroxy-1-methylcyclobutyl)amino)-6-morpholinopyridin-4-yl)-4-methylphenyl)-3-(2,2,2-trifluoroethyl)pyrrolidine-1-carboxamide, (S)—N-(3-(2-(((1S,3R)-3-hydroxy-1-methylcyclobutyl)amino)-6-morpholinopyridin-4-yl)-4-methylphenyl)-3-(2,2,2-trifluoroethyl)pyrrolidine-1-carboxamide

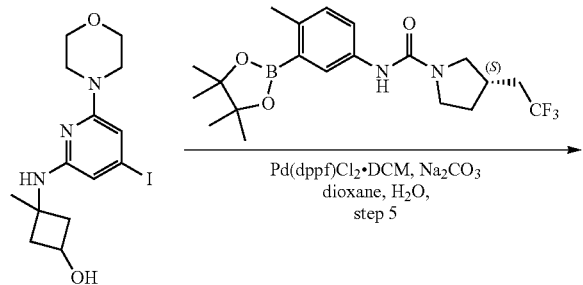

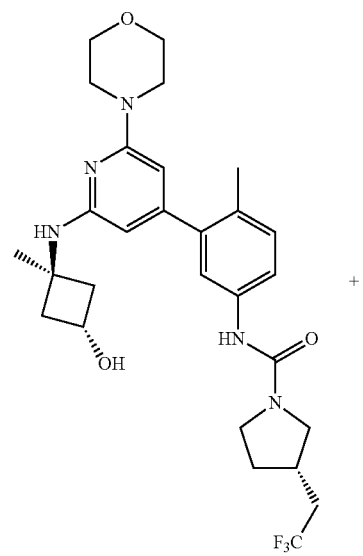

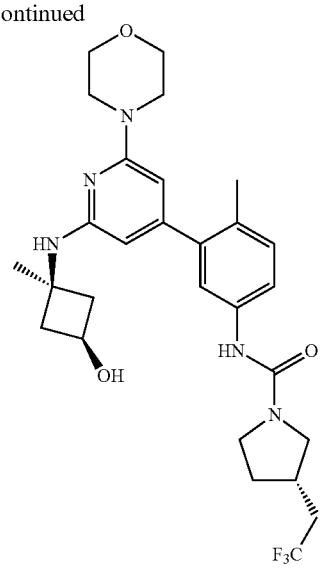

A mixture of 3-((4-iodo-6-morpholinopyridin-2-yl)amino)-3-methylcyclobutan-1-ol (200 mg, 0.514 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (212 mg, 0.514 mmol), Pd(dppf)Cl$_2$·CH$_2$Cl$_2$ (42 mg, 0.051 mmol) and Na$_2$CO$_3$ (163 mg, 1.541 mmol) in dioxane (2 mL) and H$_2$O (0.2 mL) was stirred for 3 h at 80° C. under nitrogen atmosphere. The reaction mixture was concentrated under reduced pressure. The residue was purified by silica gel column chromatography, eluted with PE/EtOAc (1/2). The resulting mixture was resolved by chiral HPLC with following conditions: Column: CHIRALPAK IE, 2*25 cm, 5 um; Mobile Phase A: Hex (0.5% 2 M NH$_3$-MeOH), Mobile Phase B: EtOH; Flow rate: 18 mL/min; A:B=70:30; 220/254 nm to afforde 14.7 mg (9%) as a light blue solid. MS ESI calculated for C$_{28}$H$_{36}$F$_3$N$_5$O$_3$ [M+H]$^+$, 548.28, found 548.25. $^1$H NMR (400 MHz, DMSO-d$_6$) δ 8.10 (s, 1H), 7.48-7.32 (m, 2H), 7.09 (d, J=8.3 Hz, 1H), 6.24 (s, 1H), 5.73 (d, J=28.8 Hz, 2H), 4.91 (d, J=5.8 Hz, 1H), 4.16 (h, J=6.7 Hz, 1H), 3.75-3.60 (m, 5H), 3.53 (ddd, J=10.4, 8.2, 2.3 Hz, 1H), 3.36 (d, J=9.6 Hz, 4H), 3.32-3.25 (m, 1H), 3.02 (t, J=9.4 Hz, 1H), 2.63 (ddd, J=10.0, 7.3, 2.6 Hz, 2H), 2.43 (dd, J=15.0, 7.1 Hz, 3H), 2.17 (s, 4H), 1.89-1.77 (m, 2H), 1.77-1.59 (m, 1H), 1.49 (s, 3H). $^{19}$F NMR (376 MHz, DMSO-d$_6$) δ −63.36, and 50.5 mg (30%) as a light blue solid. MS ESI calculated for C$_{28}$H$_{36}$F$_3$N$_5$O$_3$ [M+H]$^+$, 548.28, found 548.25. $^1$H NMR (300 MHz, DMSO-d$_6$) δ 8.11 (s, 1H), 7.49-7.30 (m, 2H), 7.09 (d, J=8.3 Hz, 1H), 6.42 (s, 1H), 5.72 (d, J=19.3 Hz, 2H), 4.93 (d, J=6.2 Hz, 1H), 4.03 (h, J=7.1 Hz, 1H), 3.80-3.62 (m, 5H), 3.53 (ddd, J=10.5, 8.3, 2.4 Hz, 1H), 3.39 (s, 1H), 3.37-3.21 (m, 3H), 3.03 (t, J=9.3 Hz, 1H), 2.50-2.34 (m, 5H), 2.17 (s, 3H), 2.05 (t, J=10.2 Hz, 3H), 1.85-1.55 (m, 1H), 1.42 (s, 3H). $^{19}$F NMR (282 MHz, DMSO-d$_6$) δ −63.36, −63.43.

313

Example 61: (3S)—N-[3-(2-[[(2R,3R)-3-hydroxybutan-2-yl]amino]-6-(morpholin-4-yl)pyridin-4-yl)-4-methylphenyl]-3-(2,2,2-trifluoroethyl)pyrrolidine-1-carboxamide

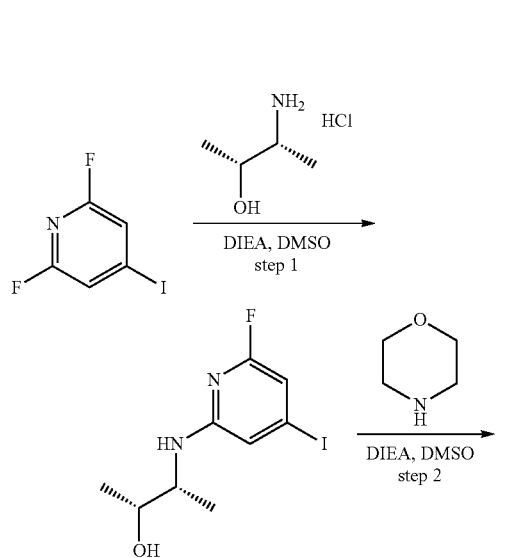

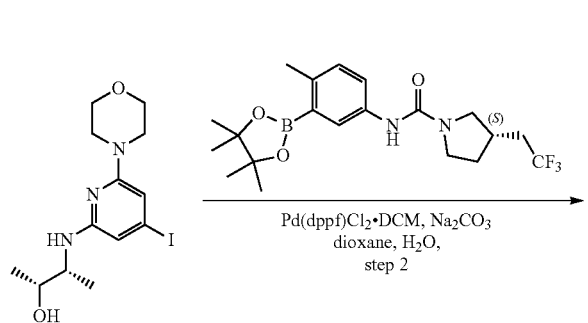

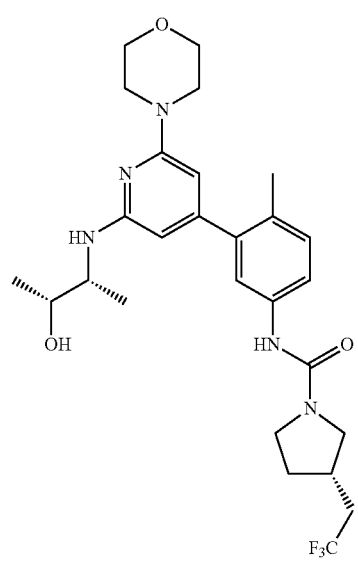

314

Preparation 61A: (2R,3R)-3-[(6-fluoro-4-iodopyridin-2-yl)amino]butan-2-ol

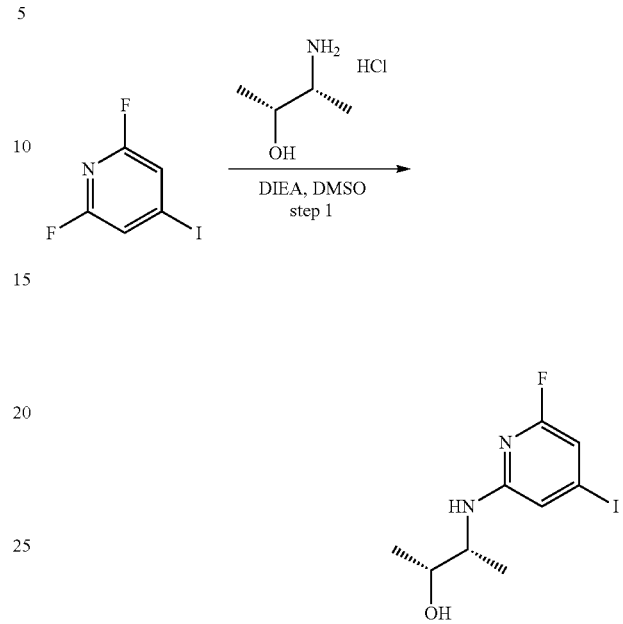

A solution of 2,6-difluoro-4-iodopyridine (300 mg, 1.245 mmol), DMSO (3 mL), (2R,3R)-3-aminobutan-2-ol (133 mg, 1.494 mmol) and DIEA (804 mg, 6.225 mmol) was stirred for 2 h at 70° C. The resulting mixture was quenched with H$_2$O (100 mL) and extracted with EtOAc (4×50 mL). The combined organic layers were washed with brine (4×50 mL), dried over anhydrous Na$_2$SO$_4$. After filtration, the filtrate was concentrated under reduced pressure. The residue was purified by silica gel column chromatography, eluted with PE/EtOAc (1:1) to afford (2R,3R)-3-[(6-fluoro-4-iodopyridin-2-yl)amino]butan-2-ol (172 mg, 44%) as a light yellow oil. MS ESI calculated for C$_9$H$_{12}$FIN$_2$O [M+H]$^+$, 311.11, found 310.90. $^1$H NMR (400 MHz, chloroform-d) δ 6.65 (s, 1H), 6.52 (m, 1H), 4.78 (s, 1H), 3.80 (m, 2H), 2.19 (s, 1H), 1.32-1.19 (m, 6H).

Preparation 61B: (2R,3R)-3-[[4-iodo-6-(morpholin-4-yl)pyridin-2-yl]amino]butan-2-ol

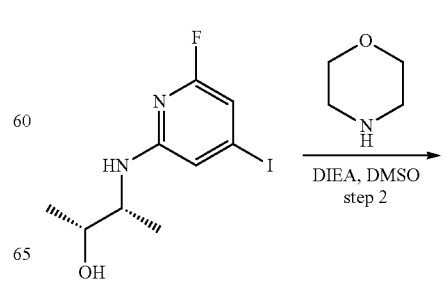

315
-continued

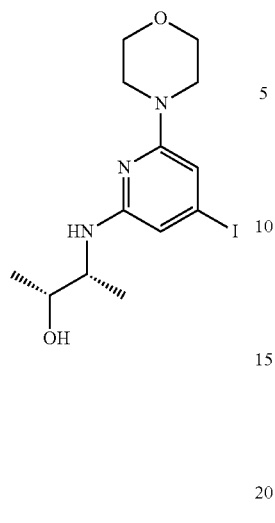

316
-continued

A mixture of (2R,3R)-3-[(6-fluoro-4-iodopyridin-2-yl)amino]butan-2-ol (110 mg, 0.355 mmol), DMSO (2 mL), morpholine (102 mg, 1.171 mmol) and DIEA (55 mg, 0.426 mmol) was stirred for 16 h at 70° C. The resulting mixture was quenched with H$_2$O (100 mL) and extracted with EtOAc (4×50 mL). The combined organic layers were washed with brine (4×50 mL), dried over anhydrous Na$_2$SO$_4$. After filtration, the filtrate was concentrated under reduced pressure. The residue was purified by silica gel column chromatography, eluted with 39% EtOAc in PE to afford (2R,3R)-3-[[4-iodo-6-(morpholin-4-yl)pyridin-2-yl]amino]butan-2-ol (110 mg, 67%) as a dark yellow oil. MS ESI calculated for C$_{13}$H$_{20}$IN$_3$O$_2$ [M+H]$^+$, 379.06, found 379.00. C$_{13}$H$_{20}$IN$_3$O$_2$: $^1$H NMR (400 MHz, chloroform-d) δ 7.28 (s, 1H), 6.28 (s, 1H), 6.24 (s, 1H), 4.44-4.20 (m, 1H), 3.79 (s, 4H), 3.72 (m, 1H), 3.43 (s, 4H), 2.07 (s, 1H), 1.29-1.20 (m, 6H).

Example 61: (3S)—N-[3-(2-[[(2R,3R)-3-hydroxybutan-2-yl]amino]-6-(morpholin-4-yl)pyridin-4-yl)-4-methylphenyl]-3-(2,2,2-trifluoroethyl)pyrrolidine-1-carboxamide A mixture of (2R,3R)-3-[[4-iodo-6-(morpholin-4-yl)pyridin-2-yl]amino]butan-2-ol (110 mg, 0.292 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (120 mg, 0.292 mmol), 1,4-dioxane (2 mL), H$_2$O (0.5 mL), Na$_2$CO$_3$ (93 mg, 0.875 mmol) and Pd(dppf)Cl$_2$·CH$_2$Cl$_2$ (24 mg, 0.029 mmol) was stirred for 2 h at 80° C. under nitrogen atmosphere. The resulting mixture was concentrated under reduced pressure. The residue was purified by silica gel column chromatography, eluted with EtOAc followed by reverse phase flash with the following conditions (column, C18 silica gel; mobile phase, MeCN in water, 5% to 95% gradient in 10 min; detector, UV 254 nm) to afford (3S)—N-[3-(2-[[(2R,3R)-3-hydroxybutan-2-yl]amino]-6-(morpholin-4-yl)pyridin-4-yl)-4-methylphenyl]-3-(2,2,2-trifluoroethyl)pyrrolidine-1-carboxamide (59 mg, 38%) as a white solid. MS ESI calculated for C$_{27}$H$_{36}$F$_3$N$_5$O$_3$ [M+H]$^+$, 536.61, found 536.15. $^1$H NMR (300 MHz, DMSO-d$_6$) δ 8.11 (s, 1H), 7.41 (m, 1H), 7.33 (s, 1H), 7.09 (s, 1H), 5.86 (s, 1H), 5.79 (s, 1H), 5.73 (s, 1H), 4.59 (s, 1H), 3.87 (s, 1H), 3.78-3.62 (m, 6H), 3.57-3.47 (m, 1H), 3.37 (sz, 4H), 3.31-3.25 (m, 1H), 3.02 (m, 1H), 2.50 (s, 3H), 2.16 (s, 3H), 2.12-1.97 (m, 1H), 1.66 (m, 1H), 1.06 (m, 6H). $^{19}$F NMR (376 MHz, DMSO-d$_6$) δ −63.4 (3F).

Example 62: (3S)—N-(3-[2-[(1-cyanopropan-2-yl)amino]-6-(morpholin-4-yl)pyridin-4-yl]-4-methylphenyl)-3-(2,2,2-trifluoroethyl)pyrrolidine-1-carboxamide

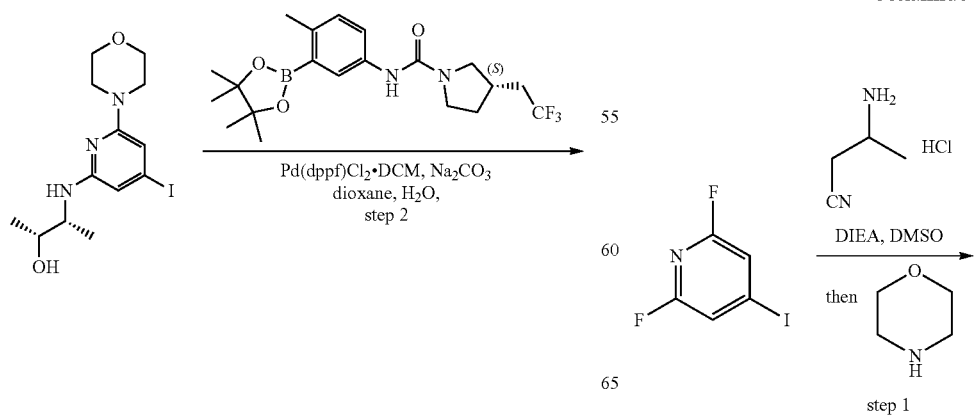

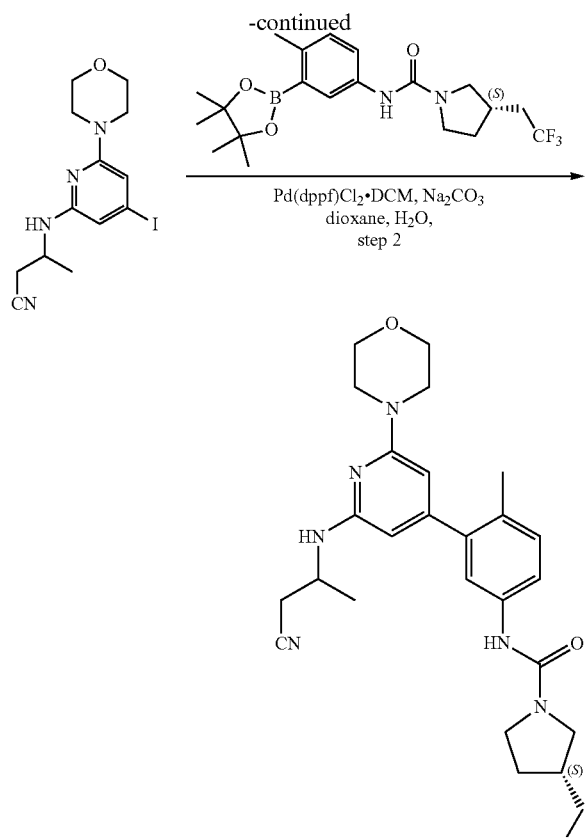

Preparation 62A: 3-[[4-iodo-6-(morpholin-4-yl)pyridin-2-yl]amino]butanenitrile

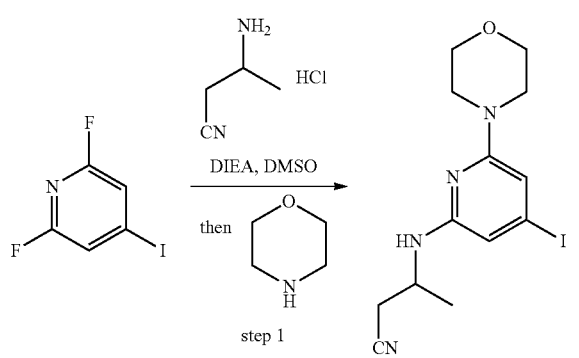

A solution of 2,6-difluoro-4-iodopyridine (300 mg, 1.245 mmol), DMSO (4 mL), 3-aminobutanenitrile hydrochloride (165 mg, 1.369 mmol) and DIEA (354 mg, 2.739 mmol) was stirred for 3 h at 70° C. To above stirred mixture was added morpholine (357 mg, 4.097 mmol). The resulting mixture was stirred for 16 h at 100° C. The resulting mixture was diluted with water (50 mL). The resulting mixture was extracted with EtOAc (3×50 mL). The combined organic layers were washed with brine (2×30 mL), dried over anhydrous $Na_2SO_4$. After filtration, the filtrate was concentrated under reduced pressure. The residue was purified by silica gel column chromatography, eluted with PE/EtOAc/EtOH=(4/3/1) to afford 3-[[4-iodo-6-(morpholin-4-yl)pyridin-2-yl]amino]butanenitrile (351 mg, 75%) as off-white solid. MS ESI calculated for $C_{13}H_{17}IN_4O$ [M+H]$^+$, 373.04, found 372.90. $^1$H NMR (300 MHz, chloroform-d) δ 6.45-6.40 (m, 1H), 6.23-6.22 (m, 1H), 4.25-4.22 (m, 1H), 3.84-3.78 (m, 5H), 3.54-3.37 (m, 4H), 2.84-2.64 (m, 2H), 1.47-1.42 (m, 3H).

Example 62: (3S)—N-(3-[2-[(1-cyanopropan-2-yl)amino]-6-(morpholin-4-yl)pyridin-4-yl]-4-methylphenyl)-3-(2,2,2-trifluoroethyl)pyrrolidine-1-carboxamide

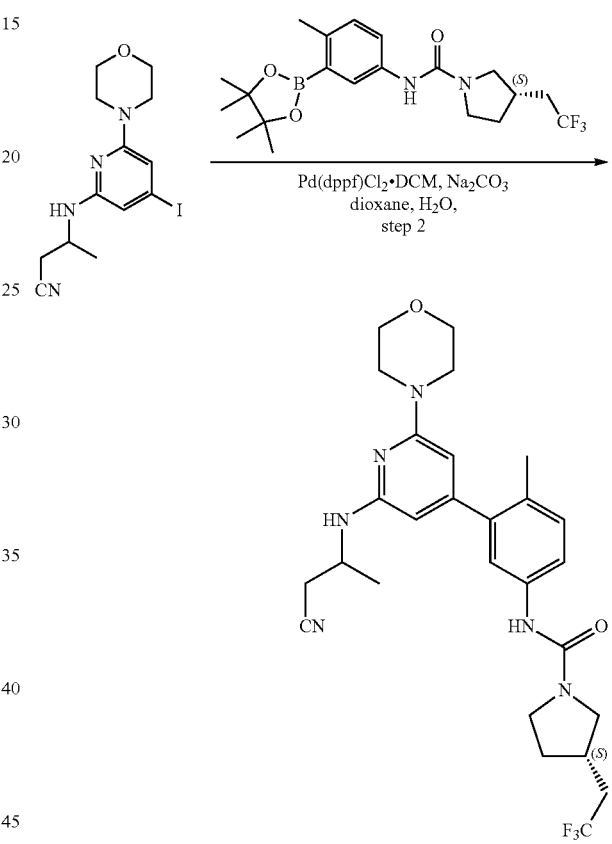

A mixture of 3-[[4-iodo-6-(morpholin-4-yl)pyridin-2-yl]amino]butanenitrile (150 mg, 0.403 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (166 mg, 0.403 mmol), $Na_2CO_3$ (128 mg, 1.209 mmol), dioxane (4 mL), $H_2O$ (1 mL) and Pd(dppf)Cl$_2$·CH$_2$Cl$_2$ (33 mg, 0.040 mmol) was stirred for 16 h at 60° C. under nitrogen atmosphere. The resulting mixture was diluted with water (50 mL) and extracted with EtOAc (3×50 mL). The combined organic layers were washed with brine (2×40 mL), dried over anhydrous $Na_2SO_4$. After filtration, the filtrate was concentrated under reduced pressure. The residue was purified by silica gel column chromatography, eluted with hexane/EtOAc/EtOH=4/3/1 followed by reverse flash chromatography with the following conditions: column, C18 silica gel; mobile phase, MeCN in water, 5% to 95% gradient in 10 min; detector, UV 254 nm to afford (3S)—N-(3-[2-[(1-cyanopropan-2-yl)amino]-6-(morpholin-4-yl)pyridin-4-yl]-4-methylphenyl)-3-(2,2,2-trifluoroethyl)pyrrolidine-1-carboxamide (149 mg, 69% as a white solid. MS ESI calculated for $C_{27}H_{33}F_3N_6O_2$ [M+H]$^+$, 531.26, found 531.15. $^1$H NMR (300 MHz, DMSO-d$_6$) δ 8.01 (s, 1H), 7.43-7.33 (m, 2H), 7.11-7.08 (m, 1H), 6.53-6.51 (m, 1H), 5.82-5.81 (m, 2H), 4.16-4.15 (m, 1H), 3.68-3.49 (m, 5H), 3.52-3.49 (m, 1H), 3.39-3.33 (m, 4H), 3.04-3.02 (m, 1H), 2.98-2.72 (m, 2H), 2.50-2.42 (m, 3H), 2.18-2.01 (m, 5H), 2.71-2.59 (m, 1H), 1.29-1.22 (m, 3H). $^{19}$F NMR (282 MHz, DMSO-d$_6$) δ −63.36 (3F).

Examples 63 and 64: (S)—N-(3-(2-(((1S,4R)-4-hydroxy-1-methylcyclohexyl)amino)-6-morpholinopyridin-4-yl)-4-methylphenyl)-3-(2,2,2-trifluoroethyl)pyrrolidine-1-carboxamide, (S)—N-(3-(2-(((1R,4S)-4-hydroxy-1-methylcyclohexyl)amino)-6-morpholinopyridin-4-yl)-4-methylphenyl)-3-(2,2,2-trifluoroethyl)pyrrolidine-1-carboxamide

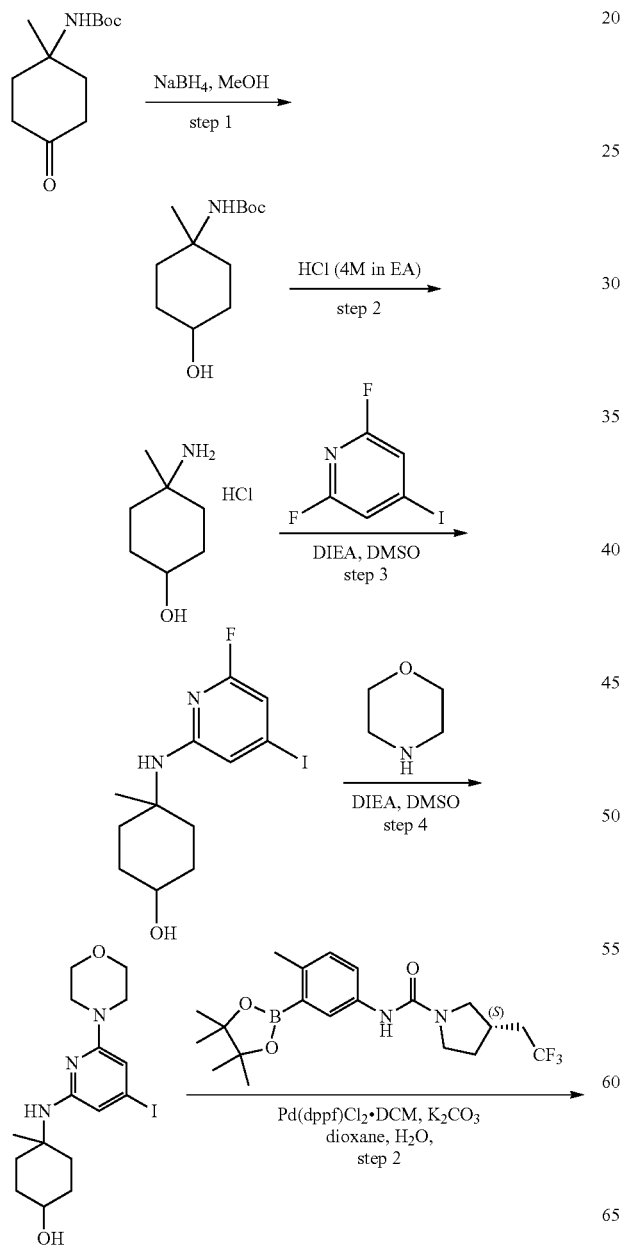

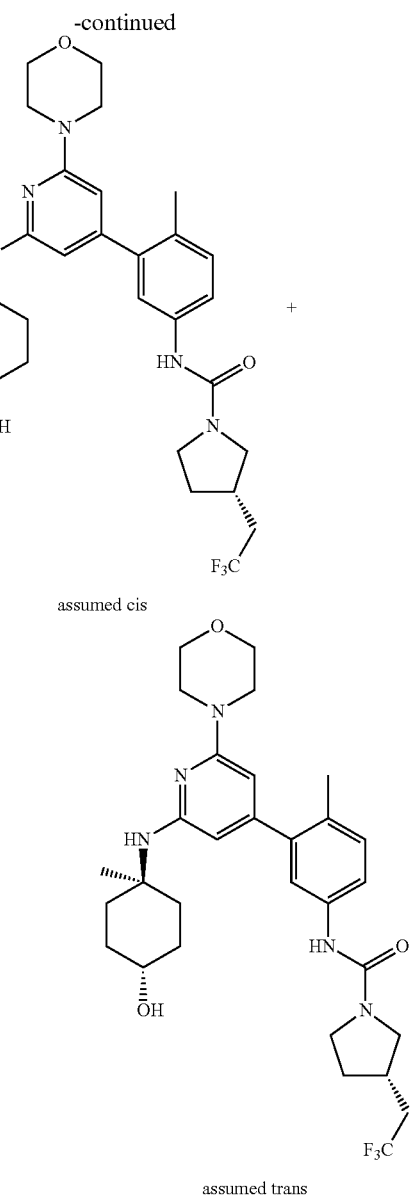

assumed cis

+ assumed trans

Preparation 63A: tert-butyl N-(4-hydroxy-1-methylcyclohexyl)carbamate

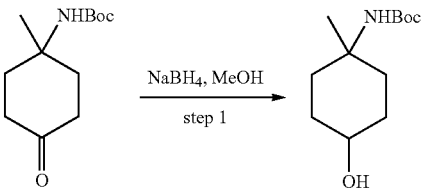 [SMILES: CC1(NC(=O)OC(C)(C)C)CCC(=O)CC1 ; CC1(NC(=O)OC(C)(C)C)CCC(O)CC1]

To a solution of tert-butyl N-(1-methyl-4-oxocyclohexyl) carbamate (700 mg, 3.080 mmol) in MeOH (10 mL) was added NaBH$_4$ (174 mg, 4.619 mmol) in ports at room temperature. The mixture was stirred at room temperature for 2 h. The reaction was quenched by the addition of water (50 mL) at 0° C. The resulting mixture was extracted with EtOAc (3×50 mL). The combined organic layers were washed with brine (3×50 mL), dried over anhydrous Na₂SO₄. After filtration, the filtrate was concentrated under reduced pressure. This resulted in tert-butyl N-(4-hydroxy-1-methylcyclohexyl)carbamate (600 mg, 85%) as colorless oil. MS ESI calculated for C₁₂H₂₃NO₃ [M+H]⁺, 230.17 found N/A. ¹H NMR (400 MHz, chloroform-d) δ 3.65 (td, J=10.1, 4.8 Hz, 1H), 1.47 (s, 3H), 1.46-1.40 (m, 8H), 1.44 (s, 9H).

Preparation 63B: 4-amino-4-methylcyclohexan-1-ol hydrochloride

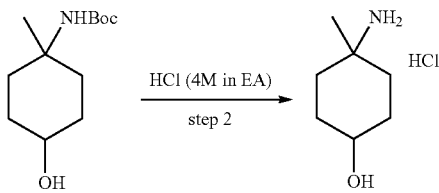

To a solution of tert-butyl N-(4-hydroxy-1-methylcyclohexyl)carbamate (600 mg, 2.616 mmol) in EtOAc (5 mL) was added HCl (gas) in EtOAc (10 mL) at room temperature. The mixture was stirred at room temperature for 2 h. The resulting mixture was concentrated under reduced pressure. This resulted in 4-amino-4-methylcyclohexan-1-ol hydrochloride (400 mg, 92%) as a white solid. The crude product was used in the next step directly without further purification. MS ESI calculated for C—H₁₅NO [M+H]⁺, 130.12 found N/A. ¹H NMR (400 MHz, methanol-d₄) δ 3.84 (td, J=6.1, 3.1 Hz, 1H), 1.93-1.66 (m, 8H), 1.37 (s, 3H).

Preparation 63C: 4-[(6-fluoro-4-iodopyridin-2-yl)amino]-4-methylcyclohexan-1-ol

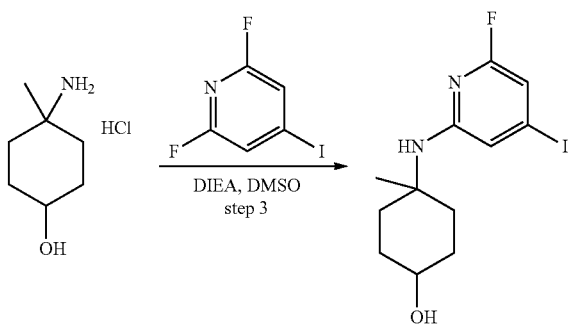

To a solution of 4-(6-fluoro-4-iodopyridin-2-yl)morpholine (744 mg, 2.415 mmol) and 4-amino-4-methylcyclohexan-1-ol hydrochloride (500 mg, 3.018 mmol) in DMSO (10 mL) was added DIEA (1.95 g, 15.091 mmol) at room temperature. The mixture was stirred at 100° C. for 3 h. The mixture was allowed to cool down to room temperature. The reaction was quenched by the addition of water (50 mL) at room temperature. The resulting mixture was extracted with EtOAc (3×50 mL). The combined organic layers were washed with brine (3×50 mL), dried over anhydrous Na₂SO₄. After filtration, the filtrate was concentrated under reduced pressure. MS ESI calculated for C₁₂H₁₆FIN₂O [M+H]⁺, 351.03, found 350.95. ¹H NMR (400 MHz, chloroform-d) δ 6.67-6.61 (m, 1H), 6.51 (dd, J=2.9, 1.0 Hz, 1H), 3.69 (td, J=9.3, 4.2 Hz, 1H), 2.33-2.25 (m, 2H), 1.94-1.78 (m, 3H), 1.49 (d, J=20.6 Hz, 3H), 1.44 (s, 3H).

Preparation 63D: 4-[[4-iodo-6-(morpholin-4-yl)pyridin-2-yl]amino]-4-methylcyclohexan-1-ol

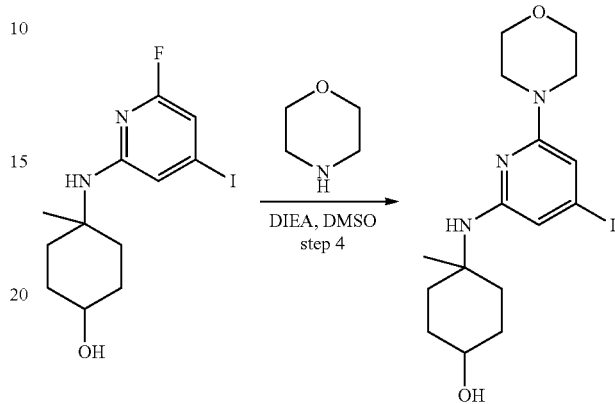

To a solution of 4-[(6-fluoro-4-iodopyridin-2-yl)amino]-4-methylcyclohexan-1-ol (130 mg, 0.371 mmol) and morpholine (48 mg, 0.557 mmol) in DMSO (5 mL) was added DIEA (96 mg, 0.742 mmol) at room temperature. The mixture was stirred at 110° C. for 16 h. The resulting solution was purified by Prep-HPLC with the following conditions (Column: XBridge Shield RP18 OBD Column, 30*150 mm, 5 um; Mobile Phase A: water (10 mmol/L NH₄HCO₃), Mobile Phase B: CH₃CN; Flow rate: 60 mL/min; Gradient:35 B to 75 B in 25 min) to afford 4-[[4-iodo-6-(morpholin-4-yl)pyridin-2-yl]amino]-4-methylcyclohexan-1-ol (80 mg, 52%) as a light yellow solid. MS ESI calculated for C₁₆H₂₄IN₃O₂ [M+H]⁺, 418.09, found 418.00. ¹H NMR (400 MHz, chloroform-d) δ 6.60-6.44 (m, 1H), 6.32 (dd, J=9.8, 1.2 Hz, 1H), 3.85 (q, J=3.9, 2.7 Hz, 5H), 3.54 (dd, J=5.7, 3.8 Hz, 4H), 2.18 (d, J=13.6 Hz, 1H), 1.99-1.76 (m, 3H), 1.70-1.44 (m, 2H), 1.42 (s, 3H), 1.32-1.30 (m, 2H).

Examples 63 and 64: (S)—N-(3-(2-(((1S,4R)-4-hydroxy-1-methylcyclohexyl)amino)-6-morpholinopyridin-4-yl)-4-methylphenyl)-3-(2,2,2-trifluoroethyl)pyrrolidine-1-carboxamide, (S)—N-(3-(2-(((1R,4S)-4-hydroxy-1-methylcyclohexyl)amino)-6-morpholinopyridin-4-yl)-4-methylphenyl)-3-(2,2,2-trifluoroethyl)pyrrolidine-1-carboxamide

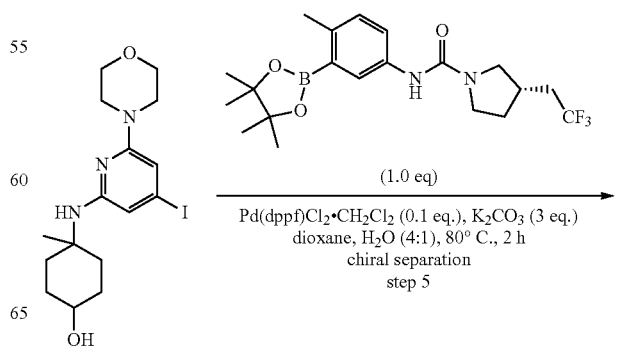

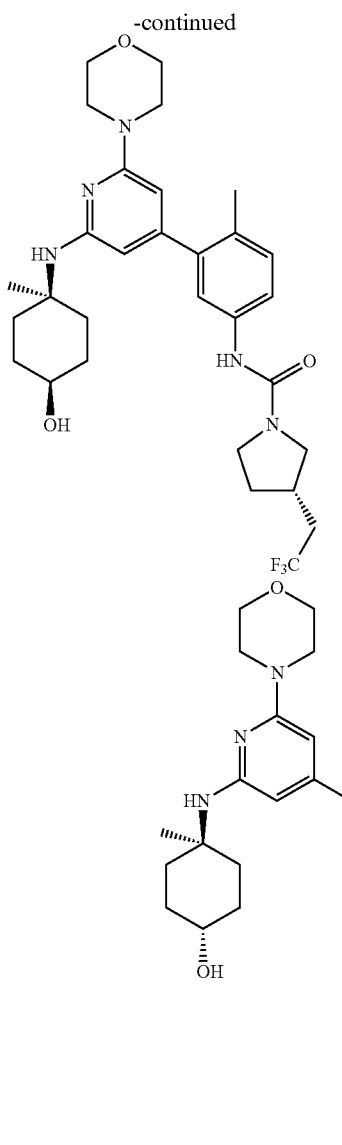

3.84-3.75 (m, 6H), 3.63 (ddd, J=10.5, 8.4, 2.3 Hz, 1H), 3.44 (h, J=6.5 Hz, 5H), 3.18-3.09 (m, 1H), 2.55 (s, 1H), 2.47-2.32 (m, 2H), 2.23 (s, 4H), 2.05 (t, J=9.4 Hz, 2H), 1.97-1.67 (m, 5H), 1.54 (q, J=8.4, 7.1 Hz, 2H), 1.49 (s, 3H). $^{19}F$ NMR (376 MHz, chloroform-d) δ −66.49 (3F). The second peak afforded 33 mg (18%) as a white solid. MS ESI calculated for $C_{30}H_{40}F_3N_5O_3$ [M+H]$^+$, 576.31, found 576.15. $^1H$ NMR (400 MHz, methanol-$d_4$) δ 7.31-7.25 (m, 2H), 7.15 (d, J=9.0 Hz, 1H), 5.93 (s, 1H), 5.84 (s, 1H), 3.84-3.75 (m, 5H), 3.68-3.53 (m, 2H), 3.49-3.38 (m, 5H), 3.13 (t, J=9.7 Hz, 1H), 2.65-2.30 (m, 5H), 2.24 (s, 4H), 1.97-1.67 (m, 3H), 1.68-1.53 (m, 2H), 1.46 (s, 3H), 1.44-1.29 (m, 2H). $^{19}F$ NMR (376 MHz, chloroform-d) δ −66.48 (3F).

Example 65: (3S)—N-(3-[2-[(1,3-dihydroxypropan-2-yl)amino]-6-(morpholin-4-yl)pyridin-4-yl]-4-methylphenyl)-3-(2,2,2-trifluoroethyl)pyrrolidine-1-carboxamide

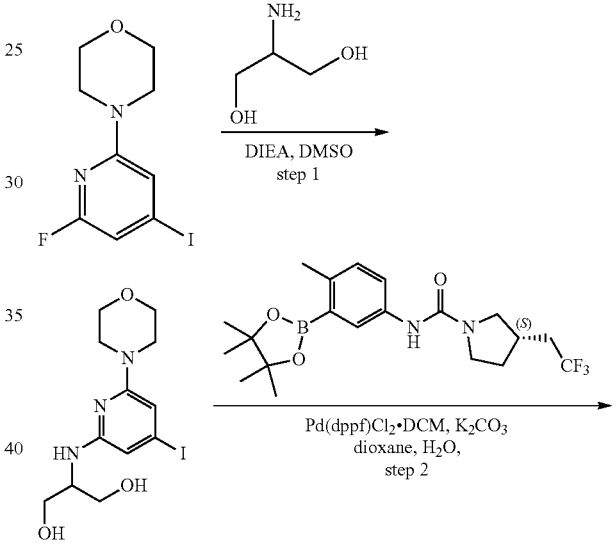

To a solution of 4-[[4-iodo-6-(morpholin-4-yl)pyridin-2-yl]amino]-4-methylcyclohexan-1-ol (130 mg, 0.312 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (128 mg, 0.312 mmol) in 1,4-dioxane (10 mL) and H₂O (1 mL) were added Pd(dppf)Cl₂·CH₂Cl₂ (25 mg, 0.031 mmol) and K₂CO₃ (129 mg, 0.935 mmol) at room temperature. The mixture was stirred at 80° C. for 2 h under nitrogen atmosphere. The resulting mixture was concentrated under vacuum. The crude product was purified by Prep-HPLC with the following conditions (Column: XBridge Shield RP18 OBD Column, 30*150 mm, 5 um; Mobile Phase A: water (10 mmoL/L NH₄HCO₃), Mobile Phase B: CH₃CN; Flow rate: 60 mL/min; Gradient:35 B to 75 B in 25 min;) to afford racemic (40 mg) as a white solid. The mixture (40 mg) was separated by Chiral-HPLC with the following conditions: Column: CHIRALPAK IH, 2.0*25 cm, 5 um; Mobile Phase A: MeOH (0.1% DEA), Mobile Phase B: CO₂; Flow rate: 50 mL/min; Gradient:50% B. The first peak afforded 8 mg (4%) as a white solid. MS ESI calculated for $C_{30}H_{40}F_3N_5O_3$ [M+H]$^+$, 576.31, found 576.15. $^1H$ NMR (400 MHz, methanol-$d_4$) δ 7.27 (dt, J=4.1, 2.4 Hz, 2H), 7.14 (d, J=8.9 Hz, 1H), 5.87 (d, J=16.9 Hz, 2H),

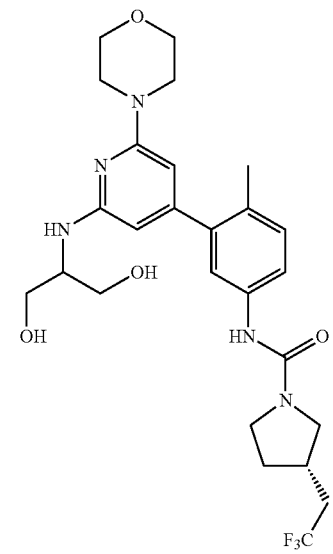

Preparation 65A: 2-((4-iodo-6-morpholinopyridin-2-yl)amino) propane-1,3-diol

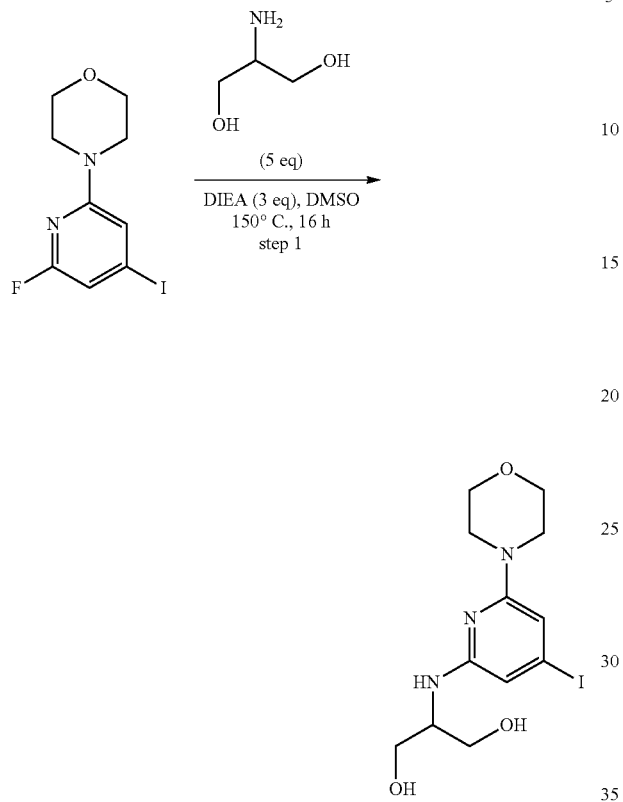

Example 65: (3S)—N-(3-[2-[(1,3-dihydroxypropan-2-yl)amino]-6-(morpholin-4-yl)pyridin-4-yl]-4-methylphenyl)-3-(2,2,2-trifluoroethyl)pyrrolidine-1-carboxamide

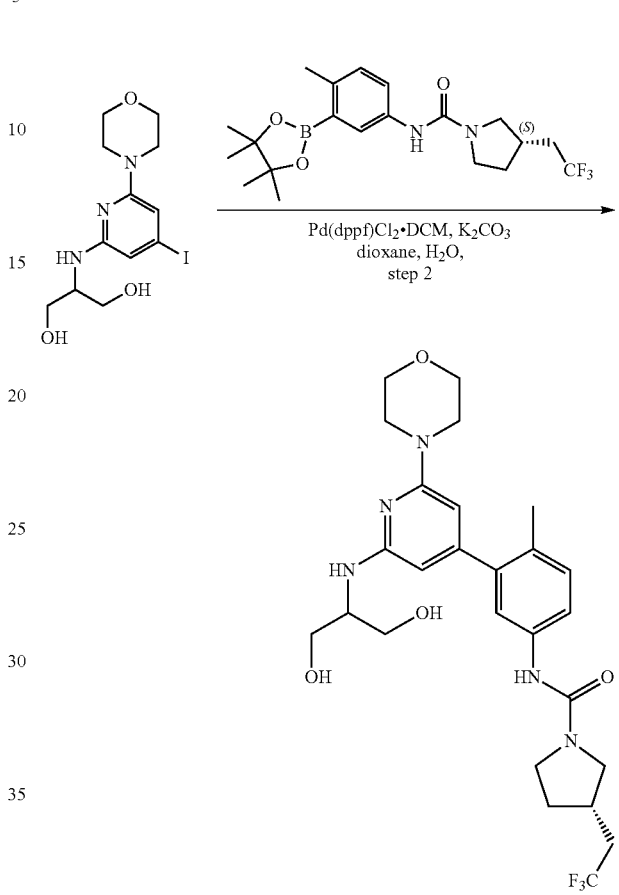

To a stirred mixture of 4-(6-fluoro-4-iodopyridin-2-yl) morpholine (300 mg, 0.974 mmol) and $K_2CO_3$ (404 mg, 2.921 mmol) in NMP (4 mL) was added 2-aminopropane-1,3-diol (443 mg, 4.869 mmol) at room temperature. The reaction mixture was stirred for 16 h at 150° C. The resulting mixture was diluted with water (50 mL). The resulting mixture was extracted with EtOAc (3×20 mL). The combined organic layers were washed with brine (3×50 mL), dried over anhydrous $Na_2SO_4$. After filtration, the filtrate was concentrated under reduced pressure. The residue was purified by reverse phase chromatography, eluted with 55% $CH_3CN$ in water (with 0.5% $NH_4HCO_3$). The fractions containing the desired product were collected and concentrated under reduced pressure to afford 2-((4-iodo-6-morpholinopyridin-2-yl)amino) propane-1,3-diol (110 mg, 25%) as a pink solid. MS ESI calculated for $C_{12}H_{18}IN_3O_3$ [M+H]$^+$, 380.04 found 380.05. $^1$H NMR (400 MHz, DMSO-$d_6$) δ 6.29 (d, J=1.0 Hz, 1H), 6.19 (d, J=1.0 Hz, 1H), 4.55 (t, J=5.5 Hz, 2H), 3.64 (t, J=4.9 Hz, 4H), 3.52-3.40 (m, 4H), 3.34 (d, J=4.9 Hz, 4H), 1.06 (t, J=7.0 Hz, 1H).

To a stirred mixture of 2-((4-iodo-6-morpholinopyridin-2-yl)amino) propane-1,3-diol (80 mg, 0.211 mmol), $K_2CO_3$ (87 mg, 0.633 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (104 mg, 0.253 mmol) in dioxane (2 mL) and $H_2O$ (0.5 mL) was added Pd(dppf)Cl$_2$·CH$_2$Cl$_2$ (17 mg, 0.021 mmol) at room temperature. The reaction mixture was stirred for 2 h at 80° C. under $N_2$ atmosphere. The resulting mixture was diluted with water (10 mL). The resulting mixture was extracted with EtOAc (3×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with 50% PE in EA. The fractions containing the desired product were collected and concentrated under reduced pressure. The crude was purified by reverse phase chromatography, eluted with 50% $CH_3CN$ in water (with 10 mmol/mL $NH_4HCO_3$). The fractions containing the desired product were collected and concentrated under reduced pressure to afford (3S)—N-(3-[2-[(1,3-dihydroxypropan-2-yl)amino]-6-(morpholin-4-yl)pyridin-4-yl]-4-methylphenyl)-3-(2,2,2-trifluoroethyl)pyrrolidine-1-carboxamide (105 mg, 98%) as an off-white solid. MS ESI calculated for $C_{26}H_{34}F_3N_5O_4$ [M+H]$^+$, 538.26 found 538.35. $^1$H NMR (400 MHz, DMSO-$d_6$) δ 8.11 (s, 1H), 7.41 (dd, J=8.3, 2.3 Hz, 1H), 7.34 (d, J=2.3 Hz, 1H), 7.09 (d, J=8.4 Hz, 1H), 5.86 (d, J=7.6 Hz, 1H), 5.81 (d, J=0.9 Hz, 1H), 5.76 (d, J=1.1 Hz, 1H), 4.58 (t, J=5.5 Hz, 2H), 3.82 (d, J=6.7 Hz, 1H), 3.67 (q, J=8.3, 6.4 Hz, 5H), 3.58-3.45 (m, 5H), 3.37 (d, J=9.6 Hz, 4H), 3.30 (d, J=10.0 Hz, 1H), 3.02 (t, J=9.4 Hz, 1H), 2.44 (t, J=10.7 Hz, 3H), 2.16 (s, 3H), 2.08 (d, J=3.7 Hz, 1H), 1.66 (p, J=9.9 Hz, 1H).

Example 66: (3S)—N-[3-[2-amino-6-(morpholin-4-yl)pyridin-4-yl]-4-methylphenyl]-3-(2,2,2-trifluoroethyl)pyrrolidine-1-carboxamide

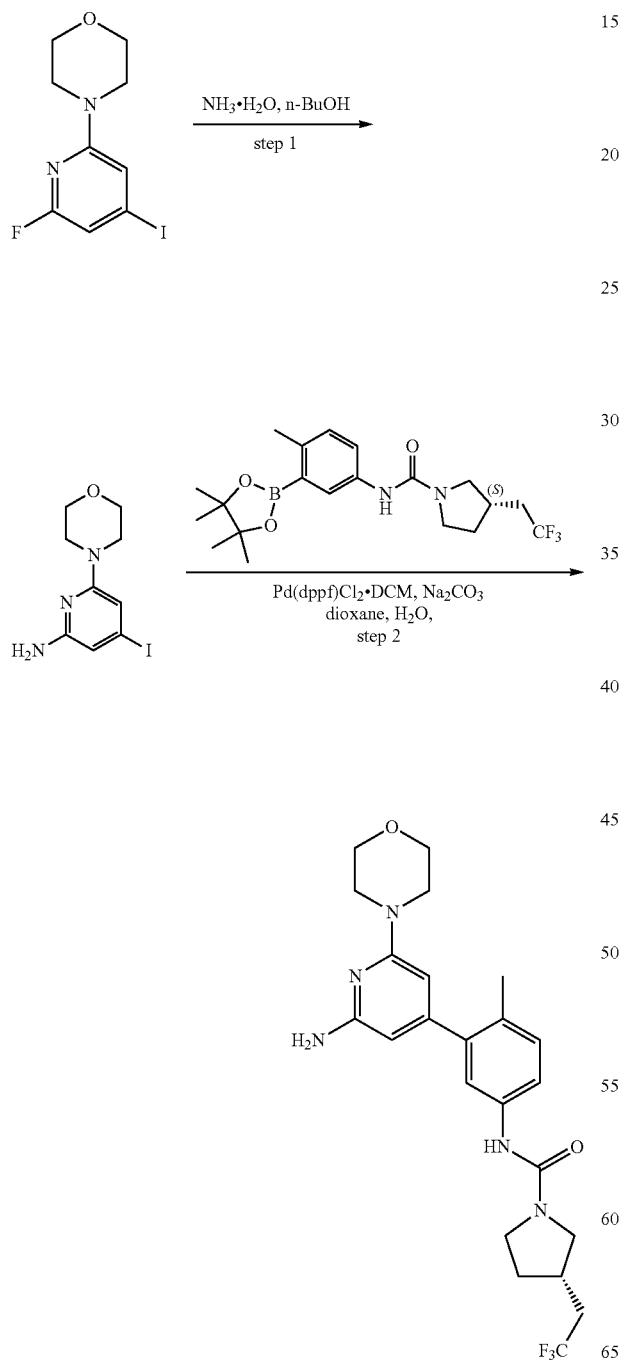

Preparation 66A: 4-iodo-6-(morpholin-4-yl)pyridin-2-amine

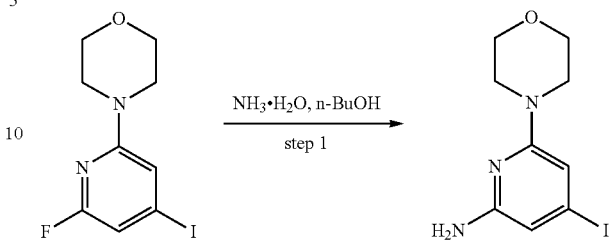

A solution of 4-(6-fluoro-4-iodopyridin-2-yl)morpholine (2.00 g, 6.492 mmol) and NH₄OH (140 mL) in n-BuOH (20 mL) was stirred for 16 h at 120° C. The mixture was allowed to cool down to room temperature. The resulting mixture was extracted with EtOAc (3×50 mL). The combined organic layers were washed with brine (3×50 mL), dried over anhydrous Na₂SO₄. After filtration, the filtrate was concentrated under reduced pressure. The residue was purified by silica gel column chromatography, eluted with PE/EtOAc (1/1) to afford 4-iodo-6-(morpholin-4-yl)pyridin-2-amine (0.70 g, 35%) as a light yellow oil. MS ESI calculated for C₉H₁₂IN₃O [M+H]⁺, 306.00, found 305.95. ¹H NMR (300 MHz, chloroform-d) δ 6.32 (dd, J=15.3, 1.0 Hz, 2H), 4.21 (s, 2H), 3.82-3.73 (m, 4H), 3.48-3.39 (m, 4H).

Example 66: (3S)—N-[3-[2-amino-6-(morpholin-4-yl)pyridin-4-yl]-4-methylphenyl]-3-(2,2,2-trifluoroethyl)pyrrolidine-1-carboxamide

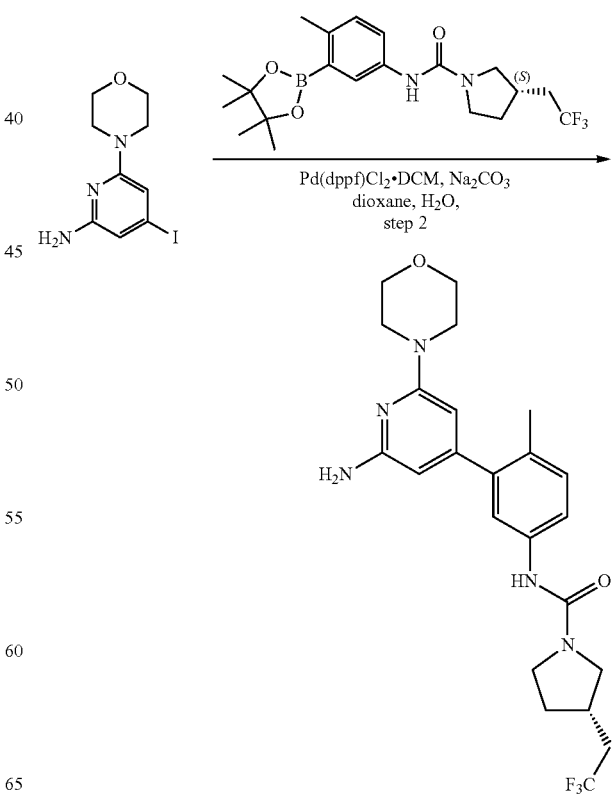

To a stirred solution of 4-iodo-6-(morpholin-4-yl)pyridin-2-amine (100 mg, 0.328 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (135 mg, 0.328 mmol) in 1,4-dioxane (1 mL) and H$_2$O (0.2 mL) were added Na$_2$CO$_3$ (104 mg, 0.983 mmol) and Pd(dppf)Cl$_2$·CH$_2$Cl$_2$ (27 mg, 0.033 mmol) at room temperature. The resulting mixture was stirred for 2 h at 80° C. under nitrogen atmosphere. The mixture was allowed to cool down to room temperature. The reaction was quenched by the addition of water (50 mL) at room temperature. The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with PE/EtOAc (1/1) to afford (3S)—N-[3-[2-amino-6-(morpholin-4-yl)pyridin-4-yl]-4-methylphenyl]-3-(2,2,2-trifluoroethyl)pyrrolidine-1-carboxamide (73 mg, 48%) as a light yellow solid. MS ESI calculated for C$_{23}$H$_{28}$F$_3$N$_5$O$_2$ [M+H]$^+$, 464.22, found 464.10. $^1$H NMR (400 MHz, DMSO-d$_6$) δ 8.11 (s, 1H), 7.42 (dd, J=8.3, 2.4 Hz, 1H), 7.34 (d, J=2.4 Hz, 1H), 7.09 (d, J=8.4 Hz, 1H), 5.77 (dd, J=17.6, 1.0 Hz, 2H), 5.64 (s, 2H), 3.71-3.63 (m, 5H), 3.55-3.49 (m, 1H), 3.41-3.35 (m, 3H), 3.32-3.26 (m, 2H), 3.02 (t, J=9.4 Hz, 1H), 2.51-2.36 (m, 3H), 2.16 (s, 3H), 2.08 (d, J=10.6 Hz, 1H), 1.67 (q, J=10.4, 10.0 Hz, 1H). $^{19}$F NMR (376 MHz, DMSO-d$_6$) δ −63.37 (3F).

Example 67: (3S)—N-[4-methyl-3-[2-(methylamino)-6-(morpholin-4-yl)pyridin-4-yl]phenyl]-3-(2,2,2-trifluoroethyl)pyrrolidine-1-carboxamide

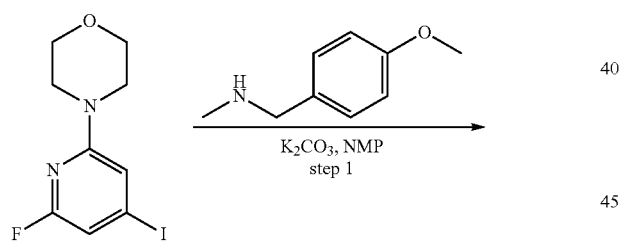

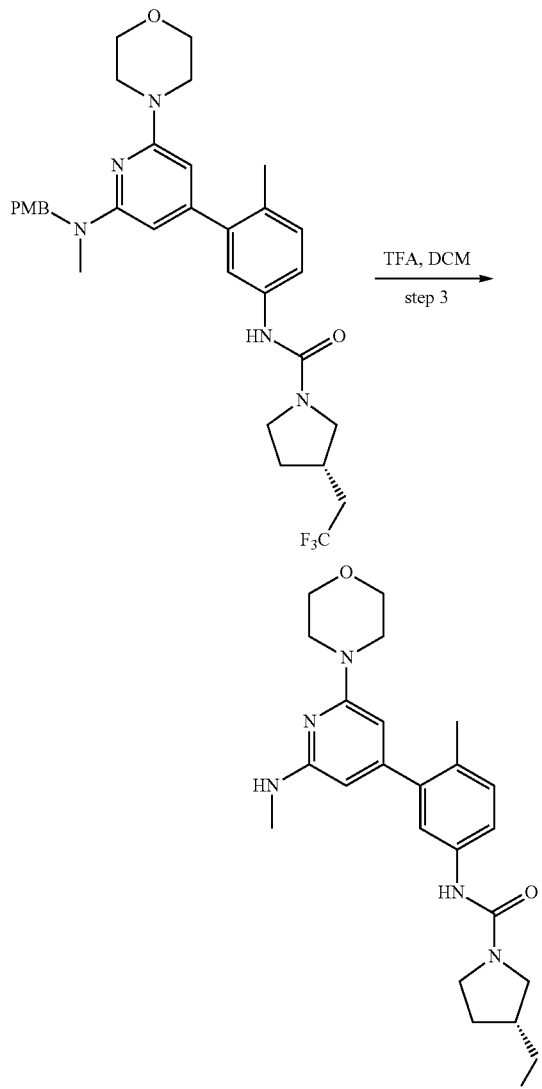

Preparation 67A: 4-iodo-N-[(4-methoxyphenyl)methyl]-N-methyl-6-(morpholin-4-yl)pyridin-2-amine

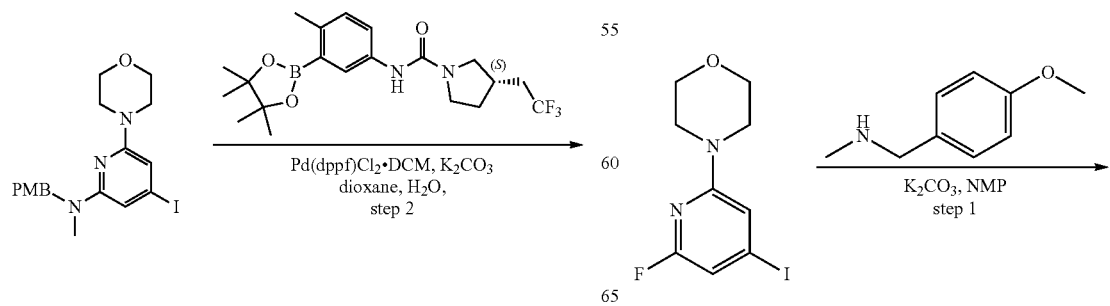

-continued

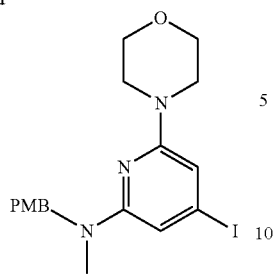

To a stirred mixture of 4-(6-fluoro-4-iodopyridin-2-yl)morpholine (320 mg, 0.974 mmol) and [(4-methoxyphenyl)methyl](methyl)amine (740 mg, 4.869 mmol) in NMP (3 mL) was added $K_2CO_3$ (670 mg, 4.869 mmol) in portions at room temperature. The resulting mixture was stirred for 16 h at 150° C. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EtOAc (5/1) to afford 4-iodo-N-[(4-methoxyphenyl)methyl]-N-methyl-6-(morpholin-4-yl)pyridin-2-amine (170 mg, 39%) as a yellow solid. MS ESI calculated for $C18H_{22}IN_3O_2$ [M+H]+, 440.08 found 440.05. $^1$H NMR (300 MHz, methanol-$d_4$) δ 7.16 (d, J=8.5 Hz, 2H), 6.86 (d, J=8.5 Hz, 2H), 6.35 (s, 1H), 4.70 (s, 2H), 3.81 (d, J=5.0 Hz, 7H), 3.46 (t, J=4.9 Hz, 3H), 2.96 (s, 3H).

Preparation 67B: (3S)—N-[3-(2-[[(4-methoxyphenyl)methyl](methyl)amino]-6-(morpholin-4-yl)pyridin-4-yl)-4-methylphenyl]-3-(2,2,2-trifluoroethyl)pyrrolidine-1-carboxamide To a stirred mixture of 4-iodo-N-[(4-methoxyphenyl)methyl]-N-methyl-6-(morpholin-4-yl)pyridin-2-amine (170 mg, 0.387 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (160 mg, 0.387 mmol) and $K_2CO_3$ (160 mg, 1.161 mmol) in dioxane (1.6 mL) and $H_2O$ (0.4 mL) was added Pd(dppf)$Cl_2$·$CH_2Cl_2$ (31 mg, 0.039 mmol) The resulting mixture was stirred for 2 h at 80° C. under nitrogen atmosphere. The resulting mixture was concentrated under reduced pressure. The residue was purified by Prep-TLC (PE/EtOAc=1/1) to afford (3S)—N-[3-(2-[[(4-methoxyphenyl)methyl](methyl)amino]-6-(morpholin-4-yl)pyridin-4-yl)-4-methylphenyl]-3-(2,2,2-trifluoroethyl)pyrrolidine-1-carboxamide (240 mg, 93%) as a light yellow solid. MS ESI calculated for $C_{32}H_{38}F_3N_5O_3$ [M+H]+, 598.29 found 598.30. $^1$H NMR (400 MHz, chloroform-d) δ 7.37 (d, J=8.3 Hz, 1H), 7.19 (dd, J=15.4, 8.2 Hz, 3H), 6.87 (d, J=8.5 Hz, 2H), 6.10 (s, 1H), 5.97 (s, 1H), 4.77 (s, 2H), 3.84 (d, J=19.9 Hz, 7H), 3.64 (t, J=8.9 Hz, 1H), 3.57-3.40 (m, 4H), 3.06 (s, 2H), 2.28 (t, J=9.5 Hz, 3H), 1.81-1.73 (m, 1H).

Example 67: (3S)—N-[4-methyl-3-[2-(methylamino)-6-(morpholin-4-yl)pyridin-4-yl]phenyl]-3-(2,2,2-trifluoroethyl)pyrrolidine-1-carboxamide

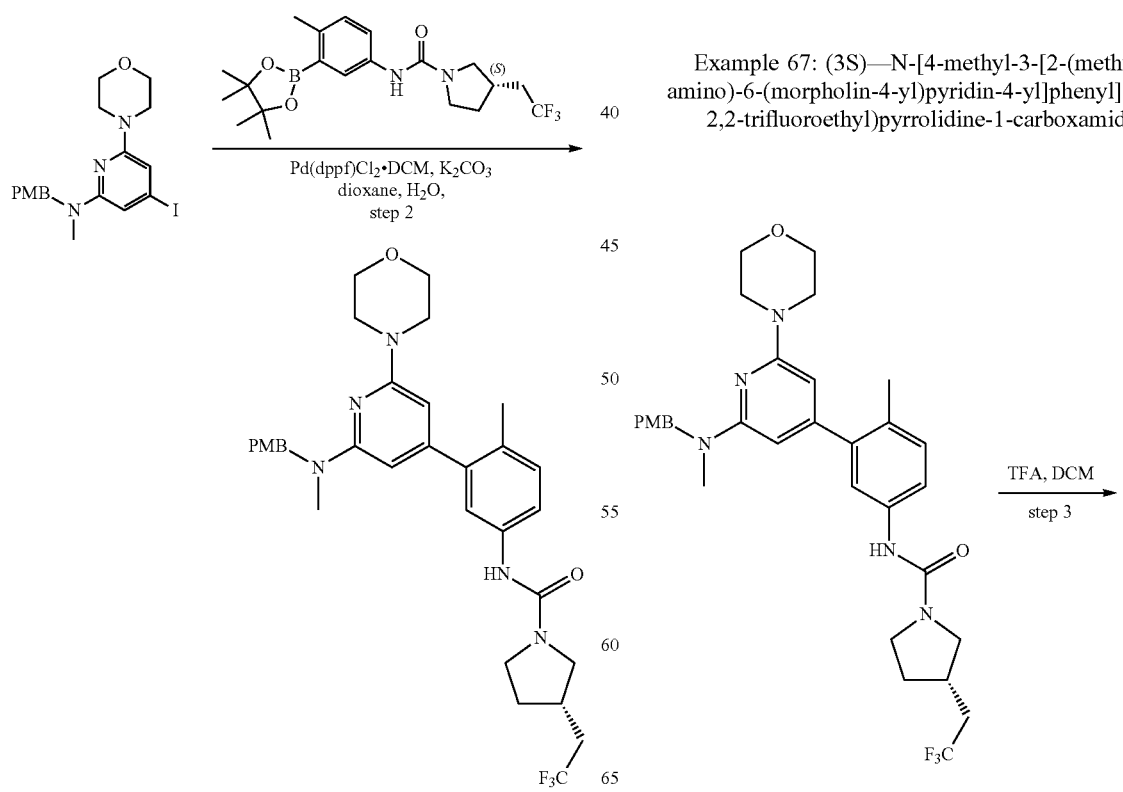

-continued

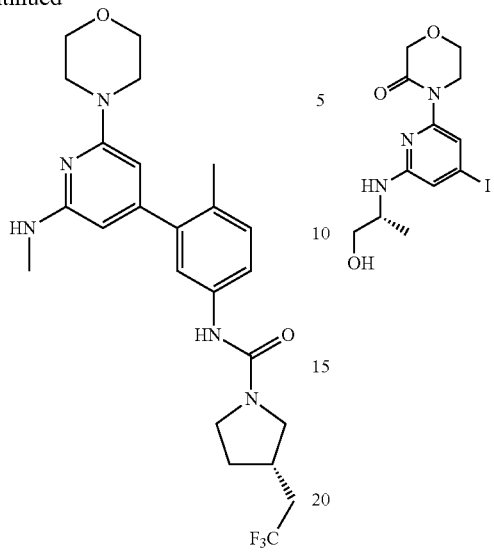

A mixture of (3S)—N-[3-(2-[[(4-methoxyphenyl)methyl](methyl)amino]-6-(morpholin-4-yl)pyridin-4-yl)-4-methylphenyl]-3-(2,2,2-trifluoroethyl)pyrrolidine-1-carboxamide (190 mg, 0.318 mmol) and TFA (1.5 mL) in DCM (1.5 mL) was stirred for 16 h at room temperature. The resulting mixture was concentrated under reduced pressure. The residue was purified by silica gel column chromatography, eluted with PE/EtOAc (1/1) to afford (3S)—N-[4-methyl-3-[2-(methylamino)-6-(morpholin-4-yl)pyridin-4-yl]phenyl]-3-(2,2,2-trifluoroethyl)pyrrolidine-1-carboxamide (90 mg, 59%) as an off-white solid. MS ESI calculated for $C_{24}H_{30}F_3N_5O_2$ [M+H]$^+$, 478.24, found 478.05. $^1$H NMR (300 MHz, methanol-$d_4$) δ 7.34-7.25 (m, 2H), 7.15 (d, J=8.6 Hz, 1H), 5.89 (d, J=1.3 Hz, 1H), 5.82 (d, J=1.2 Hz, 1H), 3.84-3.75 (m, 5H), 3.64 (t, J=9.8 Hz, 1H), 3.50-3.39 (m, 5H), 3.20-3.07 (m, 1H), 2.91-2.84 (m, 3H), 2.55 (s, 1H), 2.48-2.29 (m, 2H), 2.23 (s, 4H), 1.77 (p, J=10.9, 10.2 Hz, 1H). $^{19}$F NMR (376 MHz, methanol-$d_4$) δ −63.36 (3F).

Example 68: (3S)—N-[3-(2-[[(2R)-1-hydroxypropan-2-yl]amino]-6-(3-oxomorpholin-4-yl)pyridin-4-yl)-4-methylphenyl]-3-(2,2,2-trifluoroethyl)pyrrolidine-1-carboxamide

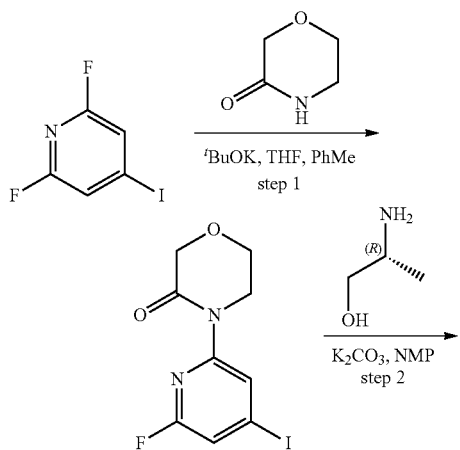

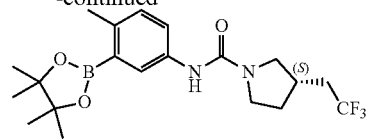

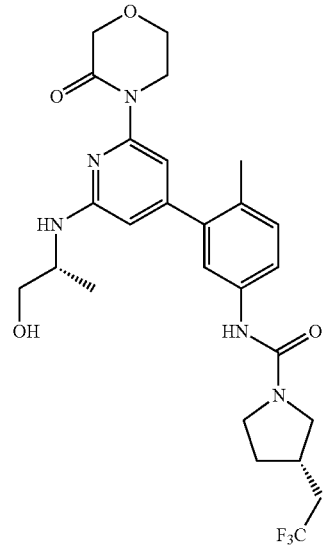

Preparation 68A: 4-(6-fluoro-4-iodopyridin-2-yl)morpholin-3-one

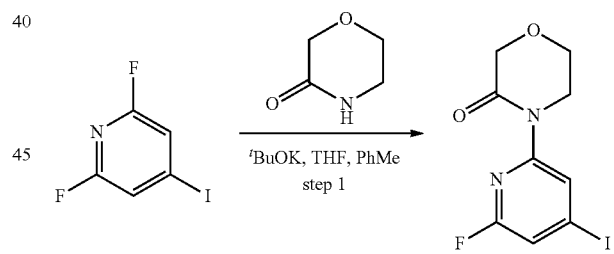

To a solution of morpholin-3-one (0.92 g, 9.13 mmol) in toluene (20 mL) was added t-BuOK in THF (8.3 mL, 8.30 mmol, 1 M) dropwise at 0° C. under nitrogen atmosphere. To the above mixture was added 2,6-difluoro-4-iodopyridine (2.00 g, 8.30 mmol) at room temperature. The resulting mixture was stirred for 5 h at 80° C. The reaction was quenched with water (20 mL) at 0° C. The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with hexane/EtOAc (1/1) to afford 4-(6-fluoro-4-iodopyridin-2-yl)morpholin-3-one (2.00 g, 74%) as a white solid. MS ESI calculated for $C_9H_8FIN_2O_2$ [M+H]$^+$, 322.96, found 323.00. $^1$H NMR (400 MHz, chloroform-d) δ 8.63 (t, J=1.2 Hz, 1H), 7.15 (dd, J=3.3, 1.0 Hz, 1H), 4.36 (s, 2H), 4.03 (s, 4H).

Preparation 68B: 4-(6-[[(2R)-1-hydroxypropan-2-yl]amino]-4-iodopyridin-2-yl) morpholin-3-one

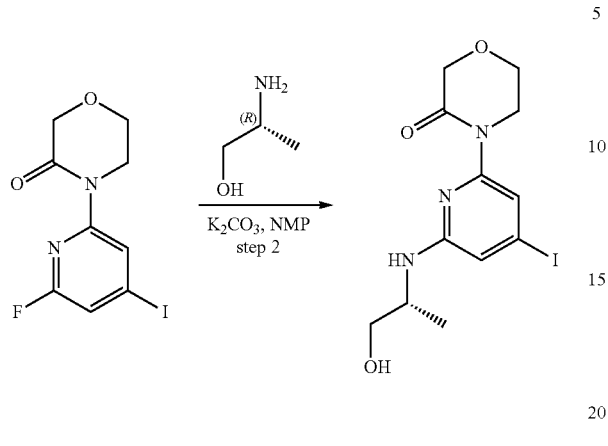

To a solution of 4-(6-fluoro-4-iodopyridin-2-yl) morpholin-3-one (1.00 g, 3.10 mmol) and (R)-(−)-2-amino-1-propanol (0.35 g, 4.66 mmol) in NMP (10 mL) was added K$_2$CO$_3$ (0.86 g, 6.21 mmol). The resulting mixture was stirred for 16 h at 100° C. The reaction was quenched by the addition of water (100 mL) at room temperature. The resulting mixture was extracted with EtOAc (3×60 mL). The combined organic layers were washed with brine (3×100 mL), dried over anhydrous Na$_2$SO$_4$. After filtration, the filtrate was concentrated under reduced pressure. The residue was purified by silica gel column chromatography, eluted with PE/EtOAc (1/1) to afford 4-(6-[[(2R)-1-hydroxypropan-2-yl]amino]-4-iodopyridin-2-yl) morpholin-3-one (0.40 g, crude) as a yellow oil. MS ESI calculated for C$_{12}$H$_{16}$IN$_3$O$_3$ [M+H]$^+$, 378.02; found 378.00.

Example 68: (3S)—N-[3-(2-[[(2R)-1-hydroxypropan-2-yl]amino]-6-(3-oxomorpholin-4-yl)pyridin-4-yl)-4-methylphenyl]-3-(2,2,2-trifluoroethyl)pyrrolidine-1-carboxamide

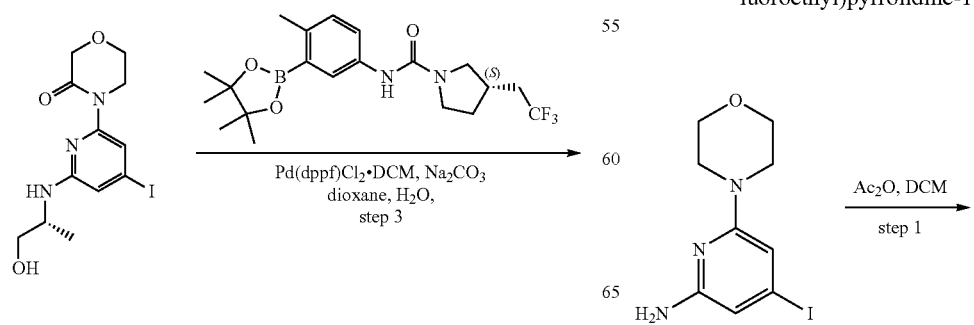

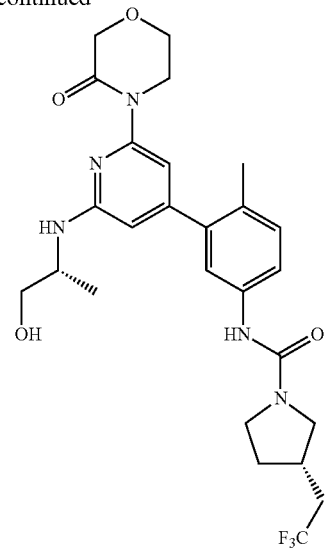

A mixture of 4-(6-[[(2R)-1-hydroxypropan-2-yl]amino]-4-iodopyridin-2-yl) morpholin-3-one (150 mg, 0.398 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (164 mg, 0.398 mmol), Pd(dppf)Cl$_2$·CH$_2$Cl$_2$ (32 mg, 0.040 mmol), Na$_2$CO$_3$ (126 mg, 1.193 mmol), dioxane (2 mL) and H$_2$O (0.2 mL). The mixture was stirred for 2 h at 80° C. under nitrogen atmosphere. The reaction mixture was concentrated under reduced pressure. The residue was purified by reverse phase chromatography with the following conditions: (Column: Spherical C18, 20-40 um, 40 g; Mobile Phase A: Water (10 mmol/mL NH$_4$HCO$_3$), Mobile Phase B: CH$_3$CN; Flow rate: 40 mL/min; 30%~60% within 20 min). The collected fractions were combined and concentrated under reduced pressure to afford (3S)—N-[3-(2-[[(2R)-1-hydroxypropan-2-yl]amino]-6-(3-oxomorpholin-4-yl)pyridin-4-yl)-4-methylphenyl]-3-(2,2,2-trifluoroethyl)pyrrolidine-1-carboxamide (45 mg, 21%) as a white solid. MS ESI calculated for C$_{26}$H$_{32}$F$_3$N$_5$O$_4$ [M+H]$^+$, 536.25 found 536.24. $^1$H NMR (300 MHz, DMSO-d$_6$) δ 8.17 (s, 1H), 7.49-7.33 (m, 2H), 7.17-7.06 (m, 2H), 6.44 (d, J=7.6 Hz, 1H), 6.26 (d, J=1.2 Hz, 1H), 4.69 (t, J=5.6 Hz, 1H), 4.21 (s, 2H), 3.97 (s, 5H), 3.68 (dd, J=10.3, 6.7 Hz, 1H), 3.59-3.46 (m, 2H), 3.32-3.25 (m, 2H), 3.03 (t, J=9.3 Hz, 1H), 2.45 (q, J=9.5, 7.6 Hz, 3H), 2.18 (s, 4H), 1.73-1.56 (m, 1H), 1.16 (d, J=6.5 Hz, 3H). $^{19}$F NMR (276 MHz, DMSO-d$_6$) δ −63.37 (3F).

Example 69: (3S)—N-[3-[2-acetamido-6-(morpholin-4-yl)pyridin-4-yl]-4-methylphenyl]-3-(2,2,2-trifluoroethyl)pyrrolidine-1-carboxamide

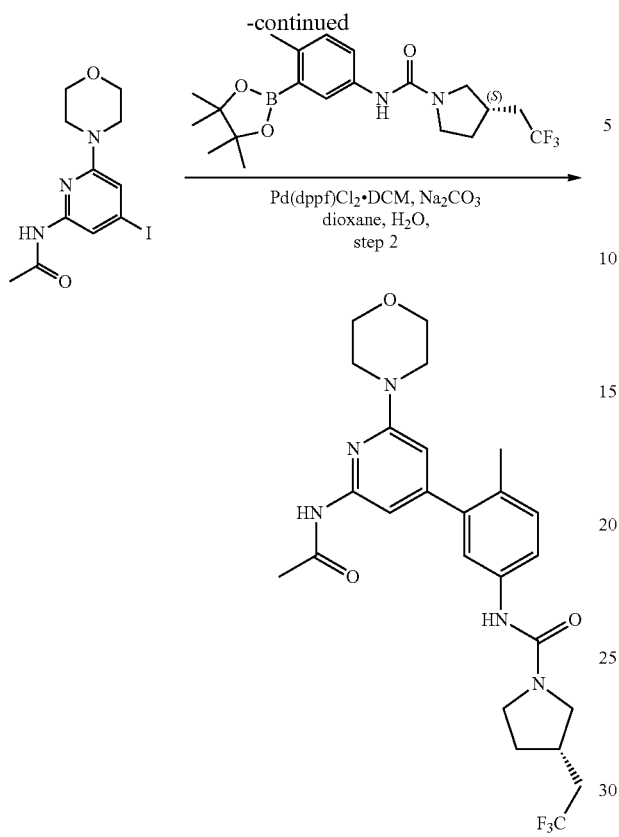

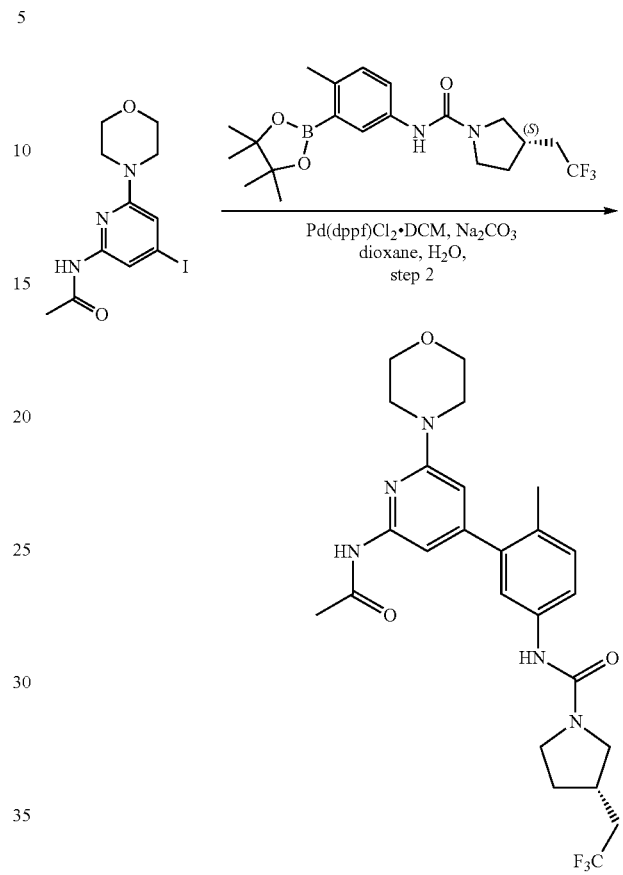

Example 69: (3S)—N-[3-[2-acetamido-6-(morpholin-4-yl)pyridin-4-yl]-4-methylphenyl]-3-(2,2,2-trifluoroethyl)pyrrolidine-1-carboxamide Preparation 69A: N-[4-iodo-6-(morpholin-4-yl)pyridin-2-yl]acetamide

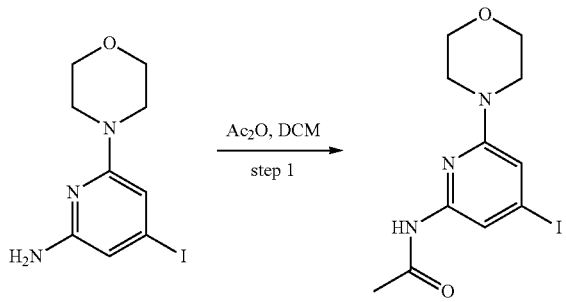 [SMILES: Nc1cc(I)cc(N2CCOCC2)n1 ; CC(=O)Nc1cc(I)cc(N2CCOCC2)n1]

To a stirred solution of 4-iodo-6-(morpholin-4-yl)pyridin-2-amine (200 mg, 0.655 mmol) in DCM (2 mL) was added 4-iodo-6-(morpholin-4-yl)pyridin-2-amine (200 mg, 0.655 mmol) at room temperature. The resulting mixture was stirred for 2 h at room temperature. The reaction was quenched by the addition of MeOH (1 mL) at room temperature. The resulting mixture was concentrated under reduced pressure. The residue was purified by silica gel column chromatography, eluted with PE/EtOAc (1/1 to 0/1) to afford N-[4-iodo-6-(morpholin-4-yl)pyridin-2-yl]acetamide (210 mg, 92%) as a white solid. MS ESI calculated for $C_{11}H_{14}IN_3O_2$ [M+H]$^+$, 348.01, found 348.00. $^1$H NMR (300 MHz, chloroform-d) δ 7.93 (s, 1H), 7.53 (s, 1H), 6.75 (d, J=1.1 Hz, 1H), 3.83-3.73 (m, 4H), 3.48-3.39 (m, 4H), 2.18 (s, 3H).

To a stirred solution of N-[4-iodo-6-(morpholin-4-yl)pyridin-2-yl]acetamide (200 mg, 0.576 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (237 mg, 0.576 mmol), 1,4-dioxane (2 mL) and H$_2$O (0.4 mL) were added Na$_2$CO$_3$ (183 mg, 1.728 mmol) and Pd(dppf)Cl$_2$·CH$_2$Cl$_2$ (47 mg, 0.058 mmol). The resulting mixture was stirred for 2 h at 80° C. under nitrogen atmosphere. The mixture was allowed to cool down to room temperature. The reaction was quenched by the addition of water (50 mL) at room temperature. The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with PE/EtOAc (1/2) to afford (3S)—N-[3-[2-acetamido-6-(morpholin-4-yl)pyridin-4-yl]-4-methylphenyl]-3-(2,2,2-trifluoroethyl)pyrrolidine-1-carboxamide (89 mg, 31%) as a light pink solid. MS ESI calculated for $C_{25}H_{30}F_3N_5O_3$ [M+H]$^+$, 506.23, found 506.10. $^1$H NMR (400 MHz, DMSO-d$_6$) δ 10.04 (s, 1H), 8.16 (s, 1H), 7.47 (dd, J=8.3, 2.4 Hz, 1H), 7.37 (d, J=2.4 Hz, 2H), 7.14 (d, J=8.4 Hz, 1H), 6.40 (d, J=1.1 Hz, 1H), 3.73-3.63 (m, 5H), 3.58-3.44 (m, 5H), 3.35-3.25 (m, 1H), 3.02 (t, J=9.5 Hz, 1H), 2.51-2.36 (m, 3H), 2.16 (s, 3H), 2.08 (s, 4H), 1.72-1.60 (m, 1H). $^{19}$F NMR (376 MHz, DMSO-d$_6$) δ −66.37 (3F).

Example 70: (S)—N-(3-(3-fluoro-2-(((R)-1-hydroxypropan-2-yl)amino)-6-morpholinopyridin-4-yl)-4-methylphenyl)-3-(2,2,2-trifluoroethyl)pyrrolidine-1-carboxamide

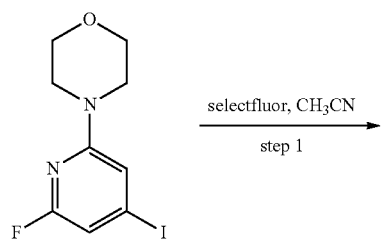

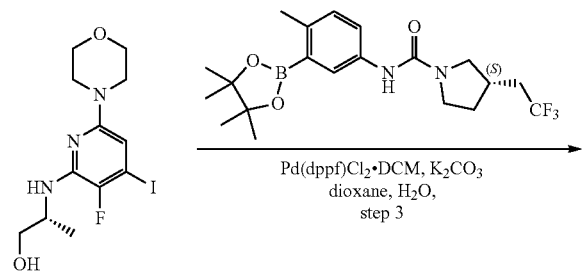

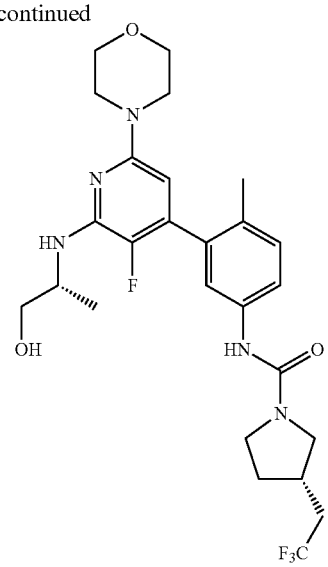

Preparation 70A: 4-(5,6-difluoro-4-iodopyridin-2-yl)morpholine and 4-(3,6-difluoro-4-iodopyridin-2-yl)morpholine

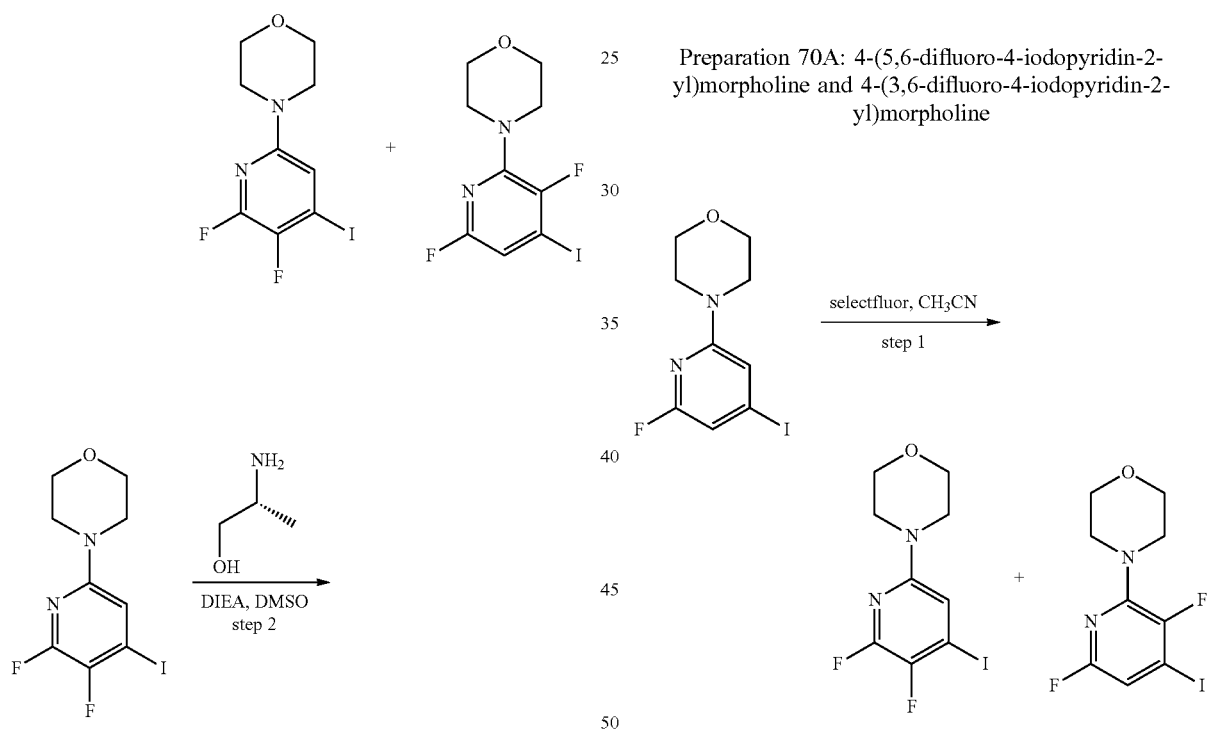

To a solution of 4-(6-fluoro-4-iodopyridin-2-yl)morpholine (6.00 g, 19.475 mmol) in MeCN (240 mL) was added selectfluor (6.9 g, 19.475 mmol) in portions at room atmosphere. The mixture was stirred for 16 h at room atmosphere. The resulting mixture was quenched with water (300 mL), and extracted with EtOAc (3×500 mL). The combined organic layers were washed with brine (2×150 mL), dried over anhydrous $Na_2SO_4$ and concentrated under reduced pressure. The residue was purified by silica gel column chromatography, eluted with EtOAc in PE (0~90%) to afford 4-(5,6-difluoro-4-iodopyridin-2-yl)morpholine (700 mg, 11%) as a white solid. MS ESI calculated for $C_9H_9F_2IN_2O$ [M+H]$^+$, 326.97, found 326.90. $^1$H NMR (400 MHz, Chloroform-d) δ 6.75 (t, J=1.8 Hz, 1H), 3.84-3.76 (m, 4H), 3.43 (dd, J=5.8, 4.1 Hz, 4H). Also afforded 4-(3,6-difluoro-4-iodopyridin-2-yl)morpholine (3.2 g, 50%) as a white solid.

MS ESI calculated for $C_9H_9F_2IN_2O$ [M+H]$^+$, 326.97, found 326.95. $^1$H NMR (400 MHz, Chloroform-d) δ 6.68 (dd, J=4.2, 2.3 Hz, 1H), 3.82-3.80 (m, 4H), 3.59-3.56 (m, 4H).

Preparation 70B: (R)-2-((3-fluoro-4-iodo-6-morpholinopyridin-2-yl)amino) propan-1-ol

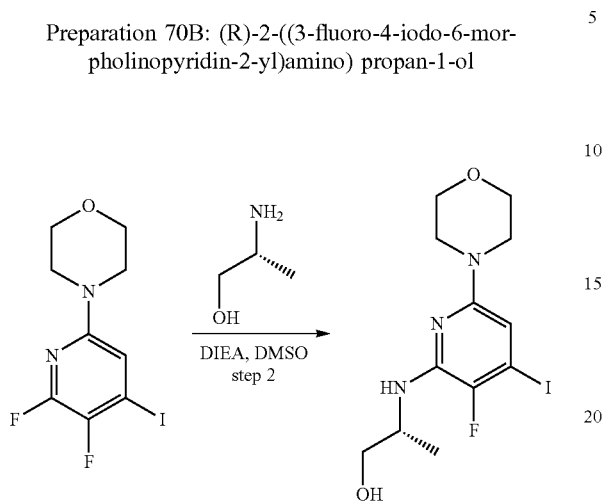

A mixture of 4-(5,6-difluoro-4-iodopyridin-2-yl)morpholine (300 mg, 0.920 mmol), (R)-(−)-2-amino-1-propanol (138 mg, 1.840 mmol) and $K_2CO_3$ (254 mg, 1.840 mmol) in NMP (5 mL) at room temperature, the mixture was stirred at 70° C. for 16 h. The mixture was allowed to cool down to room temperature. The reaction was quenched with water (50 mL) at room temperature. The resulting mixture was extracted with EtOAc (50 mL). The combined organic layers were washed with brine (3×50 mL), dried over anhydrous $Na_2SO_4$. After filtration, the filtrate was concentrated under reduced pressure. The residue was purified by Prep-TLC (PE/EtOAc/EtOH=12/3/1) to afford (2R)-2-[[3-fluoro-4-iodo-6-(morpholin-4-yl)pyridin-2-yl]amino]propan-1-ol (224 mg, 64%) as a yellow oil. MS ESI calculated for $C_{12}H_{17}FIN_3O_2$ [M+H]$^+$, 382.03, found 381.95. $^1$H NMR (400 MHz, chloroform-d) δ 6.17 (d, J=2.4 Hz, 1H), 4.28-4.20 (m, 1H), 3.84-3.80 (m, 4H), 3.80-3.75 (m, 1H), 3.62 (dd, J=10.7, 7.0 Hz, 1H), 3.37 (dd, J=5.9, 3.9 Hz, 4H), 1.31-1.28 (m, 3H).

Example 70: (S)—N-(3-(3-fluoro-2-(((R)-1-hydroxypropan-2-yl)amino)-6-morpholinopyridin-4-yl)-4-methylphenyl)-3-(2,2,2-trifluoroethyl)pyrrolidine-1-carboxamide

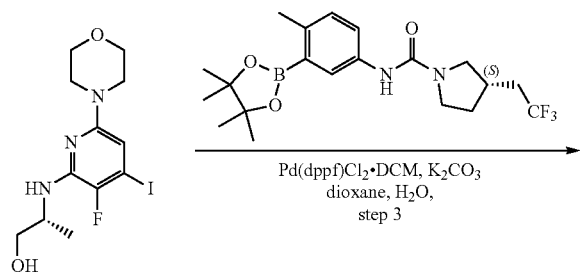

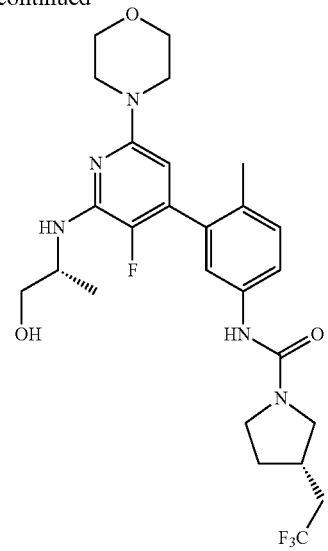

A mixture of (2R)-2-[[3-fluoro-4-iodo-6-(morpholin-4-yl)pyridin-2-yl]amino]propan-1-ol (200 mg, 0.525 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (238 mg, 0.577 mmol), Pd(dppf)Cl$_2$·CH$_2$Cl$_2$ (43 mg, 0.052 mmol) and K$_2$CO$_3$ (217 mg, 1.574 mmol) in dioxane (8 mL) and H$_2$O (2 mL) stirred at 80° C. for 2 h. The mixture was allowed to cool down to room temperature. The resulting mixture was concentrated under reduced pressure. The mixture was purified by Prep-TLC (PE/EtOAc/EtOH=4:3:1) followed by reverse flash chromatography with the following Column: C18 Column 120 g; Mobile Phase A: water (10 mmoL NH$_4$HCO$_3$), Mobile Phase B: CH$_3$CN; Flow rate: 60 mL/min; Gradient:40% to 65% B in 30 min; 254/220 nm. The fractions containing the desired product was collected at 55% B and concentrated under reduced pressure to afford (3S)—N-[3-(3-fluoro-2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide (128 mg, 45%) as a white solid. MS ESI calculated for $C_{26}H_{33}F_4N_5O_3$ [M+H]$^+$, 540.58, found 540.30. $^1$H NMR (400 MHz, DMSO-d$_6$) δ 8.15 (s, 1H), 7.45 (dd, J=8.3, 2.4 Hz, 1H), 7.37 (d, J=2.3 Hz, 1H), 7.14 (d, J=8.4 Hz, 1H), 5.89 (dd, J=7.7, 1.8 Hz, 1H), 5.63 (d, J=3.0 Hz, 1H), 4.67 (t, J=5.7 Hz, 1H), 4.07 (p, J=6.4 Hz, 1H), 3.71-3.66 (m, 4H), 3.64 (s, 1H), 3.57-3.46 (m, 2H), 3.41-3.35 (m, 1H), 3.32-3.23 (m, 4H), 3.02 (t, J=9.4 Hz, 1H), 2.50-2.35 (m, 4H), 2.09 (s, 4H), 1.66 (p, J=9.9 Hz, 1H), 1.16 (d, J=6.6 Hz, 3H). $^{19}$F NMR (376 MHz, DMSO-d$_6$) δ −63.37 (3F), −158.76 (1F).

Example 71: (3S)—N-[3-(3-fluoro-6-[[(2R)-1-hydroxypropan-2-yl]amino]-2-(morpholin-4-yl)pyridin-4-yl)-4-methylphenyl]-3-(2,2,2-trifluoroethyl)pyrrolidine-1-carboxamide

Preparation 71A: (2R)-2-[[5-fluoro-4-iodo-6-(morpholin-4-yl)pyridin-2-yl]amino]propan-1-ol

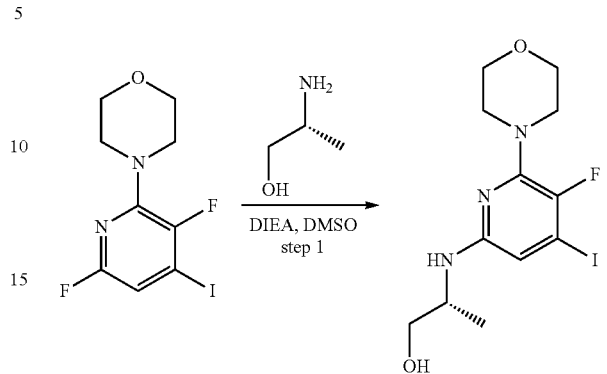

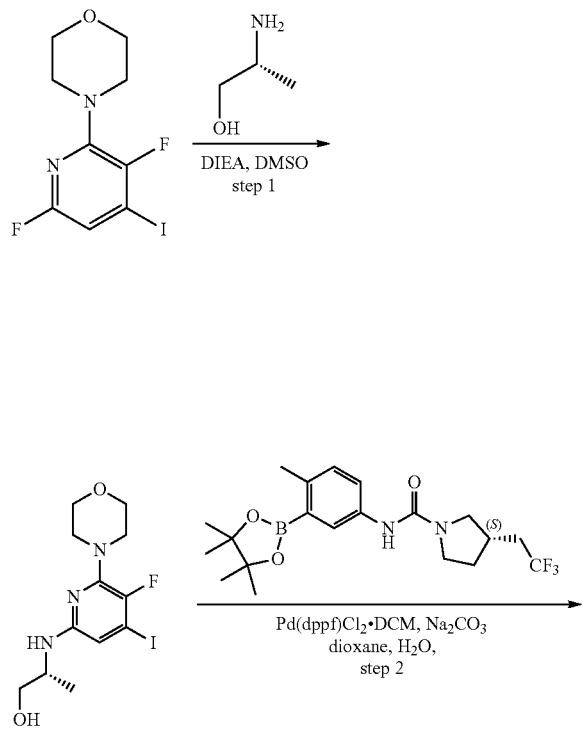

To a stirred solution of 4-(3,6-difluoro-4-iodopyridin-2-yl)morpholine (900 mg, 2.760 mmol) and (R)-(−)-2-amino-1-propanol (829 mg, 11.040 mmol) in NMP (15 mL) were added $K_2CO_3$ (763 mg, 5.520 mmol) at room temperature. The resulting mixture was stirred for 16 h at 150° C. The mixture was allowed to cool down to room temperature. The resulting mixture was extracted with EtOAc (3×50 mL). The combined organic layers were washed with water (3×100 mL), dried over anhydrous $Na_2SO_4$. After filtration, the filtrate was concentrated under reduced pressure. The residue was purified by reverse phase flash chromatography with the following conditions: Column: Spherical C18, 20-40 um, 330 g; Mobile Phase A: water (10 mM $NH_4HCO_3$); Mobile Phase B: acetonitrile; Flow rate: 80 mL/min; Gradient:50%-65% B in 20 min; Detector: 254 nm. The fractions containing desired product were collected at 55% B and concentrated under reduced pressure to afford (2R)-2-[[5-fluoro-4-iodo-6-(morpholin-4-yl)pyridin-2-yl]amino]propan-1-ol (175 mg, 16%) as a light yellow solid. MS ESI calculated for $C_{12}H_{16}FIN_2O_3$ $[M+H]^+$, 382.04; found 381.95. $^1$H NMR (300 MHz, chloroform-d) δ 6.27 (d, 1H), 4.11 (s, 1H), 3.90 (s, 1H), 3.85-3.75 (m, 4H), 3.54 (m, 1H), 3.47-3.39 (m, 3H), 1.21 (d, 3H). $^{19}$F NMR (376 MHz, chloroform-d) δ−127.54.

Example 71: (3S)—N-[3-(3-fluoro-6-[[(2R)-1-hydroxypropan-2-yl]amino]-2-(morpholin-4-yl)pyridin-4-yl)-4-methylphenyl]-3-(2,2,2-trifluoroethyl)pyrrolidine-1-carboxamide

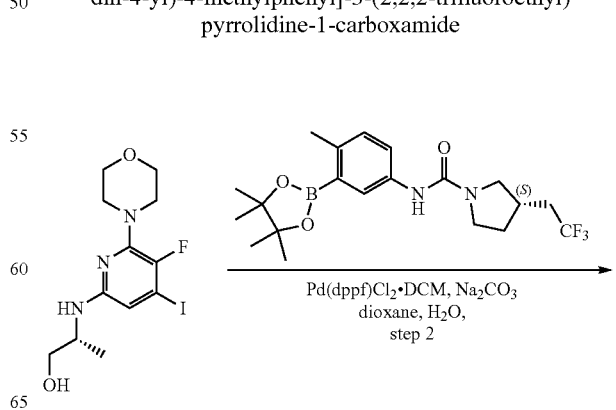

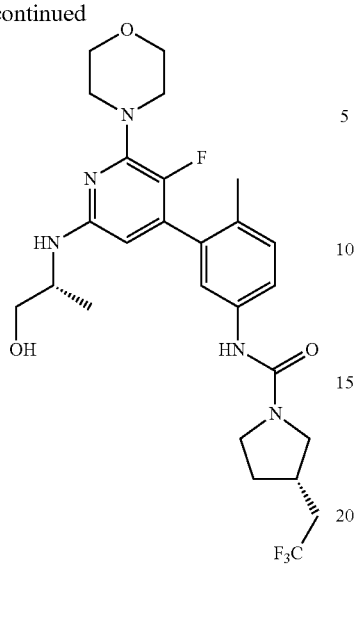

To a stirred mixture of (2R)-2-[[5-fluoro-4-iodo-6-(morpholin-4-yl)pyridin-2-yl]amino]propan-1-ol (230 mg, 0.603 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (298 mg, 0.724 mmol), Na$_2$CO$_3$ (191 mg, 1.810 mmol) in dioxane (4 mL), H$_2$O (1 mL) was added Pd(dppf)Cl$_2$·CH$_2$Cl$_2$ (49 mg, 0.060 mmol). The resulting mixture was stirred for 16 h at 100° C. under nitrogen atmosphere. The resulting mixture was quenched with water (20 mL), and extracted with EtOAc (3×100 mL). The combined organic layers were washed with brine (3×50 mL), dried over anhydrous Na$_2$SO$_4$ and concentrated under reduced pressure. The residue was purified by silica gel column chromatography, eluted with 0% to 50% EtOAc in PE to afford (3S)—N-[3-(3-fluoro-6-[[(2R)-1-hydroxypropan-2-yl]amino]-2-(morpholin-4-yl)pyridin-4-yl)-4-methylphenyl]-3-(2,2,2-trifluoroethyl)pyrrolidine-1-carboxamide (84 mg, 25%) as a yellow solid. MS ESI calculated for C$_{26}$H$_{33}$F$_4$N$_5$O$_3$ [M+H]$^+$, 540.26; found 540.25. $^1$H NMR (300 MHz, DMSO-d$_6$) δ 8.15 (s, 1H), 7.49-7.34 (m, 2H), 7.13 (m, 1H), 5.99 (m, 1H), 5.78 (m, 1H), 4.64 (m, 1H), 3.99-3.59 (m, 7H), 3.58-3.45 (m, 2H), 3.32-3.22 (m, 5H), 3.03 (m, 1H), 2.44 (m, 3H), 2.08 (s, 4H), 1.66 (m, 1H), 1.12 (m, 3H). $^{19}$F NMR (282 MHz, DMSO-d$_6$) δ −63.36 (3F), −151.86 (1F).

Example 72: (S)—N-(3-(2-(trans-3-hydroxy-2-methylazetidin-1-yl)-6-morpholinopyridin-4-yl)-4-methylphenyl)-3-(2,2,2-trifluoroethyl)pyrrolidine-1-carboxamide

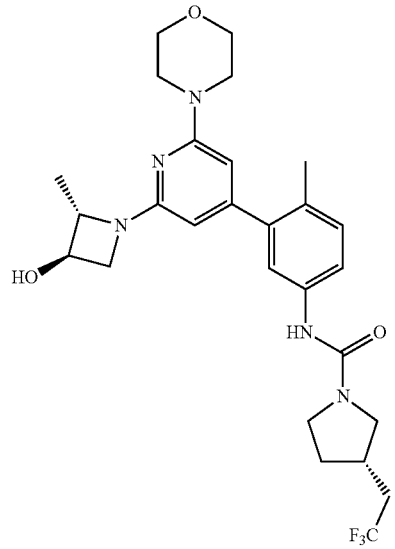 [SMILES: Cc1ccc(NC(=O)N2CC[C@@H](CC(F)(F)F)C2)cc1-c1cc(N2CCOCC2)nc(N2C[C@@H](O)[C@@H]2C)c1]

Example 73: (S)—N-(3-(2-(cis-3-hydroxy-2-methylazetidin-1-yl)-6-morpholinopyridin-4-yl)-4-methylphenyl)-3-(2,2,2-trifluoroethyl)pyrrolidine-1-carboxamide

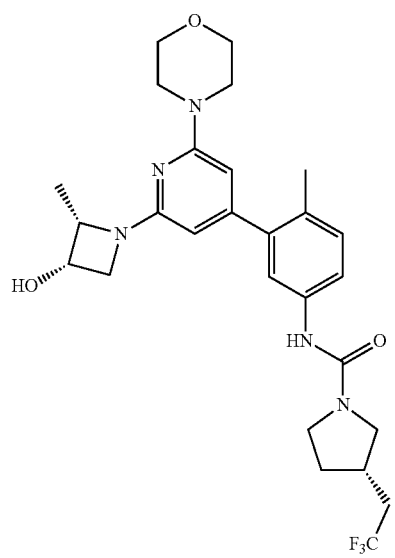 [SMILES: Cc1ccc(NC(=O)N2CC[C@@H](CC(F)(F)F)C2)cc1-c1cc(N2CCOCC2)nc(N2C[C@H](O)[C@@H]2C)c1]

Synthetic Scheme

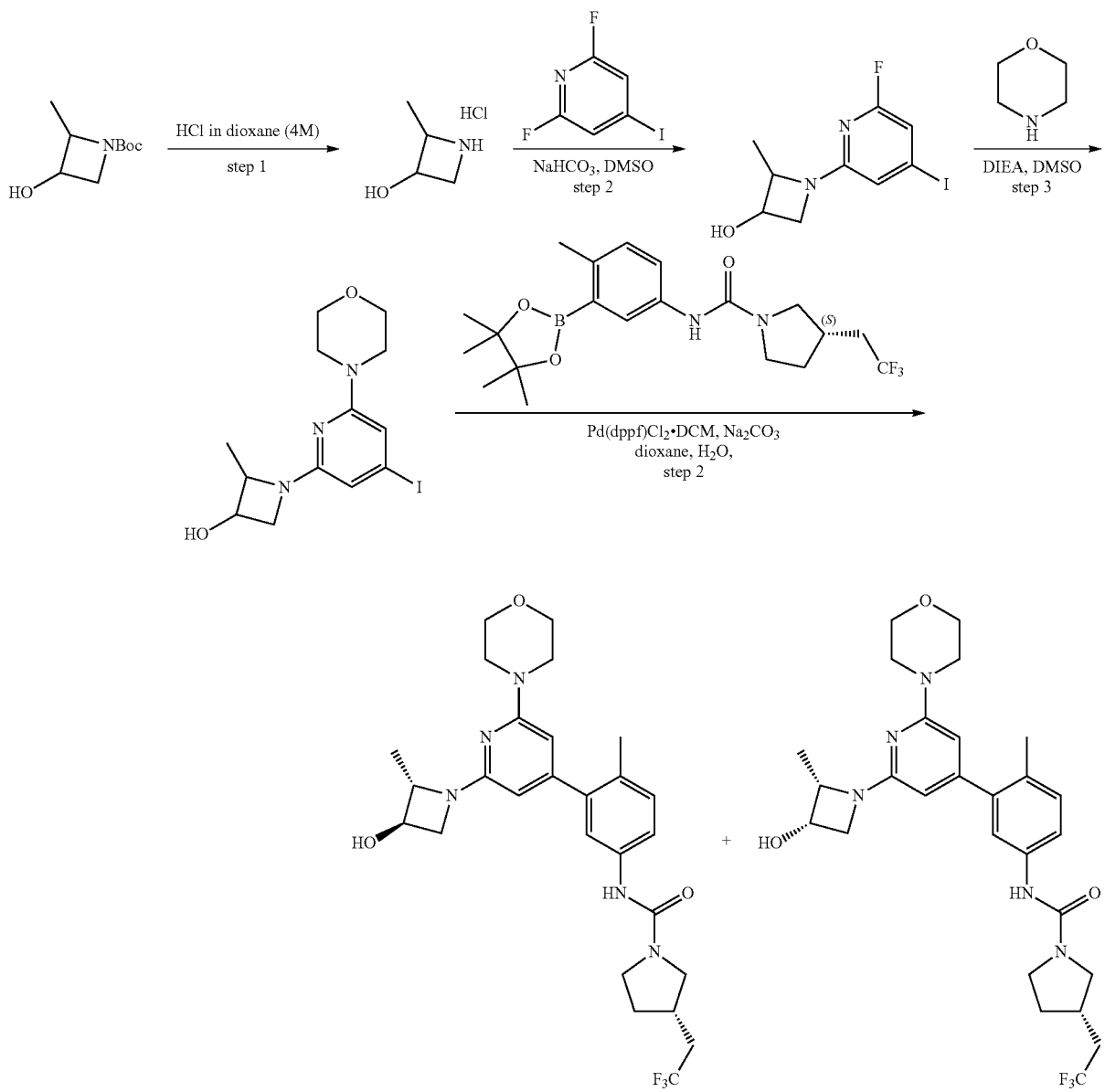

Preparation 72A: 2-methylazetidin-3-ol hydrochloride

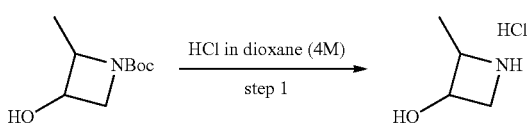

To a stirred solution of tert-butyl 3-hydroxy-2-methylazetidine-1-carboxylate (450 mg, 2.403 mmol) in 1,4-dioxane (4.5 mL) was added HCl (gas) in 1,4-dioxane (4.5 mL) dropwise at room temperature. The resulting solution was stirred for 16 h at room temperature. The reaction mixture was concentrated under reduced pressure to afford 2-methylazetidin-3-ol hydrochloride (400 mg, crude) as yellow oil.

The crude product was used directly for the next step without any other purification.

Preparation 72B: 1-(6-fluoro-4-iodopyridin-2-yl)-2-methylazetidin-3-ol

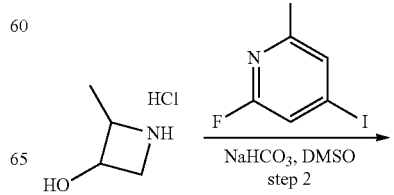

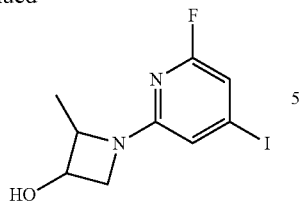

A mixture of 2,6-difluoro-4-iodopyridine (690 mg, 2.863 mmol), 2-methylazetidin-3-ol hydrochloride (389 mg, 3.150 mmol) and NaHCO$_3$ (721 mg, 8.590 mmol) in DMSO (7 mL) was stirred for 3 h at 100° C. The resulting mixture was cooled down to room temperature and diluted with water (100 mL) and extracted with EtOAc (3×50 mL). The combined organic layer was washed with brine (3×100 mL), dried over anhydrous Na$_2$SO$_4$. After filtration, the filtrate was concentrated under reduced pressure. The residue was purified by silica gel column chromatography, eluted with EtOAc in PE (40% to 50%) to afford 1-(6-fluoro-4-iodopyridin-2-yl)-2-methylazetidin-3-ol (270 mg, 33%) (mixture of cis and trans) as off-white semi-solid. MS ESI calculated for C$_9$H$_{10}$FIN$_2$O[M+H]$^+$, 308.98, found 308.85. $^1$H NMR (400 MHz, DMSO-d$_6$) δ 6.93-6.68 (m, 0.5H), 6.62 (ddt, J=4.2, 2.6, 1.4 Hz, 1H), 6.57 (t, J=1.4 Hz, 0.5H), 5.59 (dd, J=57.6, 6.2 Hz, 1H), 4.69-4.35 (m, 2H), 4.18-3.89 (m, 1H), 3.79-3.42 (m, 1H), 1.48-1.23 (m, 3H).

Preparation 72C: 1-[4-iodo-6-(morpholin-4-yl)pyridin-2-yl]-2-methylazetidin-3-ol

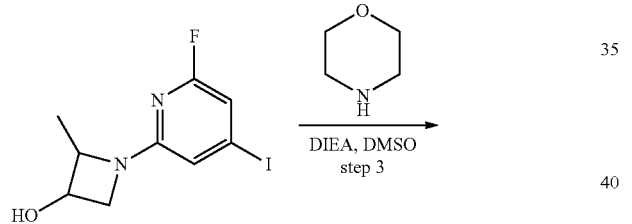

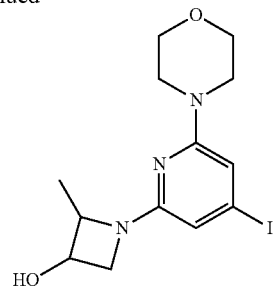

A solution of 1-(6-fluoro-4-iodopyridin-2-yl)-2-methylazetidin-3-ol (275 mg, 0.893 mmol), morpholine (85 mg, 0.982 mmol) and DIEA (230 mg, 1.785 mmol) in DMSO (3 mL) was stirred for 16 h at 100° C. The resulting mixture was cooled down to room temperature. The resulting solution was quenched with water (50 mL) and extracted with EtOAc (3×30 mL). The combined organic layer was washed with brine (1×50 mL), dried over anhydrous Na$_2$SO$_4$. After filtration, the filtrate was concentrated under reduced pressure. The residue was purified by silica gel column chromatography, eluted with EtOAc in PE (48% to 60%) to afford 1-[4-iodo-6-(morpholin-4-yl)pyridin-2-yl]-2-methylazetidin-3-ol (170 mg, 36%) (mixture of cis and trans) as a light yellow solid. MS ESI calculated for C$_{13}$H$_{18}$IN$_3$O$_2$ [M+H]$^+$, 376.04, found 375.95. $^1$H NMR (400 MHz, chloroform-d) δ 6.34 (dd, J=17.3, 1.2 Hz, 1H), 6.09 (dd, J=17.7, 1.0 Hz, 1H), 4.62 (t, J=5.4 Hz, 1H), 4.53-4.34 (m, 1H), 4.25-4.03 (m, 1H), 3.80 (q, J=5.2 Hz, 5H), 3.54-3.36 (m, 4H), 1.49 (dd, J=29.7, 6.5 Hz, 3H).

Example 72: (S)—N-(3-(2-(trans-3-hydroxy-2-methylazetidin-1-yl)-6-morpholinopyridin-4-yl)-4-methylphenyl)-3-(2,2,2-trifluoroethyl)pyrrolidine-1-carboxamide Example 73: (S)—N-(3-(2-(cis-3-hydroxy-2-methylazetidin-1-yl)-6-morpholinopyridin-4-yl)-4-methylphenyl)-3-(2,2,2-trifluoroethyl)pyrrolidine-1-carboxamide

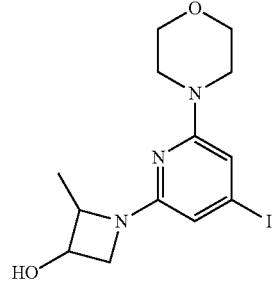

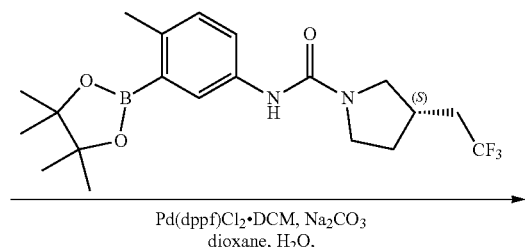

Pd(dppf)Cl$_2$·DCM, Na$_2$CO$_3$
dioxane, H$_2$O,
step 2

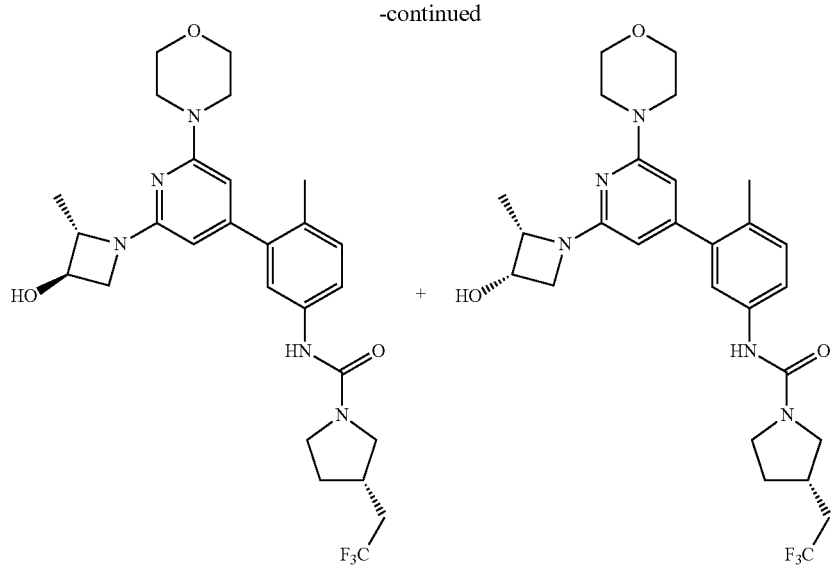

A mixture of 1-[4-iodo-6-(morpholin-4-yl)pyridin-2-yl]-2-methylazetidin-3-ol (170 mg, 0.453 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (205 mg, 0.498 mmol), Pd(dppf)Cl$_2$·CH$_2$Cl$_2$ (37 mg, 0.045 mmol), Na$_2$CO$_3$ (144 mg, 1.359 mmol), 1,4-dioxane (4 mL) and H$_2$O (1 mL) was stirred for 16 h at 60° C. The reaction mixture was cooled to room temperature and concentrated under reduced pressure. The residue was purified by silica gel column chromatography, eluted with PE/EA/EtOH (12/3/1). The crude product was purified by prep-HPLC with the following conditions: Column: Prep C18 OBD Column, 19×150 mm 5 um 10 nm; Mobile Phase A: water (0.5% TFA), Mobile Phase B: acetonitrile; Flow rate: 20 mL/min; Gradient:35%-50% B in 4.3 min; to afford (S)—N-(3-(2-(trans-3-hydroxy-2-methylazetidin-1-yl)-6-morpholinopyridin-4-yl)-4-methylphenyl)-3-(2,2,2-trifluoroethyl)pyrrolidine-1-carboxamide (73 mg, 30%) as a light yellow solid. MS ESI calculated for C$_{27}$H$_{34}$F$_3$N$_5$O$_3$ [M+H]$^+$, 534.26, found 534.25. $^1$H NMR (400 MHz, DMSO-d$_6$) δ 8.12 (s, 1H), 7.43-7.41 (m, 1H), 7.32-7.31 (m, 1H), 7.11-7.09 (m, 1H), 5.90 (s, 1H), 5.54 (s, 1H), 5.38-5.37 (m, 1H), 4.47-4.45 (m, 1H), 4.32-4.29 (m, 1H), 4.00-3.96 (m, 1H), 3.69-3.63 (m, 6H), 3.52-3.50 (m, 1H), 3.40-3.30 (m, 5H), 3.04-2.99 (m, 1H), 2.52-2.41 (m, 3H), 2.15-2.08 (m, 4H), 1.66-1.65 (m, 1H), 1.32 (d, J=6.8 Hz, 3H). $^{19}$F NMR (376 MHz, DMSO-d$_6$) δ −63.36 (3F).

Also afforded (S)—N-(3-(2-(cis-3-hydroxy-2-methylazetidin-1-yl)-6-morpholinopyridin-4-yl)-4-methylphenyl)-3-(2,2,2-trifluoroethyl)pyrrolidine-1-carboxamide (24 mg, 10%) as a light yellow solid. MS ESI calculated for C$_{27}$H$_{34}$F$_3$N$_5$O$_3$ [M+H]$^+$, 534.26, found 534.25. $^1$H NMR (300 MHz, DMSO-d$_6$) δ 8.10 (s, 1H), 7.44-7.40 (m, 1H), 7.32-7.31 (m, 1H), 7.11-7.08 (m, 1H), 5.96 (s, 1H), 5.60 (s, 1H), 5.38-5.37 (m, 1H), 4.08-3.94 (m, 2H), 3.89-3.85 (m, 1H), 3.76-3.65 (m, 5H), 3.54-3.49 (m, 2H), 3.39-3.25 (m, 5H), 3.04-3.00 (m, 1H), 2.49-2.42 (m, 3H), 2.15-2.05 (m, 4H), 1.71-1.61 (m, 1H), 1.42 (d, J=6.3 Hz, 3H). $^{19}$F NMR (376 MHz, DMSO-d$_6$) δ −63.12 (3F).

Example 74: (3S)—N-[4-methyl-3-[2-(morpholin-4-yl)-6-[[(2S)-1,1,1-trifluoro-3-hydroxypropan-2-yl]amino]pyridin-4-yl]phenyl]-3-(2,2,2-trifluoroethyl)pyrrolidine-1-carboxamide

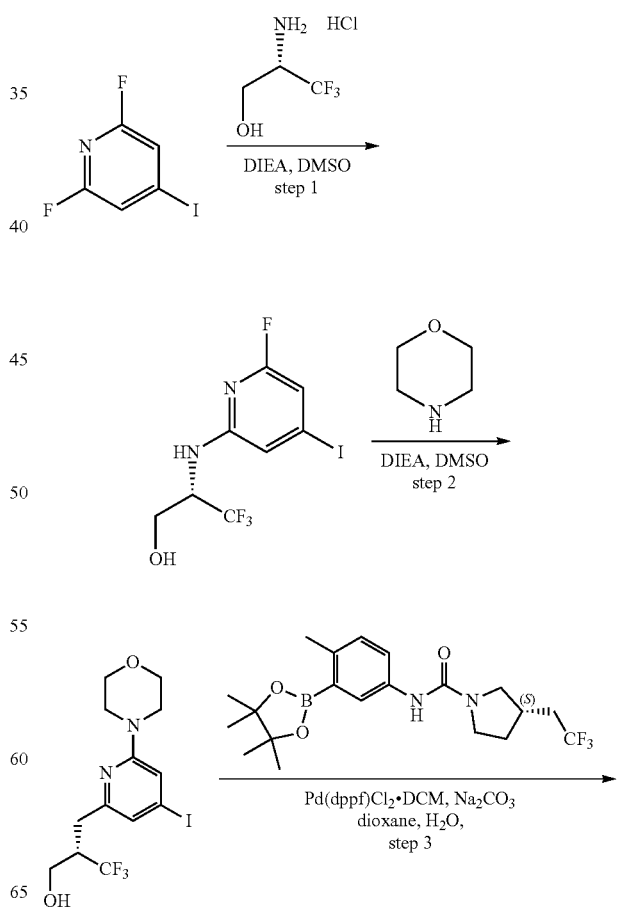

-continued

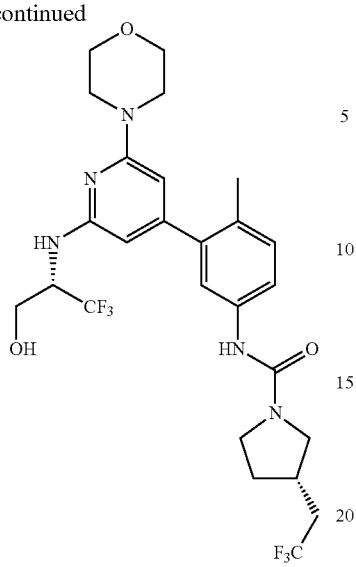

Preparation 74A: (2S)-3,3,3-trifluoro-2-[(6-fluoro-4-iodopyridin-2-yl)amino]propan-1-ol

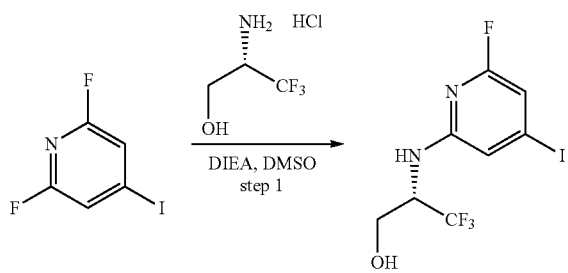 [SMILES: Cl ; Fc1cc(I)cc(F)n1 ; N[C@@H](CO)C(F)(F)F ; OC[C@H](Nc1cc(I)cc(F)n1)C(F)(F)F]

To a stirred mixture of 2,6-difluoro-4-iodopyridine (300 mg, 1.245 mmol) and (2S)-2-amino-3,3,3-trifluoropropan-1-ol (209 mg, 1.618 mmol) in DMSO (4 mL) was added $K_2CO_3$ (516 mg, 3.735 mmol) at room temperature. The resulting mixture was stirred for 2 h at 70° C. The resulting mixture was extracted with EtOAc (3×100 mL). The combined organic layers were washed with brine (3×100 mL), dried over anhydrous $Na_2SO_4$. After filtration, the filtrate was concentrated under reduced pressure. The residue was purified by silica gel column chromatography, eluted with EtOAc in PE (0% to 30%) to afford (2S)-3,3,3-trifluoro-2-[(6-fluoro-4-iodopyridin-2-yl)amino]propan-1-ol (20 mg, 5%) as a white solid. MS ESI calculated for $C_8H_7F_4IN_2O$ [M+H]$^+$, 350.95, found 350.95. $^1$H NMR (300 MHz, chloroform-d) δ 6.80 (s, 1H), 6.68 (d, J=2.7 Hz, 1H), 5.15 (d, J=9.5 Hz, 1H), 4.90-4.74 (m, 1H), 4.07 (dd, J=12.0, 3.7 Hz, 1H)

Preparation 74B: (2S)-3,3,3-trifluoro-2-[[4-iodo-6-(morpholin-4-yl)pyridin-2-yl]amino]propan-1-ol

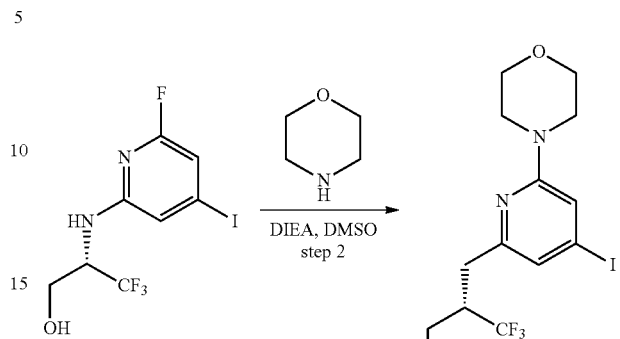

To a stirred solution of (2S)-3,3,3-trifluoro-2-[(6-fluoro-4-iodopyridin-2-yl)amino]propan-1-ol (20 mg, 0.057 mmol) and morpholine (5 mg, 0.063 mmol) in DMSO (2 mL) was added $K_2CO_3$ (24 mg, 0.171 mmol) at room temperature. The resulting mixture was stirred for 16 h at 70° C. The mixture was allowed to cool down to room temperature. The resulting mixture was diluted with water (20 mL) and extracted with EtOAc (3×30 mL). The combined organic layers were washed with brine (3×30 mL), dried over anhydrous $Na_2SO_4$. After filtration, the filtrate was concentrated under reduced pressure. The residue was purified by Prep-TLC (PE/EtOAc=2/1) to afford (2S)-3,3,3-trifluoro-2-[[4-iodo-6-(morpholin-4-yl)pyridin-2-yl]amino]propan-1-ol (10 mg, 17%) as a white solid. MS ESI calculated for $C_{12}H_{15}F_3IN_3O_2$ [M+H]$^+$, 418.02, found 417.85. $^1$H NMR (300 MHz, chloroform-d) § 6.55 (d, J=8.9 Hz, 2H), 4.54 (dd, J=11.2, 3.9 Hz, 1H), 4.36-4.25 (m, 1H), 3.88-3.74 (m, 4H), 3.66 (d, J=3.9 Hz, 1H), 3.54-3.38 (m, 4H).

Example 74: (3S)—N-[4-methyl-3-[2-(morpholin-4-yl)-6-[[(2S)-1,1,1-trifluoro-3-hydroxypropan-2-yl]amino]pyridin-4-yl]phenyl]-3-(2,2,2-trifluoroethyl)pyrrolidine-1-carboxamide

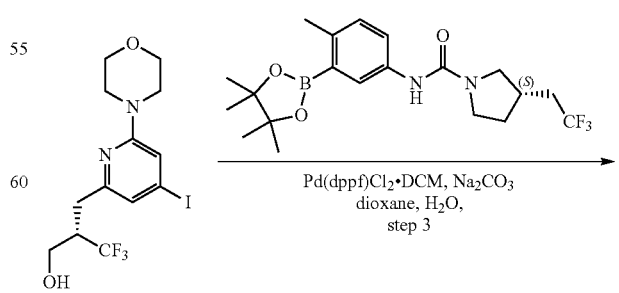

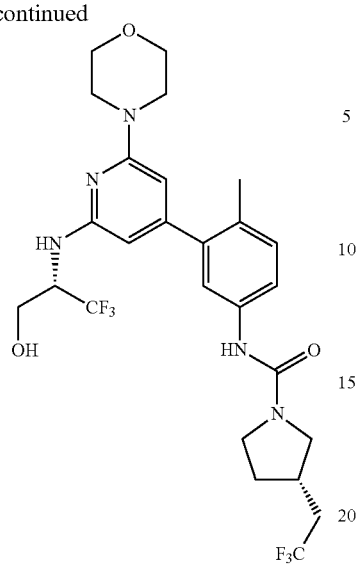

To a stirred mixture of (2S)-3,3,3-trifluoro-2-[[4-iodo-6-(morpholin-4-yl)pyridin-2-yl]amino]propan-1-ol (20 mg, 0.048 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (21 mg, 0.053 mmol), dioxane (1 mL) and H₂O (0.25 mL) were added Pd(dppf)Cl₂·CH₂Cl₂ (4 mg, 0.005 mmol) and Na₂CO₃ (15 mg, 0.144 mmol) at room temperature. The resulting mixture was stirred for 16 h at 60° C. under nitrogen atmosphere. The resulting mixture was concentrated under vacuum. The residue was purified by silica gel column chromatography, eluted with PE/EtOAc (1/1). The residue was purified by Prep-TLC (PE/EA/EtOH=8/3/1) to afford (3S)—N-[4-methyl-3-[2-(morpholin-4-yl)-6-[[(2S)-1,1,1-trifluoro-3-hydroxypropan-2-yl]amino]pyridin-4-yl]phenyl]-3-(2,2,2-trifluoroethyl)pyrrolidine-1-carboxamide (7 mg, 15%) as a white solid. MS ESI calculated for $C_{26}H_{31}F_6N_5O_3$ [M+H]⁺, 575.23, found 575.56. ¹H NMR (400 MHz, DMSO-d₆) δ 8.12 (s, 1H), 7.42 (dd, J=8.2, 2.4 Hz, 1H), 7.36 (d, J=2.3 Hz, 1H), 7.10 (d, J=8.4 Hz, 1H), 6.70 (d, J=9.0 Hz, 1H), 5.94 (d, J=1.0 Hz, 1H), 5.88 (d, J=1.0 Hz, 1H), 5.12 (t, J=5.7 Hz, 1H), 4.99-4.88 (m, 1H), 3.77-3.62 (m, J=6.2 Hz, 7H), 3.52 (t, J=2.1 Hz, 1H), 3.47-3.34 (m, 5H), 3.02 (t, J=9.4 Hz, 1H), 2.49-2.34 (m, 3H), 2.16 (s, 3H), 2.12-2.05 (m, 1H), 1.73-1.59 (m, 1H). ¹⁹F NMR (376 MHz, DMSO-d₆) δ −64.96 (3F), −73.37 (3F).

Example 75: (3S)—N-[3-[2-(2-hydroxy-2-methylpropanamido)-6-(morpholin-4-yl)pyridin-4-yl]-4-methylphenyl]-3-(2,2,2-trifluoroethyl)pyrrolidine-1-carboxamide

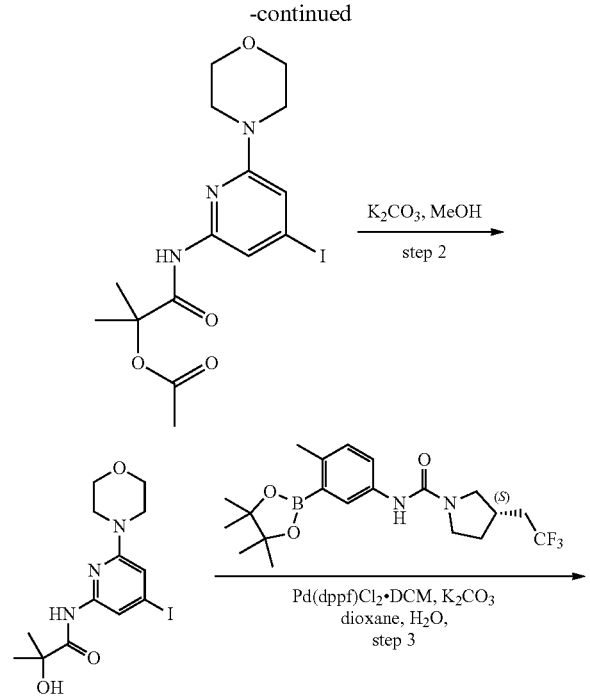

Preparation 75A: 1-[[4-iodo-6-(morpholin-4-yl)pyridin-2-yl]carbamoyl]-1-methylethyl acetate

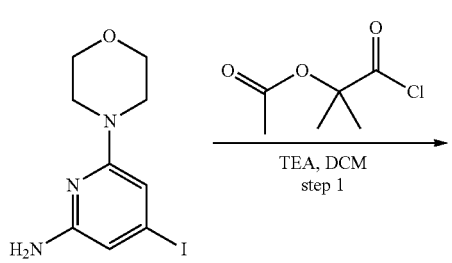

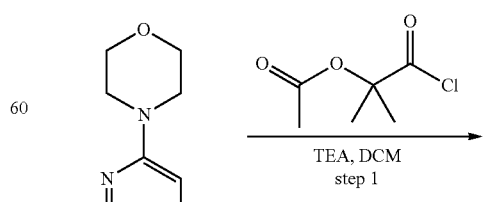

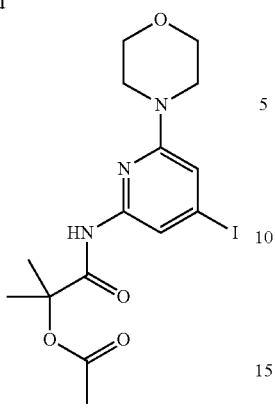

To a stirred mixture of 4-iodo-6-(morpholin-4-yl)pyridin-2-amine (250 mg, 0.819 mmol) and 1-chloro-2-methyl-1-oxopropan-2-yl acetate (202 mg, 1.229 mmol) in DCM (3 mL) was added TEA (248 mg, 2.458 mmol) at room temperature. The reaction mixture was stirred for 6 h at room temperature. The resulting mixture was diluted with water (20 mL). The resulting mixture was extracted with EtOAc (3×20 mL). The combined organic layers were washed with brine (2×30 mL), dried over anhydrous Na$_2$SO$_4$. After filtration, the filtrate was concentrated under reduced pressure to afford 1-[[4-iodo-6-(morpholin-4-yl)pyridin-2-yl]carbamoyl]-1-methylethyl acetate (400 mg, crude) as a yellow solid. MS ESI calculated for C$_{15}$H$_{20}$IN$_3$O$_4$ [M+H]$^+$, 434.05, found 434.00.

Preparation 75B: 2-hydroxy-N-[4-iodo-6-(morpholin-4-yl)pyridin-2-yl]-2-methylpropanamide

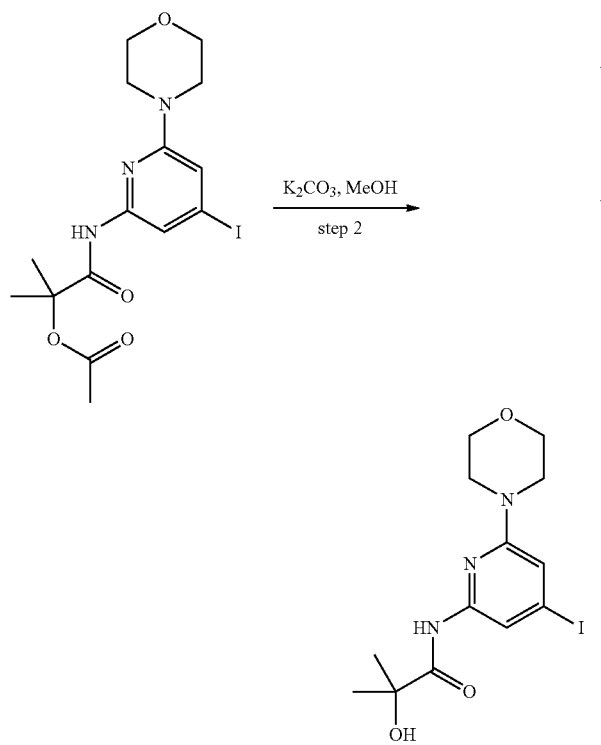

To a stirred mixture of 1-[[4-iodo-6-(morpholin-4-yl)pyridin-2-yl]carbamoyl]-1-methylethyl acetate (370 mg, 0.854 mmol) in MeOH (4 mL) was added K$_2$CO$_3$ (354 mg, 2.562 mmol) at room temperature. The reaction mixture was stirred for 16 h at room temperature. The resulting mixture was diluted with water (30 mL). The resulting mixture was extracted with EtOAc (3×40 mL). The combined organic layers were washed with brine (3×40 mL), dried over anhydrous Na$_2$SO$_4$. After filtration, the filtrate was concentrated under reduced pressure. The residue was purified by reverse phase chromatography, eluted with 65% to 80% CH$_3$CN in water (with 0.5% NH$_4$HCO$_3$). The fractions containing the desired product were collected and concentrated under reduced pressure to afford 2-hydroxy-N-[4-iodo-6-(morpholin-4-yl)pyridin-2-yl]-2-methylpropanamide (180 mg, 53%) as an off white solid. MS ESI calculated for C$_{13}$H$_{18}$IN$_3$O$_3$ [M+H]$^+$, 392.04, found 391.95; $^1$H NMR (400 MHz, DMSO-d$_6$) δ 9.09 (s, 1H), 7.81 (d, J=1.0 Hz, 1H), 6.96 (d, J=1.1 Hz, 1H), 6.03 (s, 1H), 3.66 (dd, J=5.8, 3.9 Hz, 4H), 3.43 (dd, J=5.7, 3.9 Hz, 4H), 1.34 (s, 6H).

Example 75: (3S)—N-[3-[2-(2-hydroxy-2-methyl-propanamido)-6-(morpholin-4-yl)pyridin-4-yl]-4-methylphenyl]-3-(2,2,2-trifluoroethyl)pyrrolidine-1-carboxamide

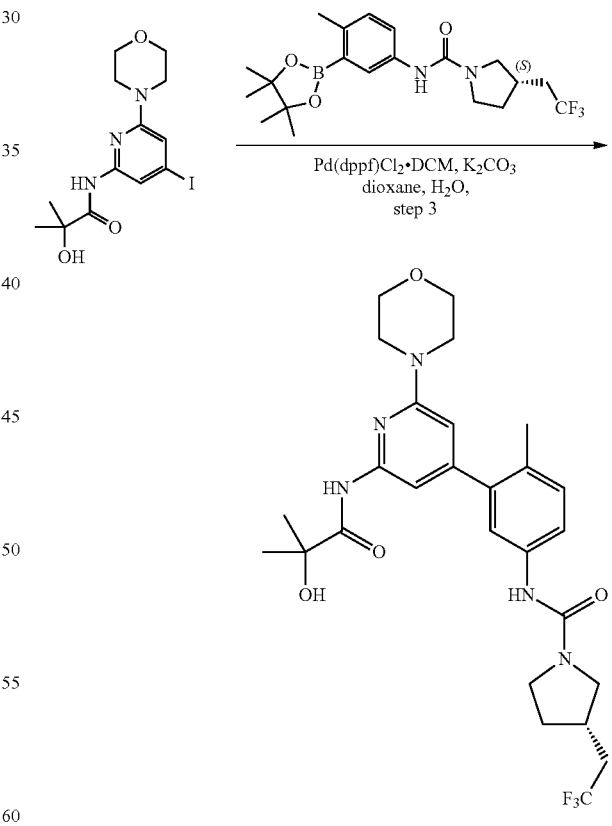

To a stirred mixture of 2-hydroxy-N-[4-iodo-6-(morpholin-4-yl)pyridin-2-yl]-2-methylpropanamide (130 mg, 0.332 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (164 mg, 0.399 mmol) and K$_2$CO$_3$ (137 mg, 0.997 mmol) in dioxane (2 mL) and H$_2$O (0.5 mL) was added Pd(dppf)Cl$_2$·CH$_2$Cl$_2$ (27 mg, 0.033 mmol). The reaction mixture was stirred for 2 h at 80° C. under N$_2$ atmosphere. The resulting mixture was diluted with water (20 mL). The resulting mixture was extracted with EtOAc (3×30 mL). The combined organic layers were washed with brine (2×30 mL), dried over anhydrous Na$_2$SO$_4$. After filtration, the filtrate was concentrated under reduced pressure. The residue was purified by silica gel column chromatography, eluted with 45% PE in EA. The fractions containing the desired product were collected and concentrated under reduced pressure. The crude was purified by reverse phase chromatography, eluted with CH$_3$CN in water (with 10 mmol/mL NH$_4$HCO$_3$). The fractions containing the desired product were collected and concentrated under reduced pressure to afford (3S)—N-[3-[2-(2-hydroxy-2-methylpropanamido)-6-(morpholin-4-yl)pyridin-4-yl]-4-methylphenyl]-3-(2,2,2-trifluoroethyl)pyrrolidine-1-carboxamide (138 mg, 73%) as a white solid. MS ESI calculated for C$_{27}$H$_{34}$F$_3$N$_5$O$_4$ [M+H]$^+$, 550.26, found 550.25; $^1$H NMR (400 MHz, DMSO-d$_6$) δ 9.16 (s, 1H), 8.18 (s, 1H), 7.49 (dd, J=8.3, 2.3 Hz, 1H), 7.40 (dd, J=6.3, 1.6 Hz, 2H), 7.15 (d, J=8.4 Hz, 1H), 6.49 (d, J=1.1 Hz, 1H), 6.03 (s, 1H), 3.73-3.63 (m, 5H), 3.58-3.43 (m, 5H), 3.33-3.26 (m, 1H), 3.03 (t, J=9.4 Hz, 1H), 2.49-2.33 (m, 3H), 2.18 (s, 3H), 2.08 (q, J=4.5, 3.8 Hz, 1H), 1.66 (dq, J=11.9, 9.7 Hz, 1H), 1.35 (s, 6H).

Example 76: (3S)—N-[2-fluoro-5-(2-[[(2R)-1-hydroxypropan-2-yl]amino]-6-(morpholin-4-yl)pyridin-4-yl]-4-methylphenyl]-3-(2,2,2-trifluoroethyl)pyrrolidine-1-carboxamide

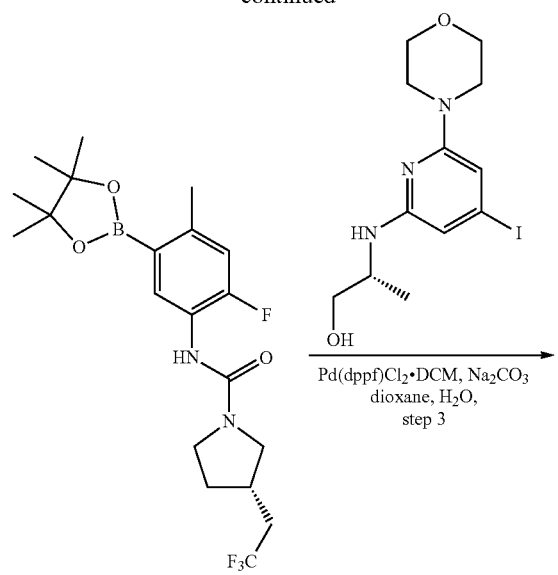

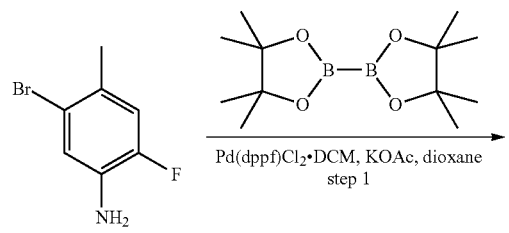

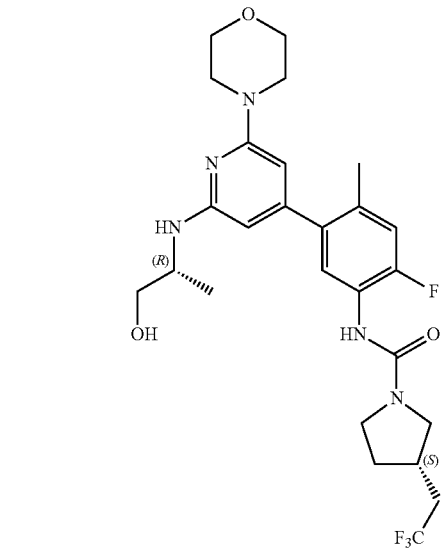

Preparation 76A: 2-fluoro-4-methyl-5-(4,4,5,5-tetramethyl-1,3,2-dioxaborolan-2-yl)aniline

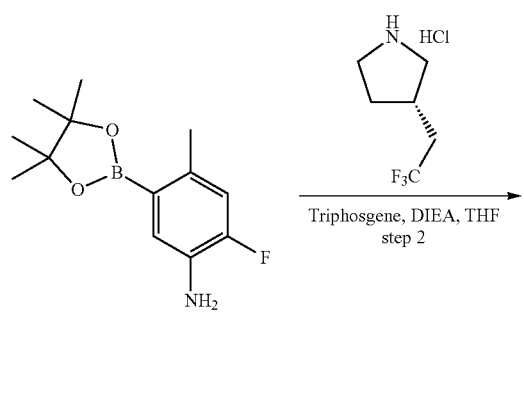

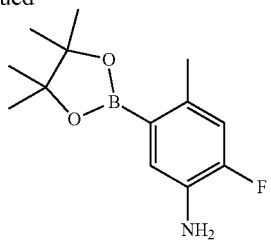

A mixture of 5-bromo-2-fluoro-4-methylaniline (50 g, 245.048 mmol), 4,4,5,5-tetramethyl-2-(tetramethyl-1,3,2-dioxaborolan-2-yl)-1,3,2-dioxaborolane (75 g, 294.057 mmol), KOAc (72 g, 735.143 mmol,) and Pd(dppf)Cl$_2$·CH$_2$Cl$_2$ (10 g, 12.252 mmol) in 1,4-dioxane (600 mL) was stirred for 16 h at 100° C. under argon atmosphere. The resulting mixture was concentrated under reduced pressure. The residue was purified by silica gel column chromatography, eluted with EtOAc in PE (0~30%) to afford 2-fluoro-4-methyl-5-(4,4,5,5-tetramethyl-1,3,2-dioxaborolan-2-yl)aniline (57 g, 93%) as an off-white solid. MS ESI calculated for C$_{13}$H$_{19}$BFNO$_2$ [M+H]$^+$, 252.15, found 252.10.

Preparation 76B: (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide

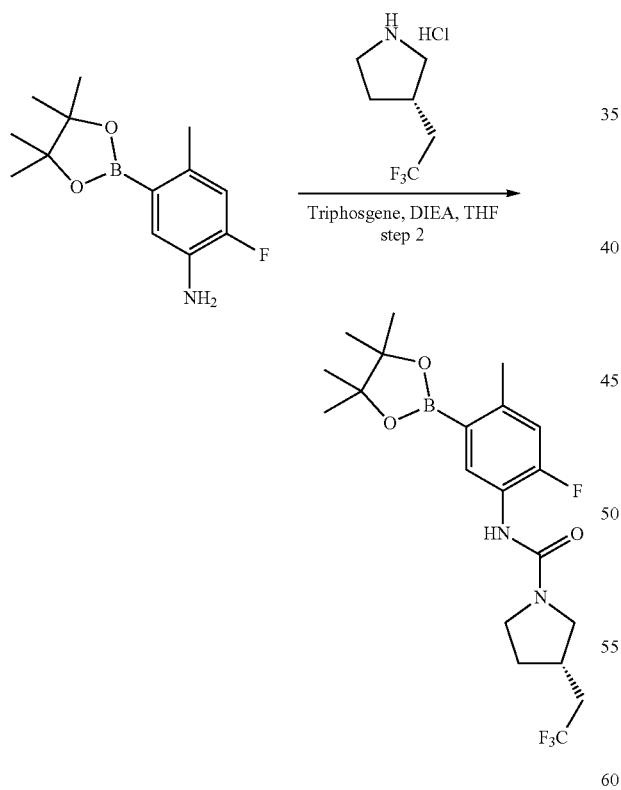

A mixture of 2-fluoro-4-methyl-5-(4,4,5,5-tetramethyl-1,3,2-dioxaborolan-2-yl)aniline (2.00 g, 7.965 mmol, 1.00 equiv), DIEA (5.15 g, 0.040 mmol, 5 equiv) and Triphosgene (0.95 g, 0.003 mmol, 0.4 equiv) in THF (19 mL) was stirred for 30 min at room temperature under nitrogen atmosphere. To the above mixture was added (3S)-3-(2,2,2-trifluoroethyl)pyrrolidine hydrochloride (1.51 g, 0.008 mmol, 1.00 equiv). The resulting mixture was stirred for additional 3 h at room temperature. The resulting mixture was concentrated under vacuum. The residue was purified by silica gel column chromatography, eluted with PE/EtOAc/EtOH (4/3/1) to afford (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (3.2 g, 75%) as an off-white solid. MS ESI calculated for C$_{20}$H$_{27}$BF$_4$N$_2$O$_3$ [M+H]$^+$, 431.21, found 431.25. $^1$H NMR (400 MHz, Chloroform-d) δ 8.38 (d, J=9.3 Hz, 1H), 6.88 (dd, J=12.3, 0.8 Hz, 1H), 6.20 (d, J=3.2 Hz, 1H), 3.83 (dd, J=9.9, 7.5 Hz, 1H), 3.67-3.63 (m, 1H), 3.46 (td, J=9.7, 6.8 Hz, 1H), 3.13 (t, J=9.5 Hz, 1H), 2.66-2.51 (m, 1H), 2.46 (s, 3H), 2.35-2.17 (m, 3H), 1.78-1.74 (m, 1H), 1.33 (s, 12H).

Example 76: (3S)—N-[2-fluoro-5-(2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide

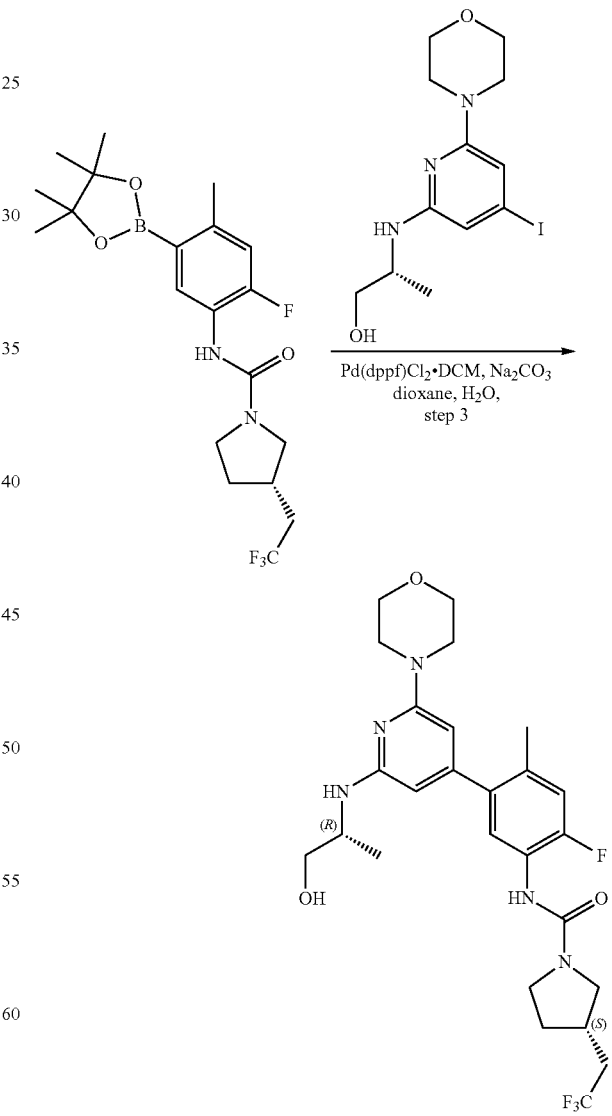

To a stirred solution of (2R)-2-[[4-iodo-6-(morpholin-4-yl)pyridin-2-yl]amino]propan-1-ol (130 mg, 0.358 mmol)

and (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (154 mg, 0.358 mmol) in 1,4-dioxane (2 mL) and H₂O (0.4 mL) were added Na₂CO₃ (113 mg, 1.074 mmol) and Pd(dppf)Cl₂·CH₂Cl₂ (29 mg, 0.036 mmol) at room temperature under nitrogen atmosphere. The resulting mixture was stirred for 16 h at 60° C. under nitrogen atmosphere. The mixture was allowed to cool down to room temperature. The reaction was quenched by the addition of water (20 mL) at room temperature. The resulting mixture was extracted with EtOAc (3×20 mL). The combined organic layers were washed with brine (3×20 mL), dried over anhydrous Na₂SO₄. After filtration, the filtrate was concentrated under reduced pressure. The residue was purified by silica gel column chromatography, eluted with PE/EtOAc (1/1) to afford (3S)—N-[2-fluoro-5-(2-[[(2R)-1-hydroxypropan-2-yl]amino]-6-(morpholin-4-yl)pyridin-4-yl)-4-methylphenyl]-3-(2,2,2-trifluoroethyl)pyrrolidine-1-carboxamide (105 mg, 54%) as a light yellow solid. MS ESI calculated for C₂₆H₃₃F₄N₅O₃ [M+H]⁺, 540.25, found 540.15. ¹H NMR (400 MHz, DMSO-d₆) δ 7.86 (s, 1H), 7.29 (d, J=8.3 Hz, 1H), 7.10 (d, J=11.7 Hz, 1H), 5.99 (d, J=7.5 Hz, 1H), 5.77-5.71 (m, 2H), 4.64 (t, J=5.6 Hz, 1H), 3.92-3.84 (m, 1H), 3.67 (dd, J=5.7, 3.9 Hz, 5H), 3.57-3.44 (m, 2H), 3.41-3.32 (m, 5H), 3.03 (t, J=9.4 Hz, 1H), 2.51-2.35 (m, 3H), 2.20 (s, 3H), 2.13-2.05 (m, 1H), 1.74-1.62 (m, 1H), 1.24 (s, 1H), 1.12 (d, J=6.6 Hz, 3H). ¹⁹F NMR (376 MHz, DMSO-d₆) δ −63.39 (3F), −125.64 (1F).

Example 77: N-[2-fluoro-5-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide Preparation 77A: (2R)-2-[[4-(5-amino-4-fluoro-2-methylphenyl)-6-(morpholin-4-yl)pyridin-2-yl]amino]propan-1-ol

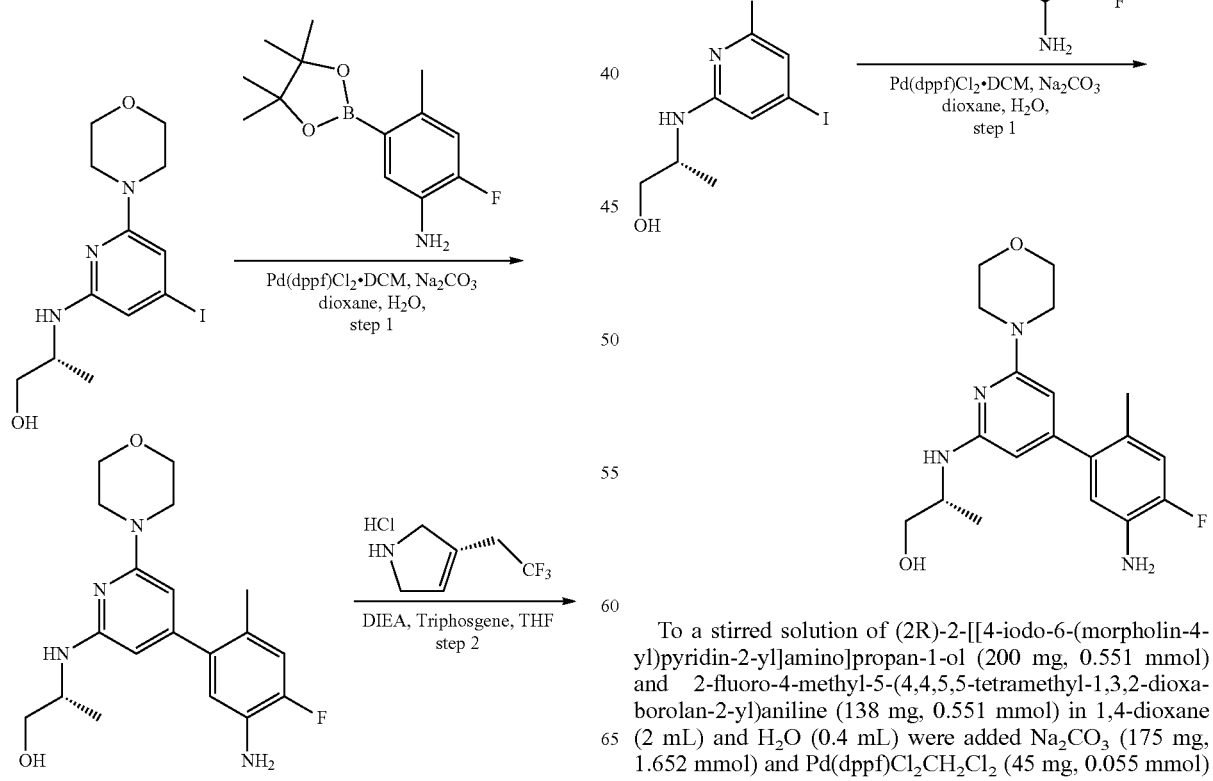

To a stirred solution of (2R)-2-[[4-iodo-6-(morpholin-4-yl)pyridin-2-yl]amino]propan-1-ol (200 mg, 0.551 mmol) and 2-fluoro-4-methyl-5-(4,4,5,5-tetramethyl-1,3,2-dioxaborolan-2-yl)aniline (138 mg, 0.551 mmol) in 1,4-dioxane (2 mL) and H₂O (0.4 mL) were added Na₂CO₃ (175 mg, 1.652 mmol) and Pd(dppf)Cl₂CH₂Cl₂ (45 mg, 0.055 mmol) at room temperature under nitrogen atmosphere. The resulting mixture was stirred for 1 h at 80° C. under nitrogen atmosphere. The mixture was allowed to cool down to room temperature. The reaction was quenched by the addition of water (20 mL) at room temperature. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EtOAc/EtOH (6/3/1) to afford (2R)-2-[[4-(5-amino-4-fluoro-2-methylphenyl)-6-(morpholin-4-yl)pyridin-2-yl]amino]propan-1-ol (140 mg, 38%) as an off-white solid. MS ESI calculated for $C_{19}H_{25}FN_4O_2$ [M+H]$^+$, 361.20, found 361.15. $^1$H NMR (300 MHz, chloroform-d) δ 6.88 (d, J=11.9 Hz, 1H), 6.64 (d, J=9.2 Hz, 1H), 5.81 (d, J=14.5 Hz, 2H), 4.08 (s, 1H), 3.88-3.73 (m, 5H), 3.68-3.53 (m, 3H), 3.49 (s, 4H), 2.17 (s, 3H), 1.25 (d, J=6.7 Hz, 3H). $^{19}$F NMR (282 MHz, chloroform-d) δ −136.65.

Example 77: N-[2-fluoro-5-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide hydrochloride (31 mg, 0.166 mmol) at room temperature. The resulting mixture was stirred for additional 3 h at room temperature. The resulting mixture was concentrated under vacuum. The residue was purified by silica gel column chromatography, eluted with (PE/EtOAc/EtOH=8/3/1) to afford mixture. The residue was purified by reverse flash chromatography with the following conditions: column, C18 silica gel; mobile phase, $CH_3CN$ in water (0.1% $NH_4HCO_3$), 10% to 50% gradient in 20 min; detector, UV 254 nm to afford N-[2-fluoro-5-(2-[[(2R)-1-hydroxypropan-2-yl]amino]-6-(morpholin-4-yl)pyridin-4-yl)-4-methylphenyl]-3-(2,2,2-trifluoroethyl)-2,5-dihydropyrrole-1-carboxamide (5 mg, 6%) as a white solid. MS ESI calculated for $C_{26}H_{31}F_4N_5O_3$ [M+H]$^+$, 538.24, found 538.05. $^1$H NMR (400 MHz, DMSO-d$_6$) δ 7.97 (s, 1H), 7.31 (d, J=8.3 Hz, 1H), 7.11 (d, J=11.7 Hz, 1H), 5.99 (d, J=7.5 Hz, 1H), 5.93 (s, 1H), 5.77-5.72 (m, 2H), 4.64 (t, J=5.5 Hz, 1H), 4.20 (s, 4H), 3.94-3.85 (m, 1H), 3.67 (t, J=4.7 Hz, 4H), 3.53-3.45 (m, 1H), 3.37 (t, J=4.9 Hz, 4H), 3.28 (d, J=13.8 Hz, 3H), 2.21 (s, 3H), 1.12 (d, J=6.6 Hz, 3H). $^{19}$F NMR (376 MHz, DMSO-d$_6$) δ −66.30 (3F), −125.50 (1F).

Example 78: (3S)—N-[3-[2-(2,5-dihydrofuran-3-yl)-6-[[(2R)-1-hydroxypropan-2-yl]amino]pyridin-4-yl]-4-methylphenyl]-3-(2,2,2-trifluoroethyl)pyrrolidine-1-carboxamide

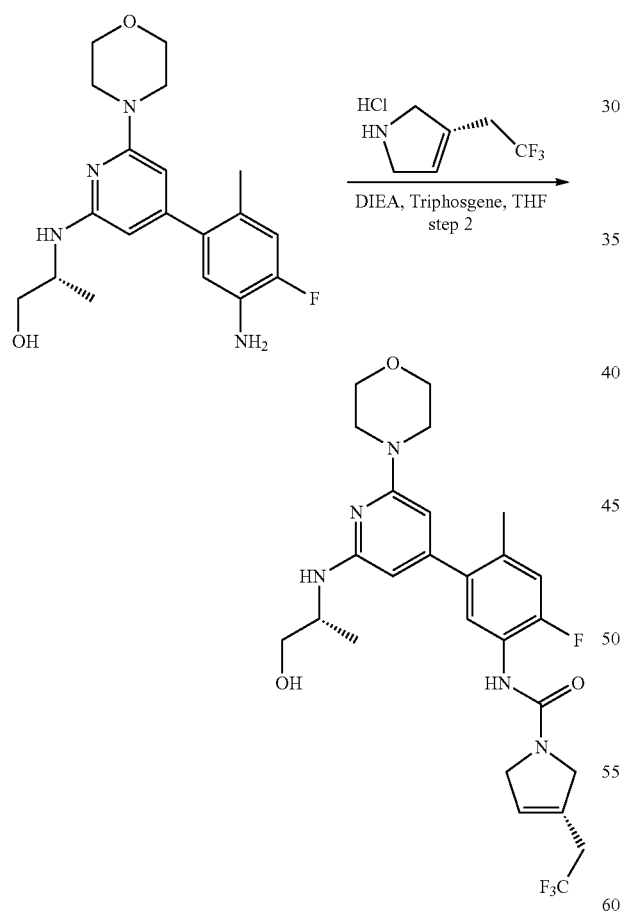

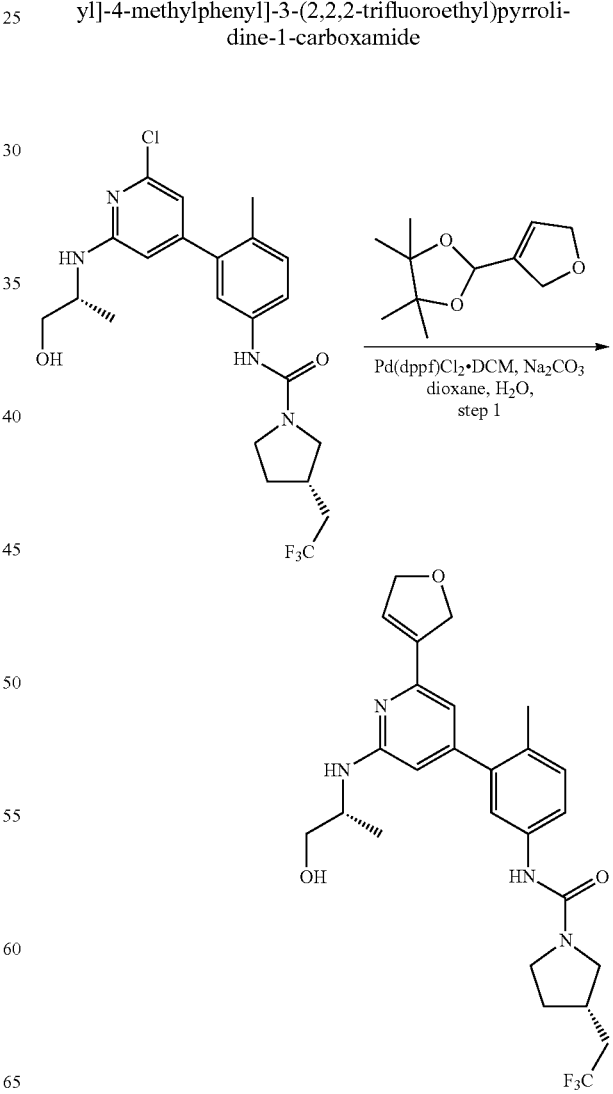

A mixture of (2R)-2-[[4-(5-amino-4-fluoro-2-methylphenyl)-6-(morpholin-4-yl)pyridin-2-yl]amino]propan-1-ol (60 mg, 0.166 mmol), DIEA (0.14 mL, 1.084 mmol) and triphosgene (20 mg, 0.067 mmol) in THF (6 mL) was stirred for 30 min at room temperature. To the above mixture was added 3-(2,2,2-trifluoroethyl)-2,5-dihydro-1H-pyrrole To a stirred mixture of (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (500 mg, 1.062 mmol) and 2-(2,5-dihydrofuran-3-yl)-4,4,5,5-tetramethyl-1,3,2-dioxaborolane (416 mg, 2.124 mmol) in 1,4-dioxane (6 mL) and H$_2$O (0.6 mL) were added Pd(dppf)Cl$_2$·CH$_2$Cl$_2$ (87 mg, 0.106 mmol) and Na$_2$CO$_3$ (338 mg, 3.185 mmol). The resulting mixture was stirred for 2 h at 80° C. under nitrogen atmosphere. The resulting mixture was concentrated under reduced pressure. The residue was purified by silica gel column chromatography, eluted with (PE/EtOAc/EtOH=12/3/1). The residue was purified by reverse phase flash chromatography with the following conditions: Column: Spherical C18, 20-40 um, 120 g; Mobile Phase A: water (5 mM NH$_4$HCO$_3$); Mobile Phase B: CH$_3$CN; Flow rate: 50 mL/min; Gradient:35%-55% B gradient in 30 min; Detector: 220 nm. The fractions containing the desired product were collected at 46% B and concentrated under reduced pressure to afford (3S)—N-[3-[2-(2,5-dihydrofuran-3-yl)-6-[[(2R)-1-hydroxypropan-2-yl]amino]pyridin-4-yl]-4-methylphenyl]-3-(2,2,2-trifluoroethyl)pyrrolidine-1-carboxamide (320 mg, 60%) as a white solid. MS ESI calculated for C$_{26}$H$_{31}$F$_3$N$_4$O$_3$ [M+H]$^+$, 505.23 found 505.25. $^1$H NMR (300 MHz, DMSO-d$_6$) δ 8.16 (s, 1H), 7.54-7.33 (m, 2H), 7.14 (d, J=8.4 Hz, 1H), 6.67-6.56 (m, 2H), 6.32 (t, J=2.0 Hz, 2H), 4.91 (td, J=5.0, 2.1 Hz, 2H), 4.75 (td, J=5.1, 2.1 Hz, 3H), 4.05-3.86 (m, 1H), 3.75-3.61 (m, 1H), 3.52 (dt, J=8.8, 2.5 Hz, 2H), 3.36 (s, 2H), 3.03 (t, J=9.3 Hz, 1H), 2.49-2.31 (m, 3H), 2.17 (s, 3H), 2.14-2.03 (m, 1H), 1.68 (d, J=10.4 Hz, 1H), 1.15 (d, J=6.6 Hz, 3H). $^{19}$F NMR (376 MHz, DMSO-d$_6$) δ −63.363 (3F).

Example 79: (3S)—N-[3-(2-[[(2R)-1-hydroxypropan-2-yl]amino]-6-(oxolan-3-yl)pyridin-4-yl)-4-methylphenyl]-3-(2,2,2-trifluoroethyl)pyrrolidine-1-carboxamide

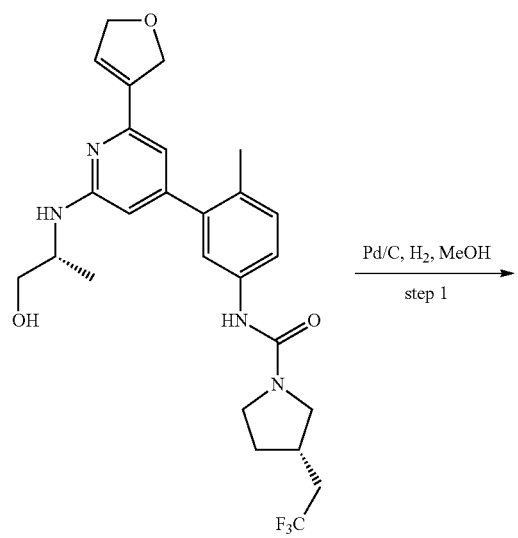

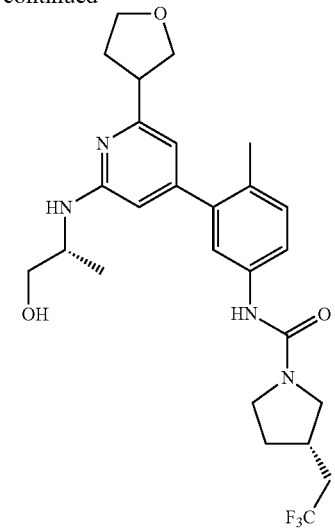

To a stirred mixture of (3S)—N-[3-[2-(2,5-dihydrofuran-3-yl)-6-[[(2R)-1-hydroxypropan-2-yl]amino]pyridin-4-yl]-4-methylphenyl]-3-(2,2,2-trifluoroethyl)pyrrolidine-1-carboxamide (100 mg, 0.198 mmol) in MeOH (5 mL) was added Pd/C (21 mg, 0.198 mmol). The resulting mixture was stirred for 16 h at room temperature under hydrogen atmosphere. The resulting mixture was filtered. The filter cake was washed with MeOH (3×20 mL). The filtrate was concentrated under reduced pressure. The residue was purified by reverse phase flash chromatography with the following conditions: Column: Spherical C18, 20-40 um, 120 g; Mobile Phase A: Water (plus 5 mmol/mL NH$_4$HCO$_3$); Mobile Phase B: CH$_3$CN; Flow rate: 60 mL/min; Gradient: 35%-55% B gradient in 25 min; Detector: 220 nm. The fractions containing the desired product were collected at 48% B and concentrated under reduced pressure to afford (3S)—N-[3-(2-[[(2R)-1-hydroxypropan-2-yl]amino]-6-(oxolan-3-yl)pyridin-4-yl)-4-methylphenyl]-3-(2,2,2-trifluoroethyl)pyrrolidine-1-carboxamide (79 mg, 79%) as a white solid. MS ESI calculated for C$_{26}$H$_{33}$F$_3$N$_4$O$_3$ [M+H]$^+$, 507.25 found 507.30. $^1$H NMR (300 MHz, DMSO-d$_6$) δ 8.13 (s, 1H), 7.44 (dd, J=8.3, 2.3 Hz, 1H), 7.37 (d, J=2.3 Hz, 1H), 7.12 (d, J=8.3 Hz, 1H), 6.33 (d, J=1.3 Hz, 1H), 6.30-6.17 (m, 2H), 4.73 (t, J=5.5 Hz, 1H), 4.03 (t, J=7.8 Hz, 1H), 3.99-3.61 (m, 5H), 3.60-3.43 (m, 2H), 3.40-3.34 (m, 3H), 3.03 (t, J=9.3 Hz, 1H), 2.44 (t, J=10.1 Hz, 3H), 2.25-2.00 (m, 6H), 1.66 (p, J=9.8 Hz, 1H), 1.15 (d, J=6.5 Hz, 3H). $^{19}$F NMR (376 MHz, DMSO-d$_6$) δ −63.360 (3F).

Example 80: (3S)—N-[3-(2-[[(2S)-1-hydroxypropan-2-yl]amino]-6-(1H-pyrazol-4-yl)pyridin-4-yl)-4-methylphenyl]-3-(2,2,2-trifluoroethyl)pyrrolidine-1-carboxamide

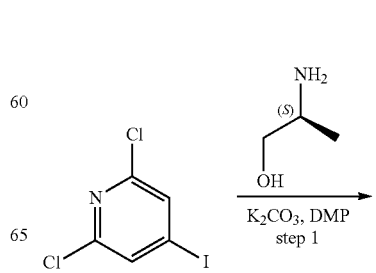

K$_2$CO$_3$, DMP
step 1

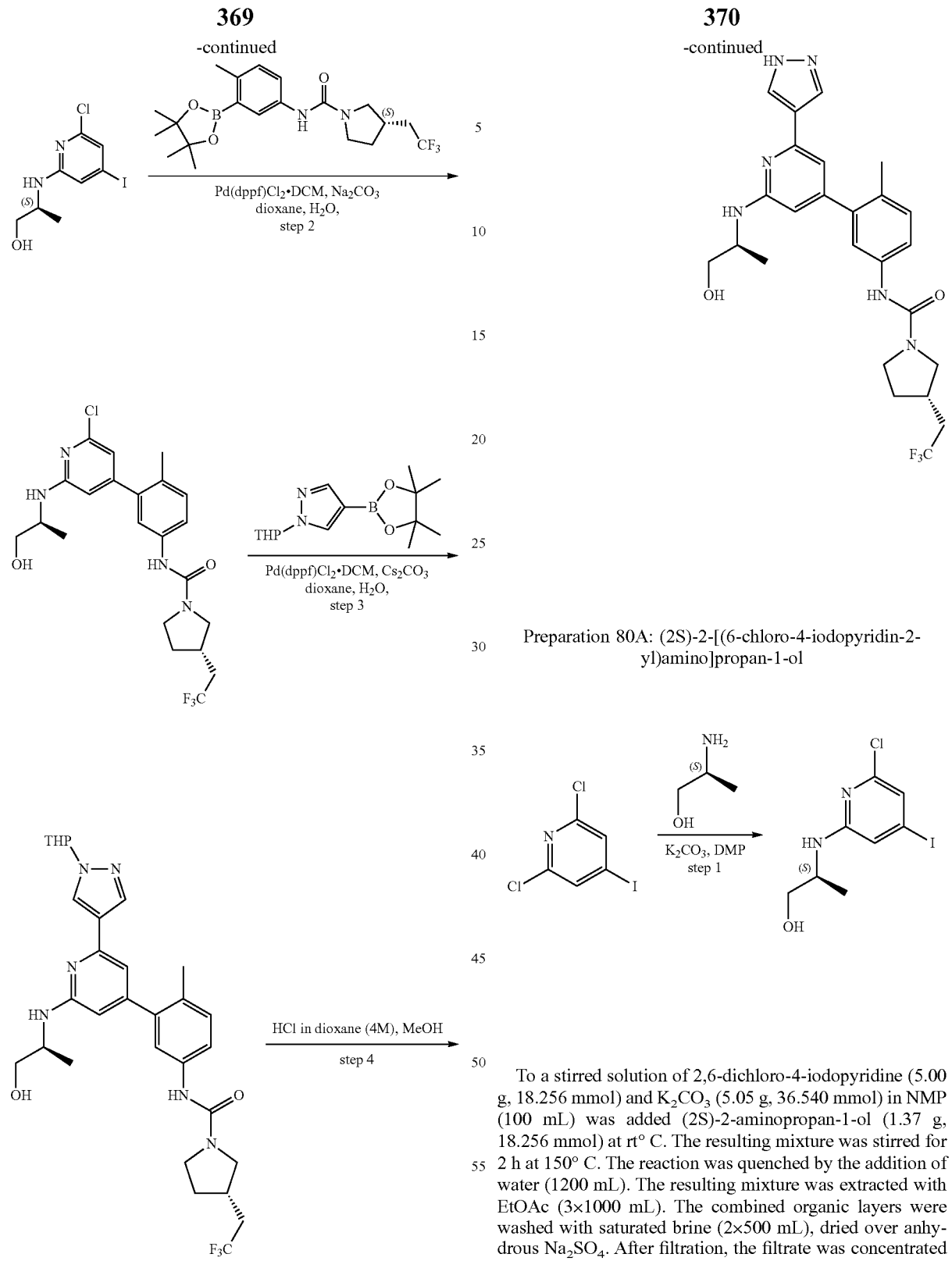

Preparation 80A: (2S)-2-[(6-chloro-4-iodopyridin-2-yl)amino]propan-1-ol

To a stirred solution of 2,6-dichloro-4-iodopyridine (5.00 g, 18.256 mmol) and K₂CO₃ (5.05 g, 36.540 mmol) in NMP (100 mL) was added (2S)-2-aminopropan-1-ol (1.37 g, 18.256 mmol) at rt° C. The resulting mixture was stirred for 2 h at 150° C. The reaction was quenched by the addition of water (1200 mL). The resulting mixture was extracted with EtOAc (3×1000 mL). The combined organic layers were washed with saturated brine (2×500 mL), dried over anhydrous Na₂SO₄. After filtration, the filtrate was concentrated under reduced pressure. The residue was purified by silica gel column chromatography, eluted with PE/EtOAc (2/1) to afford (2S)-2-[(6-chloro-4-iodopyridin-2-yl)amino]propan-1-ol (1.3 g, 23%) as a yellow oil. MS ESI calculated for C8H10ClIN2O [M+H]⁺, 312.95, found 313.05. ¹H NMR (400 MHz, Chloroform-d) δ 7.05 (s, 1H), 6.97 (s, 1H), 4.02-3.94 (m, 1H), 3.78-3.74 (m, 1H), 3.63-3.58 (m, 1H), 1.26 (d, J=10.8 Hz, 3H).

Preparation 80B: (3S)—N-[3-(2-chloro-6-[[(2S)-1-hydroxypropan-2-yl]amino]pyridin-4-yl)-4-methylphenyl]-3-(2,2,2-trifluoroethyl)pyrrolidine-1-carboxamide

Preparation 80C: (3S)—N-[3-(2-chloro-6-[[(2S)-1-hydroxypropan-2-yl]amino]pyridin-4-yl)-4-methylphenyl]-3-(2,2,2-trifluoroethyl)pyrrolidine-1-carboxamide

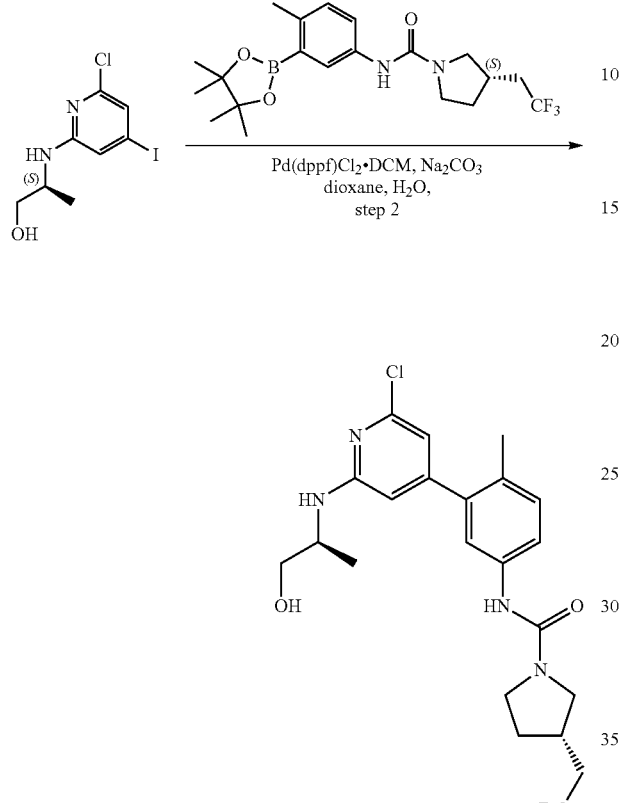

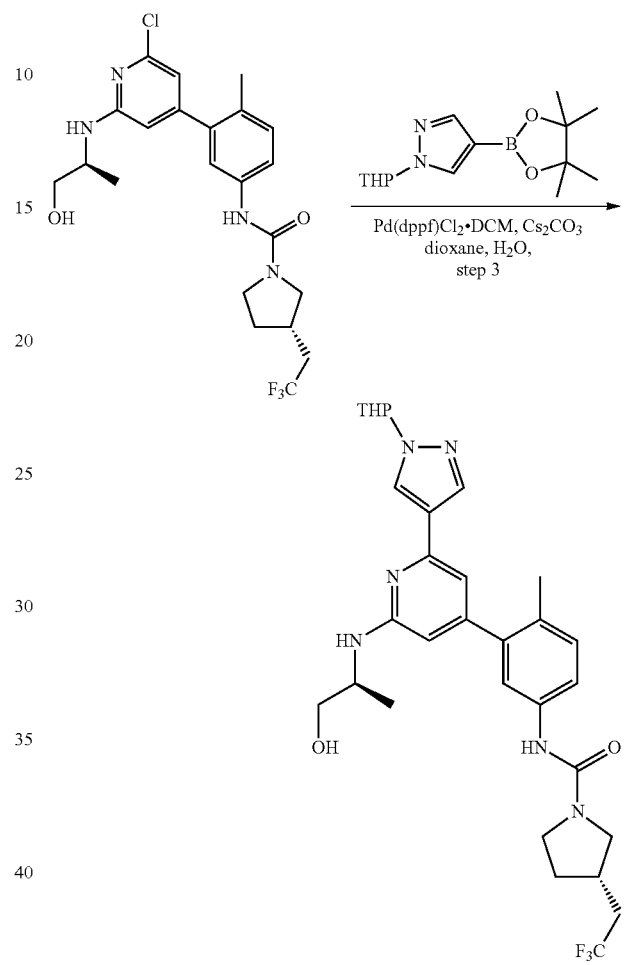

A mixture of (2S)-2-[(6-chloro-4-iodopyridin-2-yl)amino]propan-1-ol (300 mg, 0.960 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (395 mg, 0.960 mmol), Pd(dppf)Cl$_2$·CH$_2$Cl$_2$ (78 mg, 0.096 mmol) and Na$_2$CO$_3$ (305 mg, 2.880 mmol) in dioxane (3 mL) and H$_2$O (0.75 mL) was stirred for 16 h at 60° C. under nitrogen atmosphere. The reaction was quenched by the addition of water (50 mL) at room temperature. The resulting mixture was extracted with EtOAc (2×100 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with (PE/EtOAc/EtOH=8/3/1) to afford (3S)—N-[3-(2-chloro-6-[[(2S)-1-hydroxypropan-2-yl]amino]pyridin-4-yl)-4-methylphenyl]-3-(2,2,2-trifluoroethyl)pyrrolidine-1-carboxamide (410 mg, 85%) as a brown solid. MS ESI calculated for C$_{22}$H$_{26}$ClF$_3$N$_4$O$_2$ [M+H]$^+$, 471.17, found 471.20. $^1$H NMR (400 MHz, chloroform-d) δ 7.31-7.30 (m, 1H), 7.19-7.16 (m, 1H), 6.57 (s, 1H), 6.27-6.23 (m, 2H), 4.77 (s, 1H), 4.13-3.81 (m, 1H), 3.79-3.74 (m, 2H), 3.67-3.58 (m, 2H), 3.49-3.40 (m, 1H), 3.15-3.09 (m, 1H), 2.57-2.55 (m, 1H), 2.34-2.24 (m, 5H), 1.82-1.72 (m, 1H), 1.31-1.25 (m, 3H).

A mixture of (3S)—N-[3-(2-chloro-6-[[(2S)-1-hydroxypropan-2-yl]amino]pyridin-4-yl)-4-methylphenyl]-3-(2,2,2-trifluoroethyl)pyrrolidine-1-carboxamide (300 mg, 0.637 mmol), 1-(oxan-2-yl)-4-(4,4,5,5-tetramethyl-1,3,2-dioxaborolan-2-yl) pyrazole (354 mg, 1.274 mmol), Pd(dppf)Cl$_2$·CH$_2$Cl$_2$ (52 mg, 0.064 mmol) and Cs$_2$CO$_3$ (622 mg, 1.911 mmol) in dioxane (3 mL) and H$_2$O (0.3 mL) was stirred for 2 h at 80° C. under nitrogen atmosphere. The reaction was quenched by the addition of water (50 mL) at room temperature. The resulting mixture was extracted with EtOAc (3×100 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with (PE/EtOAc/EtOH=8/3/1) to afford (3S)—N-[3-(2-[[(2S)-1-hydroxypropan-2-yl]amino]-6-[1-(oxan-2-yl) pyrazol-4-yl]pyridin-4-yl)-4-methylphenyl]-3-(2,2,2-trifluoroethyl)pyrrolidine-1-carboxamide (330 mg, 79%) as a light brown solid. MS ESI calculated for C$_{30}$H$_{37}$F$_3$N$_6$O$_3$ [M+H]$^+$, 587.29, found 587.30. $^1$H NMR (300 MHz, chloroform-d) δ 8.22 (s, 1H), 7.95 (s, 1H), 7.40-7.36 (m, 2H), 7.21-7.19 (m, 1H), 6.79 (s, 1H), 6.28-6.26 (m, 2H), 5.43-5.39 (m, 1H), 4.18-4.07 (m, 2H), 3.85-3.84 (m, 1H), 3.81-3.62 (m, 5H), 3.50-3.41 (m, 1H), 3.16-3.10 (m, 1H), 2.57 (m, 1H), 2.34-2.26 (m, 3H), 2.10-2.07 (m, 2H), 1.82-1.62 (m, 6H), 1.31-1.26 (m, 3H). $^{19}$F NMR (282 MHz, chloroform-d) δ −64.58-65.56 (3F).

Example 80: (3S)—N-[3-(2-[[(2S)-1-hydroxypropan-2-yl]amino]-6-(1H-pyrazol-4-yl)pyridin-4-yl)-4-methylphenyl]-3-(2,2,2-trifluoroethyl)pyrrolidine-1-carboxamide

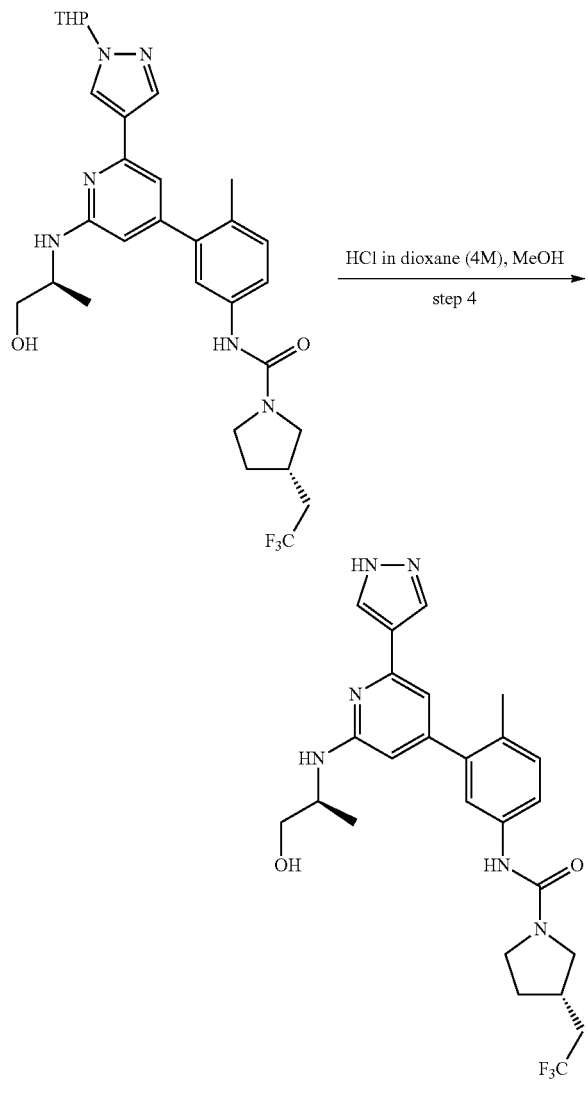

To a stirred mixture of (3S)—N-[3-(2-[[(2S)-1-hydroxypropan-2-yl]amino]-6-[1-(oxan-2-yl) pyrazol-4-yl]pyridin-4-yl)-4-methylphenyl]-3-(2,2,2-trifluoroethyl)pyrrolidine-1-carboxamide (330 mg, 0.563 mmol) in MeOH (3 mL) and THF (4 mL) was added HCl (gas) in 1,4-dioxane (1 mL) dropwise at 0° C. The resulting mixture was stirred for 30 min at room temperature. The reaction was quenched by the addition of sat. NaHCO$_3$ (aq.) (10 mL) at 0° C. The resulting mixture was extracted with EtOAc (2×20 mL). The combined organic layers were washed with brine (3×50 mL), dried over anhydrous Na$_2$SO$_4$. After filtration, the filtrate was concentrated under reduced pressure. The residue was purified by reverse flash chromatography with the following conditions: Mobile Phase A: water (10 mmol/L NH$_4$HCO$_3$), Mobile Phase B: CH$_3$CN; Flow rate: 20 mL/min; Gradient: 40 B to 65 B in 20 min. This resulted in (3S)—N-[3-(2-[[(2S)-1-hydroxypropan-2-yl]amino]-6-(1H-pyrazol-4-yl)pyridin-4-yl)-4-methylphenyl]-3-(2,2,2-trifluoroethyl)pyrrolidine-1-carboxamide (168 mg, 59%) as an off-white solid. MS ESI calculated for C$_{25}$H$_{29}$F$_3$N$_6$O$_2$ [M+H]$^+$, 503.23; found 503.30. $^1$H NMR (400 MHz, DMSO-d$_6$) δ 12.91 (s, 1H), 8.19-8.15 (m, 2H), 7.98 (s, 1H), 7.48-7.40 (m, 2H), 7.15-7.13 (m, 1H), 6.75 (s, 1H), 6.23-6.21 (m, 2H), 4.89-4.86 (m, 1H), 4.03-4.00 (m, 1H), 3.70-3.65 (m, 1H), 3.58-3.51 (m, 2H), 3.38-3.28 (m, 3H), 3.05-3.00 (m, 1H), 2.53-2.50 (m, 2H), 2.20 (s, 3H), 2.15-2.05 (m, 1H), 1.75-1.55 (m, 1H), 1.20 (s, 3H). $^{19}$F NMR (282 MHz, DMSO-d$_6$) δ −63.36 (3F).

Example 81: (3S)—N-[3-(6-[[(2R)-1-hydroxypropan-2-yl]amino]-[2,4'-bipyridin]-4-yl)-4-methylphenyl]-3-(2,2,2-trifluoroethyl)pyrrolidine-1-carboxamide

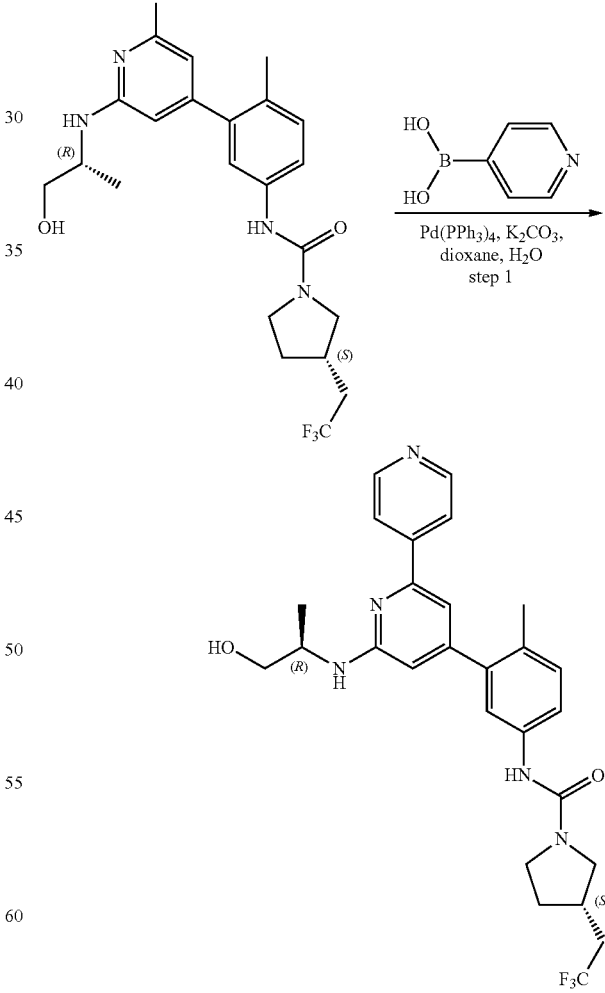

To a stirred mixture of (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (150 mg, 0.319 mmol), pyridin-4-ylboronic acid (58 mg, 0.478 mmol) and K$_2$CO$_3$ (88 mg, 0.637 mmol) in dioxane (2 mL) and H$_2$O (0.5 mL) was added Pd(PPh$_3$)$_4$ (37 mg, 0.032 mmol) at room temperature. The reaction mixture was stirred for 2 h at 80° C. under nitrogen atmosphere. The resulting mixture was diluted with water (50 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with (EA/PE/EtOH=12/3/1). The fractions containing the desired product were collected and concentrated under reduced pressure. The residue was purified by reverse phase chromatography, eluted with CH$_3$CN in water (with 10 mmol/mL NH$_4$HCO$_3$). The fractions containing the desired product were collected and concentrated under reduced pressure to afford (3S)—N-[3-(6-[[(2R)-1-hydroxypropan-2-yl]amino]-[2,4'-bipyridin]-4-yl)-4-methylphenyl]-3-(2,2,2-trifluoroethyl)pyrrolidine-1-carboxamide (141 mg, 86%) as a white solid. MS ESI calculated for C$_{27}$H$_{30}$F$_3$N$_5$O$_2$ [M+H]$^+$, 514.24, found 514.20; $^1$H NMR (400 MHz, DMSO-d$_6$) δ 8.67-8.61 (m, 2H), 8.18 (s, 1H), 8.06-8.00 (m, 2H), 7.52-7.43 (m, 2H), 7.20-7.13 (m, 2H), 6.60 (d, J=7.6 Hz, 1H), 6.51 (d, J=1.1 Hz, 1H), 4.76 (t, J=5.6 Hz, 1H), 4.16 (p, J=6.4 Hz, 1H), 3.67 (dd, J=10.2, 6.9 Hz, 1H), 3.63-3.48 (m, 2H), 3.40 (dt, J=10.4, 6.0 Hz, 1H), 3.32-3.27 (m, 1H), 3.03 (t, J=9.4 Hz, 1H), 2.48-2.36 (m, 3H), 2.22 (s, 3H), 2.09 (h, J=6.3 Hz, 1H), 1.66 (p, J=9.8 Hz, 1H), 1.21 (d, J=6.6 Hz, 3H). $^{19}$F NMR (282 MHz, DMSO-d$_6$) δ -63.37 (3F).

Example 82: (3S)—N-[3-(2'-amino-6-[[(2R)-1-hydroxypropan-2-yl]amino]-[2,4'-bipyridin]-4-yl)-4-methylphenyl]-3-(2,2,2-trifluoroethyl)pyrrolidine-1-carboxamide

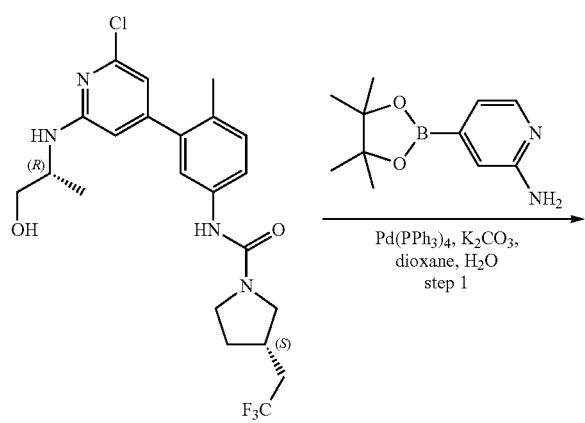

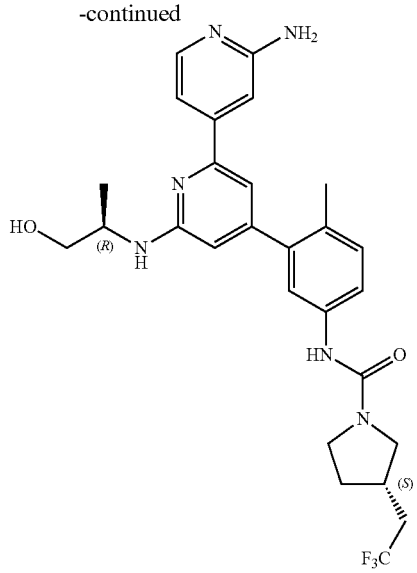

To a stirred mixture of (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (150 mg, 0.319 mmol), 4-(4,4,5,5-tetramethyl-1,3,2-dioxaborolan-2-yl)pyridin-2-amine (84 mg, 0.382 mmol) and K$_2$CO$_3$ (88 mg, 0.637 mmol) in dioxane (2 ml) and H$_2$O (0.5 ml) was added Pd(PPh$_3$)$_4$ (37 mg, 0.032 mmol). The reaction mixture was stirred for 2 h at 80° C. under N$_2$ atmosphere. The resulting mixture was diluted with water (40 mL). The resulting mixture was extracted with EtOAc (3×40 mL). The combined organic layers were washed with brine (3×40 mL), dried over anhydrous Na$_2$SO$_4$. After filtration, the filtrate was concentrated under reduced pressure. The residue was purified by silica gel column chromatography, eluted with (EA/PE/EtOH=12/3/1). The fractions containing the desired product were collected and concentrated under reduced pressure. The residue was purified by reverse phase chromatography, eluted with CH$_3$CN in water (with 10 mmol/mL NH$_4$HCO$_3$). The fractions containing the desired product were collected and concentrated under reduced pressure to afford (3S)—N-[3-(2'-amino-6-[[(2R)-1-hydroxypropan-2-yl]amino]-[2,4'-bipyridin]-4-yl)-4-methylphenyl]-3-(2,2,2-trifluoroethyl)pyrrolidine-1-carboxamide (101 mg, 58%) as a white solid. MS ESI calculated for C$_{27}$H$_{31}$F$_3$N$_6$O$_2$ [M+H]$^+$, 529.25, found 529.30; $^1$H NMR (400 MHz, DMSO-d$_6$) δ 8.17 (s, 1H), 7.95 (dd, J=5.2, 0.8 Hz, 1H), 7.51-7.42 (m, 2H), 7.19-7.07 (m, 3H), 6.90 (d, J=1.2 Hz, 1H), 6.51-6.44 (m, 2H), 5.91 (s, 2H), 4.75 (t, J=5.5 Hz, 1H), 4.14 (p, J=6.4 Hz, 1H), 3.67 (dd, J=10.2, 6.9 Hz, 1H), 3.59-3.50 (m, 2H), 3.40 (dt, J=10.4, 5.9 Hz, 1H), 3.29 (d, J=6.7 Hz, 1H), 3.03 (t, J=9.4 Hz, 1H), 2.49-2.36 (m, 3H), 2.21 (s, 3H), 2.13-2.05 (m, 1H), 1.66 (p, J=10.1 Hz, 1H), 1.20 (d, J=6.6 Hz, 3H).

Example 83: (3S)—N-[3-(2'-cyano-6-[[(2R)-1-hy-droxypropan-2-yl]amino]-[2,4'-bipyridin]-4-yl)-4-methylphenyl]-3-(2,2,2-trifluoroethyl)pyrrolidine-1-carboxamide

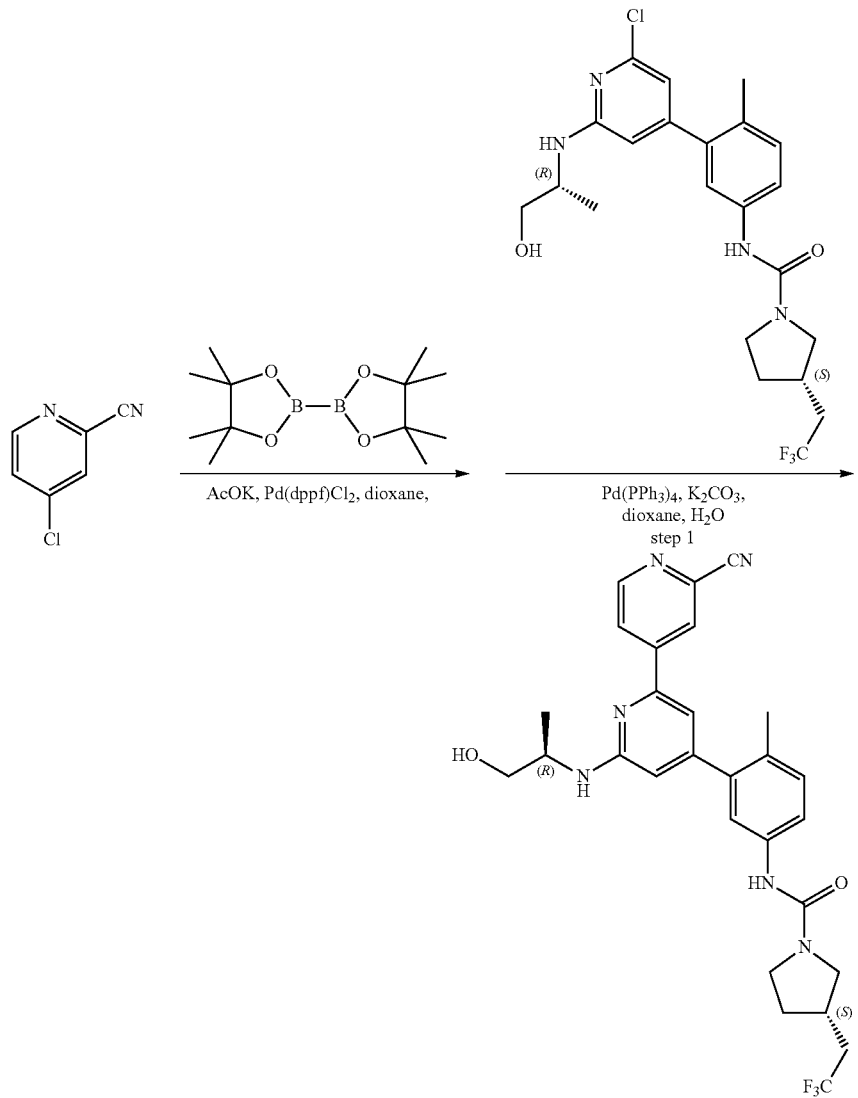

To a solution of 4-chloropyridine-2-carbonitrile (0.50 g, 3.61 mmol) and bis(pinacolato)diboron (1.83 g, 7.21 mmol) in 1,4-dioxane (10 mL) were added AcOK (1.06 g, 10.83 mmol) and Pd(dppf)Cl$_2$ (0.53 g, 0.72 mmol). After stirring for 2 h at 100° C. under a nitrogen atmosphere. To above solution were added (3S)—N-[3-(2-chloro-6-[[(2R)-1-hydroxypropan-2-yl]amino]pyridin-4-yl)-4-methylphenyl]-3-(2,2,2-trifluoroethyl)pyrrolidine-1-carboxamide (0.30 g, 0.65 mmol), 4-(4,4,5,5-tetramethyl-1,3,2-dioxaborolan-2-yl)pyridine-2-carbonitrile (0.30 g, 1.30 mmol), H$_2$O (0.4 mL), Pd(PPh$_3$)$_4$ (0.07 mg, 0.06 mmol) and K$_2$CO$_3$ (0.18 g, 1.30 mmol) at room temperature under nitrogen atmosphere. After stirring for 2 h at 80° C. The resulting mixture was concentrated under reduced pressure. The residue was purified by Prep-TLC, eluted with (PE/EtOAc/EtOH=12/3/1). The residue was purified by reverse phase flash chromatography with the following conditions: Column: Spherical C18, 20-40 um, 120 g; Mobile Phase A: Water (plus 5 mmol/mL NH$_4$HCO$_3$); Mobile Phase B: CH$_3$CN; Flow rate: 80 mL/min; Gradient:38%-60% B gradient in 25 min; Detector: 220 nm. The fractions containing the desired product were collected at 54% B to afford (3S)—N-[3-(2-cyano-6-[[(2R)-1-hydroxypropan-2-yl]amino]-[2,4-bipyridin]-4-yl)-4-methylphenyl]-3-(2,2,2-trifluoroethyl)pyrrolidine-1-carboxamide (0.12 g, 33%) as a light yellow solid. MS ESI calculated for C$_{28}$H$_{29}$F$_3$N$_6$O$_2$ [M+H]$^+$, 539.23, found 539.10. $^1$H NMR (400 MHz, DMSO-d$_6$) δ 8.81 (dd, J=5.2, 0.8 Hz, 1H), 8.67 (dd, J=1.8, 0.8 Hz, 1H), 8.40 (dd, J=5.2, 1.8 Hz, 1H), 8.19 (s, 1H), 7.52-7.44 (m, 2H), 7.34 (d, J=1.1 Hz, 1H), 7.18 (d, J=8.2 Hz, 1H), 6.71 (d, J=7.6 Hz, 1H), 6.57 (d, J=1.1 Hz, 1H), 4.76 (t, J=5.6 Hz, 1H), 4.18 (p, J=6.4 Hz, 1H), 3.68 (dd, J=10.2, 6.9 Hz, 1H), 3.63-3.48 (m, 2H), 3.39 (dt, J=10.4, 6.1 Hz, 1H), 3.30 (dd, J=10.0, 6.7 Hz, 1H), 3.03 (t, J=9.4 Hz, 1H), 2.51-2.34 (m, 3H), 2.22 (s, 3H), 2.09 (d, J=10.3 Hz, 1H), 1.66 (p, J=9.7 Hz, 1H), 1.22 (d, J=6.6 Hz, 3H). $^{19}$F NMR (376 MHz, DMSO-d$_6$) δ −63.367 (3F).

Examples 84 and 85: (3S)—N-[3-(2-[[(2R)-1-hydroxypropan-2-yl]amino]-6-[(1R,6S)-3-oxabicyclo[4.1.0]heptan-6-yl)pyridin-4-yl)-4-methylphenyl]-3-(2,2,2-trifluoroethyl)pyrrolidine-1-carboxamide, (3S)—N-[3-(2-[[(2R)-1-hydroxypropan-2-yl]amino]-6-[(1S,6R)-3-oxabicyclo[4.1.0]heptan-6-yl)pyridin-4-yl)-4-methylphenyl]-3-(2,2,2-trifluoroethyl)pyrrolidine-1-carboxamide

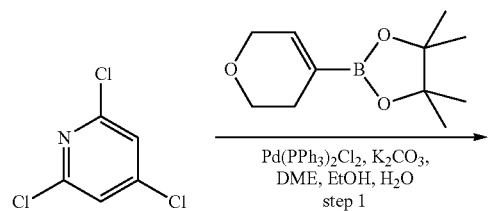

Pd(PPh₃)₂Cl₂, K₂CO₃,
DME, EtOH, H₂O
step 1

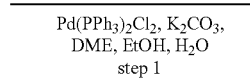

NaH, DMSO
step 2

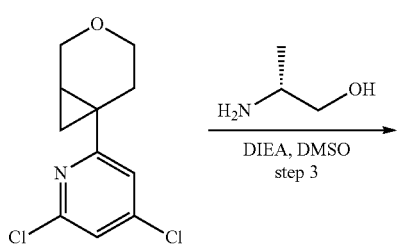

DIEA, DMSO
step 3

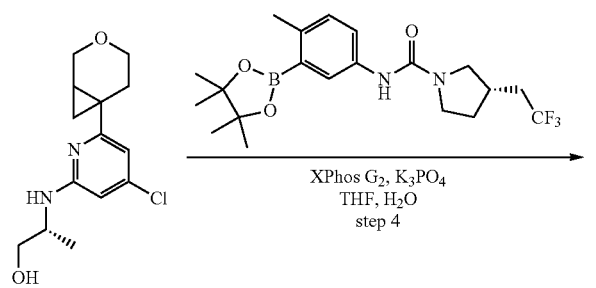

XPhos G₂, K₃PO₄
THF, H₂O
step 4

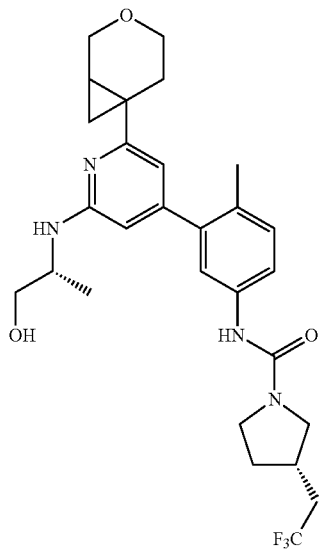

chiral separation
step 5

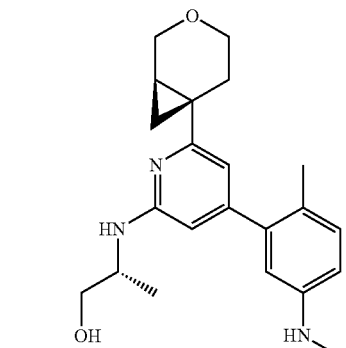

+

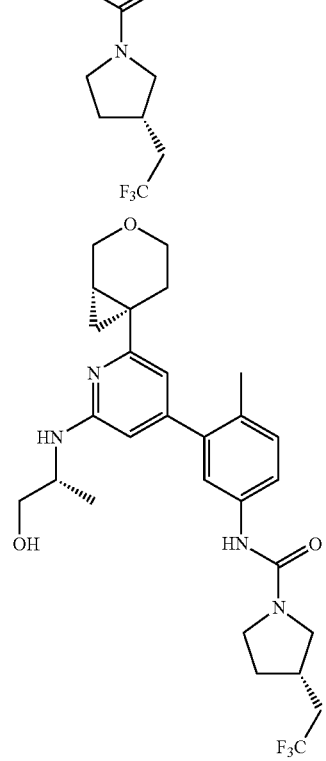

Preparation 84A: 2,4-dichloro-6-(3,6-dihydro-2H-pyran-4-yl)pyridine

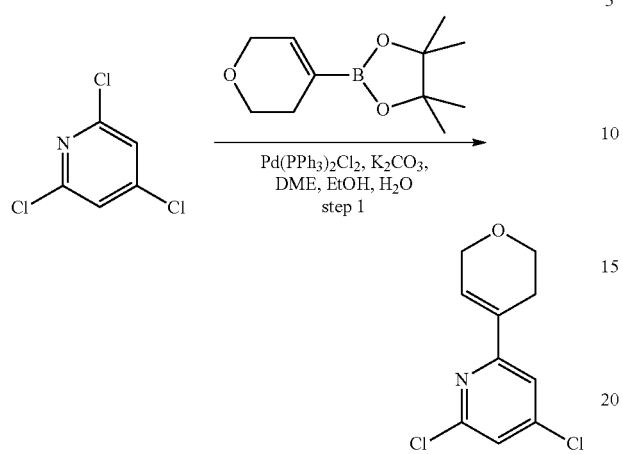

To a stirred solution of 2,4,6-trichloropyridine (5.00 g, 27.41 mmol), 2-(3,6-dihydro-2H-pyran-4-yl)-4,4,5,5-tetramethyl-1,3,2-dioxaborolane (5.76 g, 27.41 mmol) and K$_2$CO$_3$ (7.58 g, 54.82 mmol) in DME/EtOH/H$_2$O=2/1/2 (50 mL) was added Pd(PPh$_3$)$_2$Cl$_2$ (0.96 g, 1.37 mmol) at room temperature under nitrogen atmosphere. The resulting mixture was stirred for 16 h at 80° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (2/1) to afford 2,4-dichloro-6-(3,6-dihydro-2H-pyran-4-yl)pyridine (2.77 g, 44%) as an off-white solid. MS ESI calculated for C$_{10}$H$_9$Cl$_2$NO [M+H]$^+$, 230.01, found 229.90. $^1$H NMR (300 MHz, chloroform-d) δ 7.26-7.25 (m, 1H), 7.23-7.22 (m, 1H), 6.86-6.82 (m, 1H), 4.40-4.37 (m, 2H), 3.95-3.91 (m, 2H), 2.60-2.54 (m, 2H).

Preparation 84B: 2,4-dichloro-6-[3-oxabicyclo[4.1.0]heptan-6-yl]pyridine

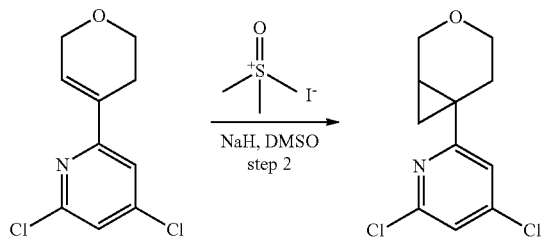

To a stirred solution of trimethylsulfoxonium iodide (7.65 g, 34.77 mmol) in DMSO (20 mL) was added NaH (1.40 g, 35.03 mmol, 60%) in portions at 0° C. under nitrogen atmosphere. The resulting mixture was stirred for 30 min at room temperature under nitrogen atmosphere. To the above mixture was added 2,4-dichloro-6-(3,6-dihydro-2H-pyran-4-yl)pyridine (2.00 g, 8.69 mmol) at room temperature. The resulting mixture was stirred for additional 16 h at 60° C. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (4/1) to afford 2,4-dichloro-6-[3-oxabicyclo[4.1.0]heptan-6-yl]pyridine (1.7 g, 80%) as an off-white solid. MS ESI calculated for C$_{11}$H$_{11}$Cl$_2$NO [M+H]$^+$. 244.02, found 243.95. $^1$H NMR (300 MHz, chloroform-d) δ 7.14-7.13 (m, 2H), 4.04-3.93 (m, 2H), 3.68-3.61 (m, 1H), 3.50-3.41 (m, 1H), 2.49-2.41 (m, 1H), 2.15-2.06 (m, 1H), 1.82-1.75 (m, 1H), 1.36-1.32 (m, 1H), 1.15-1.11 (m, 1H).

Preparation 84C: (2R)-2-[(4-chloro-6-[3-oxabicyclo[4.1.0]heptan-6-yl]pyridin-2-yl)amino]propan-1-ol

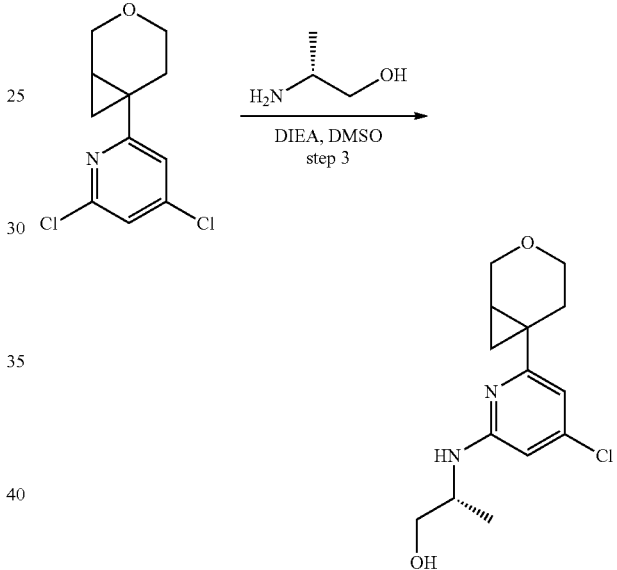

To a stirred solution of 2,4-dichloro-6-[3-oxabicyclo[4.1.0]heptan-6-yl]pyridine (1.40 g, 5.73 mmol) and (R)-(−)-2-amino-1-propanol (0.86 g, 11.47 mmol) in DMSO (15 mL) was added DIEA (1.48 g, 11.47 mmol) dropwise at room temperature under nitrogen atmosphere. The resulting mixture was stirred for 16 h at 130° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by reverse flash chromatography with the following conditions: column, C18 silica gel; mobile phase, CH$_3$CN in water (0.1% TFA), 5% to 95% gradient in 40 min; detector, UV 254 nm; to afford (2R)-2-[(4-chloro-6-[3-oxabicyclo[4.1.0]heptan-6-yl]pyridin-2-yl)amino]propan-1-ol (0.21 g, 13%) as an off-white solid. MS ESI calculated for C$_{14}$H$_{19}$ClN$_2$O$_2$ [M+H]$^+$. 283.11, found 283.20. $^1$H NMR (300 MHz, DMSO-d$_6$) δ 6.44-6.42 (m, 2H), 6.31 (m, 1H), 4.65 (s, 1H), 3.91-3.74 (m, 3H), 3.50-3.36 (m, 3H), 3.29-3.22 (m, 1H), 2.42-2.34 (m, 1H), 1.92-1.83 (m, 1H), 1.67-1.61 (m, 1H), 1.22-1.19 (m, 1H), 1.09-1.07 (m, 3H), 0.90-0.85 (m, 1H).

Preparation 84D: (3S)—N-[3-(2-[[(2R)-1-hydroxy-propan-2-yl]amino]-6-[3-oxabicyclo[4.1.0]heptan-6-yl]pyridin-4-yl)-4-methylphenyl]-3-(2,2,2-trifluoroethyl)pyrrolidine-1-carboxamide

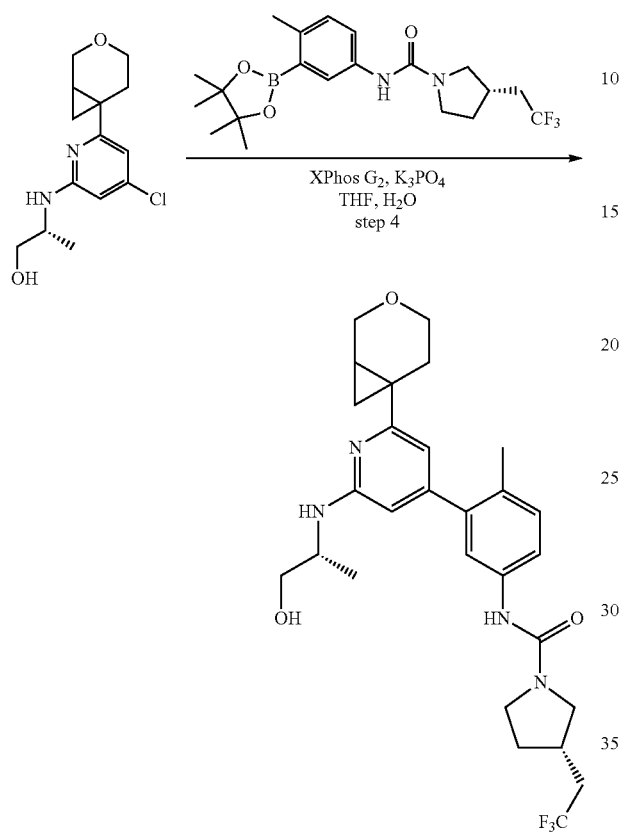

To a stirred solution of (2R)-2-[(4-chloro-6-[3-oxabicyclo[4.1.0]heptan-6-yl]pyridin-2-yl)amino]propan-1-ol (310 mg, 1.096 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (452 mg, 1.096 mmol) and K$_3$PO$_4$ (465 mg, 2.193 mmol) in THF/H$_2$O=10/1 (4 mL) was added XPhos Pd G2 (86 mg, 0.110 mmol) at room temperature under nitrogen atmosphere. The resulting mixture was stirred for 16 h at 80° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with (PE/EA/EtOH=8/3:1) to afford (3S)—N-[3-(2-[[(2R)-1-hydroxypropan-2-yl]amino]-6-[3-oxabicyclo[4.1.0]heptan-6-yl]pyridin-4-yl)-4-methylphenyl]-3-(2,2,2-trifluoroethyl)pyrrolidine-1-carboxamide (350 mg, 60%) as a light yellow solid. MS ESI calculated for C$_{28}$H$_{35}$F$_3$N$_4$O$_3$ [M+H]$^+$. 533.27, found 533.15. $^1$H NMR (300 MHz, DMSO-d$_6$) δ 8.14 (s, 1H), 7.46-7.43 (m, 1H), 7.37-7.36 (m, 1H), 7.14-7.11 (m, 1H), 6.34 (s, 1H), 6.19 (m, 2H), 4.70 (m, 1H), 3.97-3.92 (m, 2H), 3.82-3.78 (m, 1H), 3.71-3.65 (m, 1H), 3.57-3.47 (m, 3H), 3.42-3.35 (m, 2H), 3.31-3.28 (m, 1H), 3.06-3.00 (m, 1H), 2.24 (m, 3H), 2.17-2.10 (m, 4H), 2.00-1.89 (m, 1H), 1.74-1.63 (m, 3H), 1.28-1.27 (m, 1H), 1.15-1.12 (m, 3H), 0.93-0.88 (m, 1H). $^{19}$F NMR (282 MHz, DMSO-d$_6$) δ −63.36 (3F).

Examples 84 and 85: (3S)—N-[3-(2-[[(2R)-1-hydroxypropan-2-yl]amino]-6-[(1R,6S)-3-oxabicyclo[4.1.0]heptan-6-yl]pyridin-4-yl)-4-methylphenyl]-3-(2,2,2-trifluoroethyl)pyrrolidine-1-carboxamide, (3S)—N-[3-(2-[[(2R)-1-hydroxypropan-2-yl]amino]-6-[(1S,6R)-3-oxabicyclo[4.1.0]heptan-6-yl]pyridin-4-yl)-4-methylphenyl]-3-(2,2,2-trifluoroethyl)pyrrolidine-1-carboxamide

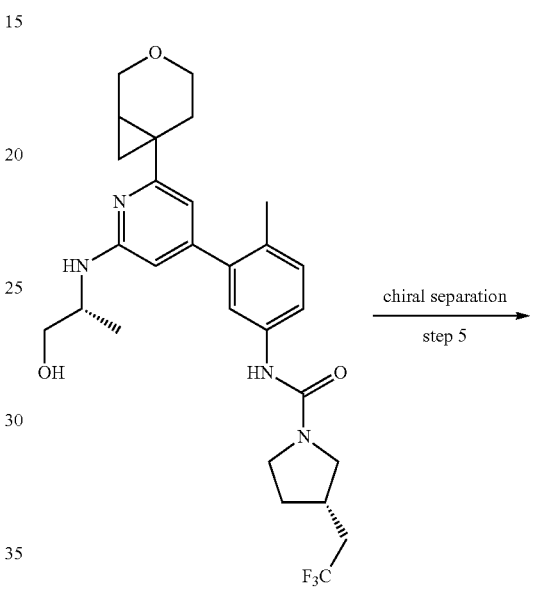

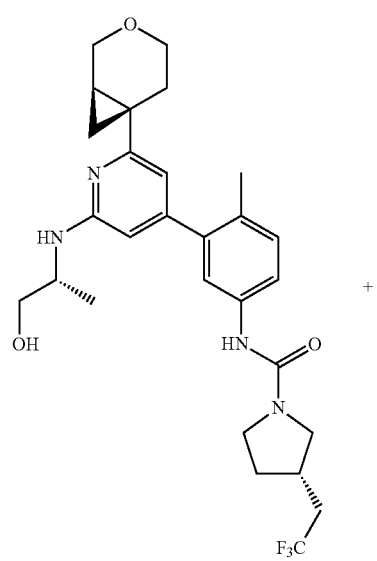

-continued

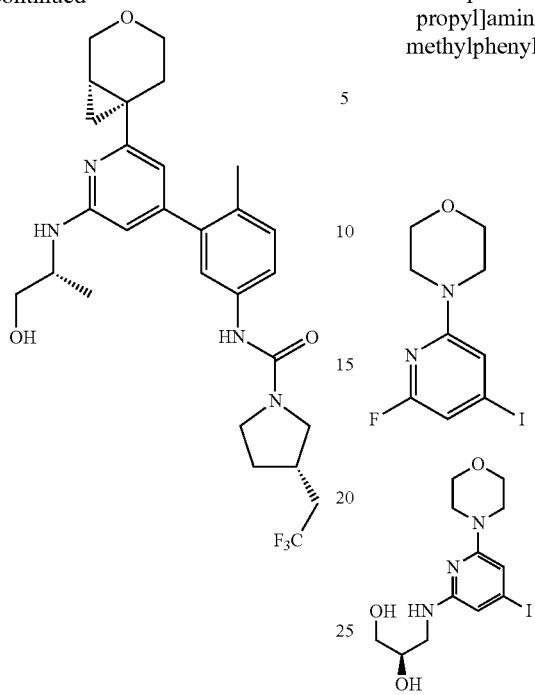

The crude product ((3S)—N-[3-(2-[[(2R)-1-hydroxypropan-2-yl]amino]-6-[3-oxabicyclo[4.1.0]heptan-6-yl]pyridin-4-yl)-4-methylphenyl]-3-(2,2,2-trifluoroethyl)pyrrolidine-1-carboxamide (350 mg, 0.657 mmol) was resolved by Chiral-Prep-HPLC with the following conditions (Column: CHIRAL ART Cellulose-SB, 2*25 cm, 5 um; Mobile Phase A: Hex (0.5% 2M NH$_3$-MeOH)-HPLC, Mobile Phase B: EtOH-HPLC; Flow rate: 20 mL/min; Gradient:20 B to 20 B in 19 min; 254/220 nm). The first peak afforded (3S)—N-[3-(2-[[(2R)-1-hydroxypropan-2-yl]amino]-6-[(1R,6S)-3-oxabicyclo[4.1.0]heptan-6-yl]pyridin-4-yl)-4-methylphenyl]-3-(2,2,2-trifluoroethyl)pyrrolidine-1-carboxamide (139 mg, 40%) as an off-white solid. MS ESI calculated for $C_{28}H_{35}F_3N_4O_3$ [M+H]$^+$. 533.27, found 533.20. $^1$H NMR (400 MHz, DMSO-d$_6$) δ 8.12 (s, 1H), 7.45-7.35 (m, 2H), 7.12-7.10 (m, 1H), 6.33-6.32 (m, 1H), 6.17-6.14 (m, 2H), 4.69-4.65 (m, 1H), 3.95-3.90 (m, 2H), 3.80-3.77 (m, 1H), 3.69-3.63 (m, 1H), 3.52-3.45 (m, 3H), 3.38-3.34 (m, 2H), 3.31-3.25 (m, 1H), 3.04-2.99 (m, 1H), 2.46-2.40 (m, 3H), 2.15-2.05 (m, 4H), 1.96-1.87 (m, 1H), 1.73-1.63 (m, 3H), 1.26-1.22 (m, 1H), 1.13-1.10 (m, 3H), 0.90-0.88 (m, 1H). $^{19}$F NMR (376 MHz, DMSO-d$_6$) δ −63.36 (3F).

The second peak afforded (3S)—N-[3-(2-[[(2R)-1-hydroxypropan-2-yl]amino]-6-[(1S,6R)-3-oxabicyclo[4.1.0]heptan-6-yl]pyridin-4-yl)-4-methylphenyl]-3-(2,2,2-trifluoroethyl)pyrrolidine-1-carboxamide (150 mg, 43%) as an off-white solid. MS ESI calculated for $C_{28}H_{35}F_3N_4O_3$ [M+H]$^+$. 533.27, found 533.20. $^1$H NMR (400 MHz, DMSO-d$_6$) δ 8.12 (s, 1H), 7.44-7.35 (m, 2H), 7.12-7.10 (m, 1H), 6.33 (m, 1H), 6.17-6.15 (m, 2H), 4.70-4.66 (m, 1H), 3.95-3.90 (m, 2H), 3.80-3.77 (m, 1H), 3.69-3.63 (m, 1H), 3.52-3.45 (m, 3H), 3.38-3.35 (m, 2H), 3.31-3.28 (m, 1H), 3.04-2.99 (m, 1H), 2.46-2.40 (m, 3H), 2.15-2.07 (m, 4H), 1.96-1.87 (m, 1H), 1.73-1.63 (m, 3H), 1.26-1.22 (m, 1H), 1.13-1.11 (m, 3H), 0.90-0.87 (m, 1H). $^{19}$F NMR (376 MHz, DMSO-d$_6$) δ −63.35 (3F).

Example 86: (3S)—N-[3-(2-[[(2R)-2,3-dihydroxypropyl]amino]-6-(morpholin-4-yl)pyridin-4-yl)-4-methylphenyl]-3-(2,2,2-trifluoroethyl)pyrrolidine-1-carboxamide

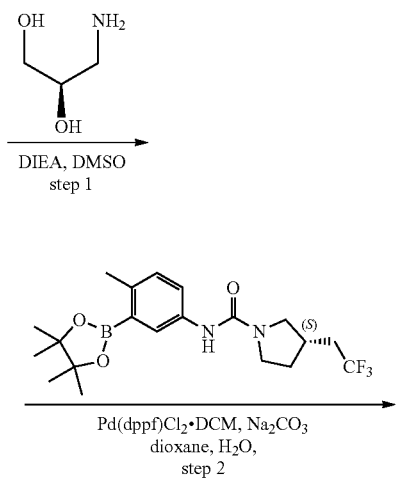

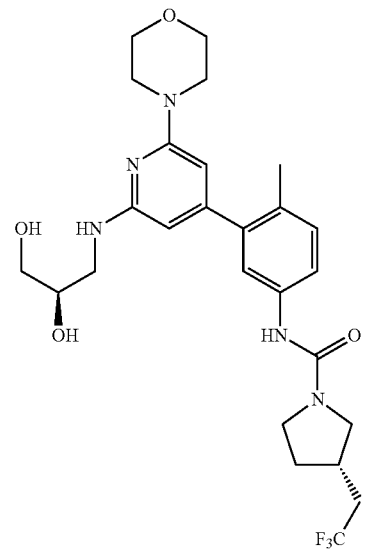

Preparation 86A: (2R)-3-[[4-iodo-6-(morpholin-4-yl)pyridin-2-yl]amino]propane-1,2-diol

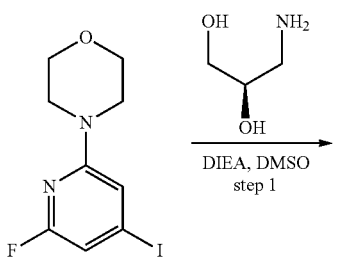

387
-continued

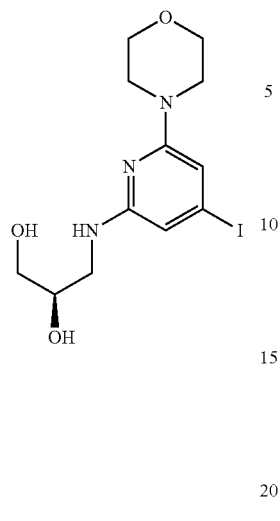

To a stirred solution of 4-(6-fluoro-4-iodopyridin-2-yl)morpholine (600 mg, 1.947 mmol) and (2R)-3-aminopropane-1,2-diol (266 mg, 2.921 mmol) in DMSO (6 mL) was added DIEA (1 mL, 7.874 mmol) under nitrogen atmosphere. The resulting mixture was stirred for 16 h at 80° C. under nitrogen atmosphere. The resulting mixture was concentrated under reduced pressure. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with (EA/PE/EtOH=12/3/1) to afford (2R)-3-[[4-iodo-6-(morpholin-4-yl)pyridin-2-yl]amino]propane-1,2-diol (350 mg, 47%) as a light yellow solid. MS ESI calculated for $C_{12}H_{18}IN_3O_3$ [M+H]$^+$, 380.19, found 380.00. $^1$H NMR (400 MHz, chloroform-d) δ 6.258-6.21 (m, 2H), 4.70 (s, 1H), 3.89-3.80 (m, 1H), 3.80-3.74 (m, 4H), 3.67-3.55 (m, 2H), 3.67-3.55 (m, 2H), 3.42-3.36 (m, 4H).

Example 86: (3S)—N-[3-(2-[[(2R)-2,3-dihydroxypropyl]amino]-6-(morpholin-4-yl)pyridin-4-yl)-4-methylphenyl]-3-(2,2,2-trifluoroethyl)pyrrolidine-1-carboxamide

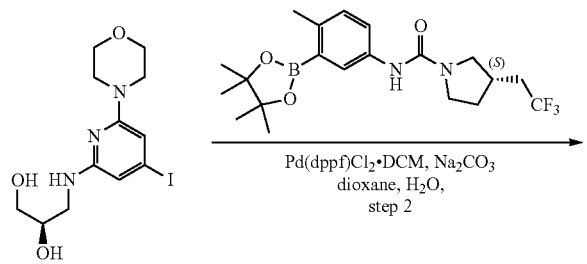

388
-continued

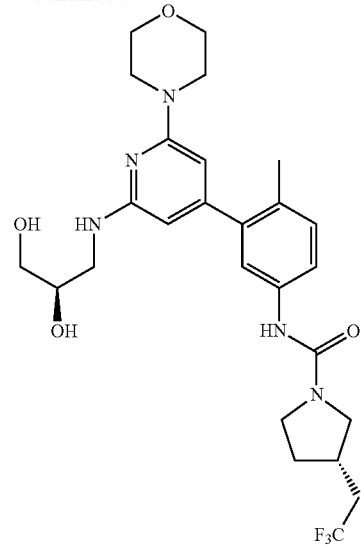

To a stirred solution of (2R)-3-[[4-iodo-6-(morpholin-4-yl)pyridin-2-yl]amino]propane-1,2-diol (200 mg, 0.527 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (217 mg, 0.527 mmol) in 1,4-dioxane (2 mL) and $H_2O$ (0.4 mL) were added $Na_2CO_3$ (167 mg, 1.582 mmol) and Pd(dppf)Cl$_2$·CH$_2$Cl$_2$ (43 mg, 0.053 mmol). The resulting mixture was stirred for 16 h at 60° C. under nitrogen atmosphere. The mixture was allowed to cool down to room temperature. The reaction was quenched by the addition of water (50 mL) at room temperature. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with (EtOAc/PE/EtOH=12/3/1) to afford (3S)—N-[3-(2-[[(2R)-2,3-dihydroxypropyl]amino]-6-(morpholin-4-yl)pyridin-4-yl)-4-methylphenyl]-3-(2,2,2-trifluoroethyl)pyrrolidine-1-carboxamide (186 mg, 66%) as an off-white solid. MS ESI calculated for $C_{26}H_{34}F_3N_5O_4$ [M+H]$^+$, 537.26, found 537.26. $^1$H NMR (400 MHz, DMSO-d$_6$) δ 8.11 (s, 1H), 7.45-7.38 (m, 1H), 7.33 (d, J=2.4 Hz, 1H), 7.09 (d, J=8.4 Hz, 1H), 6.17 (d, J=6.1 Hz, 1H), 5.81-5.74 (m, 2H), 4.80 (d, J=4.8 Hz, 1H), 4.53 (t, J=5.7 Hz, 1H), 3.71-3.58 (m, 6H), 3.57-3.48 (m, 1H), 3.44-3.25 (m, 8H), 3.19-3.08 (m, 1H), 3.02 (t, J=9.4 Hz, 1H), 2.51-2.34 (m, 3H), 2.16 (s, 3H), 2.08 (d, J=6.9 Hz, 1H), 1.73-1.58 (m, 1H). $^{19}$F NMR (376 MHz, DMSO-d$_6$) δ −63.24 (3F).

Example 87: (3S)—N-[3-(2-[[(2S)-2,3-dihydroxypropyl]amino]-6-(morpholin-4-yl)pyridin-4-yl)-4-methylphenyl]-3-(2,2,2-trifluoroethyl)pyrrolidine-1-carboxamide
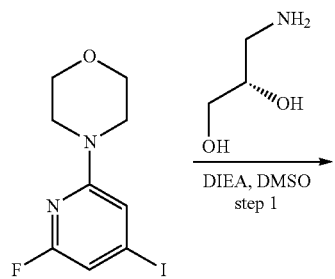
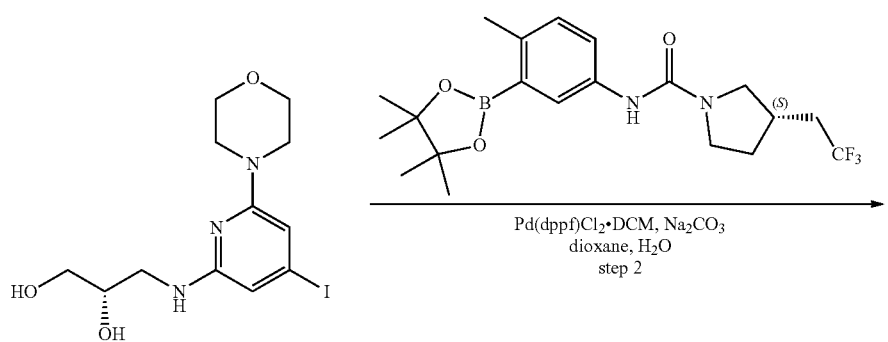
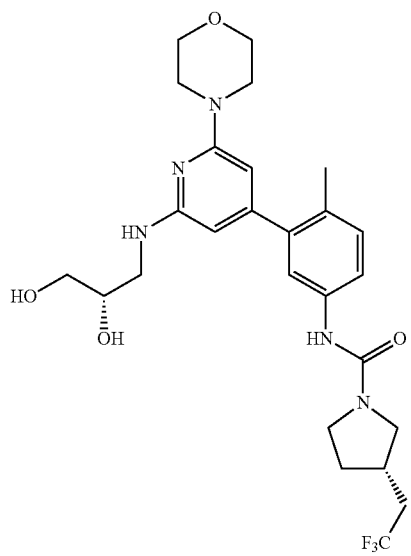

Preparation 87A: (2S)-3-[[4-iodo-6-(morpholin-4-yl)pyridin-2-yl]amino]propane-1,2-diol

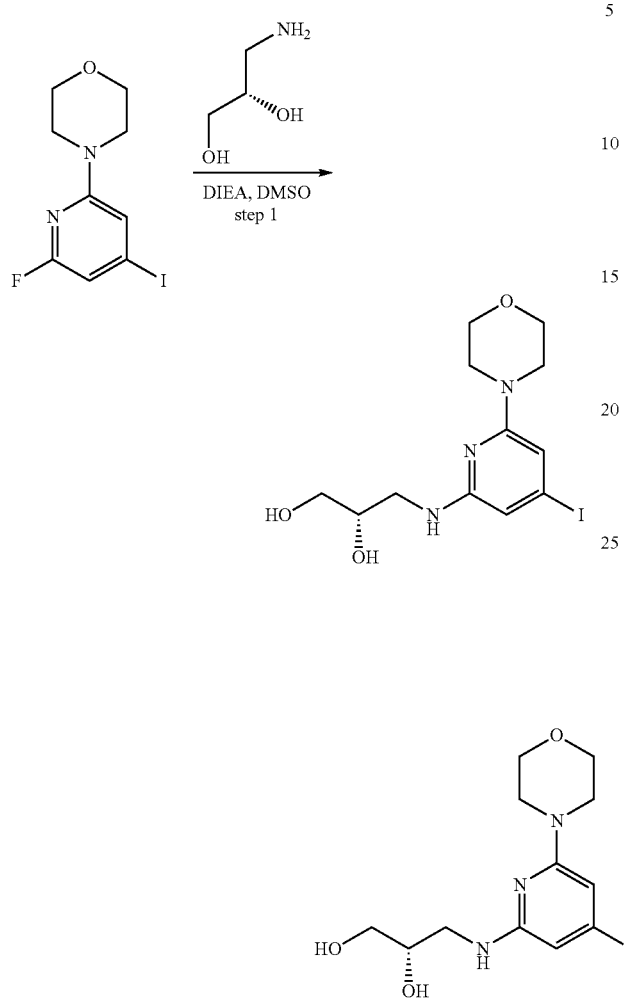

To a stirred solution of 4-(6-fluoro-4-iodopyridin-2-yl)morpholine (600 mg, 1.947 mmol) and 3-aminopropane-1,2-diol (266 mg, 2.921 mmol) in DMSO (6 mL) was added DIEA (1 mL, 5.841 mmol). The resulting mixture was stirred for 16 h at 80° C. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EtOAc (1/1) to afford (2S)-3-[[4-iodo-6-(morpholin-4-yl)pyridin-2-yl]amino]propane-1,2-diol (400 mg, 54%) as a light yellow solid. MS ESI calculated for $C_{12}H_{18}IN_3O_3$ [M+H]$^+$, 380.19, found 380.05. $^1$H NMR (400 MHz, chloroform-d) δ 6.30-6.23 (m, 2H), 4.72 (t, J=6.1 Hz, 1H), 3.91-3.82 (m, 1H), 3.82-3.75 (m, 4H), 3.69-3.57 (m, 2H), 3.57-3.45 (m, 2H), 3.45-3.38 (m, 4H).

Example 87: (3S)—N-[3-(2-[[(2S)-2,3-dihydroxypropyl]amino]-6-(morpholin-4-yl)pyridin-4-yl)-4-methylphenyl]-3-(2,2,2-trifluoroethyl)pyrrolidine-1-carboxamide

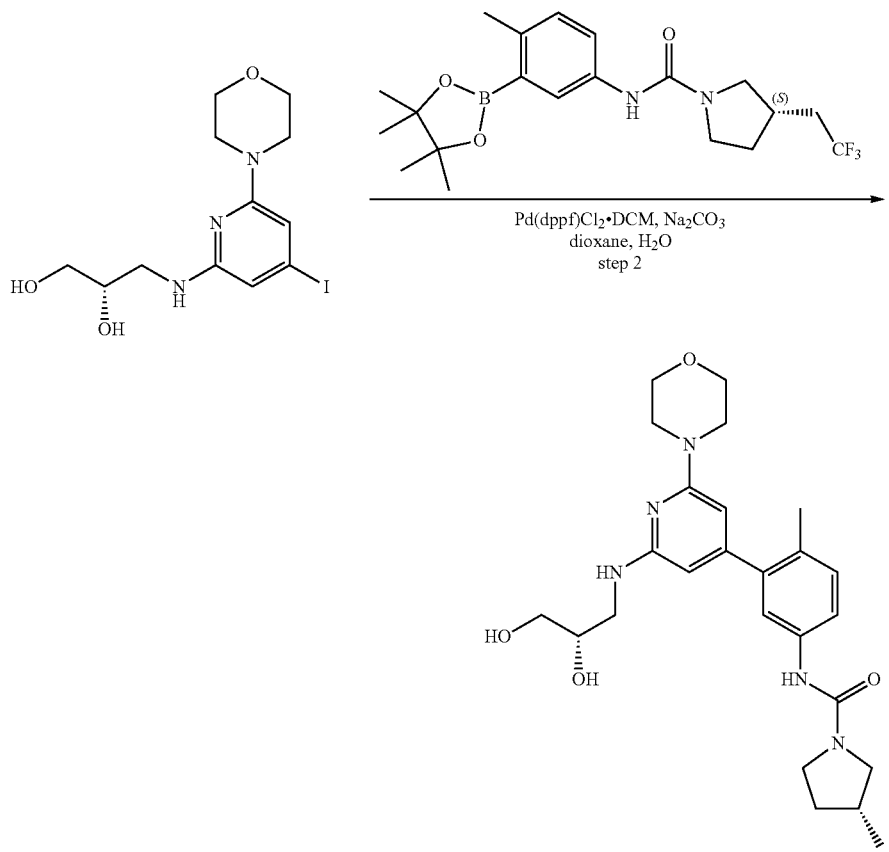

393

To a stirred solution of (2S)-3-[[4-iodo-6-(morpholin-4-yl)pyridin-2-yl]amino]propane-1,2-diol (200 mg, 0.527 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (217 mg, 0.527 mmol) in 1,4-dioxane (2 mL) and H$_2$O (0.4 mL) were added Na$_2$CO$_3$ (168 mg, 1.582 mmol) and Pd(dppf)Cl$_2$·CH$_2$Cl$_2$ (43 mg, 0.053 mmol) at room temperature under nitrogen atmosphere. The resulting mixture was stirred for 16 h at 60° C. under nitrogen atmosphere. The mixture was allowed to cool down to room temperature. The reaction was quenched by the addition of water (50 mL) at room temperature. The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with (PE/EtOAc/EtOH=12/3/1) to afford (3S)—N-[3-(2-[[(2S)-2,3-dihydroxypropyl]amino]-6-(morpholin-4-yl)pyridin-4-yl)-4-methylphenyl]-3-(2,2,2-trifluoroethyl)pyrrolidine-1-carboxamide (178 mg, 63%) as an light pink solid. MS ESI calculated for C$_{26}$H$_{34}$F$_3$N$_5$O$_4$ [M+H]$^+$, 538.26, found 538.10. $^1$H NMR (400 MHz, DMSO-d$_6$) δ 8.10 (s, 1H), 7.44-7.37 (m, 1H), 7.33 (d, J=2.4 Hz, 1H), 7.09 (d, J=8.6 Hz, 1H), 6.17 (s, 1H), 5.81-5.74 (m, 2H), 4.79 (d, J=4.7 Hz, 1H), 4.52 (t, J=5.7 Hz, 1H), 3.70-3.59 (m, 6H), 3.52 (t, J=8.5 Hz, 1H), 3.43-3.33 (m, 7H), 3.18-3.07 (m, 1H), 3.01 (t, J=9.4 Hz, 1H), 2.44 (d, J=11.2 Hz, 1H), 2.40 (s, 3H), 2.15 (s, 3H), 2.12-2.04 (m, 1H), 1.72-1.58 (m, 1H). $^{19}$F NMR (376 MHz, DMSO-d$_6$) δ −63.36 (3F).

Examples 88 and 89: (3S)—N-[3-(2-[[(2R)-1-hydroxypropan-2-yl]amino]-6-[(1S,5R)-3-oxabicyclo[3.1.0]hexan-1-yl]pyridin-4-yl)-4-methylphenyl]-3-(2,2,2-trifluoroethyl)pyrrolidine-1-carboxamide, (3S)—N-[3-(2-[[(2R)-1-hydroxypropan-2-yl]amino]-6-[(1R,5S)-3-oxabicyclo[3.1.0]hexan-1-yl]pyridin-4-yl)-4-methylphenyl]-3-(2,2,2-trifluoroethyl)pyrrolidine-1-carboxamide

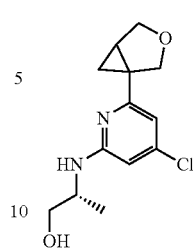

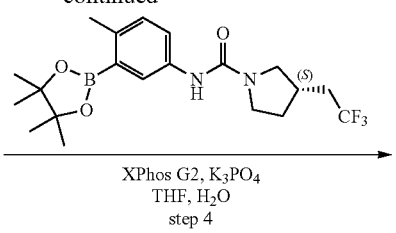

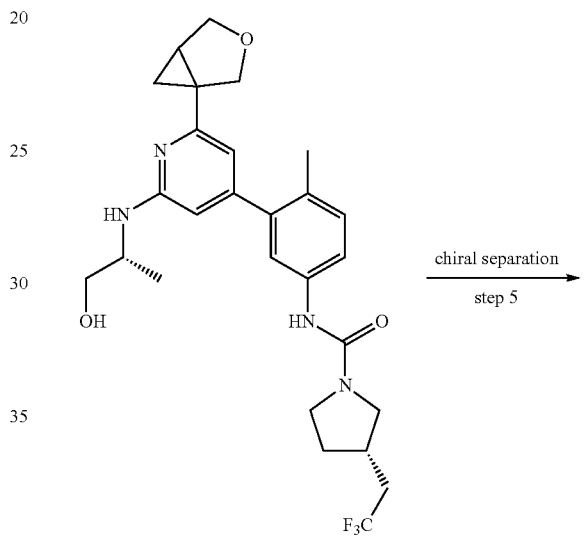

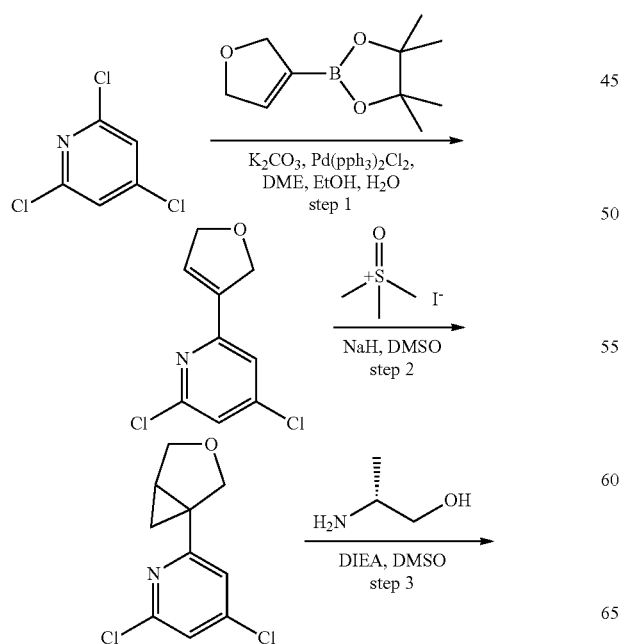

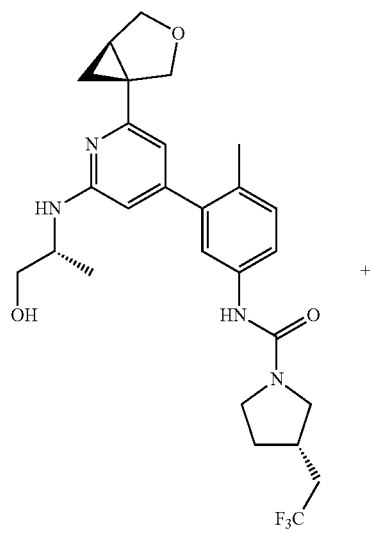

395
-continued

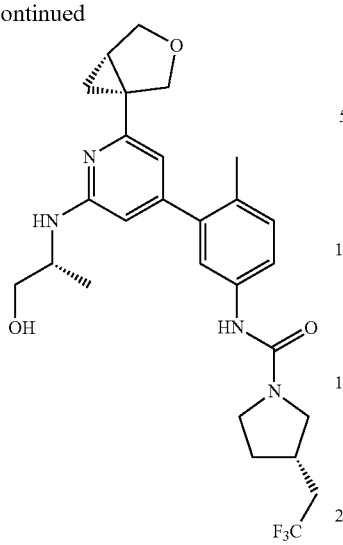

Preparation 88A:
2,4-dichloro-6-(2,5-dihydrofuran-3-yl)pyridine

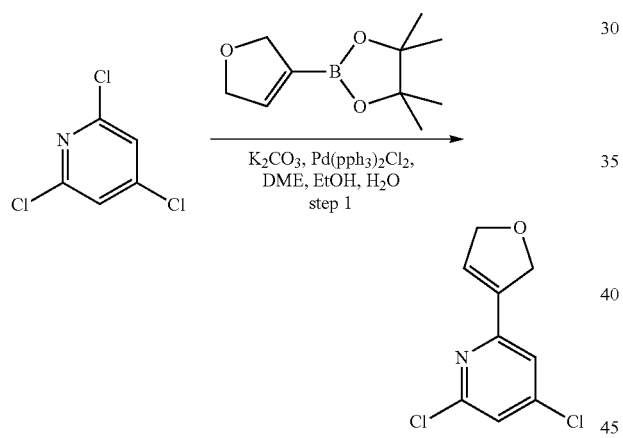

To a stirred solution of 2,4,6-trichloropyridine (5.50 g, 30.15 mmol), 2-(2,5-dihydrofuran-3-yl)-4,4,5,5-tetramethyl-1,3,2-dioxaborolane (5.91 g, 30.15 mmol) and $K_2CO_3$ (8.38 g, 60.60 mmol) in DME/EtOH/$H_2O$=2/1/2 (60 mL) was added Pd(PPh$_3$)$_2$Cl$_2$ (1.06 g, 1.51 mmol). The resulting mixture was stirred for 16 h at 80° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EtOAc (2/1) to afford 2,4-dichloro-6-(2,5-dihydrofuran-3-yl)pyridine (2.55 g, 39%) as an off-white solid. MS ESI calculated for $C_9H_7Cl_2NO$ [M+H]$^+$, 215.99, found 215.95. $^1$H NMR (300 MHz, chloroform-d) δ 7.26-7.23 (m, 2H), 6.74-6.71 (m, 1H), 5.07-5.03 (m, 2H), 3.93-3.89 (m, 2H).

396

Preparation 88B: 2,4-dichloro-6-[3-oxabicyclo [3.1.0]hexan-1-yl]pyridine

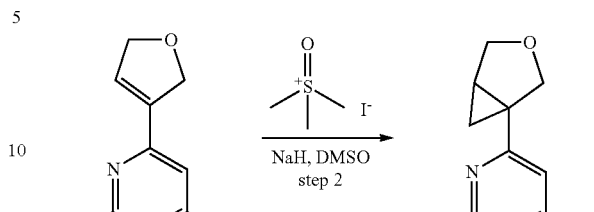

To a stirred solution of trimethylsulfoxonium iodide (10.39 g, 47.21 mmol) in DMSO (30 mL) was added NaH (1.89 g, 47.25 mmol) in portions at 0° C. The resulting mixture was stirred for 30 min at room temperature under nitrogen atmosphere. To the above mixture was added 2,4-dichloro-6-(2,5-dihydrofuran-3-yl)pyridine (2.55 g, 11.80 mmol). The resulting mixture was stirred for additional 16 h at 60° C. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with PE/EtOAc (4/1) to afford 2,4-dichloro-6-[3-oxabicyclo [3.1.0]hexan-1-yl]pyridine (2.28 g, 84%) as an off-white solid. MS ESI calculated for $C_{10}H_9Cl_2NO$ [M+H]$^+$. 230.01, found 229.95. $^1$H NMR (300 MHz, chloroform-d) δ 7.18-7.17 (m, 1H), 6.97-6.96 (m, 1H), 4.14 (s, 2H), 3.95-3.86 (m, 2H), 2.21-2.16 (m, 1H), 1.46-1.42 (m, 1H), 1.28-1.19 (m, 1H).

Preparation 88C: (2R)-2-[(4-chloro-6-[3-oxabicyclo [3.1.0]hexan-1-yl]pyridin-2-yl)amino]propan-1-ol

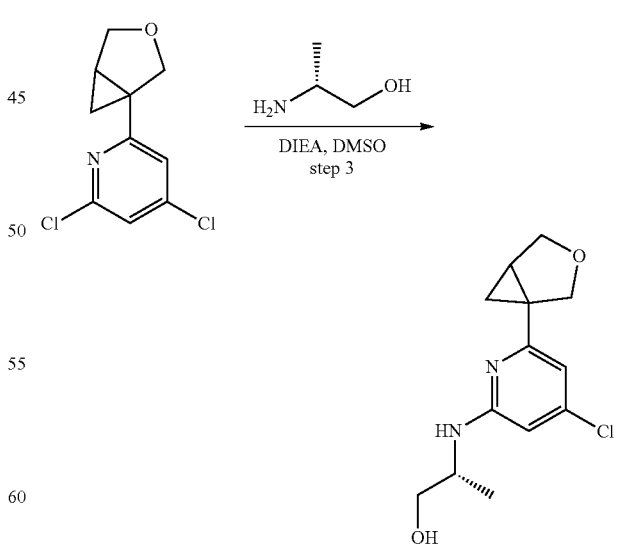

To a stirred solution of 2,4-dichloro-6-[3-oxabicyclo [3.1.0]hexan-1-yl]pyridine (2.28 g, 9.91 mmol) and (R)-(−)-2-amino-1-propanol (1.49 g, 19.82 mmol) in DMSO (25 mL) was added DIEA (2.56 g, 19.82 mmol) dropwise at room temperature. The resulting mixture was stirred for 16 h at 130° C. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by reverse flash chromatography with the following conditions: column, C18 silica gel; mobile phase, $CH_3CN$ in water (0.1% TFA), 5% to 95% gradient in 40 min; detector, UV 254 nm; to afford (2R)-2-[(4-chloro-6-[3-oxabicyclo[3.1.0]hexan-1-yl]pyridin-2-yl)amino]propan-1-ol (0.38 g, 14%) as an off-white solid. MS ESI calculated for $C_{13}H_{17}ClN_2O_2$ [M+H]$^+$. 269.10, found 269.00. $^1H$ NMR (300 MHz, chloroform-d) δ 6.38-6.36 (m, 1H), 6.31-6.30 (m, 1H), 4.72 (s, 1H), 4.09 (s, 2H), 4.04-3.84 (m, 3H), 3.78-3.73 (m, 1H), 3.61-3.54 (m, 1H), 2.14-2.07 (m, 1H), 1.38-1.31 (m, 1H), 1.28-1.24 (m, 4H), 1.11-1.07 (m, 1H).

Preparation 88D: (3S)—N-[3-(2-[[(2R)-1-hydroxypropan-2-yl]amino]-6-[3-oxabicyclo[3.1.0]hexan-1-yl]pyridin-4-yl)-4-methylphenyl]-3-(2,2,2-trifluoroethyl)pyrrolidine-1-carboxamide

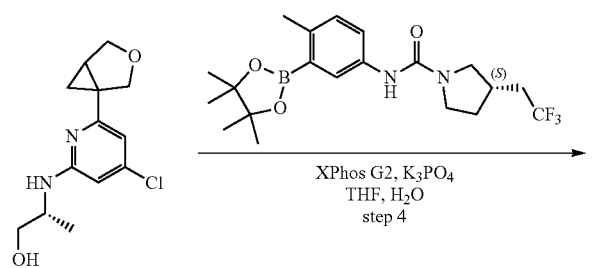

To a stirred solution of (2R)-2-[(4-chloro-6-[3-oxabicyclo[3.1.0]hexan-1-yl]pyridin-2-yl)amino]propan-1-ol (380 mg, 1.414 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (583 mg, 1.414 mmol) and $K_3PO_4$ (600 mg, 2.828 mmol) in THF/$H_2O$=10/1 (4 mL) was added XPhos Pd G2 (111 mg, 0.141 mmol) at room temperature under nitrogen atmosphere. The resulting mixture was stirred for 16 h at 80° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous $Na_2SO_4$. After filtration, the filtrate was concentrated under reduced pressure. The residue was purified by silica gel column chromatography, eluted with (EA/PE/EtOH=8/3/1) to afford (3S)—N-[3-(2-[[(2R)-1-hydroxypropan-2-yl]amino]-6-[3-oxabicyclo[3.1.0]hexan-1-yl]pyridin-4-yl)-4-methylphenyl]-3-(2,2,2-trifluoroethyl)pyrrolidine-1-carboxamide (420 mg, 57%) as a light yellow solid. MS ESI calculated for $C_{27}H_{33}F_3N_4O_3$ [M+H]$^+$. 519.25, found 519.25. $^1H$ NMR (300 MHz, chloroform-d) δ 7.31-7.29 (m, 1H), 7.19-7.16 (m, 1H), 6.34-6.32 (m, 1H), 6.24-6.22 (m, 2H), 4.59 (s, 1H), 4.18-4.04 (m, 3H), 3.93-3.75 (m, 4H), 3.67-3.55 (m, 2H), 3.49-3.40 (m, 1H), 3.15-3.08 (m, 1H), 2.62-2.49 (m, 1H), 2.34-2.11 (m, 7H), 1.81-1.68 (m, 2H), 1.40-1.30 (m, 1H), 1.27-1.24 (m, 3H), 1.09-1.05 (m, 1H). $^{19}F$ NMR (282 MHz, chloroform-d) δ −64.94 (3F).

Examples 88 and 89: (3S)—N-[3-(2-[[(2R)-1-hydroxypropan-2-yl]amino]-6-[(1S,5R)-3-oxabicyclo[3.1.0]hexan-1-yl]pyridin-4-yl)-4-methylphenyl]-3-(2,2,2-trifluoroethyl)pyrrolidine-1-carboxamide, (3S)—N-[3-(2-[[(2R)-1-hydroxypropan-2-yl]amino]-6-[(1R,5S)-3-oxabicyclo[3.1.0]hexan-1-yl]pyridin-4-yl)-4-methylphenyl]-3-(2,2,2-trifluoroethyl)pyrrolidine-1-carboxamide

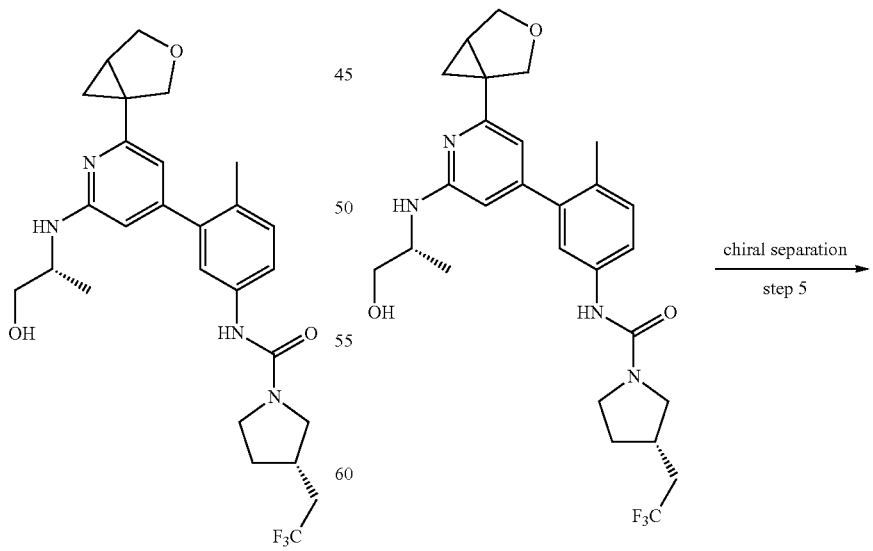

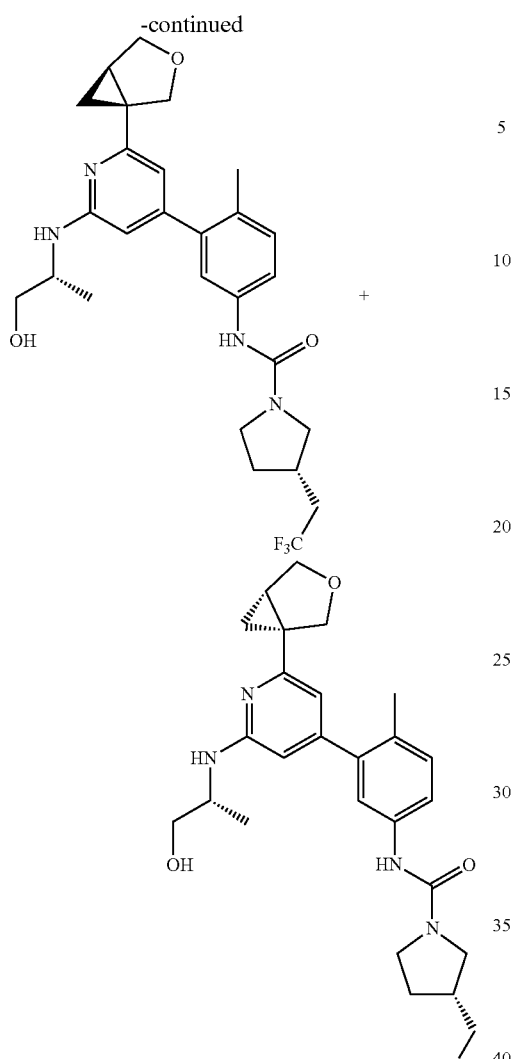

The crude product ((3S)—N-[3-(2-[[(2R)-1-hydroxypropan-2-yl]amino]-6-[3-oxabicyclo[3.1.0]hexan-1-yl]pyridin-4-yl]-4-methylphenyl]-3-(2,2,2-trifluoroethyl)pyrrolidine-1-carboxamide (420 mg, 0.810 mmol) was purified by Chiral-Prep-HPLC with the following conditions (Column: CHIRAL ART Cellulose-SB, 30*250 mm, 5 um; Mobile Phase A: $CO_2$, Mobile Phase B: IPA (0.5% 2 M $NH_3$-MeOH); Flow rate: 80 mL/min; Gradient:40% B; 220 nm). The first peak afforded 169 mg (40%) as an off-white solid. MS ESI calculated for $C_{27}H_{33}F_3N_4O_3$ [M+H]$^+$. 519.25, found 519.10. $^1$H NMR (400 MHz, chloroform-d) δ 7.28 (m, 1H), 7.17-7.14 (m, 1H), 6.31-6.30 (m, 1H), 6.21-6.19 (m, 2H), 4.99-4.56 (m, 2H), 4.09-4.02 (m, 3H), 3.91-3.73 (m, 4H), 3.62-3.53 (m, 2H), 3.44-3.40 (m, 1H), 3.13-3.07 (m, 1H), 2.60-2.49 (m, 1H), 2.32-2.09 (m, 7H), 1.80-1.67 (m, 2H), 1.39-1.35 (m, 1H), 1.24-1.22 (m, 3H), 1.08-1.05 (m, 1H). $^{19}$F NMR (376 MHz, chloroform-d) δ −64.95 (3F).

The second peak afforded 119 mg (28%) as an off-white solid. MS ESI calculated for $C_{27}H_{33}F_3N_4O_3$ [M+H]$^+$. 519.25, found 519.10. $^1$H NMR (400 MHz, chloroform-d) δ 7.31-7.30 (m, 1H), 7.20-7.17 (m, 1H), 6.35 (m, 1H), 6.25-6.19 (m, 2H), 4.63 (m, 2H), 4.11-4.04 (m, 3H), 3.94-3.75 (m, 4H), 3.64-3.56 (m, 2H), 3.47-3.43 (m, 1H), 3.19-3.10 (m, 1H), 2.58-2.55 (m, 1H), 2.32-2.14 (m, 7H), 1.83-1.72 (m, 2H), 1.35-1.31 (m, 1H), 1.28-1.24 (m, 3H), 1.09-1.06 (m, 1H). $^{19}$F NMR (376 MHz, chloroform-d) δ −64.95 (3F).

Example 90 and 91: (S)—N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide & (R)—N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide

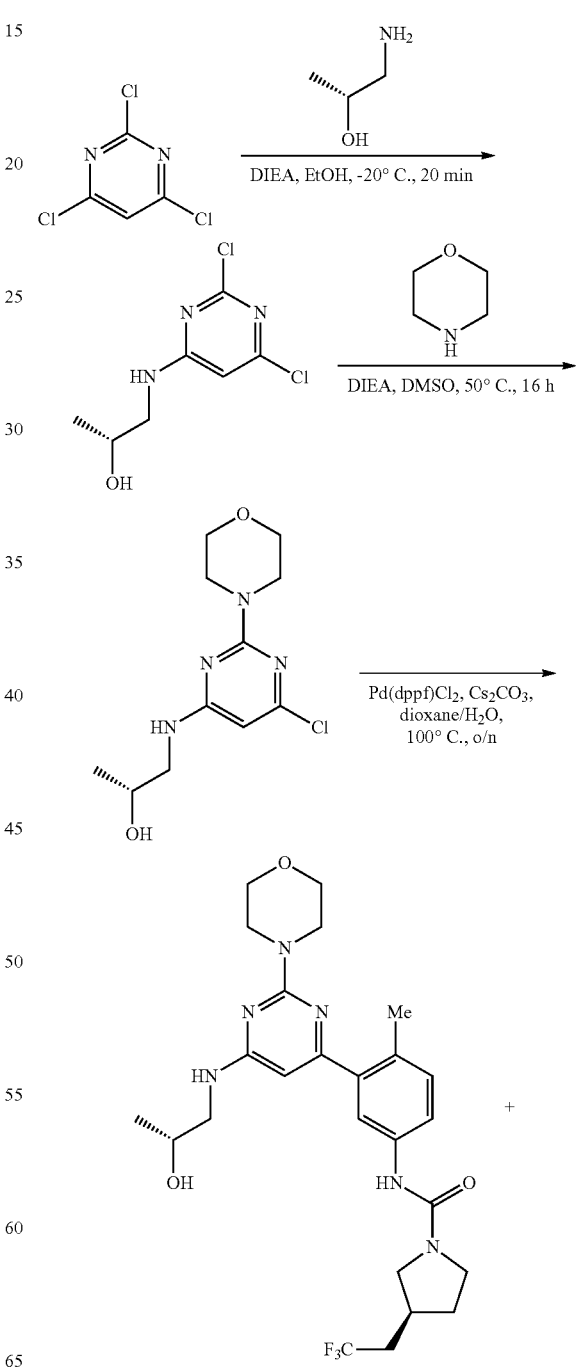

-continued

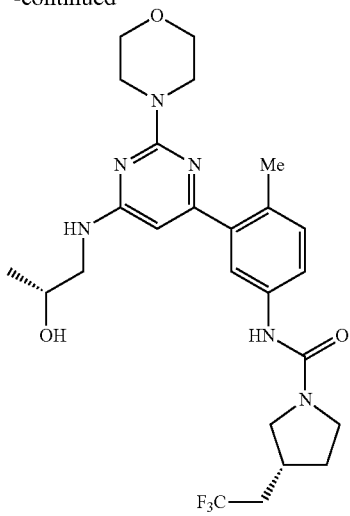

Step 1: To a stirred solution of 2,4,6-trichloropyrimidine (4.00 g, 21.85 mmol) in EtOH (70 mL) was added (R)-1-aminopropan-2-ol (1.63 g, 21.85 mmol) and DIEA (2.82 g, 21.85 mmol) at −20° C. The reaction mixture was stirred at −20° C. for 20 min. The resulting mixture was diluted with water (150 mL) and extracted with EA (300 mL×3). The combined organic layers was washed with brine (100 mL×4), dried over anhydrous $Na_2SO_4$ and filtered. The filtrate was concentrated under reduced pressure. The residue was purified by FCC (PE:EA=5:1) to afford (R)-1-((2,6-dichloropyrimidin-4-yl)amino) propan-2-ol (2.30 g, 48%) as an off-white solid. MS Calcd.: 221, MS Found: 222 ([M+H]$^+$).

Step 2: To a stirred solution of (R)-1-((2,6-dichloropyrimidin-4-yl)amino) propan-2-ol (1.00 g, 4.52 mmol) in DMSO (5 mL) were added morpholine (396 mg, 4.52 mmol) and DIEA (875 mg, 6.78 mmol) at rt. The reaction mixture was stirred at 50° C. for 16 h. The resulting mixture was cooled to rt, diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=1:2) to afford (R)-1-((6-chloro-2-morpholinopyrimidin-4-yl) amino) propan-2-ol (1.07 g, 86%) as a white solid. MS Calcd.: 272, MS Found: 273 ([M+H]$^+$).

Step 3: To a solution of (R)-1-((6-chloro-2-morpholinopyrimidin-4-yl)amino) propan-2-ol (600 mg, 2.20 mmol), N-(4-methyl-3-(4,4,5,5-tetramethyl-1,3,2-dioxaborolan-2-yl)phenyl)-3-(2,2,2-trifluoroethyl)pyrrolidine-1-carboxamide (996 mg, 2.42 mmol) and $Cs_2CO_3$ (1.79 g, 2.49 mmol) in dioxane (40 mL) and water (4 mL) was added Pd(dppf)Cl$_2$ (80 mg, 0.11 mmol) at room temperature under nitrogen atmosphere. The reaction mixture was stirred at 100° C. overnight. The mixture was cooled down to room temperature, filtered and concentrated. The residue was purified by chiral prep-SFC (Column: Chiralpak IG 5 μm*20*250 mm; Mobile Phase: $CO_2$:EtOH=70:30 at 50 g/min; Temp: 40° C.; Wavelength: 214 nm, Back pressure: 100 bar) to afford 183.8 mg (16%), RT=7.13 min, ee>98%), $^1$H NMR (400 MHz, DMSO-d$_6$): δ 8.13 (s, 1H), 7.49 (d, J=2.4 Hz, 1H), 7.42 (dd, J=2.0, 8.4 Hz, 1H), 7.07 (d, J=8.4 Hz, 2H), 5.90 (s, 1H), 4.71 (br s, 1H), 3.80-3.79 (m, 1H), 3.69-3.63 (m, 9H), 3.55-3.50 (m, 1H), 3.34-3.20 (m, 3H), 3.02 (t, J=9.2 Hz, 1H), 2.49-2.38 (m, 3H), 2.25 (s, 3H), 2.09-2.07 (m, 1H), 1.68-1.63 (m, 1H), 1.08 (d, J=6.4 Hz, 3H) and 196.7 mg, (17%), RT=6.31 min, ee>98%), $^1$H NMR (400 MHz, DMSO-d$_6$): δ 8.13 (s, 1H), 7.49 (d, J=2.4 Hz, 1H), 7.42 (dd, J=2.4, 8.4 Hz, 1H), 7.08-7.03 (m, 2H), 5.90 (s, 1H), 4.71 (d, J=4.0 Hz, 1H), 3.81-3.78 (m, 1H), 3.69-3.63 (m, 9H), 3.55-3.50 (m, 1H), 3.34-3.20 (m, 3H), 3.02 (t, J=9.2 Hz, 1H), 2.49-2.38 (m, 3H), 2.25 (s, 3H), 2.09-2.07 (m, 1H), 1.68-1.63 (m, 1H), 1.08 (d, J=6.4 Hz, 3H). MS Calcd.: 522, MS Found: 523 ([M+H]+).

Example 92: (S)—N-(3-(2-(((R)-2-hydroxypropyl)amino)-6-morpholinopyrimidin-4-yl)-4-methylphenyl)-3-(2,2,2-trifluoroethyl)pyrrolidine-1-carboxamide

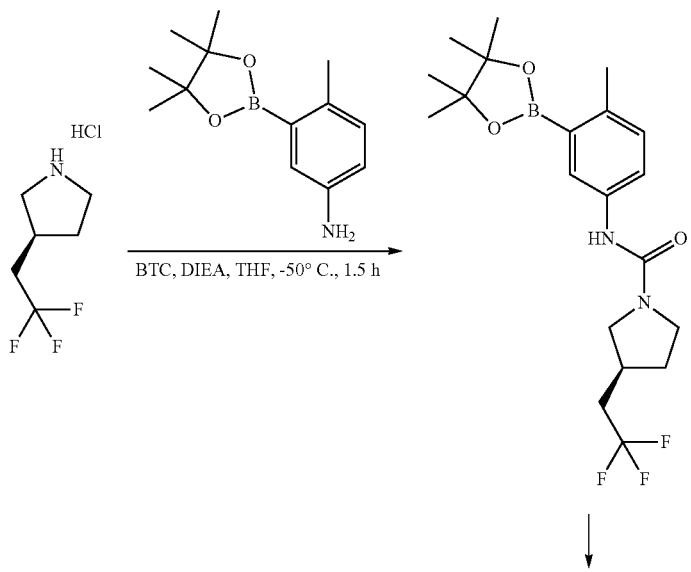

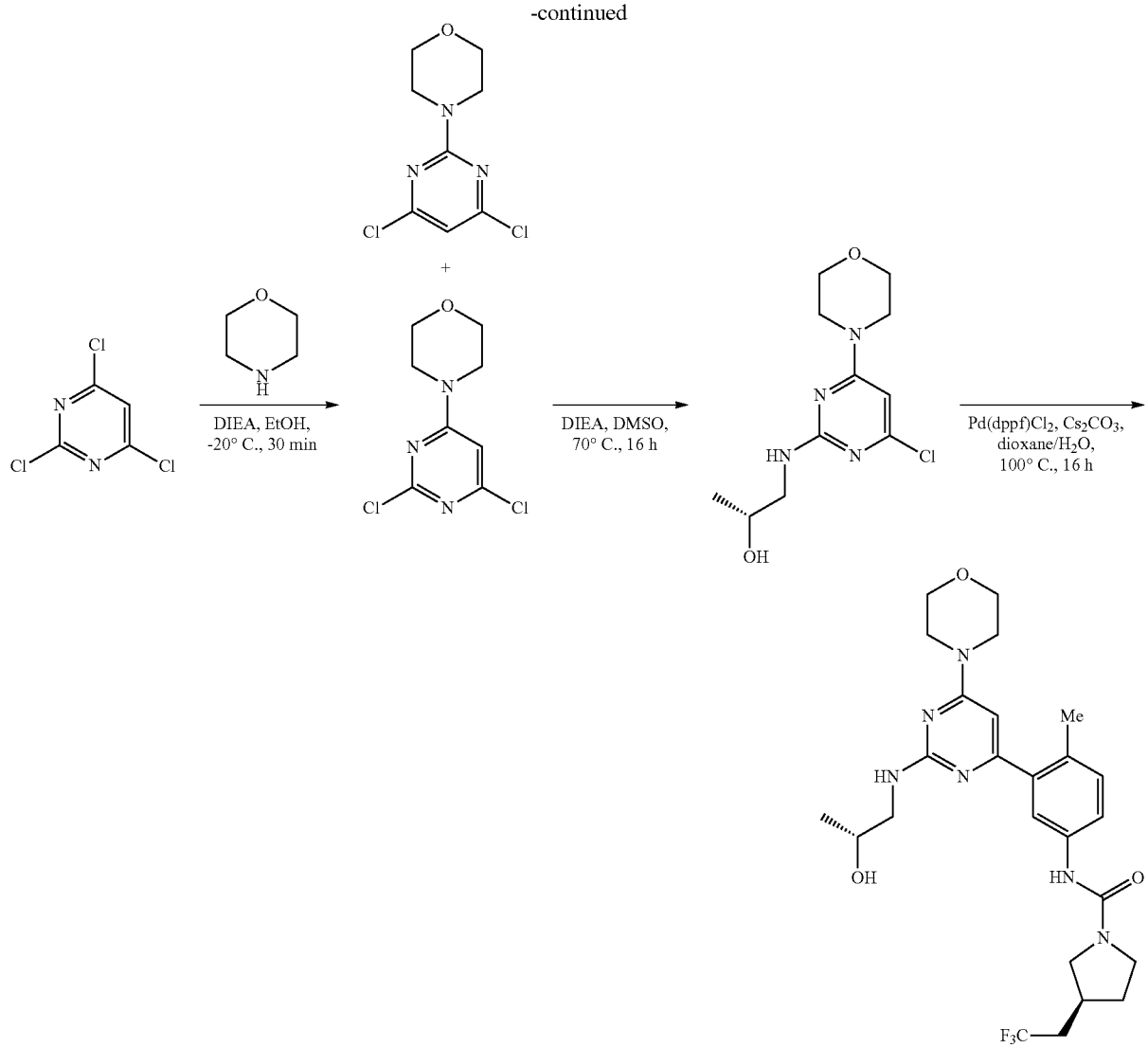

Step 1: To a solution of 4-methyl-3-(4,4,5,5-tetramethyl-1,3,2-dioxaborolan-2-yl)aniline (3.80 g, 16.31 mmol) and DIEA (10.5 g, 81.50 mmol) in THF (100 mL) was added BTC (1.9 g, 6.40 mmol) at −50° C. under nitrogen atmosphere. The mixture was stirred at −50° C. for 30 min. Then (S)-3-(2,2,2-trifluoroethyl)pyrrolidine hydrochloride (3.1 g, 16.40 mmol) was added to the mixture which was stirred at −50° C. for another 1 h. The residue was concentrated and purified by FCC (PE:EA=1:1) to afford (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (3.85 g, 57%) as a white solid. MS Calcd.: 412, MS Found: 413 ([M+H]+).

Step 2: To a stirred solution of 2,4,6-trichloropyrimidine (5.00 g, 27.47 mmol) in EtOH (70 mL) was added morpholine (2.39 g, 27.47 mmol) and DIEA (3.51 g, 27.47 mmol) at −20° C. The reaction mixture was stirred at −20° C. for 0.5 h. The resulting mixture was diluted with water (150 mL) and extracted with EA (300 mL×3). The combined organic layers was washed with brine (100 mL×4), dried over anhydrous Na2SO4 and filtered. The filtrate was concentrated under reduced pressure. The residue was purified by FCC (PE:EA=10:1) to afford 4-(4,6-dichloropyrimidin-2-yl)morpholine (1.13 g, 17%) and 4-(2,6-dichloropyrimidin-4-yl)morpholine (3.58 g, 54%) as an off-white solid. MS Calcd.: 233, MS Found: 234 ([M+H]+).

Step 3: To a stirred solution of 4-(2,6-dichloropyrimidin-2-yl)morpholine (600 mg, 2.36 mmol) in DMSO (5 mL) were added (R)-1-aminopropan-2-ol (250 mg, 3.33 mmol) and DIEA (496 mg, 3.84 mmol) at rt. The reaction mixture was stirred at 70° C. for 16 h. The resulting mixture was cooled to rt, diluted with water (10 mL) and extracted with EA (10 mL×3). The combined organic layers was washed with brine (5 mL×4), dried over anhydrous Na2SO4 and filtered. The filtrate was concentrated under reduced pressure. The residue was purified by FCC (PE:EA=1:1) to afford (R)-1-((4-chloro-6-morpholinopyrimidin-2-yl)amino) propan-2-ol (400 mg, 57%) as a white solid. MS Calcd.: 272, MS Found: 273 ([M+H]+).

Step 4: To a solution of (R)-1-((4-chloro-6-morpholino-pyrimidin-2-yl)amino) propan-2-ol (33 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and Cs2CO3 (98 mg, 0.30 mmol) in dioxane (10 mL) and water (2 mL) was added Pd(dppf)Cl₂ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(2-(((R)-2-hydroxypropyl)amino)-6-morpholinopyrimidin-4-yl)-4-methylphenyl)-3-(2,2,2-trifluoroethyl)pyrrolidine-1-carboxamide (21 mg, 33%) as a white solid. ¹H NMR (400 MHz, DMSO-d₆): δ 8.12 (s, 1H), 7.45-7.43 (m, 2H), 7.07 (dd, J=3.6, 4.8 Hz, 1H), 6.40 (s, 1H), 6.02 (s, 1H), 4.76-4.71 (m, 1H), 3.76-3.50 (m, 12H), 3.29-3.14 (m, 2H), 3.02 (t, J=9.2 Hz, 1H), 2.46-2.33 (m, 3H), 2.24 (s, 3H), 2.11-2.07 (m, 1H), 1.70-1.63 (m, 1H), 1.04 (d, J=6.0 Hz, 3H). MS Calcd.: 522, MS Found: 523 ([M+H]⁺).

Example 93: (S)—N-(3-(6-(((S)-2-hydroxypropyl)amino)-2-morpholinopyrimidin-4-yl)-4-methylphenyl)-3-(2,2,2-trifluoroethyl)pyrrolidine-1-carboxamide

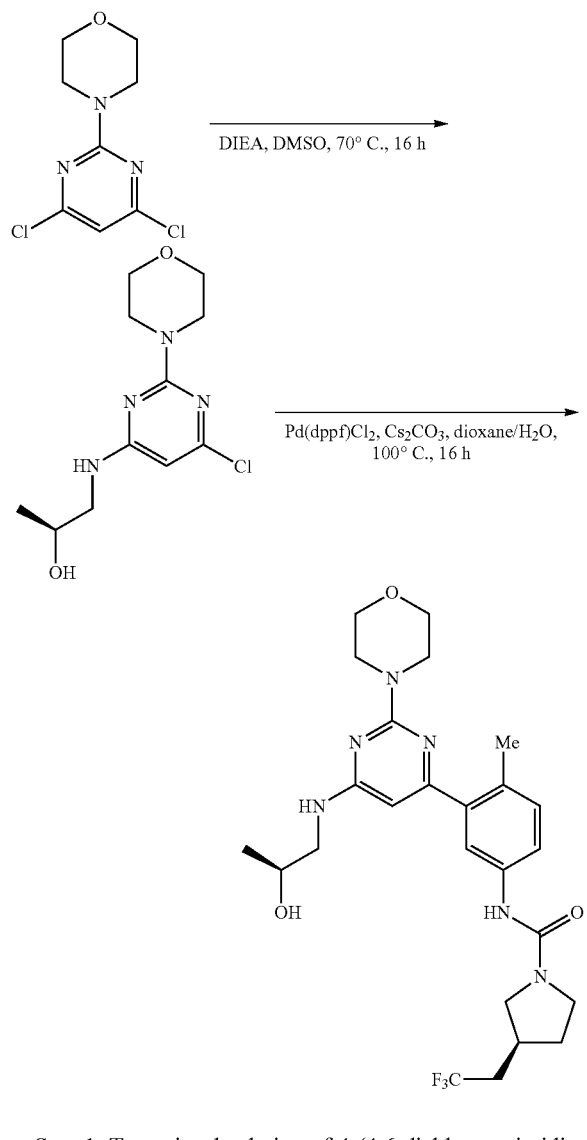

Step 1: To a stirred solution of 4-(4,6-dichloropyrimidin-2-yl)morpholine (300 mg, 1.28 mmol) in DMSO (5 mL) was added (S)-1-aminopropan-2-ol (96 mg, 1.28 mmol) and DIEA (248 mg, 1.92 mmol) at rt. The reaction mixture was stirred at 70° C. for 16 h. The resulting mixture was cooled to rt, diluted with water (10 mL) and extracted with EA (10 mL×3). The combined organic layers was washed with brine (5 mL×4), dried over anhydrous Na₂SO₄ and filtered. The filtrate was concentrated under reduced pressure. The residue was purified by FCC (PE:EA=1:1) to afford (S)-1-((6-chloro-2-morpholinopyrimidin-4-yl)amino) propan-2-ol (200 mg, 57%) as a white solid. MS Calcd.: 272, MS Found: 273 ([M+H]⁺).

Step 2: To a solution of(S)-1-((6-chloro-2-morpholinopyrimidin-4-yl)amino) propan-2-ol (33 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and Cs₂CO₃ (98 mg, 0.30 mmol) in dioxane (10 mL) and water (2 mL) was added Pd(dppf)Cl₂ (4 mg, 0.006 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(6-(((S)-2-hydroxypropyl)amino)-2-morpholinopyrimidin-4-yl)-4-methylphenyl)-3-(2,2,2-trifluoroethyl)pyrrolidine-1-carboxamide (15.7 mg, 24%) as a white solid. ¹H NMR (400 MHz, DMSO-d₆): δ 8.13 (d, J=1.6 Hz, 1H), 7.49 (d, J=2.4 Hz, 1H), 7.42 (dd, J=2.0, 8.0 Hz, 1H), 7.08-7.05 (m, 2H), 5.90 (s, 1H), 4.70 (d, J=4.4 Hz, 1H), 3.81-3.78 (m, 1H), 3.69-3.63 (m, 9H), 3.55-3.50 (m, 1H), 3.29-3.24 (m, 3H), 3.02 (t, J=9.2 Hz, 1H), 2.49-2.38 (m, 3H), 2.25 (s, 3H), 2.10-2.07 (m, 1H), 1.68-1.63 (m, 1H), 1.07 (d, J=6.0 Hz, 3H). MS Calcd.: 522, MS Found: 523 ([M+H]⁺).

Example 94: (S)—N-(3-(6-((2-hydroxyethyl)amino)-2-morpholinopyrimidin-4-yl)-4-methylphenyl)-3-(2,2,2-trifluoroethyl)pyrrolidine-1-carboxamide

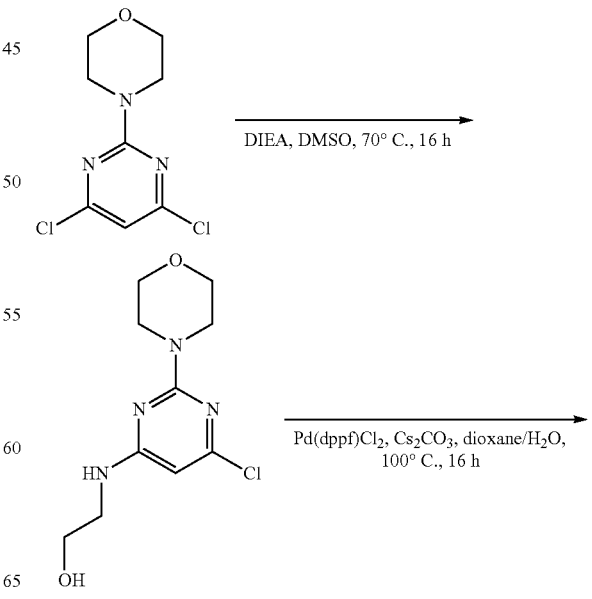

-continued

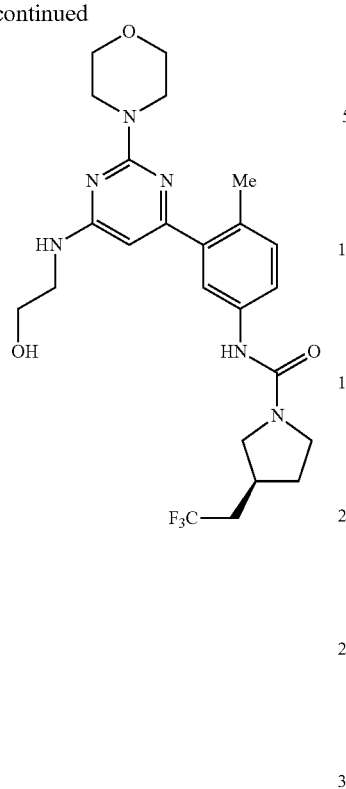

Step 1: To a stirred solution of 4-(4,6-dichloropyrimidin-2-yl)morpholine (300 mg, 1.28 mmol) in DMSO (5 mL) were added 2-aminoethanol (102 mg, 1.17 mmol) and DIEA (248 mg, 1.92 mmol) at rt. The reaction mixture was stirred at 70° C. for 16 h. The resulting mixture was cooled to rt, diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=1:1) to afford 2-((6-chloro-2-morpholinopyrimidin-4-yl)amino) ethanol (325 mg, 98%) as a white solid. MS Calcd.: 258, MS Found: 259 ([M+H]$^+$).

Step 2: To a solution of 2-((6-chloro-2-morpholinopyrimidin-4-yl)amino) ethanol (31 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and $Cs_2CO_3$ (98 mg, 0.30 mmol) in dioxane (10 mL) and water (2 mL) was added Pd(dppf)Cl$_2$ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(6-((2-hydroxyethyl)amino)-2-morpholinopyrimidin-4-yl)-4-methylphenyl)-3-(2,2,2-trifluoroethyl)pyrrolidine-1-carboxamide (17 mg, 27.4%) as a white solid. $^1$H NMR (400 MHz, DMSO-d$_6$): δ 8.13 (s, 1H), 7.49 (d, J=2.4 Hz, 1H), 7.42 (dd, J=2.0, 8.8 Hz, 1H), 7.07 (d, J=8.4 Hz, 1H), 5.88 (s, 1H), 4.69 (t, J=5.2 Hz, 1H), 3.69-3.63 (m, 9H), 3.55-3.51 (m, 3H), 3.36-3.27 (m, 3H), 3.02 (t, J=9.6 Hz, 1H), 2.49-2.38 (m, 3H), 2.25 (s, 3H), 2.09-2.07 (m, 1H), 1.68-1.63 (m, 1H). MS Calcd.: 508, MS Found: 509 ([M+H]$^+$).

Example 95: (S)—N-(3-(6-(((S)-1-hydroxypropan-2-yl)amino)-2-morpholinopyrimidin-4-yl)-4-methylphenyl)-3-(2,2,2-trifluoroethyl)pyrrolidine-1-carboxamide

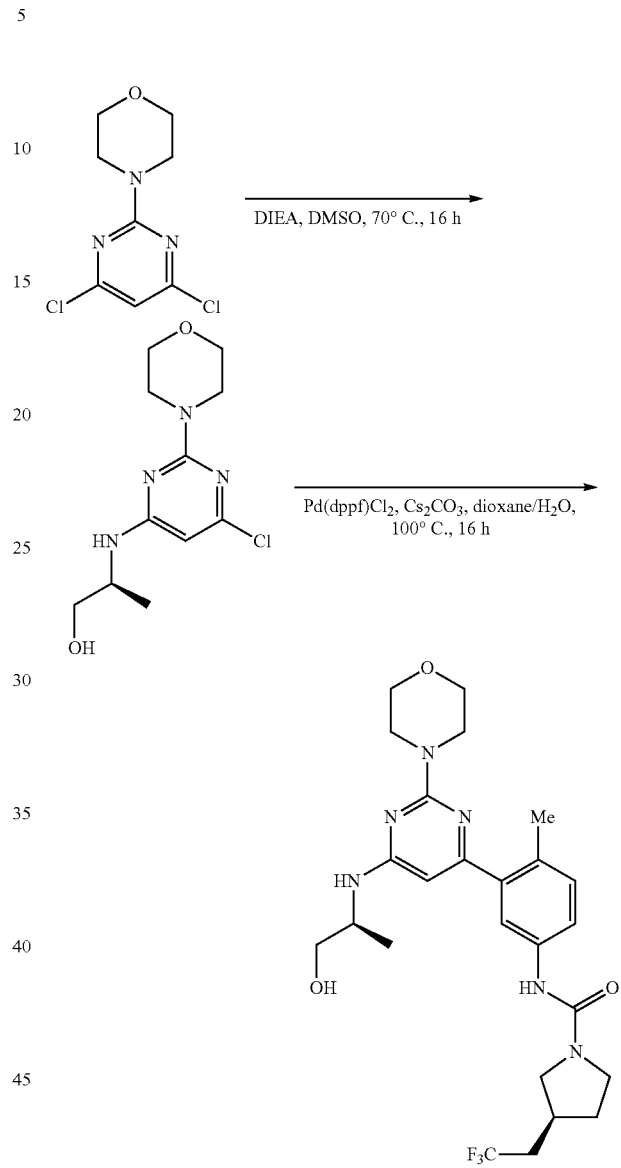

Step 1: To a stirred solution of 4-(4,6-dichloropyrimidin-2-yl)morpholine (300 mg, 1.28 mmol) in DMSO (5 mL) were added(S)-2-aminopropan-1-ol (125 mg, 1.66 mmol) and DIEA (248 mg, 1.92 mmol) at rt. The reaction mixture was stirred at 70° C. for 16 h. The resulting mixture was diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=1:1) to afford (S)-2-((6-chloro-2-morpholinopyrimidin-4-yl)amino) propan-1-ol (270 mg, 77%) as a white solid. MS Calcd.: 272, MS Found: 273 ([M+H]$^+$).

Step 2: To a solution of(S)-2-((6-chloro-2-morpholinopyrimidin-4-yl)amino) propan-1-ol (33 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1- carboxamide (50 mg, 0.12 mmol) and Cs₂CO₃ (98 mg, 0.30 mmol) in dioxane (10 mL) and water (2 mL) was added Pd(dppf)Cl₂ (4 mg, 0.006 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(6-(((S)-1-hydroxypropan-2-yl)amino)-2-morpholinopyrimidin-4-yl)-4-methylphenyl)-3-(2,2,2-trifluoroethyl)pyrrolidine-1-carboxamide (11.4 mg, 18%) as a white solid. ¹H NMR (400 MHz, DMSO-d₆): δ 8.12 (s, 1H), 7.50 (s, 1H), 7.41 (d, J=8.4 Hz, 1H), 7.08-6.81 (m, 2H), 5.85 (s, 1H), 4.70-4.69 (m, 1H), 4.03 (br s, 1H), 3.69-3.63 (m, 9H), 3.55-3.45 (m, 1H), 3.38-3.27 (m, 3H), 3.02 (t, J=9.2 Hz, 1H), 2.49-2.38 (m, 3H), 2.26 (s, 3H), 2.10-2.07 (m, 1H), 1.68-1.63 (m, 1H), 1.13 (d, J=6.8 Hz, 3H). MS Calcd.: 522, MS Found: 523 ([M+H]⁺).

Example 96: (S)—N-(3-(6-((2-hydroxy-2-methylpropyl)amino)-2-morpholinopyrimidin-4-yl)-4-methylphenyl)-3-(2,2,2-trifluoroethyl)pyrrolidine-1-carboxamide

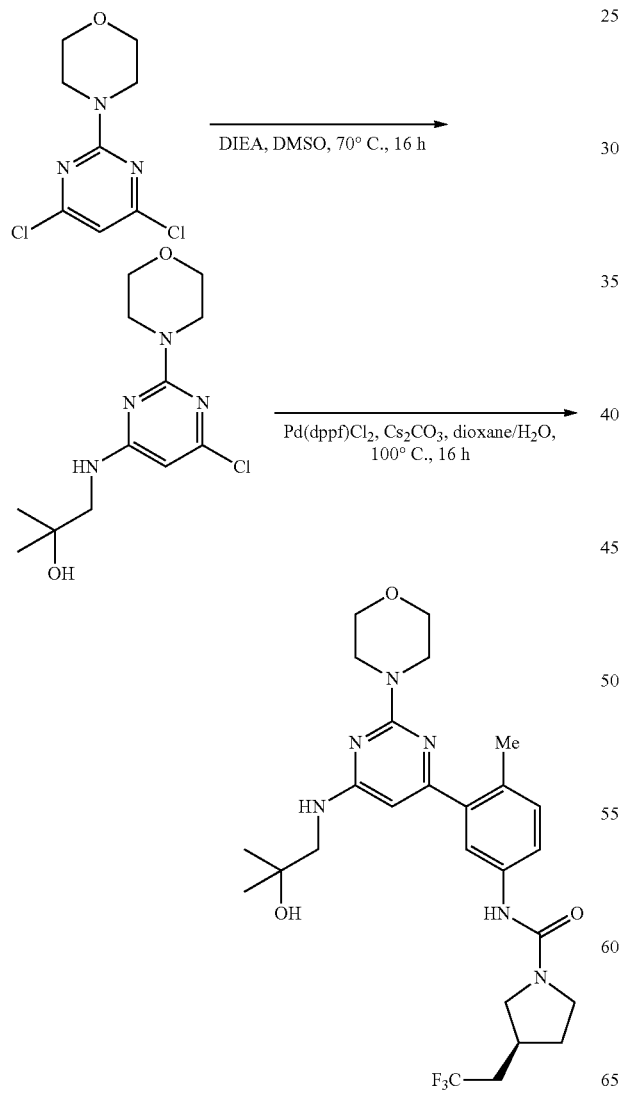

Step 1: To a stirred solution of 4-(4,6-dichloropyrimidin-2-yl)morpholine (200 mg, 0.85 mmol) in DMSO (5 mL) were added 1-amino-2-methylpropan-2-ol (91 mg, 1.03 mmol) and DIEA (165 mg, 1.28 mmol) at rt. The reaction mixture was stirred at 70° C. for 16 h. The resulting mixture was diluted with water (10 mL) and extracted with EA (10 mL×3). The combined organic layers was washed with brine (5 mL×4), dried over anhydrous Na₂SO₄ and filtered. The filtrate was concentrated under reduced pressure. The residue was purified by FCC (PE:EA=2:1) to afford 1-((6-chloro-2-morpholinopyrimidin-4-yl)amino)-2-methylpropan-2-ol (150 mg, 61%) as a white solid. MS Calcd.: 286, MS Found: 287 ([M+H]⁺).

Step 2: To a solution of 1-((6-chloro-2-morpholinopyrimidin-4-yl)amino)-2-methylpropan-2-ol (35 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and Cs₂CO₃ (98 mg, 0.30 mmol) in dioxane (10 mL) and water (2 mL) was added Pd(dppf)Cl₂ (4 mg, 0.006 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(6-((2-hydroxy-2-methylpropyl)amino)-2-morpholinopyrimidin-4-yl)-4-methylphenyl)-3-(2,2,2-trifluoroethyl)pyrrolidine-1-carboxamide (7.9 mg, 12%) as a white solid. ¹H NMR (400 MHz, DMSO-d₆): δ 8.13 (s, 1H), 7.50 (d, J=2.0 Hz, 1H), 7.43 (dd, J=2.4, 8.4 Hz, 1H), 7.08-6.64 (m, 2H), 5.98 (s, 1H), 4.53 (s, 1H), 3.69-3.50 (m, 10H), 3.37-3.23 (m, 3H), 3.02 (t, J=9.2 Hz, 1H), 2.46-2.33 (m, 3H), 2.26 (s, 3H), 2.11-2.07 (m, 1H), 1.70-1.60 (m, 1H), 1.07 (s, 6H). MS Calcd.: 536, MS Found: 537 ([M+H]⁺).

Example 97: (S)—N-(3-(2-((2-hydroxyethyl)amino)-6-morpholinopyrimidin-4-yl)-4-methylphenyl)-3-(2,2,2-trifluoroethyl)pyrrolidine-1-carboxamide formate

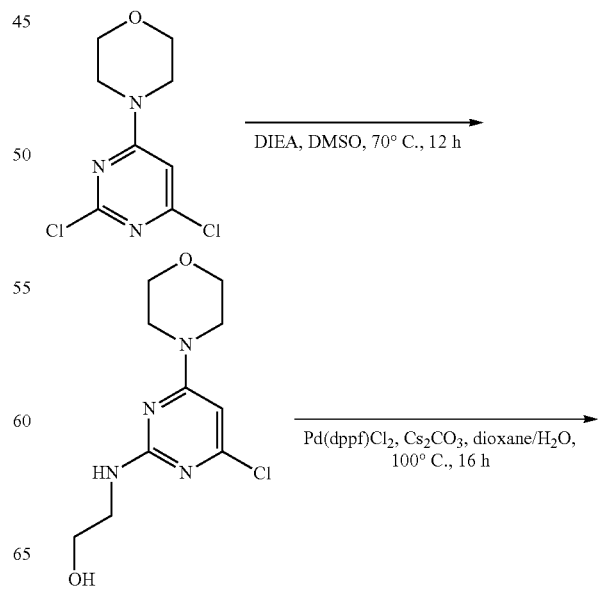

-continued

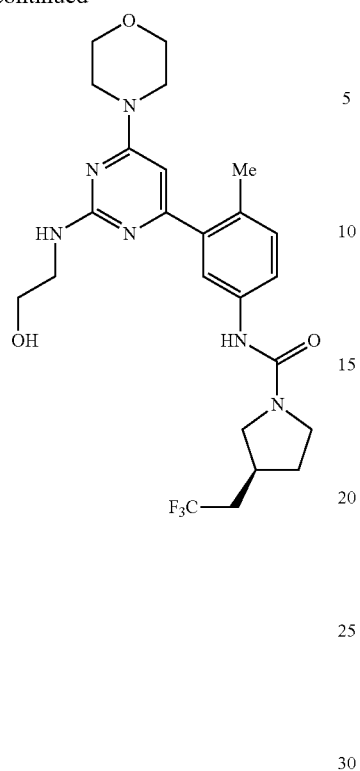

Step 1: To a stirred solution of 4-(2,6-dichloropyrimidin-4-yl)morpholine (500 mg, 2.14 mmol) in DMSO (5 mL) were added 2-aminoethanol (170 mg, 2.78 mmol) and DIEA (415 mg, 3.21 mmol) at rt. The reaction mixture was stirred at 70° C. for 12 h. The resulting mixture was diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=2:1) to afford 2-((4-chloro-6-morpholinopyrimidin-2-yl)amino) ethanol (360 mg, 65%) as a white solid. MS Calcd.: 258, MS Found: 259 ([M+H]$^+$).

Step 2: To a solution of 2-((4-chloro-6-morpholinopyrimidin-2-yl)amino) ethanol (32 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and $Cs_2CO_3$ (98 mg, 0.30 mmol) in dioxane (10 mL) and water (2 mL) was added Pd(dppf)Cl$_2$ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(2-((2-hydroxyethyl)amino)-6-morpholinopyrimidin-4-yl)-4-methylphenyl)-3-(2,2,2-trifluoroethyl)pyrrolidine-1-carboxamide formate (15.8 mg, 25%) as a yellow solid. $^1$H NMR (400 MHz, DMSO-d$_6$): δ 8.17 (s, 1H), 8.12 (s, 1H), 7.45-7.43 (m, 2H), 7.07 (d, J=9.2 Hz, 1H), 6.43 (br s, 1H), 6.02 (s, 1H), 4.62 (br, 0.5H), 3.69-3.64 (m, 5H), 3.54-3.46 (m, 7H), 3.41-3.30 (m, 3H), 3.02 (t, J=9.2 Hz, 1H), 2.46-2.36 (m, 3H), 2.24 (s, 3H), 2.10-2.07 (m, 1H), 1.68-1.63 (m, 1H). MS Calcd.: 508, MS Found: 509 ([M+H]$^+$).

Example 98: (S)—N-(3-(2-(((R)-1-hydroxypropan-2-yl)amino)-6-morpholinopyrimidin-4-yl)-4-methylphenyl)-3-(2,2,2-trifluoroethyl)pyrrolidine-1-carboxamide

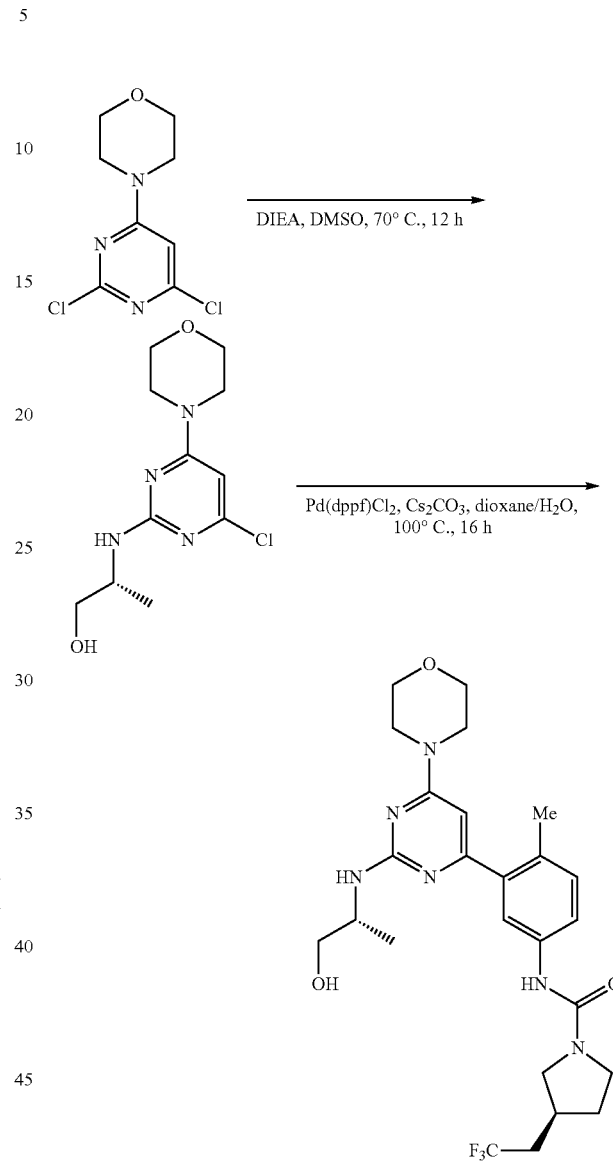

Step 1: To a stirred solution of 4-(2,6-dichloropyrimidin-4-yl)morpholine (500 mg, 2.14 mmol) in DMSO (5 mL) were added (R)-2-aminopropan-1-ol (210 mg, 2.78 mmol) and DIEA (415 mg, 3.21 mmol) at rt. The reaction mixture was stirred at 70° C. for 12 h. The resulting mixture was cooled to rt, diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=1:1) to afford (R)-2-((4-chloro-6-morpholinopyrimidin-2-yl)amino) propan-1-ol (180 mg, 31%) as a yellow solid. MS Calcd.: 272, MS Found: 273 ([M+H]$^+$).

Step 2: To a solution of (R)-2-((4-chloro-6-morpholinopyrimidin-2-yl)amino) propan-1-ol (32 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and Cs₂CO₃ (98 mg, 0.30 mmol) in dioxane (10 mL) and water (2 mL) was added Pd(dppf)Cl₂ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(2-(((R)-1-hydroxypropan-2-yl)amino)-6-morpholinopyrimidin-4-yl)-4-methylphenyl)-3-(2,2,2-trifluoroethyl)pyrrolidine-1-carboxamide (4.18 mg, 6%) as a pink solid. ¹H NMR (400 MHz, DMSO-d₆): δ 8.12 (s, 1H), 7.46-7.43 (m, 2H), 7.08 (d, J=8.0 Hz, 1H), 6.17-6.15 (m, 1H), 6.02 (s, 1H), 4.64 (br s, 1H), 3.98-3.91 (m, 1H), 3.69-3.59 (m, 5H), 3.54-3.43 (m, 6H), 3.31-3.29 (m, 2H), 3.04-2.98 (m, 1H), 2.46-2.32 (m, 3H), 2.25 (s, 3H), 2.10-2.07 (m, 1H), 1.68-1.63 (m, 1H), 1.11 (d, J=6.8 Hz, 3H). MS Calcd.: 522, MS Found: 523 ([M+H]⁺).

Example 99: (S)—N-(3-(2-((2-hydroxy-2-methylpropyl)amino)-6-morpholinopyrimidin-4-yl)-4-methylphenyl)-3-(2,2,2-trifluoroethyl)pyrrolidine-1-carboxamide

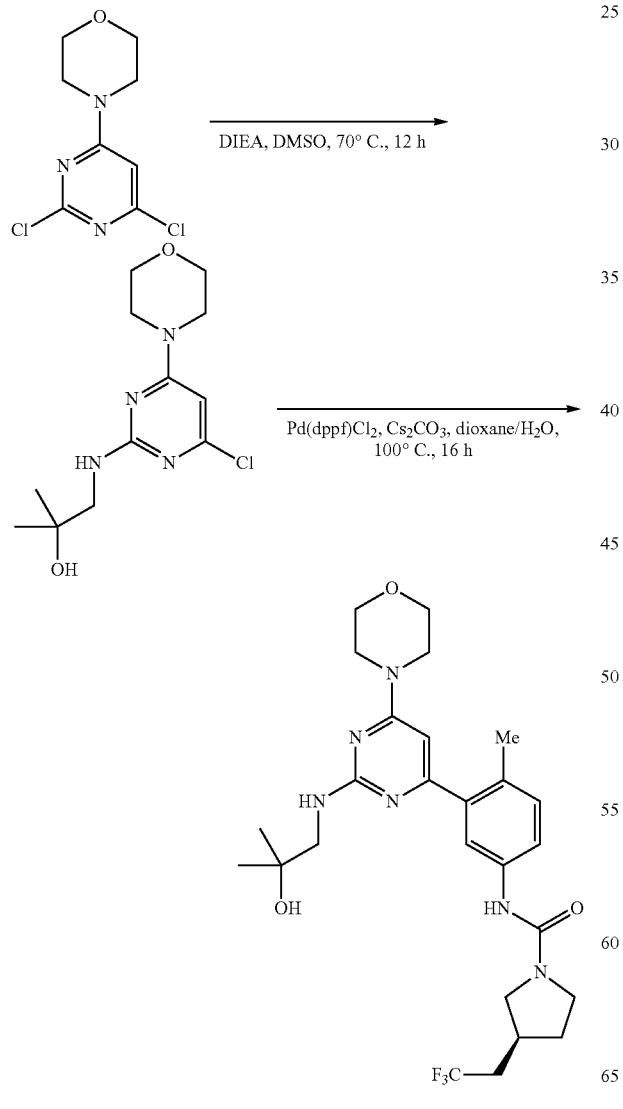

Step 1: To a stirred solution of 4-(2,6-dichloropyrimidin-4-yl)morpholine (500 mg, 2.14 mmol) in DMSO (5 mL) were added 1-amino-2-methylpropan-2-ol (250 mg, 2.78 mmol) and DIEA (415 mg, 3.21 mmol) at rt. The reaction mixture was stirred at 70° C. for 12 h. The resulting mixture was diluted with water (10 mL) and extracted with EA (10 mL×3). The combined organic layers was washed with brine (5 mL×4), dried over anhydrous Na₂SO₄ and filtered. The filtrate was concentrated under reduced pressure. The residue was purified by FCC (PE:EA=1:1) to afford 1-((4-chloro-6-morpholinopyrimidin-2-yl)amino)-2-methylpropan-2-ol (280 mg, 46%) as a yellow solid. MS Calcd.: 286, MS Found: 287 ([M+H]⁺).

Step 2: To a solution of 1-((4-chloro-6-morpholinopyrimidin-2-yl)amino)-2-methylpropan-2-ol (39 mg, 0.12 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (50 mg, 0.12 mmol) and Cs₂CO₃ (98 mg, 0.30 mmol) in dioxane (10 mL) and water (2 mL) was added Pd(dppf)Cl₂ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(2-((2-hydroxy-2-methylpropyl)amino)-6-morpholinopyrimidin-4-yl)-4-methylphenyl)-3-(2,2,2-trifluoroethyl)pyrrolidine-1-carboxamide (14.3 mg, 22%) as a yellow solid. ¹H NMR (400 MHz, DMSO-d₆): δ 8.13 (s, 1H), 7.46-7.44 (m, 2H), 7.08 (d, J=9.2 Hz, 1H), 6.26 (br s, 1H), 6.03 (s, 1H), 3.69-3.64 (m, 5H), 3.55-3.50 (m, 5H), 3.30-3.25 (m, 3H), 3.02 (t, J=9.2 Hz, 1H), 2.48-2.38 (m, 3H), 2.24 (s, 3H), 2.10-2.07 (m, 1H), 1.68-1.65 (m, 1H), 1.04 (s, 6H). MS Calcd.: 536, MS Found: 537 ([M+H]⁺).

Example 100: (S)—N-(3-(6-(((R)-1-hydroxypropan-2-yl)amino)-2-morpholinopyrimidin-4-yl)-4-methylphenyl)-3-(2,2,2-trifluoroethyl)pyrrolidine-1-carboxamide formate

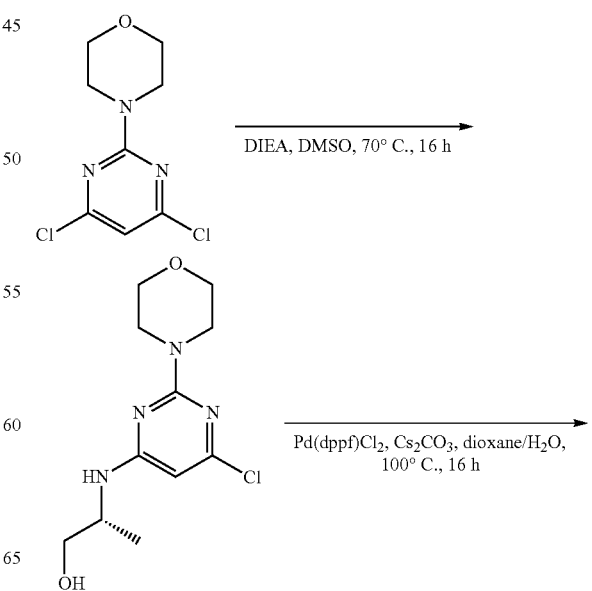

415

-continued

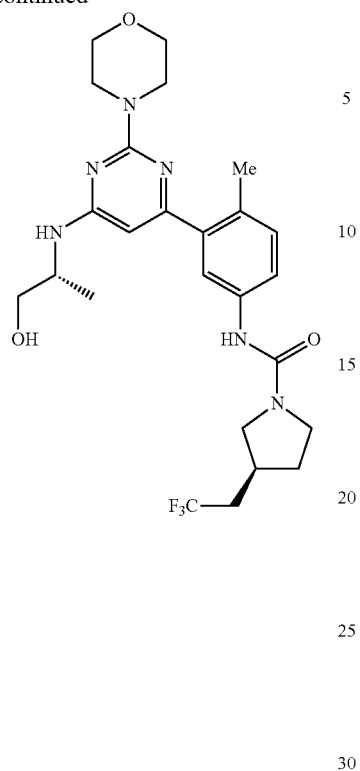

Step 1: To a stirred solution of 4-(4,6-dichloropyrimidin-2-yl)morpholine (300 mg, 1.28 mmol) in DMSO (5 mL) were added (R)-2-aminopropan-1-ol (125 mg, 1.66 mmol) and DIEA (248 mg, 1.92 mmol) at rt. The reaction mixture was stirred at 70° C. for 16 h. The resulting mixture was diluted with water (10 mL) and extracted with EA (10 mL×3). The combined organic layers was washed with brine (5 mL×4), dried over anhydrous $Na_2SO_4$ and filtered. The filtrate was concentrated under reduced pressure. The residue was purified by FCC (PE:EA=1:1) to afford (R)-2-((6-chloro-2-morpholinopyrimidin-4-yl)amino) propan-1-ol (270 mg, 77%) as a white solid. MS Calcd.: 272, MS Found: 273 ([M+H]$^+$).

Step 2: To a solution of (R)-2-((6-chloro-2-morpholinopyrimidin-4-yl)amino) propan-1-ol (66 mg, 0.24 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (100 mg, 0.24 mmol) and $Cs_2CO_3$ (198 mg, 0.61 mmol) in dioxane (10 mL) and water (2 mL) was added $Pd(dppf)Cl_2$ (9 mg, 0.012 mmol) at room temperature under nitrogen atmosphere. The reaction mixture was stirred at 100° C. for 16 h. The mixture was cooled down to room temperature, filtered and concentrated. The residue was purified by prep-HPLC to afford (S)—N-(3-(6-(((R)-1-hydroxypropan-2-yl)amino)-2-morpholinopyrimidin-4-yl)-4-methylphenyl)-3-(2,2,2-trifluoroethyl)pyrrolidine-1-carboxamide formate (29.4 mg, 23%) as a white solid. $^1$H NMR (400 MHz, DMSO-$d_6$): δ 8.21 (s, 0.3H), 8.12 (s, 1H), 7.50 (d, J=2.4 Hz, 1H), 7.41 (dd, J=2.0, 8.0 Hz, 1H), 7.06 (d, J=4.4 Hz, 1H), 6.82 (br s, 1H), 5.86 (s, 1H), 4.70 (br s, 1H), 3.98 (br s, 1H), 3.69-3.63 (m, 9H), 3.55-3.46 (m, 2H), 3.34-3.27 (m, 2H), 3.02 (t, J=9.2 Hz, 1H), 2.49-2.41 (m, 3H), 2.26 (s, 3H), 2.10-2.07 (m, 1H), 1.68-1.63 (m, 1H), 1.13 (d, J=6.8 Hz, 3H). MS Calcd.: 522, MS Found: 523 ([M+H]$^+$).

416

Example 101: (S)—N-(3-(2-(((S)-1-hydroxypropan-2-yl)amino)-6-morpholinopyrimidin-4-yl)-4-methylphenyl)-3-(2,2,2-trifluoroethyl)pyrrolidine-1-carboxamide

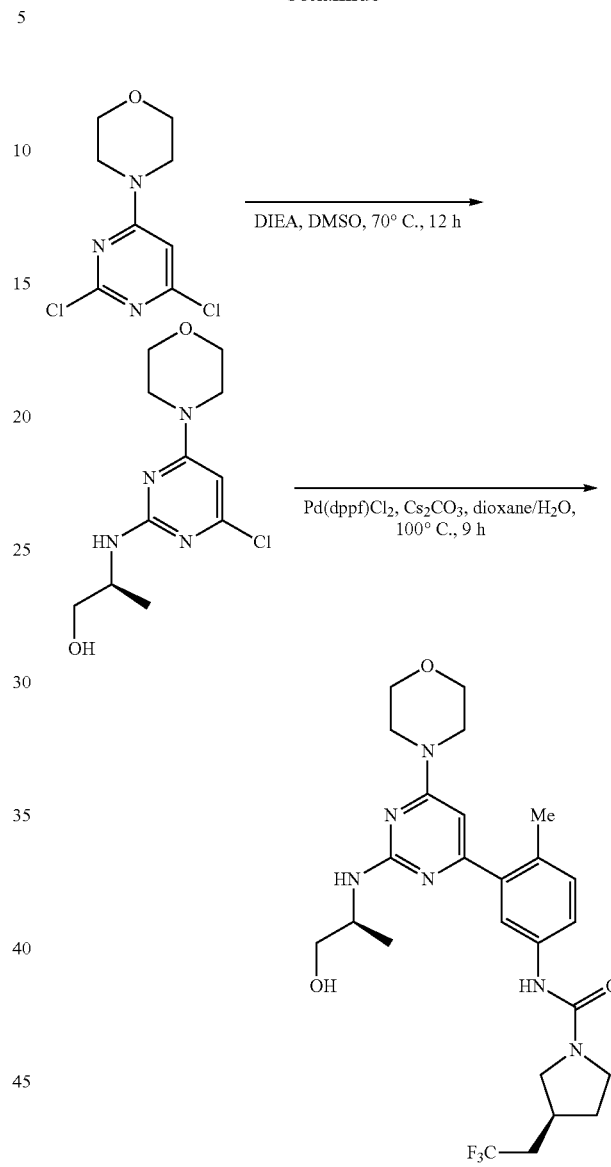

Step 1: To a stirred solution of 4-(2,6-dichloropyrimidin-4-yl)morpholine (1.0 g, 4.28 mmol) in DMSO (15 mL) were added (S)-2-aminopropan-1-ol (420 mg, 5.56 mmol) and DIEA (830 mg, 6.42 mmol) at rt. The reaction mixture was stirred at 70° C. for 12 h. The resulting mixture was cooled to rt, diluted with water (30 mL) and extracted with EA (15 mL×3). The combined organic layers was washed with brine (15 mL×4), dried over anhydrous $Na_2SO_4$ and filtered. The filtrate was concentrated under reduced pressure. The residue was purified by FCC (PE:EA=1:1) to afford (S)-2-((4-chloro-6-morpholinopyrimidin-2-yl)amino) propan-1-ol (580 mg, 50%) as a white solid. MS Calcd.: 272, MS Found: 273 ([M+H]$^+$).

Step 2: To a solution of(S)-2-((4-chloro-6-morpholinopyrimidin-2-yl)amino) propan-1-ol (50 mg, 0.18 mmol), (S)—N-(4-methyl-3-(4,4,5,5-tetramethyl-1,3,2-dioxaborolan-2-yl)phenyl)-3-(2,2,2-trifluoroethyl)pyrrolidine-1- carboxamide (75 mg, 0.18 mmol) and Cs₂CO₃ (150 mg, 0.46 mmol) in dioxane (10 mL) and water (2 mL) was added Pd(dppf)Cl₂ (27 mg, 0.036 mmol) at room temperature under nitrogen atmosphere. The reaction mixture was stirred at 100° C. for 9 h. The mixture was cooled down to room temperature, filtered and concentrated. The residue was purified by prep-HPLC to afford (S)—N-(3-(2-(((R)-1-hydroxypropan-2-yl)amino)-6-morpholinopyrimidin-4-yl)-4-methylphenyl)-3-(2,2,2-trifluoroethyl)pyrrolidine-1-carboxamide (7.3 mg, 7.6%) as a white solid. ¹H NMR (400 MHz, DMSO-d₆): δ 8.12 (s, 1H), 7.46-7.43 (m, 2H), 7.07 (d, J=8.4 Hz, 1H), 6.16 (br s, 1H), 6.01 (s, 1H), 4.63-4.62 (m, 1H), 3.92-3.91 (m, 1H), 3.69-3.64 (m, 5H), 3.59-3.43 (m, 6H), 3.31-3.24 (m, 2H), 3.02 (t, J=9.2 Hz, 1H), 2.46-2.32 (m, 3H), 2.25 (s, 3H), 2.11-2.07 (m, 1H), 1.70-1.60 (m, 1H), 1.11 (d, J=6.4 Hz, 3H). MS Calcd.: 522, MS Found: 523 ([M+H]⁺).

Examples 102 & 103: (R)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide & (S)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide

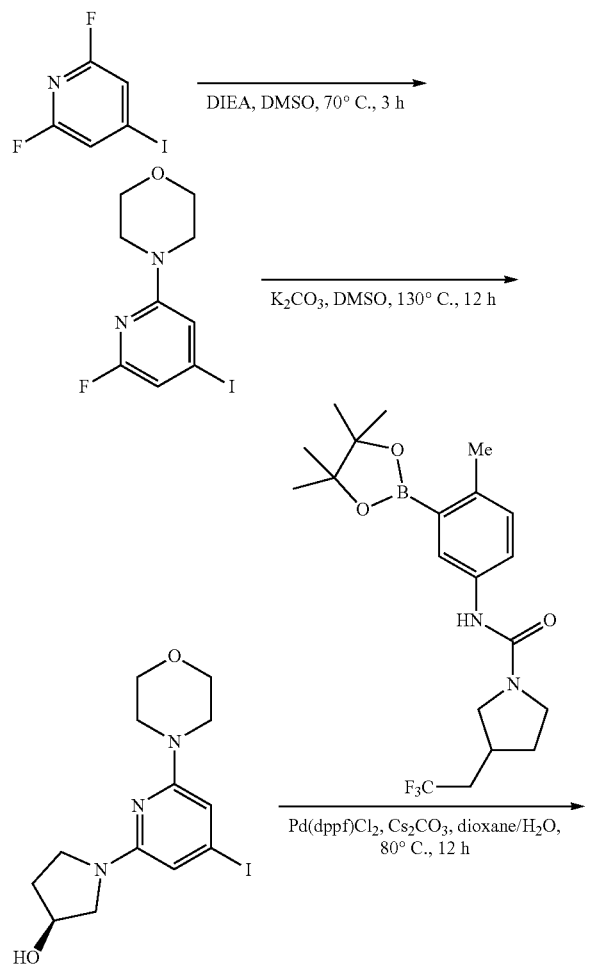

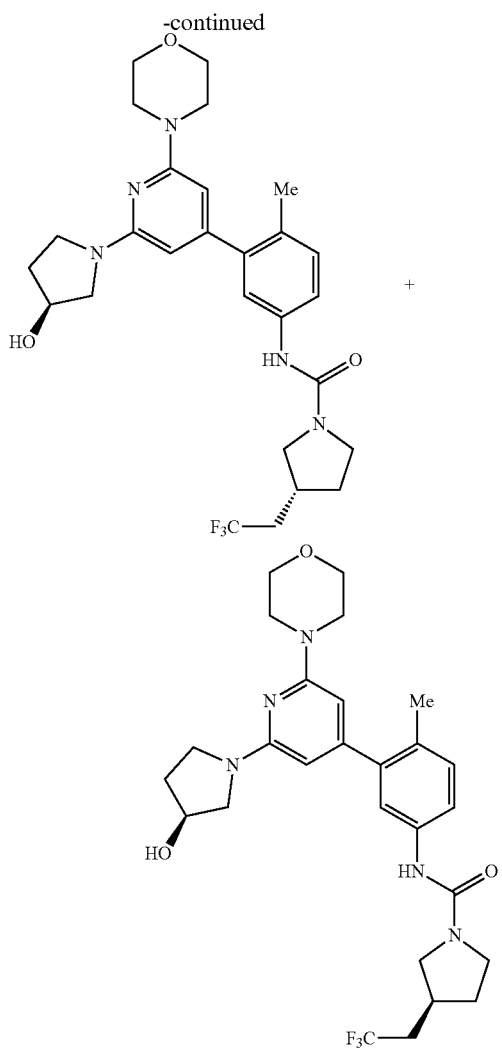

Step 1: To a stirred solution of 2,6-difluoro-4-iodopyridine (16.00 g, 66.40 mmol) in DMSO (240 mL) were added morpholine (5.49 mL, 63.04 mmol) and DIEA (12.07 mL, 93.40 mmol) at room temperature under nitrogen atmosphere. The reaction mixture was stirred at 70° C. for 3 h. The resulting mixture was cooled to rt, diluted with water (150 mL) and extracted with EA (300 mL×3). The combined organic layers was washed with brine (100 mL×4), dried over anhydrous Na₂SO₄, filtered and concentrated under reduced pressure. The residue was purified by silica gel column chromatography eluting with 30% EA in PE to afford 4-(6-fluoro-4-iodopyridin-2-yl)morpholine (17.60 g, 86%) as an off-white solid. MS Calcd.: 308, MS Found: 309 ([M+H]⁺).

Step 2: To a stirred solution of 4-(6-fluoro-4-iodopyridin-2-yl)morpholine (600 mg, 1.95 mmol) in DMSO (15 mL) was added (S)-pyrrolidin-3-ol (254 mg, 2.92 mmol) and K₂CO₃ (538 mg, 3.89 mmol) at rt. The reaction mixture was stirred at 130° C. for 12 h. The resulting mixture was cooled to rt, diluted with water (30 mL) and extracted with EA (15 mL×3). The combined organic layers was washed with brine (15 mL×4), dried over anhydrous Na₂SO₄ and filtered. The filtrate was concentrated under reduced pressure. The residue was purified by FCC (PE:EA=5:1) to afford (S)-1-(4-iodo-6-morpholinopyridin-2-yl) pyrrolidin-3-ol (500 mg, 68%) as a white solid. MS Calcd.: 375, MS Found: 376 ([M+H]⁺).

Step 3: To a solution of (S)-1-(4-iodo-6-morpholinopyridin-2-yl) pyrrolidin-3-ol (300 mg, 0.80 mmol), N-(4-methyl-3-(4,4,5,5-tetramethyl-1,3,2-dioxaborolan-2-yl)phenyl)-3-(2,2,2-trifluoroethyl)pyrrolidine-1-carboxamide (330 mg, 0.80 mmol) and $Cs_2CO_3$ (650 mg, 1.99 mmol) in dioxane (40 mL) and water (4 mL) was added $Pd(dppf)Cl_2$ (60 mg, 0.08 mmol) at room temperature under nitrogen atmosphere. The reaction mixture was stirred at 80° C. for 12 h. The mixture was cooled down to room temperature, filtered and concentrated. The residue was purified by chiral prep-SFC (Column: Chiralpak IC 5 μm*20*250 mm; Mobile Phase: $CO_2$:MeOH=65:35; Temp: 40° C.; Wavelength: 214 nm, Back pressure: 100 bar) to afford (R)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide (111.4 mg, 26%, RT=7.31 min, ee>98%) and (S)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide (114.6 mg, 27%, RT=6.45 min, ee>98%) as a white solid. (R)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide: 1H NMR (400 MHz, DMSO-$d_6$): δ 8.10 (s, 1H), 7.42 (dd, J=2.4, 8.4 Hz, 1H), 7.33 (d, J=2.0 Hz, 1H), 7.10 (d, J=8.4 Hz, 1H), 5.83 (s, 1H), 5.63 (s, 1H), 4.88 (d, J=4.0 Hz, 1H), 4.35 (br s, 1H), 3.68-3.64 (m, 5H), 3.54-3.39 (m, 8H), 3.29-3.27 (m, 2H), 3.02 (t, J=9.2 Hz, 1H), 2.49-2.36 (m, 3H), 2.16 (s, 3H), 2.09-1.95 (m, 2H), 1.87-1.85 (m, 1H), 1.68-1.63 (m, 1H). (S)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide: 1H NMR (400 MHz, DMSO-$d_6$): δ 8.10 (s, 1H), 7.42 (dd, J=2.4, 8.4 Hz, 1H), 7.33 (d, J=2.4 Hz, 1H), 7.10 (d, J=8.4 Hz, 1H), 5.83 (s, 1H), 5.63 (s, 1H), 4.88 (d, J=3.6 Hz, 1H), 4.35 (br s, 1H), 3.69-3.64 (m, 5H), 3.54-3.39 (m, 8H), 3.29-3.27 (m, 2H), 3.02 (t, J=9.2 Hz, 1H), 2.49-2.37 (m, 3H), 2.16 (s, 3H), 2.11-1.96 (m, 2H), 1.87-1.85 (m, 1H), 1.68-1.62 (m, 1H). MS Calcd.: 533, MS Found: 534 ([M+H]$^+$).

Example 104: (S)—N-(3-(2-(((S)-2-hydroxypropyl)amino)-6-morpholinopyrimidin-4-yl)-4-methylphenyl)-3-(2,2,2-trifluoroethyl)pyrrolidine-1-carboxamide

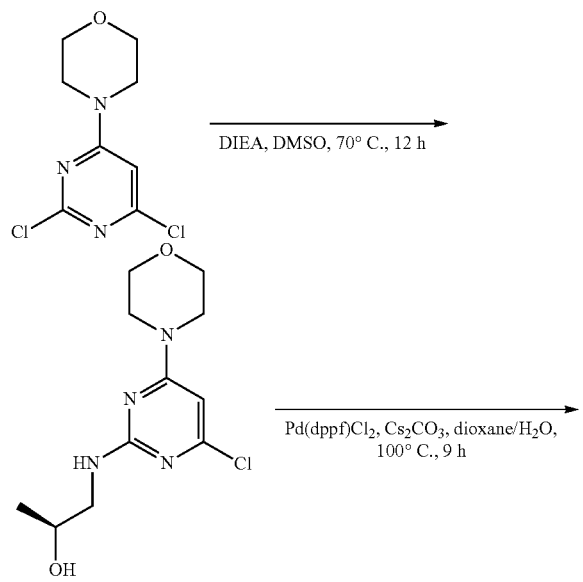

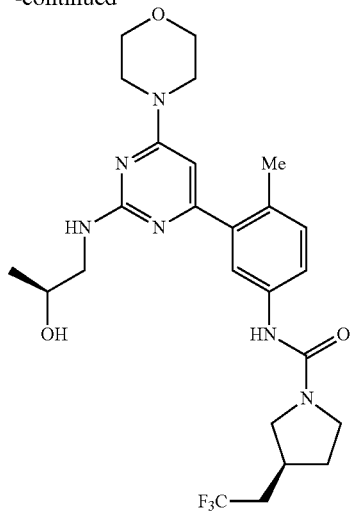

Step 1: To a stirred solution of 4-(2,6-dichloropyrimidin-4-yl)morpholine (500 mg, 2.14 mmol) in DMSO (15 mL) were added (S)-1-aminopropan-2-ol (210 mg, 2.78 mmol) and DIEA (400 mg, 3.21 mmol) at rt. The reaction mixture was stirred at 70° C. for 12 h. The resulting mixture was cooled to rt, diluted with water (30 mL) and extracted with EA (15 mL×3). The combined organic layers were washed with brine (15 mL×4), dried over anhydrous $Na_2SO_4$ and filtered. The filtrate was concentrated under reduced pressure. The residue was purified by FCC (PE:EA=1:1) to afford (S)-1-((4-chloro-6-morpholinopyrimidin-2-yl)amino)propan-2-ol (260 mg, 45%) as a white solid. MS Calcd.: 272, MS Found: 273 ([M+H]$^+$).

Step 2: To a solution of (S)-1-((4-chloro-6-morpholinopyrimidin-2-yl)amino) propan-2-ol (50 mg, 0.18 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (75 mg, 0.18 mmol) and $Cs_2CO_3$ (150 mg, 0.46 mmol) in dioxane (10 mL) and water (2 mL) was added $Pd(dppf)Cl_2$ (27 mg, 0.036 mmol) at room temperature under nitrogen atmosphere. The reaction mixture was stirred at 100° C. for 9 h. The mixture was cooled down to room temperature, filtered and concentrated. The residue was purified by prep-HPLC to afford (S)—N-(3-(2-(((S)-2-hydroxypropyl)amino)-6-morpholinopyrimidin-4-yl)-4-methylphenyl)-3-(2,2,2-trifluoroethyl)pyrrolidine-1-carboxamide (7.6 mg, 8%) as a white solid. $^1$H NMR (400 MHz, DMSO-$d_6$): δ 8.12 (s, 1H), 7.45-7.43 (m, 2H), 7.09-7.06 (m, 1H), 6.40-6.37 (m, 1H), 6.02 (s, 1H), 4.74-4.70 (m, 1H), 3.78-3.76 (m, 1H), 3.69-3.64 (m, 5H), 3.55-3.50 (m, 5H), 3.26-3.14 (m, 3H), 3.02 (t, J=9.2 Hz, 1H), 2.46-2.38 (m, 3H), 2.24 (s, 3H), 2.10-2.04 (m, 1H), 1.70-1.60 (m, 1H), 1.04 (d, J=6.0 Hz, 3H). MS Calcd.: 522, MS Found: 523 ([M+H]$^+$).

Example 105: (3S)—N-(3-[2-[(3R)-3-aminopyrrolidin-1-yl]-6-(morpholin-4-yl)pyridin-4-yl]-4-methylphenyl)-3-(2,2,2-trifluoroethyl)pyrrolidine-1-carboxamide
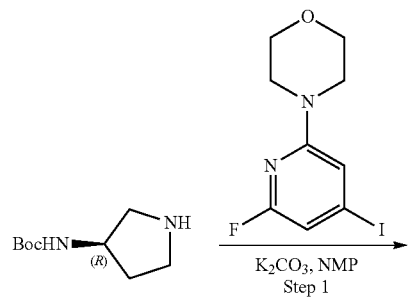
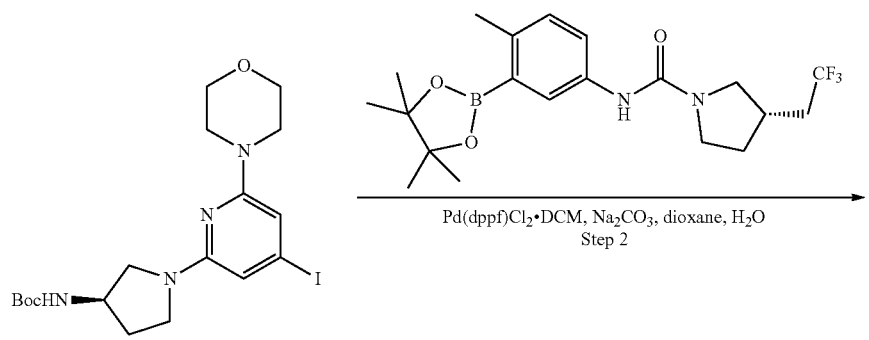
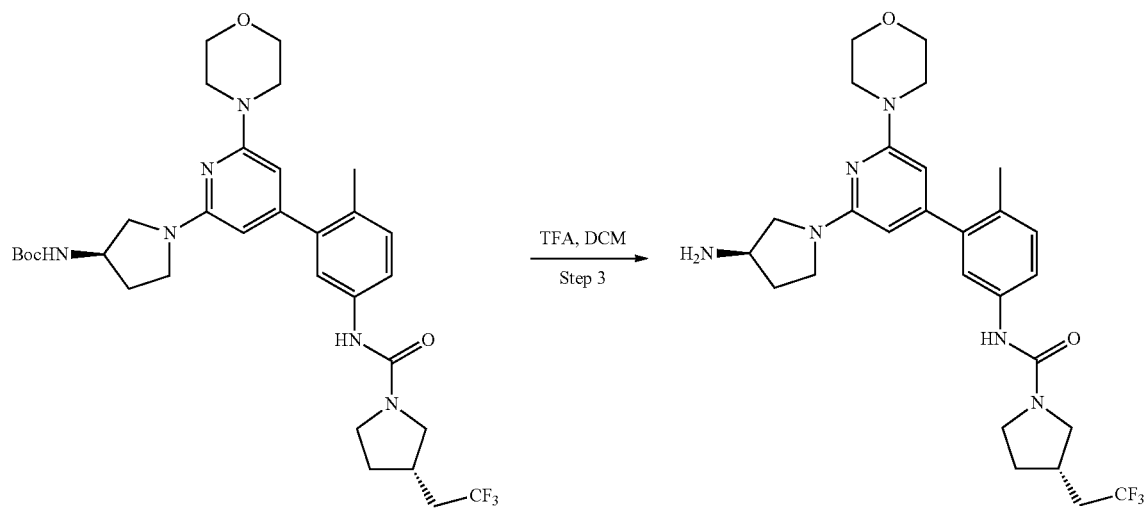

423

Preparation 105A: tert-butyl N-[(3R)-1-[4-iodo-6-(morpholin-4-yl)pyridin-2-yl]pyrrolidin-3-yl]carbamate

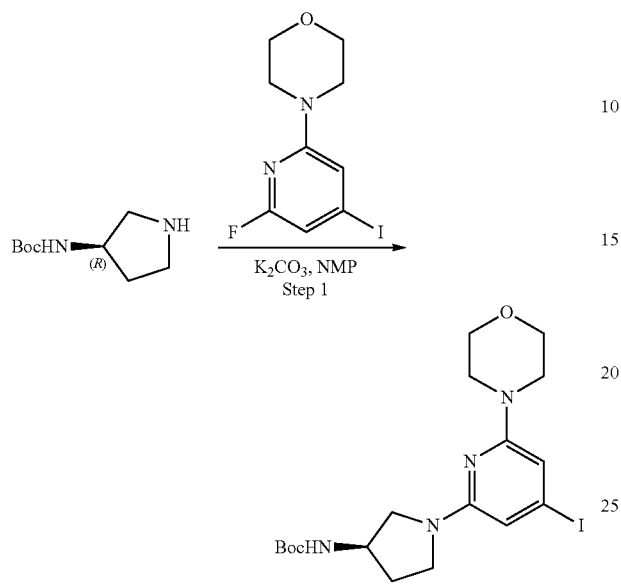

424

A mixture of 4-(6-fluoro-4-iodopyridin-2-yl)morpholine (500 mg, 1.623 mmol), tert-butyl N-[(3R)-pyrrolidin-3-yl]carbamate (453 mg, 2.434 mmol) and $K_2CO_3$ (449 mg, 3.246 mmol9) in NMP (5 mL) was stirred at 150° C. for 2 h. The reaction was quenched by the addition of water (100 mL). The resulting mixture was extracted with EtOAc (3×50 mL). The combined organic layers were washed with brine (3×20 mL), dried over anhydrous $Na_2SO_4$. After filtration, the filtrate was concentrated under reduced pressure. The residue was purified by silica gel column chromatography, eluted with PE/EtOAc (5/1) to afford tert-butyl N-[(3R)-1-[4-iodo-6-(morpholin-4-yl)pyridin-2-yl]pyrrolidin-3-yl]carbamate (588 mg, 76%) as a white solid. MS ESI calculated for $C_{18}H_{27}IN_4O_3$ $[M+H]^+$, 475.11; found 475.10. $^1$H NMR (400 MHz, Chloroform-d) δ 6.28 (d, J=1.2 Hz, 1H), 6.16 (d, J=1.2 Hz, 1H), 4.71-4.67 (m, 1H), 4.35-4.25 (m, 1H), 3.82-3.76 (m, 4H), 3.70-3.68 (m, 1H), 3.55-3.44 (m, 6H), 3.34-3.24 (m, 1H), 2.24-2.20 (m, 1H), 1.93-1.91 (m, 1H), 1.47 (s, 9H).

Preparation 105B: tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate

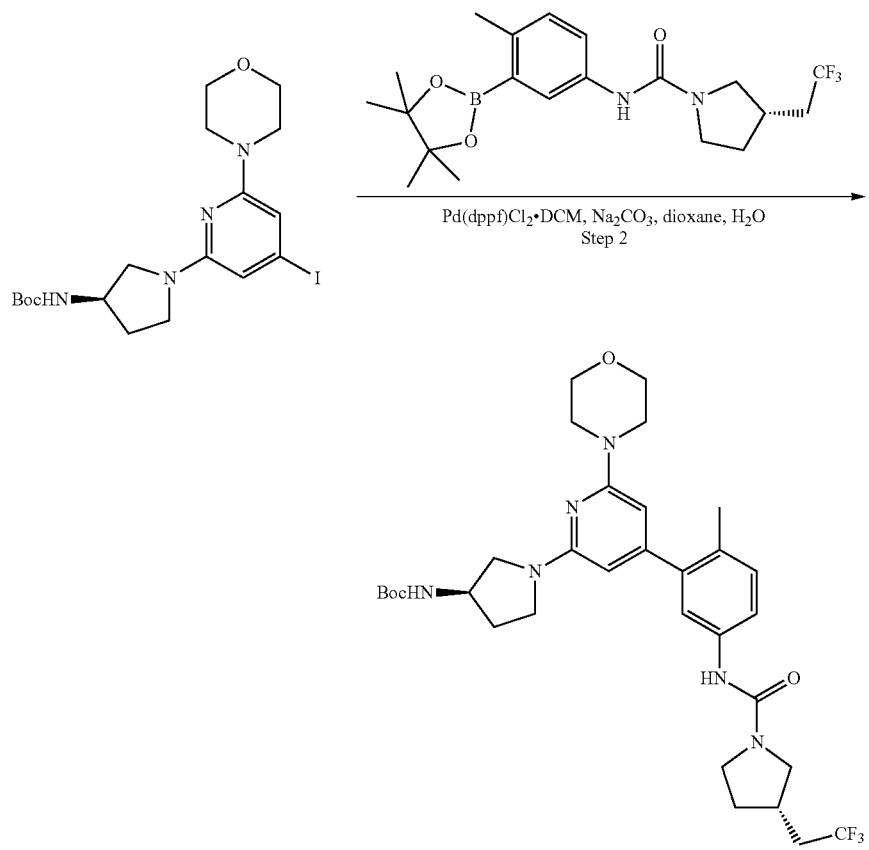

A mixture of tert-butyl N-[(3S)-1-[4-iodo-6-(morpholin-4-yl)pyridin-2-yl]pyrrolidin-3-yl]carbamate (173 mg, 0.364 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (150 mg, 0.364 mmol), Pd(dppf)Cl$_2$·CH$_2$Cl$_2$ (30 mg, 0.036 mmol) and Na$_2$CO$_3$ (116 mg, 1.092 mmol) in dioxane (4 mL) and H$_2$O (1 mL) was stirred at 60° C. for 16 h under nitrogen atmosphere. The mixture was allowed to cool down to room temperature. The reaction was quenched by the addition of water (100 mL). The resulting mixture was extracted with EtOAc (3×50 mL). The combined organic layers were washed with brine (3×20 mL), dried over anhydrous Na$_2$SO$_4$. After filtration, the filtrate was concentrated under reduced pressure. The residue was purified by Prep-TLC with PE/EtOAc (1/1) to afford tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (200 mg, 87%) as a light yellow solid. MS ESI calculated for C$_{32}$H$_{43}$F$_3$N$_6$O$_4$ [M+H]$^+$, 633.33, found 633.10. $^1$H NMR (400 MHz, Chloroform-d) δ 7.42-7.41 (m, 1H), 7.19-7.17 (m, 2H), 6.14 (s, 1H), 5.87 (s, 1H), 5.73 (s, 1H), 4.77-4.73 (m, 1H), 4.34-4.32 (m, 1H), 3.85-3.80 (m, 5H), 3.74-3.72 (m, 1H), 3.66-3.63 (m, 1H), 3.57-3.45 (m, 7H), 3.38-3.36 (m, 1H), 3.13-3.11 (m, 1H), 2.56-2.52 (m, 1H), 2.31-2.21 (m, 7H), 1.95-1.93 m, 1H), 1.79-1.71 (m, 1H), 1.47 (s, 9H).

Example 105: (3S)—N-(3-[2-[(3R)-3-aminopyrrolidin-1-yl]-6-(morpholin-4-yl)pyridin-4-yl]-4-methylphenyl)-3-(2,2,2-trifluoroethyl)pyrrolidine-1-carboxamide

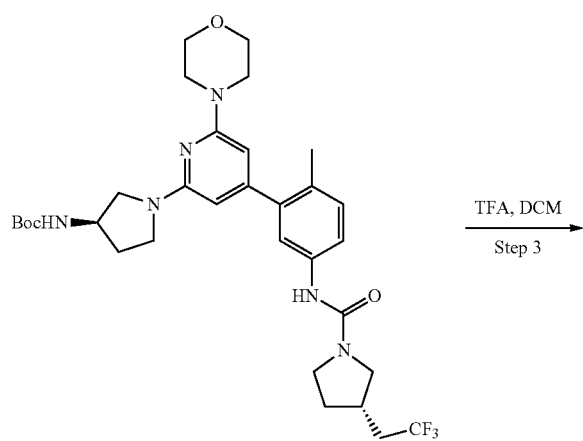

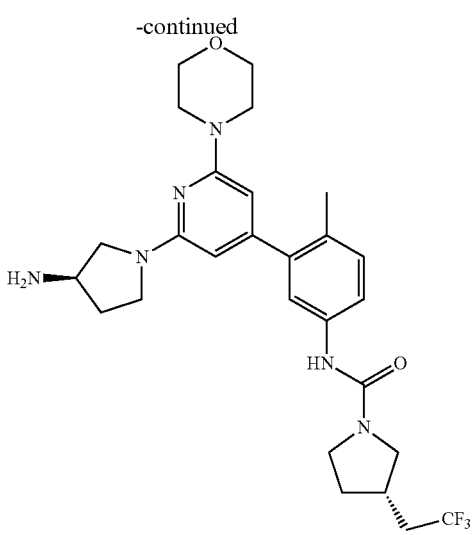

A mixture of tert-butyl N-[(3R)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (233 mg, 0.368 mmol) and TFA (1 mL) in DCM (5 mL) was stirred for 1 h at room temperature. The reaction mixture was concentrated under reduced pressure and basified to pH 8 with saturated NaHCO$_3$. The resulting mixture was extracted with EtOAc (3×50 mL). The combined organic layers were washed with brine (3×20 mL), dried over anhydrous Na$_2$SO$_4$. After filtration, the filtrate was concentrated under reduced pressure. The residue was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient:30% B to 50% B; 254/220 nm to afford (3S)—N-(3-[2-[(3R)-3-aminopyrrolidin-1-yl]-6-(morpholin-4-yl)pyridin-4-yl]-4-methylphenyl)-3-(2,2,2-trifluoroethyl)pyrrolidine-1-carboxamide (94 mg, 48%) as a white solid. MS ESI calculated for C$_{27}$H$_{35}$F$_3$N$_6$O$_2$ [M+H]$^+$, 533.28, found 533.40. $^1$H NMR (400 MHz, DMSO-d$_6$) δ 8.12 (s, 1H), 7.43 (dd, J=8.4, 2.4 Hz, 1H), 7.34 (d, J=2.4 Hz, 1H), 7.10 (d, J=8.4 Hz, 1H), 5.83 (s, 1H), 5.61 (s, 1H), 3.72-3.63 (m, 5H), 3.57-3.45 (m, 4H), 3.42-3.26 (m, 6H), 3.03-3.00 (m, 2H), 2.48-2.35 (m, 3H), 2.17 (s, 3H), 2.05-2.00 (m, 2H), 1.84-1.58 (m, 4H). $^{19}$F NMR (376 MHz, DMSO-d$_6$) δ -63.37 (3F).

Example 106: (3S)—N-(3-[2-[(3S)-3-aminopyrrolidin-1-yl]-6-(morpholin-4-yl)pyridin-4-yl]-4-methylphenyl)-3-(2,2,2-trifluoroethyl)pyrrolidine-1-carboxamide

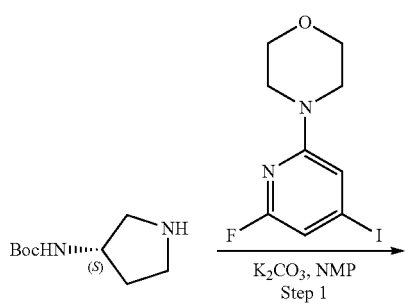

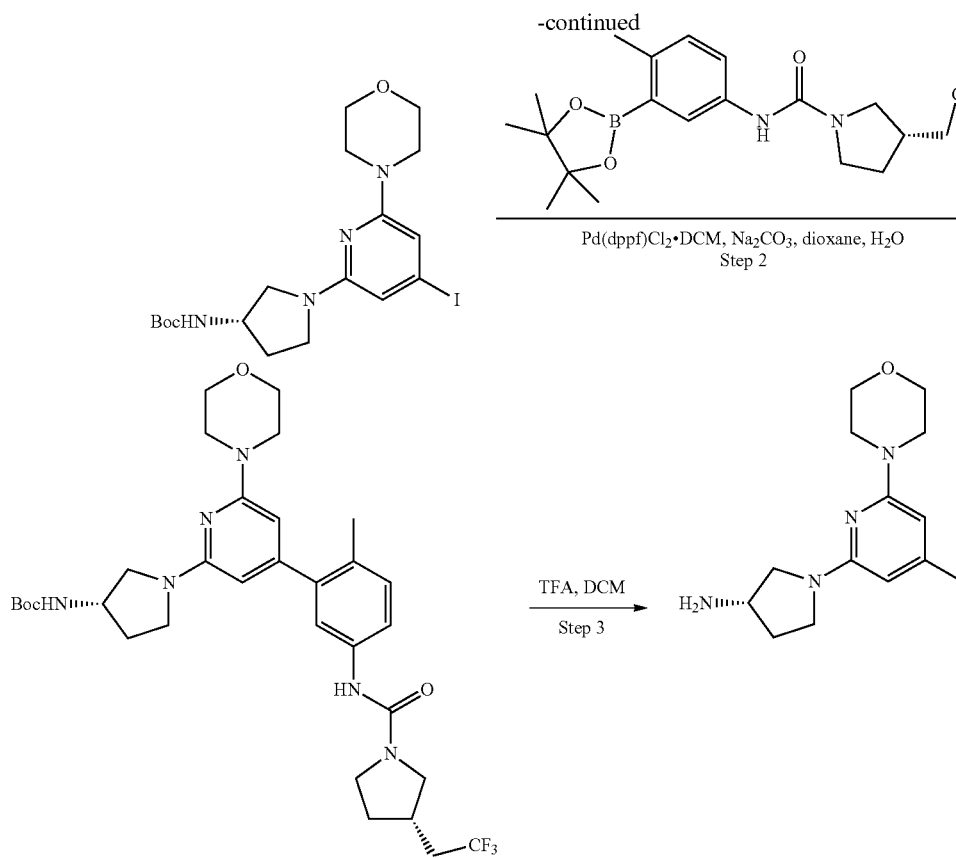

Preparation 106A: tert-butyl N-[(3S)-1-[4-iodo-6-(morpholin-4-yl)pyridin-2-yl]pyrrolidin-3-yl]carbamate

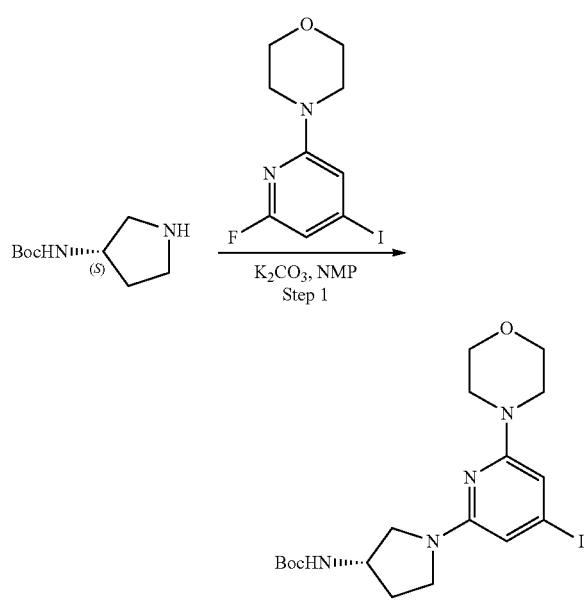

A mixture of 4-(6-fluoro-4-iodopyridin-2-yl)morpholine (500 mg, 1.623 mmol), tert-butyl N-[(3S)-pyrrolidin-3-yl]carbamate (453 mg, 2.434 mmol) and $K_2CO_3$ (449 mg, 3.246 mmol) in NMP (5 mL) was stirred at 150° C. for 2 h. The reaction was quenched by the addition of water (100 mL) at room temperature. The resulting mixture was extracted with EtOAc (3×50 mL). The combined organic layers were washed with brine (3×20 mL), dried over anhydrous $Na_2SO_4$. After filtration, the filtrate was concentrated under reduced pressure. The residue was purified by silica gel column chromatography, eluted with PE/EtOAc (5/1) to afford tert-butyl N-[(3S)-1-[4-iodo-6-(morpholin-4-yl)pyridin-2-yl]pyrrolidin-3-yl]carbamate (577 mg, 75%) as a white solid. MS ESI calculated for $C18H_{27}IN_4O_3$ [M+H]$^+$, 475.11, found 475.15. $^1$H NMR (400 MHz, Chloroform-d) δ 6.28 (d, J=1.2 Hz, 1H), 6.16 (d, J=1.2 Hz, 1H), 4.71-4.67 (s, 1H), 4.35-4.25 (m, 1H), 3.82-3.76 (m, 4H), 3.70-3.68 (m, 1H), 3.55-3.48 (m, 1H), 3.48-3.44 (m, 4H), 3.34-3.24 (m, 1H), 2.24-2.20 (m, 1H), 1.93-1.91 (m, 1H), 1.47 (s, 9H).

Preparation 106B: tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate

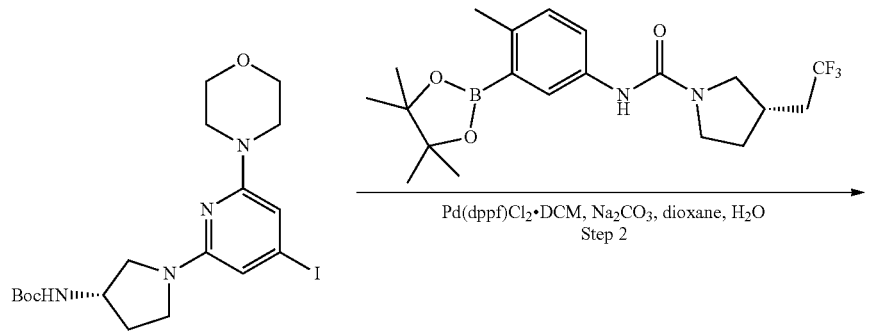

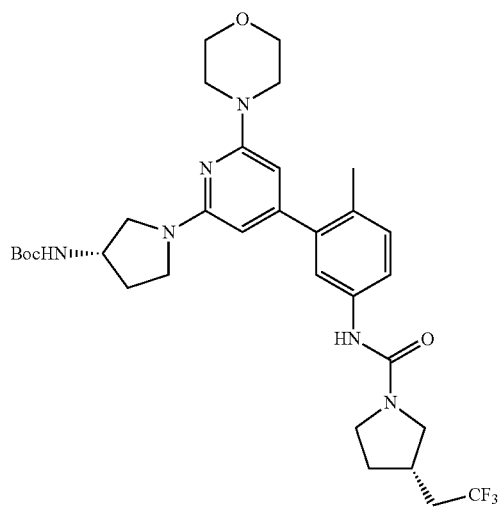

A mixture of tert-butyl N-[(3S)-1-[4-iodo-6-(morpholin-4-yl)pyridin-2-yl]pyrrolidin-3-yl]carbamate (173 mg, 0.364 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (150 mg, 0.364 mmol), Pd(dppf)Cl$_2$·CH$_2$Cl$_2$ (30 mg, 0.036 mmol) and Na$_2$CO$_3$ (116 mg, 1.092 mmol) in dioxane (4 mL) and H$_2$O (1 mL) was stirred at 60° C. for 3 h under nitrogen atmosphere. The resulting mixture was concentrated under reduced pressure. The residue was purified by Prep-TLC with PE/EtOAc (1/1) to afford tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (200 mg, 87%) as a light yellow solid. MS ESI calculated for C$_{32}$H$_{43}$F$_3$N$_6$O$_4$ [M+H]$^+$, 633.33, found 633.10. $^1$H NMR (400 MHz, Chloroform-d) δ 7.42-7.41 (m, 1H), 7.19-7.17 (m, 2H), 6.14 (s, 1H), 5.87 (s, 1H), 5.73 (s, 1H), 4.77-4.73 (m, 1H), 4.34-4.32 (m, 1H), 3.85-3.80 (m, 5H), 3.74-3.72 (m, 1H), 3.66-3.63 (m, 1H), 3.57-3.45 (m, 6H), 3.38-3.36 (m, 2H), 3.13-3.11 (m, 1H), 2.56-2.52 (m, 1H), 2.31-2.21 (m, 7H), 1.95-1.93 m, 1H), 1.79-1.71 (m, 1H), 1.47 (s, 9H).

Example 106: (3S)—N-(3-[2-[(3S)-3-aminopyrrolidin-1-yl]-6-(morpholin-4-yl)pyridin-4-yl]-4-methylphenyl)-3-(2,2,2-trifluoroethyl)pyrrolidine-1-carboxamide

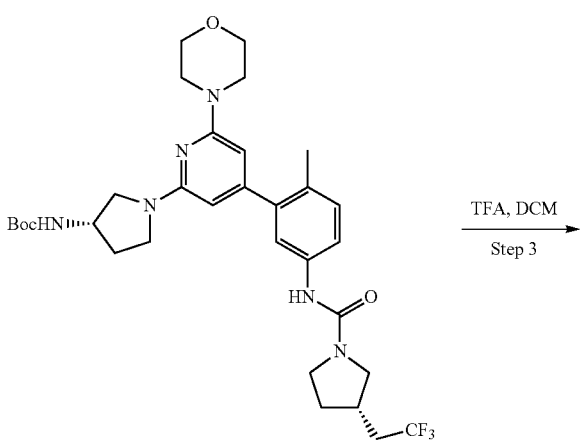

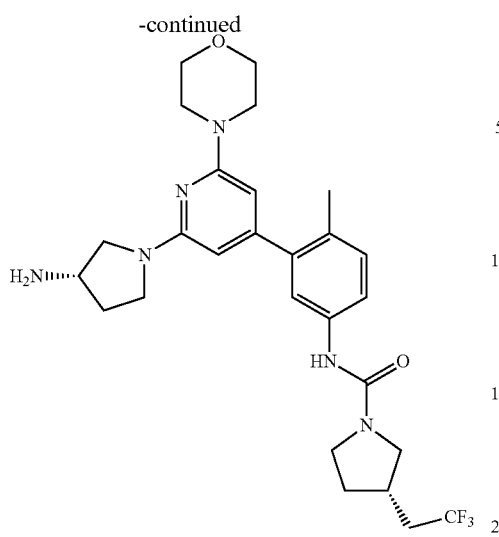

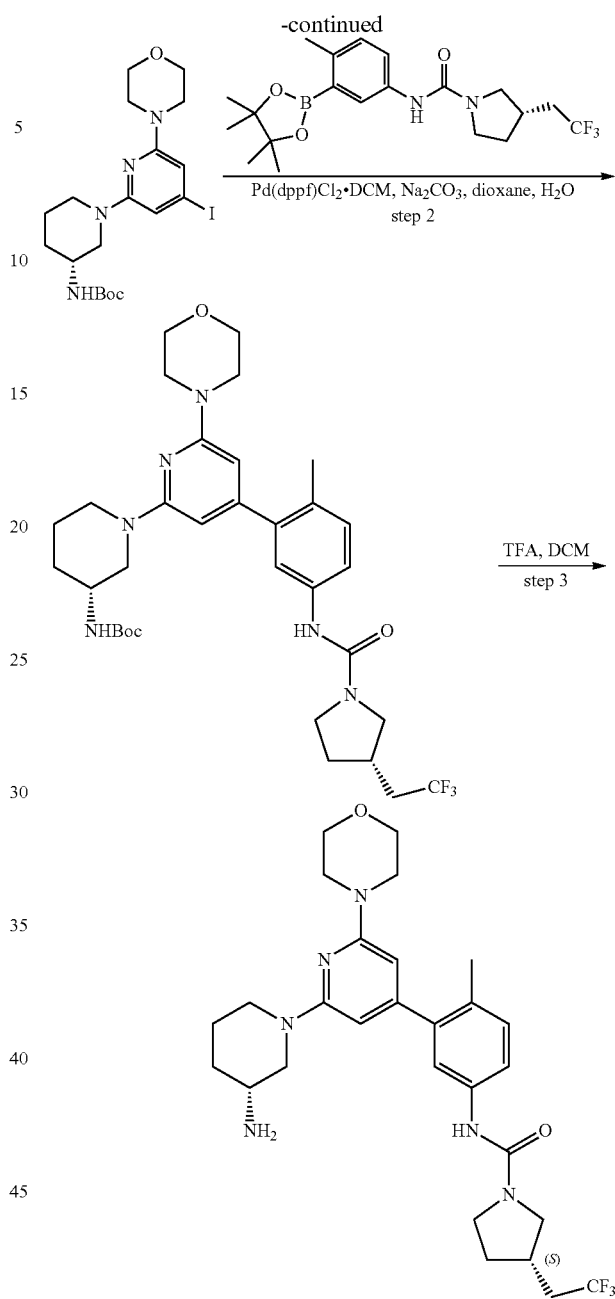

A mixture of tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (223 mg, 0.368 mmol) and TFA (1 mL) in DCM (5 mL) was stirred for 1 h at room temperature. The reaction mixture was concentrated under reduced pressure and basified to pH 8 with saturated NaHCO$_3$. The resulting mixture was extracted with EtOAc (50 mL). The combined organic layers were washed with brine (3×20 mL), dried over anhydrous Na$_2$SO$_4$. After filtration, the filtrate was concentrated under reduced pressure. The residue was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient:30% B to 50% B in 25 min; 254/220 nm to afford (3S)—N-(3-[2-[(3S)-3-aminopyrrolidin-1-yl]-6-(morpholin-4-yl)pyridin-4-yl]-4-methylphenyl)-3-(2,2,2-trifluoroethyl)pyrrolidine-1-carboxamide (81 mg, 48%) as a white solid. MS ESI calculated for C$_{27}$H$_{35}$F$_3$N$_6$O$_2$ [M+H]$^+$, 533.28, found 533.15. $^1$H NMR (400 MHz, DMSO-d$_6$) δ 8.12 (s, 1H), 7.43 (dd, J=8.4, 2.4 Hz, 1H), 7.34 (d, J=2.4 Hz, 1H), 7.10 (d, J=8.4 Hz, 1H), 5.83 (s, 1H), 5.61 (s, 1H), 3.72-3.63 (m, 5H), 3.57-3.45 (m, 4H), 3.42-3.26 (m, 6H), 3.03-3.00 (m, 2H), 2.48-2.35 (m, 3H), 2.17 (s, 3H), 2.05-2.00 (m, 2H), 1.94-1.60 (m, 4H). $^{19}$F NMR (376 MHz, DMSO-d$_6$) δ −63.37 (3F).

Example 107: (3S)—N-(3-[2-[(3R)-3-aminopiperidin-1-yl]-6-(morpholin-4-yl)pyridin-4-yl]-4-methylphenyl)-3-(2,2,2-trifluoroethyl)pyrrolidine-1-carboxamide Preparation 107A: tert-butyl N-[(3R)-1-[4-iodo-6-(morpholin-4-yl)pyridin-2-yl]piperidin-3-yl]carbamate

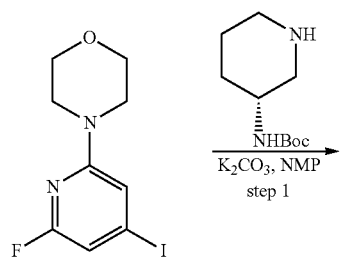

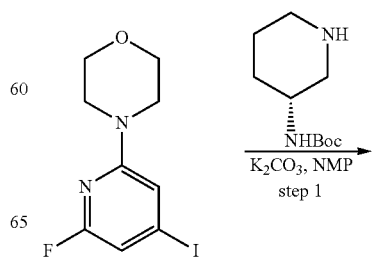

-continued

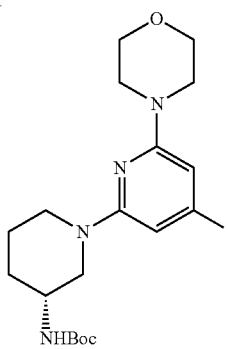

A mixture of 4-(6-fluoro-4-iodopyridin-2-yl)morpholine (500 mg, 1.623 mmol), tert-butyl N-[(3R)-piperidin-3-yl]carbamate (486 mg, 2.435 mmol) in NMP (5 mL) and $K_2CO_3$ (449 mg, 3.246 mmol) was stirred for 2 h at 150° C. The reaction was quenched by the addition of water (30 mL). The resulting mixture was extracted with EtOAc (3×40 mL). The combined organic layers were washed with brine (30 mL), dried over anhydrous $Na_2SO_4$. After filtration, the filtrate was concentrated under reduced pressure. The residue was purified by silica gel column chromatography, eluted with PE/EtOAc (3/1) to afford tert-butyl N-[(3R)-1-[4-iodo-6-(morpholin-4-yl)pyridin-2-yl]piperidin-3-yl]carbamate (450 mg, 57%) as a white solid. MS ESI calculated for $C_{19}H_{29}IN_4O_3$ $[M+H]^+$, 489.13; found 488.95.

Preparation 107B: tert-butyl N-[(3R)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate

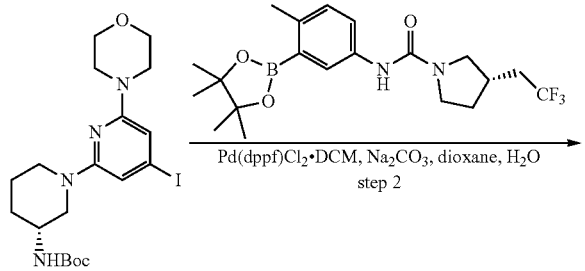

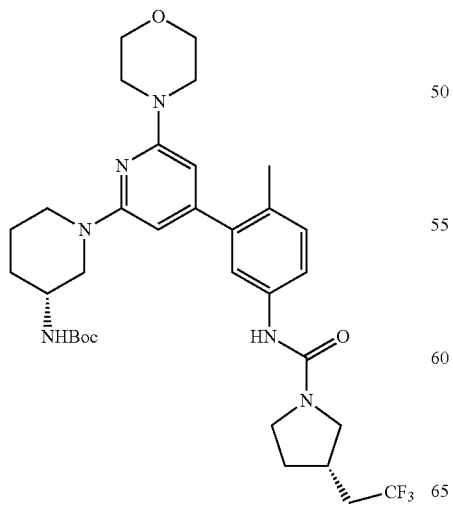

A mixture of tert-butyl N-[(3R)-1-[4-iodo-6-(morpholin-4-yl)pyridin-2-yl]piperidin-3-yl]carbamate (200 mg, 0.410 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (169 mg, 0.410 mmol), 1,4-dioxane (2 mL), $H_2O$ (0.4 mL), $Na_2CO_3$ (130 mg, 1.229 mmol) and $Pd(dppf)Cl_2 \cdot CH_2Cl_2$ (39 mg, 0.041 mmol) was stirred for 16 h at 80° C. under nitrogen atmosphere. The reaction was quenched by the addition of water (25 mL) at room temperature. The resulting mixture was extracted with EtOAc (3×25 mL). The combined organic layers were washed with brine (15 mL), dried over anhydrous $Na_2SO_4$. After filtration, the filtrate was concentrated under reduced pressure. The residue was purified by silica gel column chromatography, eluted with PE/EtOAc (1/1) to afford tert-butyl N-[(3R)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (200 mg, 76%) as a light brown solid. MS ESI calculated for $C_{33}H_{45}F_3N_6O_4$ $[M+H]^+$, 647.35, found 647.40.

Example 107: (3S)—N-(3-[2-[(3R)-3-aminopiperidin-1-yl]-6-(morpholin-4-yl)pyridin-4-yl]-4-methylphenyl)-3-(2,2,2-trifluoroethyl)pyrrolidine-1-carboxamide

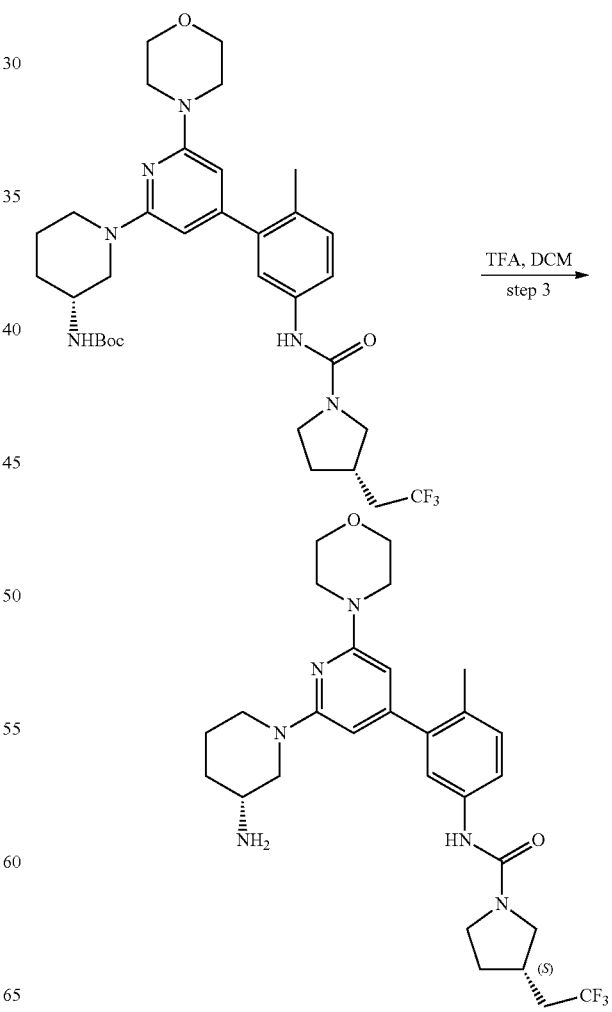

To a stirred solution of tert-butyl N-[(3R)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (200 mg, 0.309 mmol) in DCM (3 mL) was added TFA (1 mL) at room temperature. The resulting mixture was stirred for 1 h at room temperature. The resulting mixture was concentrated under reduced pressure. The mixture was basified to pH 8 with saturated NaHCO$_3$. The resulting mixture was extracted with DCM (3×20 mL). The combined organic layers were washed with brine (2×10 mL), dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford (3S)—N-(3-[2-[(3R)-3-aminopiperidin-1-yl]-6-(morpholin-4-yl)pyridin-4-yl]-4-methylphenyl)-3-(2,2,2-trifluoroethyl)pyrrolidine-1-carboxamide (94 mg, 55%) as a light yellow solid. MS ESI calculated for C$_{28}$H$_{37}$F$_3$N$_6$O$_2$ [M+H]$^+$, 547.29, found 547.15. $^1$H NMR (400 MHz, DMSO-d$_6$) δ 8.14 (s, 1H), 7.43 (dd, J=8.4, 2.4 Hz, 1H), 7.35 (d, J=2.4 Hz, 1H), 7.11 (d, J=8.4 Hz, 1H), 6.00 (s, 1H), 5.92 (s, 1H), 4.15-4.12 (m, 1H), 4.07-4.03 (m, 1H), 3.72-3.63 (m, 4H), 3.53-3.50 (m, 2H), 3.44-3.37 (m, 4H), 3.31-3.30 (m, 1H), 3.02-3.00 (m, 1H), 2.85-2.75 (m, 2H), 2.79-2.71 (m, 1H), 2.51-2.34 (m, 3H), 2.16 (s, 3H), 2.14-2.03 (m, 1H), 1.88-1.86 (m, 1H), 1.74-1.58 (m, 2H), 1.53-1.37 (m, 1H), 1.37-1.24 (m, 3H). $^{19}$F NMR (282 MHz, Chloroform-d) δ −64.92 (3F).

Example 108: (3S)—N-(3-[2-[(3S)-3-aminopiperidin-1-yl]-6-(morpholin-4-yl)pyridin-4-yl]-4-methylphenyl)-3-(2,2,2-trifluoroethyl)pyrrolidine-1-carboxamide

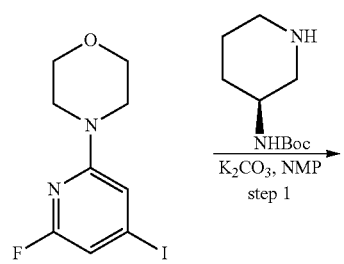

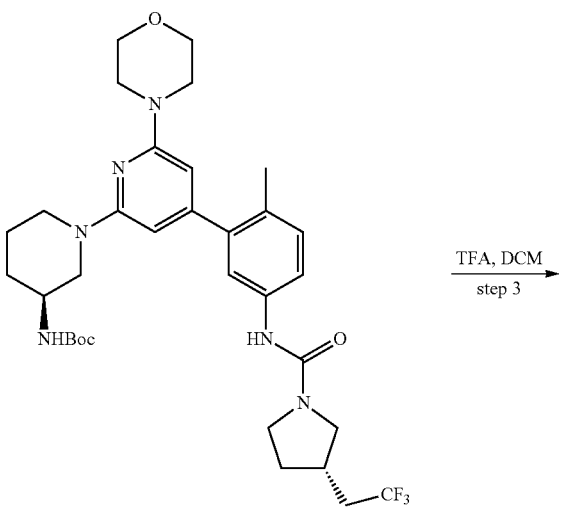

Preparation 108A: tert-butyl N-[(3S)-1-[4-iodo-6-(morpholin-4-yl)pyridin-2-yl]piperidin-3-yl]carbamate

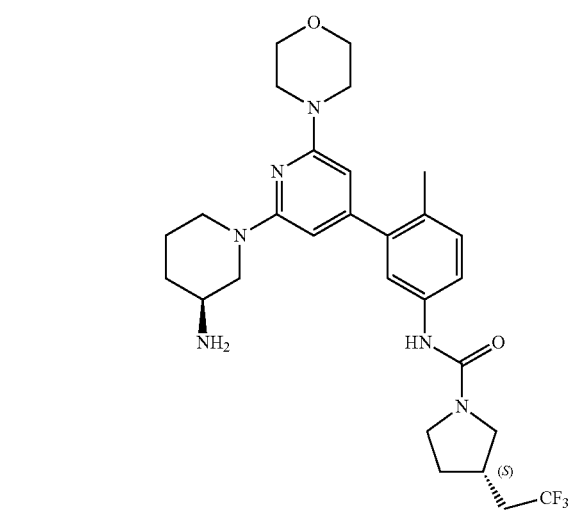

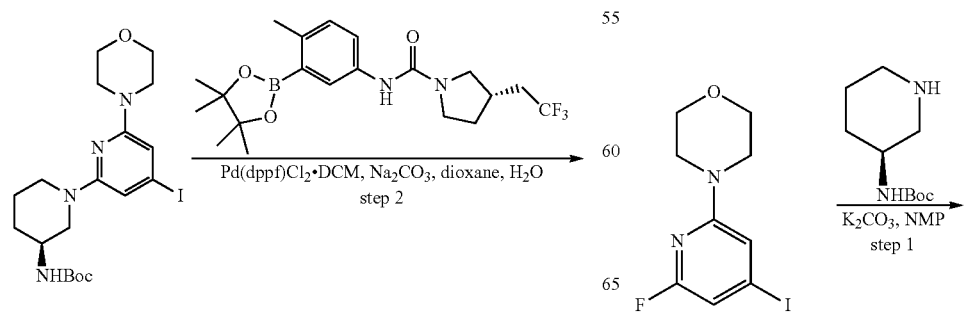

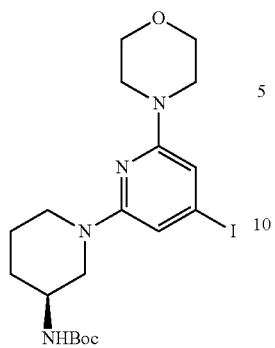

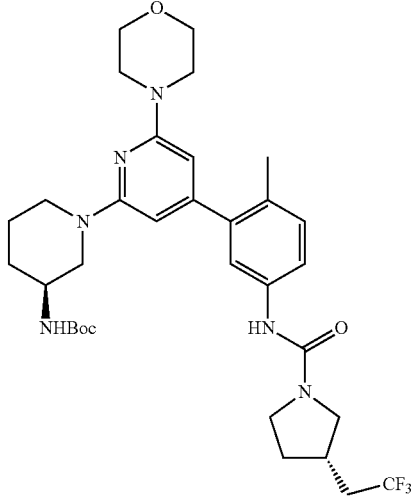

A mixture of 4-(6-fluoro-4-iodopyridin-2-yl)morpholine (500 mg, 1.623 mmol), tert-butyl N-[(3S)-piperidin-3-yl]carbamate (486 mg, 2.435 mmol) in NMP (5 mL) and K$_2$CO$_3$ (449 mg, 3.246 mmol) was stirred for 2 h at 150° C. The reaction was quenched by the addition of water (30 mL). The resulting mixture was extracted with EtOAc (3×40 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EtOAc (3/1) to afford tert-butyl N-[(3S)-1-[4-iodo-6-(morpholin-4-yl)pyridin-2-yl]piperidin-3-yl]carbamate (480 mg, 61%) as a white solid. MS ESI calculated for C$_{19}$H$_{29}$IN$_4$O$_3$ [M+H]$^+$, 489.13; found 488.95. $^1$H NMR (300 MHz, Chloroform-d) δ 6.42 (s, 1H), 6.31 (s, 1H), 4.86-4.83 (m, 1H), 3.80-3.75 (m, 4H), 3.62-3.56 (m, 2H), 3.46-3.42 (m, 6H), 1.85-1.63 (m, 4H), 1.46 (s, 9H).

Preparation 108B: tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate

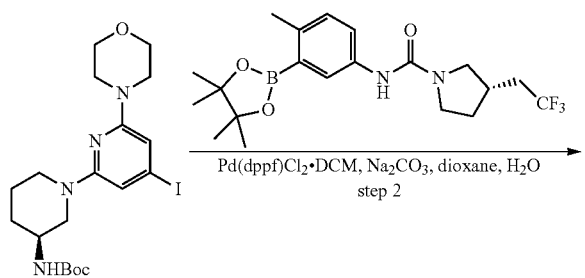

A mixture of tert-butyl N-[(3S)-1-[4-iodo-6-(morpholin-4-yl)pyridin-2-yl]piperidin-3-yl]carbamate (200 mg, 0.410 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (169 mg, 0.410 mmol), 1,4-dioxane (2 mL), H$_2$O (0.4 mL), Na$_2$CO$_3$ (130 mg, 1.229 mmol) and Pd(dppf)Cl$_2$·CH$_2$Cl$_2$ (39 mg, 0.041 mmol) was stirred for 16 h at 80° C. under nitrogen atmosphere. The reaction was quenched by the addition of water (25 mL). The resulting mixture was extracted with EtOAc (3×25 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EtOAc/EtOH (8/3/1) to afford tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (210 mg, 79%) as a light brown solid. MS ESI calculated for C$_{33}$H$_{45}$F$_3$N$_6$O$_4$ [M+H]$^+$, 647.35, found 647.45. $^1$H NMR (400 MHz, Chloroform-d) δ 7.43-7.40 (m, 1H), 7.21-7.14 (m, 2H), 6.12 (s, 1H), 6.02 (s, 1H), 5.92 (s, 1H), 4.99-4.94 (m, 1H), 3.85-3.77 (m, 6H), 3.64-3.62 (m, 2H), 3.56-3.39 (m, 8H), 3.15-3.10 (m, 1H), 2.56-2.53 (m, 1H), 2.37-2.22 (m, 5H), 1.85-1.58 (m, 5H), 1.45 (s, 9H).

Example 108: (3S)—N-(3-[2-[(3S)-3-aminopiperidin-1-yl]-6-(morpholin-4-yl)pyridin-4-yl]-4-methylphenyl)-3-(2,2,2-trifluoroethyl)pyrrolidine-1-carboxamide

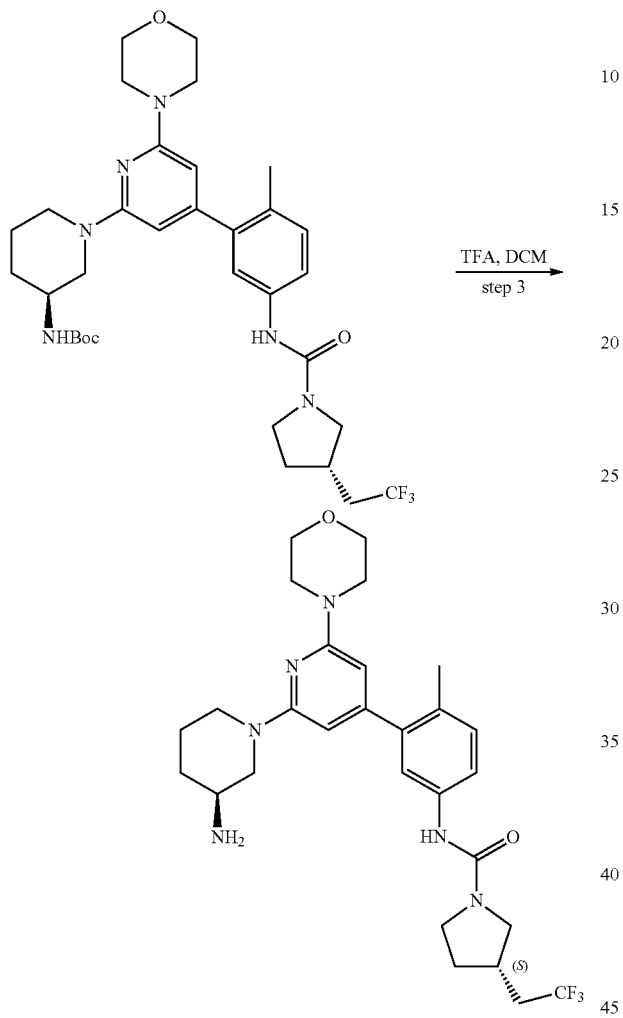

To a stirred solution of tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (200 mg, 0.309 mmol) in DCM (3 mL) was added TFA (1 mL). The resulting mixture was stirred for 1 h at room temperature. The resulting mixture was concentrated under reduced pressure. The mixture was basified to pH 8 with saturated NaHCO₃. The resulting mixture was extracted with DCM (3×20 mL). The combined organic layers were washed with brine (2×10 mL), dried over anhydrous Na₂SO₄. After filtration, the filtrate was concentrated under reduced pressure. The residue was purified by silica gel column chromatography, eluted with CH₂Cl₂/MeOH (10/1) to afford (3S)—N-(3-[2-[(3S)-3-aminopiperidin-1-yl]-6-(morpholin-4-yl)pyridin-4-yl]-4-methylphenyl)-3-(2,2,2-trifluoroethyl)pyrrolidine-1-carboxamide (107 mg, 63%) as a light yellow solid. MS ESI calculated for $C_{28}H_{37}F_3N_6O_2$ [M+H]⁺, 547.29, found 547.15. ¹H NMR (400 MHz, DMSO-d₆) δ 8.14 (s, 1H), 7.43 (dd, J=8.4, 2.0 Hz, 1H), 7.35 (d, J=2.0 Hz, 1H), 7.11 (d, J=8.4 Hz, 1H), 5.99 (s, 1H), 5.91 (s, 1H), 4.15-4.05 (m, 2H), 3.72-3.63 (m, 5H), 3.53-3.50 (m, 1H), 3.44-3.37 (m, 4H), 3.31-3.29 (m, 1H), 3.02-3.00 (m, 1H), 2.85-2.75 (m, 2H), 2.79-2.71 (m, 1H), 2.51-2.34 (m, 3H), 2.16 (s, 3H), 2.14-2.03 (m, 1H), 1.88-1.86 (m, 1H), 1.74-1.58 (m, 2H), 1.53-1.37 (m, 1H), 1.37-1.24 (m, 2H). ¹⁹F NMR (282 MHz, Chloroform-d) δ −64.93 (3F).

Example 109: (3S)—N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide

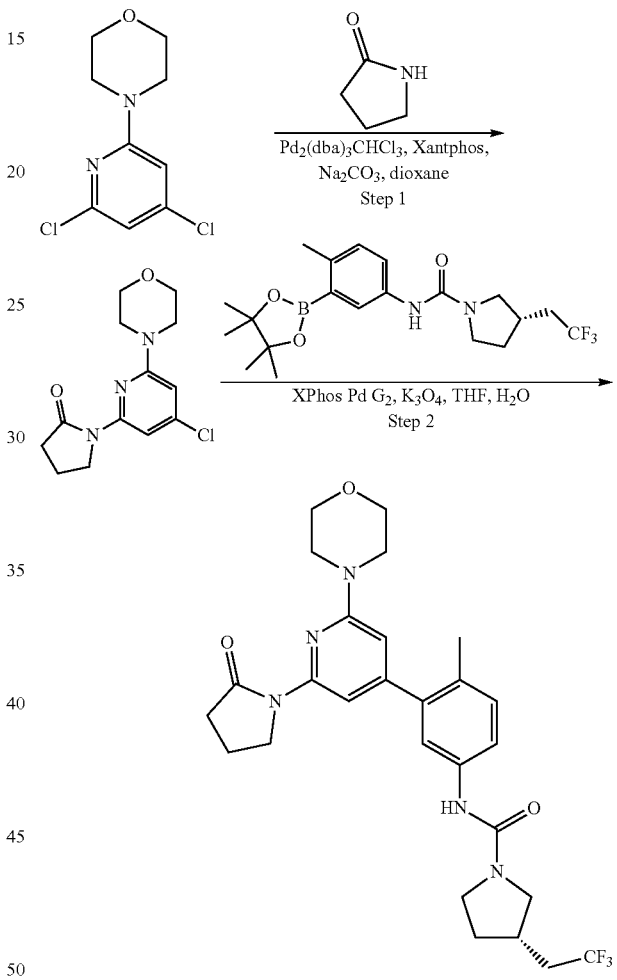

Preparation 109A: 1-[4-chloro-6-(morpholin-4-yl)pyridin-2-yl]pyrrolidin-2-one

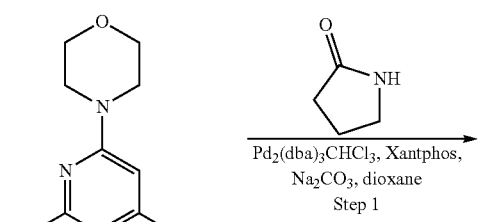

441
-continued

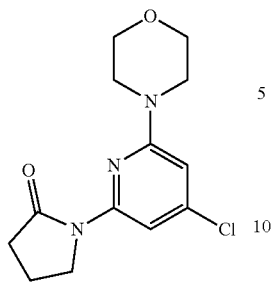

A mixture of 4-(4,6-dichloropyridin-2-yl)morpholine (1.00 g, 4.29 mmol) and pyrrolidone (0.55 g, 6.435 mmol), 1,4-dioxane (20 mL), Na$_2$CO$_3$ (0.91 g, 8.58 mmol), XantPhos (0.50 g, 0.86 mmol) and Pd$_2$(dba)$_3$·CHCl$_3$ (0.44 g, 0.43 mmol) was stirred for 16 h at 100° C. under nitrogen atmosphere. The reaction was quenched by the addition of water (100 mL). The resulting mixture was extracted with EtOAc (3×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with PE/EtOAc/EtOH (9/3/1) to afford 1-[4-chloro-6-(morpholin-4-yl)pyridin-2-yl]pyrrolidin-2-one (690 mg, 57%) as a light yellow solid. MS ESI calculated for C$_{13}$H$_{16}$ClN$_3$O$_2$ [M+H]$^+$, 282.09, found 282.15. $^1$H NMR (400 MHz, Chloroform-d) δ 7.86 (d, J=1.2 Hz, 1H), 6.38 (d, J=1.2 Hz, 1H), 4.10-4.02 (m, 2H), 3.86-3.79 (m, 4H), 3.52-3.45 (m, 4H), 2.66-2.64 (m, 2H), 2.17-2.05 (m, 2H).

Example 109: (3S)—N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide

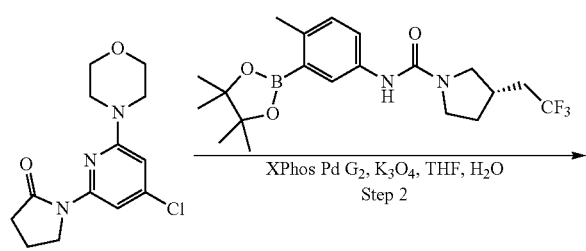

442
-continued

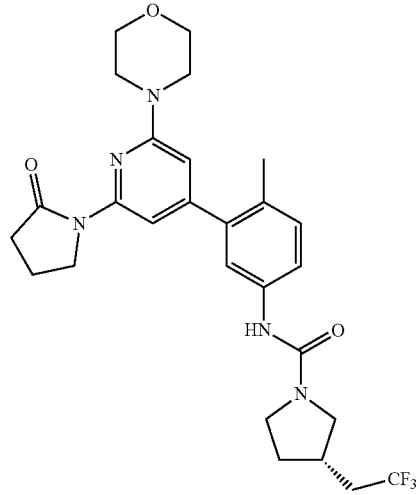

A mixture of 1-[4-chloro-6-(morpholin-4-yl)pyridin-2-yl]pyrrolidin-2-one (150 mg, 0.532 mmol,), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (219 mg, 0.532 mmol), 1,4-dioxane (2 mL), H$_2$O (0.4 mL), K$_3$PO$_4$ (38 mg, 0.355 mmol) and 2$^{nd}$ XPhos Precatalyst (14 mg, 0.018 mmol) was stirred for 16 h at 80° C. under nitrogen atmosphere. The mixture was allowed to cool down to room temperature. The reaction was quenched by the addition of water (10 mL). The resulting mixture was extracted with EtOAc (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc/EtOH (4/3/1) to afford (3S)—N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide (117.7 mg, 42%) as a white solid. MS ESI calculated for C$_{27}$H$_{32}$F$_3$N$_5$O$_3$ [M+H]$^+$, 532.25, found 532.20. $^1$H NMR (400 MHz, DMSO-d$_6$) δ 8.17 (s, 1H), 7.58 (s, 1H), 7.47 (dd, J=8.4, 2.4 Hz, 1H), 7.38 (d, J=2.4 Hz, 1H), 7.14 (d, J=8.4 Hz, 1H), 6.44 (s, 1H), 4.02 (t, J=7.2 Hz, 2H), 3.74-3.63 (m, 5H), 3.58-3.43 (m, 5H), 3.34-3.32 (m, 1H), 3.04-3.02 (m, 1H), 2.61-2.51 (m, 2H), 2.50-2.30 (m, 3H), 2.16 (s, 3H), 2.13-1.95 (m, 3H), 1.66-1.64 (m, 1H). $^{19}$F NMR (376 MHz, DMSO-d$_6$) δ −63.37 (3F).

Example 110: (3S)—N-(3-[2-[(3R)-3-hydroxypyrrolidin-1-yl]-6-(morpholin-4-yl)pyridin-4-yl]-4-methylphenyl)-3-(2,2,2-trifluoroethyl)pyrrolidine-1-carboxamide

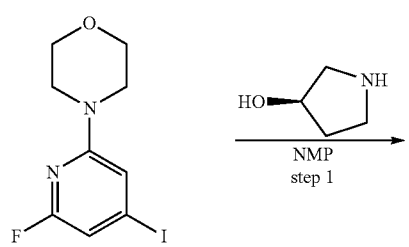

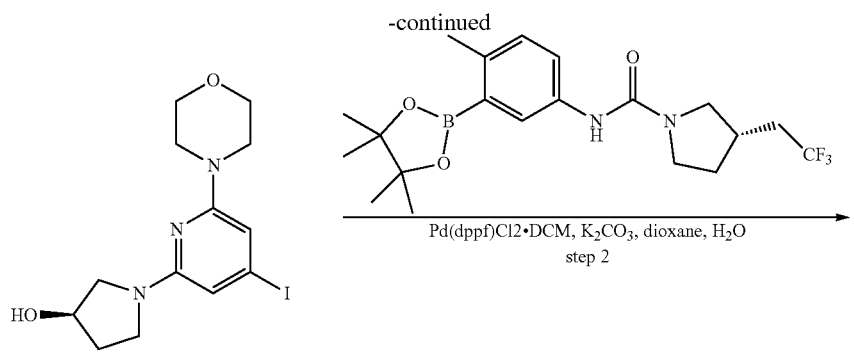

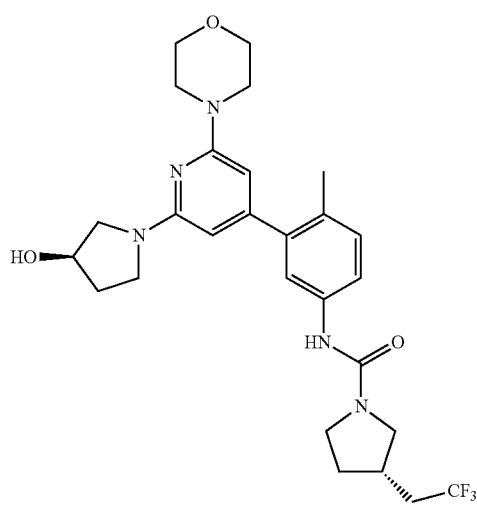

Preparation 110A: (3R)-1-[4-iodo-6-(morpholin-4-yl)pyridin-2-yl]pyrrolidin-3-ol

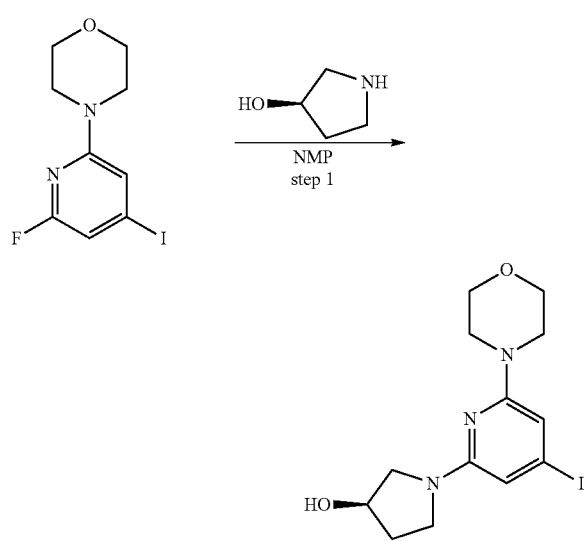

A mixture of 4-(6-fluoro-4-iodopyridin-2-yl)morpholine (500 mg, 1.623 mmol) and (3R)-pyrrolidin-3-ol (212 mg, 2.434 mmol) in NMP (6 mL) and K$_2$CO$_3$ (448 mg, 3.246 mmol) was stirred for 2 h at 150° C. under nitrogen atmosphere. The reaction was quenched by the addition of water (100 mL). The resulting mixture was extracted with EtOAc (3×300 mL). The combined organic layers were washed with brine (3×200 mL), dried over anhydrous Na$_2$SO$_4$. After filtration, the filtrate was concentrated under reduced pressure. The residue was purified by silica gel column chromatography, eluted with PE/EtOAc (1/1) to afford (3R)-1-[4-iodo-6-(morpholin-4-yl)pyridin-2-yl]pyrrolidin-3-ol (572 mg, 94%) as an off-white solid. MS ESI calculated for C$_{13}$H$_{18}$IN$_3$O$_2$ [M+H]$^+$, 376.04, found 376.00. $^1$H NMR (400 MHz, DMSO-d$_6$) δ 6.30 (s, 1H), 6.10 (s, 1H), 4.90 (d, J=3.6 Hz, 1H), 4.38-4.28 (m, 1H), 3.65-3.63 (m, 4H), 3.45-3.33 (m, 7H), 3.23-3.21 (m, 1H), 2.00-1.95 (m, 1H), 1.89-1.78 (m, 1H).

Example 110: (3S)—N-(3-[2-[(3R)-3-hydroxypyrrolidin-1-yl]-6-(morpholin-4-yl)pyridin-4-yl]-4-methylphenyl)-3-(2,2,2-trifluoroethyl)pyrrolidine-1-carboxamide

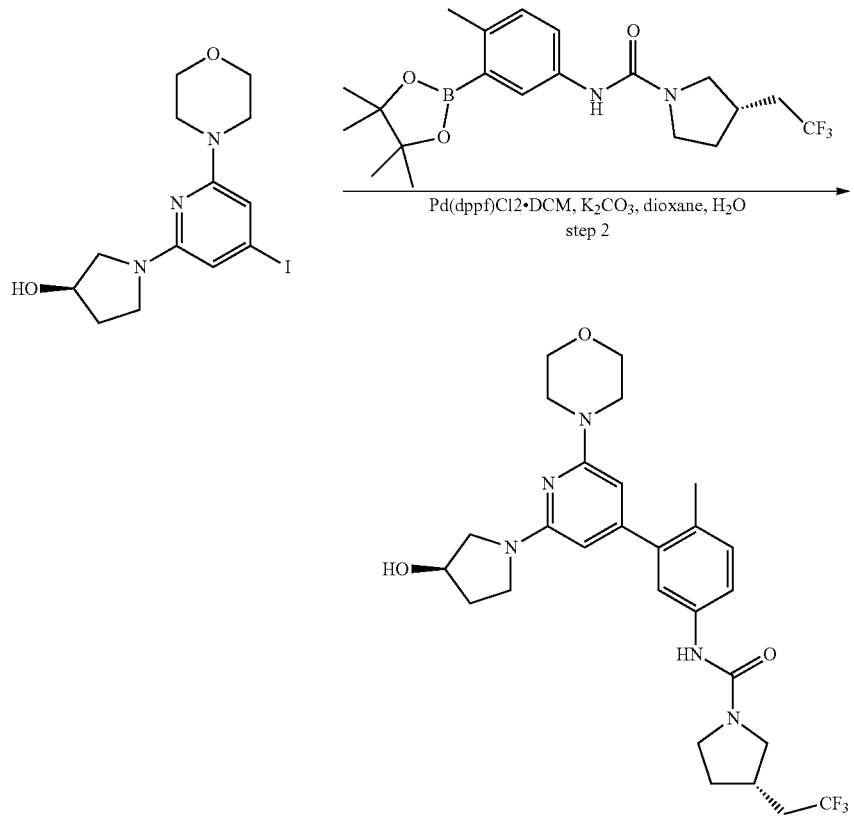

A mixture of (3R)-1-[4-iodo-6-(morpholin-4-yl)pyridin-2-yl]pyrrolidin-3-ol (120 mg, 0.320 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (105 mg, 0.256 mmol) in dioxane (4 mL) and H$_2$O (1 mL), Pd(dppf)Cl$_2$·CH$_2$Cl$_2$ (26 mg, 0.032 mmol) and Na$_2$CO$_3$ (102 mg, 0.959 mmol) was stirred for 2 h at 60° C. under nitrogen atmosphere. The reaction mixture was concentrated under reduced pressure. The residue was purified by Prep-TLC with PE/EtOAc (1/1). The crude product was purified by Prep-HPLC with the following conditions (Column: XBridge Prep Phenyl OBD Column, 19×150 mm, 5 um, 13 nm; Mobile Phase A: water (10 mmol/L NH$_4$HCO$_3$), Mobile Phase B: CH$_3$CN; Flow rate: 20 mL/min; Gradient:40% B to 60% B in 4.3 min; 254/210 nm to afford (3S)—N-(3-[2-[(3R)-3-hydroxypyrrolidin-1-yl]-6-(morpholin-4-yl)pyridin-4-yl]-4-methylphenyl)-3-(2,2,2-trifluoroethyl)pyrrolidine-1-carboxamide (53.7 mg, 31%) as an light blue solid. MS ESI calculated for C$_{27}$H$_{34}$F$_3$N$_5$O$_3$ [M+H]$^+$, 534.26, found 534.20. $^1$H NMR (400 MHz, DMSO-d$_6$) δ 8.12 (s, 1H), 7.43 (dd, J=8.4, 2.4 Hz, 1H), 7.34 (d, J=2.4 Hz, 1H), 7.10 (d, J=8.4 Hz, 1H), 5.84 (s, 1H), 5.64 (s, 1H), 4.90 (d, J=3.6 Hz, 1H), 4.36-4.34 (m, 1H), 3.72-3.63 (m, 5H), 3.53-3.42 (m, 8H), 3.33-3.30 (m, 2H), 3.04-3.00 (m, 1H), 2.50-2.34 (m, 3H), 2.17 (s, 3H), 2.10-1.94 (m 2H), 1.88-1.82 (m, 1H), 1.73-1.58 (m, 1H). $^{19}$F NMR (376 MHz, DMSO-d$_6$) δ −63.37 (3F).

Example 111: (3S)—N-[4-methyl-3-[2-(3-methyl-2-oxoimidazolidin-1-yl)-6-(morpholin-4-yl)pyridin-4-yl]phenyl]-3-(2,2,2-trifluoroethyl)pyrrolidine-1-carboxamide

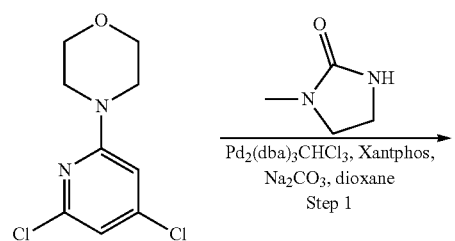

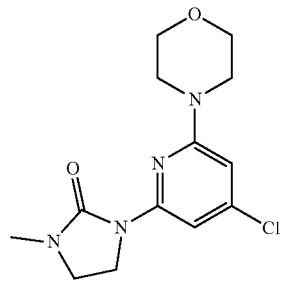
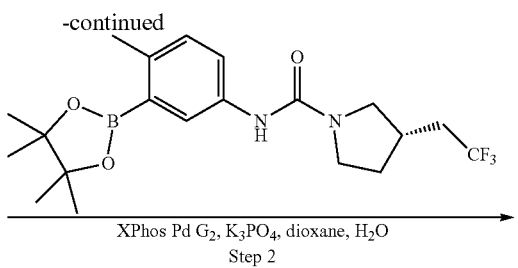

XPhos Pd G$_2$, K$_3$PO$_4$, dioxane, H$_2$O
Step 2

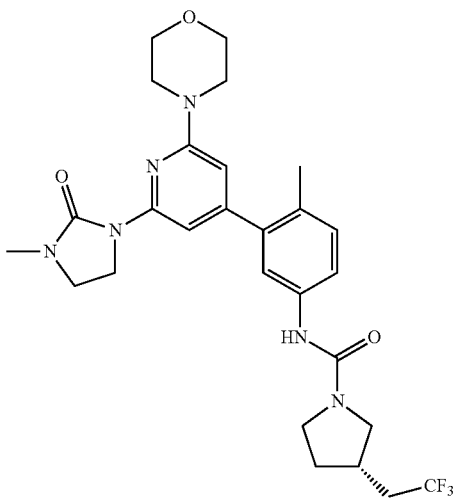

Preparation 111A: 1-[4-chloro-6-(morpholin-4-yl)pyridin-2-yl]-3-methylimidazolidin-2-one

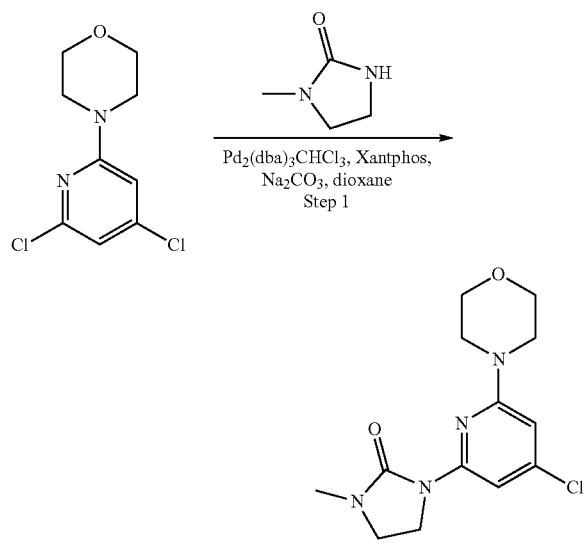

To a stirred solution of 4-(4,6-dichloropyridin-2-yl)morpholine (500 mg, 2.145 mmol) and 1-methylimidazolidin-2-one (322 mg, 3.218 mmol) in 1,4-dioxane (5 mL) were added Na$_2$CO$_3$ (682 mg, 6.435 mmol), XantPhos (248 mg, 0.429 mmol) and Pd$_2$(dba)$_3$CHCl$_3$ (222 mg, 0.215 mmol) under nitrogen atmosphere. The resulting mixture was stirred for 16 h at 100° C. under nitrogen atmosphere. The reaction was quenched by the addition of water (20 mL). The resulting mixture was extracted with EtOAc (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc (1/1) to afford 1-[4-chloro-6-(morpholin-4-yl)pyridin-2-yl]-3-methylimidazolidin-2-one (500 mg, 79%) as a light yellow solid. MS ESI calculated for C$_{13}$H$_{17}$ClN$_4$O$_2$ [M+H]$^+$, 297.10; found 297.15. $^1$H NMR (400 MHz, Chloroform-d) δ 7.74 (d, J=1.2 Hz, 1H), 6.23 (d, J=1.2 Hz, 1H), 4.03-3.99 (m, 2H), 3.83-3.80 (m, 4H), 3.48-3.43 (m, 6H), 2.92 (s, 3H).

Example 111: (3S)—N-[4-methyl-3-[2-(3-methyl-2-oxoimidazolidin-1-yl)-6-(morpholin-4-yl)pyridin-4-yl]phenyl]-3-(2,2,2-trifluoroethyl)pyrrolidine-1-carboxamide

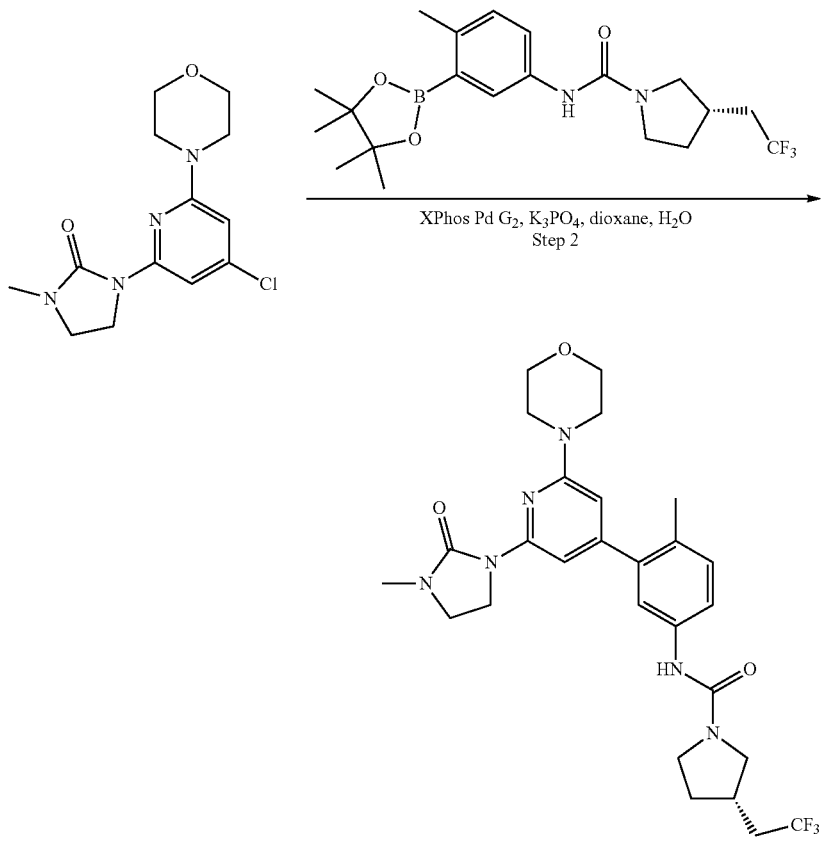

To a stirred solution of 1-[4-chloro-6-(morpholin-4-yl)pyridin-2-yl]pyrrolidin-2-one (150 mg, 0.532 mmol,) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (219 mg, 0.532 mmol) in 1,4-dioxane (2 mL) and $H_2O$ (0.4 mL) were added $K_3PO_4$ (38 mg, 0.355 mmol) and $2^{nd}$ XPhos Precatalyst (14 mg, 0.018 mmol) under nitrogen atmosphere. The resulting mixture was stirred for 16 h at 80° C. under nitrogen atmosphere. The reaction was quenched by the addition of water (10 mL). The resulting mixture was extracted with EtOAc (3×20 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EtOAc/EtOH (4/3/1) to afford (3S)—N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide (113.5 mg, 41%) as a white solid. MS ESI calculated for $C_{27}H_{33}F_3N_6O_3$ [M+H]⁺, 547.26, found 547.15. ¹H NMR (400 MHz, DMSO-$d_6$) δ 8.16 (s, 1H), 7.47-7.44 (m, 2H), 7.37 (s, 1H), 7.13 (d, J=8.8 Hz, 1H), 6.28 (s, 1H), 3.99-3.91 (m, 2H), 3.72-3.63 (m, 5H), 3.56-3.38 (m, 7H), 3.34-3.25 (m, 1H), 3.03 (t, J=9.6 Hz, 1H), 2.77 (s, 3H), 2.51-2.34 (m, 3H), 2.16 (s, 3H), 2.11-2.07 (m, 1H), 1.70-1.60 (m, 1H). ¹⁹F NMR (282 MHz, DMSO-$d_6$) δ -69.69 (3F).

Example 112: (3S)—N-[4-methyl-3-[2-(N-methylacetamido)-6-(morpholin-4-yl)pyridin-4-yl]phenyl]-3-(2,2,2-trifluoroethyl)pyrrolidine-1-carboxamide

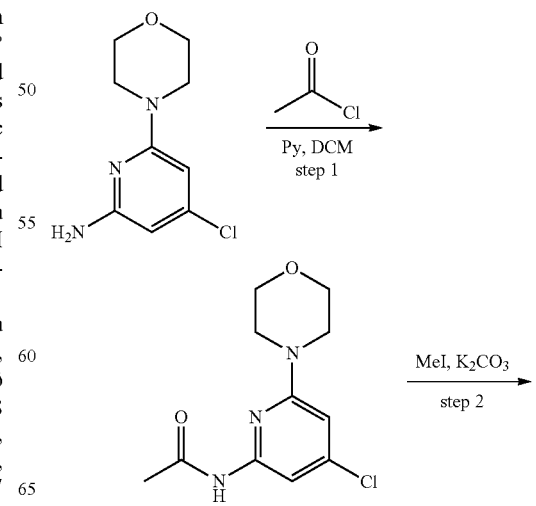

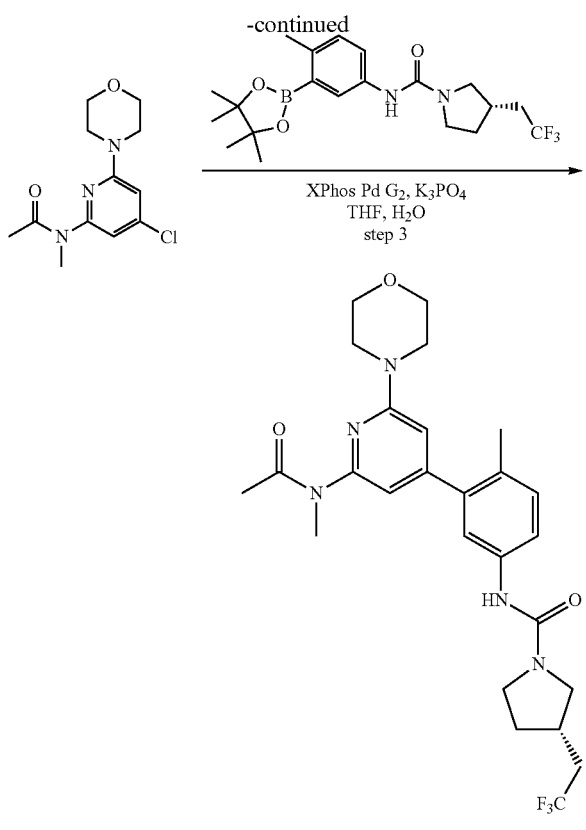

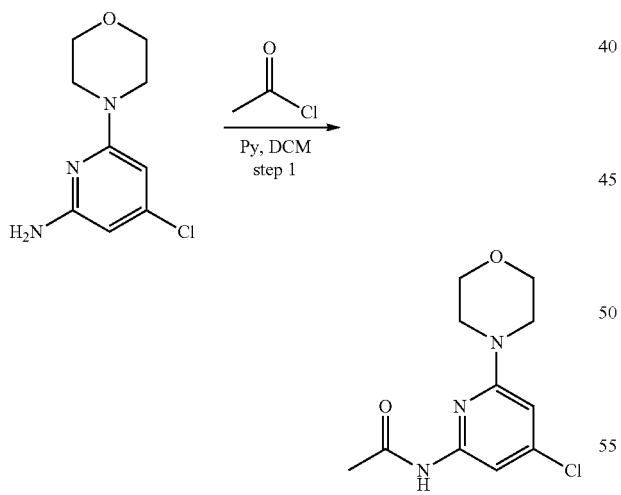

Preparation 112A: tert-butyl N-[4-chloro-6-(morpholin-4-yl)pyridin-2-yl]acetamide To a stirred mixture of 4-chloro-6-(morpholin-4-yl)pyridin-2-amine (300 mg, 1.404 mmol) and Pyridine (222 mg, 2.808 mmol) in DCM (5 mL) was added acetyl chloride (220 mg, 2.808 mmol) at 0° C. The resulting mixture was stirred for 2 h at room temperature. The reaction was quenched by the addition of water (10 mL). The resulting mixture was extracted with EtOAc (3×10 mL). The combined organic layers were washed with brine (2×5 mL), dried over anhydrous $Na_2SO_4$. After filtration, the filtrate was concentrated under reduced pressure. The residue was purified by silica gel column chromatography, eluted with PE/EtOAc (1/1) to afford N-[4-chloro-6-(morpholin-4-yl)pyridin-2-yl]acetamide (224 mg, 62%) as an off-white solid. MS ESI calculated for $C_{11}H_{14}ClN_3O_2$ [M+H]$^+$, 256.08, found 256.10. $^1$H NMR (400 MHz, DMSO-d$_6$) δ 7.41 (s, 1H), 6.59 (s, 1H), 3.66 (m, 4H), 3.47 (m, 4H), 2.06 (s, 3H).

Preparation 112B: N-[4-chloro-6-(morpholin-4-yl)pyridin-2-yl]-N-methylacetamide

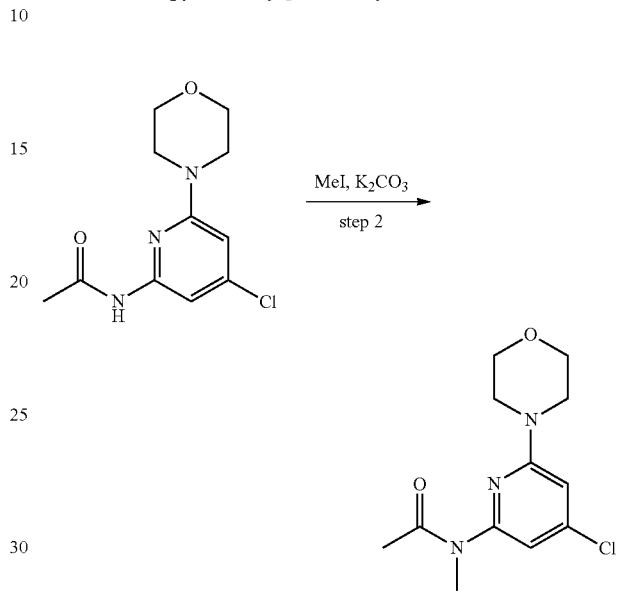

To a stirred mixture of N-[4-chloro-6-(morpholin-4-yl)pyridin-2-yl]acetamide (200 mg, 0.782 mmol) and NaH (28 mg, 1.173 mmol) in DMF (8 mL) was added MeI (167 mg, 1.173 mmol) dropwise at 0° C. The resulting mixture was stirred for 5 h at room temperature under nitrogen atmosphere. The resulting mixture was diluted with water (20 mL). The resulting mixture was extracted with EtOAc (3×10 mL). The combined organic layers were washed with brine (2×10 mL), dried over anhydrous $Na_2SO_4$. After filtration, the filtrate was concentrated under reduced pressure. The residue was purified by silica gel column chromatography, eluted with PE/EtOAc (1/1) to afford N-[4-chloro-6-(morpholin-4-yl)pyridin-2-yl]-N-methylacetamide (166 mg, 79%) as an off-white solid. MS ESI calculated for $C_{12}H_{16}ClN_3O_2$ [M+H]$^+$, 270.09, found 270.20. $^1$H NMR (300 MHz, Chloroform-d) δ 6.63 (s, 1H), 6.49 (s, 1H), 3.87-3.78 (m, 4H), 3.57-3.47 (m, 4H), 3.33 (s, 3H), 2.16 (s, 3H).

Example 112: (3S)—N-[4-methyl-3-[2-(N-methylacetamido)-6-(morpholin-4-yl)pyridin-4-yl]phenyl]-3-(2,2,2-trifluoroethyl)pyrrolidine-1-carboxamide

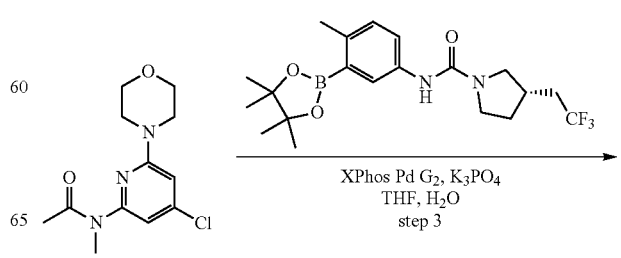

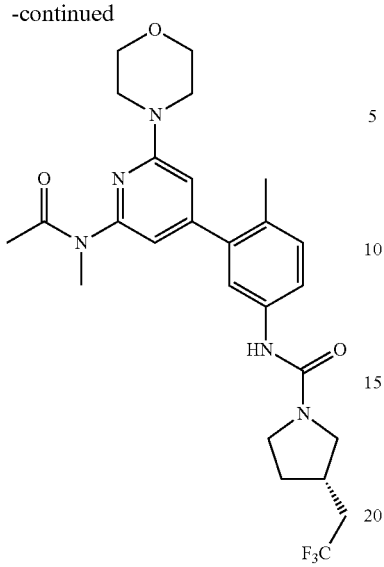

To a stirred solution of N-[4-chloro-6-(morpholin-4-yl)pyridin-2-yl]-N-methylacetamide (140 mg, 0.519 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (148 mg, 0.519 mmol) in THF (5 mL) and H$_2$O (0.5 mL) were added 2$^{nd}$ XPhos Precatalyst (41 mg, 0.052 mmol) and K$_3$PO$_4$ (220 mg, 1.038 mmol). The resulting mixture was stirred for 1 h at 50° C. under nitrogen atmosphere. The resulting mixture was diluted with water (30 mL). The resulting mixture was extracted with EtOAc (3×10 mL). The combined organic layers were washed with brine (2×10 mL), dried over anhydrous Na$_2$SO$_4$. After filtration, the filtrate was concentrated under reduced pressure. The residue was purified by Prep-TLC with PE/EtOAc (1/1) to afford (3S)—N-[4-methyl-3-[2-(N-methylacetamido)-6-(morpholin-4-yl)pyridin-4-yl]phenyl]-3-(2,2,2-trifluoroethyl)pyrrolidine-1-carboxamide (113 mg, 41%) as an off-white solid. MS ESI calculated for C$_{26}$H$_{32}$F$_3$N$_5$O$_3$ [M+H]$^+$, 520.25, found 520.15. $^1$H NMR (400 MHz, Chloroform-d) δ 7.54 (s, 1H), 7.42-7.41 (m, 1H), 7.28-7.02 (m, 1H), 6.53 (s, 1H), 6.48 (s, 1H), 6.17 (s, 1H), 3.86-3.80 (m, 5H), 3.67-3.65 (m, 1H), 3.63-3.54 (m, 4H), 3.49-3.43 (m, 1H), 3.36 (s, 3H), 3.14 (t, J=9.6 Hz, 1H), 2.63-2.54 (m, 1H), 2.35-2.28 (m, 2H), 2.24 (s, 3H), 2.16 (s, 3H), 1.90-1.77 (m, 2H). $^{19}$F NMR (376 MHz, Chloroform-d) δ −64.96 (3F).

Example 113: (3S)—N-[3-[2-methanesulfonamido-6-(morpholin-4-yl)pyridin-4-yl]-4-methylphenyl]-3-(2,2,2-trifluoroethyl)pyrrolidine-1-carboxamide

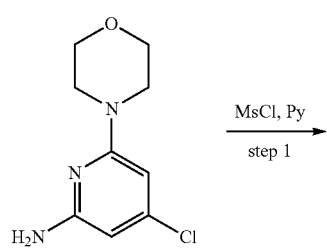

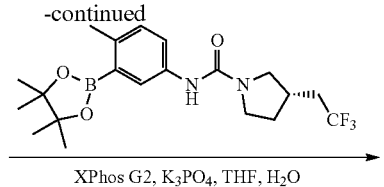

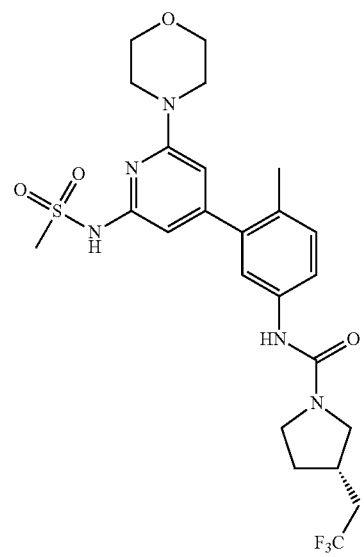

Preparation 113A: N-[4-chloro-6-(morpholin-4-yl)pyridin-2-yl]methanesulfonamide

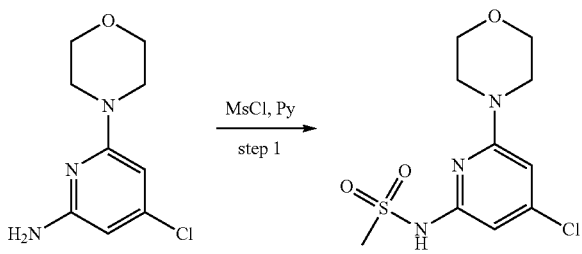 [SMILES: Nc1cc(Cl)cc(N2CCOCC2)n1 ; CS(=O)(=O)Nc1cc(Cl)cc(N2CCOCC2)n1]

A mixture of 4-chloro-6-(morpholin-4-yl)pyridin-2-amine (300 mg, 1.404 mmol), MsCl (209 mg, 1.8 mmol) in pyridine (5 mL) was stirred for 2 h at 80° C. The resulting mixture was concentrated under reduced pressure. The residue was purified by silica gel column chromatography, eluted with EtOAc/EtOH (3/1) in petroleum ether (70%) to afford N-[4-chloro-6-(morpholin-4-yl)pyridin-2-yl]methanesulfonamide (350 mg, 85%) as a light pink solid. MS ESI calculated for C$_{10}$H$_{14}$ClN$_3$O$_3$S [M+H]$^+$, 292.04, found 291.95. $^1$H NMR (400 MHz, Chloroform-d) δ 6.51 (d, J=1.2 Hz, 1H), 6.35 (d, J=1.2 Hz, 1H), 3.85-3.78 (m, 4H), 3.54-3.47 (m, 4H), 3.25 (s, 3H).

Example 113: (3S)—N-[3-[2-methanesulfonamido-6-(morpholin-4-yl)pyridin-4-yl]-4-methylphenyl]-3-(2,2,2-trifluoroethyl)pyrrolidine-1-carboxamide

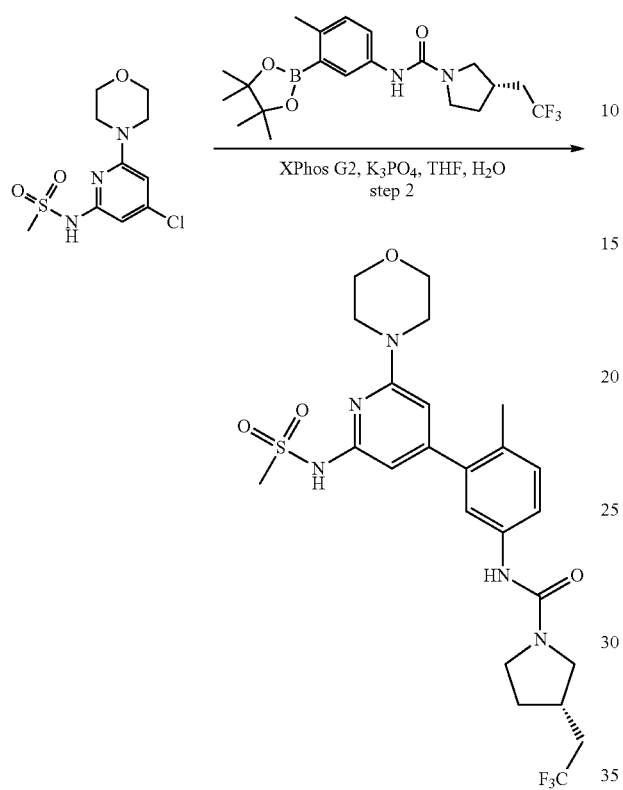

A mixture of N-[4-chloro-6-(morpholin-4-yl)pyridin-2-yl]methanesulfonamide (170 mg, 0.6 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (192 mg, 0.5 mmol), $K_3PO_4$ (371 mg, 1.8 mmol) and $2^{nd}$ XPhos Precatalyst (46 mg, 0.06 mmol) in and $H_2O$ (0.4 mL), THF (4 mL) was stirred for 2 h at 80° C. under nitrogen atmosphere. The resulting mixture was concentrated under reduced pressure. The residue was purified by silica gel column chromatography, eluted with PE/EtOAc/EtOH (6/3/1). The crude product was purified by prep-HPLC with the following conditions: Column: SunFire Prep C18 OBD Column, 19×150 mm, 5 μm; Mobile Phase A: water (0.05% FA), Mobile Phase B: $CH_3CN$; Flow rate: 20 mL/min; Gradient:55% B to 75% B to afford (3S)—N-[3-[2-methanesulfonamido-6-(morpholin-4-yl)pyridin-4-yl]-4-methylphenyl]-3-(2,2,2-trifluoroethyl)pyrrolidine-1-carboxamide (129 mg, 46%) as an off-white solid. MS ESI calculated for $C_{24}H_{30}F_3N_5O_4S$ [M+H]$^+$, 542.20, found 542.20. $^1$H NMR (400 MHz, Chloroform-d) δ 7.31-7.28 (m, 2H), 7.18-7.16 (m, 1H), 7.09 (s, 1H), 6.37 (s, 1H), 6.28 (s, 1H), 6.23 (s, 1H), 3.84-3.79 (m, 5H), 3.67-3.62 (m, 1H), 3.52-3.48 (m, 4H), 3.47-3.42 (m, 1H), 3.27 (s, 3H), 3.13 (t, J=9.6 Hz, 1H), 2.57-2.55 (m, 1H), 2.31-2.21 (m, 6H), 1.78-1.73 (m, 1H). $^{19}$F NMR (376 MHz, Chloroform-d) δ −64.94 (3F).

Example 114: (3S)—N-[3-[2-(3-hydroxy-2-oxopyrrolidin-1-yl)-6-(morpholin-4-yl)pyridin-4-yl]-4-methylphenyl]-3-(2,2,2-trifluoroethyl)pyrrolidine-1-carboxamide

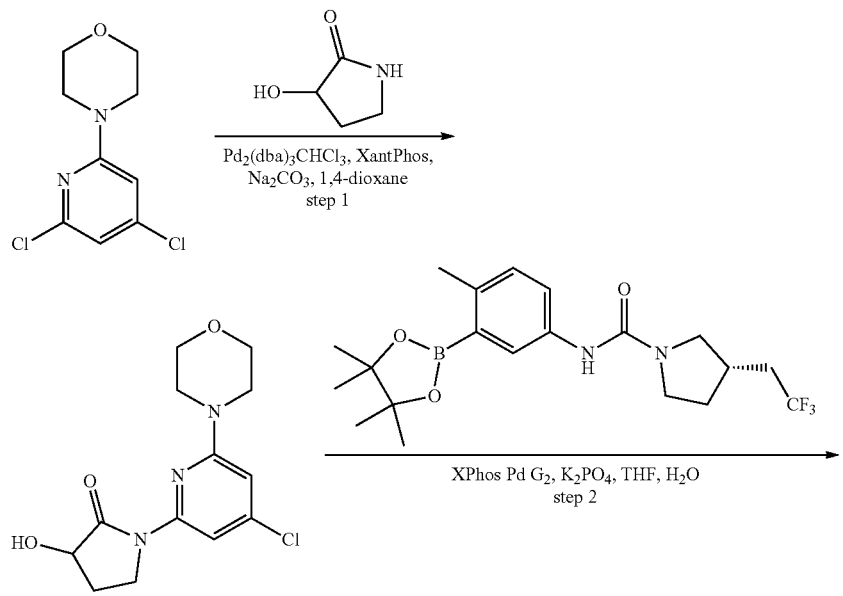

-continued

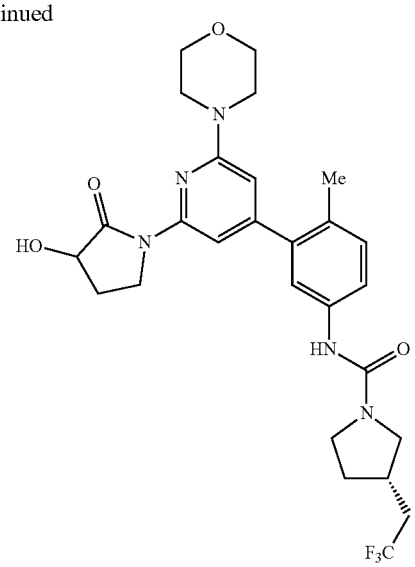

Preparation 114A: 1-[4-chloro-6-(morpholin-4-yl)pyridin-2-yl]-3-hydroxypyrrolidin-2-one

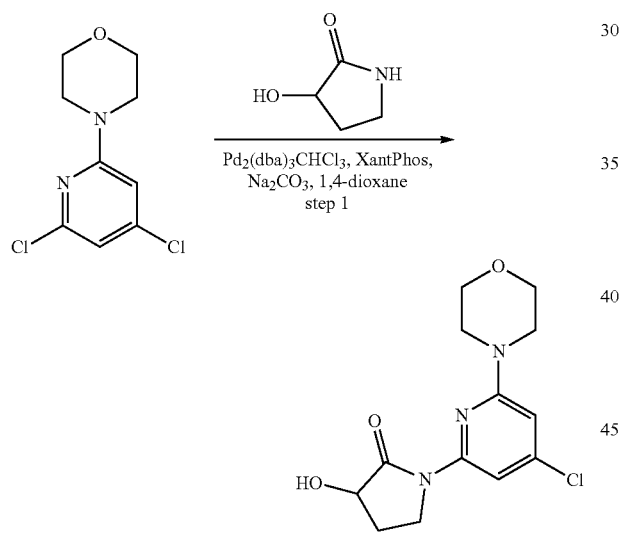

To a stirred mixture of 4-(4,6-dichloropyridin-2-yl)morpholine (600 mg, 2.574 mmol), Na$_2$CO$_3$ (546 mg, 5.148 mmol) and 3-hydroxypyrrolidin-2-one (390 mg, 3.861 mmol) in 1,4-dioxane (5 mL) were added XantPhos (298 mg, 0.515 mmol) and Pd$_2$(dba)$_3$CHCl$_3$ (266 mg, 0.257 mmol) under nitrogen atmosphere. The resulting mixture was stirred for 16 h at 100° C. under nitrogen atmosphere. The resulting mixture was diluted with H$_2$O (100 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with PE/EtOAc (3/1) to afford 1-[4-chloro-6-(morpholin-4-yl)pyridin-2-yl]-3-hydroxypyrrolidin-2-one (440 mg, 57%) as a brown solid. MS ESI calculated for C$_{13}$H$_{16}$ClN$_3$O$_3$ [M+H]$^+$, 298.09; found 298.05. $^1$H NMR (400 MHz, Chloroform-d) δ 7.81 (s, 1H), 6.40-6.39 (m, 1H), 4.55-4.50 (m, 1H), 4.23-4.18 (m, 1H), 3.88-3.68 (m, 5H), 3.57-3.47 (m, 5H), 2.60-2.53 (m, 1H), 2.10-1.76 (m, 1H).

Example 114: (3S)—N-[3-[2-(3-hydroxy-2-oxopyrrolidin-1-yl)-6-(morpholin-4-yl)pyridin-4-yl]-4-methylphenyl]-3-(2,2,2-trifluoroethyl)pyrrolidine-1-carboxamide

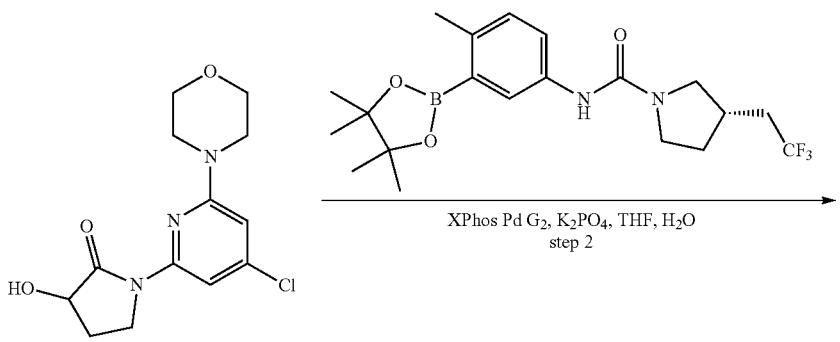

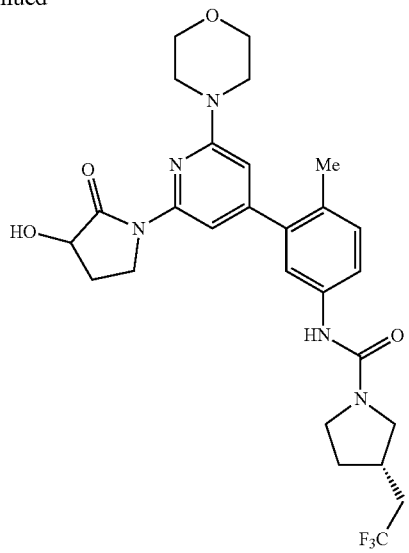

A mixture of 1-[4-chloro-6-(morpholin-4-yl)pyridin-2-yl]-3-hydroxypyrrolidin-2-one (100 mg, 0.336 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (111 mg, 0.269 mmol), 2$^{nd}$ XPhos Precatalyst (26 mg, 0.034 mmol), K$_3$PO$_4$ (143 mg, 0.672 mmol), THF (2 mL) and H$_2$O (0.2 mL) was stirred for 2 h at 80° C. under nitrogen atmosphere. The resulting mixture was diluted with H$_2$O (100 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure. The not pure product was purified by Prep-TLC with PE/EtOAc/EtOH (8/3/1) to afford (3S)—N-[3-[2-(3-hydroxy-2-oxopyrrolidin-1-yl)-6-(morpholin-4-yl)pyridin-4-yl]-4-methylphenyl]-3-(2,2,2-trifluoroethyl)pyrrolidine-1-carboxamide (76 mg, 41%) as an off-white solid. MS ESI calculated for C$_{27}$H$_{32}$F$_3$N$_5$O$_4$ [M+H]$^+$, 548.24; found 548.30. $^1$H NMR (300 MHz, Chloroform-d) δ 7.73 (s, 1H), 7.40-7.39 (m, 1H), 7.29-7.26 (m, 1H), 7.21-7.18 (m, 1H), 6.40 (s, 1H), 6.20 (s, 1H), 4.54-4.47 (m, 1H), 4.34-4.26 (m, 1H), 3.87-3.79 (m, 6H), 3.65-3.61 (m, 1H), 3.54-3.43 (m, 5H), 3.16-3.10 (m, 1H), 2.61-2.55 (m, 2H), 2.34-2.25 (m, 6H), 2.09-2.02 (m, 1H), 1.80-1.69 (m, 1H). $^{19}$F NMR (282 MHz, Chloroform-d) δ −64.95 (3F).

Example 115: (3S)—N-[4-methyl-3-[2-(morpholin-4-yl)-6-(2-oxo-1,3-oxazolidin-3-yl)pyridin-4-yl]phenyl]-3-(2,2,2-trifluoroethyl)pyrrolidine-1-carboxamide

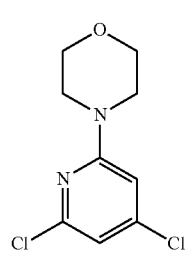

Pd$_2$(dba)$_3$·CHCl$_3$, Xantphos, Na$_2$CO$_3$, diaoxane
step 1

-continued

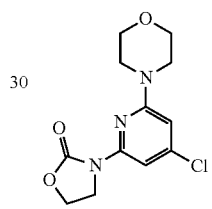

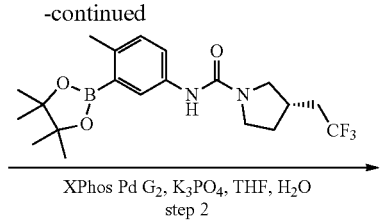

XPhos Pd G$_2$, K$_3$PO$_4$, THF, H$_2$O
step 2

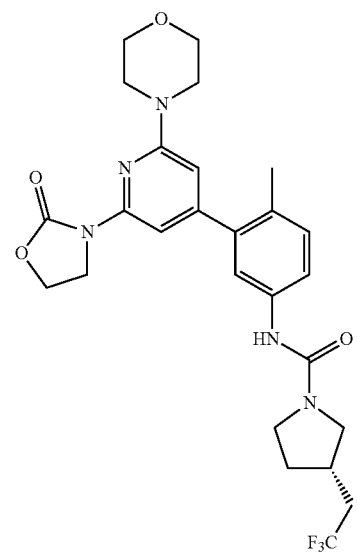

Preparation 115A: 3-[4-chloro-6-(morpholin-4-yl)pyridin-2-yl]-1,3-oxazolidin-2-one

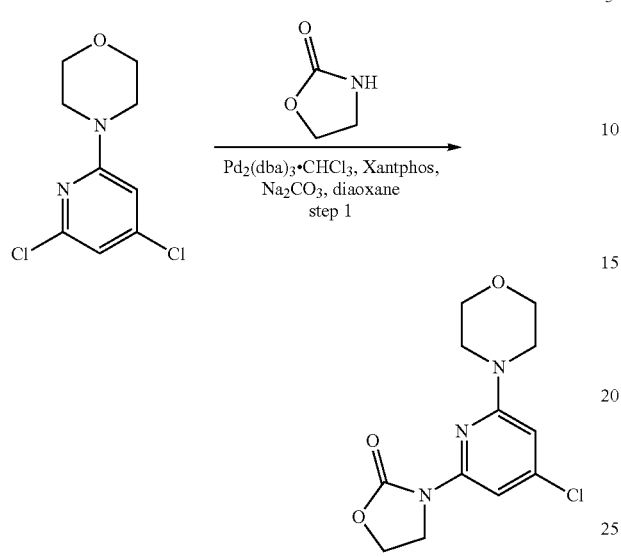

To a stirred solution of 4-(4,6-dichloropyridin-2-yl)morpholine (200 mg, 0.858 mmol), Na$_2$CO$_3$ (182 mg, 1.716 mmol) and oxazolidinone (112 mg, 1.287 mmol) in 1,4-dioxane (2 mL) was added Pd$_2$(dba)$_3$·CHCl$_3$ (89 mg, 0.086 mmol) and XantPhos (99 mg, 0.172 mmol) under nitrogen atmosphere. The resulting mixture was stirred for 16 h at 100° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (1/1) to afford 3-[4-chloro-6-(morpholin-4-yl)pyridin-2-yl]-1,3-oxazolidin-2-one (130 mg, 53%) as a brown solid. MS ESI calculated for C$_{12}$H$_{14}$ClN$_3$O$_3$ [M+H]$^+$. 284.07, found 284.05. $^1$H NMR (400 MHz, Chloroform-d) δ 7.62 (d, J=1.2 Hz, 1H), 6.34 d, J=1.2 Hz, 1H), 4.49-4.45 (m, 2H), 4.25-4.21 (m, 2H), 3.83-3.80 (m, 4H), 3.49-3.47 (m, 4H).

Example 115: (3S)—N-[4-methyl-3-[2-(morpholin-4-yl)-6-(2-oxo-1,3-oxazolidin-3-yl)pyridin-4-yl]phenyl]-3-(2,2,2-trifluoroethyl)pyrrolidine-1-carboxamide

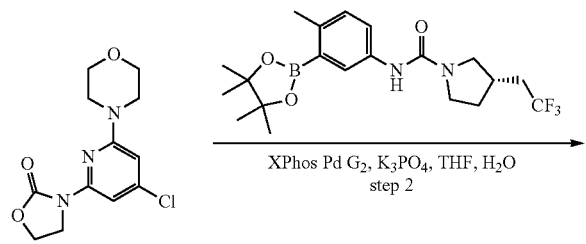

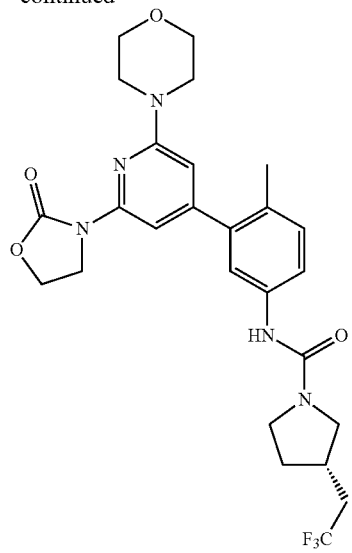

To a stirred solution of 3-[4-chloro-6-(morpholin-4-yl)pyridin-2-yl]-1,3-oxazolidin-2-one (130 mg, 0.458 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (189 mg, 0.458 mmol) and K$_3$PO$_4$ (195 mg, 0.916 mmol) in THF (2 mL) and H$_2$O (0.2 mL) was added 2$^{nd}$ XPhos Precatalyst (36 mg, 0.046 mmol) under nitrogen atmosphere. The resulting mixture was stirred for 2 h at 80° C. under nitrogen atmosphere. The reaction was quenched by the addition of water (100 mL). The resulting mixture was extracted with EtOAc (3×50 mL). The combined organic layers were washed with saturated brine (3×50 mL), dried over anhydrous Na$_2$SO$_4$. After filtration, the filtrate was concentrated under reduced pressure. The residue was purified by silica gel column chromatography, eluted with PE/EtOAc (1/1). The crude product was purified by reverse flash chromatography with the following conditions: column, C$^{18}$ silica gel; mobile phase, CH$_3$CN in water (10 mmol/L NH$_4$HCO$_3$), 5% to 95% gradient; detector, UV 254 nm to afford (3S)—N-[4-methyl-3-[2-(morpholin-4-yl)-6-(2-oxo-1,3-oxazolidin-3-yl)pyridin-4-yl]phenyl]-3-(2,2,2-trifluoroethyl)pyrrolidine-1-carboxamide (122 mg, 50%) as an off-white solid. MS ESI calculated for C$_{26}$H$_{30}$F$_3$N$_5$O$_4$ [M+H]$^+$. 534.22, found 534.30. $^1$H NMR (300 MHz, Chloroform-d) δ 7.52 (s, 1H), 7.38 (dd, J=2.4, 8.4 Hz, 1H), 7.22 (d, J=2.1 Hz, 1H), 7.16 (d, J=8.4 Hz, 1H), 6.32 (s, 1H), 6.18 (s, 1H), 4.49-4.44 (m, 2H), 4.31-4.26 (m, 2H), 3.84-3.76 (m, 5H), 3.65-3.59 (m, 1H), 3.50-3.38 (m, 5H), 3.13-3.07 (m, 1H), 2.60-2.50 (m, 1H), 2.31-2.18 (m, 6H), 1.77-1.73 (m, 1H). $^{19}$F NMR (282 MHz, Chloroform-d) δ −64.95 (3F).

Example 116: (3S)—N-(3-[2-[5-hydroxy-2-oxopiperidin-1-yl]-6-(morpholin-4-yl)pyridin-4-yl]-4-methylphenyl)-3-(2,2,2-trifluoroethyl)pyrrolidine-1-carboxamide

Preparation 116A: tert-butyl 1-[4-chloro-6-(morpholin-4-yl)pyridin-2-yl]-5-hydroxypiperidin-2-one

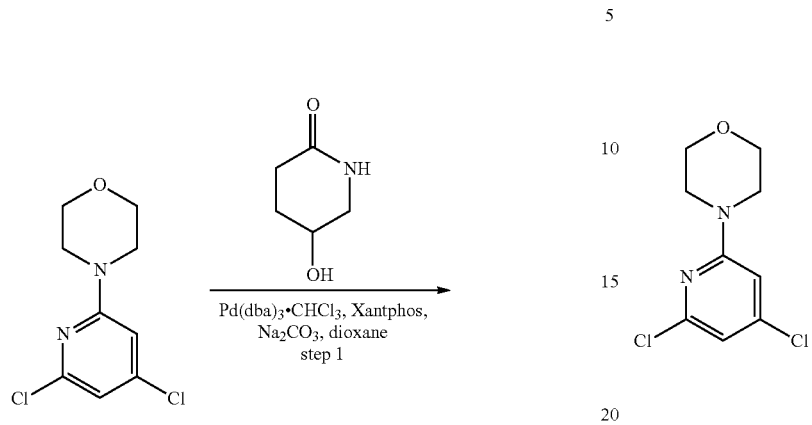

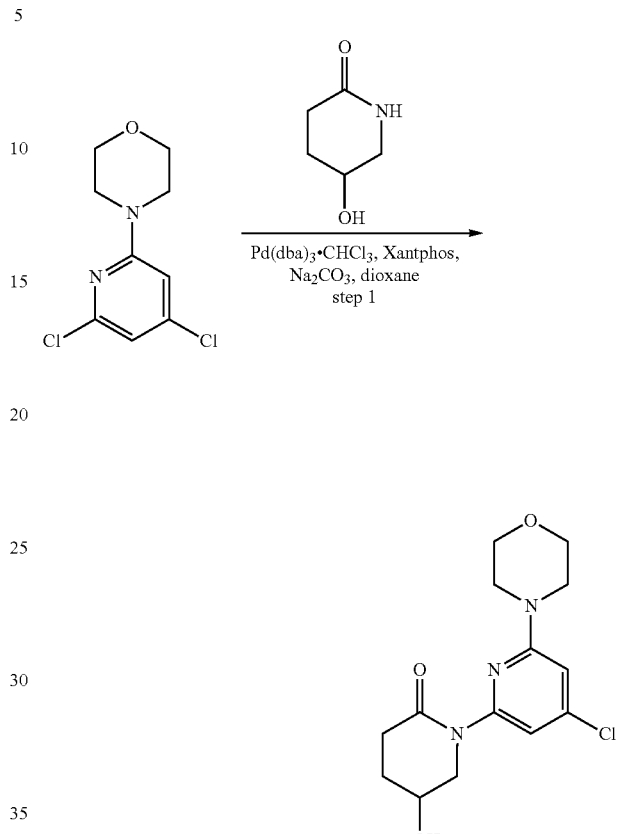

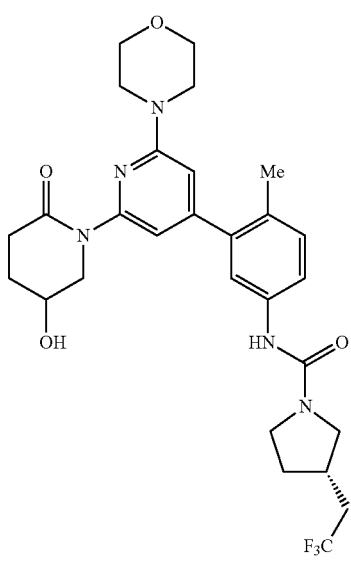

To a mixture of 4-(4,6-dichloropyridin-2-yl)morpholine (500 mg, 2.145 mmol) and 5-hydroxypiperidin-2-one (370 mg, 3.218 mmol) in dioxane (7 mL) were added XantPhos (248 mg, 0.429 mmol) and $Na_2CO_3$ (455 mg, 4.290 mmol) and $Pd_2(dba)_3CHCl_3$ (222 mg, 0.215 mmol). The resulting mixture was stirred for 16 h at 100° C. under nitrogen atmosphere. The resulting mixture was diluted with water (15 mL). The resulting mixture was extracted with EtOAc (3×15 mL). The combined organic layers were washed with brine (2×10 mL), dried over anhydrous $Na_2SO_4$. After filtration, the filtrate was concentrated under reduced pressure. The residue was purified by silica gel column chromatography, eluted with PE/EtOAc (1/1) to afford 1-[4-chloro-6-(morpholin-4-yl)pyridin-2-yl]-5-hydroxypiperidin-2-one (498 mg, 74%) as an off-white solid. MS ESI calculated for $C_{14}H_{18}ClN_3O_3$ $[M+H]^+$. 312.10, found 312.05. $^1H$ NMR (300 MHz, DMSO-$d_6$) δ 7.29 (d, J=1.2 Hz, 1H), 6.70 (d, J=1.5 Hz, 1H), 5.09 (d, J=3.6 Hz, 1H), 4.09 (s, 1H), 3.90-3.81 (m, 1H), 3.79-3.75 (m, 1H), 3.71-3.68 (m, 4H), 3.48-3.45 (m, 4H), 2.62-2.40 (m, 2H), 1.98-1.97 (m, 1H), 1.80-1.73 (m, 1H).

Example 116: (3S)—N-[3-[2-(5-hydroxy-2-oxopiperidin-1-yl)-6-(morpholin-4-yl)pyridin-4-yl]-4-methylphenyl]-3-(2,2,2-trifluoroethyl)pyrrolidine-1-carboxamide Example 117: (3S)—N-(4-methyl-3-(2-morpholino-6-(2-oxo-3-azabicyclo[3.1.0]hexan-3-yl)pyridin-4-yl)phenyl)-3-(2,2,2-trifluoroethyl)pyrrolidine-1-carboxamide

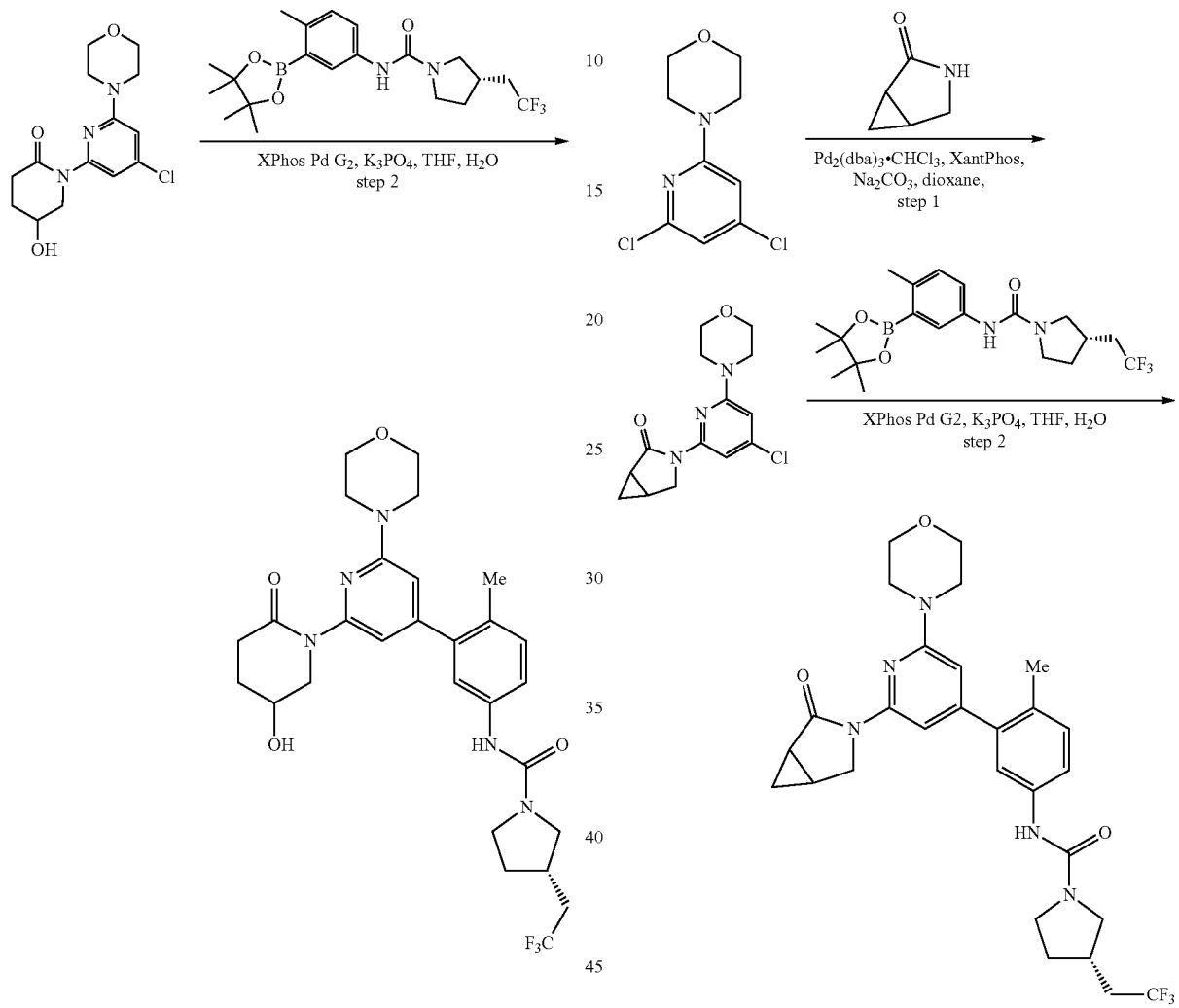

To a stirred mixture of 1-[4-chloro-6-(morpholin-4-yl)pyridin-2-yl]-5-hydroxypiperidin-2-one (250 mg, 0.802 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (264 mg, 0.641 mmol) in THF (8 mL) and H$_2$O (0.8 mL) were added K$_3$PO$_4$ (340 mg, 1.604 mmol) and 2$^{nd}$ XPhos Precatalyst (63 mg, 0.080 mmol). The resulting mixture was stirred for 2 h at 80° C. under nitrogen atmosphere. The resulting mixture was diluted with water (30 mL). The resulting mixture was extracted with EtO Ac (3×20 mL). The combined organic layers were washed with brine (2×10 mL), dried over anhydrous Na$_2$SO$_4$. After filtration, the filtrate was concentrated under reduced pressure. The residue was purified by silica gel column chromatography, eluted with PE/EtOAc (1/1) to afford (3S)—N-[3-[2-(5-hydroxy-2-oxopiperidin-1-yl)-6-(morpholin-4-yl)pyridin-4-yl]-4-methylphenyl]-3-(2,2,2-trifluoroethyl)pyrrolidine-1-carboxamide (274 mg, 61%) as an off-white solid. MS ESI calculated for C$_{28}$H$_{34}$F$_3$N$_5$O$_4$ [M+H]$^+$ 562.26, found 562.20.

Preparation 117A: 3-[4-chloro-6-(morpholin-4-yl)pyridin-2-yl]-3-azabicyclo[3.1.0]hexan-2-one

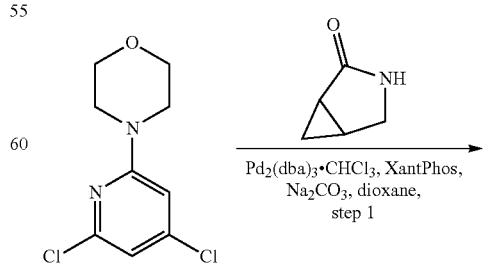

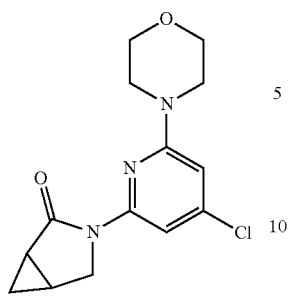

A mixture of 4-(4,6-dichloropyridin-2-yl)morpholine (500 mg, 2.145 mmol), 3-azabicyclo[3.1.0]hexan-2-one (187 mg, 1.931 mmol), Pd$_2$(dba)$_3$·CHCl$_3$ (222 mg, 0.215 mmol), XantPhos (248 mg, 0.429 mmol) and Na$_2$CO$_3$ (455 mg, 4.290 mmol) in dioxane (5 mL) was stirred for 3 h at 100° C. under nitrogen atmosphere. The resulting mixture was concentrated under reduced pressure. The residue was purified by silica gel column chromatography, eluted with PE/EtOAc (1/1) to afford 3-[4-chloro-6-(morpholin-4-yl)pyridin-2-yl]-3-azabicyclo[3.1.0]hexan-2-one (810 mg, 86%) as a red solid. MS ESI calculated for C$_{14}$H$_{16}$ClN$_3$O$_2$ [M+H]$^+$, 294.09, found 294.05. $^1$H NMR (400 MHz, Chloroform-d) δ 7.74 (s, 1H), 6.32 (s, 1H), 4.07-4.03 (m, 2H), 3.82-3.80 (m, 4H), 3.47-3.45 (m, 4H), 2.15-2.11 (m, 1H), 2.01-1.95 (m, 1H), 1.24-1.19 (m, 1H), 0.80-0.77 (m, 1H).

Example 117: (3S)—N-[4-methyl-3-[2-(morpholin-4-yl)-6-[2-oxo-3-azabicyclo[3.1.0]hexan-3-yl]pyridin-4-yl]phenyl]-3-(2,2,2-trifluoroethyl)pyrrolidine-1-carboxamide

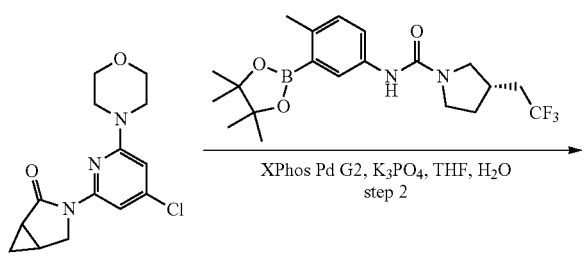

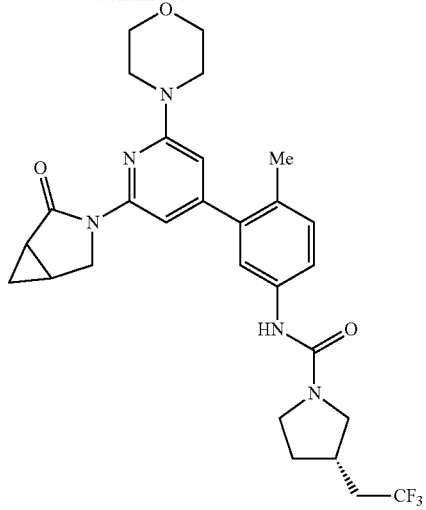

A mixture of 3-[4-chloro-6-(morpholin-4-yl)pyridin-2-yl]-3-azabicyclo[3.1.0]hexan-2-one (200 mg, 0.681 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (225 mg, 0.545 mmol), 2$^{nd}$ XPhos Precatalyst (54 mg, 0.068 mmol) and K$_3$PO$_4$ (289 mg, 1.362 mmol) in THF (2 mL) and H$_2$O (0.2 mL) was stirred for 2 h at 80° C. under nitrogen atmosphere. The reaction was quenched by the addition of water (10 mL). The resulting mixture was extracted with EtOAc (2×5 mL). The combined organic layers were washed with brine (5 mL), dried over anhydrous Na$_2$SO$_4$. After filtration, the filtrate was concentrated under reduced pressure. The residue was purified by silica gel column chromatography, eluted with PE/EtOAc (1/1) to afford (3S)—N-[4-methyl-3-[2-(morpholin-4-yl)-6-[2-oxo-3-azabicyclo[3.1.0]hexan-3-yl]pyridin-4-yl]phenyl]-3-(2,2,2-trifluoroethyl)pyrrolidine-1-carboxamide (109 mg, 29%) as an off-white solid. MS ESI calculated for C$_{28}$H$_{32}$F$_3$N$_5$O$_3$ [M+H]$^+$, 544.25, found 544.35. $^1$H NMR (300 MHz, Chloroform-d) δ 7.63 (s, 1H), 7.40 (dd, J=2.1, 8.1 Hz, 1H), 7.26-7.14 (m, 2H), 6.27 (s, 1H), 6.18 (s, 1H), 4.13 (s, 1H), 4.11 (s, 1H), 3.83-3.76 (m, 5H), 3.61-3.58 (m, 1H), 3.48-3.38 (m, 5H), 3.13-3.07 (m, 1H), 2.31-2.28 (m, 1H), 2.25-2.22 (m, 6H), 2.18-2.06 (m, 1H), 1.98-1.95 (m, 1H), 1.76-1.73 (m, 1H), 1.21-1.15 (m, 1H), 0.81-0.77 (m, 1H). $^{19}$F NMR (282 MHz, Chloroform-d) δ −64.94 (3F).

Example 118: (3S)—N-(3-[2-[(3S,4S)-3,4-dihydroxypyrrolidin-1-yl]-6-(morpholin-4-yl)pyridin-4-yl]-4-methylphenyl)-3-(2,2,2-trifluoroethyl)pyrrolidine-1-carboxamide

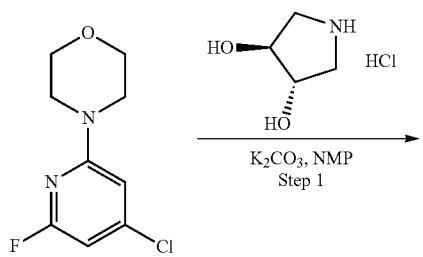

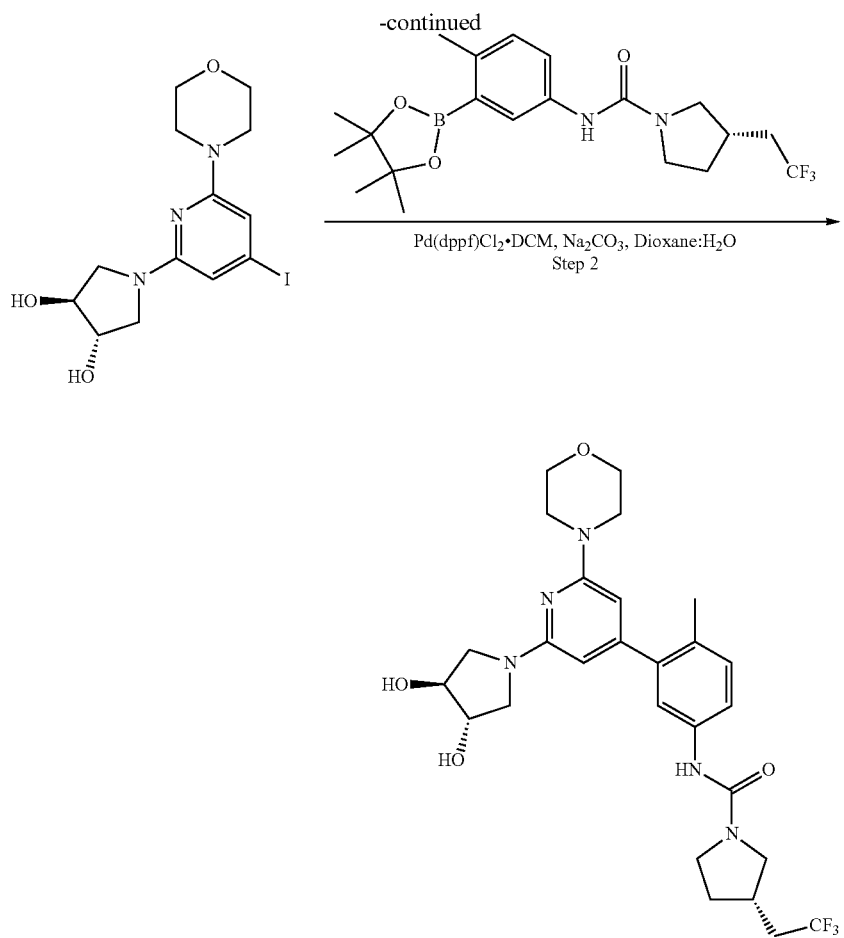

Preparation 118A: (3S,4S)-1-[4-iodo-6-(morpholin-4-yl)pyridin-2-yl]pyrrolidine-3,4-diol

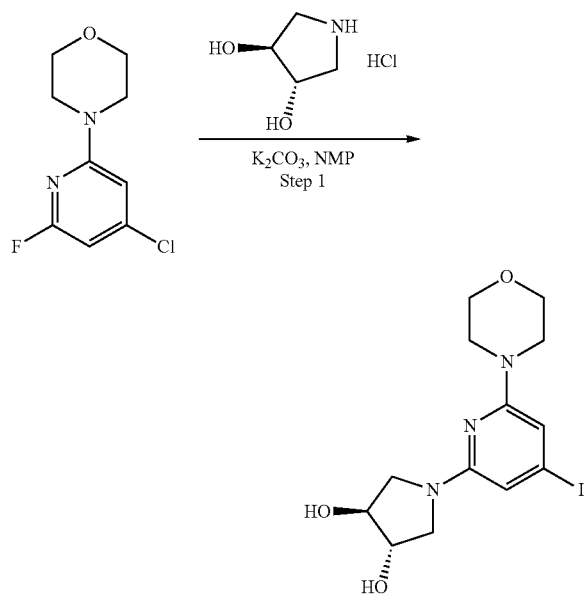

A mixture of 4-(6-fluoro-4-iodopyridin-2-yl)morpholine (200 mg, 0.649 mmol), K$_2$CO$_3$ (358 mg, 2.597 mmol) and (3S,4S)-pyrrolidine-3,4-diol hydrochloride (181 mg, 1.298 mmol) in NMP (1.6 mL) was stirred for 16 h at 100° C. under nitrogen atmosphere. The resulting mixture was diluted with water (100 mL). The resulting mixture was extracted with EtOAc (3×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with hexane/EtOAc/EtOH (4/3/1) to afford (3S,4S)-1-[4-iodo-6-(morpholin-4-yl)pyridin-2-yl]pyrrolidine-3,4-diol (237 mg, 93%) as a white solid. MS ESI calculated for C$_{13}$H$_{18}$IN$_3$O$_3$ [M+H]$^+$, 392.04 found 391.95. $^1$H NMR (300 MHz, DMSO-d$_6$) δ 6.31 (s, 1H), 6.10 (s, 1H), 5.06 (s, 2H), 3.99-3.98 (m, 2H), 3.68-3.65 (m, 4H), 3.50-3.49 (m, 2H), 3.46-3.45 (m, 4H), 3.27-3.23 (m, 2H).

Example 118: (3S)—N-(3-[2-[(3S,4S)-3,4-dihydroxypyrrolidin-1-yl]-6-(morpholin-4-yl)pyridin-4-yl]-4-methylphenyl)-3-(2,2,2-trifluoroethyl)pyrrolidine-1-carboxamide

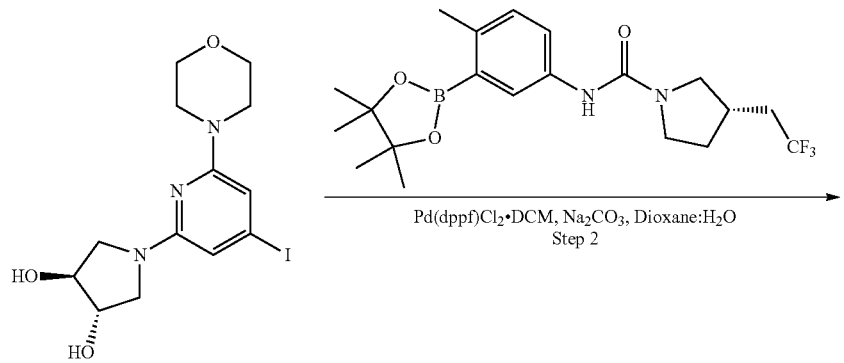

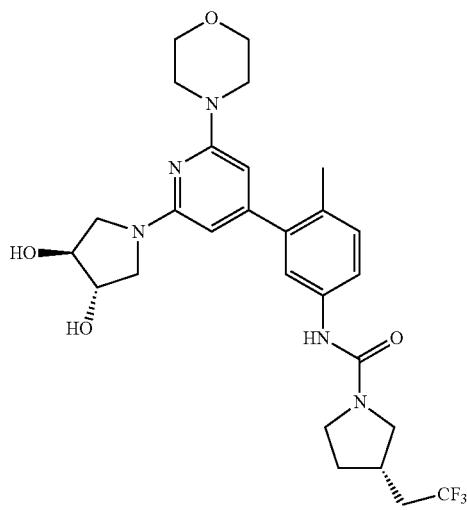

A mixture of (3S,4S)-1-[4-iodo-6-(morpholin-4-yl)pyridin-2-yl]pyrrolidine-3,4-diol (120 mg, 0.307 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (113 mg, 0.276 mmol), $Na_2CO_3$ (98 mg, 0.920 mmol), dioxane (3 mL), $H_2O$ (0.75 mL) and Pd(dppf)Cl$_2$CH$_2$Cl$_2$ (25 mg, 0.031 mmol) was stirred for 3 h at 60° C. under nitrogen atmosphere. The resulting mixture was diluted with water (50 mL). The resulting mixture was extracted with EtOAc (3×50 mL). The combined organic layers were washed with brine (2×50 mL), dried over anhydrous $Na_2SO_4$. After filtration, the filtrate was concentrated under reduced pressure. The residue was purified by Prep-TLC with $CH_2Cl_2/CH_3OH$ (10:1) to afford (3S)—N-(3-[2-[(3S,4S)-3,4-dihydroxypyrrolidin-1-yl]-6-(morpholin-4-yl)pyridin-4-yl]-4-methylphenyl)-3-(2,2,2-trifluoroethyl)pyrrolidine-1-carboxamide (76.3 mg, 45%) as an off-white solid. MS ESI calculated for $C_{27}H_{34}F_3N_5O_4$ [M+H]$^+$, 550.26 found 550.30. $^1$H NMR (400 MHz, DMSO-d$_6$) δ 8.12 (s, 1H), 7.43 (dd, J=2.0, 8.4 Hz, 1H), 7.34 (d, J=2.0 Hz, 1H), 7.10 (d, J=8.4 Hz, 1H), 5.84 (s, 1H), 5.62 (s, 1H), 5.04 (d, J=3.2 Hz, 2H), 4.01 (s, 2H), 3.70-3.65 (m, 5H), 3.54-3.51 (m, 3H), 3.42-3.40 (m, 4H), 3.30-3.29 (m, 3H), 3.05-3.00 (m, 1H), 2.48-2.41 (m, 3H), 2.17 (s, 3H), 2.10-2.07 (m, 1H), 1.69-1.62 (m, 1H). $^{19}$F NMR (376 MHz, DMSO-d$_6$) δ −63.36 (3F).

Example 119: (3S)—N-(3-[2-[(3S,4S)-3-fluoro-4-hydroxypyrrolidin-1-yl]-6-(morpholin-4-yl)pyridin-4-yl]-4-methylphenyl)-3-(2,2,2-trifluoroethyl)pyrrolidine-1-carboxamide
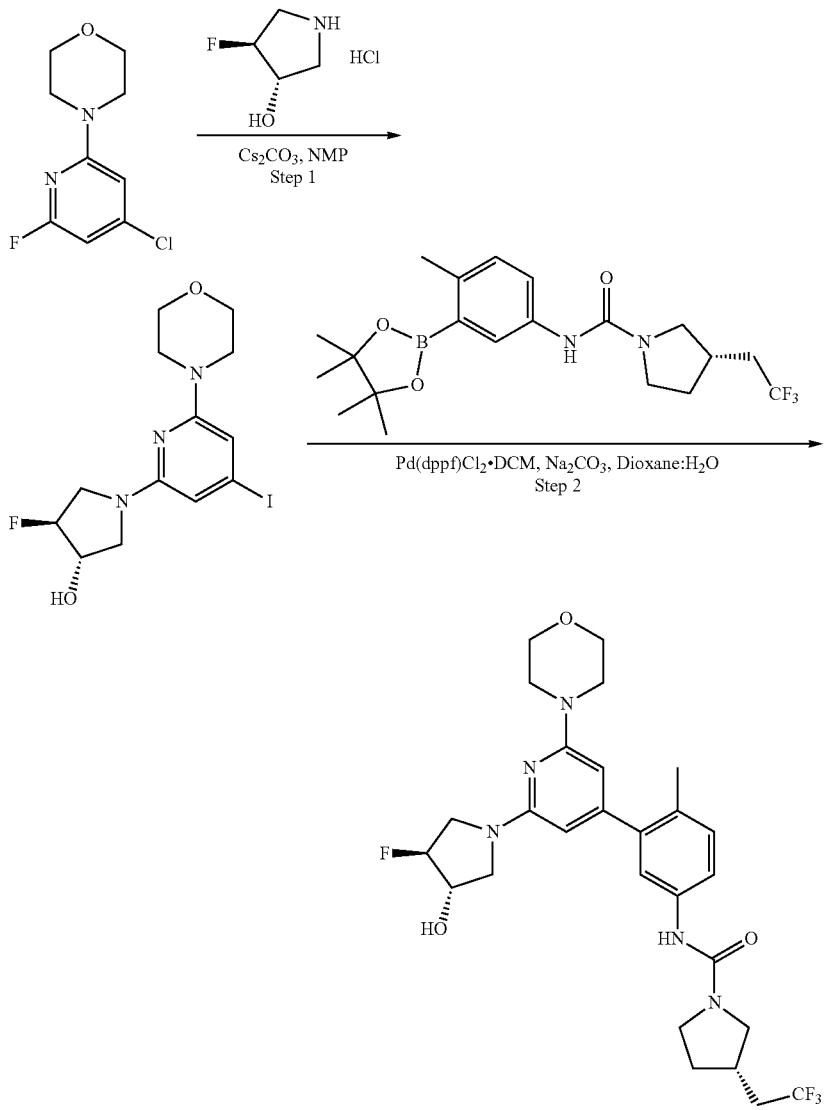
Preparation 119A: (3S,4S)-4-fluoro-1-[4-iodo-6-(morpholin-4-yl)pyridin-2-yl]pyrrolidin-3-ol
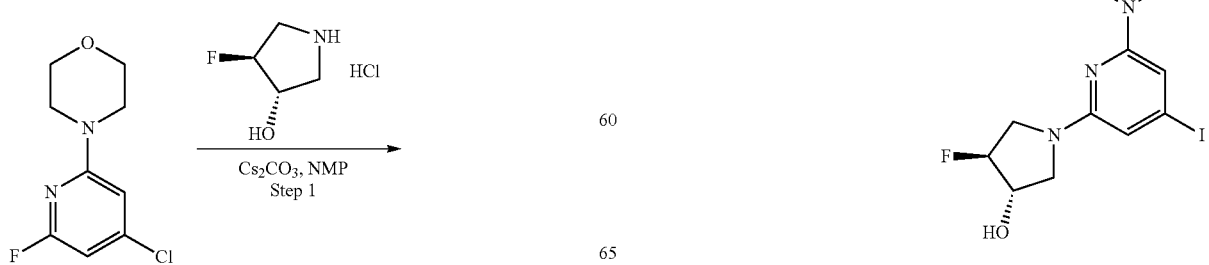
-continued To a stirred mixture of 4-(6-fluoro-4-iodopyridin-2-yl)morpholine (300 mg, 0.974 mmol) and (3S,4S)-4-fluoropyrrolidin-3-ol hydrochloride (165 mg, 1.168 mmol) in NMP (3 mL) was added $Cs_2CO_3$ (635 mg, 1.947 mmol) was stirred for 2 h in portions at 130° C. under nitrogen atmosphere. The reaction was quenched by the addition of water (20 mL) at room temperature. The resulting mixture was extracted with EtOAc (3×20 mL). The combined organic layers were washed with brine (2×5 mL), dried over anhydrous $Na_2SO_4$. After filtration, the filtrate was concentrated under reduced pressure. The residue was purified by silica gel column chromatography, eluted with PE/EtOAc (5/1) to afford (3S,4S)-4-fluoro-1-[4-iodo-6-(morpholin-4-yl)pyridin-2-yl]pyrrolidin-3-ol (113 mg, 29%) as a light yellow solid. MS ESI calculated for $C_{13}H_{17}FIN_3O_2$ $[M+H]^+$, 394.04 found 394.00. $^1H$ NMR (400 MHz, Chloroform-d) δ 6.32 (s, 1H), 6.19 (s, 1H), 5.06 (d, J=51.2 Hz, 1H), 4.55-4.51 (m, 1H), 3.85-3.66 (m, 7H), 3.62-3.58 (m, 1H), 3.52-3.44 (m, 4H).

Example 119: (3S)—N-(3-[2-[(3S,4S)-3-fluoro-4-hydroxypyrrolidin-1-yl]-6-(morpholin-4-yl)pyridin-4-yl]-4-methylphenyl)-3-(2,2,2-trifluoroethyl)pyrrolidine-1-carboxamide A mixture of (3S,4S)-4-fluoro-1-[4-iodo-6-(morpholin-4-yl)pyridin-2-yl]pyrrolidin-3-ol (90 mg, 0.218 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (90 mg, 0.218 mmol), 1,4-dioxane (1.8 mL), $H_2O$ (0.45 mL), $Na_2CO_3$ (69 mg, 0.653 mmol) and Pd(dppf)$Cl_2 \cdot CH_2Cl_2$ (18 mg, 0.022 mmol) was stirred for 16 h at 60° C. under nitrogen atmosphere. The reaction was quenched by the addition of water (5 mL). The resulting mixture was extracted with EtOAc (3×20 mL). The combined organic layers were washed with brine (3×4 mL), dried over anhydrous $Na_2SO_4$. After filtration, the filtrate was concentrated under reduced pressure. The residue was purified by silica gel column chromatography, eluted with PE/EtOAc (5/1) to afford (3S)—N-(3-[2-[(3S,4S)-3-fluoro-4-hydroxypyrrolidin-1-yl]-6-(morpholin-4-yl)pyridin-4-yl]-4-methylphenyl)-3-(2,2,2-trifluoroethyl)pyrrolidine-1-carboxamide (74.9 mg, 62%) as an off-white solid. MS ESI calculated for $C_{27}H_{33}F_4N_5O_3$ $[M+H]^+$, 552.25 found 552.35. $^1H$ NMR (400 MHz, Chloroform-d) δ 7.37 (dd, J=2.4, 8.4 Hz, 1H), 7.23 (d, J=2.4 Hz, 1H), 7.18 (d, J=8.4 Hz, 1H), 6.21 (s, 1H), 5.90 (s, 1H), 5.74 (s, 1H), 5.07 (d, J=50.8 Hz, 1H), 4.52-4.50 (m, 1H), 3.92-3.71 (m, 8H), 3.65-3.61 (m, 2H), 3.52-3.50 (m, 4H), 3.46-3.41 (m, 1H), 3.11-3.07 (m, 1H), 2.61-2.49 (m, 1H), 2.33-2.20 (m, 6H), 1.78-1.70 (m, 1H), 1.70-1.66 (m, 1H). $^{19}F$ NMR (376 MHz, Chloroform-d) δ −63.93 (3F), −182.75 (1F).

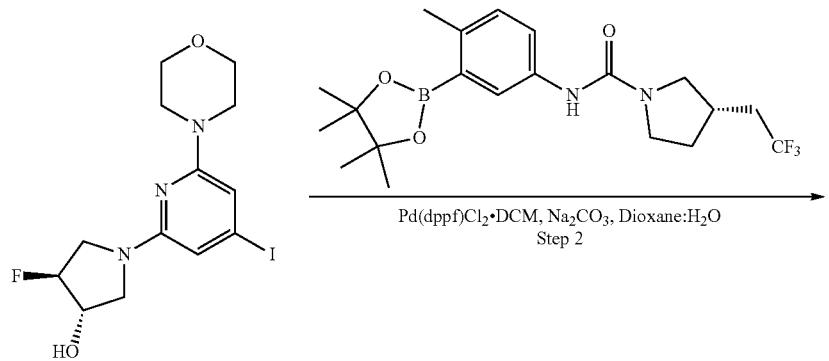

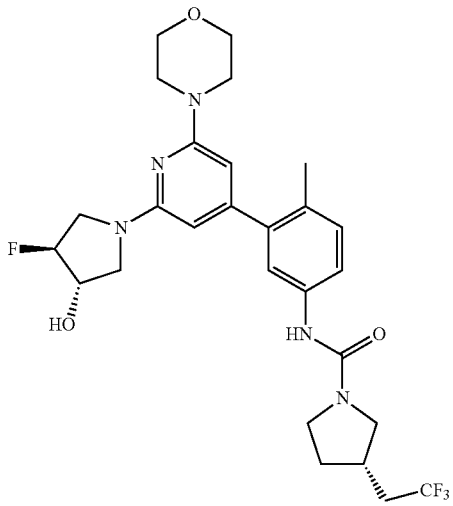

Example 120: (3S)—N-[3-[2-cyclopropanesulfona-
mido-6-(morpholin-4-yl)pyridin-4-yl]-4-methylphe-
nyl]-3-(2,2,2 trifluoroethyl)pyrrolidine-1-carboxam-
ide

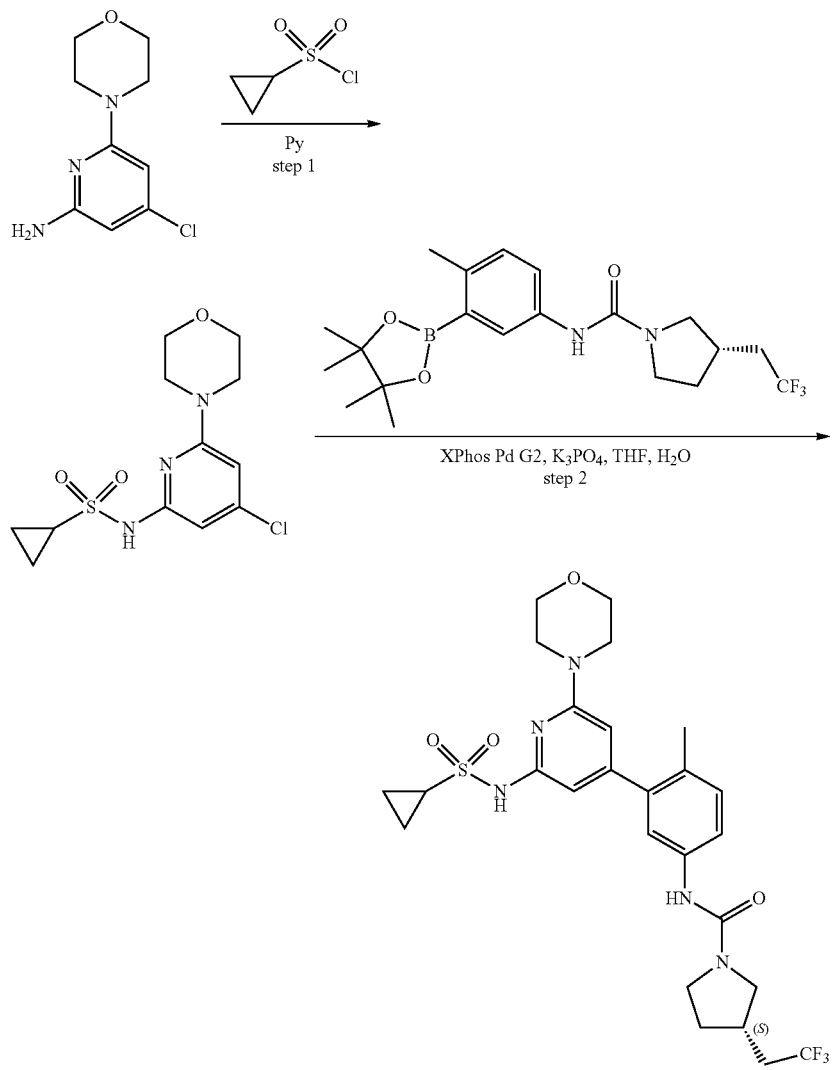

Preparation 120A: N-[4-chloro-6-(morpholin-4-yl)
pyridin-2-yl]cyclopropanesulfonamide

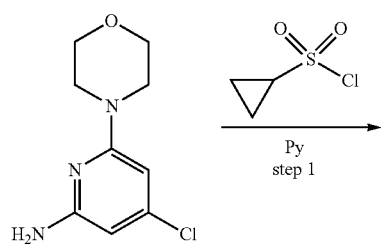

-continued

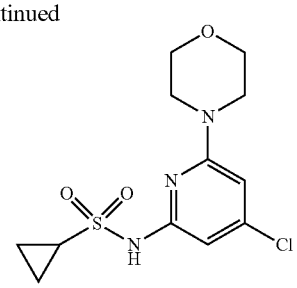

A mixture of 4-chloro-6-(morpholin-4-yl)pyridin-2-amine (200 mg, 0.936 mmol) in pyridine (6 mL) and cyclopropanesulfonyl chloride (197 mg, 1.404 mmol) was stirred for 48 h at room temperature. The reaction mixture was concentrated under reduced pressure. The residue was purified by reverse flash chromatography with the following conditions: column, C18 silica gel; mobile phase, CH$_3$CN in water (with 10 mmol/L NH$_4$HCO$_3$), gradient 10% to 95%; detector, UV 254 nm to afford N-[4-chloro-6-(morpholin-4-yl)pyridin-2-yl]cyclopropanesulfonamide (127 mg, 17%) as an off-white solid. MS ESI calculated for C$_{12}$H$_{16}$ClN$_3$O$_3$S [M+H]$^+$, 318.06, found 318.10. $^1$H NMR (400 MHz, Chloroform-d) δ 6.65 (s, 1H), 6.34 (s, 1H), 3.91-3.71 (m, 4H), 3.59-3.39 (m, 4H), 2.80-2.76 m, 1H), 1.41-1.23 (m, 2H), 1.19-0.97 (m, 2H).

Example 120: (3S)—N-[3-[2-cyclopropanesulfonamido-6-(morpholin-4-yl)pyridin-4-yl]-4-methylphenyl]-3-(2,2,2 trifluoroethyl)pyrrolidine-1-carboxamide

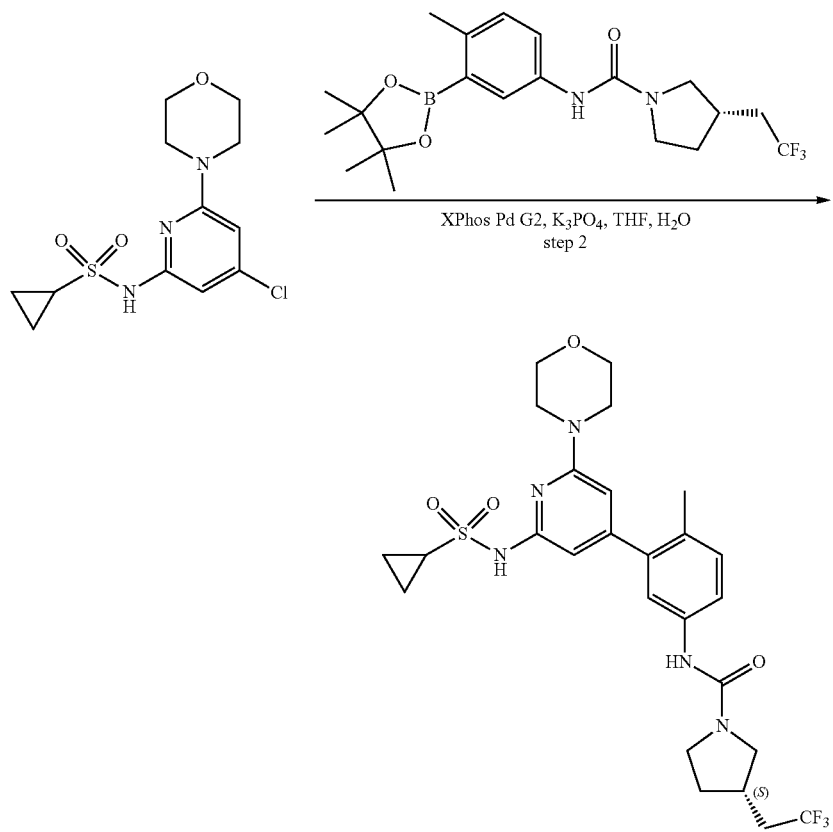

A mixture of N-[4-chloro-6-(morpholin-4-yl)pyridin-2-yl]cyclopropanesulfonamide (100 mg, 0.300 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (116.8 mg, 0.300 mmol), 2$^{nd}$ XPhos Precatalyst (24 mg, 0.030 mmol) and K$_3$PO$_4$ (135 mg, 0.640 mmol) in THF (5 mL) and H$_2$O (0.5 mL) was stirred for 2 h at 80° C. under nitrogen atmosphere. The resulting mixture was concentrated under reduced pressure. The residue was purified by silica gel column chromatography, eluted with PE/EtOAc (1/1) to afford (3S)—N-[3-[2-cyclopropanesulfonamido-6-(morpholin-4-yl)pyridin-4-yl]-4-methylphenyl]-3-(2,2,2 trifluoroethyl)pyrrolidine-1-carboxamide (69 mg, 38%) as an off-white solid. MS ESI calculated for C$_{26}$H$_{32}$F$_3$N$_5$O$_4$S [M+H]$^+$, 568.21, found 568.15. $^1$H NMR (400 MHz, DMSO-d$_6$) δ 10.29 (s, 1H), 8.17 (s, 1H), 7.46 (dd, J=8.4, 2.4 Hz, 1H), 7.37 (d, J=2.4 Hz, 1H), 7.14 (d, J=8.4 Hz, 1H), 6.32 (s, 1H), 6.18 (s, 1H), 3.86-3.62 (m, 5H), 3.60-3.41 (m, 5H), 3.32-3.27 (m, 1H), 3.17-2.93 (m, 2H), 2.50-2.29 (m, 3H), 2.16 (s, 3H), 2.09-2.07 (m, 1H), 1.74-1.55 (m, 1H), 1.04-1.02 (m, 4H). $^{19}$F NMR (282 MHz, DMSO-d$_6$) δ −63.36 (3F).

Example 121: (3S)—N-(3-[2-[(3S)-3-amino-2-oxopyrrolidin-1-yl]-6-(morpholin-4-yl)pyridin-4-yl]-4-methylphenyl)-3-(2,2,2-trifluoroethyl)pyrrolidine-1-carboxamide
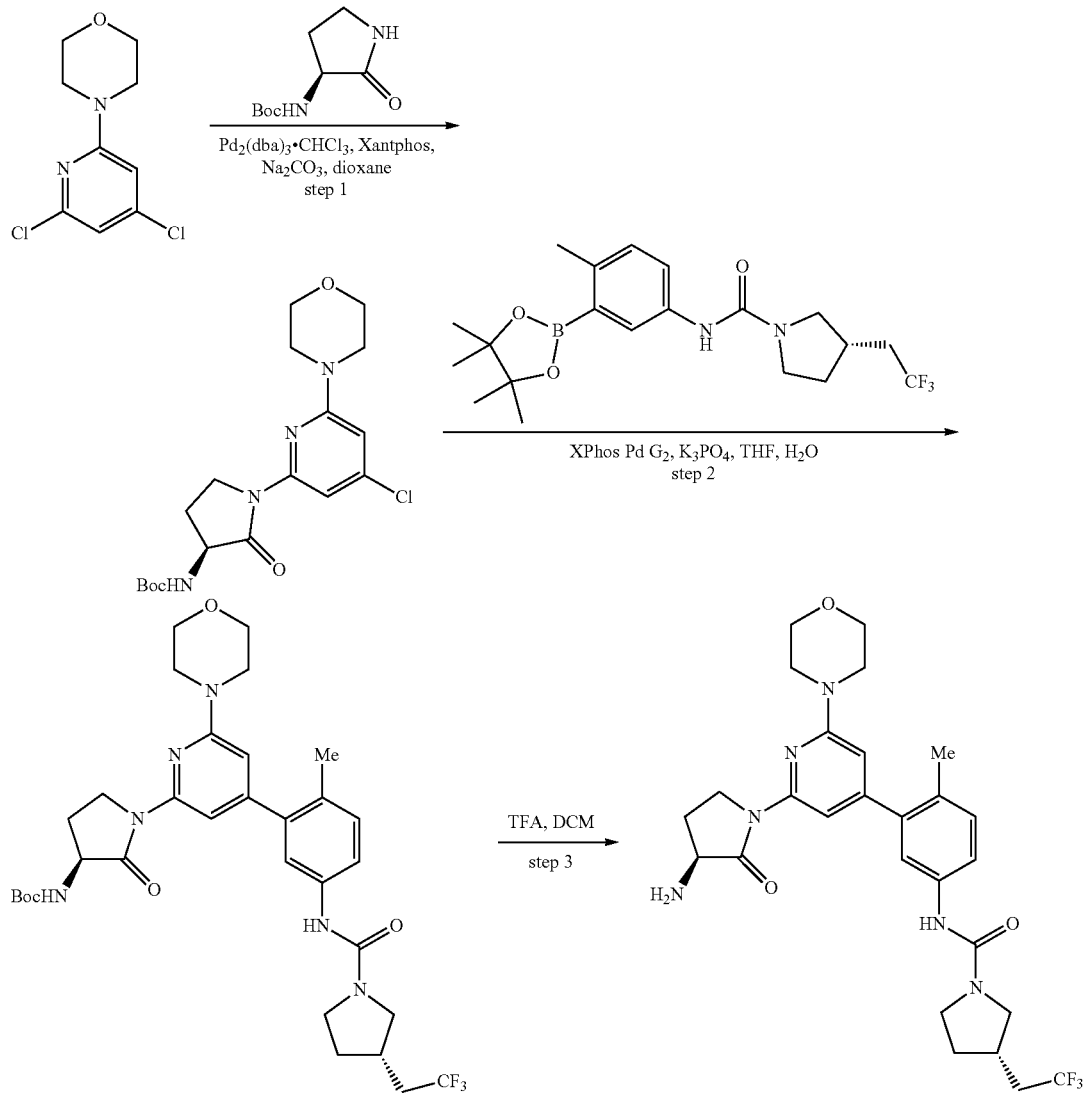
Preparation 121A: tert-butyl N-[(3S)-1-[4-chloro-6-(morpholin-4-yl)pyridin-2-yl]-2-oxopyrrolidin-3-yl] carbamate
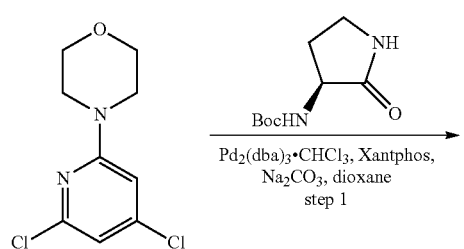
-continued
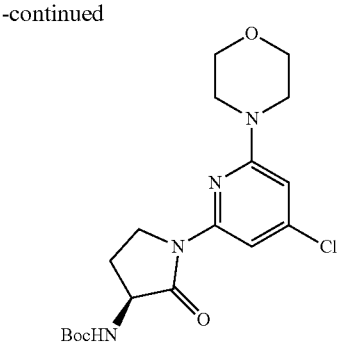
A mixture of 4-(4,6-dichloropyridin-2-yl)morpholine (500 mg, 2.145 mmol), tert-butyl N-[(3S)-2-oxopyrrolidin- 3-yl]carbamate (644 mg, 3.218 mmol), dioxane (5 mL), Pd$_2$(dba)$_3$·CHCl$_3$ (222 mg, 0.215 mmol), XantPhos (248 mg, 0.429 mmol) and Na$_2$CO$_3$ (682 mg, 6.435 mmol) was stirred for 2 h at 100° C. under nitrogen atmosphere. The resulting mixture was quenched with water (50 mL). The resulting mixture was extracted with EtOAc (3×50 mL). The combined organic layers were washed with brine (50 mL), dried over anhydrous Na$_2$SO$_4$. After filtration, the filtrate was concentrated under reduced pressure. The residue was purified by silica gel column chromatography, eluted with PE/EtOAc (1/1) to afford tert-butyl N-[(3S)-1-[4-chloro-6-(morpholin-4-yl)pyridin-2-yl]-2-oxopyrrolidin-3-yl]carbamate (740 mg, 86%) as a yellow solid. MS ESI calculated for C18H25ClN4O4 [M+H]$^+$, 397.16, found 397.25. $^1$H NMR (400 MHz, Chloroform-d) δ 7.80 (d, J=1.2 Hz, 1H), 6.38 (d, J=1.2 Hz, 1H), 5.22 (s, 1H), 4.43-4.40 (m, 1H), 4.26-4.16 (m, 1H), 3.85-3.78 (m, 4H), 3.75-3.71 (m, 1H), 3.55-3.42 (m, 4H), 2.74-2.70 (m, 1H), 1.93-1.90 (m, 1H), 1.49 (s, 9H).

Preparation 121B: tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-2-oxopyrrolidin-3-yl]carbamate

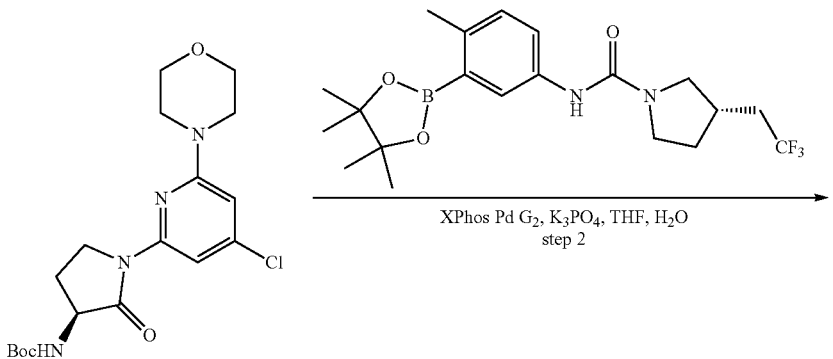

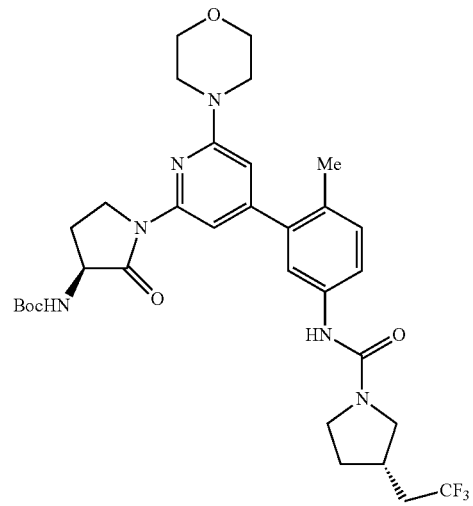

A mixture of tert-butyl N-[(3S)-1-[4-chloro-6-(morpholin-4-yl)pyridin-2-yl]-2-oxopyrrolidin-3-yl]carbamate (200 mg, 0.504 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (228 mg, 0.554 mmol), THF (5 mL), H$_2$O (0.5 mL), 2$^{nd}$ XPhos Precatalyst (39 mg, 0.050 mmol) and K$_3$PO$_4$ (213 mg, 1.008 mmol) was stirred for 2 h at 80° C. under a nitrogen atmosphere. The resulting mixture was concentrated under reduced pressure. The residue was purified by Prep-TLC with PE/EtOAc/EtOH (4/3/1) to afford tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-2-oxopyrrolidin-3-yl]carbamate (300 mg, 92%) as a yellow oil. MS ESI calculated for C$_{32}$H$_{41}$F$_3$N$_6$O$_5$ [M+H]$^+$, 647.31, found 647.35.

Example 121: (3S)—N-(3-[2-[(3S)-3-amino-2-oxopyrrolidin-1-yl]-6-(morpholin-4-yl)pyridin-4-yl]-4-methylphenyl)-3-(2,2,2-trifluoroethyl)pyrrolidine-1-carboxamide

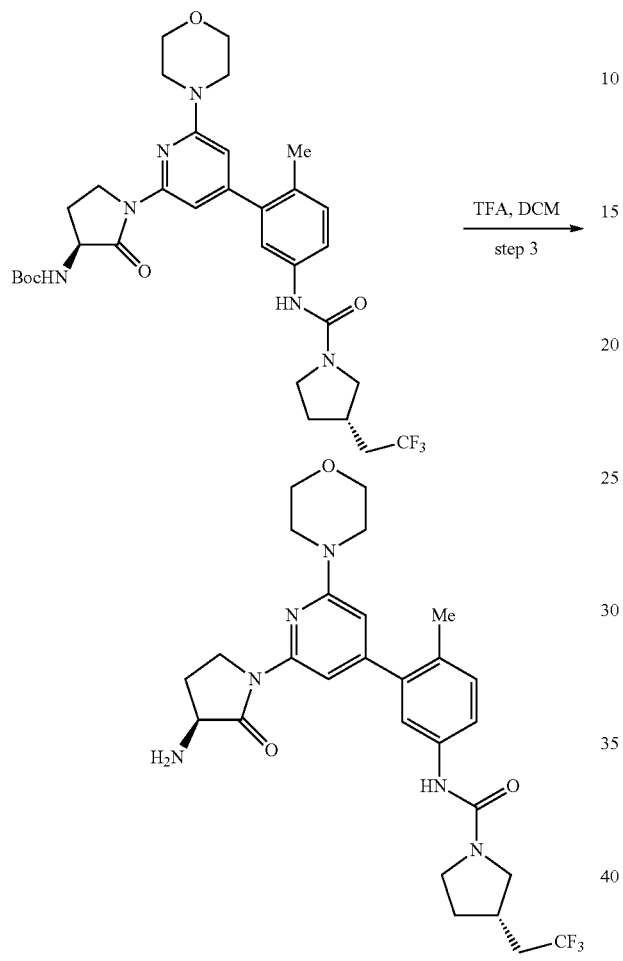

A solution of tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-2-oxopyrrolidin-3-yl]carbamate (200 mg, 0.309 mmol) and TFA (1 mL) in DCM (5 mL) was stirred for 1 h at room temperature. The resulting mixture was concentrated under reduced pressure. The crude product was purified by reverse phase flash with the following conditions: Column: Spherical C18, 20~40 μm, 120 g; Mobile Phase A: water (plus 0.05% FA); Mobile Phase B: $CH_3CN$; Flow rate: 60 mL/min; Gradient:35% B to 75%, Detector: 220 nm. The resulting mixture was diluted with $Na_2CO_3$ (1 M, 10 mL). The resulting mixture was extracted with EtOAc (2×15 mL). The combined organic layers were washed with brine (15 mL), dried over anhydrous $Na_2SO_4$. After filtration, the filtrate was concentrated under reduced pressure to afford (3S)—N-(3-[2-[(3S)-3-amino-2-oxopyrrolidin-1-yl]-6-(morpholin-4-yl)pyridin-4-yl]-4-methylphenyl)-3-(2,2,2-trifluoroethyl)pyrrolidine-1-carboxamide (129 mg, 76%) as an off-white solid. MS ESI calculated for $C_{27}H_{33}F_3N_6O_3$ [M+H]$^+$, 547.26, found 547.25. $^1$H NMR (400 MHz, DMSO-d$_6$) δ 8.19 (s, 1H), 7.62 (s, 1H), 7.47 (dd, J=2.0, 8.4 Hz, 1H), 7.39 (d, J=2.0 Hz, 1H), 7.15 (d, J=8.4 Hz, 1H), 6.45 (s, 1H), 4.13-4.04 (m, 1H), 3.77-3.65 (m, 6H), 3.61-3.46 (m, 6H), 3.31-3.27 (m, 1H), 3.05-3.00 (m, 1H), 2.51-2.40 (m, 3H), 2.35-2.31 (m, 1H), 2.17 (s, 3H), 2.12-2.05 (m, 1H), 1.91 (s, 2H), 1.78-1.56 (m, 2H). $^{19}$F NMR (376 MHz, DMSO-d$_6$) δ −63.37 (3F).

Example 122: (3S)—N-(3-[2-[(4S)-4-amino-2-oxopyrrolidin-1-yl]-6-(morpholin-4-yl)pyridin-4-yl]-4-methylphenyl)-3-(2,2,2-trifluoroethyl)pyrrolidine-1-carboxamide

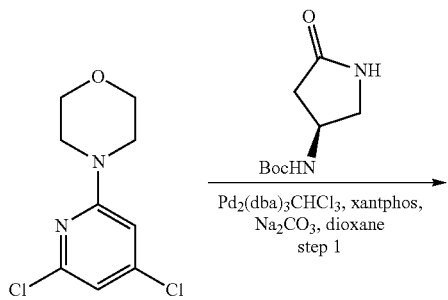

487

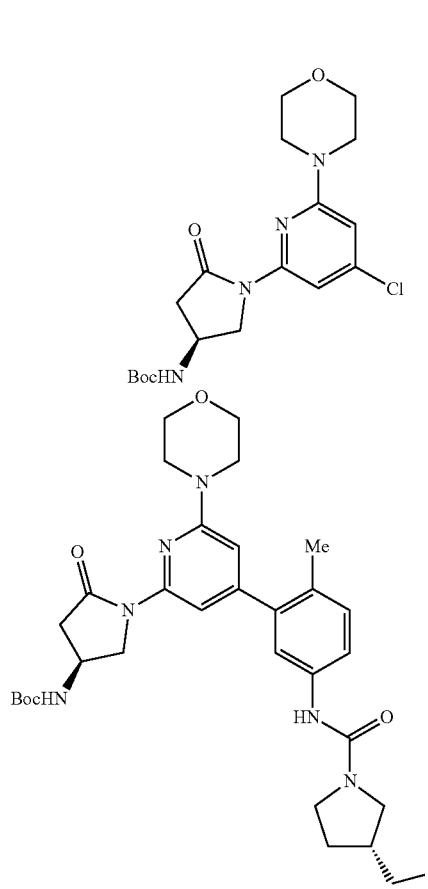

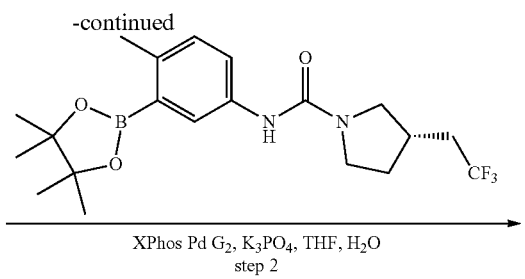

Preparation 122A: tert-butyl N-[(3S)-1-[4-chloro-6-(morpholin-4-yl)pyridin-2-yl]-5-oxopyrrolidin-3-yl]carbamate

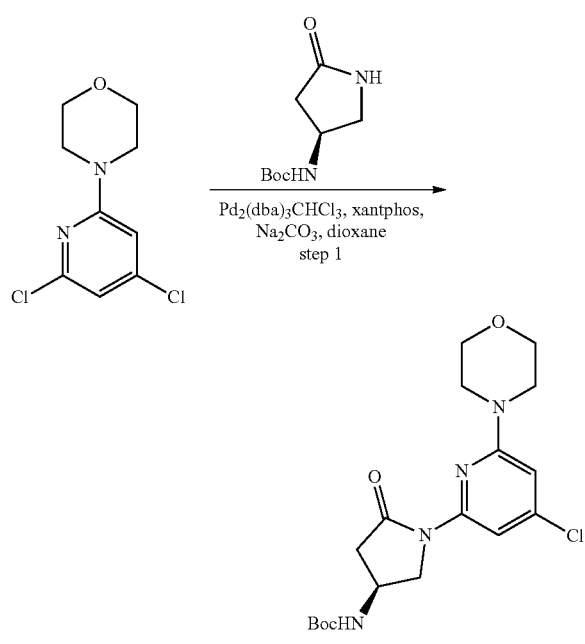

488

A mixture of 4-(4,6-dichloropyridin-2-yl)morpholine (500 mg, 2.145 mmol), tert-butyl N-[(3S)-5-oxopyrrolidin-3-yl]carbamate (644 mg, 3.218 mmol), Pd$_2$(dba)$_3$·CHCl$_3$ (222 mg, 0.215 mmol), Na$_2$CO$_3$ (682 mg, 6.435 mmol) and XantPhos (248 mg, 0.429 mmol) in dioxane (5 mL) was stirred for 2 h at 100° C. under nitrogen atmosphere. The resulting mixture was diluted with water (30 mL). The resulting mixture was extracted with EtOAc (3×30 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EtOAc (1/1) to afford tert-butyl N-[(3S)-1-[4-chloro-6-(morpholin-4-yl)pyridin-2-yl]-5-oxopyrrolidin-3-yl]carbamate (750 mg, 88%) as a light yellow solid. MS ESI calculated for C$_{18}$H$_{25}$ClN$_4$O$_4$ [M+H]$^+$, 397.16, found 397.20. $^1$H NMR (400 MHz, Chloroform-d) δ 7.80 (d, J=1.2 Hz, 1H), 6.40 (d, J=1.2 Hz, 1H), 4.85-4.83 (m, 1H), 4.40-4.38 (m, 1H), 4.31-4.27 (m, 1H), 4.01-3.93 (m, 1H), 3.86-3.79 (m, 4H), 3.54-3.45 (m, 4H), 3.04-3.01 (m, 1H), 2.58-2.54 (m, 1H), 1.47 (s, 9H).

Preparation 122B: tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-5-oxopyrrolidin-3-yl]carbamate

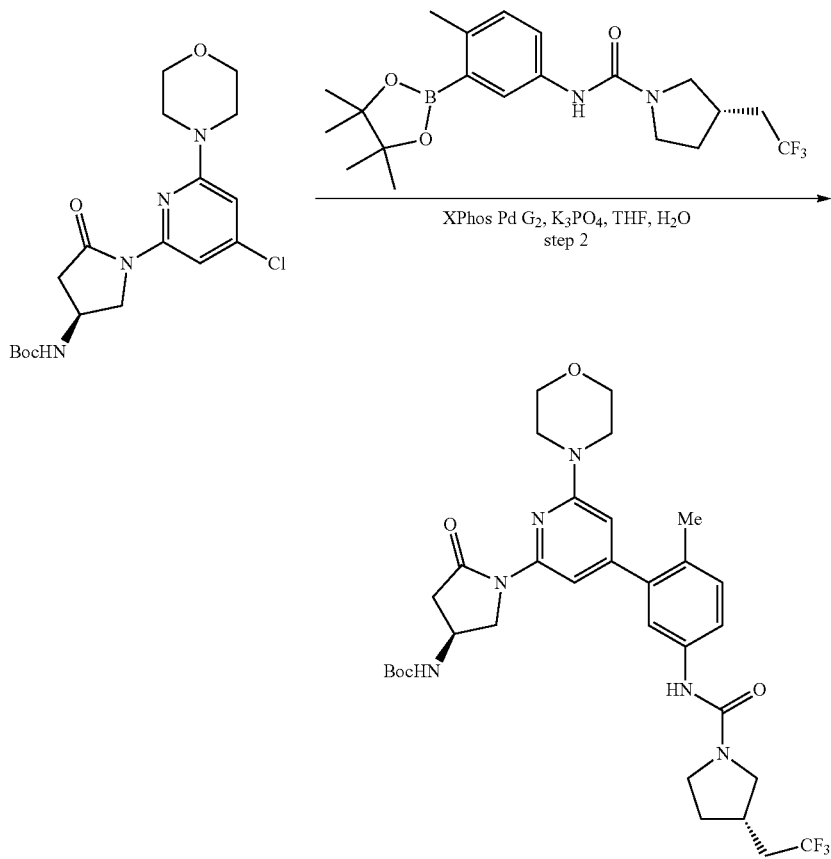

To a stirred mixture of tert-butyl N-[(3S)-1-[4-chloro-6-(morpholin-4-yl)pyridin-2-yl]-5-oxopyrrolidin-3-yl]carbamate (200 mg, 0.504 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (249 mg, 0.605 mmol) in THF (6 mL) and H$_2$O (0.6 mL) were added 2$^{nd}$ XPhos Precatalyst (39 mg, 0.050 mmol) and K$_3$PO$_4$ (213 mg, 1.008 mmol. The resulting mixture was stirred for 2 h at 80° C. under nitrogen atmosphere. The resulting mixture was concentrated under reduced pressure. The residue was purified by silica gel column chromatography, eluted with PE/EtOAc/EtOH (4/3/1) to afford tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-5-oxopyrrolidin-3-yl]carbamate (300 mg, 92%) as a light yellow solid. MS ESI calculated for C$_{32}$H$_{41}$F$_3$N$_6$O$_5$ [M+H]$^+$, 647.31, found 647.15.

Example 122: (3S)—N-(3-[2-[(4S)-4-amino-2-oxopyrrolidin-1-yl]-6-(morpholin-4-yl)pyridin-4-yl]-4-methylphenyl)-3-(2,2,2-trifluoroethyl)pyrrolidine-1-carboxamide

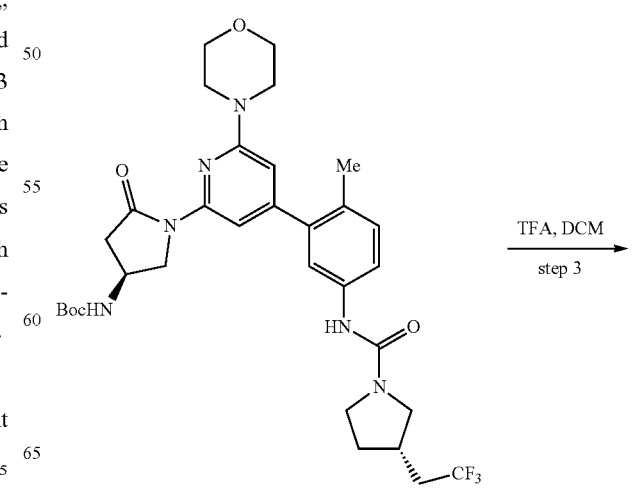

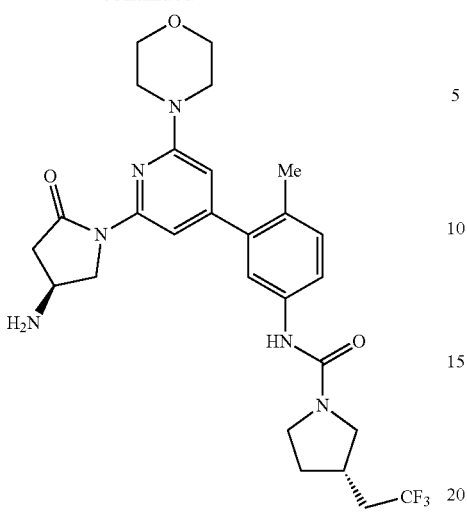

To a stirred solution of tert-butyl N-[(3S)-1-(4-[2-methyl-5-[(3S)-3-(2,2,2-trifluoroethyl)pyrrolidine-1-carbonylamino]phenyl]-6-(morpholin-4-yl)pyridin-2-yl)-5-oxopyrrolidin-3-yl]carbamate (200 mg, 0.309 mmol) in DCM (4 mL) was added TFA (0.8 mL) at room temperature. The resulting mixture was stirred for 1 h at room temperature. The resulting mixture was concentrated under reduced pressure. The crude product was purified by reverse phase flash with the following conditions: Column: Spherical C18, 20~40 μm, 120 g; Mobile Phase A: Water (plus 0.05% FA); Mobile Phase B: CH$_3$CN; Flow rate: 60 mL/min; Gradient: 25% B to 55% B, Detector: 220 nm to afford (3S)—N-(3-[2-[(4S)-4-amino-2-oxopyrrolidin-1-yl]-6-(morpholin-4-yl)pyridin-4-yl]-4-methylphenyl)-3-(2,2,2-trifluoroethyl)pyrrolidine-1-carboxamide (66 mg, 39%) as an off-white solid. MS ESI calculated for C$_{27}$H$_{33}$F$_3$N$_6$O$_3$ [M+H]$^+$, 547.26, found 547.30. $^1$H NMR (400 MHz, DMSO-d$_6$) δ 8.17 (s, 1H), 7.59 (s, 1H), 7.47 (dd, J=2.4, 8.4 Hz, 1H), 7.38 (d, J=2.4 Hz, 1H), 7.14 (d, J=8.8 Hz, 1H), 6.43 (s, 1H), 4.08-4.04 (m, 1H), 3.76-3.59 (m, 6H), 3.63-3.53 (m, 1H), 3.56-3.43 (m, 5H), 3.03 (t, J=9.6 Hz, 1H), 2.78-2.74 (m, 1H), 2.48-2.36 (m, 3H), 2.25-2.22 (m, 1H), 2.16 (s, 3H), 2.10-2.06 (m, 1H), 1.85 (brs, 2H), 1.66-1.55 (m, 1H). $^{19}$F NMR (282 MHz, Chloroform-d) δ −64.94 (3F).

Example 123: (3S)—N-(3-[2-[(3S)-3-amino-3-methylpyrrolidin-1-yl]-6-(morpholin-4-yl)pyridin-4-yl]-4-methylphenyl)-3-(2,2,2-trifluoroethyl)pyrrolidine-1-carboxamide

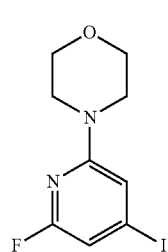

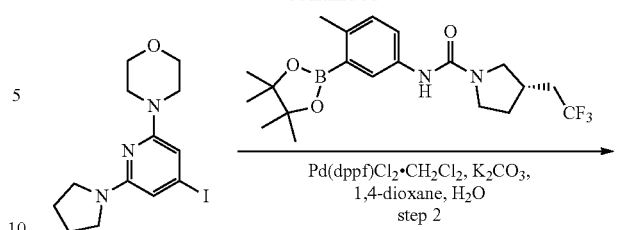

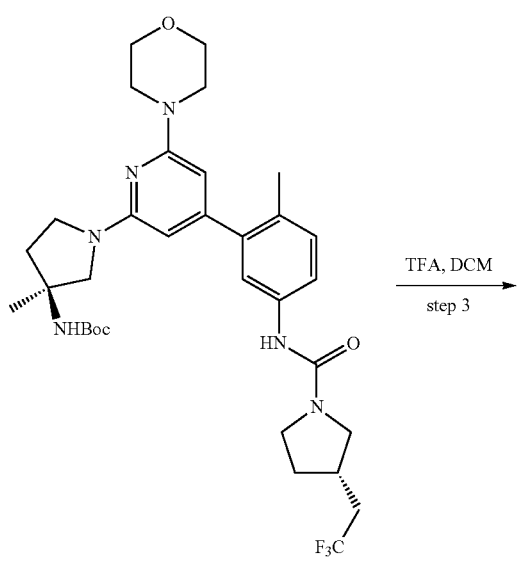

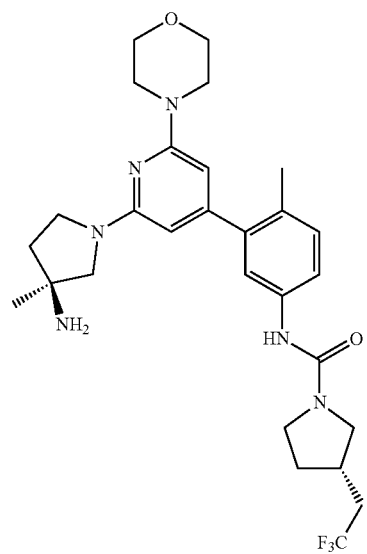 [SMILES: Cc1ccc(NC(=O)N2CC[C@@H](CC(F)(F)F)C2)cc1-c1cc(N2CCOCC2)nc(N2CC[C@](C)(N)C2)c1]

Preparation 123A: tert-butyl N-[(3S)-1-[4-iodo-6-(morpholin-4-yl)pyridin-2-yl]-3-methylpyrrolidin-3-yl]carbamate

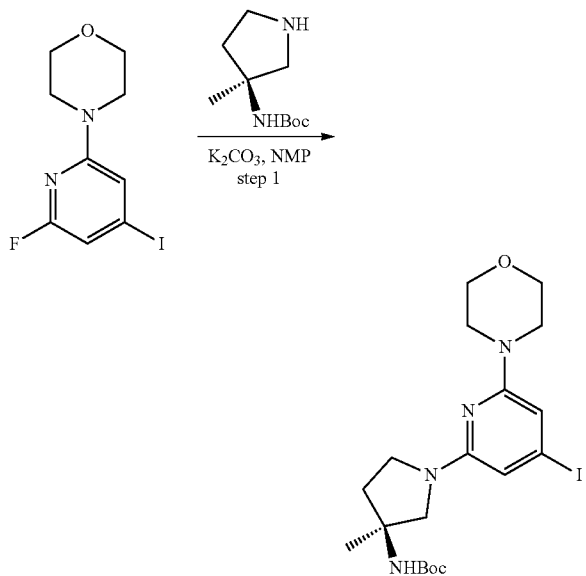

To a stirred solution of 4-(6-fluoro-4-iodopyridin-2-yl) morpholine (693 mg, 2.249 mmol) and tert-butyl N-[(3S)-3-methylpyrrolidin-3-yl]carbamate (450 mg, 2.249 mmol) in NMP (15 mL) was added $K_2CO_3$ (932 mg, 6.748 mmol). The resulting mixture was stirred for 2 h at 150° C. under nitrogen atmosphere. The resulting mixture was diluted with EtOAc (50 mL). The combined organic layers were washed with brine (3×20 mL), dried over anhydrous $Na_2SO_4$. After filtration, the filtrate was concentrated under reduced pressure. The residue was purified by silica gel column chromatography, eluted with PE/EtOAc (3/1) to afford tert-butyl N-[(3S)-1-[4-iodo-6-(morpholin-4-yl)pyridin-2-yl]-3-methylpyrrolidin-3-yl]carbamate (700 mg, 63%) as a white solid. MS ESI calculated for $C_{19}H_{29}IN_4O_3$ [M+H]$^+$, 489.13, found 489.05. $^1$H NMR (400 MHz, Chloroform-d) δ 6.26 (d, J=0.8 Hz, 1H), 6.15 (d, J=0.8 Hz, 1H), 4.66 (s, 1H), 3.85-3.76 (m, 4H), 3.64 (d, J=10.8 Hz, 1H), 3.54-3.43 (m, 6H), 3.39 (d, J=10.8 Hz, 1H), 2.43-2.33 (m, 1H), 1.95-1.88 (m, 1H), 1.51 (s, 3H), 1.45 (s, 9H).

Preparation 123B: tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate

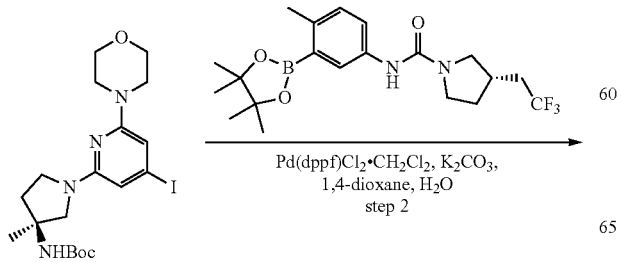

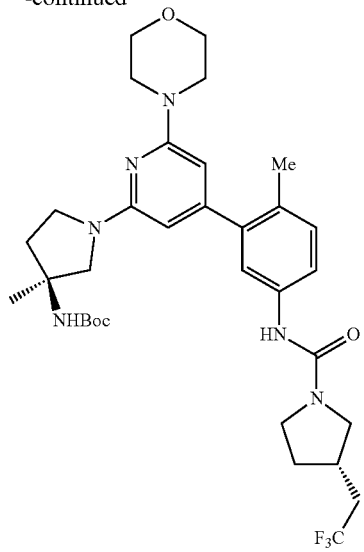

To a stirred solution of tert-butyl N-[(3S)-1-[4-iodo-6-(morpholin-4-yl)pyridin-2-yl]-3-methylpyrrolidin-3-yl]carbamate (200 mg, 0.410 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (185 mg, 0.450 mmo) in dioxane (6 mL) and $H_2O$ (1.5 mL) were added Pd(dppf)Cl$_2$·CH$_2$Cl$_2$ (33 mg, 0.041 mmol) and Na$_2$CO$_3$ (130 mg, 1.230 mmol) at room temperature. The resulting mixture was stirred for 2 h at 60° C. under nitrogen atmosphere. The residue was purified by Prep-TLC (PE/EtOAc=1/1) to afford tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (220 mg, 83%) as a light brown solid. MS ESI calculated for $C_{33}H_{45}F_3N_6O_4$ [M+H]$^+$, 647.35, found 647.30.

Example 123: (3S)—N-(3-[2-[(3S)-3-amino-3-methylpyrrolidin-1-yl]-6-(morpholin-4-yl)pyridin-4-yl]-4-methylphenyl)-3-(2,2,2-trifluoroethyl)pyrrolidine-1-carboxamide

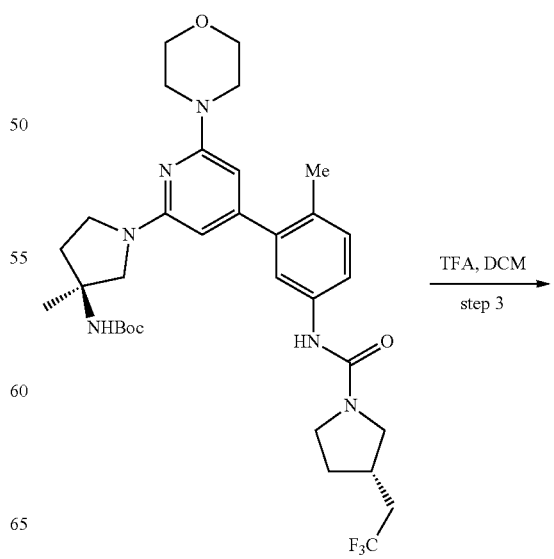

495

-continued

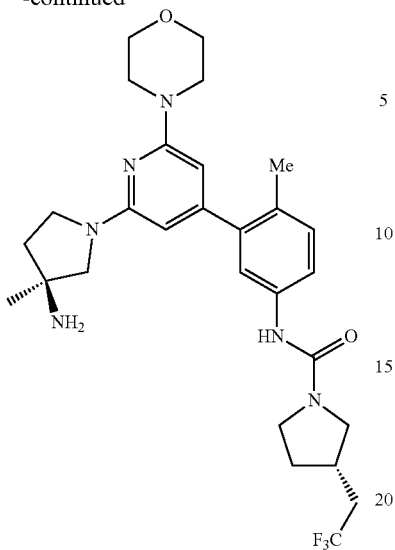

A solution of tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) pyrrolidin-3-yl]carbamate (200 mg, 0.309 mmol) and TFA (1 mL) in DCM (5 mL) was stirred for 1 h at room temperature. The resulting mixture was concentrated under reduced pressure. The resulting mixture was diluted with EtOAc (30 mL). The combined organic layers were washed with brine (10 mL), dried over anhydrous Na$_2$SO$_4$. After filtration, the filtrate was concentrated under reduced pressure. The crude product was purified by reverse phase flash with the following conditions: Column: Spherical C18, 20~40 μm, 120 g; Mobile Phase A: Water (plus 10 mM NH$_4$CO$_3$); Mobile Phase B: CH$_3$CN; Flow rate: 60 mL/min; Gradient:25% B to 55% B, Detector: 220 nm to afford (3S)—N-(3-[2-[(3S)-3-amino-3-methylpyrrolidin-1-yl]-6-(morpholin-4-yl)pyridin-4-yl]-4-methylphenyl)-3-(2,2,2-trifluoroethyl)pyrrolidine-1-carboxamide (88 mg, 52%) as a light green solid. MS ESI calculated for C$_{28}$H$_{37}$F$_3$N$_6$O$_2$ [M+H]$^+$, 547.29, found 547.30. $^1$H NMR (300 MHz, DMSO-d$_6$) δ 8.13 (s, 1H), 7.44 (dd, J=2.4, 8.4 Hz, 1H), 7.35 (d, J=2.4 Hz, 1H), 7.11 (d, J=8.4 Hz, 1H), 5.84 (s, 1H), 5.61 (s, 1H), 3.72-3.68 (m, 5H), 3.55-3.23 (m, 10H), 3.04 (t, J=9.3 Hz, 1H), 2.49-2.37 (m, 3H), 2.18 (s, 3H), 2.11-2.07 (m, 1H), 1.81-1.60 (m, 5H), 1.25 (s, 3H). $^{19}$F NMR (282 MHz, DMSO-d$_6$) δ −63.35 (3F).

Example 124: (3S)—N-(3-[2-[(3S)-3-amino-3-methylpiperidin-1-yl]-6-(morpholin-4-yl)pyridin-4-yl]-4-methylphenyl)-3-(2,2,2-trifluoroethyl)pyrrolidine-1-carboxamide

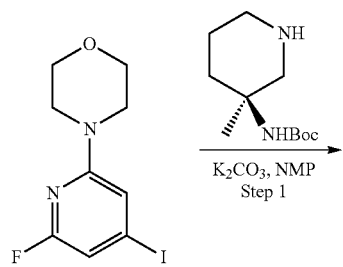

496

-continued

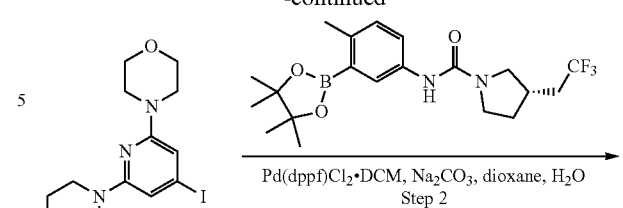

Pd(dppf)Cl$_2$·DCM, Na$_2$CO$_3$, dioxane, H$_2$O
Step 2

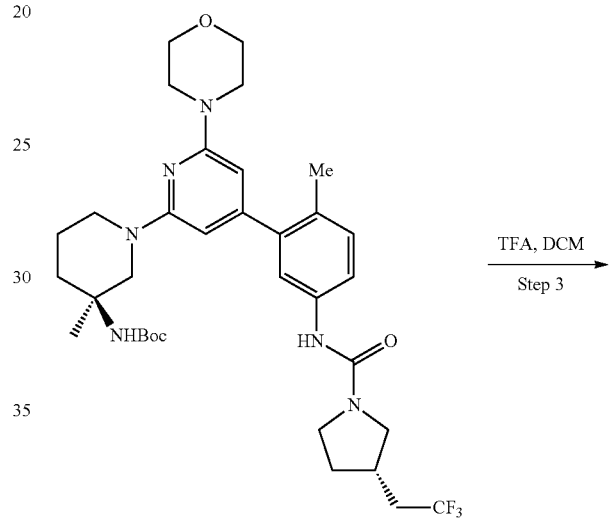

TFA, DCM
Step 3

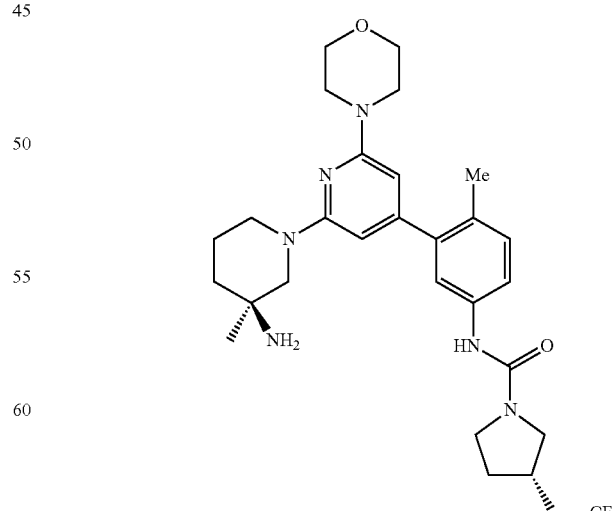

Preparation 124A: tert-butyl N-[(3S)-1-[4-iodo-6-(morpholin-4-yl)pyridin-2-yl]-3-methylpiperidin-3-yl]carbamate

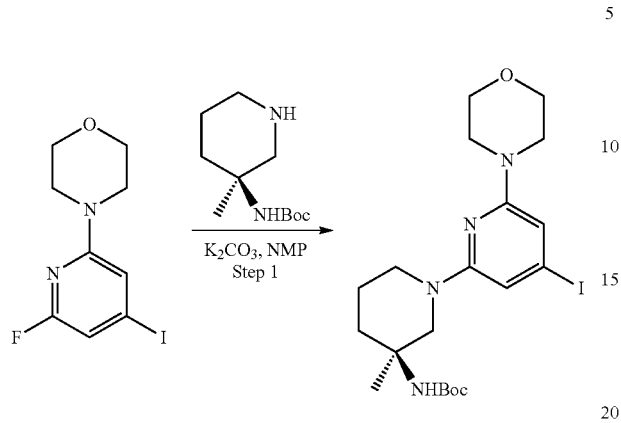

To a stirred solution of 4-(6-fluoro-4-iodopyridin-2-yl)morpholine (646 mg, 2.100 mmol) and tert-butyl N-[(3S)-3-methylpiperidin-3-yl]carbamate (450 mg, 2.100 mmol) in NMP (5 mL) was added $K_2CO_3$ (870 mg, 6.299 mmol). The resulting mixture was stirred for 2 h at 150° C. under nitrogen atmosphere. The resulting mixture was diluted with EtOAc (30 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EtOAc/EtOH (12/3/1) to afford tert-butyl N-[(3S)-1-[4-iodo-6-(morpholin-4-yl)pyridin-2-yl]-3-methylpiperidin-3-yl]carbamate (270 mg, 25%) as a light yellow solid. MS ESI calculated for $C_{20}H_{31}IN_4O_3$ [M+H]$^+$, 503.14, found 503.00. $^1$H NMR (400 MHz, Chloroform-d) δ 6.46 (s, 1H), 6.31 (s, 1H), 5.07 (s, 1H), 4.20 (d, J=13.2 Hz, 1H), 3.97 (d, J=12.9 Hz, 1H), 3.83-3.79 (m, 4H), 3.48-3.42 (m, 4H), 3.03-2.82 (m, 1H), 2.77 (d, J=13.2 Hz, 1H), 2.40-2.32 (m, 1H), 1.75-1.55 (m, 3H), 1.43 (s, 9H), 1.39 (s, 3H).

Preparation 124B: tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate

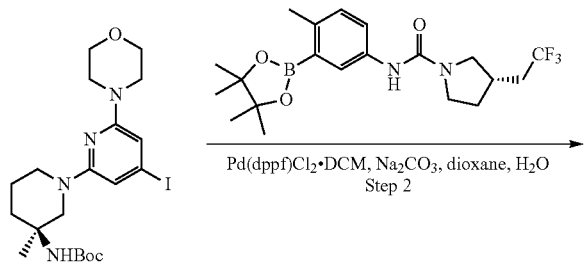

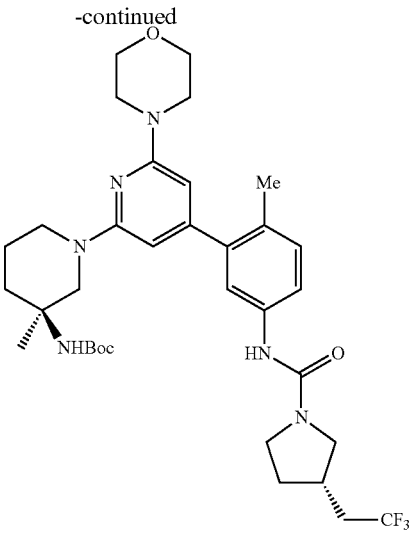

To a stirred solution of tert-butyl N-[(3S)-1-[4-iodo-6-(morpholin-4-yl)pyridin-2-yl]-3-methylpiperidin-3-yl]carbamate (200 mg, 0.398 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (180 mg, 0.438 mmol) in 1,4-dioxane (2 mL) and $H_2O$ (0.5 mL) were added Pd(dppf)Cl$_2$·CH$_2$Cl$_2$ (32 mg, 0.040 mmol) and Na$_2$CO$_3$ (126.58 mg, 1.194 mmol). The resulting mixture was stirred for 2 h at 60° C. under nitrogen atmosphere. The resulting mixture was concentrated under reduced pressure. The residue was purified by Prep-TLC with PE/EtOAc (1/1) to afford tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (230 mg, 87%) as a light brown solid. MS ESI calculated for $C_{34}H_{47}F_3N_6O_4$ [M+H]$^+$, 661.36, found 661.40.

Example 124: (3S)—N-(3-[2-[(3S)-3-amino-3-methylpiperidin-1-yl]-6-(morpholin-4-yl)pyridin-4-yl]-4-methylphenyl)-3-(2,2,2-trifluoroethyl)pyrrolidine-1-carboxamide

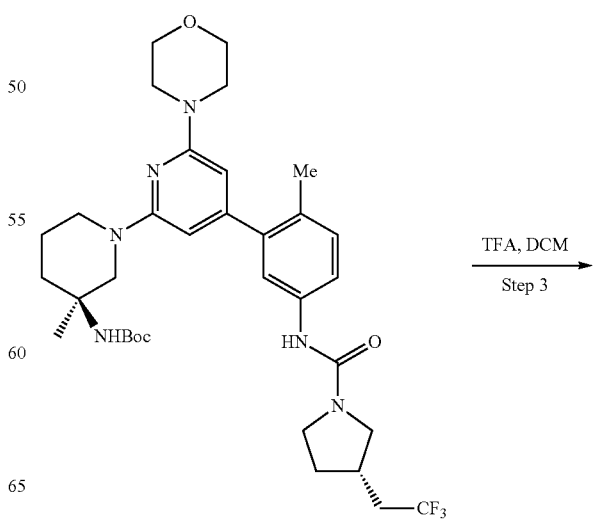

499

-continued

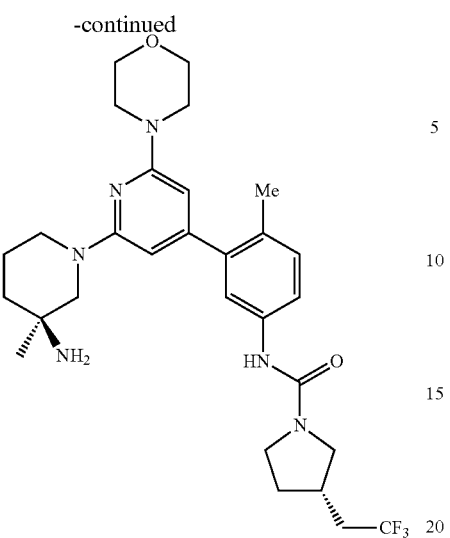

A solution of tert-butyl N-[(3S)-3-methyl-1-(4-[2-methyl-5-[(3S)-3-(2,2,2-trifluoroethyl)pyrrolidine-1-carbonylamino]phenyl]-6-(morpholin-4-yl)pyridin-2-yl) piperidin-3-yl]carbamate (200 mg, 0.303 mmol) and TFA (0.4 mL) in DCM (2 mL) was stirred for 1 h at room temperature. The resulting mixture was concentrated under reduced pressure. The residue was purified by silica gel column chromatography, eluted with $CH_2Cl_2$/MeOH (8/1). The crude product was purified by Prep-HPLC with the following conditions: Column: XBridge Prep Phenyl OBD Column, 19×150 mm, 5 μm; Mobile Phase A: water (10 mmol/L $NH_4HCO_3$), Mobile Phase B: $CH_3CN$; Flow rate: 20 mL/min; Gradient:40% B to 50% B; 254/210 nm to afford (3S)—N-(3-[2-[(3S)-3-amino-3-methylpiperidin-1-yl]-6-(morpholin-4-yl)pyridin-4-yl]-4-methylphenyl)-3-(2,2,2-trifluoroethyl)pyrrolidine-1-carboxamide (29 mg, 17%) as a white solid. MS ESI calculated for $C_{29}H_{39}F_3N_6O_2$ [M+H]$^+$, 560.31, found 561.30. $^1$H NMR (400 MHz, DMSO-$d_6$) δ 8.13 (s, 1H), 7.43 (dd, J=8.4, 2.4 Hz, 1H), 7.34 (d, J=2.4 Hz, 1H), 7.11 (d, J=8.4 Hz, 1H), 6.01 (s, 1H), 5.91 (s, 1H), 3.73-3.62 (m, 5H), 3.54-3.52 (m, 2H), 3.42-3.38 (m, 5H), 3.30-3.25 (m, 3H), 3.02 (t, J=9.6 Hz, 1H), 2.50-2.42 (m, 4H), 2.16 (s, 3H), 2.10-2.06 (m, 1H), 1.67-1.60 (m, 2H), 1.55-1.50 (m, 3H), 1.07 (s, 3H). $^{19}$F NMR (376 MHz, DMSO-$d_6$) δ −63.37 (3F).

Example 125: (3S)—N-(3-[2-[(4R)-4-hydroxy-2-oxopyrrolidin-1-yl]-6-(morpholin-4-yl)pyridin-4-yl]-4-methylphenyl)-3-(2,2,2-trifluoroethyl)pyrrolidine-1-carboxamide

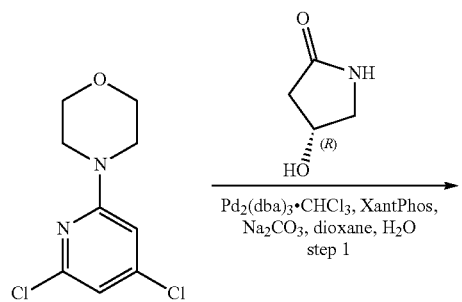

500

-continued

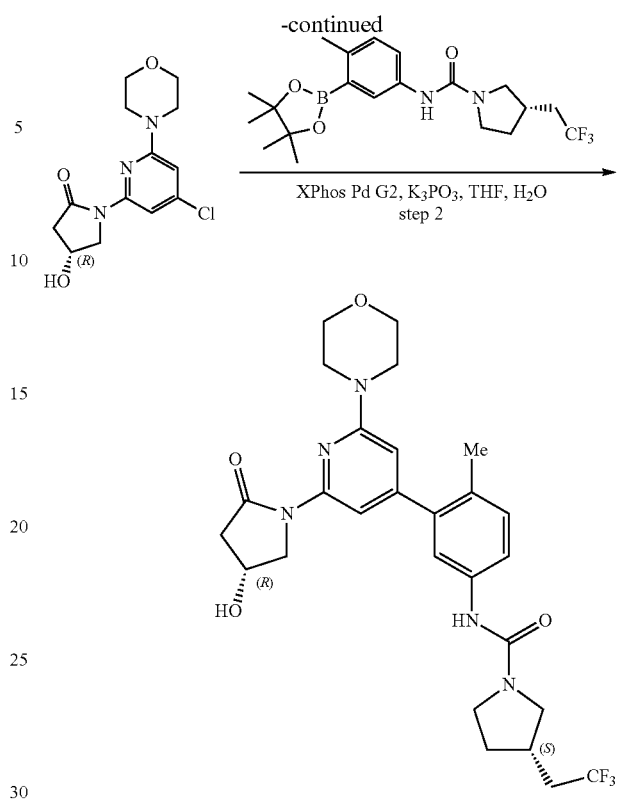

Preparation 125A: (4R)-1-[4-chloro-6-(morpholin-4-yl)pyridin-2-yl]-4-hydroxypyrrolidin-2-one

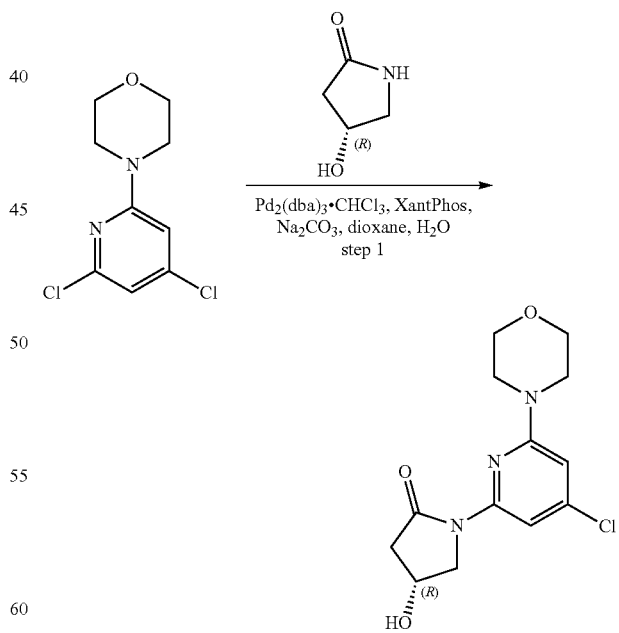

A mixture of 4-(4,6-dichloropyridin-2-yl)morpholine (500 mg, 2.145 mmol), (4R)-4-hydroxypyrrolidin-2-one (195 mg, 1.931 mmol), Pd$_2$(dba)$_3$·CHCl$_3$ (222 mg, 0.215 mmol), XantPhos (248 mg, 0.429 mmol) and Na$_2$CO$_3$ (455 mg, 4.290 mmol) in dioxane (5 mL) was stirred for 2 h at 100° C. under nitrogen atmosphere. The resulting mixture was concentrated under reduced pressure. The residue was purified by silica gel column chromatography, eluted with PE/EtOAc (1/1) to afford (4R)-1-[4-chloro-6-(morpholin-4-yl)pyridin-2-yl]-4-hydroxypyrrolidin-2-one (550 mg, 78%) as a brown solid. MS ESI calculated for $C_{13}H_{16}ClN_3O_3$ [M+H]$^+$, 298.09, found 298.05. $^1$H NMR (400 MHz, Chloroform-d) δ 7.83 (s, 1H), 6.36 (s, 1H), 4.60 (s, 1H), 4.19 (dd, J=12.4, 5.2 Hz, 1H), 4.14-4.09 (m, 1H), 3.87-3.79 (m, 4H), 3.52-3.45 (m, 4H), 2.97 (dd, J=17.6, 6.3 Hz, 1H), 2.68-2.62 (m, 1H), 2.10 (s, 1H).

Example 125: (3S)—N-(3-[2-[(4R)-4-hydroxy-2-oxopyrrolidin-1-yl]-6-(morpholin-4-yl)pyridin-4-yl]-4-methylphenyl)-3-(2,2,2-trifluoroethyl)pyrrolidine-1-carboxamide

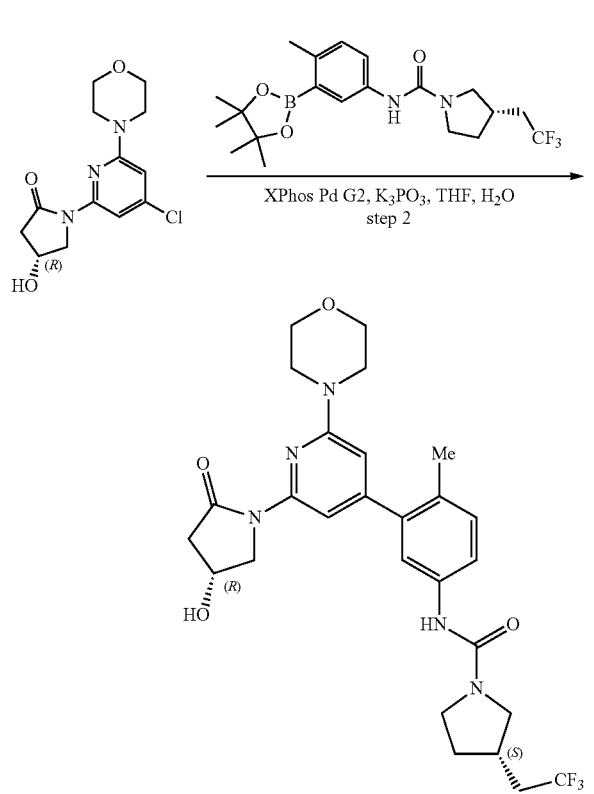

A mixture of (4R)-1-[4-chloro-6-(morpholin-4-yl)pyridin-2-yl]-4-hydroxypyrrolidin-2-one (150 mg, 0.504 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (166 mg, 0.403 mmol), 2$^{nd}$ XPhos Precatalyst (40 mg, 0.050 mmol) and K$_3$PO$_4$ (214 mg, 1.008 mmol) in THF (1.5 mL) and H$_2$O (0.2 mL) was stirred for 2 h at 80° C. under nitrogen atmosphere. The reaction was quenched by the addition of water (10 mL). The resulting mixture was extracted with EtOAc (2×20 mL). The combined organic layers were washed with brine (10 mL), dried over anhydrous Na$_2$SO$_4$. After filtration, the filtrate was concentrated under reduced pressure. The residue was purified by Prep-TLC with PE/EtOAc/EtOH (8/3/1) to afford (3S)—N-(3-[2-[(4R)-4-hydroxy-2-oxopyrrolidin-1-yl]-6-(morpholin-4-yl)pyridin-4-yl]-4-methylphenyl)-3-(2,2,2-trifluoroethyl)pyrrolidine-1-carboxamide (126 mg, 45%) as an off-white solid. MS ESI calculated for $C_{27}H_{32}F_3N_5O_4$ [M+H]$^+$, 548.24, found 548.25. $^1$H NMR (400 MHz, DMSO-d$_6$) δ 8.18 (s, 1H), 7.60 (s, 1H), 7.48 (dd, J=8.4, 2.4 Hz, 1H), 7.38 (d, J=2.4 Hz, 1H), 7.14 (d, J=8.4 Hz, 1H), 6.44 (s, 1H), 5.27 (s, 1H), 4.37-4.35 (m, 1H), 4.09-4.05 (m, 1H), 4.00-3.97 (m, 1H), 3.73-3.70 (m, 5H), 3.68-3.46 (m, 5H), 3.33-3.28 (m, 1H), 3.05-2.91 (m, 1H), 2.89-2.87 (m, 1H), 2.53-2.32 (m, 4H), 2.16 (s, 3H), 2.10-2.07 (m, 1H), 1.68-1.63 (m, 1H). $^{19}$F NMR (376 MHz, DMSO-d$_6$) δ −63.37 (3F).

Example 126: (3S)—N-[3-[2-(1,1-dioxo-1lambda6,2-thiazolidin-2-yl)-6-(morpholin-4-yl)pyridin-4-yl]-4-methylphenyl]-3-(2,2,2-trifluoroethyl)pyrrolidine-1-carboxamide

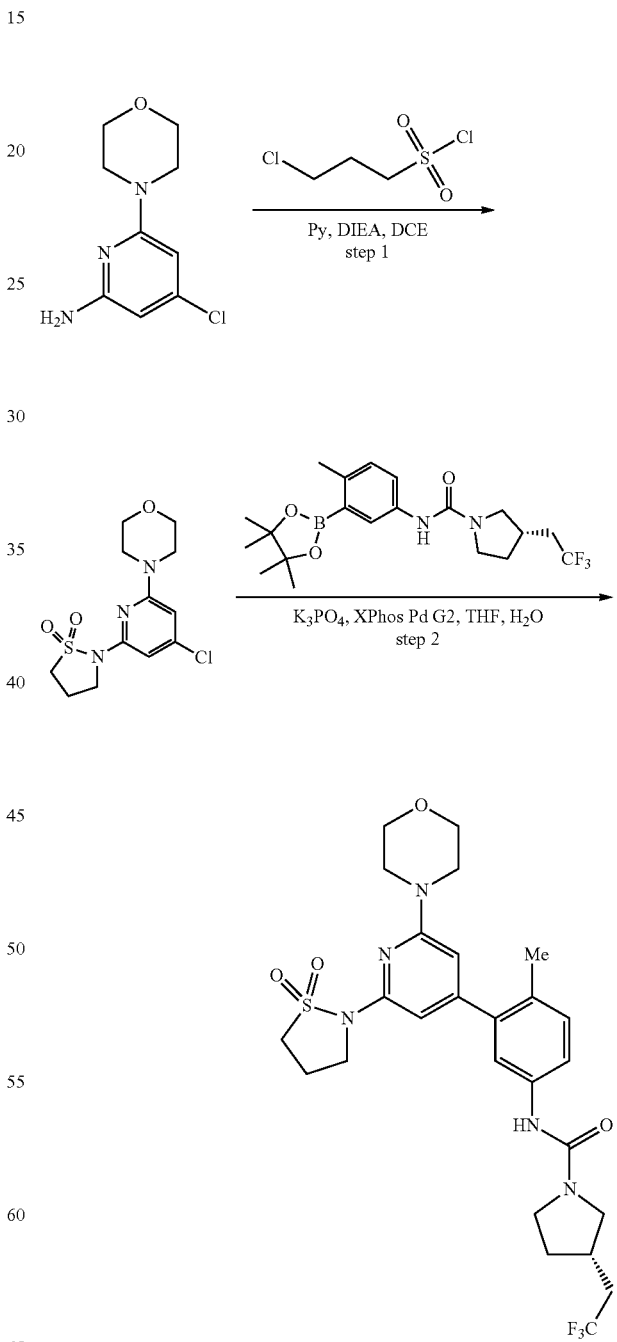

Preparation 126A: 2-[6-(morpholin-4-yl)pyridin-2-yl]-1lambda6,2-thiazolidine-1,1-dione To a stirred mixture of 4-chloro-6-(morpholin-4-yl)pyridin-2-amine (250 mg, 1.200 mmol), pyridine (0.5 mL) and DIEA (756 mg, 6.000 mmol) in DCE (5 mL) was added 3-chloropropane-1-sulfonyl chloride (414 mg, 2.300 mmol) dropwise at 0° C. The reaction mixture was stirred for 3 h and quenched with sat. Na$_2$CO$_3$ (50 mL). The resulting mixture was extracted with EtOAc (3×50 mL). The combined organic layers were washed with brine (50 mL), dried over anhydrous Na$_2$SO$_4$. After filtration, the filtrate was concentrated under reduced pressure. The residue was purified by silica gel column chromatography, eluted with PE/EtOAc (1/1) to afford 2-[6-(morpholin-4-yl)pyridin-2-yl]-1lambda6,2-thiazolidine-1,1-dione (200 mg, 34%) as an off-white solid. MS ESI calculated for C$_{12}$H$_{16}$ClN$_3$O$_3$S [M+H]$^+$, 318.06, found 318.05. $^1$H NMR (300 MHz, Chloroform-d) δ 6.52 (d, J=1.2 Hz, 1H), 6.29 (d, J=1.2 Hz, 1H), 3.94 (t, J=6.8 Hz, 2H), 3.86-3.74 (m, 4H), 3.51-3.49 (m, 4H), 3.41 (t, J=7.2 Hz, 2H), 2.51-2.46 (m, 2H).

Example 126: (3S)—N-[3-[2-(1,1-dioxo-1lambda6,2-thiazolidin-2-yl)-6-(morpholin-4-yl)pyridin-4-yl]-4-methylphenyl]-3-(2,2,2-trifluoroethyl)pyrrolidine-1-carboxamide A mixture of 2-[4-chloro-6-(morpholin-4-yl)pyridin-2-yl]-1lambda6,2-thiazolidine-1,1-dione (200 mg, 0.630 mmol), (3S)—N-[4-methyl-3-(4,4,5-trimethyl-1,3,2-dioxaborolan-2-yl)phenyl]-3-(2,2,2-trifluoroethyl)pyrrolidine-1-carboxamide (200 mg, 0.500 mmol), K$_3$PO$_4$ (267 mg, 0.130 mmol) and 2$^{nd}$ XPhos Precatalyst (53 mg, 0.006 mmol) in THF (2 mL) and H$_2$O (0.2 mL) was stirred for 2 h at 80° C. under nitrogen atmosphere. The resulting mixture was concentrated under reduced pressure. The residue was purified by silica gel column chromatography, eluted with PE/EtOAc (1/1) to afford (3S)—N-[3-[2-(1,1-dioxo-1lambda6,2-thiazolidin-2-yl)-6-(morpholin-4-yl)pyridin-4-yl]-4-methylphenyl]-3-(2,2,2-trifluoroethyl)pyrrolidine-1-carboxamide (115 mg, 32%) as an off-white solid. MS ESI calculated for C$_{26}$H$_{32}$F$_3$N$_5$O$_4$S [M+H]$^+$, 568.21, found 568.15. $^1$H NMR (400 MHz, Chloroform-d) δ 7.43 (dd, J=8.0, 2.4 Hz, 1H), 7.24-7.12 (m, 2H), 6.48 (s, 1H), 6.25 (s, 1H), 6.18 (s, 1H), 4.00 (t, J=6.8 Hz, 2H), 3.93-3.69 (m, 5H), 3.67-3.62 (m, 1H), 3.58-3.48 (m, 4H), 3.48-3.37 (m, 3H), 3.15-3.10 (m, 1H), 2.62-2.47 (m, 3H), 2.34-2.21 (m, 6H), 1.81-1.70 (m, 1H). $^{19}$F NMR (376 MHz, Chloroform-d) δ −64.95 (3F).

Example 127: (S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide
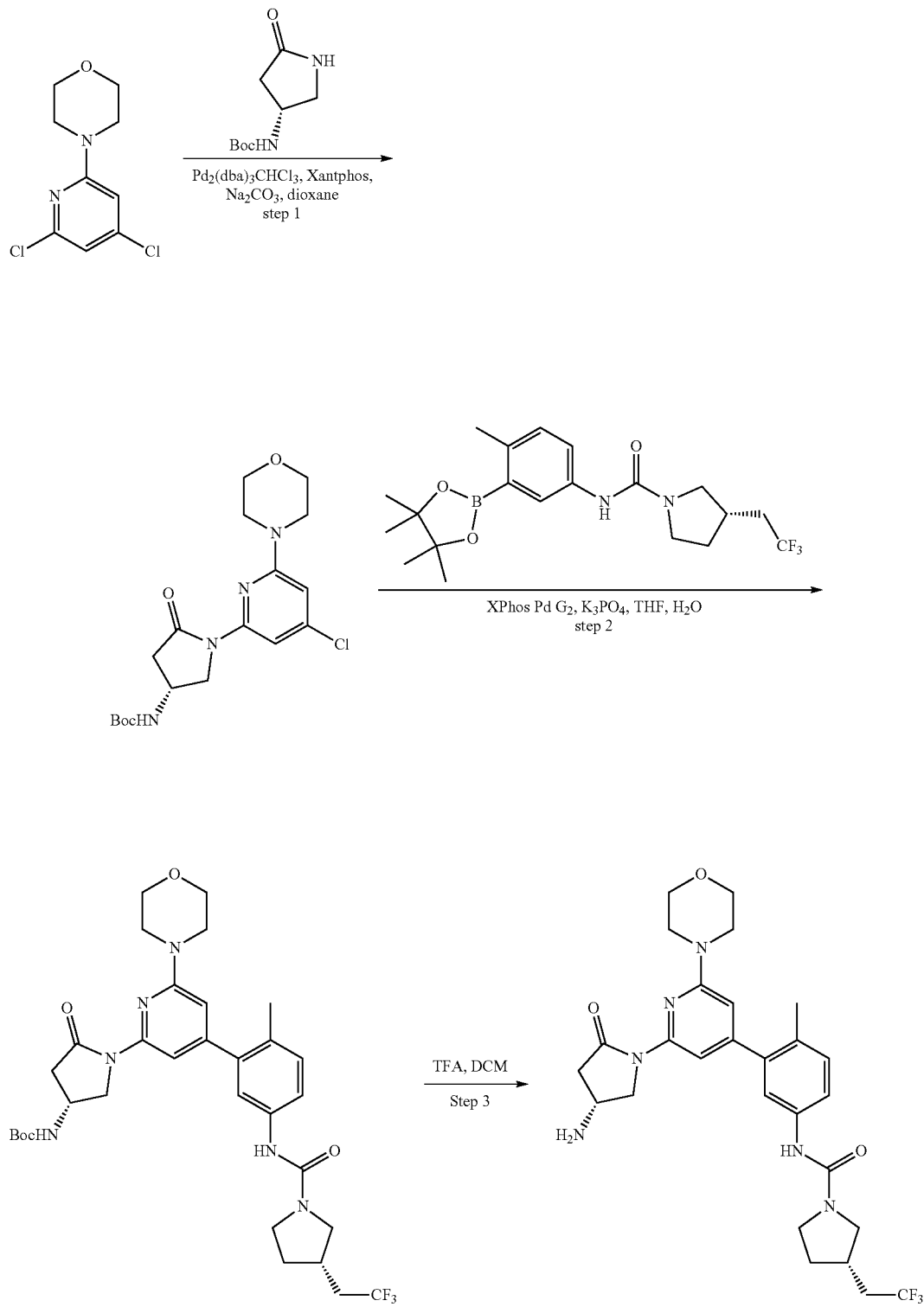

Preparation 127A: tert-butyl (R)-(1-(4-chloro-6-morpholinopyridin-2-yl)-5-oxopyrrolidin-3-yl)carbamate

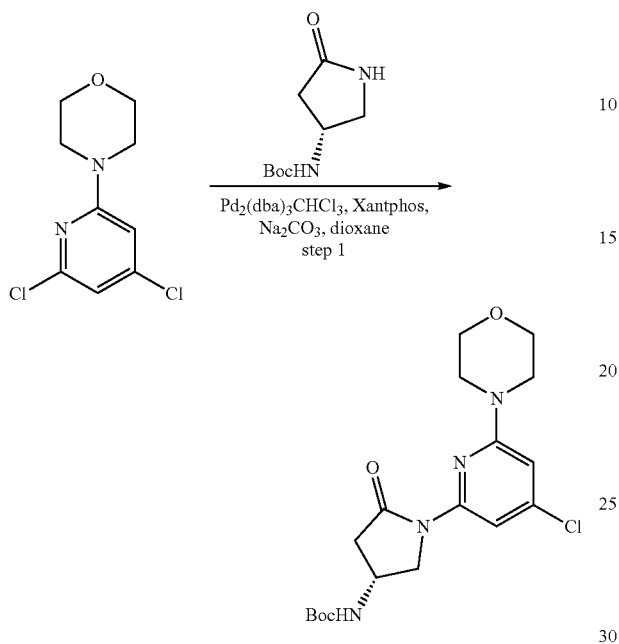

A mixture of 4-(4,6-dichloropyridin-2-yl)morpholine (500 mg, 2.160 mmol) and tert-butyl (R)-(5-oxopyrrolidin-3-yl)carbamate (648 mg, 3.240 mmol), dioxane (5 mL), $Pd_2(dba)_3 \cdot CHCl_3$ (228 mg, 0.220 mmol), Xantphos (254 mg, 0.440 mmol) and $Na_2CO_3$ (687 mg, 6.480 mmol) was stirred for 2 h at 100° C. under nitrogen atmosphere. The resulting mixture was concentrated under reduced pressure. The residue was purified by silica gel column chromatography, eluted with EtOAc/PE (1/4) to afford tert-butyl (R)-(1-(4-chloro-6-morpholinopyridin-2-yl)-5-oxopyrrolidin-3-yl)carbamate (567.8 mg, 67%) as a yellow solid. MS ESI calculated for $C18H_{25}ClN_4O_4$ $[M+H]^+$, 397.16, found 397.10. $^1H$ NMR (400 MHz, Chloroform-$d_6$) δ7.76 (s, 1H), 6.35 (s, 1H), 4.92 (s, 1H), 4.37 (s, 1H), 4.26 (dd, J=12.0, 6.4 Hz, 1H), 3.94 (dd, J=12.0, 3.2 Hz, 1H), 3.82-3.76 (m, 4H), 3.48-3.41 (m, 4H), 3.03-2.97 (m, 1H), 2.56-2.51 (m, 1H), 1.45 (s, 9H).

Preparation 127B: tert-butyl ((R)-1-(4-(2-methyl-5-((S)-3-(2,2,2-trifluoroethyl)pyrrolidine-1-carboxamido)phenyl)-6-morpholinopyridin-2-yl)-5-oxopyrrolidin-3-yl)carbamate

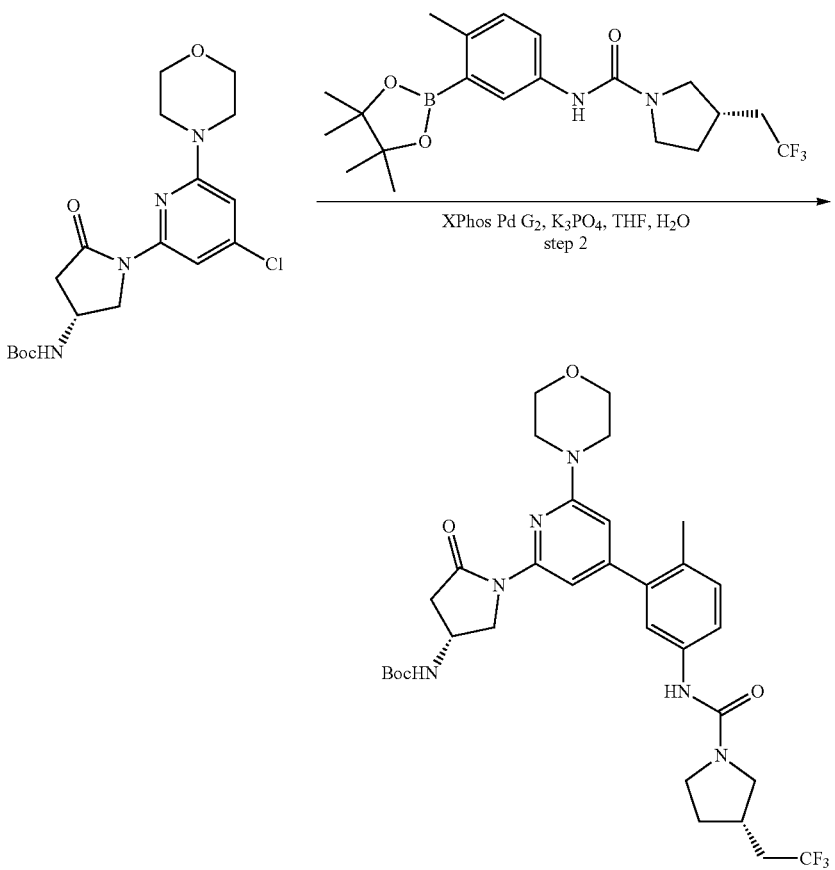

A mixture of tert-butyl (R)-(1-(4-chloro-6-morpholino-pyridin-2-yl)-5-oxopyrrolidin-3-yl)carbamate (200 mg, 0.505 mmol) and (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (250 mg, 0.606 mmol), 2$^{nd}$ XPhos Precatalyst (40 mg, 0.051 mmol) and $K_3PO_4$ (212 mg, 1.010 mmol) in THF (5 mL) and $H_2O$ (0.5 mL) was stirred for 3 h at 80° C. under nitrogen atmosphere. The resulting mixture was concentrated under reduced pressure. The residue was purified by silica gel column chromatography, eluted with EtOAc/PE (1/1) to afford tert-butyl ((R)-1-(4-(2-methyl-5-((S)-3-(2,2,2-trifluoroethyl)pyrrolidine-1-carboxamido)phenyl)-6-morpholinopyridin-2-yl)-5-oxopyrrolidin-3-yl)carbamate (293 mg, 90%) as a light yellow solid. MS ESI calculated for $C_{32}H_{41}F_3N_6O_5$+[M+H]$^+$, 647.31, found 647.20.

Example 127: (S)—N-(3-(2-((R)-4-amino-2-oxopyr-rolidin-1-yl)-6-morpholinopyridin-4-yl)-4-methylphenyl)-3-(2,2,2-trifluoroethyl)pyrrolidine-1-carboxamide

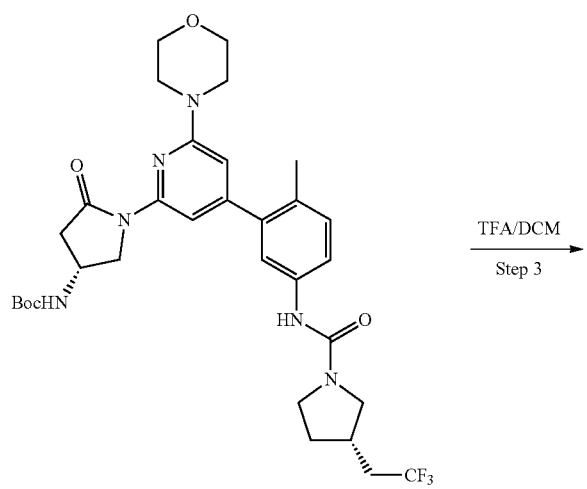

TFA/DCM
Step 3

-continued

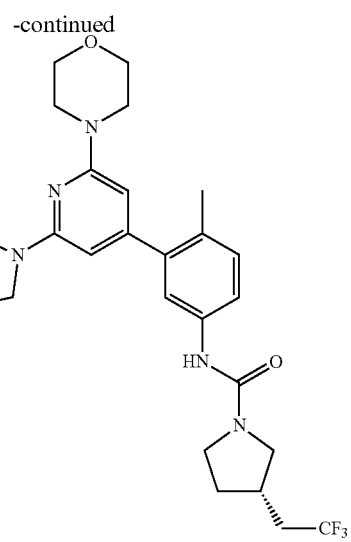

A mixture of tert-butyl ((R)-1-(4-(2-methyl-5-((S)-3-(2,2,2-trifluoroethyl)pyrrolidine-1-carboxamido)phenyl)-6-morpholinopyridin-2-yl)-5-oxopyrrolidin-3-yl)carbamate (200 mg, 0.309 mmol), DCM (5.0 mL) and TFA (0.5 mL) was stirred for 30 min at room temperature. The resulting mixture was concentrated under reduced pressure. The residue was purified by Prep-HPLC with following conditions: Column: Spherical C18, 20~40 μm, 120 g; Mobile Phase A: water (plus 10 mM $NH_4CO_3$); Mobile Phase B: $CH_3CN$; Flow rate: 60 mL/min; Gradient:35% B to 65% B; Detector: 220 nm to afford (S)—N-(3-(2-((R)-4-amino-2-oxopyrroli-din-1-yl)-6-morpholinopyridin-4-yl)-4-methylphenyl)-3-(2,2,2-trifluoroethyl)pyrrolidine-1-carboxamide (90.5 mg, 53%) as a white solid. MS ESI calculated for $C_{27}H_{33}F_3N_6O_3$ [M+H]$^+$, 547.26, found 547.30. $^1$H NMR (400 MHz, Chloroform-d$_6$) δ7.75 (s, 1H), 7.36 (dd, J=8.4, 2.4 Hz, 1H), 7.22 (d, J=2.4 Hz, 1H), 7.16 (d, J=8.4 Hz, 1H), 6.31 (s, 1H), 6.20 (s, 1H), 4.32-4.27 (m, 1H), 3.93-3.87 (m, 1H), 3.82-3.78 (m, 6H), 3.63-3.60 (m, 1H), 3.49-3.37 (m, 5H), 3.12-3.08 (m, 1H), 2.94-2.90 (m, 1H), 2.60-2.43 (m, 2H), 2.29-2.20 (m, 6H), 1.76-1.63 (m, 3H). $^{19}$F NMR (376 MHz, Chloroform-d$_6$) δ −64.94 (3F).

Examples 128 and 129: (3S)—N-(3-{2-[(4R)-3,3-difluoro-4-hydroxypyrrolidin-1-yl]-6-(morpholin-4-yl)pyridin-4-yl}-4-methylphenyl)-3-(2,2,2-trifluoro-ethyl)pyrrolidine-1-carboxamide and (3S)—N-(3-{2-[(4S)-3,3-difluoro-4-hydroxypyrrolidin-1-yl]-6-(morpholin-4-yl)pyridin-4-yl}-4-methylphenyl)-3-(2,2,2-trifluoroethyl)pyrrolidine-1-carboxamide

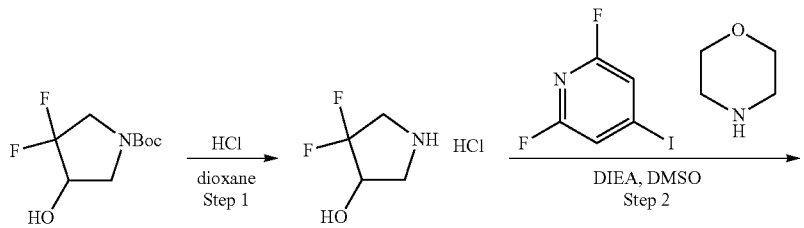

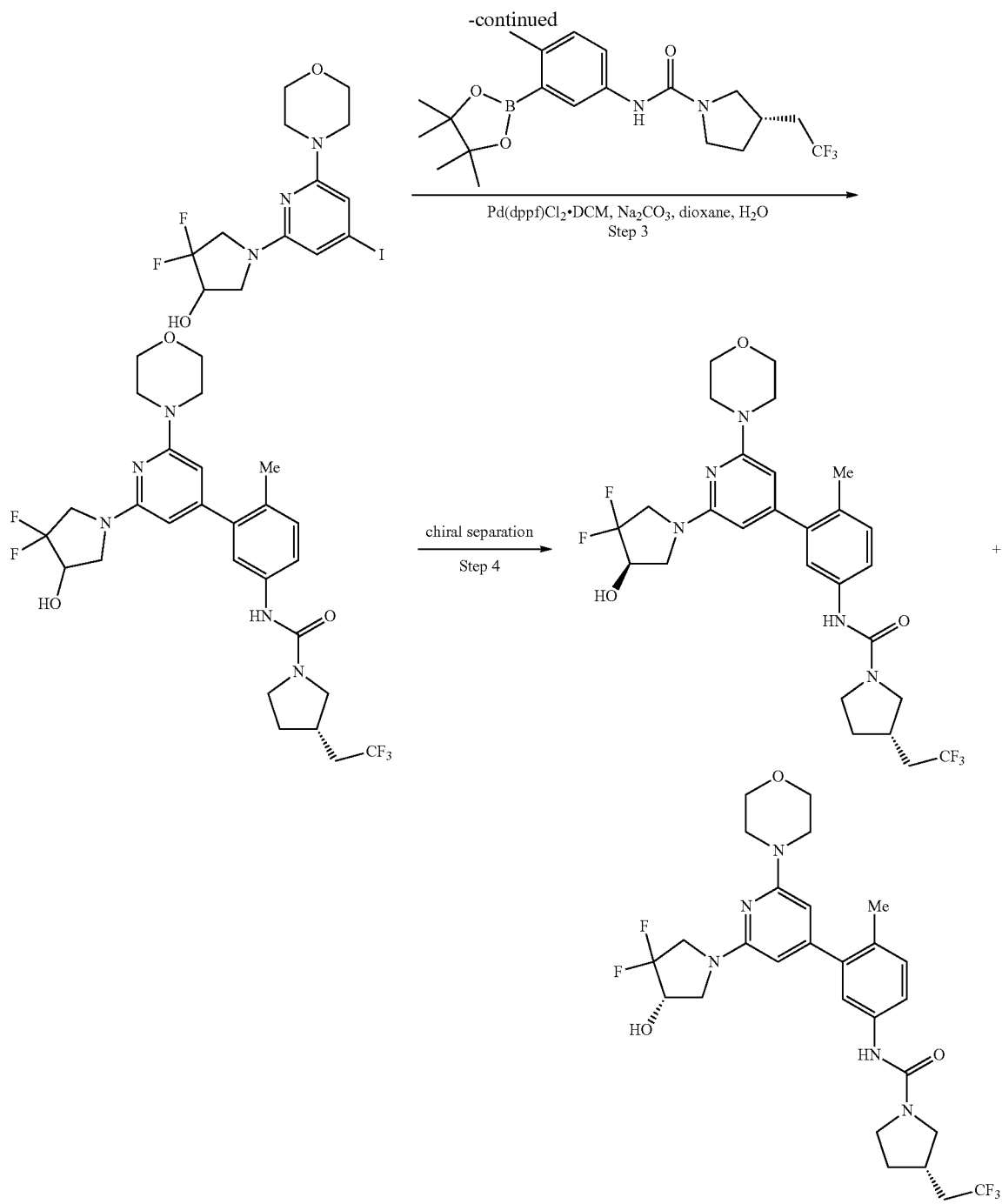

Preparation 128A: 4,4-difluoropyrrolidin-3-ol hydrochloride

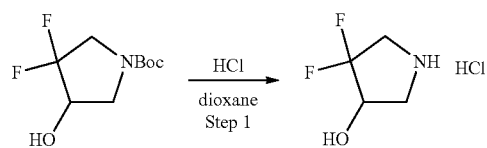 [SMILES: CC(C)(C)OC(=O)N1CC(O)C(F)(F)C1 ; Cl ; OC1CNCC1(F)F ; Cl]

To a stirred solution of tert-butyl 3,3-difluoro-4-hydroxy-pyrrolidine-1-carboxylate (300 mg, 1.344 mmol) in DCM (5 mL) was added HCl in dioxane (1 mL, 1 M) dropwise at 0° C. The resulting mixture was stirred for 2 h at room temperature. The resulting mixture was concentrated under reduced pressure to afford 4,4-difluoropyrrolidin-3-ol hydrochloride (350 mg, crude) as yellow oil. $C_4H_8ClF_2NO$, $^1H$ NMR (400 MHz, DMSO-$d_6$) δ 4.33-4.31 (m, 1H), 3.59-3.52 (m, 2H), 3.51-3.45 (m, 1H), 3.29-3.26 (m, 1H).

Preparation 128B: 4-iodo-N-(4-methyloxan-4-yl)-6-(morpholin-4-yl)pyridin-2-amine

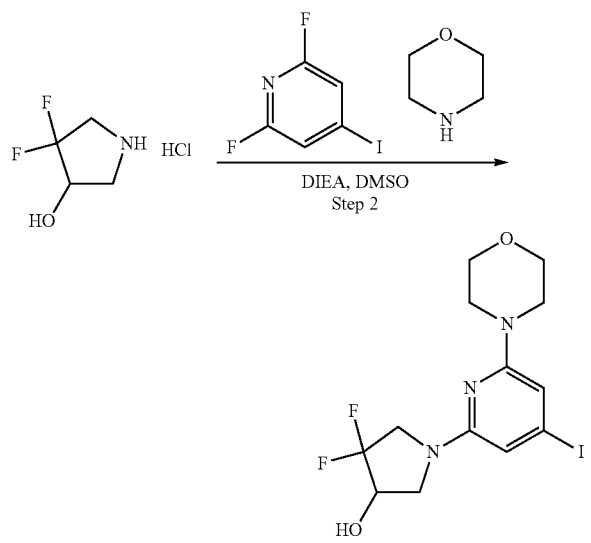

To a stirred solution of 2,6-difluoro-4-iodopyridine (350 mg, 1.452 mmol) and 4,4-difluoropyrrolidin-3-ol hydrochloride (214 mg, 1.742 mmol) in DMSO (5 mL) was added DIEA (412 mg, 3.194 mmol) at room temperature. The resulting mixture was stirred for 4 h at 80° C. To this was added morpholine (632 mg, 7.260 mmol). The resulting mixture was stirred for 16 h at 80° C. The mixture was allowed to cool down to room temperature. The resulting mixture was diluted with $H_2O$ (50 mL) and extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EtOAc (4/1) to afford 4-iodo-N-(4-methyloxan-4-yl)-6-(morpholin-4-yl)pyridin-2-amine (240 mg, 40%) as a yellow solid. MS ESI calculated for $C_{13}H_{16}F_2IN_3O_2$ $[M+H]^+$, 412.03, found 412.05. $^1H$ NMR (400 MHz, Chloroform-d) δ 6.36 (s, 1H), 6.14 (s, 1H), 4.40-4.36 (m, 1H), 3.88-3.74 (m, 7H), 3.55-3.53 (m, 1H), 3.50-3.42 (m, 4H). Preparation 128C: (3S)—N-[3-[2-(3,3-difluoro-4-hydroxypyrrolidin-1-yl)-6-(morpholin-4-yl)pyridin-4-yl]-4-methylphenyl]-3-(2,2,2-trifluoroethyl)pyrrolidine-1-carboxamide

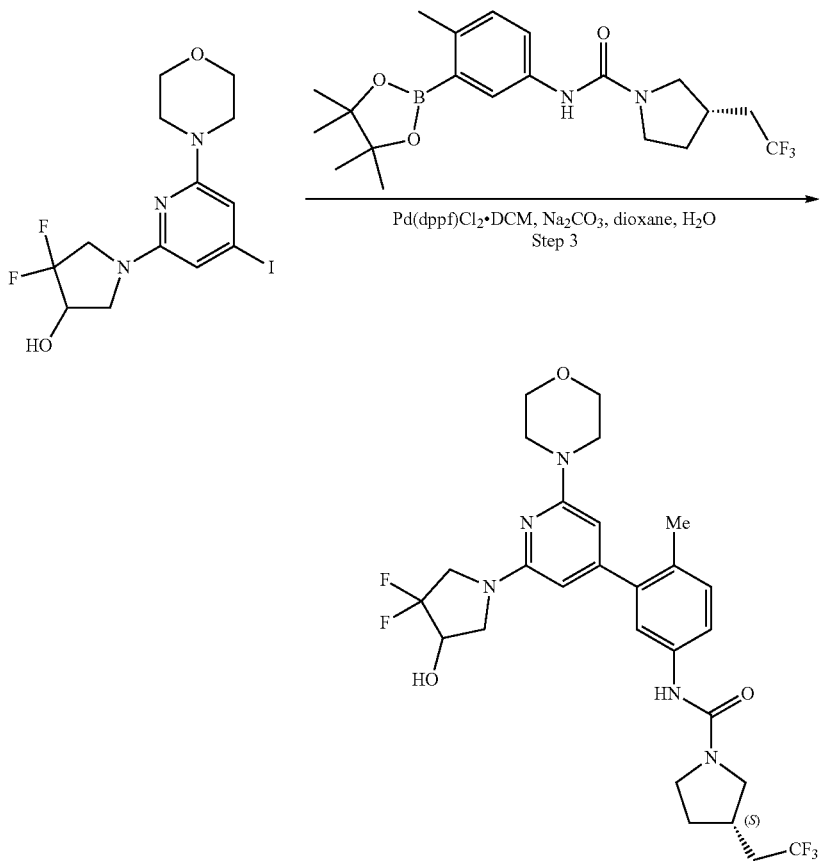

A mixture of 4,4-difluoro-1-[4-iodo-6-(morpholin-4-yl)pyridin-2-yl]pyrrolidin-3-ol (240 mg, 0.584 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (240 mg, 0.582 mmol), 1,4-dioxane (2.4 mL), H$_2$O (0.6 mL), Pd(dppf)Cl$_2$·CH$_2$Cl$_2$ (47 mg, 0.058 mmol) and Na$_2$CO$_3$ (185 mg, 1.752 mmol) was stirred for 2 h at 60° C. under nitrogen atmosphere. The reaction was quenched with water (50 mL). The resulting mixture was extracted with EtOAc (3×50 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EtOAc/EtOH (2/3/1) to afford (3S)—N-[3-[2-(3,3-difluoro-4-hydroxypyrrolidin-1-yl)-6-(morpholin-4-yl)pyridin-4-yl]-4-methylphenyl]-3-(2,2,2-trifluoroethyl)pyrrolidine-1-carboxamide (265 mg, 79%) as a white solid. MS ESI calculated for C$_{27}$H$_{32}$F$_5$N$_5$O$_3$ [M+H]$^+$, 570.24, found 570.30.

Examples 128 and 129: (3S)—N-(3-{2-[(4R)-3,3-difluoro-4-hydroxypyrrolidin-1-yl]-6-(morpholin-4-yl)pyridin-4-yl}-4-methylphenyl)-3-(2,2,2-trifluoroethyl)pyrrolidine-1-carboxamide and (3S)—N-(3-{2-[(4S)-3,3-difluoro-4-hydroxypyrrolidin-1-yl]-6-(morpholin-4-yl)pyridin-4-yl}-4-methylphenyl)-3-(2,2,2-trifluoroethyl)pyrrolidine-1-carboxamide

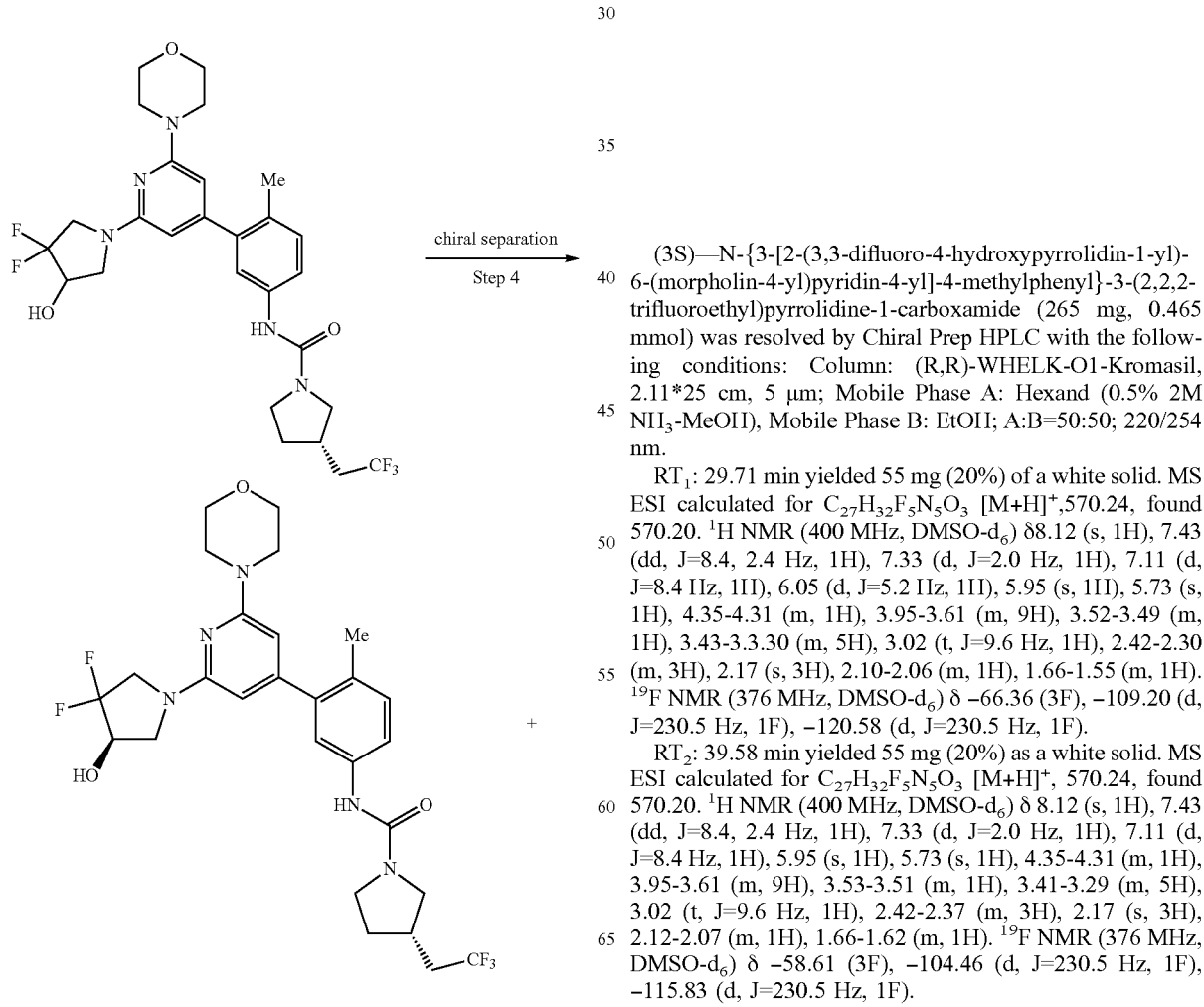

(3S)—N-{3-[2-(3,3-difluoro-4-hydroxypyrrolidin-1-yl)-6-(morpholin-4-yl)pyridin-4-yl]-4-methylphenyl}-3-(2,2,2-trifluoroethyl)pyrrolidine-1-carboxamide (265 mg, 0.465 mmol) was resolved by Chiral Prep HPLC with the following conditions: Column: (R,R)-WHELK-O1-Kromasil, 2.11*25 cm, 5 μm; Mobile Phase A: Hexand (0.5% 2M NH$_3$-MeOH), Mobile Phase B: EtOH; A:B=50:50; 220/254 nm.

RT$_1$: 29.71 min yielded 55 mg (20%) of a white solid. MS ESI calculated for C$_{27}$H$_{32}$F$_5$N$_5$O$_3$ [M+H]$^+$, 570.24, found 570.20. $^1$H NMR (400 MHz, DMSO-d$_6$) δ 8.12 (s, 1H), 7.43 (dd, J=8.4, 2.4 Hz, 1H), 7.33 (d, J=2.0 Hz, 1H), 7.11 (d, J=8.4 Hz, 1H), 6.05 (d, J=5.2 Hz, 1H), 5.95 (s, 1H), 5.73 (s, 1H), 4.35-4.31 (m, 1H), 3.95-3.61 (m, 9H), 3.52-3.49 (m, 1H), 3.43-3.3.30 (m, 5H), 3.02 (t, J=9.6 Hz, 1H), 2.42-2.30 (m, 3H), 2.17 (s, 3H), 2.10-2.06 (m, 1H), 1.66-1.55 (m, 1H). $^{19}$F NMR (376 MHz, DMSO-d$_6$) δ −66.36 (3F), −109.20 (d, J=230.5 Hz, 1F), −120.58 (d, J=230.5 Hz, 1F).

RT$_2$: 39.58 min yielded 55 mg (20%) as a white solid. MS ESI calculated for C$_{27}$H$_{32}$F$_5$N$_5$O$_3$ [M+H]$^+$, 570.24, found 570.20. $^1$H NMR (400 MHz, DMSO-d$_6$) δ 8.12 (s, 1H), 7.43 (dd, J=8.4, 2.4 Hz, 1H), 7.33 (d, J=2.0 Hz, 1H), 7.11 (d, J=8.4 Hz, 1H), 5.95 (s, 1H), 5.73 (s, 1H), 4.35-4.31 (m, 1H), 3.95-3.61 (m, 9H), 3.53-3.51 (m, 1H), 3.41-3.29 (m, 5H), 3.02 (t, J=9.6 Hz, 1H), 2.42-2.37 (m, 3H), 2.17 (s, 3H), 2.12-2.07 (m, 1H), 1.66-1.62 (m, 1H). $^{19}$F NMR (376 MHz, DMSO-d$_6$) δ −58.61 (3F), −104.46 (d, J=230.5 Hz, 1F), −115.83 (d, J=230.5 Hz, 1F).

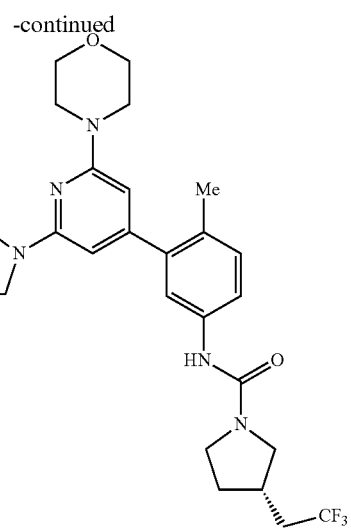

Examples 130 and 131: (3S)—N-(3-{2-[(1R)-1-amino-3-azabicyclo[3.1.0]hexan-3-yl]-6-(morpholin-4-yl)pyridin-4-yl}-4-methylphenyl)-3-(2,2,2-trifluoroethyl)pyrrolidine-1-carboxamide and (3S)—N-(3-{2-[(1S)-1-amino-3-azabicyclo[3.1.0]hexan-3-yl]-6-(morpholin-4-yl)pyridin-4-yl}-4-methylphenyl)-3-(2,2,2-trifluoroethyl)pyrrolidine-1-carboxamide
-continued
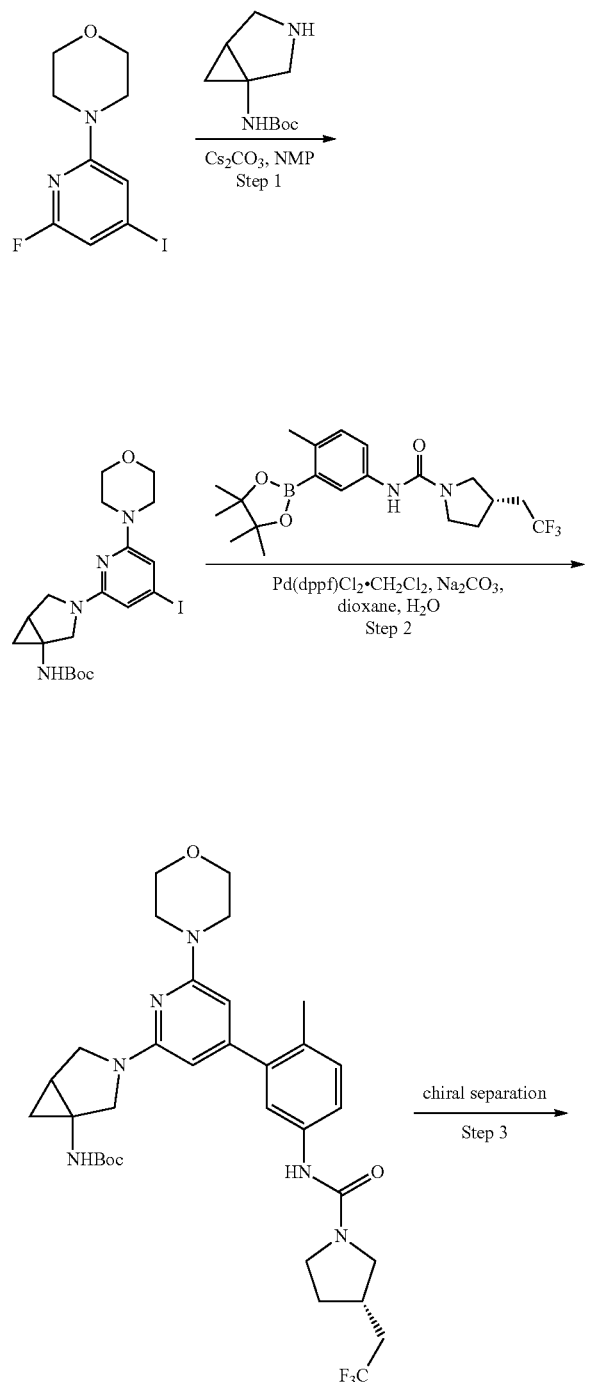
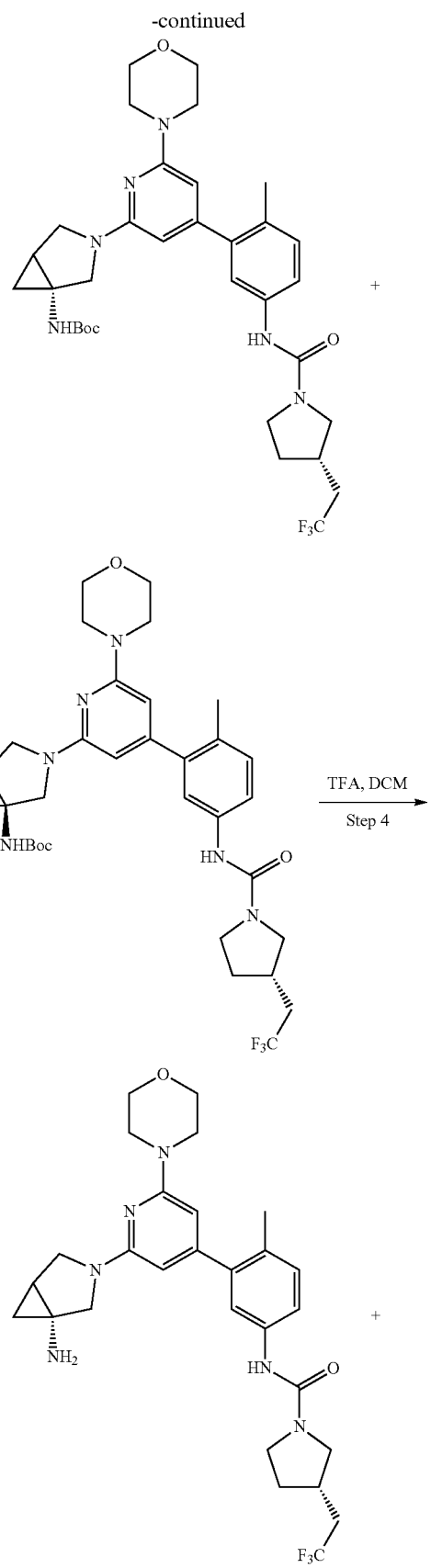

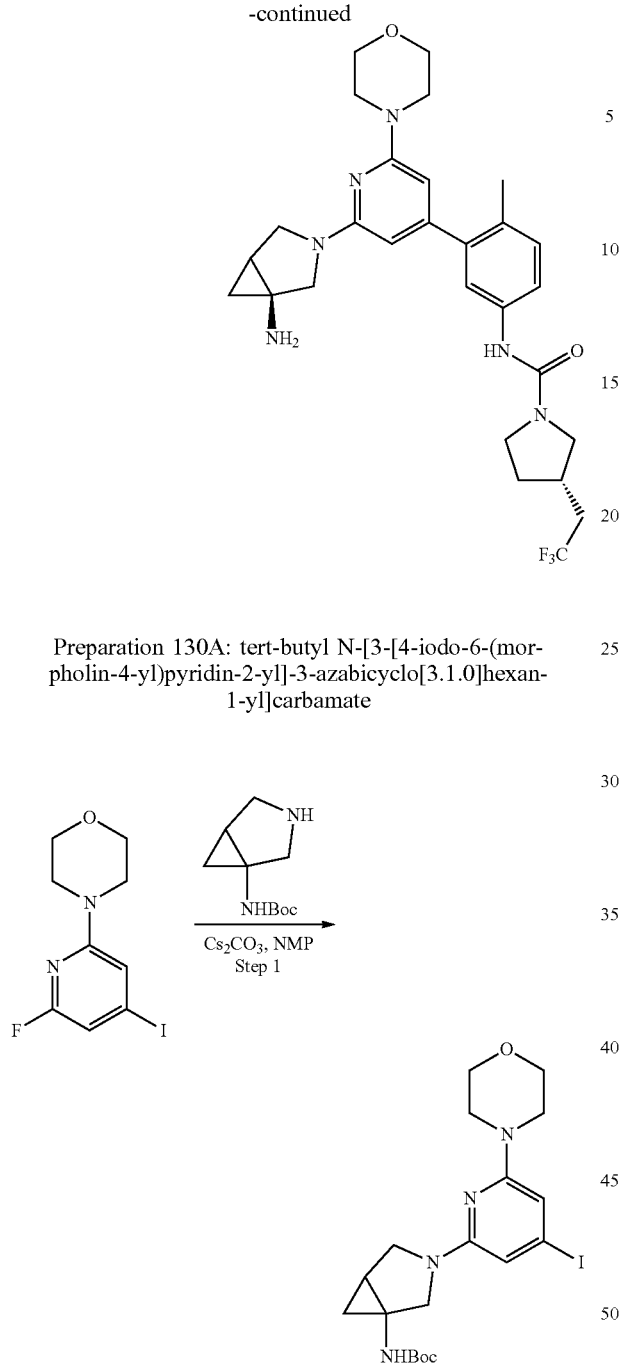

Preparation 130A: tert-butyl N-[3-[4-iodo-6-(morpholin-4-yl)pyridin-2-yl]-3-azabicyclo[3.1.0]hexan-1-yl]carbamate To a stirred mixture of 4-(6-fluoro-4-iodopyridin-2-yl)morpholine (400 mg, 1.298 mmol) and tert-butyl N-[3-azabicyclo[3.1.0]hexan-1-yl]carbamate (309 mg, 1.558 mmol) in NMP (4 mL) was added Cs$_2$CO$_3$ (1.27 g, 3.895 mmol). The reaction mixture was stirred for 2 h at 130° C. under nitrogen atmosphere. The reaction was quenched with water (20 mL). The resulting mixture was extracted with EtOAc (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc (5/1) to afford tert-butyl N-[3-[4-iodo-6-(morpholin-4-yl)pyridin-2-yl]-3-azabicyclo[3.1.0]hexan-1-yl]carbamate (100 mg, 16%) as a light yellow solid. MS ESI calculated for C$_{19}$H$_{27}$IN$_4$O$_3$ [M+H]$^+$487.11; found 487.05. $^1$H NMR (400 MHz, Chloroform-d) δ 6.30 (s, 1H), 6.15 (s, 1H), 5.05 (brs, 1H), 3.93-3.91 (m, 1H), 3.85-3.78 (m, 4H), 3.62-3.60 (m, 2H), 3.45-3.41 (m, 5H), 1.81-1.79 (m, 1H), 1.47 (s, 9H), 1.10-1.08 (m, 1H), 0.76-0.74 (m, 1H).

Preparation 130B: tert-butyl N-[3-(4-[2-methyl-5-[(3S)-3-(2,2,2-trifluoroethyl)pyrrolidine-1-carbonylamino]phenyl]-6-(morpholin-4-yl)pyridin-2-yl)-3-azabicyclo[3.1.0]hexan-1-yl]carbamate

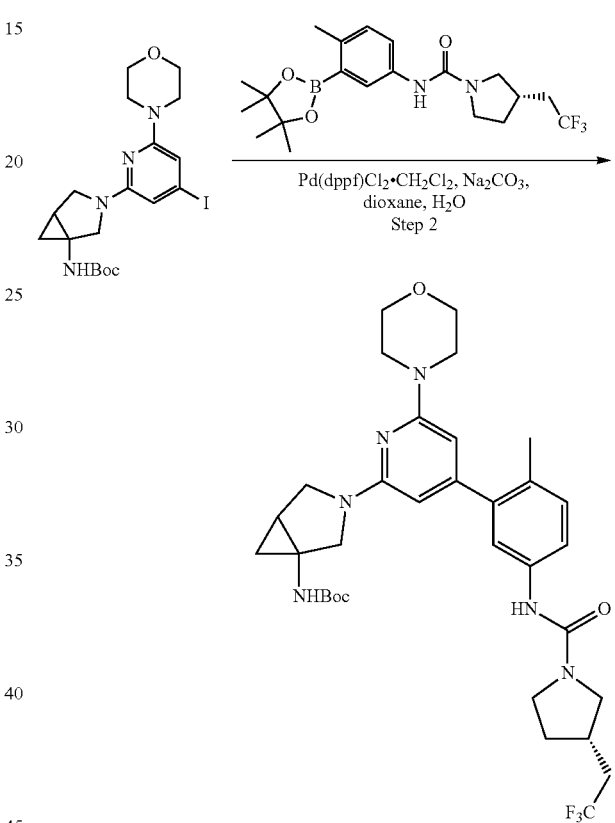

To a stirred mixture of tert-butyl (3-(4-iodo-6-morpholinopyridin-2-yl)-3-azabicyclo[3.1.0]hexan-1-yl)carbamate (150 mg, 0.316 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (130 mg, 0.316 mmol) in 1,4-dioxane (2 mL) and H$_2$O (0.5 mL) were added Na$_2$CO$_3$ (100 mg, 0.949 mmol) and Pd(dppf)Cl$_2$·CH$_2$Cl$_2$ (26 mg, 0.032 mmol) was stirred for 16 h in portions at 60° C. under nitrogen atmosphere. The reaction was quenched with water (10 mL) at room temperature. The resulting mixture was extracted with EtOAc (3×20 mL). The combined organic layers were washed with brine (10 mL), dried over anhydrous Na$_2$SO$_4$. After filtration, the filtrate was concentrated under reduced pressure. The residue was purified by Prep-TLC with PE/EtOAc (1/1) to afford tert-butyl N-[3-(4-[2-methyl-5-[(3S)-3-(2,2,2-trifluoroethyl)pyrrolidine-1-carbonylamino]phenyl]-6-(morpholin-4-yl)pyridin-2-yl)-3-azabicyclo[3.1.0]hexan-1-yl]carbamate (144 mg, 71%) as an off-white solid. MS ESI calculated for C$_{33}$H$_{43}$F$_3$N$_6$O$_4$ [M+H]$^+$645.33; found 645.25.

Preparations 130C/131C: tert-butyl N-[(1R)-3-(4-{2-methyl-5-[(3S)-3-(2,2,2-trifluoroethyl)pyrrolidine-1-carbonylamino]phenyl}-6-(morpholin-4-yl)pyridin-2-yl)-3-azabicyclo[3.1.0]hexan-1-yl]carbamate and tert-butyl N-[(1S)-3-(4-{2-methyl-5-[(3S)-3-(2,2,2-trifluoroethyl)pyrrolidine-1-carbonylamino]phenyl}-6-(morpholin-4-yl)pyridin-2-yl)-3-azabicyclo[3.1.0]hexan-1-yl]carbamate

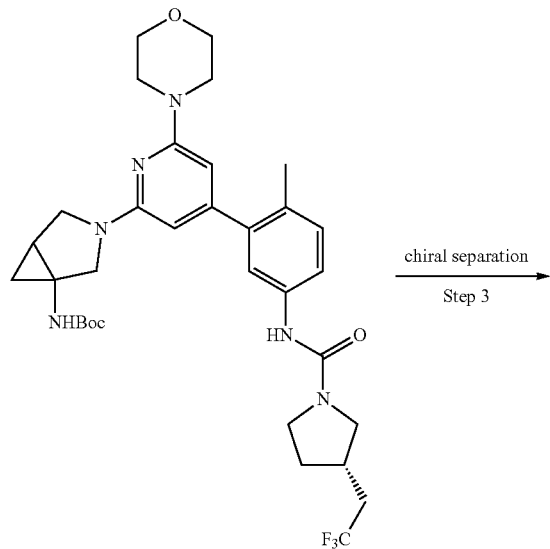

chiral separation
Step 3

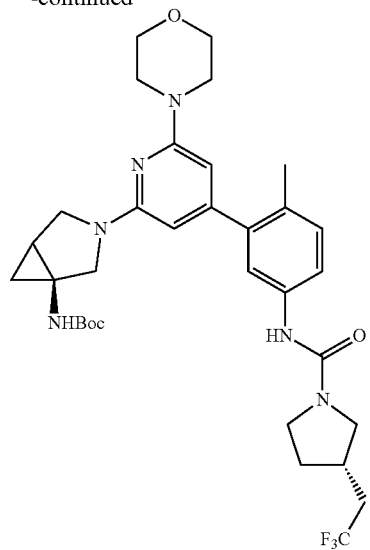

tert-butyl N-[3-(4-{2-methyl-5-[(3S)-3-(2,2,2-trifluoroethyl)pyrrolidine-1-carbonylamino]phenyl}-6-(morpholin-4-yl)pyridin-2-yl)-3-azabicyclo[3.1.0]hexan-1-yl]carbamate (144 mg, 0.223 mmol) was resolved by chiral Prep-HPLC with the following conditions: Column: (R,R)-WHELK-O1-Kromasil, 2.11×25 cm, 5 μm; Mobile Phase A: MTBE (0.5% 2M NH₃-MeOH), Mobile Phase B: EtOH; Flow rate: 20 mL/min; Gradient:10% B; 220/254 nm. $RT_1$: 20.89 min yielded 67 mg (46%) of Preparation 130C. $RT_2$: 24.627 min yielded 76 mg (53%) of Preparation 131C as an off-white solid.

Examples 130/131: (3S)—N-(3-{2-[(1R)-1-amino-3-azabicyclo[3.1.0]hexan-3-yl]-6-(morpholin-4-yl)pyridin-4-yl}-4-methylphenyl)-3-(2,2,2-trifluoroethyl)pyrrolidine-1-carboxamide and (3S)—N-(3-{2-[(1S)-1-amino-3-azabicyclo[3.1.0]hexan-3-yl]-6-(morpholin-4-yl)pyridin-4-yl}-4-methylphenyl)-3-(2,2,2-trifluoroethyl)pyrrolidine-1-carboxamide

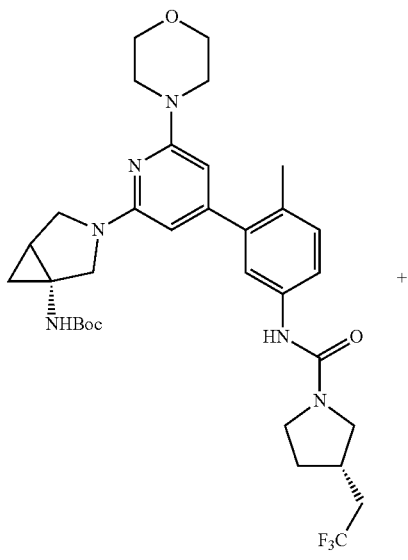 + 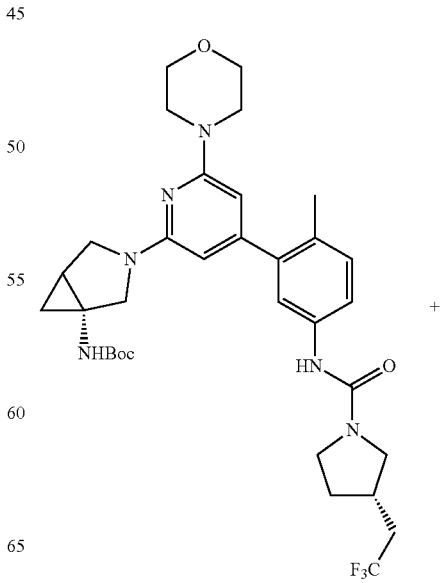 +

-continued

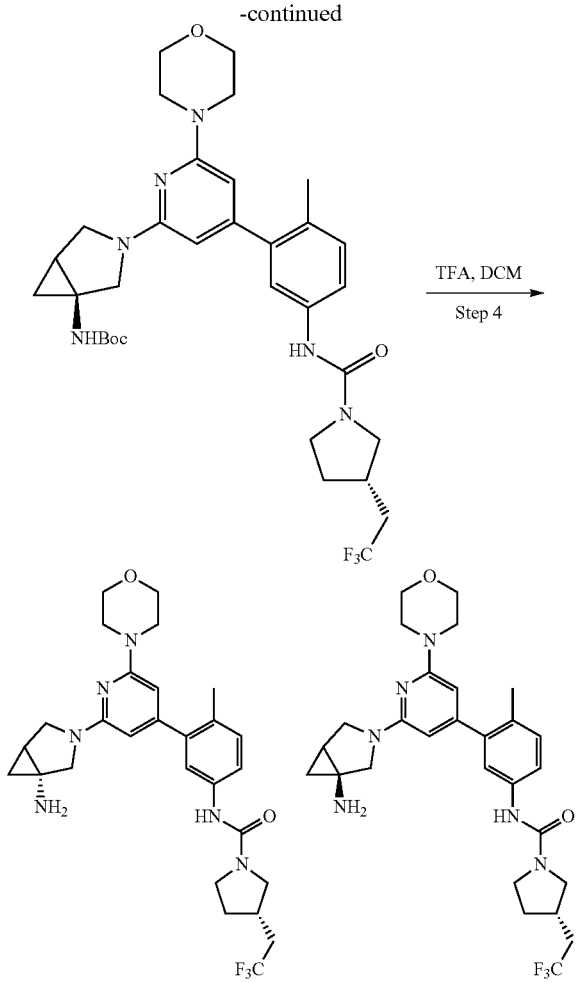

A mixture of Preparation 130C (60 mg, 0.093 mmol) in DCM (1.5 mL) and TFA (0.3 mL) was stirred for 1 h at room temperature. The resulting mixture was concentrated under reduced pressure. The residue was purified by reverse flash chromatography with the following conditions: column, C18 column; mobile phase, CH$_3$CN in water, 10% to 50%; detector, UV 254 nm to afford Example 130 (34.2 mg, 67%) as an off-white solid. MS ESI calculated for C$_{28}$H$_{35}$F$_3$N$_6$O$_2$ [M+H]$^+$545.28; found 545.20. $^1$H NMR (300 MHz, Chloroform-d) δ 7.40-7.38 (m, 1H), 7.28-7.17 (m, 2H), 6.11 (s, 1H), 5.85 (s, 1H), 5.68 (s, 1H), 3.95 (d, J=9.6 Hz, 1H), 3.85-3.82 (m, 5H), 3.79-3.70 (m, 2H), 3.69-3.43 (m, 6H), 3.34 (d, J=9.6 Hz, 1H), 3.12 (t, J=9.6 Hz, 1H), 2.65-2.50 (m, 1H), 2.30-2.23 (m, 6H), 1.57-1.53 (m, 2H), 1.06-1.01 (m, 1H), 0.69-0.66 (m, 1H). $^{19}$F NMR (282 MHz, Chloroform-d) δ −64.95 (3F).

A mixture of Preparation 131C in DCM (1.5 mL) and TFA (0.3 mL) was stirred for 1 h at room temperature under air atmosphere. The resulting mixture was concentrated under reduced pressure. The residue was purified by reverse flash chromatography with the following conditions: column, silica gel; mobile phase, MeCN in water, 10% to 50% gradient in 10 min; detector, UV 254 nm to afford Example 131 (40.3 mg, 68%) as an off-white solid. MS ESI calculated for C$_{28}$H$_{35}$F$_3$N$_6$O$_2$ [M+H]$^+$545.28; found 545.25. $^1$H NMR (400 MHz, Chloroform-d) δ 7.40-7.38 (m, 1H), 7.28-7.17 (m, 2H), 6.11 (s, 1H), 5.83 (s, 1H), 5.66 (s, 1H), 3.93 (d, J=9.6 Hz, 1H), 3.84-3.78 (m, 5H), 3.68-3.52 (m, 2H), 3.50-3.40 (m, 6H), 3.33 (d, J=10.0 Hz, 1H), 3.12 (t, J=9.6 Hz, 1H), 2.58-2.50 (m, 1H), 2.28-2.18 (m, 6H), 1.57-1.53 (m, 1H), 1.06-1.01 (m, 1H), 0.69-0.66 (m, 1H). $^{19}$F NMR (376 MHz, Chloroform-d) δ −64.95 (3F).

Example 132: (S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide formate

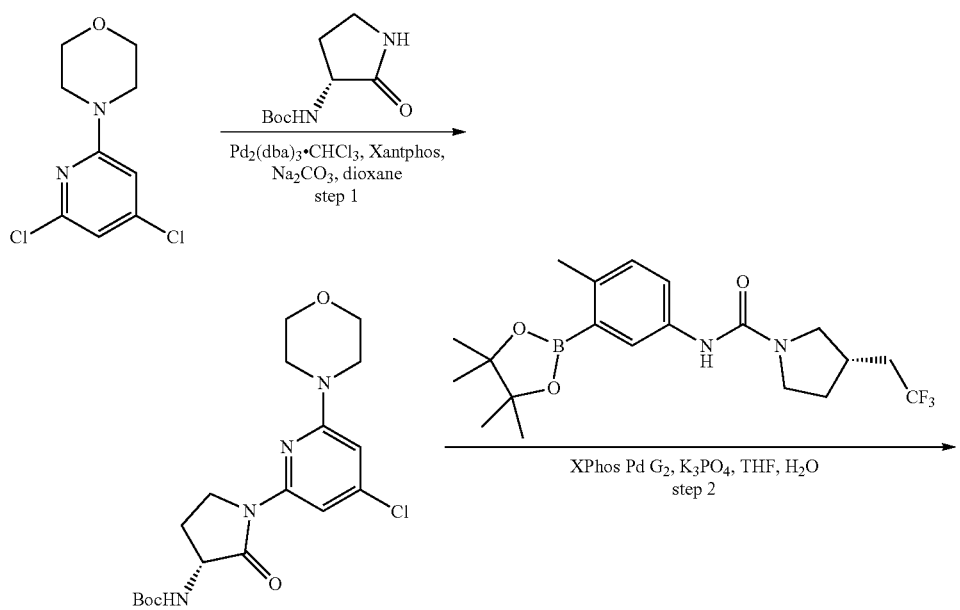

-continued

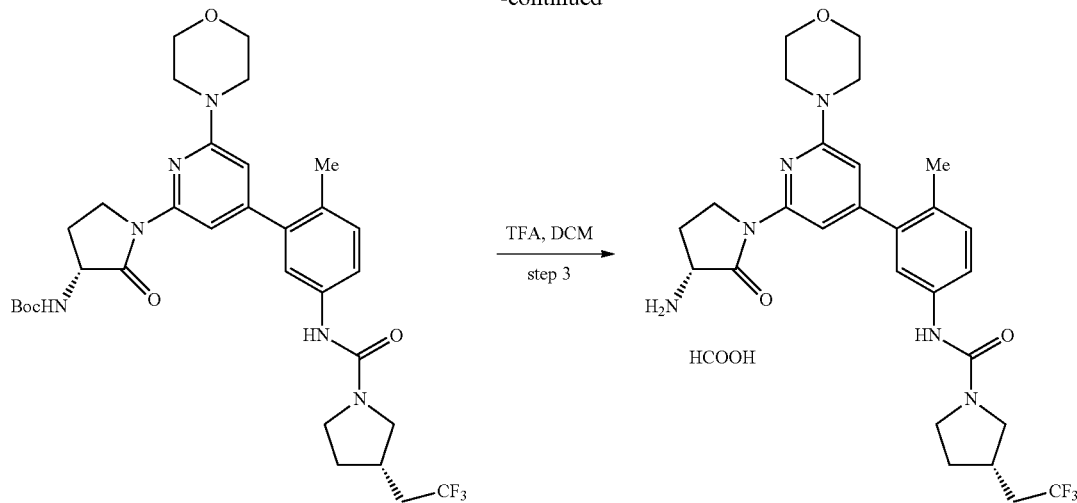

TFA, DCM
step 3

HCOOH

Preparation 132A: tert-butyl (R)-(1-(4-chloro-6-morpholinopyridin-2-yl)-2-oxopyrrolidin-3-yl)carbamate

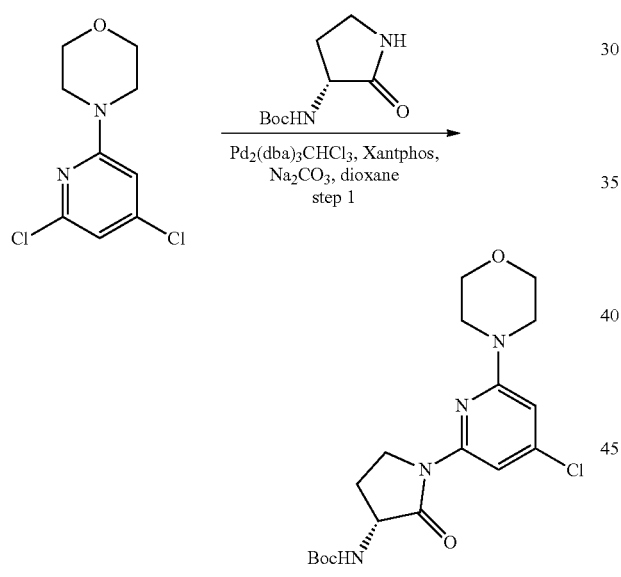

Pd₂(dba)₃CHCl₃, Xantphos, Na₂CO₃, dioxane
step 1

A mixture of 4-(4,6-dichloropyridin-2-yl)morpholine (500 mg, 2.160 mmol) and tert-butyl (R)-(2-oxopyrrolidin-3-yl)carbamate (648 mg, 3.240 mmol), Pd₂(dba)₃·CHCl₃ (228 mg, 0.220 mmol), Xantphos (254 mg, 0.440 mmol) and Na₂CO₃ (687 mg, 6.480 mmol) in dioxane (5 mL) was stirred for 2 h at 100° C. under nitrogen atmosphere. The resulting mixture was concentrated under reduced pressure. The residue was purified by silica gel column chromatography, eluted with EtOAc/PE (1/4) to afford tert-butyl (R)-(1-(4-chloro-6-morpholinopyridin-2-yl)-2-oxopyrrolidin-3-yl)carbamate (680 mg, 80%) as a yellow solid. MS ESI calculated for C18H25ClN4O4 [M+H]⁺, 397.16, found 397.05. ¹H NMR (400 MHz, Chloroform-d) δ 7.79 (s, 1H), 6.37 (s, 1H), 5.19 (s, 1H), 4.39-4.37 (m, 1H), 4.20-4.17 (m, 1H), 3.82-3.78 (m, 4H), 3.76-3.69 (m, 1H), 3.47-3.45 (m, 4H), 2.73-2.70 (m, 1H), 1.94-1.90 (m, 1H), 1.47 (s, 9H).

Preparation 132B: tert-butyl ((R)-1-(4-(2-methyl-5-((S)-3-(2,2,2-trifluoroethyl)pyrrolidine-1-carboxamido)phenyl)-6-morpholinopyridin-2-yl)-2-oxopyrrolidin-3-yl)carbamate

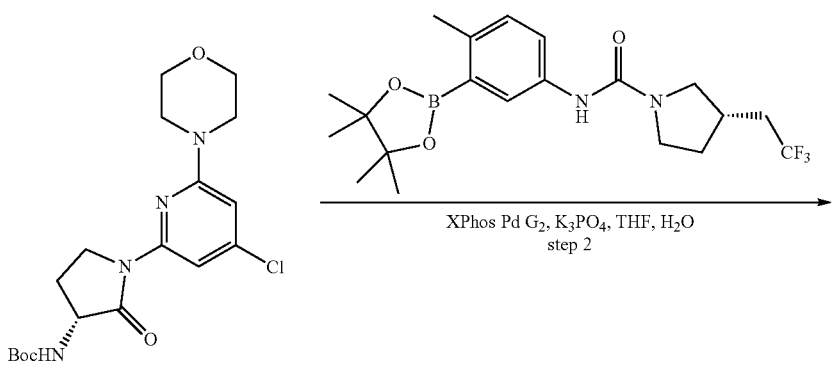

XPhos Pd G₂, K₃PO₄, THF, H₂O
step 2

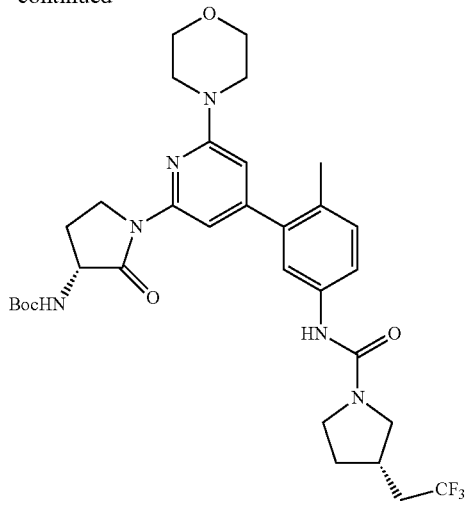

A mixture of tert-butyl (R)-(1-(4-chloro-6-morpholinopyridin-2-yl)-2-oxopyrrolidin-3-yl)carbamate (200 mg, 0.505 mmol), (S)—N-(4-methyl-3-(4,4,5,5-tetramethyl-1,3,2-dioxaborolan-2-yl)phenyl)-3-(2,2,2-trifluoroethyl)pyrrolidine-1-carboxamide (250 mg, 0.606 mmol), $2^{nd}$ XPhos Precatalyst (40 mg, 0.051 mmol) and $K_3PO_4$ (212 mg, 1.010 mmol) in THF (5.0 mL) and $H_2O$ (0.5 mL) was stirred for 3 h at 80° C. under nitrogen atmosphere. The resulting mixture was concentrated under reduced pressure. The residue was purified by silica gel column chromatography, eluted with EtOAc/PE (1/1) to afford tert-butyl ((R)-1-(4-(2-methyl-5-((S)-3-(2,2,2-trifluoroethyl)pyrrolidine-1-carboxamido)phenyl)-6-morpholinopyridin-2-yl)-2-oxopyrrolidin-3-yl)carbamate (309 mg, 96%) as a light yellow solid. MS ESI calculated for $C_{32}H_{41}F_3N_6O_5$ [M+H]$^+$, 647.31, found 647.20.

Example 132: (S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide formate

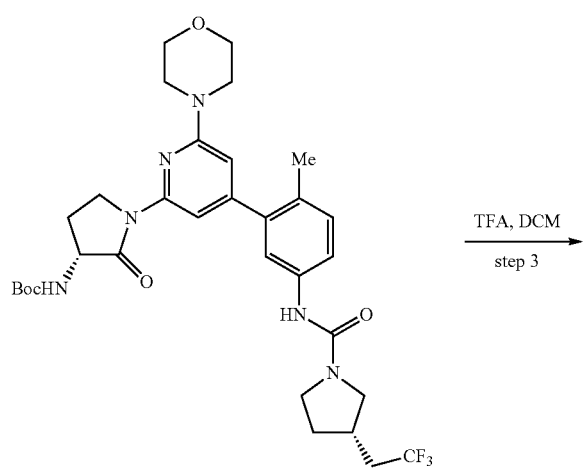

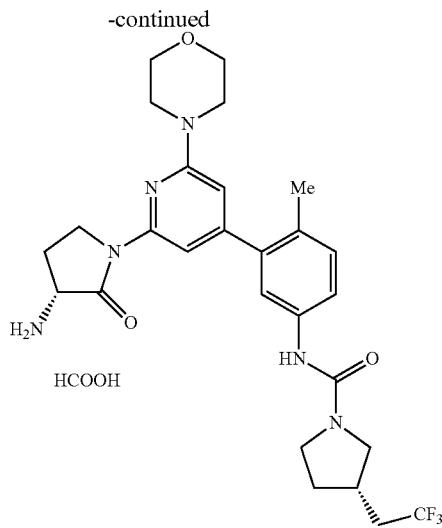

A mixture of tert-butyl ((R)-1-(4-(2-methyl-5-((S)-3-(2,2,2-trifluoroethyl)pyrrolidine-1-carboxamido)phenyl)-6-morpholinopyridin-2-yl)-2-oxopyrrolidin-3-yl)carbamate (200 mg, 0.309 mmol), DCM (5 mL) and TFA (0.5 mL) was stirred for 30 min at room temperature. The resulting mixture was concentrated under reduced pressure. The residue was purified by Prep-HPLC with following conditions: Column: Spherical C18, 20~40 μm, 120 g; Mobile Phase A: water (plus 10 mM FA); Mobile Phase B: $CH_3CN$; Flow rate: 60 mL/min; Gradient:35% B to 65% B; Detector: 220 nm to afford (S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide formate (100.2 mg, 59%) as a white solid. MS ESI calculated for $C_{28}H_{35}F_3N_6O_5$ [M−HCOO]$^+$, 547.26, found 547.30. $^1$H NMR (400 MHz, Chloroform-d) δ 8.18 (s, 1H), 7.68 (s, 1H), 7.36 (dd, J=8.4, 2.4 Hz, 1H), 7.22 (d, J=2.4 Hz, 1H), 7.14 (d, J=8.4 Hz, 1H), 6.47 (s, 1H), 6.34 (s, 1H), 4.26-4.15 (m, 1H), 3.95-3.68 (m, 7H), 3.65-3.56 (m, 1H), 3.49-3.46 (m, 4H), 3.42-3.20 (m, 3H), 3.09-3.06 (m, 1H), 2.55-2.50 (m, 2H), 2.32-2.10 (m, 6H), 1.97-1.86 (m, 1H), 1.73-1.61 (m, 1H). $^{19}$F NMR (376 MHz, Chloroform-$d_6$) δ −64.92 (3F).

Examples 133 and 134: (3S)—N-(3-{2-[(4R)-4-amino-3,3-difluoropyrrolidin-1-yl]-6-(morpholin-4-yl)pyridin-4-yl}-4-methylphenyl)-3-(2,2,2-trifluoroethyl)pyrrolidine-1-carboxamide and (3S)—N-(3-{2-[(4S)-4-amino-3,3-difluoropyrrolidin-1-yl]-6-(morpholin-4-yl)pyridin-4-yl}-4-methylphenyl)-3-(2,2,2-trifluoroethyl)pyrrolidine-1-carboxamide
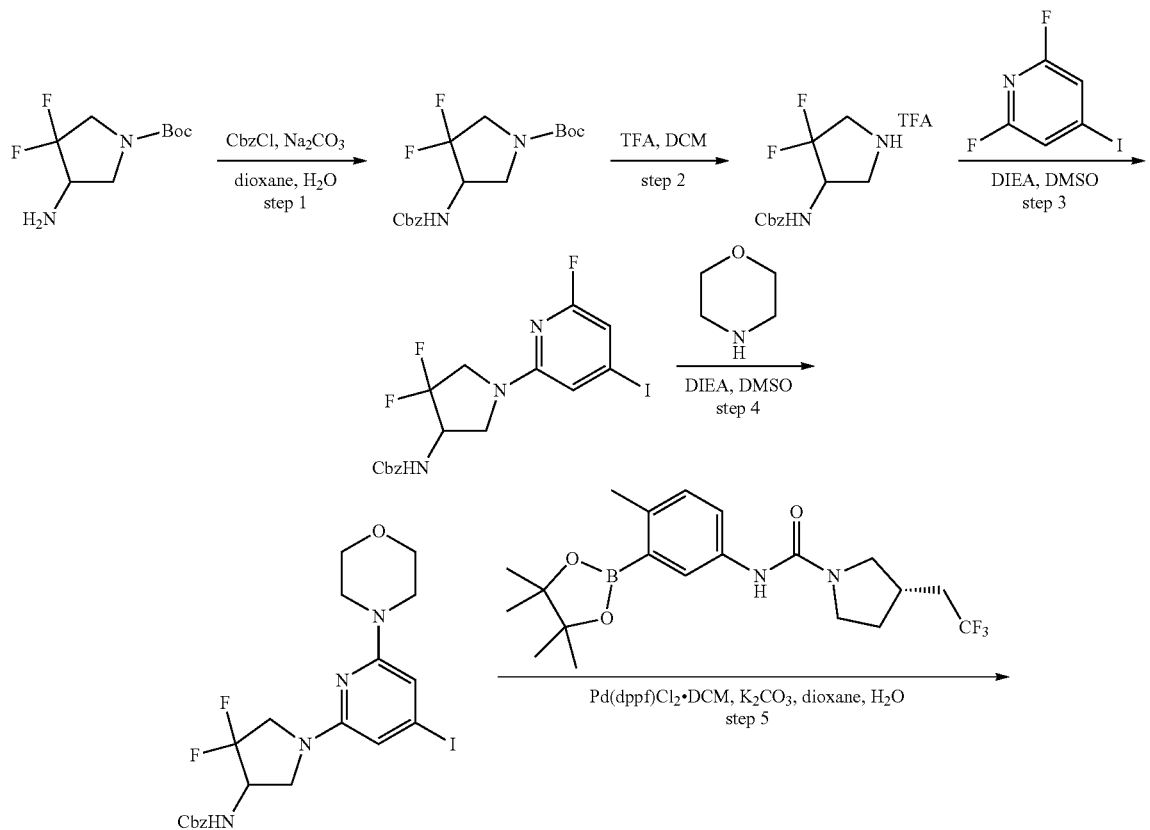
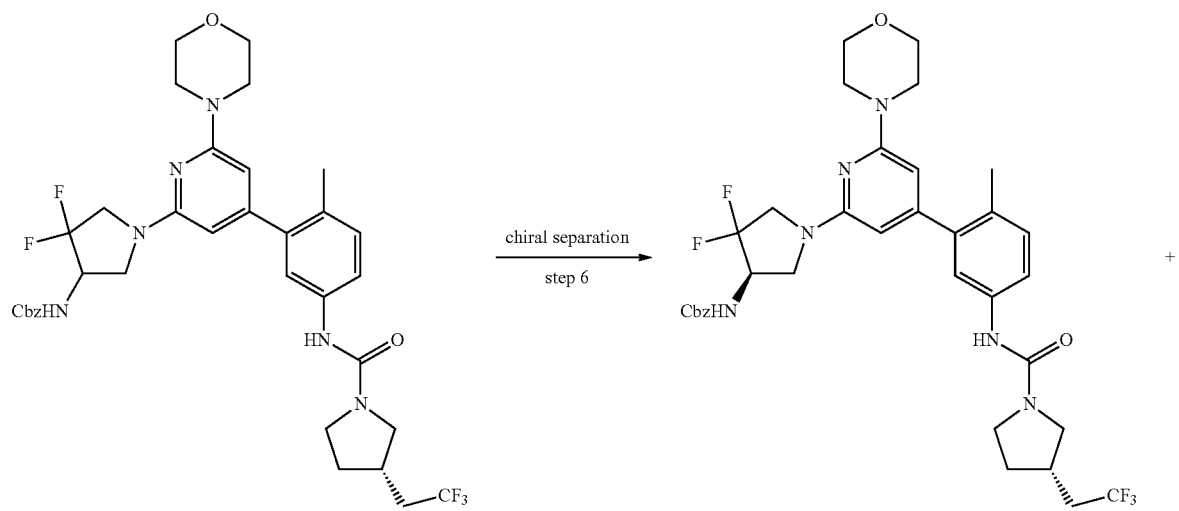

531 532

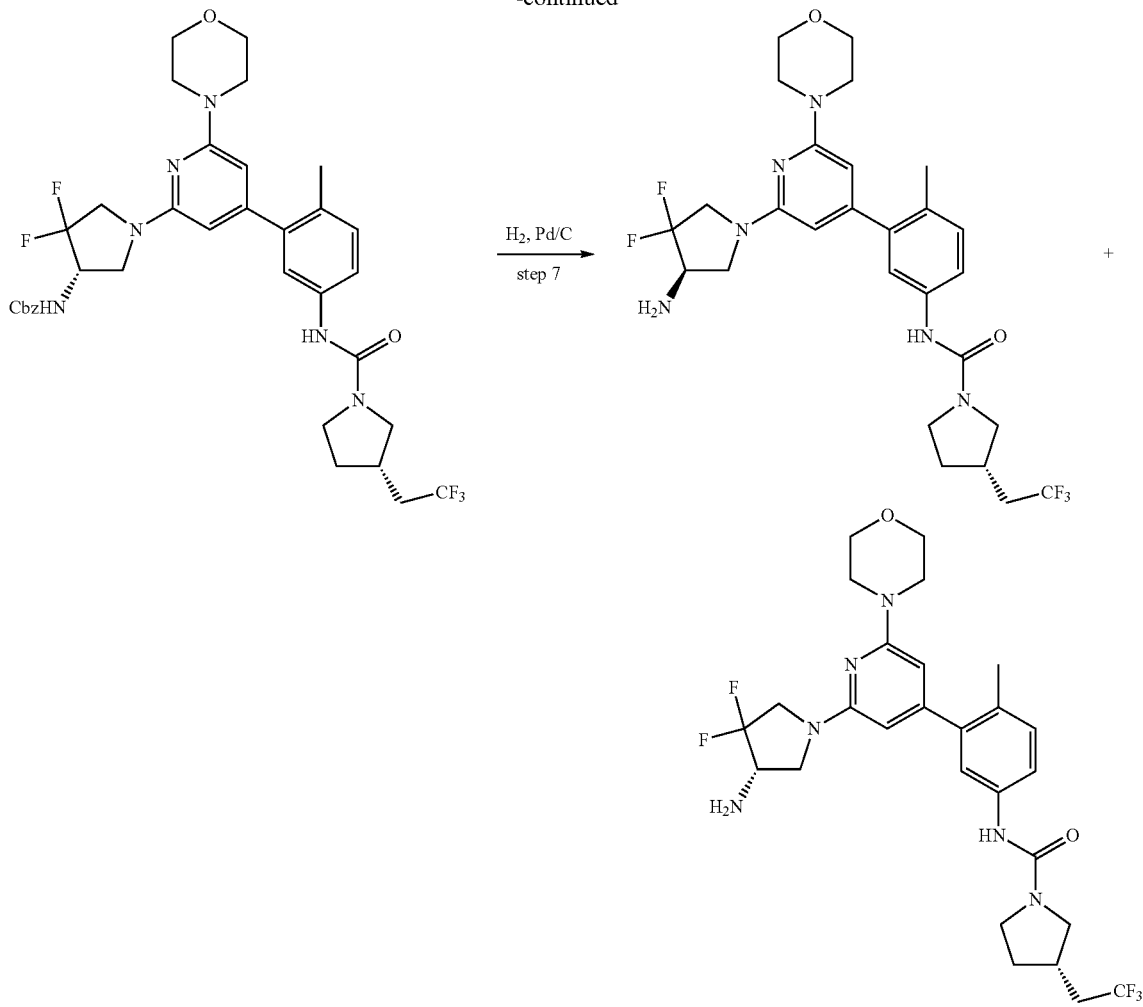

Preparation 133A: tert-butyl 4-{[(benzyloxy)carbonyl]amino}-3,3-difluoropyrrolidine-1-carboxylate

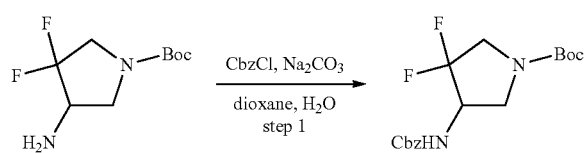

To a stirred solution of tert-butyl 4-amino-3,3-difluoropyrrolidine-1-carboxylate (200 mg, 0.900 mmol) and Na$_2$CO$_3$ (114 mg, 1.080 mmol) in 1,4-dioxane (2 mL) and H$_2$O (2 mL) was added Cbz-Cl (184 mg, 1.080 mmol) at 0° C. The resulting mixture was stirred for 4 h at room temperature. The reaction mixture was diluted with water (30 mL). The resulting mixture was extracted with EtOAc (3×30 mL). The combined organic layers were washed with brine (30 mL), dried over anhydrous Na$_2$SO$_4$. After filtration, the filtrate was concentrated under reduced pressure to afford tert-butyl 4-{[(benzyloxy)carbonyl]amino}-3,3-difluoropyrrolidine-1-carboxylate (700 mg, crude) as yellow oil. MS ESI calculated for C$_{17}$H$_{22}$F$_2$N$_2$O$_4$ [M-Boc+H]$^+$, 257.15; found 257.10.

Preparation 133B: benzyl N-(4,4-difluoropyrrolidin-3-yl)carbamate 2,2,2-trifluoroacetate

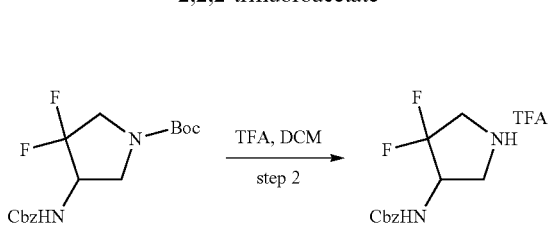

To a stirred solution of tert-butyl 4-{[(benzyloxy)carbonyl]amino}-3,3-difluoropyrrolidine-1-carboxylate (700 mg, 1.964 mmol) in DCM (10 mL) was added TFA (2 mL) dropwise at 0° C. The resulting mixture was stirred for 2 h at room temperature. The resulting mixture was concentrated under reduced pressure to afford benzyl N-(4,4-difluoropyrrolidin-3-yl)carbamate 2,2,2-trifluoroacetate (750 mg, crude) as yellow oil. MS ESI calculated for C$_{14}$H$_{15}$F$_5$N$_2$O$_4$ [M-CF$_3$COO]$^+$, 257.10, found 257.10.

Preparation 133C: 6-fluoro-4-iodo-N-(4-methyl-oxan-4-yl)pyridin-2-amine

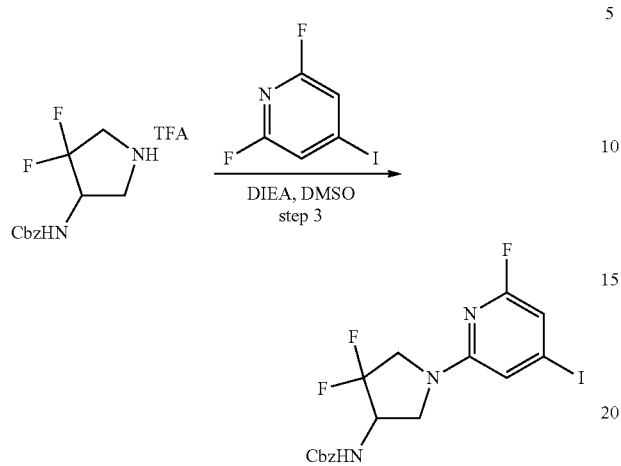

A solution of 2,6-difluoro-4-iodopyridine (700 mg, 2.905 mmol), benzyl N-(4,4-difluoropyrrolidin-3-yl)carbamate 2,2,2-trifluoroacetate (893 mg, 3.486 mmol) in DMSO (7 mL) and DIEA (825 mg, 6.391 mmol) was stirred for 4 h at 80° C. The resulting mixture was diluted with H$_2$O (50 mL) and extracted with EtOAc (3×50 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EtOAc (4/1) to afford 6-fluoro-4-iodo-N-(4-methyloxan-4-yl)pyridin-2-amine (550 mg, 56%) as a yellow solid. MS ESI calculated for C$_{17}$H$_{15}$F$_3$IN$_3$O$_2$ [M+H]$^+$, 478.02, found 477.90.

Preparation 133D: benzyl N-[4,4-difluoro-1-[4-iodo-6-(morpholin-4-yl)pyridin-2-yl]pyrrolidin-3-yl]carbamate

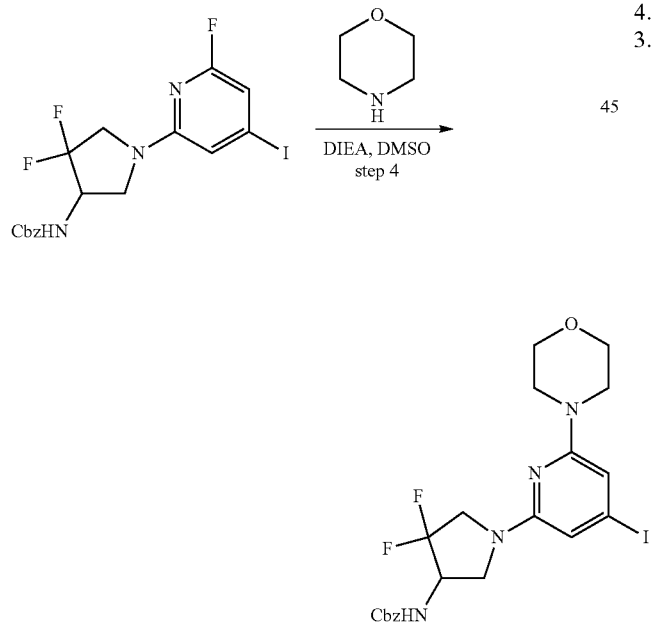

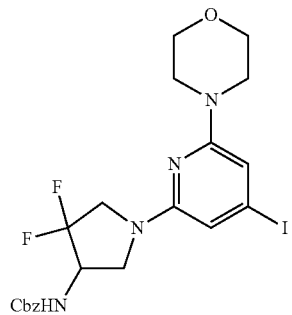

To a stirred solution of benzyl N-[4,4-difluoro-1-(6-fluoro-4-iodopyridin-2-yl) pyrrolidin-3-yl]carbamate (500 mg, 1.048 mmol) and morpholine (109 mg, 1.257 mmol) in DMSO (5.00 mL) was added DIEA (203 mg, 1.572 mmol) at room temperature. The resulting mixture was stirred for 16 h at 80° C. The reaction was quenched with water (50 mL). The resulting mixture was extracted with EtOAc (3×50 mL). The combined organic layers were washed with brine (2×30 mL), dried over anhydrous Na$_2$SO$_4$. After filtration, the filtrate was concentrated under reduced pressure. The residue was purified by silica gel column chromatography, eluted with PE/EA (2/1) to afford benzyl N-[4,4-difluoro-1-[4-iodo-6-(morpholin-4-yl)pyridin-2-yl]pyrrolidin-3-yl]carbamate (480 mg, 84%) as a white solid. MS ESI calculated for C$_{21}$H$_{23}$F$_2$IN$_4$O$_3$ [M+H]$^+$, 545.08, found 545.10. $^1$H NMR (400 MHz, Chloroform-d) δ 7.40-7.30 (m, 5H), 6.36 (s, 1H), 6.10 (s, 1H), 5.15 (s, 2H), 4.66-4.62 (m, 1H), 4.04-3.98 (m, 1H), 3.90-3.67 (m, 7H), 3.49-3.40 (m, 4H), 3.24-3.20 (m, 1H).

Preparation 133E: benzyl N-[4,4-difluoro-1-(4-{2-methyl-5-[(3S)-3-(2,2,2-trifluoroethyl)pyrrolidine-1-carbonylamino]phenyl}-6-(morpholin-4-yl)pyridin-2-yl) pyrrolidin-3-yl]carbamate

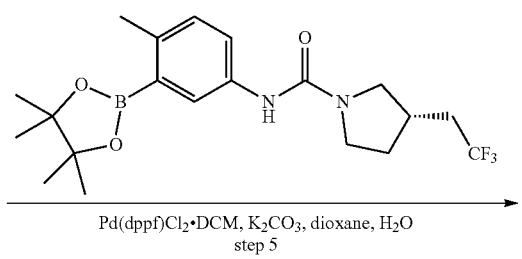

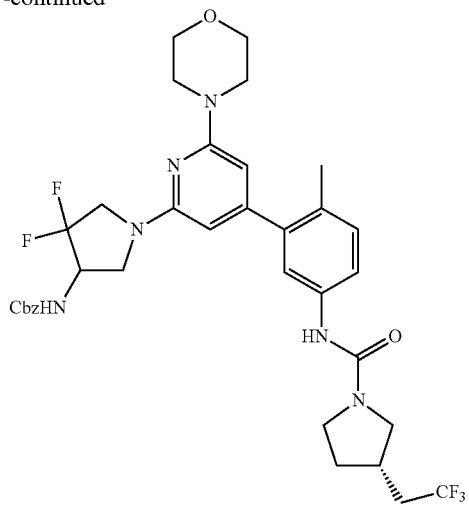

A mixture of benzyl N-{4,4-difluoro-1-[4-iodo-6-(morpholin-4-yl)pyridin-2-yl]pyrrolidin-3-yl}carbamate (300 mg, 0.551 mmol), N-[4-methyl-3-(4,4,5,5-tetramethyl-1,3,2-dioxaborolan-2-yl)phenyl]-2-(trifluoromethyl)pyridine-4-carboxamide (223 mg, 0.551 mmol), 1,4-dioxane (3 mL), H$_2$O (0.7 mL), Pd(dppf)Cl$_2$·CH$_2$Cl$_2$ (45 mg, 0.055 mmol) and K$_2$CO$_3$ (152 mg, 1.101 mmol) was stirred for 2 h at 80° C. under nitrogen atmosphere. The reaction was quenched with water (50 mL). The resulting mixture was extracted with EtOAc (3×50 mL). The combined organic layers were washed with brine (2×30 mL), dried over anhydrous Na$_2$SO$_4$. After filtration, the filtrate was concentrated under reduced pressure. The residue was purified by silica gel column chromatography, eluted with PE/EtOAc/EtOH (2/3/1) to afford benzyl N-[4,4-difluoro-1-(4-{2-methyl-5-[(3S)-3-(2,2,2-trifluoroethyl)pyrrolidine-1-carbonylamino]phenyl}-6-(morpholin-4-yl)pyridin-2-yl) pyrrolidin-3-yl]carbamate (300 mg, 77%) as yellow oil. MS ESI calculated for C$_{35}$H$_{39}$F$_5$N$_6$O$_4$ [M+H]$^+$, 703.30, found 703.15. $^1$H NMR (400 MHz, Chloroform-d) δ 7.42-7.35 (m, 6H), 7.23 (d, J=2.4 Hz, 1H), 7.18 (d, J=8.4 Hz, 1H), 6.14 (s, 1H), 5.99 (s, 1H), 5.71 (s, 1H), 5.21-5.17 (m, 3H), 4.74-4.68 (m, 1H), 4.12-4.07 (m, 1H), 3.98-3.77 (m, 7H), 3.64 (t, J=8.8 Hz, 1H), 3.50-3.42 (m, 5H), 3.31 (t, J=9.2 Hz, 1H), 3.12 (t, J=9.2 Hz, 1H), 2.56-2.53 (m, 1H), 2.31-2.20 (m, 5H), 1.77-1.71 (m, 1H).

Preparations 133F/134F: Benzyl N-[(3R)-4,4-difluoro-1-(4-{2-methyl-5-[(3S)-3-(2,2,2-trifluoroethyl) pyrrolidine-1-carbonylamino]phenyl}-6-(morpholin-4-yl)pyridin-2-yl) pyrrolidin-3-yl]carbamate and benzyl N-[(3S)-4,4-difluoro-1-(4-{2-methyl-5-[(3S)-3-(2,2,2-trifluoroethyl)pyrrolidine-1-carbonylamino] phenyl}-6-(morpholin-4-yl)pyridin-2-yl) pyrrolidin-3-yl]carbamate

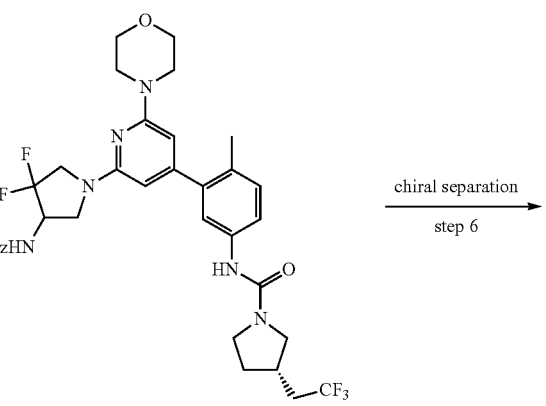

chiral separation
step 6

-continued

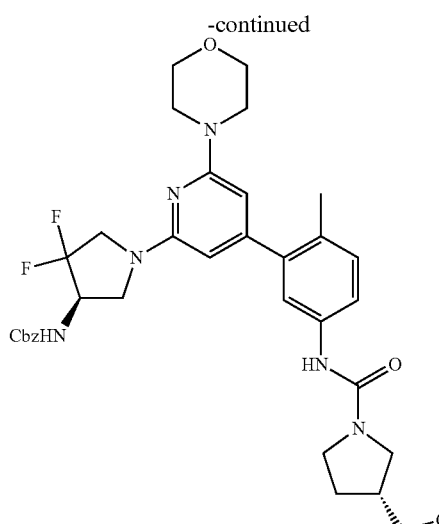

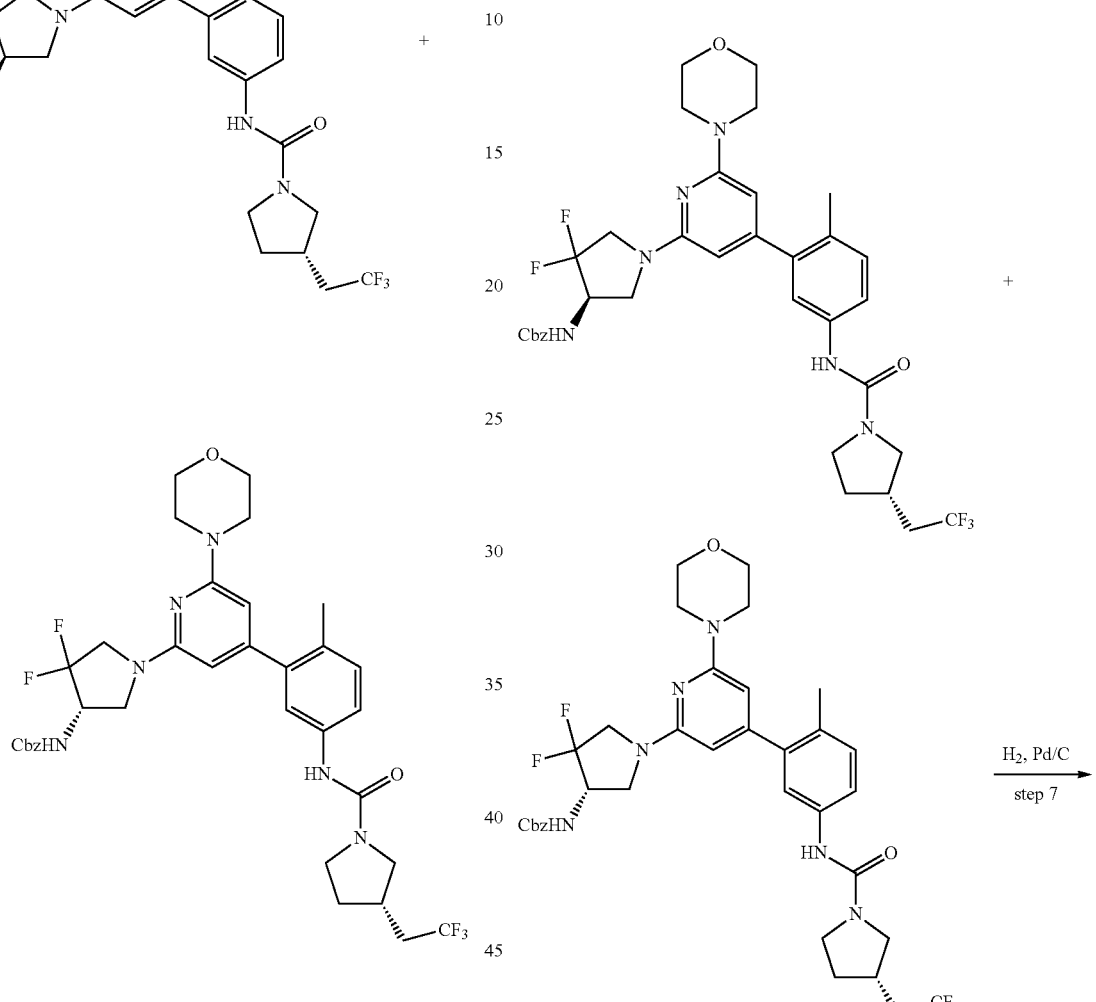

Benzyl N-[4,4-difluoro-1-(4-{2-methyl-5-[(3S)-3-(2,2,2-trifluoroethyl)pyrrolidine-1-carbonylamino]phenyl}-6-(morpholin-4-yl)pyridin-2-yl) pyrrolidin-3-yl]carbamate (330 mg, 0.470 mmol) was resolved by chiral Prep-HPLC with the following conditions: Column: CHIRALPAK IE, 2*25 cm, 5 μm; Mobile Phase A: Hexane (0.5% 2M NH$_3$-MeOH), Mobile Phase B: EtOH; Flow rate: 20 mL/min; Gradient: A:B=70:30; 220/254 nm. RT$_1$: 16.88 min gave 100 mg (30%) of Preparation 133F as a white solid. MS ESI calculated for $C_{35}H_{39}F_5N_6O_4$ [M+H]$^+$, 703.30, found 703.35. And RT$_2$: 22.22 min gave 110 mg (33%) of Preparation 134F as a white solid. MS ESI calculated for $C_{35}H_{39}F_5N_6O_4$ [M+H]$^+$, 703.30, found 703.40.

Examples 133 and 134: (3S)—N-(3-{2-[(4R)-4-amino-3,3-difluoropyrrolidin-1-yl]-6-(morpholin-4-yl)pyridin-4-yl}-4-methylphenyl)-3-(2,2,2-trifluoroethyl)pyrrolidine-1-carboxamide and (3S)—N-(3-{2-[(4S)-4-amino-3,3-difluoropyrrolidin-1-yl]-6-(morpholin-4-yl)pyridin-4-yl}-4-methylphenyl)-3-(2,2,2-trifluoroethyl)pyrrolidine-1-carboxamide

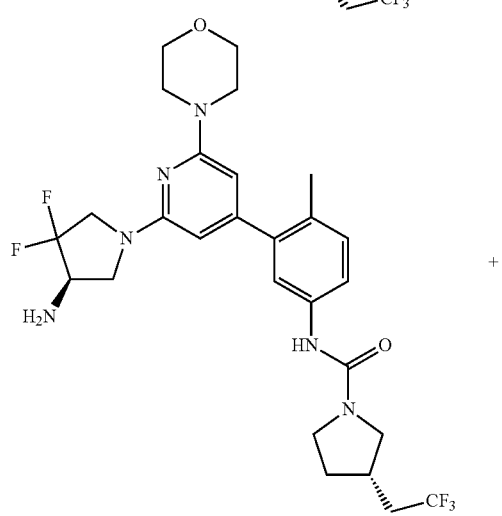

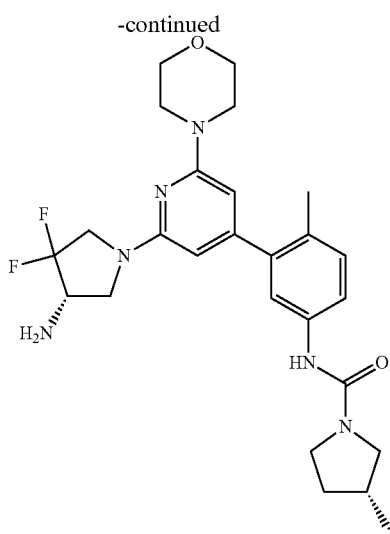

A mixture of Preparation 133F (110 mg, 0.157 mmol) in MeOH (3 mL) and Pd/C (50 mg) was stirred for 30 min at room temperature under hydrogen atmosphere. The resulting mixture was filtered and washed with MeOH (3×10 mL). The filtrate was concentrated under reduced pressure to afford Example 133 (70 mg, 78%) as a white solid. MS ESI calculated for $C_{27}H_{33}F_5N_6O_2$ [M+H]$^+$, 569.26, found 569.25. $^1$H NMR (400 MHz, DMSO-d$_6$) δ 8.12 (s, 1H), 7.43 (dd, J=2.4, 8.4 Hz, 1H), 7.33 (d, J=2.4 Hz, 1H), 7.11 (d, J=8.4 Hz, 1H), 5.95 (s, 1H), 5.70 (s, 1H), 3.90-3.73 (m, 3H), 3.72-3.63 (m, 6H), 3.52 (t, J=9.2 Hz, 1H), 3.42-3.40 (m, 4H), 3.31-3.29 (m, 1H) 3.15 (t, J=8.8 Hz, 1H), 3.02 (t, J=9.6 Hz, 1H), 2.45-2.52 (m, 3H), 2.17 (s, 3H), 2.10-2.07 (m, 1H), 1.94 (s, 1H), 1.70-1.62 (m, 1H). $^{19}$F NMR (376 MHz, DMSO-d$_6$) δ −66.37 (3F), −110.15 (d, J=224.8 Hz, 1F), −117.55 (d, J=224.8 Hz, 1F).

A mixture of Preparation 134F (110 mg, 0.157 mmol), MeOH (3 mL) and Pd/C (50 mg) was stirred for 30 min at room temperature under hydrogen atmosphere. The resulting mixture was filtered and washed with MeOH (3×10 mL). The resulting mixture was concentrated under reduced pressure to afford Example 134 (72 mg, 88%) as a white solid. MS ESI calculated for $C_{27}H_{33}F_5N_6O_2$ [M+H]$^+$, 569.26, found 569.20. $^1$H NMR (400 MHz, DMSO-d$_6$) δ 8.12 (s, 1H), 7.43 (dd, J=2.4, 8.4 Hz, 1H), 7.34 (d, J=2.4 Hz, 1H), 7.11 (d, J=8.4 Hz, 1H), 5.95 (s, 1H), 5.70 (s, 1H), 3.90-3.73 (m, 3H), 3.72-3.63 (m, 6H), 3.52 (t, J=9.2 Hz, 1H), 3.42-3.40 (m, 4H), 3.31-3.29 (m, 1H) 3.15 (t, J=8.8 Hz, 1H), 3.02 (t, J=9.6 Hz, 1H), 2.45-2.52 (m, 3H), 2.17 (s, 3H), 2.10-2.05 (m, 1H), 1.94 (s, 1H), 1.69-1.63 (m, 1H). $^{19}$F NMR (376 MHz, DMSO-d$_6$) δ −63.36 (3F), −110.13 (d, J=224.8 Hz, 1F), −117.54 (d, J=224.8 Hz, 1F).

Examples 135 and 136: (3S)—N-(3-{2-[(3R,4R)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide and (3S)—N-(3-{2-[(3S,4S)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide

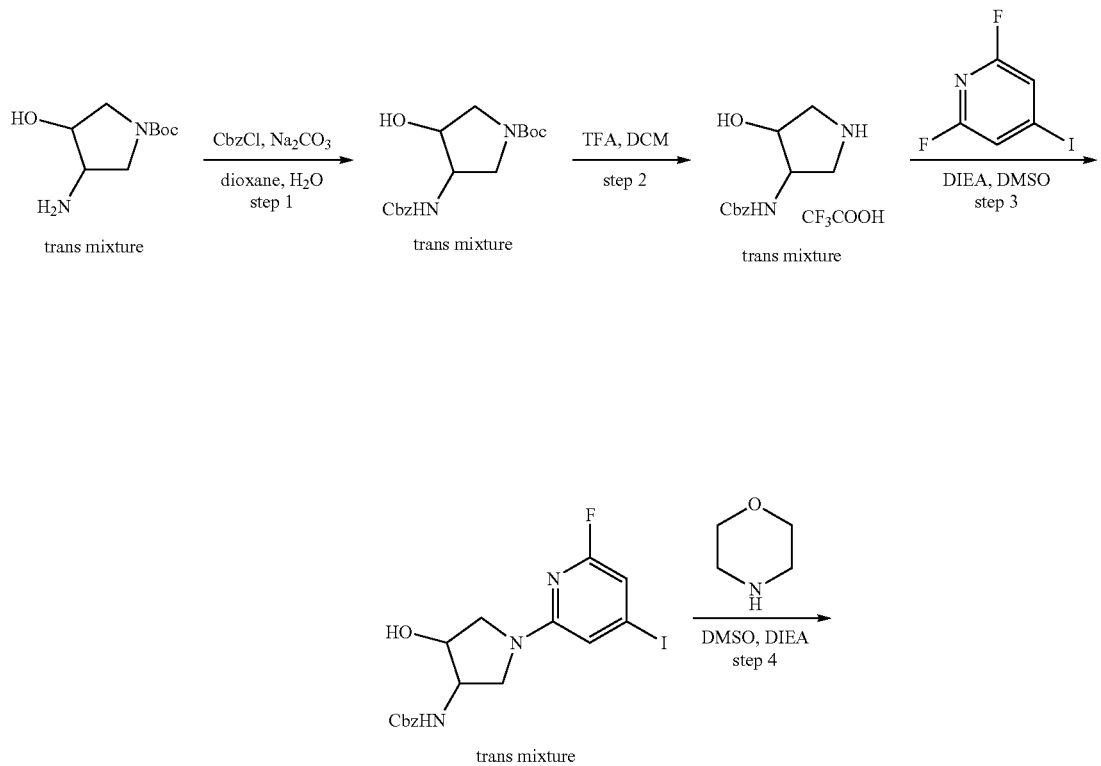

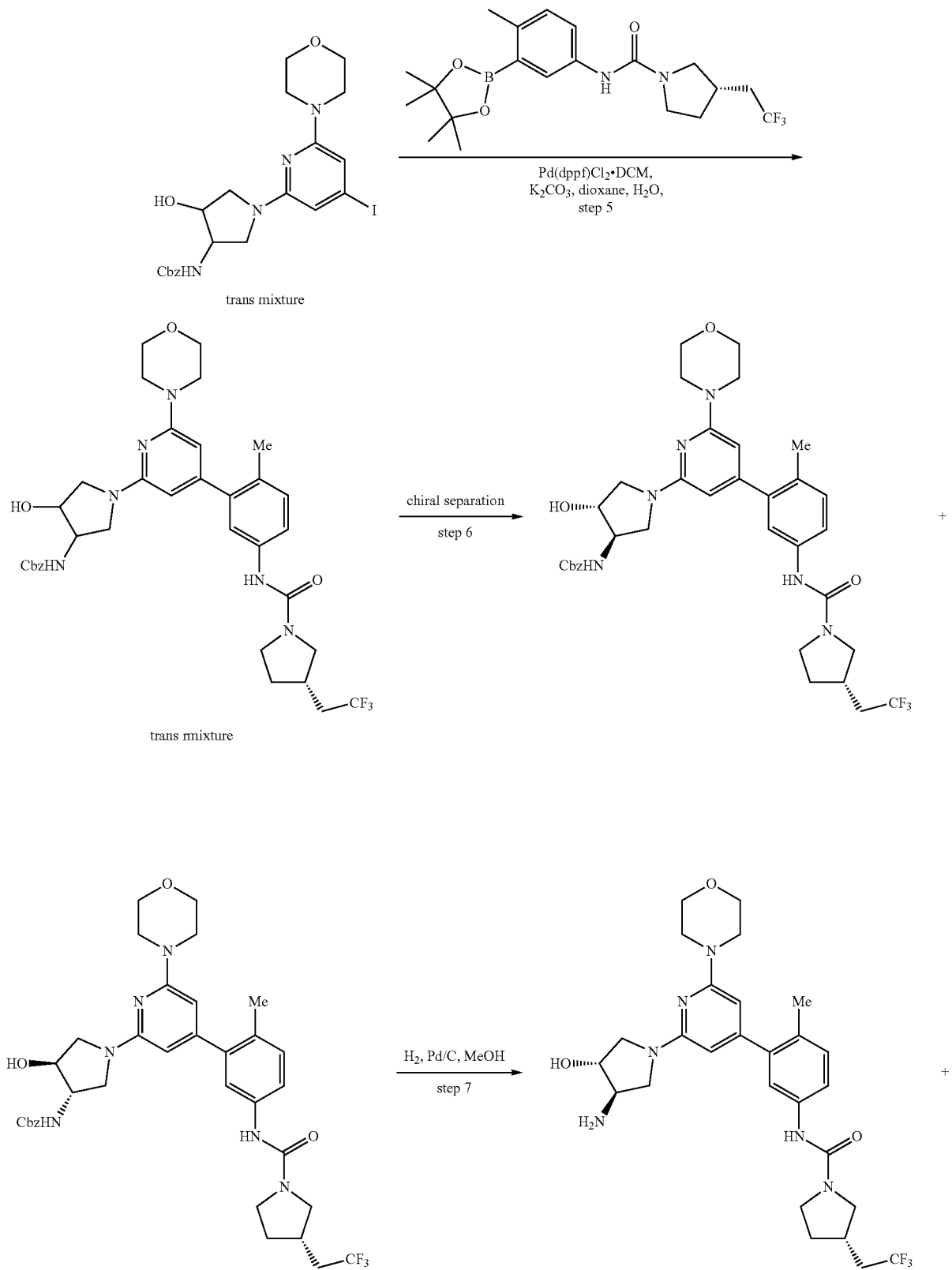

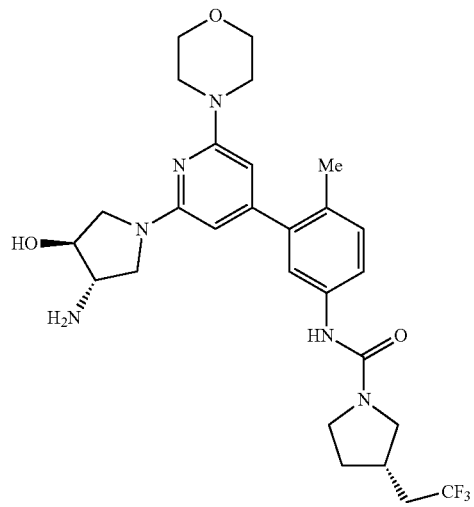

Preparation 135A: Trans-tert-butyl-3-[[(benzyloxy)carbonyl]amino]-4-hydroxypyrrolidine-1-carboxylate

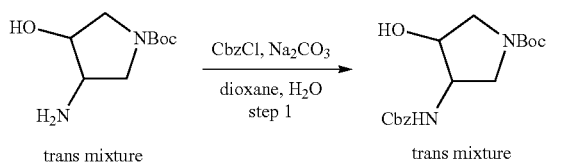 [SMILES: CC(C)(C)OC(=O)N1CC(N)C(O)C1 ; CC(C)(C)OC(=O)N1CC(O)C(NC(=O)OCc2ccccc2)C1]

To a stirred mixture of trans-tert-butyl-3-amino-4-hydroxypyrrolidine-1-carboxylate (5 g, 24.721 mmol) and Na$_2$CO$_3$ (3 g, 29.666 mmol) in dioxane (57 mL) and H$_2$O (57 mL) was added Cbz-Cl (5 g, 29.661 mmol) dropwise at 0° C. The resulting mixture was stirred for 3 h at room temperature. The reaction mixture was diluted with water (100 mL). The resulting mixture was extracted with EtOAc (2×200 mL). The combined organic layers were washed with brine (50 mL), dried over anhydrous Na$_2$SO$_4$. After filtration, the filtrate was concentrated under reduced pressure. The residue was purified by silica gel column chromatography, eluted with PE/EtOAc/EtOH (4/3/1) to afford trans-tert-butyl-3-[[(benzyloxy)carbonyl]amino]-4-hydroxypyrrolidine-1-carboxylate (7.2 g, 78%) as an off-white solid. MS ESI calculated for C$_{17}$H$_{24}$N$_2$O$_5$ [M-Boc+H], 237.17, found 237.10. $^1$H NMR (300 MHz, Chloroform-d) δ 7.40-7.33 (m, 5H), 5.11 (s, 2H), 4.27-4.23 (m, 1H), 4.02-3.98 (m, 1H), 3.79 (m, 1H), 3.65 (m, 1H), 3.33-3.24 (m, 2H), 1.46 (s, 9H).

Preparation 135B: Trans-benzyl (4-hydroxypyrrolidin-3-yl)carbamate 2,2,2-trifluoroacetate

To a stirred mixture of trans-tert-butyl-3-[[(benzyloxy)carbonyl]amino]-4-hydroxypyrrolidine-1-carboxylate (2 g, 5.946 mmol) in DCM (20 mL) was added TFA (4 mL, 53.852 mmol) dropwise at 0° C. The resulting mixture was stirred for 30 min at room temperature. The resulting mixture was concentrated under reduced pressure to afford trans-benzyl (4-hydroxypyrrolidin-3-yl)carbamate 2,2,2-trifluoroacetate (3 g, crude) as a light brown oil. MS ESI calculated for C$_{14}$H$_{17}$F$_3$N$_2$O$_5$ [M-CF$_3$COO]$^+$, 237.12, found 237.10.

Preparation 135C: Trans-benzyl [1-(6-fluoro-4-iodopyridin-2-yl)-4-hydroxypyrrolidin-3-yl]carbamate

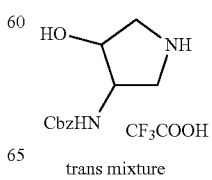

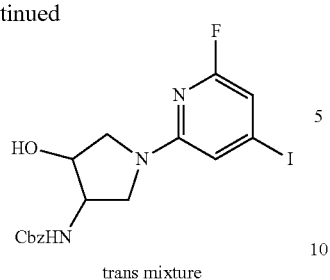

trans mixture

A mixture of 2,6-difluoro-4-iodopyridine (1.5 g, 6.225 mmol), trans-benzyl (4-hydroxypyrrolidin-3-yl)carbamate 2,2,2-trifluoroacetate (2.2 g, 6.223 mmol) and DIEA (4 g, 31.104 mmol) in DMSO (15 mL) was stirred for 16 h at 80° C. under nitrogen atmosphere. The reaction was quenched with water (80 mL). The resulting mixture was extracted with EtOAc (2×30 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EtOAc (1/1) to afford trans-benzyl [1-(6-fluoro-4-iodopyridin-2-yl)-4-hydroxypyrrolidin-3-yl]carbamate (2.1 g, 66%) as an off-white solid. MS ESI calculated for $C_{17}H_{17}FIN_3O_3$ [M+H]$^+$, 458.03, found 458.10. $^1$H NMR (300 MHz, Chloroform-d) δ 7.40-7.36 (m, 5H), 6.58-6.56 (m, 2H), 5.15 (s, 2H), 4.95-4.91 (m, 1H), 4.45-4.43 (m, 1H), 4.18-4.11 (m, 1H), 3.96-3.90 (m, 1H), 3.79-3.74 (m, 1H), 3.43-3.35 (m, 2H).

Preparation 135D: Trans-benzyl (4-hydroxy-1-(4-iodo-6-morpholinopyridin-2-yl) pyrrolidin-3-yl) carbamate

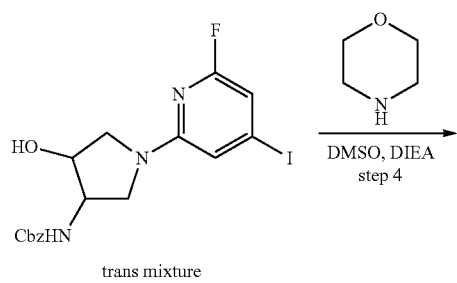

trans mixture

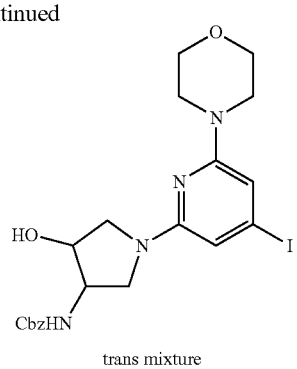

trans mixture

A mixture of trans-benzyl [1-(6-fluoro-4-iodopyridin-2-yl)-4-hydroxypyrrolidin-3-yl]carbamate (1 g, 2.187 mmol), morpholine (1.9 g, 21.914 mmol) and DIEA (0.85 g, 6.577 mmol) in DMSO (10 mL) was stirred for 16 h at 80° C. under nitrogen atmosphere. The mixture was quenched with water (50 mL). The resulting mixture was extracted with EtOAc (2×30 mL). The combined organic layers were washed with brine (10 mL), dried over anhydrous $Na_2SO_4$. After filtration, the filtrate was concentrated under reduced pressure. The residue was triturated in ethyl acetate (20 mL) to afford trans-benzyl (4-hydroxy-1-(4-iodo-6-morpholinopyridin-2-yl) pyrrolidin-3-yl)carbamate (760 mg, 60%) as an off-white solid. MS ESI calculated for $C_{21}H_{25}IN_4O_4$ [M+H]$^+$, 525.09, found 525.25. $^1$H NMR (400 MHz, DMSO-d$_6$) δ 7.39-7.30 (m, 5H), 6.32 (s, 1H), 6.09 (s, 1H), 5.03 (s, 2H), 4.10-4.04 (m, 1H), 3.90-3.87 (m, 1H), 3.65-3.58 (m, 4H), 3.57-3.52 (m, 1H), 3.37-3.35 (m, 5H), 3.25-3.17 (m, 2H).

Preparation 135E: Trans-benzyl (4-hydroxy-1-(4-(2-methyl-5-((S)-3-(2,2,2-trifluoroethyl)pyrrolidine-1-carboxamido)phenyl)-6-morpholinopyridin-2-yl) pyrrolidin-3-yl)carbamate

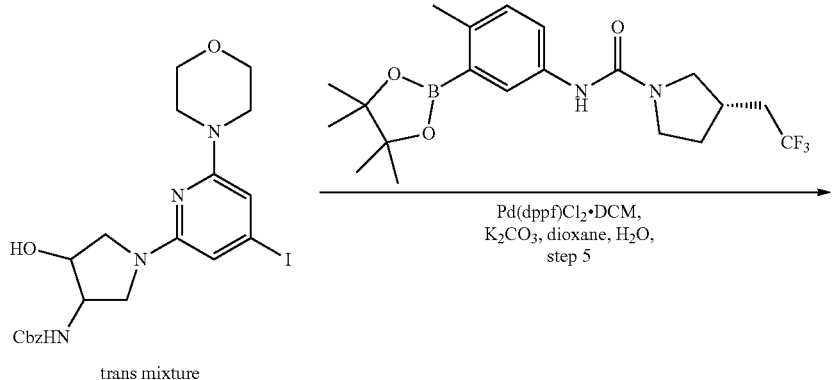

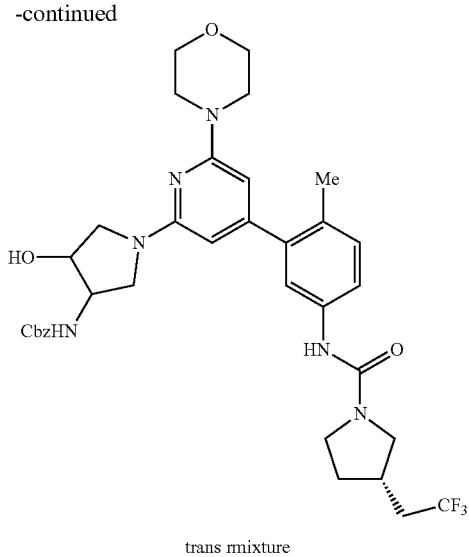

trans rmixture

A mixture of trans-benzyl (4-hydroxy-1-(4-iodo-6-morpholinopyridin-2-yl) pyrrolidin-3-yl)carbamate (300 mg, 0.572 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (236 mg, 0.572 mmol), K$_2$CO$_3$ (237 mg, 1.716 mmol) and Pd (dppf)Cl$_2$·CH$_2$Cl$_2$ (47 mg, 0.057 mmol) in dioxane (3 mL) and H$_2$O (0.75 mL) was stirred for 16 h at 80° C. under nitrogen atmosphere. The resulting mixture was concentrated under reduced pressure. The residue was purified by silica gel column chromatography, eluted with PE/EtOAc/EtOH (8/3/1) to afford trans-benzyl (4-hydroxy-1-(4-(2-methyl-5-((S)-3-(2,2,2-trifluoroethyl) pyrrolidine-1-carboxamido)phenyl)-6-morpholinopyridin-2-yl) pyrrolidin-3-yl)carbamate (270 mg, 66%) as an off-white solid. MS ESI calculated for C$_{35}$H$_{41}$F$_3$N$_6$O$_5$ [M+H]$^+$, 683.31, found 683.70. $^1$H NMR (300 MHz, Chloroform-d) δ 7.40-7.35 (m, 5H), 7.22-7.17 (m, 2H), 6.16 (s, 1H), 5.90 (s, 1H), 5.74 (s, 1H), 5.14 (s, 2H), 4.40-4.30 (m, 1H), 3.99-3.94 (m, 1H), 3.83-3.68 (m, 7H), 3.67-3.62 (m, 1H), 3.51-3.43 (m, 7H), 3.23-3.09 (m, 2H), 2.56-2.50 (m, 1H), 2.30-2.23 (m, 5H), 1.77-1.73 (m, 2H).

Preparations 135F/136F: Benzyl ((3R,4R)-4-hydroxy-1-(4-(2-methyl-5-((S)-3-(2,2,2-trifluoroethyl) pyrrolidine-1-carboxamido)phenyl)-6-morpholinopyridin-2-yl) pyrrolidin-3-yl)carbamate and benzyl ((3S,4S)-4-hydroxy-1-(4-(2-methyl-5-((S)-3-(2,2,2-trifluoroethyl)pyrrolidine-1-carboxamido)phenyl)-6-morpholinopyridin-2-yl) pyrrolidin-3-yl)carbamate

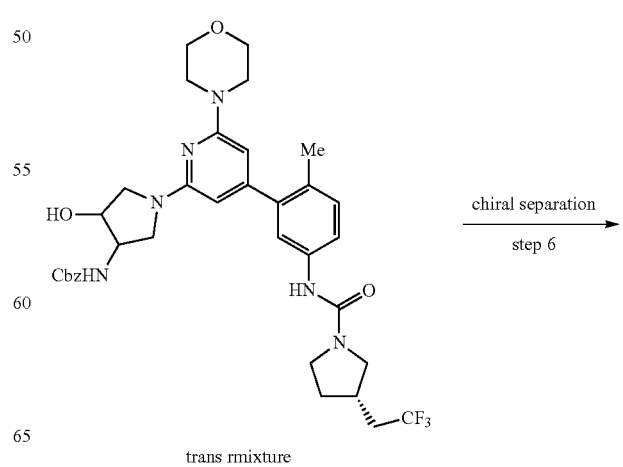

trans rmixture chiral separation
step 6

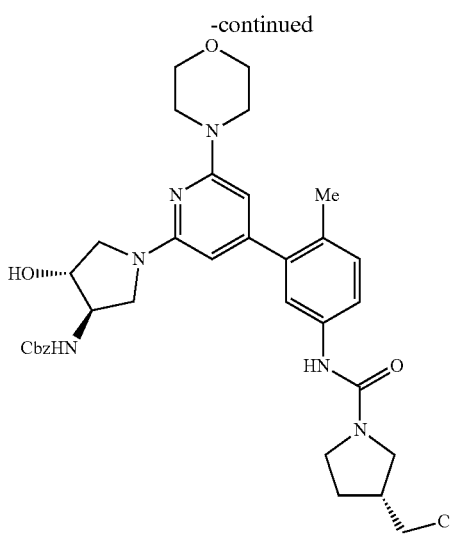

Trans-benzyl (4-hydroxy-1-(4-(2-methyl-5-((S)-3-(2,2,2-trifluoroethyl)pyrrolidine-1-carboxamido)phenyl)-6-morpholinopyridin-2-yl) pyrrolidin-3-yl)carbamate (270 mg) was resolved by Chiral-Prep-HPLC with the following conditions: Column: (R,R)-WHELK-O1-Kromasil, 2.12×25 cm, 5 μm; Mobile Phase A: MTBE (0.5% 2M $NH_3$-MeOH), Mobile Phase B: EtOH; Flow rate: 20 mL/min; Gradient: A:B=70:30; 220/254 nm. $RT_1$: 13.7 min gave 100 mg (35%) of Preparations 135F as an off-white solid, MS ESI calculated for $C_{35}H_{41}F_3N_6O_5$ [M+H]$^+$, 683.31, found 683.35.

And $RT_2$: 18.3 min gave 70 mg (24%) of Preparations 136F as an off-white solid. MS ESI calculated for $C_{35}H_{41}F_3N_6O_5$ [M+H]$^+$, 683.31, found 683.35.

Examples 135 and 136: (3S)—N-(3-{2-[(3R,4R)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide and (3S)—N-(3-{2-[(3S,4S)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide

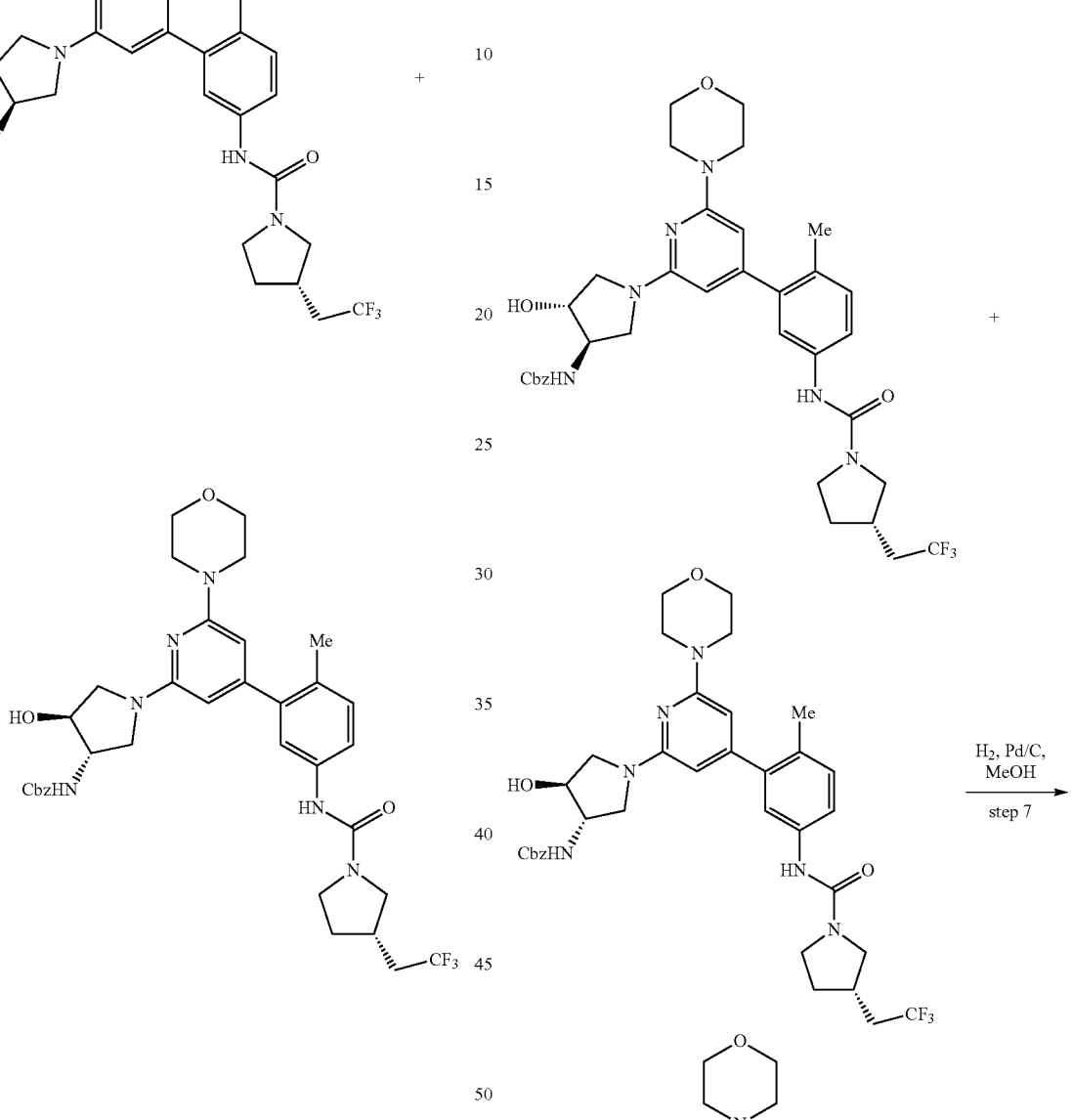

-continued

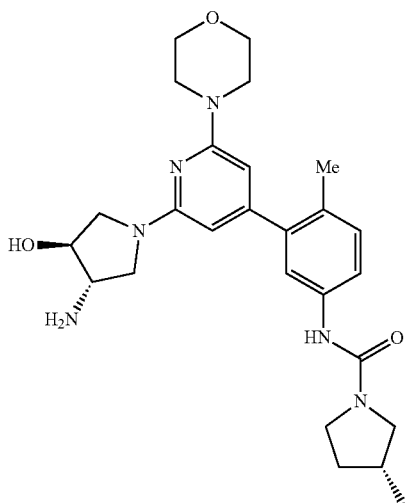

A mixture of Preparations 135F (100 mg, 0.146 mmol) and Pd/C (50 mg, 0.470 mmol) in MeOH (2 mL) was stirred for 30 min at room temperature under $H_2$ atmosphere. The resulting mixture was filtered and washed with MeOH (3×5 mL). The filtrate was concentrated under reduced pressure to afford Example 135 (27 mg, 32%) as an off-white solid. MS ESI calculated for $C_{27}H_{35}F_3N_6O_3$ [M+H]$^+$, 549.27, found 549.25. $^1$H NMR (300 MHz, DMSO-$d_6$) δ 8.12 (s, 1H), 7.51-7.35 (m, 2H), 7.16-7.10 (m, 1H), 5.89-5.84 (m, 1H), 5.66-5.61 (m, 1H), 5.00 (s, 1H), 3.90-3.86 (m, 1H), 3.69-3.51 (m, 8H), 3.42-3.33 (m, 4H), 3.28-3.13 (m, 3H), 3.09-2.94 (m, 2H), 2.74-2.47 (m, 3H), 2.29 (s, 3H), 2.18-2.02 (m, 1H), 1.72-1.58 (m, 2H). $^{19}$F NMR (282 MHz, DMSO-$d_6$) δ −63.35 (3F).

A mixture of Preparations 136F (75 mg, 0.110 mmol) and Pd/C (50 mg, 0.470 mmol) in MeOH (2 mL) was stirred for 30 min at room temperature under $H_2$ atmosphere. The resulting mixture was filtered and washed with MeOH (3×5 mL). The filtrate was concentrated under reduced pressure to afford Example 136 (29 mg, 46%) as an off-white solid. MS ESI calculated for $C_{27}H_{35}F_3N_6O_3$ [M+H]$^+$, 549.27, found 549.25. $^1$H NMR (400 MHz, DMSO-$d_6$) δ 8.11 (s, 1H), 7.42 (dd, J=2.4, 8.4 Hz, 1H), 7.33 (d, J=2.0 Hz, 1H), 7.09 (d, J=8.4 Hz, 1H), 5.82 (s, 1H), 5.60 (s, 1H), 4.99 (s, 1H), 3.86 (s, 1H), 3.68-3.60 (m, 6H), 3.59-3.53 (m, 2H), 3.50-3.39 (m, 4H), 3.32-3.29 (m, 1H), 3.25-3.19 (m, 2H), 3.12-2.99 (m, 2H), 2.52-2.43 (m, 3H), 2.16 (s, 3H), 2.09-2.08 (m, 1H), 1.75-1.55 (m, 2H). $^{19}$F NMR (376 MHz, DMSO-$d_6$) δ −63.37 (3F).

Example 137: (S)—N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide

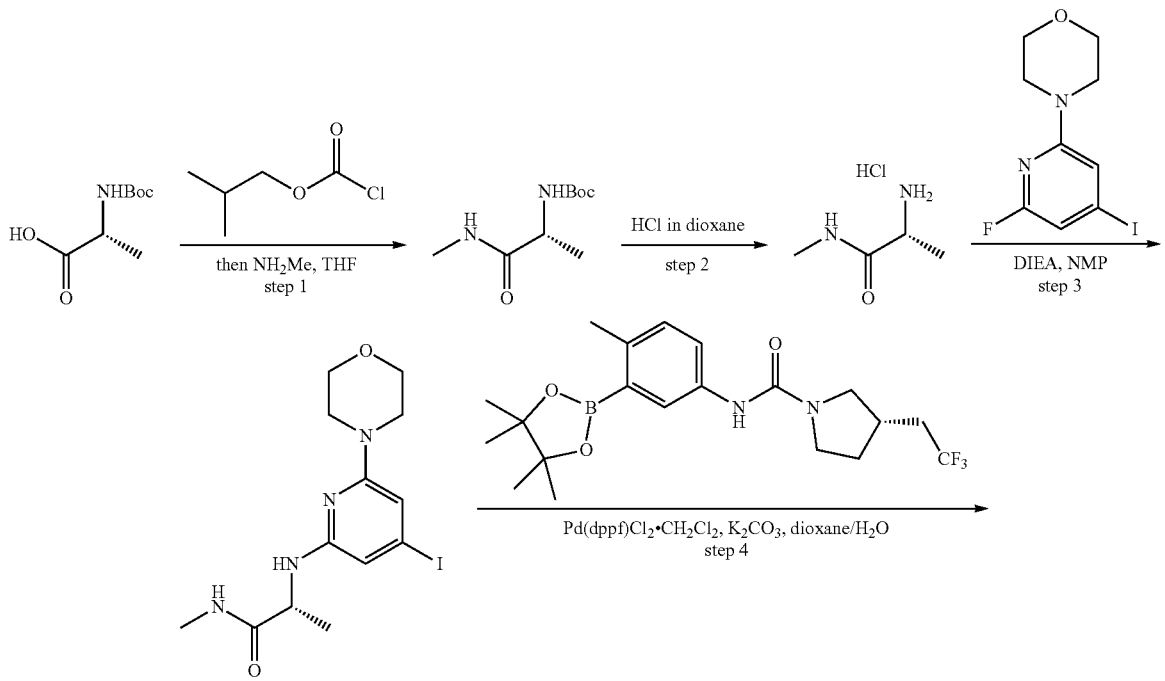

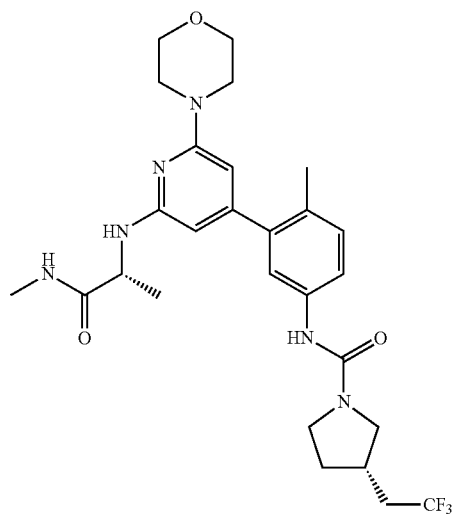

Preparation 137A: tert-butyl N-[(1R)-1-(methylcarbamoyl)ethyl]carbamate

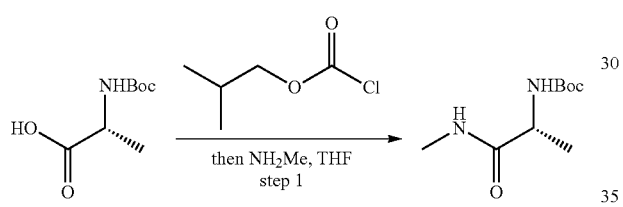

To a stirred solution of (tert-butoxycarbonyl)-D-alanine (3.00 g, 15.86 mmol) in THF (30 mL) was added isobutyl carbonochloridate (2.26 mL, 17.45 mmol) and N-methyl morphofine (1.9 mL, 17.45 mmol) at 0° C. The resulting mixture was stirred for 1 h at 0° C. To this was added methylamine (16.8 mL, 79.30 mmol). The resulting mixture was stirred for 1 h at 0° C. under nitrogen atmosphere. The reaction was quenched by the addition of water (30 mL). The resulting mixture was concentrated under reduced pressure to afford tert-butyl N-[(1R)-1-(methylcarbamoyl)ethyl]carbamate (3 g, crude) as a light yellow solid. $C_9H_{18}N_2O_3$, $^1$H NMR (400 MHz, Chloroform-d) δ 3.74-3.70 (m, 1H), 3.23-3.19 (m, 1H), 2.80 (s, 3H), 1.44 (s, 9H), 1.35 (d, J=7.2 Hz, 3H).

Preparation 137B: (R)-2-amino-N-methylpropanamide hydrochloride

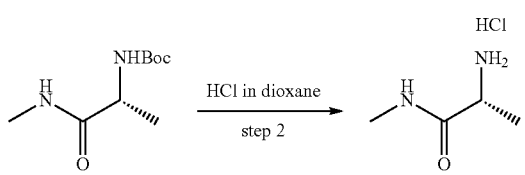

To a solution of tert-butyl N-[(1R)-1-(methylcarbamoyl) ethyl]carbamate (680 mg, 3.360 mmol) in 1,4-dioxane (15 mL) was added HCl (4 M in dioxane, 4 mL). The reaction mixture was stirred for 1 h at room temperature. The precipitated solids were collected by filtration and washed with diethyl ether (3×50 mL) to afford (R)-2-amino-N-methylpropanamide hydrochloride (630 mg, 95%). $C_4H_{11}ClN_2O$, $^1$H NMR (300 MHz, DMSO-d$_6$) δ 8.57 (brs, 1H), 8.29 (brs, 3H), 3.82-3.76 (m, 1H), 2.67-3.73 (m, 3H), 1.35 (d, J=7.2 Hz, 3H).

Preparation 137C: (2R)-2-{[4-iodo-6-(morpholin-4-yl)pyridin-2-yl]amino}-N-methylpropanamide

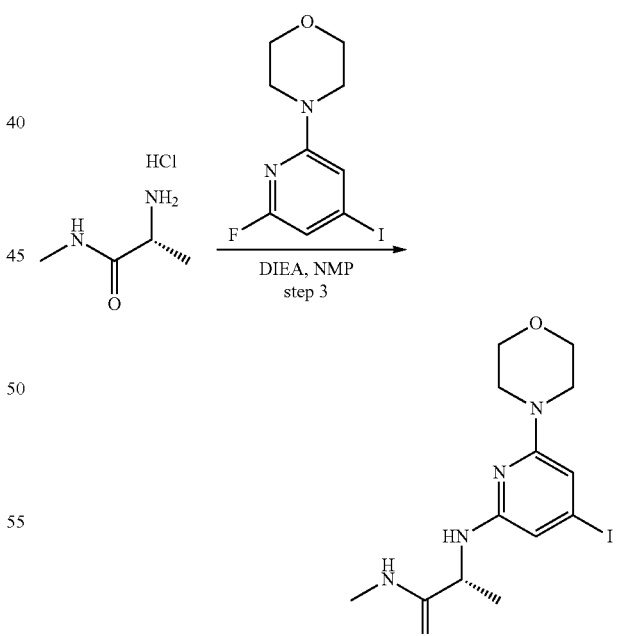

A solution of (R)-2-amino-N-methylpropanamide hydrochloride (315 mg, 2.270 mmol), 4-(6-fluoro-4-iodopyridin-2-yl)morpholine (350 mg, 1.140 mmol), NMP (5 mL) and DIEA (0.86 mL, 4.45 mmol) was stirred for 16 h at 160° C. The reaction was quenched with water (30 mL). The residue was extracted with EtOAc (3×30 mL). The resulting mixture was concentrated under reduced pressure. The residue was purified by silica gel column chromatography, eluted with PE/EtOAc (1/1) to afford (2R)-2-{[4-iodo-6-(morpholin-4-yl)pyridin-2-yl]amino}-N-methylpropanamide (151 mg, 34%) as a brown solid. MS ESI calculated for $C_{13}H_{19}IN_4O_2$ [M+H]$^+$, 391.06, found 391.00. $^1$H NMR (300 MHz, Chloroform-d) δ 6.42 (brs, 1H), 6.35 (s, 1H), 6.21 (s, 1H), 4.44-4.40 (m, 1H), 4.19-4.15 (m, 1H), 3.79-3.75 (m, 4H), 3.43-3.40 (m, 4H), 2.78 (d, J=4.8 Hz, 3H), 1.46 (d, J=7.2 Hz, 3H).

Example 137: (S)—N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide

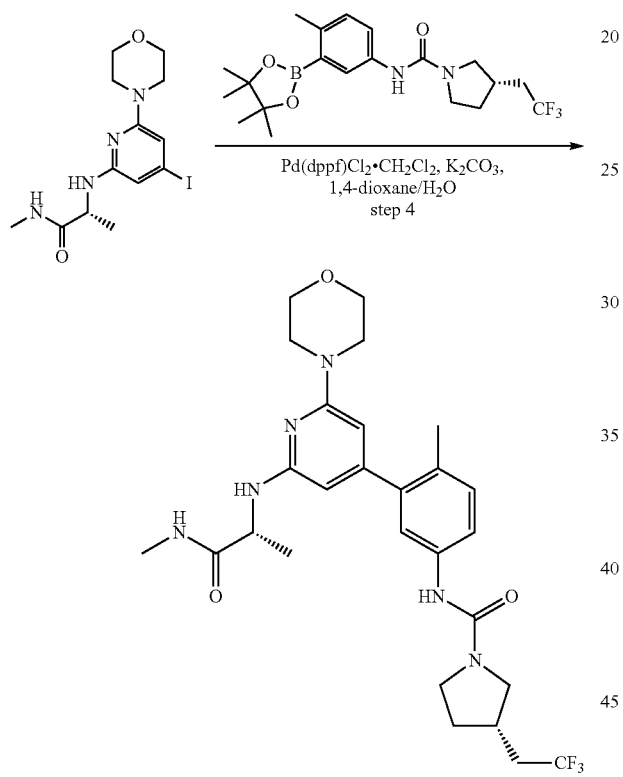

A mixture of (2R)-2-{[4-iodo-6-(morpholin-4-yl)pyridin-2-yl]amino}-N-methylpropanamide (100 mg, 0.260 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (127 mg, 0.310 mmol), 1,4-dioxane (2 mL), $H_2O$ (0.5 mL), Pd (dppf)Cl$_2$·CH$_2$Cl$_2$ (31 mg, 0.026 mmol) and $K_2CO_3$ (106 mg, 0.770 mmol) was stirred for 2 h at 80° C. under nitrogen atmosphere. The reaction was quenched by the addition of water (10 mL). The resulting mixture was concentrated under reduced pressure. The residue was purified by silica gel column chromatography, eluted with EtOAc. The crude product was resolved by Chiral-Prep-HPLC with the following conditions (Column: CHIRALPAK AD-H, 2×25 cm, 5 μm; Mobile Phase A: Hexane (0.5% 2M NH$_3$-MeOH), Mobile Phase B: IPA; Flow rate: 20 mL/min; Gradient: A:B=70:30; 220/254 nm; RT$_1$: 12.12 min; to afford (S)—N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide (13.9 mg, 9%) as an white solid and RT$_2$: 18.73 min afforded (S)—N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide (124.7 mg, 87%) as a white solid. MS ESI calculated for $C_{27}H_{35}F_3N_6O_3$ [M+H]$^+$, 549.27, found 549.35. $^1$H NMR (400 MHz, DMSO-d$_6$) δ 8.11 (s, 1H), 7.74-7.72 (m, 1H), 7.40-7.38 (m, 2H), 7.09 (d, J=8.4 Hz, 1H), 6.43 (d, J=6.4 Hz, 1H), 5.82 (s, 1H), 5.79 (s, 1H), 4.23-4.17 (m, 1H), 3.66-3.55 (m, 5H), 3.52-3.50 (m, 1H), 3.36-3.30 (m, 4H), 3.04-3.01 (m, 1H), 2.58-2.50 (m, 3H), 2.45-2.40 (m, 3H), 2.15 (s, 3H), 2.14-2.10 (m, 1H), 1.70-1.65 (m, 1H), 1.26 (d, J=7.2 Hz, 3H). $^{19}$F NMR (282 MHz, DMSO-d$_6$) δ −63.35 (3F).

Example 138: (S)—N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide

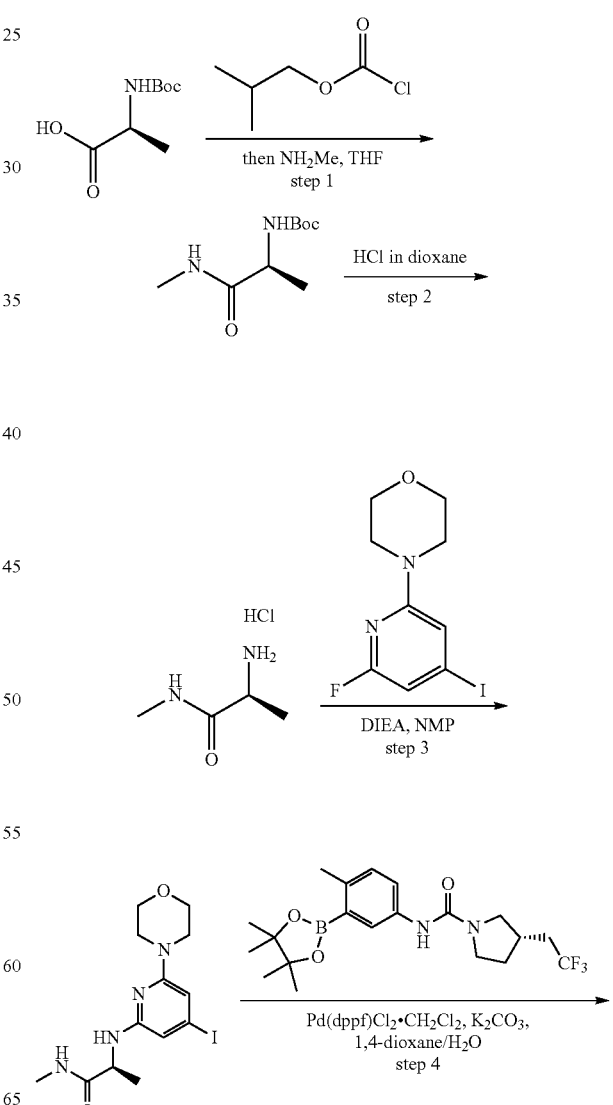

-continued

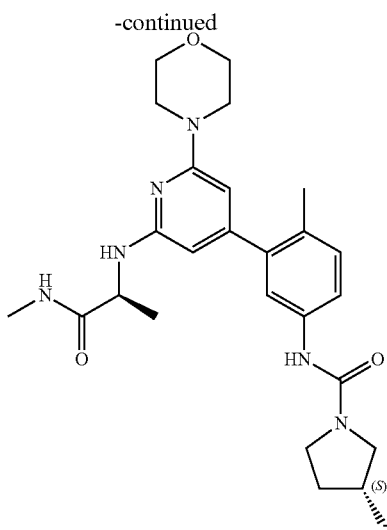

Preparation 138A: tert-butyl N—[(S)-1-(methylcarbamoyl)ethyl]carbamate

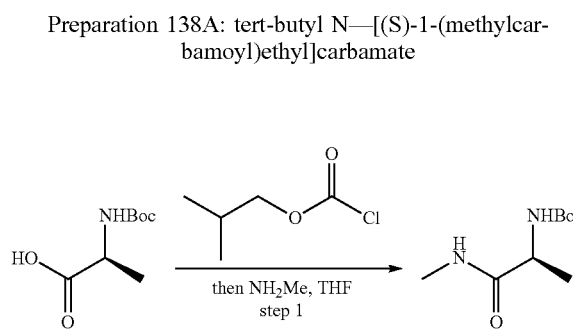

To a stirred solution of (tert-butoxycarbonyl)-L-alanine (2.00 g, 10.58 mmol) in THF (20 mL) was added isobutyl carbonochloridate (1.51 mL, 11.64 mmol) and N-methyl morphofine (1.28 mL, 11.64 mmol) at 0° C. for 1 h. The resulting mixture was stirred for 1.0 h at 0° C. under nitrogen atmosphere when methylamine (6.56 mL, 52.9 mmol) was added. The reaction was quenched by the addition of water (30 mL) at room temperature. The resulting mixture was concentrated under reduced pressure to afford tert-butyl N—[(S)-1-(methylcarbamoyl)ethyl]carbamate (2 g crude) as a light yellow solid.

Preparation 138B: (S)-2-amino-N-methylpropanamide hydrochloride

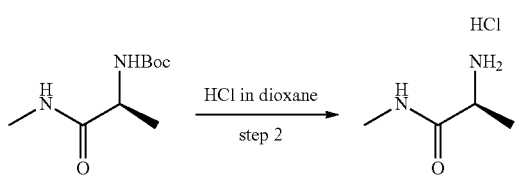

To a stirred solution of tert-butyl N—[(S)-1-(methylcarbamoyl)ethyl]carbamate (1.00 g, 4.94 mmol) in 1,4-dioxane were added HCl (4 M in dioxane, 5 mL) dropwise at room temperature under air atmosphere. The precipitated solids were collected by filtration and washed with diethyl ether (3×50 mL) to afford (S)-2-amino-N-methylpropanamide hydrochloride (920 mg, 95%) as a white solid.

Preparation 138C: (S)-2-{[4-iodo-6-(morpholin-4-yl)pyridin-2-yl]amino}-N-methylpropanamide

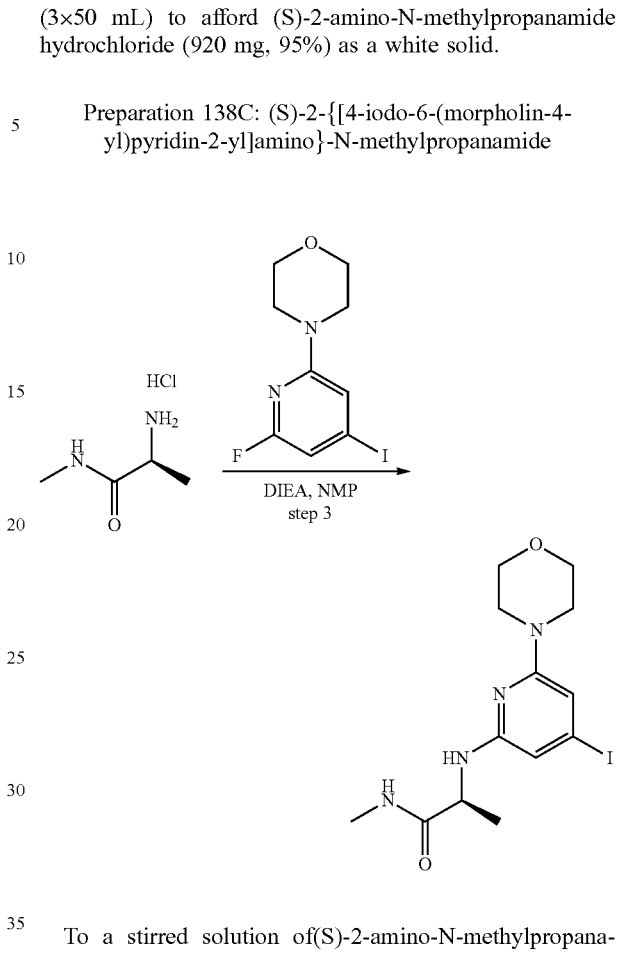

To a stirred solution of(S)-2-amino-N-methylpropanamide hydrochloride (450 mg, 3.246 mmol) and 4-(6-fluoro-4-iodopyridin-2-yl)morpholine (500 mg, 1.623 mmol) in NMP were added DIEA (839 mg, 6.492 mmol). The resulting mixture was stirred for 24 h at 170° C. The reaction was quenched with water (30 mL). The residue was washed with ethyl acetate (3×30 mL). The resulting mixture was concentrated under reduced pressure. The residue was purified by silica gel column chromatography, eluted with PE/EtOAc (1/1) to afford (S)-2-{[4-iodo-6-(morpholin-4-yl)pyridin-2-yl]amino}-N-methylpropanamide (204 mg, 32%) as a brown solid. MS ESI calculated for $C_{13}H_{19}IN_4O_2$ [M+H]$^+$, 391.06, found 391.00.

Example 138: (S)—N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide

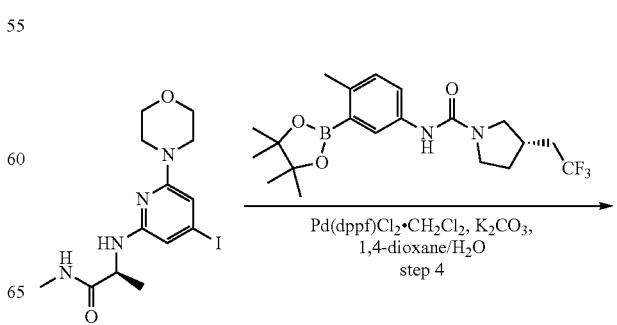

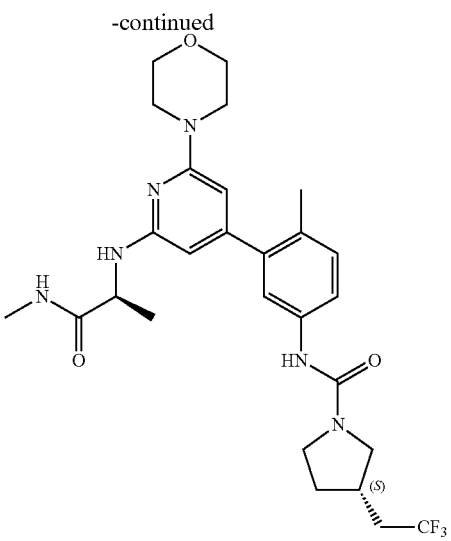

To a stirred solution/mixture of (2S)-2-{[4-iodo-6-(morpholin-4-yl)pyridin-2-yl]amino}-N-methylpropanamide (117 mg, 0.300 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (123.61 mg, 0.300 mmol) in 1,4-dioxane and H$_2$O were added Pd(dppf)Cl$_2$·CH$_2$Cl$_2$ (26.3 mg, 0.032 mmol) and K$_2$CO$_3$ (124.31 mg, 0.900 mmol). The resulting mixture was stirred for 2 h at 80° C. under nitrogen atmosphere. The resulting mixture was concentrated under reduced pressure. The residue was purified by silica gel column chromatography, eluted with EtOAc. The crude was resolved by Chiral-Prep-HPLC with the following conditions (Column: CHIRALPAK AD-H, 2×25 cm, 5 μm; Mobile Phase A: Hexane (0.5% 2M NH$_3$-MeOH), Mobile Phase B: IPA; Flow rate: 20 mL/min; Gradient: A:B=70:30; 220/254 nm; RT$_1$: 12.12 min to afford (S)—N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide (51 mg, 31%) as an white solid. MS ESI calculated for C$_{27}$H$_{35}$F$_3$N$_6$O$_3$ [M+H]$^+$, 549.27, found 549.20. $^1$H NMR (400 MHz, DMSO-d$_6$) δ 8.11 (s, 1H), 7.74-7.72 (m, 1H), 7.40-7.38 (m, 2H), 7.09 (d, J=8.4 Hz, 1H), 6.43 (d, J=6.0 Hz, 1H), 5.82 (s, 1H), 5.79 (s, 1H), 4.23-4.17 (m, 1H), 3.66-3.55 (m, 5H), 3.52-3.50 (m, 1H), 3.36-3.28 (m, 4H), 3.04-3.01 (m, 1H), 2.58-2.50 (m, 3H), 2.45-2.40 (m, 4H), 2.15 (s, 3H), 2.14-2.10 (m, 1H), 1.70-1.65 (m, 1H), 1.26 (d, J=7.2 Hz, 3H). $^{19}$F NMR (282 MHz, DMSO-d$_6$) δ −63.35 (3F). And RT$_2$: 18.73 min afforded (S)—N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide (5.7 mg, 4%) as a white solid.

Example 139: (3S)—N-{3-[2-ethanesulfonamido-6-(morpholin-4-yl)pyridin-4-yl]-4-methylphenyl}-3-(2,2,2-trifluoroethyl)pyrrolidine-1-carboxamide

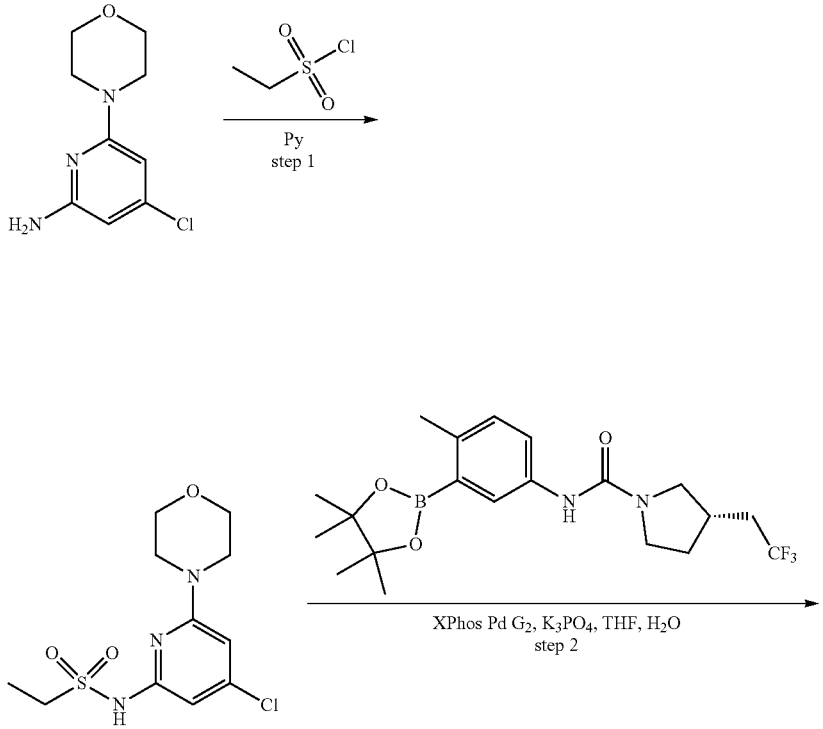

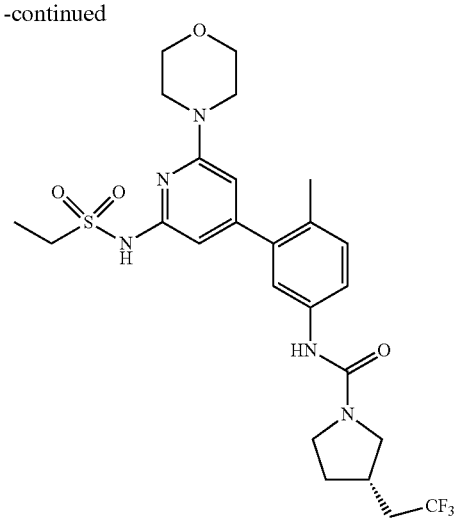

Preparation 139A: N-[4-chloro-6-(morpholin-4-yl)pyridin-2-yl]ethanesulfonamide

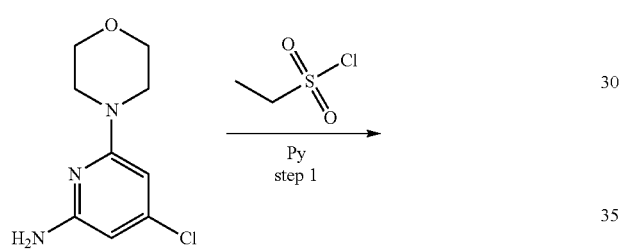

A mixture of 4-chloro-6-(morpholin-4-yl)pyridin-2-amine (500 mg, 2.340 mmol) and ethanesulfonyl chloride (451 mg, 3.510 mmol) in pyridine (7.5 mL) was stirred for 16 h at 80° C. The resulting mixture was concentrated under reduced pressure. The residue was purified by silica gel column chromatography, eluted with PE/EtOAc (1/1) to afford N-[4-chloro-6-(morpholin-4-yl)pyridin-2-yl]ethanesulfonamide (120 mg, 15%) as a brown solid. MS ESI calculated for $C_{11}H_{16}ClN_3O_3S$ $[M+H]^+$, 306.06, found 306.10. $^1$H NMR (400 MHz, Chloroform-d) δ 6.84 (brs, 1H), 6.51 (s, 1H), 6.31 (s, 1H), 3.80-3.77 (m, 4H), 3.48-3.46 (m, 4H), 3.35 (q, J=7.2 Hz, 2H), 1.41 (t, J=7.2 Hz, 3H).

Example 139: (3S)—N-{3-[2-ethanesulfonamido-6-(morpholin-4-yl)pyridin-4-yl]-4-methylphenyl}-3-(2,2,2-trifluoroethyl)pyrrolidine-1-carboxamide

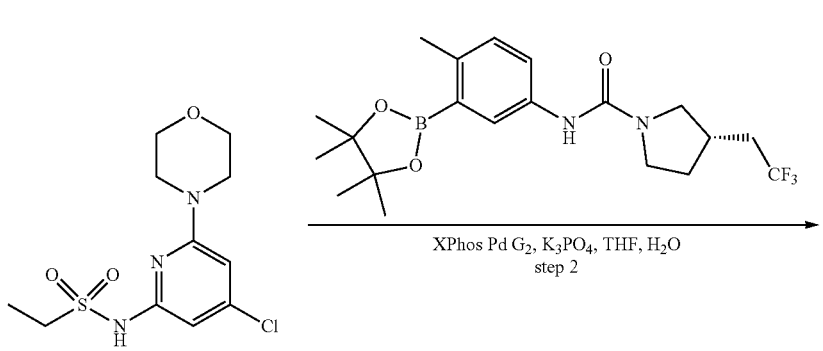

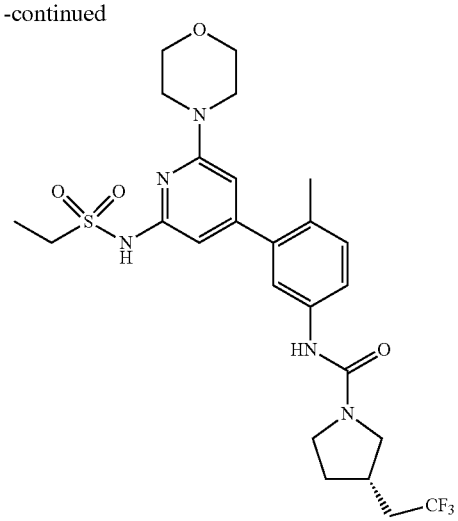

A mixture of N-[4-chloro-6-(morpholin-4-yl)pyridin-2-yl]ethanesulfonamide (100 mg, 0.327 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (108 mg, 0.262 mmol), $K_3PO_4$ (139 mg, 0.654 mmol) and $2^{nd}$ XPhos Precatalyst (26 mg, 0.033 mmol) in THF (1 mL) and $H_2O$ (0.1 mL) was stirred for 2 h at 80° C. under nitrogen atmosphere. The resulting mixture was concentrated under reduced pressure. The residue was purified by Prep-TLC with PE/EtOAc/EtOH (8/3/1) to afford (3S)—N-{3-[2-ethanesulfonamido-6-(morpholin-4-yl)pyridin-4-yl]-4-methylphenyl}-3-(2,2,2-trifluoroethyl)pyrrolidine-1-carboxamide (87 mg, 46%) as an off-white solid. MS ESI calculated for $C_{25}H_{32}F_3N_5O_4S$ [M+H]$^+$, 556.21, found 556.30. $^1H$ NMR (400 MHz, DMSO-$d_6$) δ 10.25 (brs, 1H), 8.16 (s, 1H), 7.46 (dd, J=2.4, 8.4 Hz, 1H), 7.36 (d, J=2.4 Hz, 1H), 7.14 (d, J=8.4 Hz, 1H), 6.32 (s, 1H), 6.15 (s, 1H), 3.71-3.65 (m, 5H), 3.53-3.43 (m, 7H), 3.32-3.30 (m, 1H), 3.02-3.00 (m, 1H), 2.53-2.33 (m, 3H), 2.20 (s, 3H), 2.12-2.00 (m, 1H), 2.75-2.65 (m, 1H), 1.26 (t, J=7.2 Hz, 3H). $^{19}F$ NMR (376 MHz, DMSO-$d_6$) δ −63.37 (3F).

Example 140: (3S)—N-{4-methyl-3-[2-(morpholin-4-yl)-6-(propane-2-sulfonamido)pyridin-4-yl]phenyl}-3-(2,2,2-trifluoroethyl)pyrrolidine-1-carboxamide

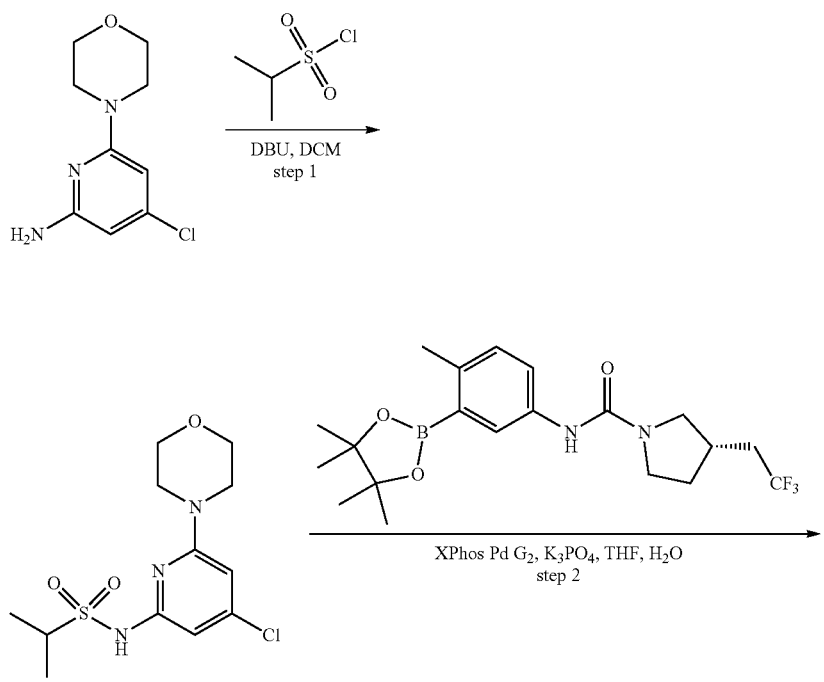

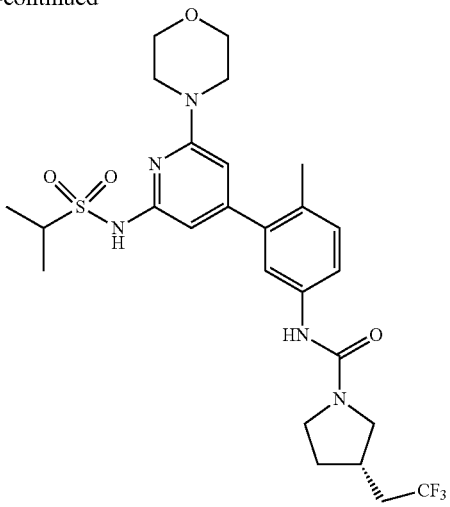

Preparation 140A: N-[4-chloro-6-(morpholin-4-yl)pyridin-2-yl]propane-2-sulfonamide

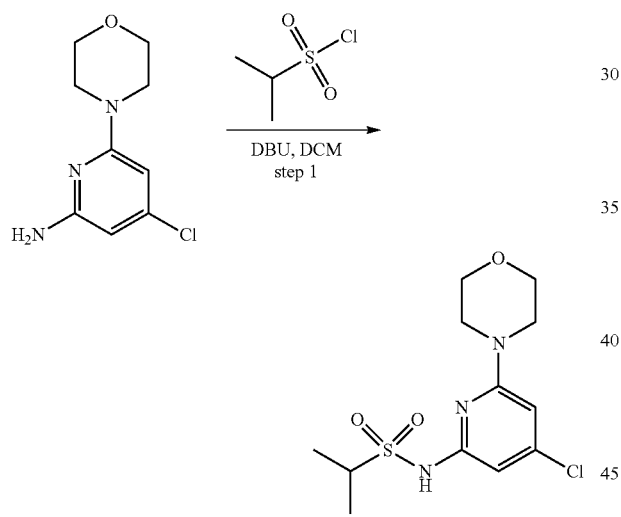

To a stirred mixture of 4-chloro-6-(morpholin-4-yl)pyridin-2-amine (500 mg, 2.340 mmol) and DBU (1.43 g, 9.393 mmol) in DCM (7 mL) was added propane-2-sulfonyl chloride (350 mg, 9.360 mmol) dropwise at −30° C. The reaction mixture was stirred for 3 h at −30° C. The resulting mixture was diluted with water (30 mL). The resulting mixture was extracted with DCM (3×20 mL). The combined organic layers were washed with brine (2×20 mL), dried over anhydrous $Na_2SO_4$. After filtration, the filtrate was concentrated under reduced pressure. The residue was purified by reverse phase chromatography, eluted with 40% $CH_3CN$ in water (plus 0.5% TFA) to afford N-[4-chloro-6-(morpholin-4-yl)pyridin-2-yl]propane-2-sulfonamide (350 mg, 47%) as a light yellow solid. MS ESI calculated for $C_{12}H_{18}ClN_3O_3S$ [M+H]$^+$, 320.08; found 320.10. $^1$H NMR (400 MHz, Chloroform-d) δ 6.62 (d, J=1.2 Hz, 1H), 6.33 (d, J=1.2 Hz, 1H), 3.84-3.77 (m, 4H), 3.62-3.45 (m, 5H), 1.45 (d, J=6.8 Hz, 6H).

Example 140: (3S)—N-{4-methyl-3-[2-(morpholin-4-yl)-6-(propane-2-sulfonamido)pyridin-4-yl]phenyl}-3-(2,2,2-trifluoroethyl)pyrrolidine-1-carboxamide

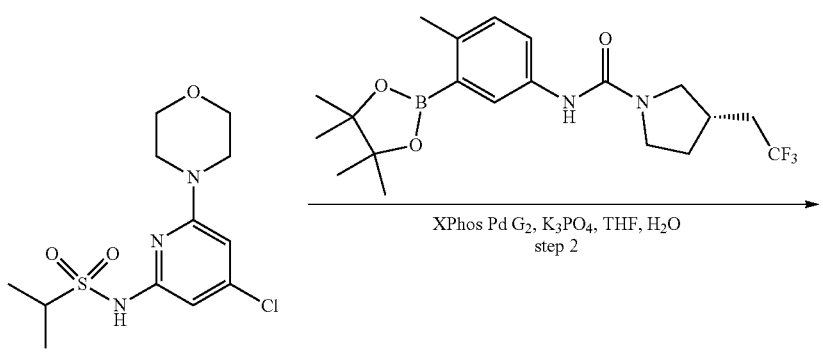

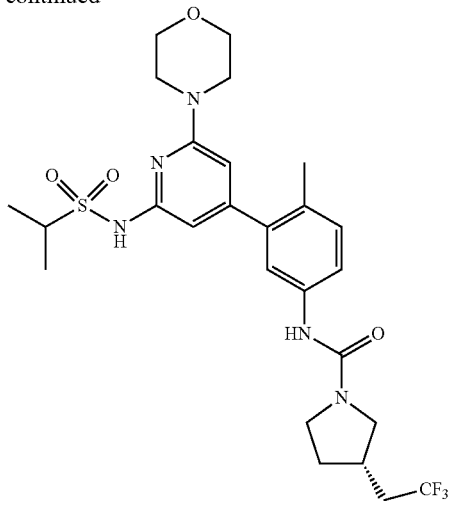

A mixture of N-[4-chloro-6-(morpholin-4-yl)pyridin-2-yl]propane-2-sulfonamide (120 mg, 0.375 mmol), K$_3$PO$_4$ (239 mg, 1.125 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (155 mg, 0.375 mmol) in THF (2 mL) and H$_2$O (0.2 mL) was added 2$^{nd}$ XPhos Precatalyst (29 mg, 0.038 mmol) was stirred for 2 h at 80° C. under nitrogen atmosphere. The resulting mixture was concentrated under reduced pressure. The residue was purified by silica gel column chromatography, eluted with PE/EtOAc (2/3) and reverse phase chromatography, eluted with 45% CH$_3$CN in water (0.05% NH$_4$HCO$_3$) to afford (3S)—N-{4-methyl-3-[2-(morpholin-4-yl)-6-(propane-2-sulfonamido)pyridin-4-yl]phenyl}-3-(2,2,2-trifluoroethyl) pyrrolidine-1-carboxamide (145.2 mg, 66%) as a white solid. MS ESI calculated for C$_{26}$H$_{34}$F$_3$N$_5$O$_4$S [M+H]$^+$, 570.23; found 570.30. $^1$H NMR (300 MHz, Chloroform-d) δ 7.33-7.30 (m, 2H), 7.19 (d, J=8.4 Hz, 1H), 6.58 (brs, 1H), 6.30 (s, 1H), 6.17 (s, 1H), 3.85-3.80 (m, 5H), 3.68-3.43 (m, 7H), 3.14-3.11 (m, 1H), 2.64-2.53 (m, 1H), 2.35-2.15 (m, 6H), 1.84-1.66 (m, 1H), 1.46 (d, J=6.9 Hz, 6H). $^{19}$F NMR (282 MHz, Chloroform-d) δ −64.95 (3F).

Example 141: (3S)—N-{4-methyl-3-[2-(1-methylcyclopropanesulfonamido)-6-(morpholin-4-yl)pyridin-4-yl]phenyl}-3-(2,2,2-trifluoroethyl)pyrrolidine-1-carboxamide

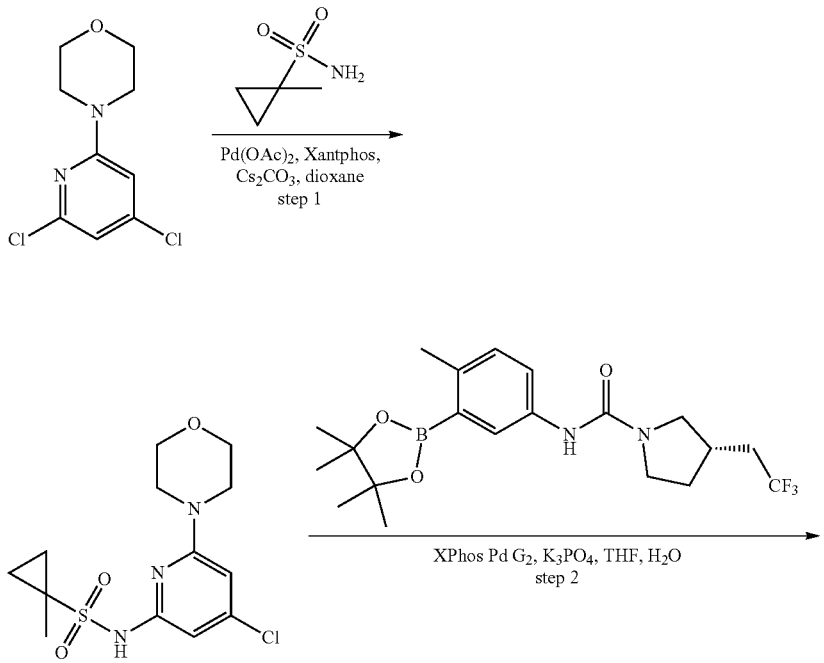

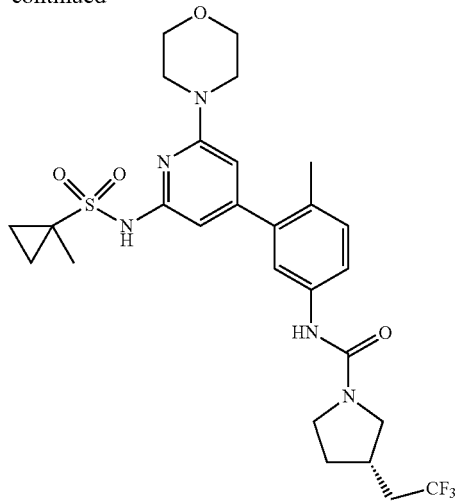

Preparation 141A: N-[4-chloro-6-(morpholin-4-yl)pyridin-2-yl]-1-methylcyclopropane-1-sulfonamide

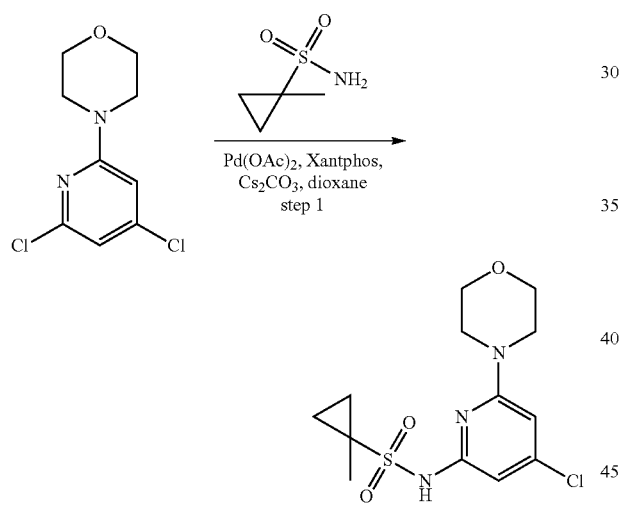

A mixture of 4-(4,6-dichloropyridin-2-yl)morpholine (1.00 g, 4.29 mmol), 1-methylcyclopropane-1-sulfonamide (0.58 g, 4.29 mmol), dioxane (12 mL), XantPhos (0.25 g, 0.43 mmol) $Cs_2CO_3$ (4.2 g, 12.87 mmol) and Pd(OAc) 2 (0.10 g, 0.43 mmol) was stirred for 16 h at 100° C. under nitrogen atmosphere. The resulting mixture was diluted with water (50 mL). The resulting mixture was extracted with EtOAc (3×30 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EtOAc (1/1) to afford N-[4-chloro-6-(morpholin-4-yl)pyridin-2-yl]-1-methylcyclopropane-1-sulfonamide (1.00 g, 70%). MS ESI calculated for $C_{13}H_{18}ClN_3O_3S$ [M+H]$^+$, 332.08; found 332.10. $^1$H NMR (400 MHz, Methanol-$d_4$) δ 11.11 (s, 1H), 7.34 (s, 1H), 7.20 (s, 1H), 4.49-4.47 (m, 4H), 4.29-4.27 (m, 4H), 2.23 (s, 3H), 2.14-2.03 (m, 2H), 1.71-1.63 (m, 2H).

Example 141: (3S)—N-{4-methyl-3-[2-(1-methylcyclopropanesulfonamido)-6-(morpholin-4-yl)pyridin-4-yl]phenyl}-3-(2,2,2-trifluoroethyl)pyrrolidine-1-carboxamide

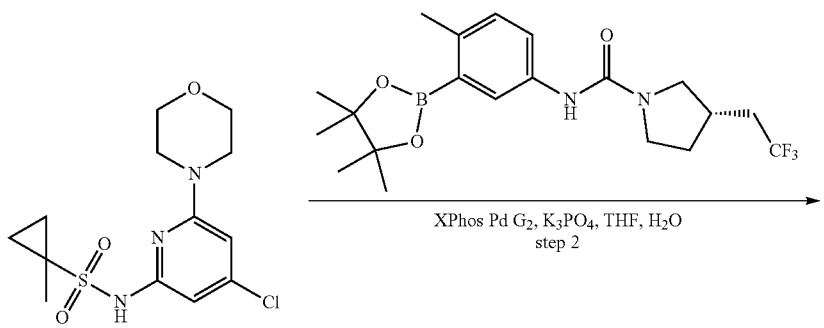

-continued

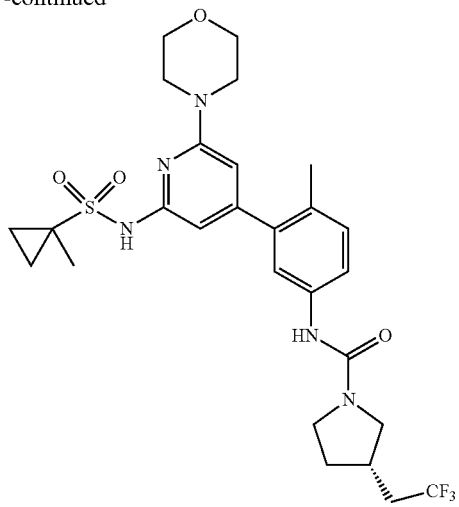

A mixture of N-[4-chloro-6-(morpholin-4-yl)pyridin-2-yl]-1-methylcyclopropane-1-sulfonamide (150 mg, 0.452 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (186 mg, 0.452 mmol), THF (2 mL), $H_2O$ (0.2 mL), $K_3PO_4$ (288 mg, 1.356 mmol) and $2^{nd}$ XPhos Precatalyst (35 mg, 0.045 mmol) was stirred for 2 h at 80° C. under nitrogen atmosphere. The resulting mixture was concentrated under reduced pressure. The residue was purified by silica gel column chromatography, eluted with PE/EtOAc/EtOH (4/3/1) and reverse phase chromatography, eluted with 55% $CH_3CN$ in water (0.05% $NH_4HCO_3$) to afford (3S)—N-{4-methyl-3-[2-(1-methylcyclopropane-sulfonamido)-6-(morpholin-4-yl)pyridin-4-yl]phenyl}-3-(2,2,2-trifluoroethyl)pyrrolidine-1-carboxamide (71 mg, 27%) as a white solid. MS ESI calculated for $C_{27}H_{34}F_3N_5O_4S$ $[M+H]^+$, 582.23; found 582.30. $^1H$ NMR (300 MHz, Chloroform-d) δ 7.35-7.29 (m, 2H), 7.19 (d, J=8.4 Hz, 1H), 6.71 (brs, 2H), 6.31 (s, 1H), 6.16 (s, 1H), 3.85-3.82 (m, 5H), 3.68-3.63 (m, 1H), 3.60-3.40 (m, 5H), 3.17-3.11 (m, 1H), 2.64-2.53 (m, 1H), 2.39-2.18 (m, 6H), 1.84-1.77 (m, 1H), 1.58 (s, 3H), 1.48-1.46 (m, 2H), 0.84-0.82 (m, 2H). $^{19}F$ NMR (282 MHz, Chloroform-d) δ −64.95 (3F).

II. Biological Evaluation

Enzymatic RAF1 Kinase Activity Determination:

Small molecule inhibition of RAF1 kinases was measured using ADP-Glo assay. In the assay, ADP is converted to ATP in the presence of test kinase and substrate, resulting in luciferase reaction and luminescent readout with light generated proportional to the relative kinase activity. Compounds diluted in DMSO were used in 10-point, 3-fold dose curve for both assays. Final concentrations of 3 nM RAF1 (CarnaBio, Cat. 09-125) and 30 nM MEK1 substrate (Millipore, Cat. 14-420) were incubated with 3 μM ATP, 10 mM MgCl2, 0.003% Brij-35, 2 mM DTT, 0.05% BSA, 1 mM EGTA, and 50 mM HEPES for 90 minutes at room temp prior to addition of ADP-Glo reagent (Promega, Cat. V9102) for 40 minutes, and detection reagent for 45 minutes. Luminescence was read on an Envision plate reader (PerkinElmer) and percent remaining activity was used to calculate IC50 using a four-parameter fit model using Dotmatics Knowledge Solutions Studies curve fitting (Dotmatics, Bishops Stortford, UK, CM23). Representative data for exemplary compounds is presented in Table 2.

TABLE 2

| Synthetic Chemistry Example | RAF-1 $IC_{50}$ |
|---|---|
| 1 | A |
| 2 | A |
| 3 | A |
| 4 | A |
| 5 | A |
| 6 | A |
| 7 | B |
| 8 | A |
| 9 | A |
| 10 | B |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | B |
| 41 | B |
| 42 | A |
| 43 | A |
| 44 | A |
| 45 | A |
| 46 | A |
| 47 | A |
| 48 | A |

TABLE 2-continued

| Synthetic Chemistry Example | RAF-1 IC$_{50}$ |
|---|---|
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | B |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | B |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |

Note:
Biochemical assay IC$_{50}$ data are designated within the following ranges:
A: ≤0.010 μM
B: >0.010 μM to ≤0.100 μM
C: >0.100 μM to ≤1 μM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:
1. A compound, or pharmaceutically acceptable salt or solvate thereof, selected from the group consisting of:
(3S)—N-(3-(6-((3,3-difluorocyclopentyl)amino)-2-morpholinopyrimidin-4-yl)-4-methylphenyl)-3-(2,2,2-trifluoroethyl)pyrrolidine-1-carboxamide;
(S)—N-(3-(6-(((R)-3,3-difluorocyclopentyl)amino)-2-morpholinopyrimidin-4-yl)-4-methylphenyl)-3-(2,2,2-trifluoroethyl)pyrrolidine-1-carboxamide;
(S)—N-(3-(6-(((S)-3,3-difluorocyclopentyl)amino)-2-morpholinopyrimidin-4-yl)-4-methylphenyl)-3-(2,2,2-trifluoroethyl)pyrrolidine-1-carboxamide;
(S)—N-(3-(2-(((1S,3S)-3-hydroxycyclopentyl)amino)-6-morpholinopyrimidin-4-yl)-4-methylphenyl)-3-(2,2,2-trifluoroethyl)pyrrolidine-1-carboxamide;
(S)—N-(3-(2-(((1R,3R)-3-hydroxycyclopentyl)amino)-6-morpholinopyrimidin-4-yl)-4-methylphenyl)-3-(2,2,2-trifluoroethyl)pyrrolidine-1-carboxamide;

(S)—N-(3-(2-(((3-hydroxyoxetan-3-yl)methyl)amino)-6-morpholinopyridin-4-yl)-4-methylphenyl)-3-(2,2,2-trifluoroethyl)pyrrolidine-1-carboxamide;

(3S)—N-(3-(2-((3,3-difluorocyclopentyl)amino)-6-morpholinopyrimidin-4-yl)-4-methylphenyl)-3-(2,2,2-trifluoroethyl)pyrrolidine-1-carboxamide;

(S)—N-(3-(2-(((R)-3,3-difluorocyclopentyl)amino)-6-morpholinopyrimidin-4-yl)-4-methylphenyl)-3-(2,2,2-trifluoroethyl)pyrrolidine-1-carboxamide;

(S)—N-(3-(2-(((S)-3,3-difluorocyclopentyl)amino)-6-morpholinopyrimidin-4-yl)-4-methylphenyl)-3-(2,2,2-trifluoroethyl)pyrrolidine-1-carboxamide;

(3S)—N-[3-(2-[[(cis-3-hydroxycyclopentyl]amino]-6-(morpholin-4-yl)pyrimidin-4-yl)-4-methylphenyl]-3-(2,2,2-trifluoroethyl)pyrrolidine-1-carboxamide;

(S)—N-(3-(2-(((1S,3R)-3-hydroxycyclopentyl)amino)-6-morpholinopyrimidin-4-yl)-4-methylphenyl)-3-(2,2,2-trifluoroethyl)pyrrolidine-1-carboxamide;

(S)—N-(3-(2-(((1R,3S)-3-hydroxycyclopentyl)amino)-6-morpholinopyrimidin-4-yl)-4-methylphenyl)-3-(2,2,2-trifluoroethyl)pyrrolidine-1-carboxamide;

(S)—N-(3-(2-(((R)-2-hydroxypropyl)amino)-6-morpholinopyridin-4-yl)-4-methylphenyl)-3-(2,2,2-trifluoroethyl)pyrrolidine-1-carboxamide;

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide;

(S)—N-(3-(2-(3-hydroxyazetidin-1-yl)-6-morpholinopyrimidin-4-yl)-4-methylphenyl)-3-(2,2,2-trifluoroethyl)pyrrolidine-1-carboxamide;

(S)—N-(3-(2-(3-hydroxyazetidin-1-yl)-6-morpholinopyridin-4-yl)-4-methylphenyl)-3-(2,2,2-trifluoroethyl)pyrrolidine-1-carboxamide;

(R)—N-(3-(2-(((R)-1-hydroxypropan-2-yl)amino)-6-morpholinopyridin-4-yl)-4-methylphenyl)-3-(trifluoromethoxy)pyrrolidine-1-carboxamide;

(R)—N-(3-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide;

(S)—N-(3-(2-((2-hydroxyethyl)amino)-6-morpholinopyridin-4-yl)-4-methylphenyl)-3-(2,2,2-trifluoroethyl)pyrrolidine-1-carboxamide;

N-(3-(2-((2-hydroxyethyl)amino)-6-morpholinopyridin-4-yl)-4-methylphenyl)-3-(2,2,2-trifluoroethyl)-2,5-dihydro-1H-pyrrole-1-carboxamide;

(S)—N-(3-(2-((2-hydroxyethyl)(methyl)amino)-6-morpholinopyridin-4-yl)-4-methylphenyl)-3-(2,2,2-trifluoroethyl)pyrrolidine-1-carboxamide;

(R)—N-(3-(2-((2-hydroxyethyl)amino)-6-morpholinopyridin-4-yl)-4-methylphenyl)-3-(trifluoromethoxy)pyrrolidine-1-carboxamide;

(R)—N-(3-(2-(((R)-2-hydroxypropyl)amino)-6-morpholinopyridin-4-yl)-4-methylphenyl)-3-(trifluoromethoxy)pyrrolidine-1-carboxamide;

(R)—N-(3-(2-((2-hydroxypropyl)amino)-6-morpholinopyridin-4-yl)-4-methylphenyl)-3-(2,2,2-trifluoroethyl)-2,5-dihydro-1H-pyrrole-1-carboxamide;

(S)—N-(3-(2-(((R)-2-hydroxypropyl)(methyl)amino)-6-morpholinopyridin-4-yl)-4-methylphenyl)-3-(2,2,2-trifluoroethyl)pyrrolidine-1-carboxamide;

(S)—N-(3-(2-(3,6-dihydro-2H-pyran-4-yl)-6-(((R)-2-hydroxypropyl)amino)pyridin-4-yl)-4-methylphenyl)-3-(2,2,2-trifluoroethyl)pyrrolidine-1-carboxamide;

(S)—N-(3-(2-(((R)-2-hydroxypropyl)amino)-6-(tetrahydro-2H-pyran-4-yl)pyridin-4-yl)-4-methylphenyl)-3-(2,2,2-trifluoroethyl)pyrrolidine-1-carboxamide;

(R)—N-(3-(2-((2-hydroxypropyl)amino)-6-morpholinopyridin-4-yl)-4-methylphenyl)-3-(trifluoromethyl)-2,5-dihydro-1H-pyrrole-1-carboxamide;

(R)—N-(3-(2-((1-hydroxypropan-2-yl)amino)-6-morpholinopyridin-4-yl)-4-methylphenyl)-3-(trifluoromethyl)-2,5-dihydro-1H-pyrrole-1-carboxamide;

(S)—N-(3-(2-(((S)-1-hydroxypropan-2-yl)amino)-6-morpholinopyridin-4-yl)-4-methylphenyl)-3-(2,2,2-trifluoroethyl)pyrrolidine-1-carboxamide;

(S)—N-(3-(2-(((S)-2-hydroxypropyl)amino)-6-morpholinopyridin-4-yl)-4-methylphenyl)-3-(2,2,2-trifluoroethyl)pyrrolidine-1-carboxamide;

(S)—N-(3-(2-(3,6-dihydro-2H-pyran-4-yl)-6-(((R)-1-hydroxypropan-2-yl)amino)pyridin-4-yl)-4-methylphenyl)-3-(2,2,2-trifluoroethyl)pyrrolidine-1-carboxamide;

(S)—N-(3-(2-(((R)-1-hydroxypropan-2-yl)amino)-6-(tetrahydro-2H-pyran-4-yl)pyridin-4-yl)-4-methylphenyl)-3-(2,2,2-trifluoroethyl)pyrrolidine-1-carboxamide;

(S)—N-(3-(2-(((1S,3R)-3-hydroxy-3-methylcyclobutyl)amino)-6-morpholinopyridin-4-yl)-4-methylphenyl)-3-(2,2,2-trifluoroethyl)pyrrolidine-1-carboxamide;

(S)—N-(3-(2-(((1R,3S)-3-hydroxy-3-methylcyclobutyl)amino)-6-morpholinopyridin-4-yl)-4-methylphenyl)-3-(2,2,2-trifluoroethyl)pyrrolidine-1-carboxamide;

(S)—N-(3-(2-(((1S,4R)-4-hydroxy-4-methylcyclohexyl)amino)-6-morpholinopyridin-4-yl)-4-methylphenyl)-3-(2,2,2-trifluoroethyl)pyrrolidine-1-carboxamide;

(S)—N-(3-(2-(((1R,4S)-4-hydroxy-4-methylcyclohexyl)amino)-6-morpholinopyridin-4-yl)-4-methylphenyl)-3-(2,2,2-trifluoroethyl)pyrrolidine-1-carboxamide;

(S)—N-(3-(2-(3-hydroxy-3-methylazetidin-1-yl)-6-morpholinopyridin-4-yl)-4-methylphenyl)-3-(2,2,2-trifluoroethyl)pyrrolidine-1-carboxamide;

(S)—N-(3-(2-(isopropylamino)-6-morpholinopyridin-4-yl)-4-methylphenyl)-3-(2,2,2-trifluoroethyl)pyrrolidine-1-carboxamide;

(S)—N-(3-(2-(tert-butylamino)-6-morpholinopyridin-4-yl)-4-methylphenyl)-3-(2,2,2-trifluoroethyl)pyrrolidine-1-carboxamide;

(S)—N-(3-(2-((1-hydroxy-2-methylpropan-2-yl)amino)-6-morpholinopyridin-4-yl)-4-methylphenyl)-3-(2,2,2-trifluoroethyl)pyrrolidine-1-carboxamide;

(S)—N-(4-methyl-3-(2-morpholino-6-(oxetan-3-ylamino)pyridin-4-yl)phenyl)-3-(2,2,2-trifluoroethyl)pyrrolidine-1-carboxamide;

(S)—N-(4-methyl-3-(2-morpholino-6-(((R)-tetrahydrofuran-3-yl)amino)pyridin-4-yl)phenyl)-3-(2,2,2-trifluoroethyl)pyrrolidine-1-carboxamide;

(S)—N-(4-methyl-3-(2-morpholino-6-(((S)-tetrahydrofuran-3-yl)amino)pyridin-4-yl)phenyl)-3-(2,2,2-trifluoroethyl)pyrrolidine-1-carboxamide;

(S)—N-(4-methyl-3-(2-morpholino-6-(((R)-tetrahydro-2H-pyran-3-yl)amino)pyridin-4-yl)phenyl)-3-(2,2,2-trifluoroethyl)pyrrolidine-1-carboxamide;

(S)—N-(4-methyl-3-(2-morpholino-6-((tetrahydro-2H-pyran-4-yl)amino)pyridin-4-yl)phenyl)-3-(2,2,2-trifluoroethyl)pyrrolidine-1-carboxamide;

(S)—N-(3-(2-(((1S,3R)-3-hydroxycyclobutyl)amino)-6-morpholinopyridin-4-yl)-4-methylphenyl)-3-(2,2,2-trifluoroethyl)pyrrolidine-1-carboxamide;

(S)—N-(3-(2-(((1R,3S)-3-hydroxycyclobutyl)amino)-6-morpholinopyridin-4-yl)-4-methylphenyl)-3-(2,2,2-trifluoroethyl)pyrrolidine-1-carboxamide;

(S)—N-(3-(2-(((R)-1-hydroxybutan-2-yl)amino)-6-morpholinopyridin-4-yl)-4-methylphenyl)-3-(2,2,2-trifluoroethyl)pyrrolidine-1-carboxamide;

(S)—N-(3-(2-(((R)-1-methoxypropan-2-yl)amino)-6-morpholinopyridin-4-yl)-4-methylphenyl)-3-(2,2,2-trifluoroethyl)pyrrolidine-1-carboxamide;

(S)—N-(3-(2-(((S)-2-methoxypropyl)amino)-6-morpholinopyridin-4-yl)-4-methylphenyl)-3-(2,2,2-trifluoroethyl)pyrrolidine-1-carboxamide;

(S)—N-(4-methyl-3-(2-morpholino-6-(((S)-tetrahydro-2H-pyran-3-yl)amino)pyridin-4-yl)phenyl)-3-(2,2,2-trifluoroethyl)pyrrolidine-1-carboxamide;

(3S)—N-(4-methyl-3-(2-((3-methyltetrahydrofuran-3-yl)amino)-6-morpholinopyridin-4-yl)phenyl)-3-(2,2,2-trifluoroethyl)pyrrolidine-1-carboxamide;

(S)—N-(3-(2-((1-(hydroxymethyl)cyclobutyl)amino)-6-morpholinopyridin-4-yl)-4-methylphenyl)-3-(2,2,2-trifluoroethyl)pyrrolidine-1-carboxamide;

(S)—N-(3-(2-((3-(hydroxymethyl)oxetan-3-yl)amino)-6-morpholinopyridin-4-yl)-4-methylphenyl)-3-(2,2,2-trifluoroethyl)pyrrolidine-1-carboxamide;

(S)—N-(4-methyl-3-(2-((3-methyloxetan-3-yl)amino)-6-morpholinopyridin-4-yl)phenyl)-3-(2,2,2-trifluoroethyl)pyrrolidine-1-carboxamide;

(S)—N-(4-methyl-3-(2-((4-methyltetrahydro-2H-pyran-4-yl)amino)-6-morpholinopyridin-4-yl)phenyl)-3-(2,2,2-trifluoroethyl)pyrrolidine-1-carboxamide;

(S)—N-(3-(2-((1-(hydroxymethyl)cyclopropyl)amino)-6-morpholinopyridin-4-yl)-4-methylphenyl)-3-(2,2,2-trifluoroethyl)pyrrolidine-1-carboxamide;

(S)—N-(3-(2-(((1R,3S)-3-hydroxy-1-methylcyclobutyl)amino)-6-morpholinopyridin-4-yl)-4-methylphenyl)-3-(2,2,2-trifluoroethyl)pyrrolidine-1-carboxamide;

(S)—N-(3-(2-(((1S,3R)-3-hydroxy-1-methylcyclobutyl)amino)-6-morpholinopyridin-4-yl)-4-methylphenyl)-3-(2,2,2-trifluoroethyl)pyrrolidine-1-carboxamide;

(S)—N-(3-(2-(((2R,3R)-3-hydroxybutan-2-yl)amino)-6-morpholinopyridin-4-yl)-4-methylphenyl)-3-(2,2,2-trifluoroethyl)pyrrolidine-1-carboxamide;

(3S)—N-(3-(2-((1-cyanopropan-2-yl)amino)-6-morpholinopyridin-4-yl)-4-methylphenyl)-3-(2,2,2-trifluoroethyl)pyrrolidine-1-carboxamide;

(S)—N-(3-(2-(((1S,4R)-4-hydroxy-1-methylcyclohexyl)amino)-6-morpholinopyridin-4-yl)-4-methylphenyl)-3-(2,2,2-trifluoroethyl)pyrrolidine-1-carboxamide;

And(S)—N-(3-(2-(((1R,4S)-4-hydroxy-1-methylcyclohexyl)amino)-6-morpholinopyridin-4-yl)-4-methylphenyl)-3-(2,2,2-trifluoroethyl)pyrrolidine-1-carboxamide;

(S)—N-(3-(2-((1,3-dihydroxypropan-2-yl)amino)-6-morpholinopyridin-4-yl)-4-methylphenyl)-3-(2,2,2-trifluoroethyl)pyrrolidine-1-carboxamide;

(S)—N-(3-(2-amino-6-morpholinopyridin-4-yl)-4-methylphenyl)-3-(2,2,2-trifluoroethyl)pyrrolidine-1-carboxamide;

(S)—N-(4-methyl-3-(2-(methylamino)-6-morpholinopyridin-4-yl)phenyl)-3-(2,2,2-trifluoroethyl)pyrrolidine-1-carboxamide;

(S)—N-(3-(2-(((R)-1-hydroxypropan-2-yl)amino)-6-(3-oxomorpholino)pyridin-4-yl)-4-methylphenyl)-3-(2,2,2-trifluoroethyl)pyrrolidine-1-carboxamide;

(S)—N-(3-(2-acetamido-6-morpholinopyridin-4-yl)-4-methylphenyl)-3-(2,2,2-trifluoroethyl)pyrrolidine-1-carboxamide;

(S)—N-(3-(3-fluoro-2-(((R)-1-hydroxypropan-2-yl)amino)-6-morpholinopyridin-4-yl)-4-methylphenyl)-3-(2,2,2-trifluoroethyl)pyrrolidine-1-carboxamide;

(S)—N-(3-(3-fluoro-6-(((R)-1-hydroxypropan-2-yl)amino)-2-morpholinopyridin-4-yl)-4-methylphenyl)-3-(2,2,2-trifluoroethyl)pyrrolidine-1-carboxamide;

(S)—N-(3-(2-((2S,3R)-3-hydroxy-2-methylazetidin-1-yl)-6-morpholinopyridin-4-yl)-4-methylphenyl)-3-(2,2,2-trifluoroethyl)pyrrolidine-1-carboxamide;

(S)—N-(3-(2-((2S,3S)-3-hydroxy-2-methylazetidin-1-yl)-6-morpholinopyridin-4-yl)-4-methylphenyl)-3-(2,2,2-trifluoroethyl)pyrrolidine-1-carboxamide;

(S)—N-(4-methyl-3-(2-morpholino-6-(((S)-1,1,1-trifluoro-3-hydroxypropan-2-yl)amino)pyridin-4-yl)phenyl)-3-(2,2,2-trifluoroethyl)pyrrolidine-1-carboxamide;

(S)—N-(3-(2-(2-hydroxy-2-methylpropanamido)-6-morpholinopyridin-4-yl)-4-methylphenyl)-3-(2,2,2-trifluoroethyl)pyrrolidine-1-carboxamide;

(S)—N-(2-fluoro-5-(2-(((R)-1-hydroxypropan-2-yl)amino)-6-morpholinopyridin-4-yl)-4-methylphenyl)-3-(2,2,2-trifluoroethyl)pyrrolidine-1-carboxamide;

(R)—N-(2-fluoro-5-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide;

(S)—N-(3-(2-(2,5-dihydrofuran-3-yl)-6-(((R)-1-hydroxypropan-2-yl)amino)pyridin-4-yl)-4-methylphenyl)-3-(2,2,2-trifluoroethyl)pyrrolidine-1-carboxamide;

(3S)—N-(3-(2-(((R)-1-hydroxypropan-2-yl)amino)-6-(tetrahydrofuran-3-yl)pyridin-4-yl)-4-methylphenyl)-3-(2,2,2-trifluoroethyl)pyrrolidine-1-carboxamide;

(S)—N-(3-(2-(((S)-1-hydroxypropan-2-yl)amino)-6-(1H-pyrazol-4-yl)pyridin-4-yl)-4-methylphenyl)-3-(2,2,2-trifluoroethyl)pyrrolidine-1-carboxamide;

(S)—N-(3-(6-(((R)-1-hydroxypropan-2-yl)amino)-[2,4'-bipyridin]-4-yl)-4-methylphenyl)-3-(2,2,2-trifluoroethyl)pyrrolidine-1-carboxamide;

(S)—N-(3-(2'-amino-6-(((R)-1-hydroxypropan-2-yl)amino)-[2,4'-bipyridin]-4-yl)-4-methylphenyl)-3-(2,2,2-trifluoroethyl)pyrrolidine-1-carboxamide;

(S)—N-(3-(2'-cyano-6-(((R)-1-hydroxypropan-2-yl)amino)-[2,4'-bipyridin]-4-yl)-4-methylphenyl)-3-(2,2,2-trifluoroethyl)pyrrolidine-1-carboxamide;

(S)—N-(3-(2-((1R,6S)-3-oxabicyclo[4.1.0]heptan-6-yl)-6-(((R)-1-hydroxypropan-2-yl)amino)pyridin-4-yl)-4-methylphenyl)-3-(2,2,2-trifluoroethyl)pyrrolidine-1-carboxamide;

(S)—N-(3-(2-((1S,6R)-3-oxabicyclo[4.1.0]heptan-6-yl)-6-(((R)-1-hydroxypropan-2-yl)amino)pyridin-4-yl)-4-methylphenyl)-3-(2,2,2-trifluoroethyl)pyrrolidine-1-carboxamide;

(S)—N-(3-(2-(((R)-2,3-dihydroxypropyl)amino)-6-morpholinopyridin-4-yl)-4-methylphenyl)-3-(2,2,2-trifluoroethyl)pyrrolidine-1-carboxamide;

(S)—N-(3-(2-(((S)-2,3-dihydroxypropyl)amino)-6-morpholinopyridin-4-yl)-4-methylphenyl)-3-(2,2,2-trifluoroethyl)pyrrolidine-1-carboxamide;

(S)—N-(3-(2-((1S,5R)-3-oxabicyclo[3.1.0]hexan-1-yl)-6-(((R)-1-hydroxypropan-2-yl)amino)pyridin-4-yl)-4-methylphenyl)-3-(2,2,2-trifluoroethyl)pyrrolidine-1-carboxamide;

(S)—N-(3-(2-((1R,5S)-3-oxabicyclo[3.1.0]hexan-1-yl)-6-(((R)-1-hydroxypropan-2-yl)amino)pyridin-4-yl)-4-methylphenyl)-3-(2,2,2-trifluoroethyl)pyrrolidine-1-carboxamide;

(S)—N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide;

(R)—N-(3-(6-(((R)-2-hydroxypropyl)amino)-2-morpholinopyrimidin-4-yl)-4-methylphenyl)-3-(2,2,2-trifluoroethyl)pyrrolidine-1-carboxamide;

(S)—N-(3-(2-(((R)-2-hydroxypropyl)amino)-6-morpholinopyrimidin-4-yl)-4-methylphenyl)-3-(2,2,2-trifluoroethyl)pyrrolidine-1-carboxamide;

(S)—N-(3-(6-(((S)-2-hydroxypropyl)amino)-2-morpholinopyrimidin-4-yl)-4-methylphenyl)-3-(2,2,2-trifluoroethyl)pyrrolidine-1-carboxamide;

(S)—N-(3-(6-((2-hydroxyethyl)amino)-2-morpholinopyrimidin-4-yl)-4-methylphenyl)-3-(2,2,2-trifluoroethyl)pyrrolidine-1-carboxamide;

(S)—N-(3-(6-(((S)-1-hydroxypropan-2-yl)amino)-2-morpholinopyrimidin-4-yl)-4-methylphenyl)-3-(2,2,2-trifluoroethyl)pyrrolidine-1-carboxamide;

(S)—N-(3-(6-((2-hydroxy-2-methylpropyl)amino)-2-morpholinopyrimidin-4-yl)-4-methylphenyl)-3-(2,2,2-trifluoroethyl)pyrrolidine-1-carboxamide;

(S)—N-(3-(2-((2-hydroxyethyl)amino)-6-morpholinopyrimidin-4-yl)-4-methylphenyl)-3-(2,2,2-trifluoroethyl)pyrrolidine-1-carboxamide;

(S)—N-(3-(2-(((R)-1-hydroxypropan-2-yl)amino)-6-morpholinopyrimidin-4-yl)-4-methylphenyl)-3-(2,2,2-trifluoroethyl)pyrrolidine-1-carboxamide;

(S)—N-(3-(2-((2-hydroxy-2-methylpropyl)amino)-6-morpholinopyrimidin-4-yl)-4-methylphenyl)-3-(2,2,2-trifluoroethyl)pyrrolidine-1-carboxamide;

(S)—N-(3-(6-(((R)-1-hydroxypropan-2-yl)amino)-2-morpholinopyrimidin-4-yl)-4-methylphenyl)-3-(2,2,2-trifluoroethyl)pyrrolidine-1-carboxamide;

(S)—N-(3-(2-(((S)-1-hydroxypropan-2-yl)amino)-6-morpholinopyrimidin-4-yl)-4-methylphenyl)-3-(2,2,2-trifluoroethyl)pyrrolidine-1-carboxamide;

(R)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-3-hydroxypyrrolidin-1-yl)-6-morpholinopyridin-4-yl)-4-methylphenyl)-3-(2,2,2-trifluoroethyl)pyrrolidine-1-carboxamide;

(S)—N-(3-(2-(((S)-2-hydroxypropyl)amino)-6-morpholinopyrimidin-4-yl)-4-methylphenyl)-3-(2,2,2-trifluoroethyl)pyrrolidine-1-carboxamide;

(3S)—N-(3-[2-[(3R)-3-aminopyrrolidin-1-yl]-6-(morpholin-4-yl)pyridin-4-yl]-4-methylphenyl)-3-(2,2,2-trifluoroethyl)pyrrolidine-1-carboxamide;

(3S)—N-(3-[2-[(3S)-3-aminopyrrolidin-1-yl]-6-(morpholin-4-yl)pyridin-4-yl]-4-methylphenyl)-3-(2,2,2-trifluoroethyl)pyrrolidine-1-carboxamide;

(3S)—N-(3-[2-[(3R)-3-aminopiperidin-1-yl]-6-(morpholin-4-yl)pyridin-4-yl]-4-methylphenyl)-3-(2,2,2-trifluoroethyl)pyrrolidine-1-carboxamide;

(3S)—N-(3-[2-[(3S)-3-aminopiperidin-1-yl]-6-(morpholin-4-yl)pyridin-4-yl]-4-methylphenyl)-3-(2,2,2-trifluoroethyl)pyrrolidine-1-carboxamide;

(3S)—N-[4-methyl-3-[2-(morpholin-4-yl)-6-(2-oxopyrrolidin-1-yl)pyridin-4-yl]phenyl]-3-(2,2,2-trifluoroethyl)pyrrolidine-1-carboxamide;

(3S)—N-(3-[2-[(3R)-3-hydroxypyrrolidin-1-yl]-6-(morpholin-4-yl)pyridin-4-yl]-4-methylphenyl)-3-(2,2,2-trifluoroethyl)pyrrolidine-1-carboxamide;

(3S)—N-[4-methyl-3-[2-(3-methyl-2-oxoimidazolidin-1-yl)-6-(morpholin-4-yl)pyridin-4-yl]phenyl]-3-(2,2,2-trifluoroethyl)pyrrolidine-1-carboxamide;

(3S)—N-[4-methyl-3-[2-(N-methylacetamido)-6-(morpholin-4-yl)pyridin-4-yl]phenyl]-3-(2,2,2-trifluoroethyl)pyrrolidine-1-carboxamide;

(3S)—N-[3-[2-methanesulfonamido-6-(morpholin-4-yl)pyridin-4-yl]-4-methylphenyl]-3-(2,2,2-trifluoroethyl)pyrrolidine-1-carboxamide;

(3S)—N-[3-[2-(3-hydroxy-2-oxopyrrolidin-1-yl)-6-(morpholin-4-yl)pyridin-4-yl]-4-methylphenyl]-3-(2,2,2-trifluoroethyl)pyrrolidine-1-carboxamide;

(3S)—N-[4-methyl-3-[2-(morpholin-4-yl)-6-(2-oxo-1,3-oxazolidin-3-yl)pyridin-4-yl]phenyl]-3-(2,2,2-trifluoroethyl)pyrrolidine-1-carboxamide;

(3S)—N-(3-[2-[(5R)-5-hydroxy-2-oxopiperidin-1-yl]-6-(morpholin-4-yl)pyridin-4-yl]-4-methylphenyl)-3-(2,2,2-trifluoroethyl)pyrrolidine-1-carboxamide;

(3S)—N-(4-methyl-3-(2-morpholino-6-(2-oxo-3-azabicyclo[3.1.0]hexan-3-yl)pyridin-4-yl)phenyl)-3-(2,2,2-trifluoroethyl)pyrrolidine-1-carboxamide;

(S)—N-(3-(2-((3S,4S)-3,4-dihydroxypyrrolidin-1-yl)-6-morpholinopyridin-4-yl)-4-methylphenyl)-3-(2,2,2-trifluoroethyl)pyrrolidine-1-carboxamide;

(S)—N-(3-(2-((3S,4S)-3-fluoro-4-hydroxypyrrolidin-1-yl)-6-morpholinopyridin-4-yl)-4-methylphenyl)-3-(2,2,2-trifluoroethyl)pyrrolidine-1-carboxamide;

(3S)—N-[3-[2-cyclopropanesulfonamido-6-(morpholin-4-yl)pyridin-4-yl]-4-methylphenyl]-3-(2,2,2 trifluoroethyl)pyrrolidine-1-carboxamide;

(S)—N-(3-(2-((S)-3-amino-2-oxopyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-4-amino-2-oxopyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-3-amino-3-methylpyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-3-amino-3-methylpiperidin-1-yl)-6-morpholinopyridin-4-yl)-4-methylphenyl)-3-(2,2,2-trifluoroethyl)pyrrolidine-1-carboxamide;

(3S)—N-(3-[2-[(4R)-4-hydroxy-2-oxopyrrolidin-1-yl]-6-(morpholin-4-yl)pyridin-4-yl]-4-methylphenyl)-3-(2,2,2-trifluoroethyl)pyrrolidine-1-carboxamide;

(3S)—N-[3-[2-(1,1-dioxo-1lambda6,2-thiazolidin-2-yl)-6-(morpholin-4-yl)pyridin-4-yl]-4-methylphenyl]-3-(2,2,2-trifluoroethyl)pyrrolidine-1-carboxamide;

(S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide;

(S)—N-(3-(2-((R)-3,3-difluoro-4-hydroxypyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-3,3-difluoro-4-hydroxypyrrolidin-1-yl)-6-morpholinopyridin-4-yl)-4-methylphenyl)-3-(2,2,2-trifluoroethyl)pyrrolidine-1-carboxamide;

(3S)—N-(3-(2-((1R)-1-amino-3-azabicyclo[3.1.0]hexan-3-yl)-6-morpholinopyridin-4-yl)-4-methylphenyl)-3-(2,2,2-trifluoroethyl)pyrrolidine-1-carboxamide;

(3S)—N-(3-(2-((1S)-1-amino-3-azabicyclo[3.1.0]hexan-3-yl)-6-morpholinopyridin-4-yl)-4-methylphenyl)-3-(2,2,2-trifluoroethyl)pyrrolidine-1-carboxamide;

(S)—N-(3-(2-((R)-4-amino-2-oxopyrrolidin-1-yl)-6-morpholinopyridin-4-yl)-4-methylphenyl)-3-(2,2,2-trifluoroethyl)pyrrolidine-1-carboxamide;

(S)—N-(3-(2-((R)-4-amino-3,3-difluoropyrrolidin-1-yl)-6-morpholinopyridin-4-yl)-4-methylphenyl)-3-(2,2,2-trifluoroethyl)pyrrolidine-1-carboxamide;

(S)—N-(3-(2-((S)-4-amino-3,3-difluoropyrrolidin-1-yl)-6-morpholinopyridin-4-yl)-4-methylphenyl)-3-(2,2,2-trifluoroethyl)pyrrolidine-1-carboxamide;

(3S)—N-(3-{2-[(3R,4R)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide;

(3S)—N-(3-{2-[(3S,4S)-3-amino-4-hydroxypyrrolidin-1-yl]-6-(morpholin-4-yl)pyridin-4-yl}-4-methylphenyl)-3-(2,2,2-trifluoroethyl)pyrrolidine-1-carboxamide;

(S)—N-(4-methyl-3-(2-(((R)-1-(methylamino)-1-oxopropan-2-yl)amino)-6-morpholinopyridin-4-yl)phenyl)-3-(2,2,2-trifluoroethyl)pyrrolidine-1-carboxamide;

(S)—N-(4-methyl-3-(2-(((S)-1-(methylamino)-1-oxopropan-2-yl)amino)-6-morpholinopyridin-4-yl)phenyl)-3-(2,2,2-trifluoroethyl)pyrrolidine-1-carboxamide;

(3S)—N-{3-[2-ethanesulfonamido-6-(morpholin-4-yl)pyridin-4-yl]-4-methylphenyl}-3-(2,2,2-trifluoroethyl)pyrrolidine-1-carboxamide;

(3S)—N-{4-methyl-3-[2-(morpholin-4-yl)-6-(propane-2-sulfonamido)pyridin-4-yl]phenyl}-3-(2,2,2-trifluoroethyl)pyrrolidine-1-carboxamide; and (3S)—N-{4-methyl-3-[2-(1-methylcyclopropanesulfonamido)-6-(morpholin-4-yl)pyridin-4-yl]phenyl}-3-(2,2,2-trifluoroethyl)pyrrolidine-1-carboxamide.

2. The compound of claim 1, or pharmaceutically acceptable salt or solvate thereof, wherein the compound is: (S)—N-(3-(2-(((R)-2-hydroxypropyl)amino)-6-morpholinopyridin-4-yl)-4-methylphenyl)-3-(2,2,2-trifluoroethyl)pyrrolidine-1-carboxamide.

3. The compound of claim 1, or pharmaceutically acceptable salt or solvate thereof, wherein the compound is: (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide.

4. The compound of claim 1, or pharmaceutically acceptable salt or solvate thereof, wherein the compound is: (R)—N-(3-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide.

5. The compound of claim 1, or pharmaceutically acceptable salt or solvate thereof, wherein the compound is: (R)—N-(3-(2-((2-hydroxyethyl)amino)-6-morpholinopyridin-4-yl)-4-methylphenyl)-3-(trifluoromethoxy)pyrrolidine-1-carboxamide.

6. The compound of claim 1, or pharmaceutically acceptable salt or solvate thereof, wherein the compound is: (R)—N-(3-(2-(((R)-2-hydroxypropyl)amino)-6-morpholinopyridin-4-yl)-4-methylphenyl)-3-(trifluoromethoxy)pyrrolidine-1-carboxamide.

7. The compound of claim 1, or pharmaceutically acceptable salt or solvate thereof, wherein the compound is: (R)—N-(3-(2-((2-hydroxypropyl)amino)-6-morpholinopyridin-4-yl)-4-methylphenyl)-3-(2,2,2-trifluoroethyl)-2,5-dihydro-1H-pyrrole-1-carboxamide.

8. The compound of claim 1, or pharmaceutically acceptable salt or solvate thereof, wherein the compound is: (R)—N-(3-(2-((1-hydroxypropan-2-yl)amino)-6-morpholinopyridin-4-yl)-4-methylphenyl)-3-(trifluoromethyl)-2,5-dihydro-1H-pyrrole-1-carboxamide.

9. The compound of claim 1, or pharmaceutically acceptable salt or solvate thereof, wherein the compound is: (S)—N-(3-(2-(((S)-2-hydroxypropyl)amino)-6-morpholinopyridin-4-yl)-4-methylphenyl)-3-(2,2,2-trifluoroethyl)pyrrolidine-1-carboxamide.

10. The compound of claim 1, or pharmaceutically acceptable salt or solvate thereof, wherein the compound is: (S)—N-(3-(2-(((R)-2,3-dihydroxypropyl)amino)-6-morpholinopyridin-4-yl)-4-methylphenyl)-3-(2,2,2-trifluoroethyl)pyrrolidine-1-carboxamide, or(S)—N-(3-(2-(((S)-2,3-dihydroxypropyl)amino)-6-morpholinopyridin-4-yl)-4-methylphenyl)-3-(2,2,2-trifluoroethyl)pyrrolidine-1-carboxamide.

11. A pharmaceutical composition comprising a compound of claim 1, or pharmaceutically acceptable salt or solvate thereof, and at least one pharmaceutically acceptable excipient.

12. The pharmaceutical composition of claim 11, wherein the compound is: (S)—N-(3-(2-(((R)-2-hydroxypropyl)amino)-6-morpholinopyridin-4-yl)-4-methylphenyl)-3-(2,2,2-trifluoroethyl)pyrrolidine-1-carboxamide.

13. The pharmaceutical composition of claim 11, wherein the compound is: (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide.

14. The pharmaceutical composition of claim 11, wherein the compound is: (R)—N-(3-(2-((1-hydroxypropan-2-yl)amino)-6-morpholinopyridin-4-yl)-4-methylphenyl)-3-(2,2,2-trifluoroethyl)-2,5-dihydro-1H-pyrrole-1-carboxamide.

15. The pharmaceutical composition of claim 11, wherein the compound is: (R)—N-(3-(2-((2-hydroxyethyl)amino)-6-morpholinopyridin-4-yl)-4-methylphenyl)-3-(trifluoromethoxy)pyrrolidine-1-carboxamide.

16. The pharmaceutical composition of claim 11, wherein the compound is: (R)—N-(3-(2-(((R)-2-hydroxypropyl)amino)-6-morpholinopyridin-4-yl)-4-methylphenyl)-3-(trifluoromethoxy)pyrrolidine-1-carboxamide.

17. The pharmaceutical composition of claim 11, wherein the compound is: (R)—N-(3-(2-((2-hydroxypropyl)amino)-6-morpholinopyridin-4-yl)-4-methylphenyl)-3-(2,2,2-trifluoroethyl)-2,5-dihydro-1H-pyrrole-1-carboxamide.

18. The pharmaceutical composition of claim 11, wherein the compound is: (R)—N-(3-(2-((1-hydroxypropan-2-yl)amino)-6-morpholinopyridin-4-yl)-4-methylphenyl)-3-(trifluoromethyl)-2,5-dihydro-1H-pyrrole-1-carboxamide.

19. The pharmaceutical composition of claim 11, wherein the compound is: (S)—N-(3-(2-(((S)-2-hydroxypropyl)amino)-6-morpholinopyridin-4-yl)-4-methylphenyl)-3-(2,2,2-trifluoroethyl)pyrrolidine-1-carboxamide.

20. The pharmaceutical composition of claim 11, wherein the compound is: (S)—N-(3-(2-(((R)-2,3-dihydroxypropyl)amino)-6-morpholinopyridin-4-yl)-4-methylphenyl)-3-(2,2,2-trifluoroethyl)pyrrolidine-1-carboxamide, or(S)—N-(3-(2-(((S)-2,3-dihydroxypropyl)amino)-6-morpholinopyridin-4-yl)-4-methylphenyl)-3-(2,2,2-trifluoroethyl)pyrrolidine-1-carboxamide.

* * * * *